United States Patent
Abudayyeh et al.

(10) Patent No.: US 11,834,658 B2
(45) Date of Patent: *Dec. 5, 2023

(54) SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

(71) Applicant: Massachusetts Institute of Technology, Cambridge, MA (US)

(72) Inventors: Omar Abudayyeh, Cambridge, MA (US); Jonathan Gootenberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 46 days.

This patent is subject to a terminal disclaimer.

(21) Appl. No.: 18/066,233

(22) Filed: Dec. 14, 2022

(65) Prior Publication Data
US 2023/0135673 A1    May 4, 2023

Related U.S. Application Data

(63) Continuation of application No. 17/649,308, filed on Jan. 28, 2022, now Pat. No. 11,572,556, which is a continuation of application No. 17/451,734, filed on Oct. 21, 2021, now abandoned.

(60) Provisional application No. 63/222,550, filed on Jul. 16, 2021, provisional application No. 63/094,803, filed on Oct. 21, 2020.

(51) Int. Cl.
| | |
|---|---|
| *C12N 15/85* | (2006.01) |
| *C12N 15/11* | (2006.01) |
| *A61K 31/7105* | (2006.01) |
| *C12N 9/12* | (2006.01) |
| *C12N 9/22* | (2006.01) |
| *C12N 15/10* | (2006.01) |
| *C12N 15/113* | (2010.01) |
| *C12N 15/90* | (2006.01) |

(52) U.S. Cl.
CPC ........ *C12N 15/111* (2013.01); *A61K 31/7105* (2013.01); *C12N 9/1276* (2013.01); *C12N 9/22* (2013.01); *C12N 15/102* (2013.01); *C12N 15/113* (2013.01); *C12N 15/85* (2013.01); *C12N 15/907* (2013.01); *C12N 2310/20* (2017.05); *C12N 2310/3519* (2013.01); *C12Y 207/07049* (2013.01)

(58) Field of Classification Search
None
See application file for complete search history.

(56) References Cited

FOREIGN PATENT DOCUMENTS

WO    WO-2020191249 A1 *   9/2020

OTHER PUBLICATIONS

Ata-Abadi et al., Construction of a New Minicircle DNA Carrying an Enhanced Green Florescent Protein Reporter Gene for Efficient Expression into Mammalian Cell Lines, Mol Biol Rep (2015) 42:1175-1185, DOi 10.1007/s11033-015-3864-z, Mar. 4, 2015.
U.S. Appl. No. 18/066,223, Non-Final Office Action dated Mar. 16, 2023.

* cited by examiner

*Primary Examiner* — Celine X Qian
(74) *Attorney, Agent, or Firm* — Lathrop GPM LLP; Laura A. Labeots

(57) ABSTRACT

This disclosure provides systems, methods, and compositions for site-specific genetic engineering using Programmable Addition via Site-Specific Targeting Elements (PASTE). PASTE comprises the addition of an integration site into a target genome followed by the insertion of one or more genes of interest or one or more nucleic acid sequences of interest at the site. PASTE combines gene editing technologies and integrase technologies to achieve unidirectional incorporation of genes in a genome for the treatment of diseases and diagnosis of disease.

22 Claims, 145 Drawing Sheets
Specification includes a Sequence Listing.

PASTE     literature
ACTB (cytoskeletal)
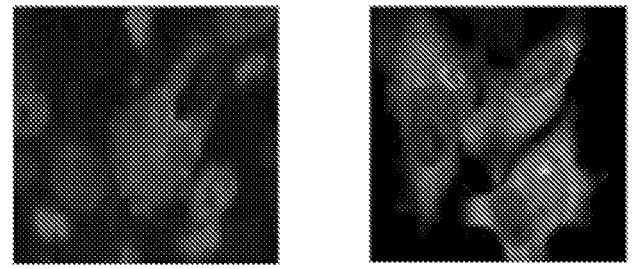
SUPT16H (nucleus)
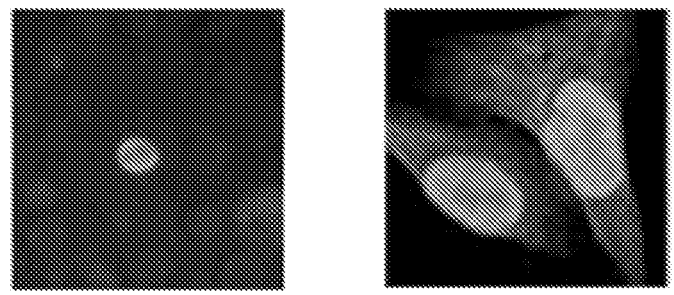
FIG. 28A PASTE  literature
NOLC1 (fibrillar center)
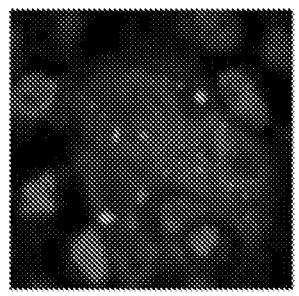 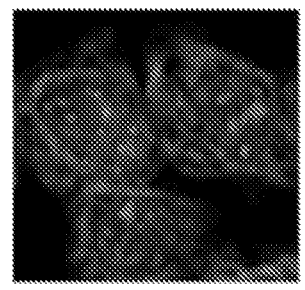
SRRM2 (nuclear speckles)
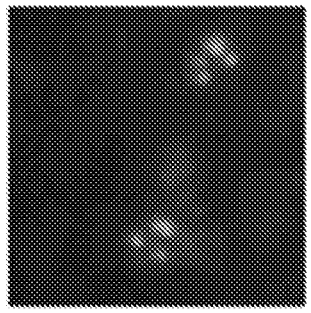 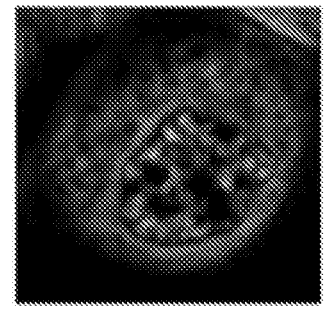
FIG. 28B PASTE literature
LMNB1 (nuclear membrane)
 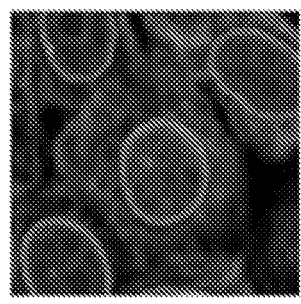
DEPDC4 (aggresome)
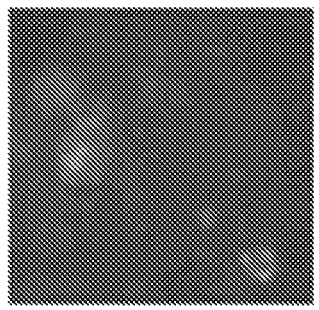 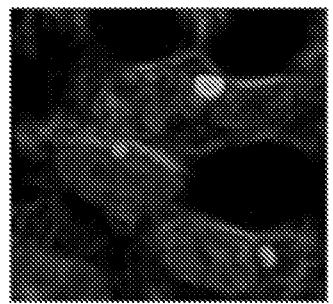
FIG. 28C

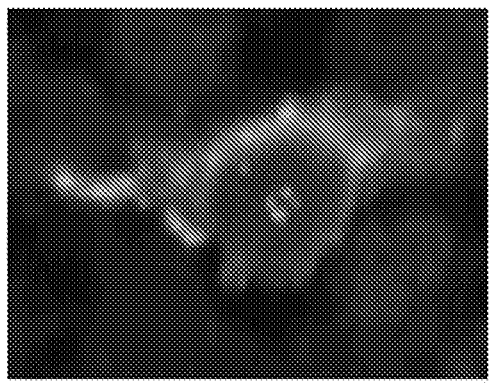 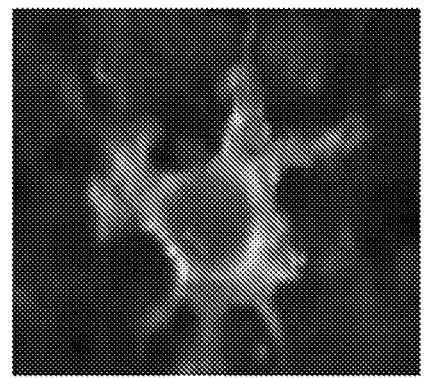
FIG. 28F

PASTE pegRNA Design
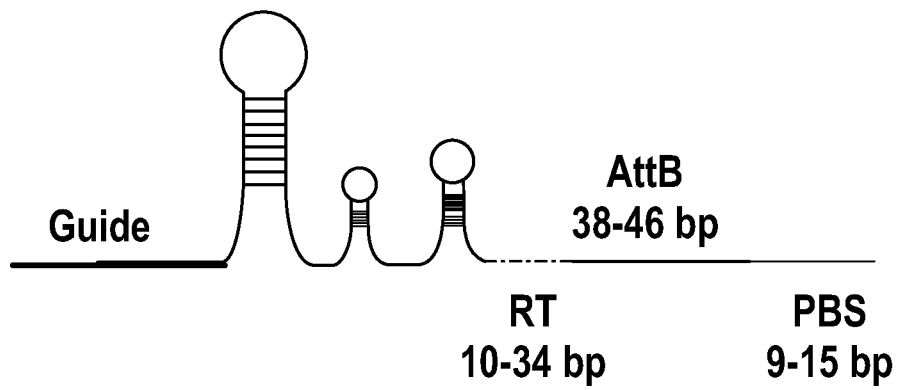
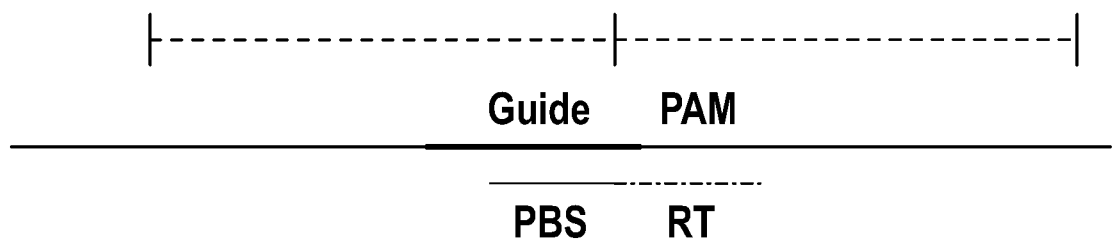
Target Considerations
FIG. 31A

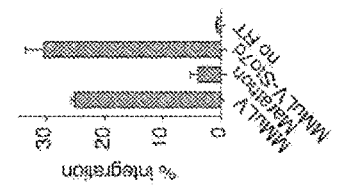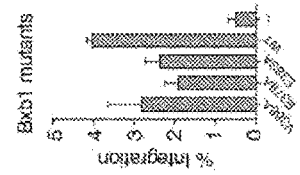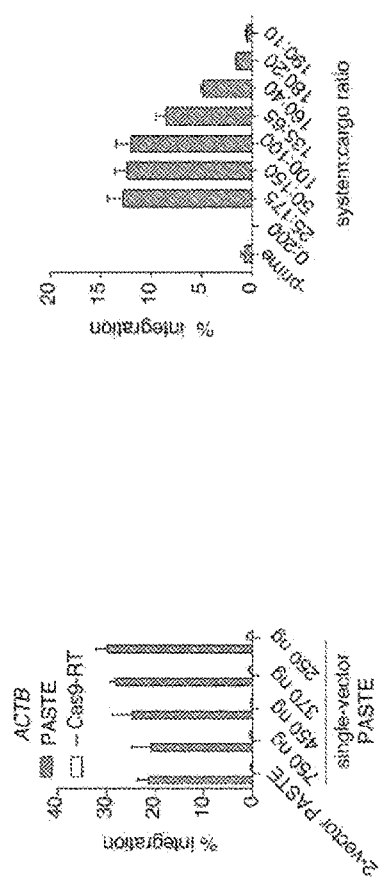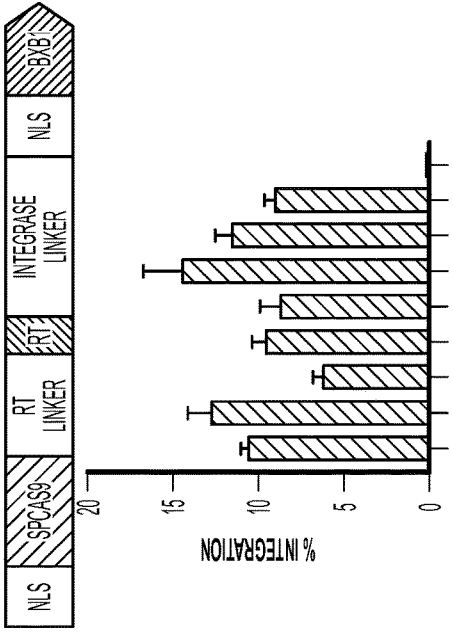
FIG. 49A FIG. 49B FIG. 49C FIG. 49D FIG. 49E FIG. 49F

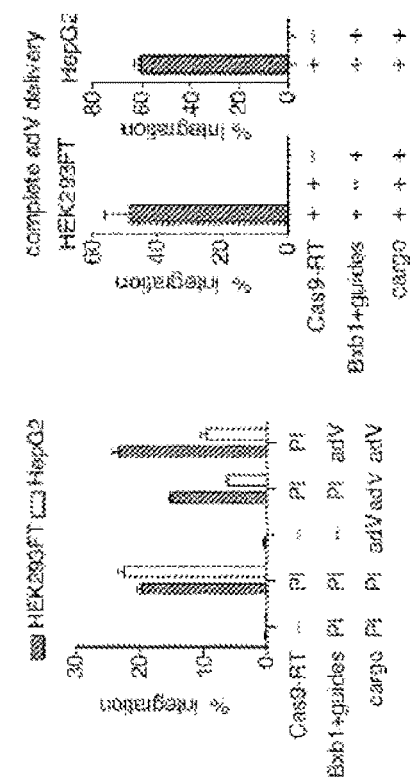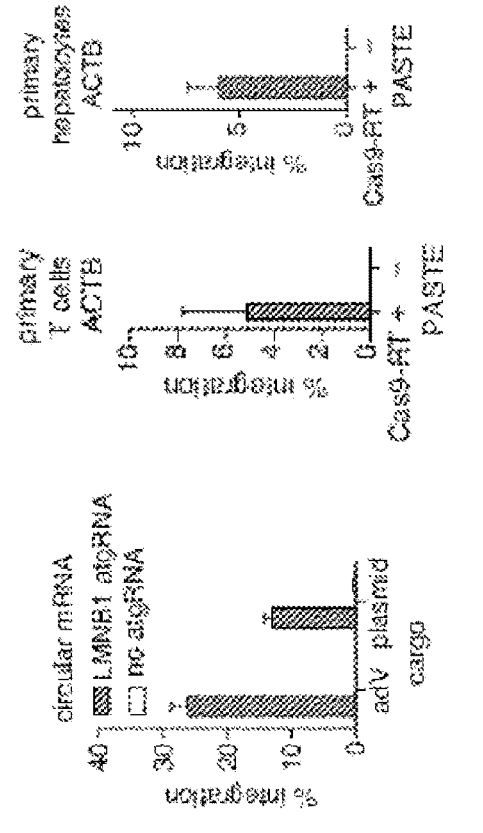

SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

CROSS REFERENCE TO RELATED APPLICATIONS

This application is a continuation of U.S. application Ser. No. 17/649,308, filed Jan. 28, 2022, which is a continuation of U.S. application Ser. No. 17/451,734, filed Oct. 21, 2021, which claims the benefit of U.S. Provisional Patent Application Ser. No. 63/222,550, filed Jul. 16, 2021 and U.S. Provisional Patent Application Ser. No. 63/094,803, filed Oct. 21, 2020. The entire contents of the above-referenced patent applications are incorporated by reference in their entirety herein.

SEQUENCE LISTING

The instant application contains a Sequence Listing which has been submitted electronically in XML format and is hereby incorporated by reference in its entirety. Said XML file, created on Dec. 14, 2022, is named 737607_083474_016CON2_SL_ST26v2.xml.txt and is 775 kilobytes in size.

FIELD OF DISCLOSURE

The subject matter disclosed herein is generally directed to systems, methods, and compositions for site-specific genetic engineering using Programmable Addition via Site-Specific Targeting Elements (PASTE) for the treatment of diseases and diagnostics.

BACKGROUND

Editing genomes using the RNA-guided DNA targeting principle of CRISPR-Cas (Clustered Regularly Interspaced Short Palindromic Repeats-CRISPR associated proteins) immunity has been widely exploited and has become a powerful genome editing means for a wide variety of applications. The main advantage of CRISPR-Cas system lies in the minimal requirement for programmable DNA interference: an endonuclease, such as a Cas9, Cas12, or any programmable nucleases, guided by a customizable dual-RNA structure. Cas9 is a multi-domain enzyme that uses an HNH nuclease domain to cleave the target strand. The CRISPR/Cas9 protein-RNA complex is localized on the target by a guide RNA (guide RNA), then cleaved to generate a DNA double strand break (dsDNA break, DSB). After cleavage, DNA repair mechanisms are activated to repair the cleaved strand. Repair mechanisms are generally from one of two types: non-homologous end joining (NHEJ) or homologous recombination (HR). In general, NHEJ dominates the repair, and, being error prone, generates random indels (insertions or deletions) causing frame shift mutations, among others. In contrast, HR has a more precise repairing capability and is potentially capable of incorporating the exact substitution or insertion. To enhance HR, several techniques have been tried, for example: combination of fusion proteins of Cas9 nuclease with homology-directed repair (HDR) effectors to enforce their localization at DSBs, introducing an overlapping homology arm, or suppression of NHEJ. Most of these techniques rely on the host DNA repair systems.

Recently, new guided editors have been developed, such as guided prime editors (PE) PE1, PE2, and PE3, e.g., Liu, D. et al., Nature 2019, 576, 149-157. These PEs are reverse transcriptase (RT) fused with Cas 9 H 840A nickase (Cas9n (H840A)), and the genome editing is achieved using a prime-editing guide RNA (pegRNA). Despite these developments, programmable gene integration is still generally dependent on cellular pathways or repair processes.

Therefore, there is a need for more effective tools for gene editing and delivery.

SUMMARY

The present disclosure provides a method of site-specific integration of a nucleic acid into a cell genome. The method comprises incorporating an integration site at a desired location in the cell genome by introducing into the cell a DNA binding nuclease linked to a reverse transcriptase domain, wherein the DNA binding nuclease comprises a nickase activity; and a guide RNA (gRNA) comprising a primer binding sequence linked to an integration sequence, wherein the gRNA interacts with the DNA binding nuclease and targets the desired location in the cell genome, wherein the DNA binding nuclease nicks a strand of the cell genome and the reverse transcriptase domain incorporates the integration sequence of the gRNA into the nicked site, thereby providing the integration site at the desired location of the cell genome. The method further comprises integrating the nucleic acid into the cell genome by introducing into the cell a DNA or RNA strand comprising the nucleic acid linked to a sequence that is complementary or associated to the integration site, and an integration enzyme, wherein the integration enzyme incorporates the nucleic acid into the cell genome at the integration site by integration, recombination, or reverse transcription of the sequence that is complementary or associated to the integration site, thereby introducing the nucleic acid into the desired location of the cell genome of the cell.

In some embodiments, the gRNA can be hybridized to a complementary strand of the cell genome to the genomic strand that is nicked by the DNA binding nuclease.

In some embodiments, the integration enzyme can be introduced as a peptide or a nucleic acid encoding the same.

In some embodiments, the DNA binding nuclease can be introduced as a peptide or a nucleic acid encoding the same.

In some embodiments, the DNA or RNA strand comprising the nucleic acid can be introduced into the cell as a minicircle, a plasmid, mRNA or a linear DNA.

In some embodiments, the DNA or RNA strand comprising the nucleic acid can be between 1000 bp and 10,000 bp.

In some embodiments, the DNA or RNA strand comprising the nucleic acid can be more than 10,000 bp.

In some embodiments, the DNA or RNA strand comprising the nucleic acid can be less than 1000 bp.

In some embodiments, the DNA comprising the nucleic acid can be introduced into the cell as a minicircle.

In some embodiment, the minicircle cannot comprise sequences of a bacterial origin.

In some embodiments, the DNA binding nuclease can be linked to a reverse transcriptase domain and the integration enzyme can be linked via a linker. The linker can be cleavable. The linker can be non-cleavable. The linker can be replaced by two associating binding domains of the DNA binding nuclease linked to a reverse transcriptase.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, To12 Tc1, Tc3, Mariner (Himar 1), Mariner (mos 1), and Minos, and any mutants thereof.

In some embodiments, the integration enzyme can be Bxb1 or a mutant thereof.

In some embodiments, the integration site can be selected from an attB site, an attP site, an attL site, an attR site, a lox71 site a Vox site, or a FRT site.

In some embodiments, the DNA binding nuclease comprising a nickase activity can be selected from Cas9-D10A, Cas9-H840A, and Cas12a/b nickase.

In some embodiments, the reverse transcriptase domain can be selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium* rectale maturase RT (MarathonRT).

In some embodiments, the reverse transcriptase domain can comprise a mutation relative to the wild-type sequence.

In some embodiments, the M-MLV reverse transcriptase domain can comprise one or more mutations selected from the group consisting of D200N, T306K, W313F, T330P and L603W.

In some embodiments, the method can further comprise introducing a second nicking guide RNA (ngRNA). The ngRNA can direct nicking at 90 bases downstream of the gRNA nick on a complementary strand.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced into a cell in a single reaction.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced using a virus, a RNP, an mRNA, a lipid, or a polymeric nanoparticle.

In some embodiments, the nucleic acid can be a reporter gene. The reporter gene can be a fluorescent protein.

In some embodiments, the cell can be a dividing cell.

In some embodiments, the cell can be a non-dividing cell.

In some embodiments, the desired location in the cell genome can be the locus of a mutated gene.

In some embodiments, the nucleic acid can be a degradation tag for programmable knockdown of proteins in the presence of small molecules.

In some embodiments, the cell can be a mammalian cell, a bacterial cell or a plant cell.

In some embodiments, nucleic acid can be a T-cell receptor (TCR), a chimeric antigen receptor (CAR), an interleukin, a cytokine, or an immune checkpoint gene for integration into a T-cell or natural killer (NK) cell. The TCR, the CAR, the interleukin, the cytokine, or the immune checkpoint gene can be incorporated into the target site of the T-cell or NK cell genome using a minicircle DNA.

In some embodiments, the nucleic acid can be a beta hemoglobin (HBB) gene and the cell can be a hematopoietic stem cell (HSC). The HBB gene can be incorporated into the target site in the HSC genome using a minicircle DNA. The nucleic acid can be a gene responsible for beta thalassemia or sickle cell anemia.

In some embodiments, the nucleic acid can be a metabolic gene. The metabolic gene can be involved in alpha-1 antitrypsin deficiency or ornithine transcarbamylase (OTC) deficiency. The metabolic gene can be a gene involved in inherited diseases.

In some embodiments, the nucleic acid can be a gene involved in an inherited disease or an inherited syndrome. The inherited disease can be cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

The present disclosure provides a vector comprising a nucleic acid encoding a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the linker can comprise two associating binding domains of the DNA binding nuclease linked to a reverse transcriptase.

In some embodiments, the integration enzyme can comprise a conditional activation domain or conditional expression domain.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, MarathonRT, or a RTX. The reverse transcriptase can be a modified M-MLV reverse transcriptase relative to the wildtype M-MLV reverse transcriptase. The M-MLV reverse transcriptase domain can comprise one or more of the mutations selected from the group consisting of D200N, T306K, W313F, T330P and L603W.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, To12 Tc1, Tc3, Mariner (Himar 1), Mariner (mos 1), and Minos, and any mutants thereof.

In some embodiments, the recombinase or integrase can be Bxb1 or a mutant thereof.

The present disclosure provides a cell comprising a vector comprising a nucleic acid encoding a DNA binding nuclease comprising a nickase activity C-terminally linked to a reverse transcriptase linked to an integration enzyme via a linker. The cell further comprises a gRNA comprising a primer binding sequence, an integration sequence, and a guide sequence, wherein the gRNA can interact with the encoded nuclease comprising a nickase activity. The cell further comprising a DNA minicircle comprising a nucleic acid and a sequence recognized by the encoded integrase, recombinase, or reverse transcriptase. The cell further comprising a nicking guide RNA (ngRNA) capable of binding the encoded nuclease comprising a nickase activity, and wherein the ngRNA targets a sequence away from the gRNA.

In some embodiments, the minicircle cannot comprise a sequence of bacterial origin.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, WO, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA binding nuclease comprising a nickase activity can be selected from the group consisting of Cas9-D10A, Cas9-H840A and Cas12a.

In some embodiments, the reverse transcriptase can be a M-MLV reverse transcriptase. The reverse transcriptase can be a modified M-MLV reverse transcriptase. The amino acid sequence of the M-MLV reverse transcriptase can comprise one or more mutations selected from the group consisting of D200N, T306K, W313F, T330P, and L603W.

In some embodiments, the cell can further comprise introducing ngRNA to the cell. The ngRNA can be a +90 ngRNA. The +90 ngRNA can direct nicking at 90 bases downstream of the gRNA nick on a complementary strand.

The present disclosure provides a polypeptide comprising a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, a MarathonRT, or a XRT. The reverse transcriptase can be a modified M-MLV relative to a wild-type M-MLV reverse transcriptase. The M-MLV reverse transcriptase domain can comprise one or more of mutations selected from the group consisting of D200N, T306K, W313F, T330P, and L603W.

In some embodiments, the integration enzyme can be selected from group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

The present disclosure provides a gRNA that specifically binds to a DNA binding nuclease comprising nickase activity, the gRNA comprising a primer binding site, which hybridizes to a nicked DNA strand, a recognition site for an integration enzyme, and a target recognition sequence recognizing a target site in a cell genome and hybridizing to a genomic strand complementary to the strand that is nicked by the DNA binding nuclease.

In some embodiments, the DNA binding nuclease comprising a nickase activity can be selected from the group consisting of Cas9-D10A, Cas9-H840A, and Cas12a/b.

In some embodiments, the primer binding site can hybridize to the 3' end of the nicked DNA strand.

In some embodiments, the recognition site for the integration enzyme can be selected from an attB site, an attP site, an attL site, an attR site, a lox71 site, and a FRT site.

In some embodiments, the recognition site for the integration enzyme can be a Bxb1 site.

The present disclosure provides a method of site-specific integration of two or more nucleic acids into a cell genome. The method comprises incorporating two integration sites at desired locations in the cell genome by introducing into the cell a DNA binding nuclease linked to a reverse transcriptase domain, wherein the DNA binding nuclease comprises a nickase activity, and two guide RNAs (gRNAs), each comprising, a primer binding sequence, linked to a unique integration sequence, wherein the gRNA interacts with the DNA binding nuclease and targets the desired locations in the cell genome, wherein the DNA binding nuclease nicks a strand of the cell genome and the reverse transcriptase domain incorporates each of the integration sequence of the gRNA into the nicked site, thereby providing the integration site at the desired locations of the cell genome. The method further comprises integrating the nucleic acid by introducing into the cell two or more DNA or RNA comprising the nucleic acids, wherein each DNA is flanked by orthogonal integration sites, and an integration enzyme, wherein the integration enzyme incorporates the nucleic acids into the cell genome at the integration sites by integrase, recombinase, or reverse transcriptase of the sequence that is complementary or associated to the integration site, thereby introducing the nucleic acids into the desired locations of the cell genome of the cell.

In some embodiments, each of the two different integration sites inserted into the cell genome can be attB sequences comprising different palindromic or non-palindromic central dinucleotide.

In some embodiments, each of the two different integration sites inserted into the cell genome can be attP sequences comprising different palindromic or non-palindromic central dinucleotide.

In some embodiments, the integration enzyme can enable each of the two or more DNA or RNA comprising the nucleic acids to directionally enable integration of the nucleic acids into a genome via recombination of a pair of orthogonal attB site sequence and an attP site sequence.

In some embodiments, the integration enzyme can be selected from the group consisting of Cre, Dre, Vika, Bxb1, φC31, RDF, FLP, φBT1, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, retrotransposases encoded by R1, R2, R3, R4, R5, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA comprising genes can be genes involved in a cell maintenance pathway, cell-division, or a signal transduction pathway.

In some embodiments, the reverse transcriptase domain can comprise Moloney Murine Leukemia Virus (M-MLV) reverse transcriptase domain, transcription xenopolymerase (RTX), avian myeloblastosis virus reverse transcriptase (AMV-RT), or *Eubacterium* rectale maturase RT (MarathonRT).

In some embodiments, the DNA binding nuclease comprising a nickase activity can be selected from the group consisting of Cas9-D10A, Cas9-H840A, and Cas12a/b.

In some embodiments, the pair of an attB site sequence and an attP site sequence can be selected from the group consisting of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34 and SEQ ID NO: 35 and SEQ ID NO: 36.

The present disclosure provides a cell comprising a vector comprising a nucleic acid encoding a DNA binding nuclease comprising a nickase activity, wherein the DNA binding nuclease is C-terminally linked to a reverse transcriptase, wherein the reverse transcriptase is linked to a recombinase or integrase via a linker. The cell further comprises two guide RNAs (gRNAs) comprising a primer binding sequence, an integration sequence and a guide sequence, wherein the gRNA can interact with the encoded DNA binding nuclease comprising a nickase activity. The cell further comprises two or more DNA or RNA strands comprising a nucleic acid and a pair of flanking attB site sequence and an attP site sequence recognized by the encoded integrase or recombinase. The cell optionally further comprises a nicking guide RNA (ngRNA) capable of binding the encoded nuclease comprising a nickase activity, and wherein the ngRNA targets a sequence away from the gRNA.

The present disclosure provides a cell comprising a modified genome, wherein the modification comprises incorporation of two orthogonal integration sites within the cell genome by introducing into the cell a: vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA.

The present disclosure provides a method of integrating two or more nucleic acids into the cell genome of cell of claim 90, the method comprising introducing into the cell: two or more DNA, each comprising a nucleic acid and a pair of flanking orthogonal integration site sequences; an integration enzyme that can recognize the integration site sequence enabling directional linking of the two or more DNA comprising nucleic acid; and enabling incorporation of the nucleic acids into the cell genome by integrating the 5' orthogonal integration sequence of the first DNA with the first genomic integration sequence and 3' orthogonal integration sequence of the last DNA with the last genomic integration sequence, thereby incorporating the two or more nucleic acids into the cell genome.

The present disclosure provides a cell comprising a modified genome, wherein the modification comprises incorporation of two orthogonal integration sites within the cell genome by introducing into the cell: a vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA; two or more DNA or RNA comprising the nucleic acids, wherein each DNA is flanked by orthogonal integration sites; and an integration enzyme, wherein the integration enzyme incorporates the nucleic acids into the cell genome at the integration sites.

BRIEF DESCRIPTION OF THE DRAWINGS

Aspects, features, benefits and advantages of the embodiments described herein will be apparent with regard to the following description, appended claims, and accompanying drawings where:

FIG. 28A shows fluorescent images of the GFP tagging of ACTB and SUPT16H genes with PASTE according to embodiments of the present teachings;

FIG. 28B shows fluorescent images of the GFP tagging of NOLC1 and SRRM2 genes with PASTE according to embodiments of the present teachings;

FIG. 28C shows fluorescent images of the GFP tagging of LMNB1 and DEPDC4 genes with PASTE according to embodiments of the present teachings;

FIG. 28F shows fluorescent images of two single cells with multiplexed gene tagging of ACTB (EGFP) and NOLC1 (mCherry) using PASTE according to embodiments of the present teachings;

FIG. 29E discloses SEQ ID NOS 428-431, respectively, in order of appearance;

FIG. 31A shows a schematic of various parameters that affect PASTE integration of ~1 kb GFP insert, wherein on the pegRNA, the PBS, RT, and attB lengths can alter the efficiency of attB insertion, and nicking guide selection also affects overall gene integration efficiency according to embodiments of the present teachings;

FIG. 40C shows the validation of ddPCR assays for detecting editing at predicted PASTE ACTB Cas9 guide off-target sites using synthetic amplicons according to embodiments of the present teachings;

FIG. 40D shows the validation of ddPCR assays for detecting editing at predicted HITI ACTB Cas9 guide off-target sites using synthetic amplicons according to embodiments of the present teachings;

FIG. 41A shows a number of significant differentially regulated genes in HEK293FT cells expressing Bxb1 integrase, PASTE targeting ACTB integration of EGFP, or Prime editing targeting ACTB for EGFP insertion without Bxb1 expression according to embodiments of the present teachings;

Figure 41A:
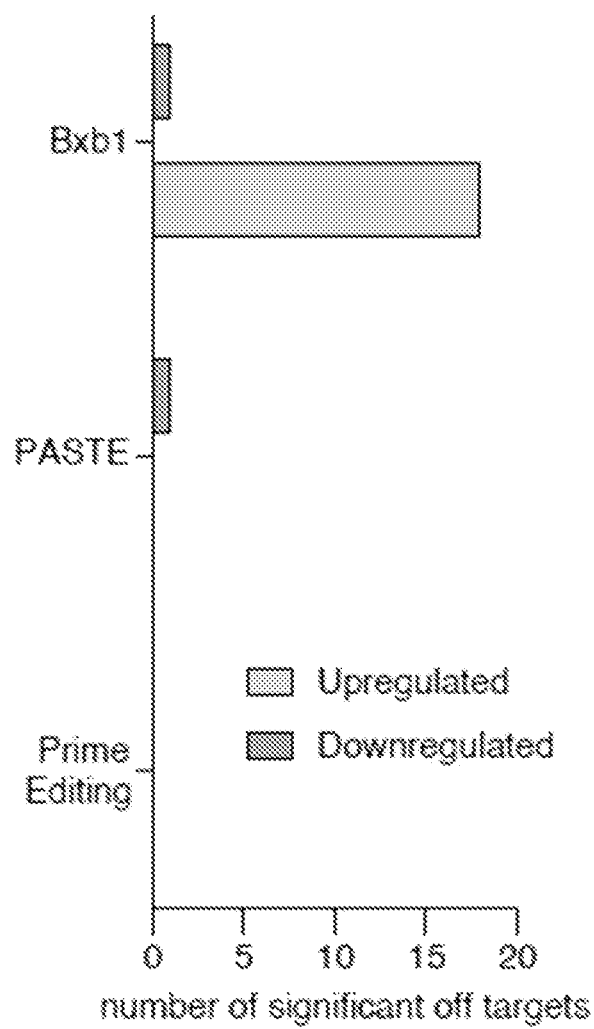
Figure 41B:
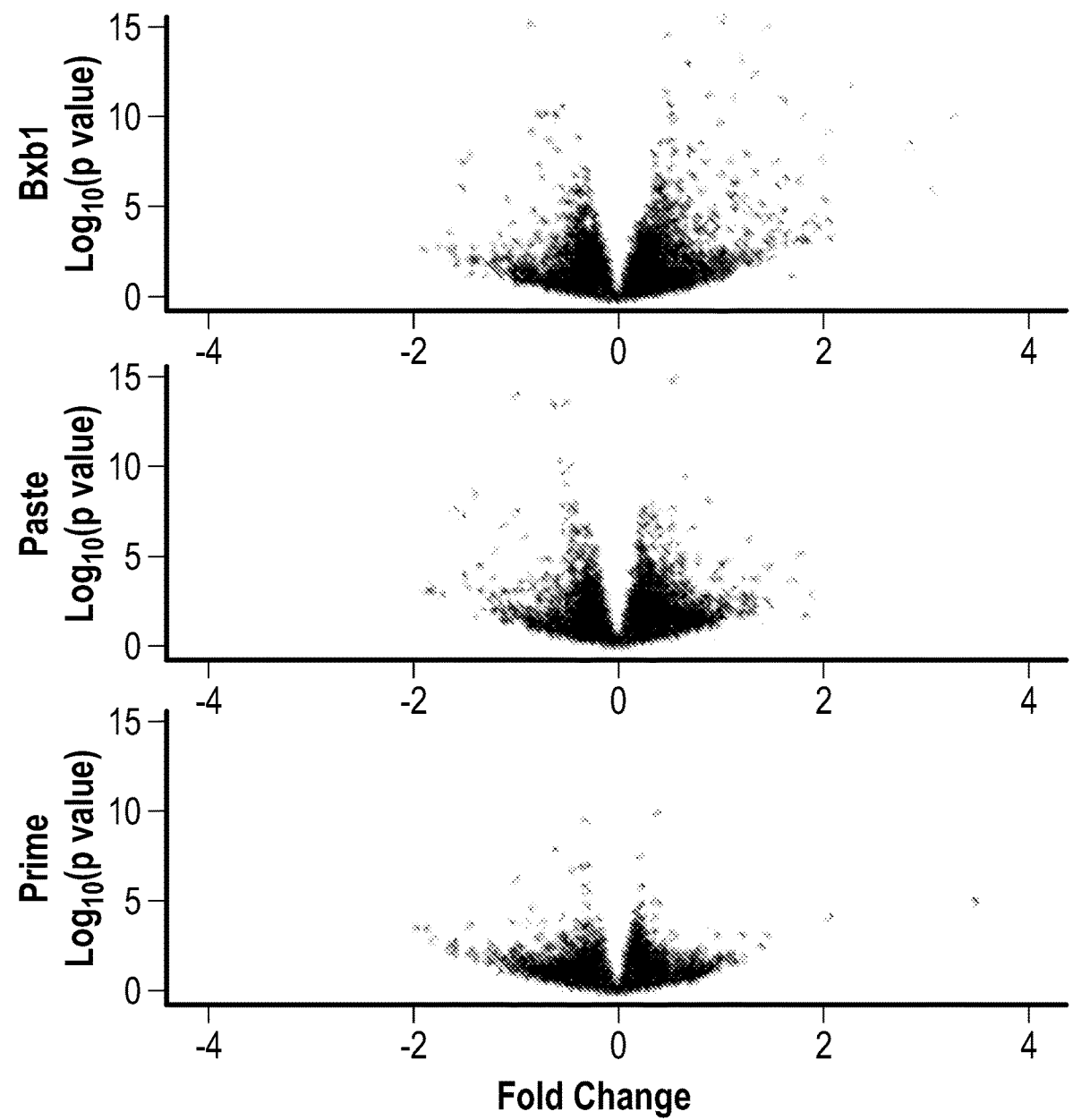
Figure 41C:
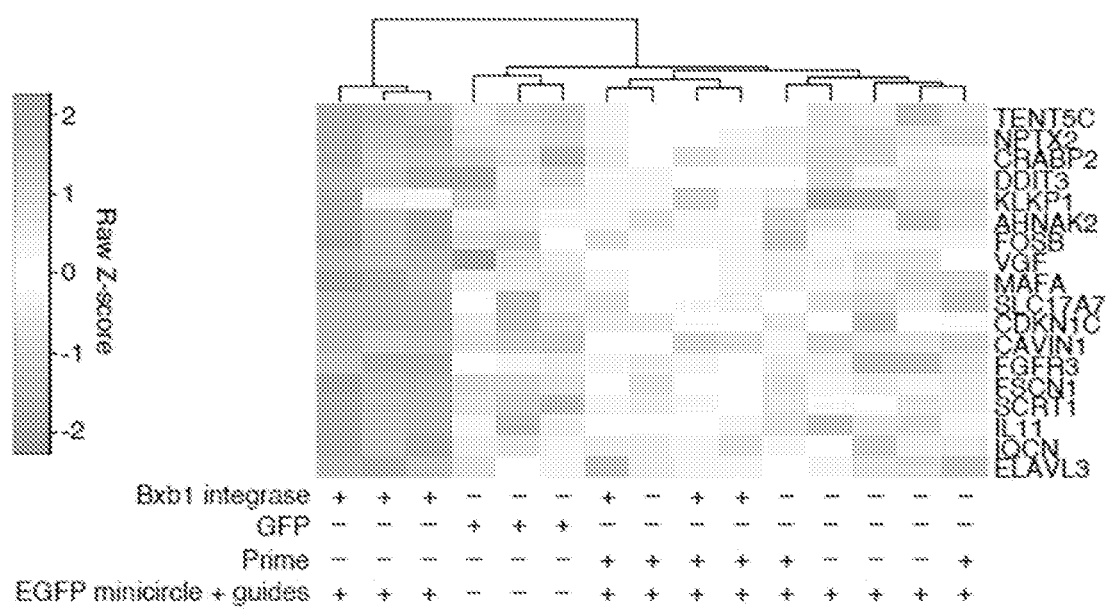
Figure 42A:
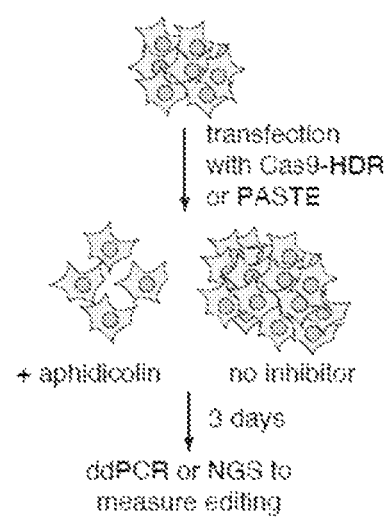
Figure 42B:
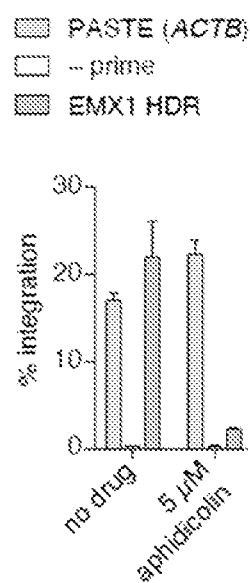
Figure 42C:
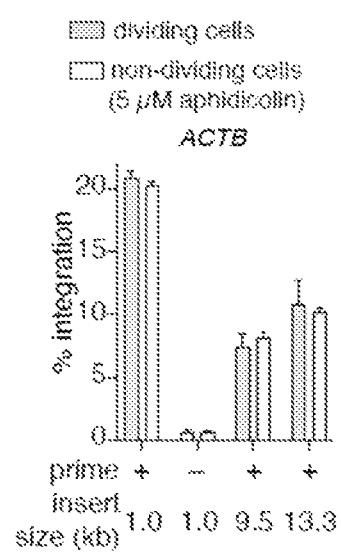
Figure 42D:
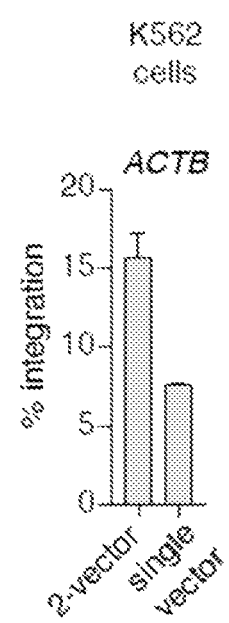
Figure 42E:
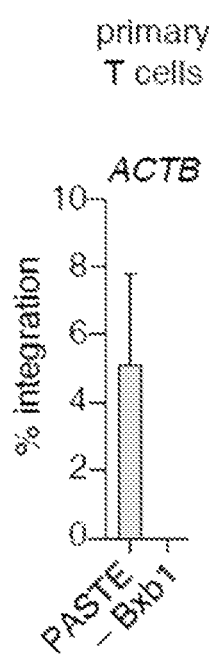
Figure 42F:
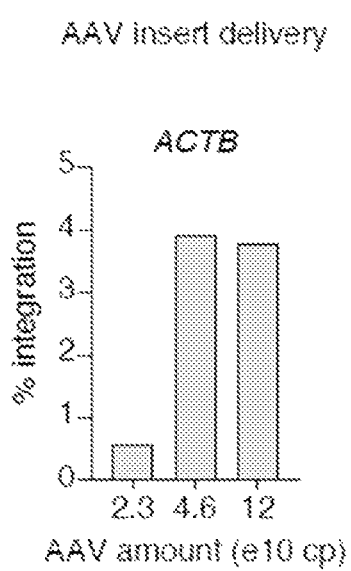
Figure 42G:
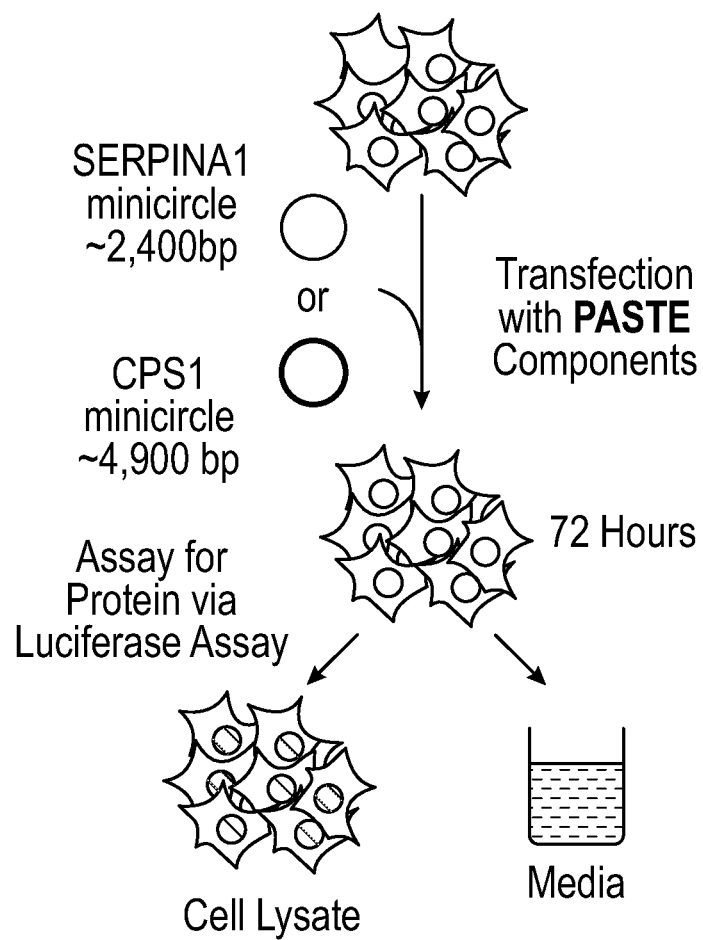
Figure 42H:
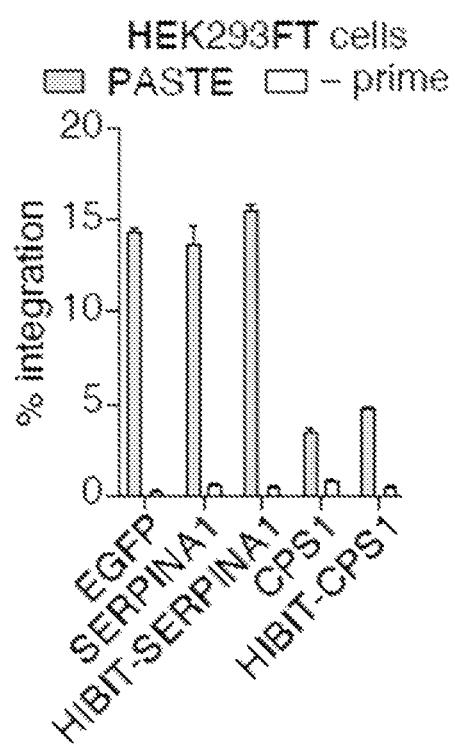
Figure 42I:
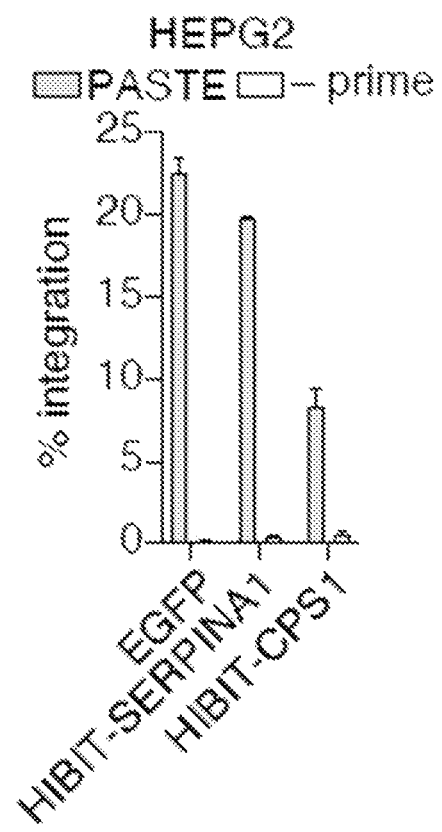
Figure 42J:
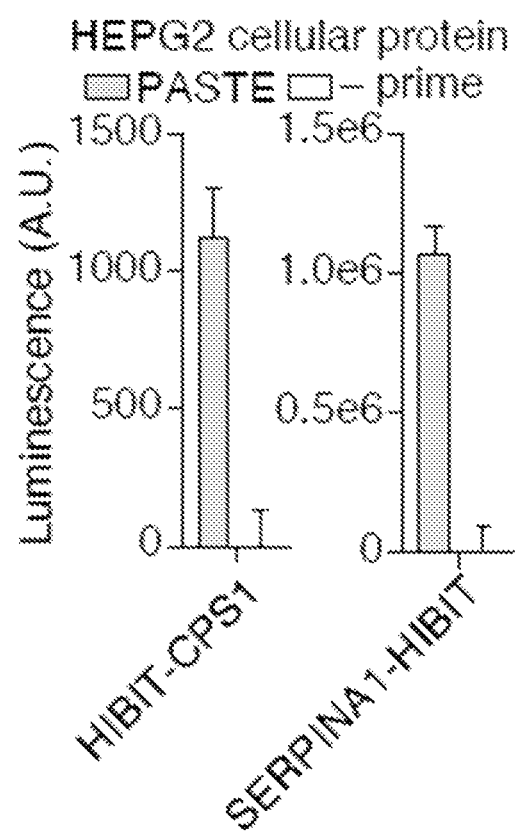
Figure 42K:
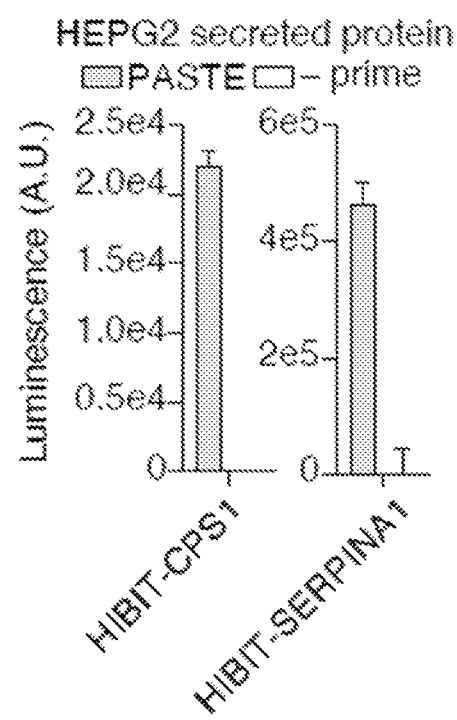
Figure 43A:
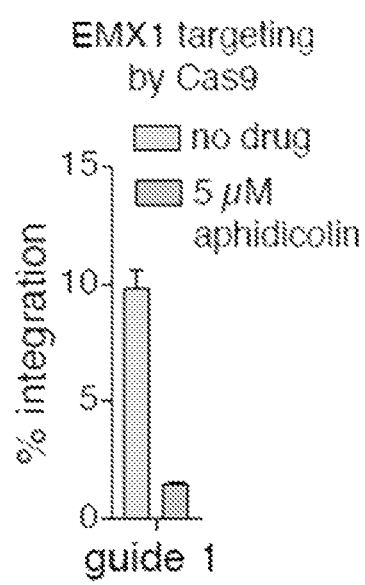
Figure 43B:
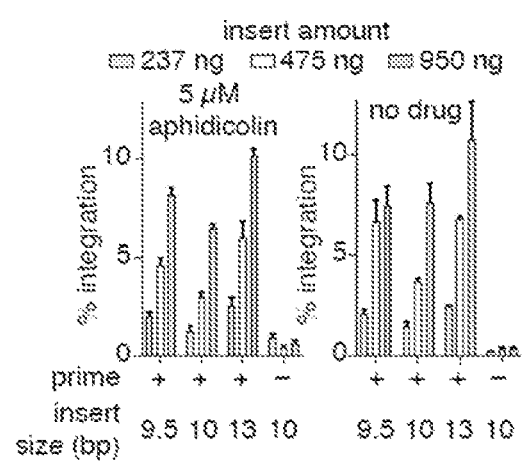
Figure 43C:
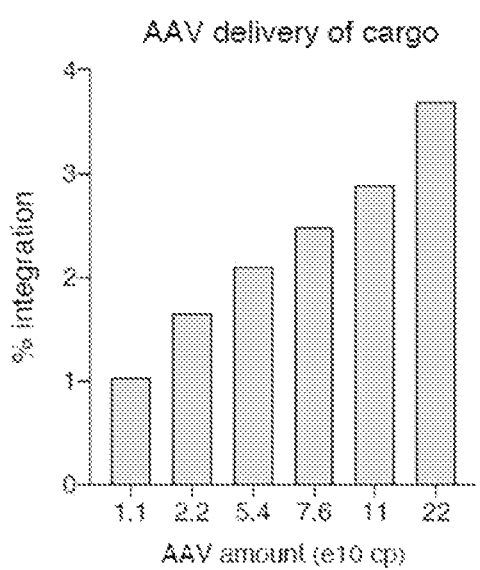
Figure 44A:
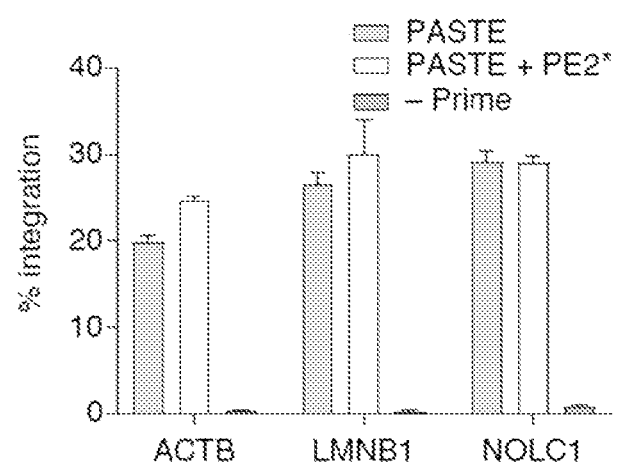
Figure 44B:
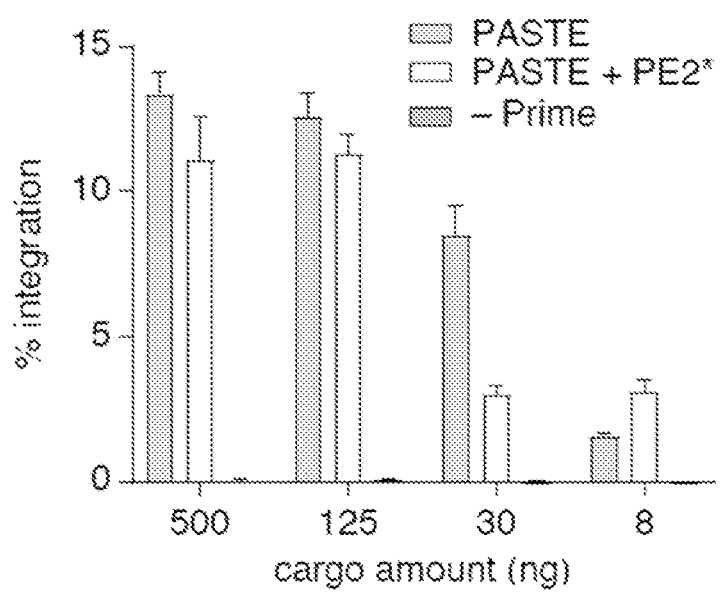
Figure 45:
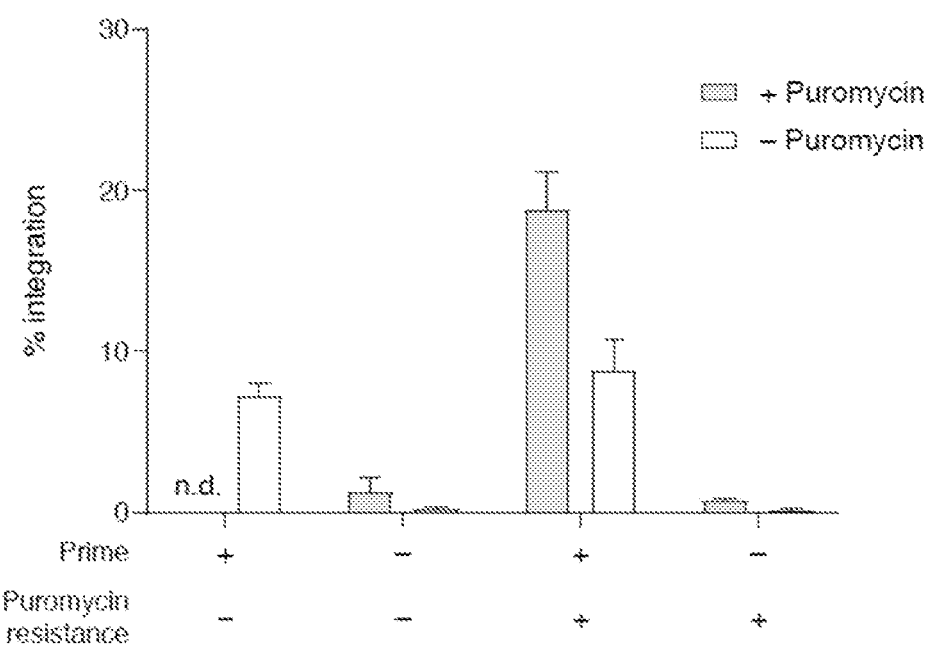
Figure 46A:
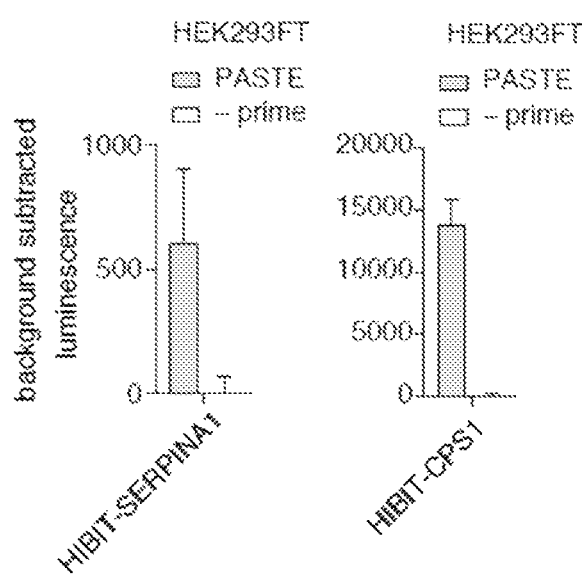
Figure 46B:
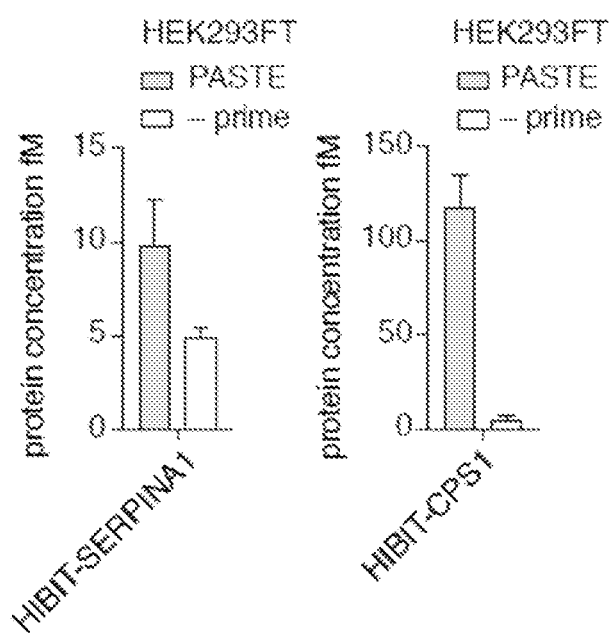
Figure 47A:
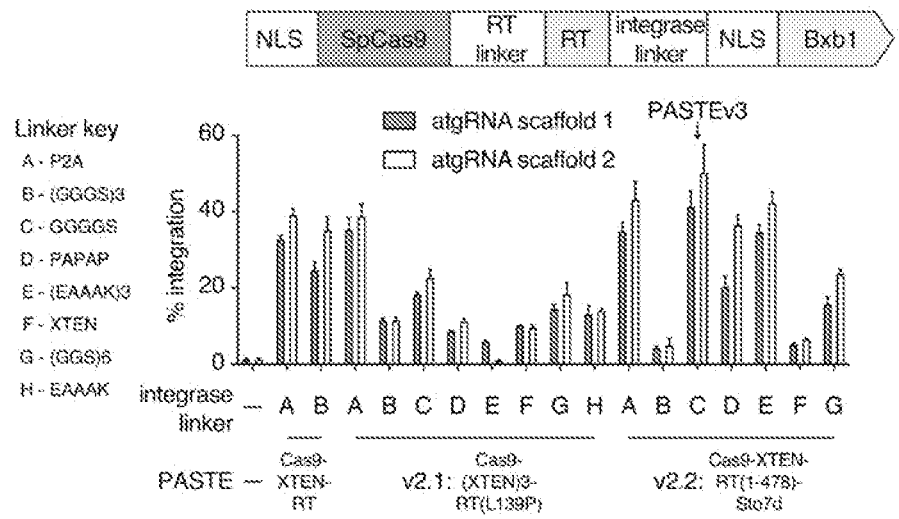
Figure 47B:
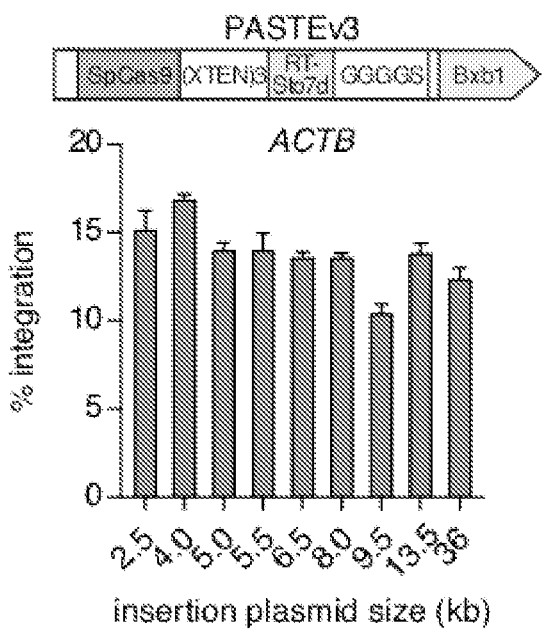
Figure 48A:
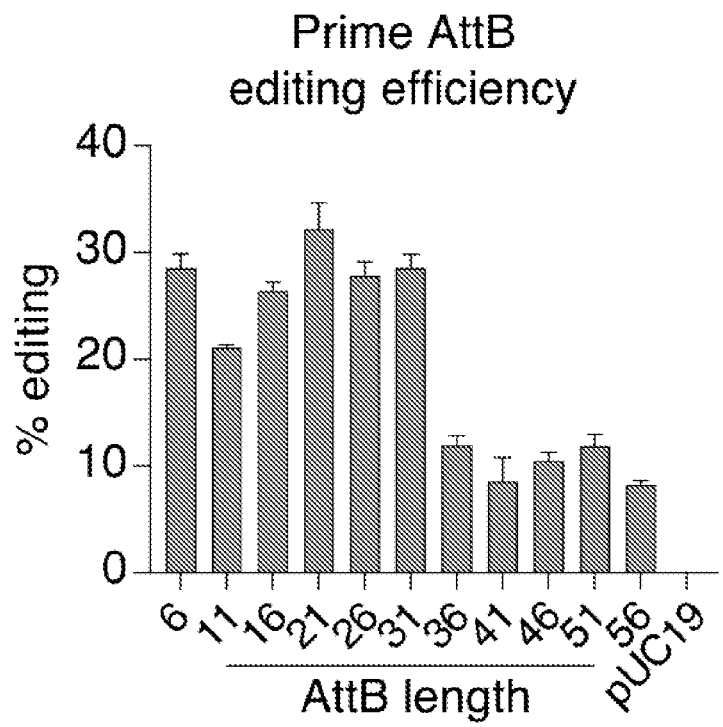
Figure 48B:
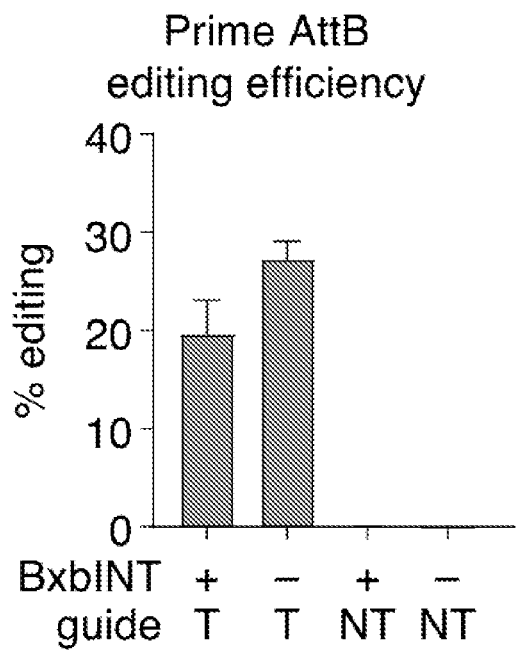
Figure 48C:
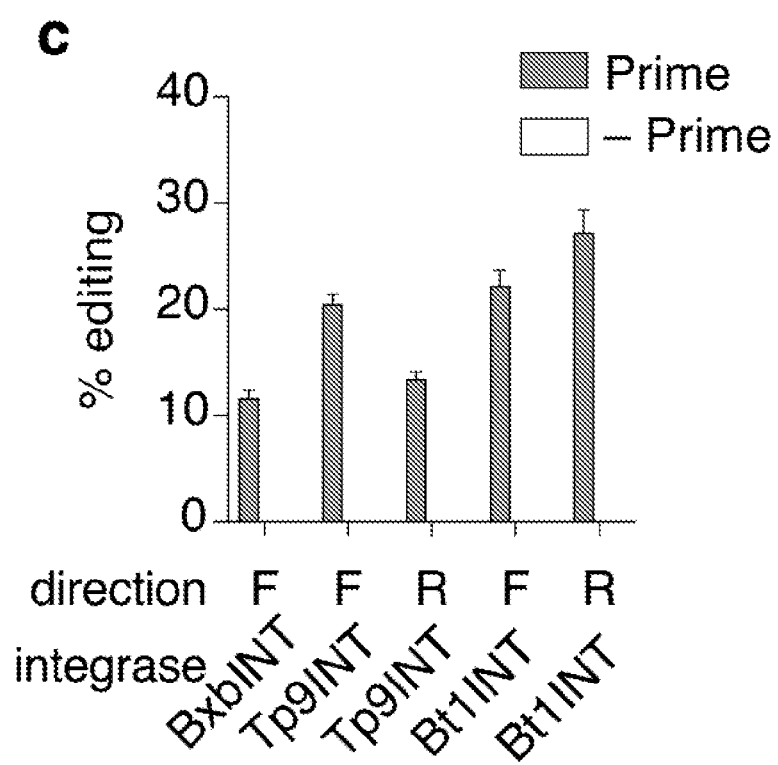
Figure 48D:
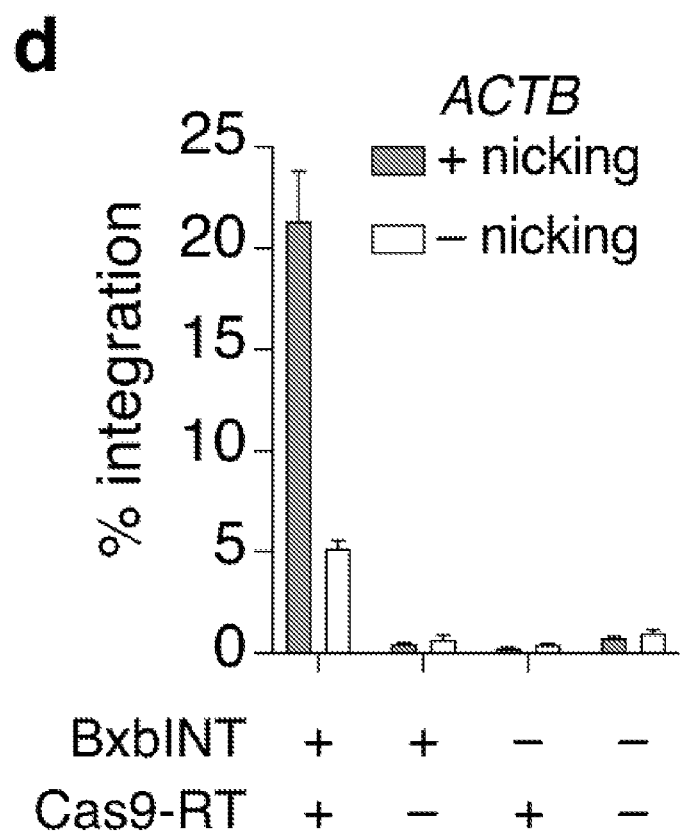

FIG. 41B shows Volcano plots depicting the fold expression change of sequenced mRNAs versus significance (p-value), wherein each dot represents a unique mRNA transcript and significant transcripts are shaded according to either upregulation (red) or downregulation (blue), and wherein fold expression change is measured against ACTB-targeting guide-only expression (including cargo) according to embodiments of the present teachings;

FIG. 41C shows top significantly upregulated and down-regulated genes for Bxb1-only conditions, wherein genes are shown with their corresponding Z-scores of counts per million (cpm) for Bxb1 only expression, GFP-only expression, PASTE targeting ACTB for EGFP insertion, Prime targeting ACTB for EGFP expression without Bxb1, and guide/cargo only according to embodiments of the present teachings;

FIG. 42A shows a schematic of PASTE performance in the presence of cell cycle inhibition, wherein cells are transfected with plasmids for insertion with PASTE or Cas9-induced HDR and treated with aphidicolin to arrest cell division, and wherein the efficiency of PASTE and HDR are read out with ddPCR or amplicon sequencing respectively according to embodiments of the present teachings;

FIG. 42B shows the editing efficiency of single mutations by HDR at EMX1 locus with two Cas9 guides in the presence or absence of cell division read out with amplicon sequencing according to embodiments of the present teachings;

FIG. 42C shows the integration efficiency of various sized GFP inserts up to 13.3 kb at the ACTB locus with PASTE in the presence or absence of cell division according to embodiments of the present teachings;

FIG. 42D shows the PASTE editing efficiency with two vector (PE2 and Bxb1) and single vector (PE2-P2A-Bxb1) designs in K562 cells according to embodiments of the present teachings;

FIG. 42E shows the PASTE editing efficiency with single vector (PE2-P2A-Bxb1) designs in primary human T cells according to embodiments of the present teachings;

FIG. 42F shows the integration efficiency of therapeutically relevant genes at the ACTB locus according to embodiments of the present teachings;

FIG. 42G shows a schematic of protein production assay for PASTE-integrated transgene, wherein SERPINA1 and CPS1 transgenes are tagged with HIBIT luciferase for readout with both ddPCR and luminescence according to embodiments of the present teachings;

FIG. 42H shows the integration efficiency of SERPINA1 and CPS1 transgenes in HEK293FT cells at the ACTB locus according to embodiments of the present teachings;

FIG. 42I shows the integration efficiency of SERPINA1 and CPS1 transgenes in HepG2 cells at the ACTB locus according to embodiments of the present teachings;

FIG. 42J shows the intracellular levels of SERPINA1-HIBIT and CPS1-HIBIT in HepG2 cells according to embodiments of the present teachings;

FIG. 42K shows the secreted levels of SERPINA1-HIBIT and CPS1-HIBIT in HepG2 cells according to embodiments of the present teachings;

FIG. 43A shows the HDR mediated editing of the EMX1 locus that is significantly diminished in non-dividing HEK293FT cells blocked by 5 μM aphidicolin treatment according to embodiments of the present teachings;

FIG. 43B shows the effect of insert minicircle DNA amount on PASTE-mediated insertion at the ACTB locus in dividing and nondividing HEK293FT cells blocked by 5 μM aphidicolin treatment according to embodiments of the present teachings;

FIG. 43C shows the PASTE integration of GFP at the ACTB locus with the GFP template delivered via AAV, showing dose dependence of integration efficiency according to embodiments of the present teachings;

FIG. 44A shows the PASTE integration activity at three endogenous loci comparing the normal PASTE SV40 NLS to a c-Myc NLS/variable bi-partite SV40 NLS design according to embodiments of the present teachings;

FIG. 44B shows the PASTE integration activity at the ACTB locus with different GFP minicircle template amounts comparing the normal PASTE SV40 NLS to a c-Myc NLS/variable bi-partite SV40 NLS design according to embodiments of the present teachings;

FIG. 45 shows the improvement of the PASTE editing activity using a puromycin growth selection marker according to embodiments of the present teachings;

FIG. 46A shows the integration of SERPINA1 and CPS1 genes that are HIBIT tagged as measured by a protein expression luciferase assay according to embodiments of the present teachings;

FIG. 46B shows the integration of SERPINA1 and CPS1 genes that are HIBIT tagged as measured by a protein expression luciferase assay normalized to a standardized HIBIT ladder, enabling accurate quantification of protein levels according to embodiments of the present teachings;

FIG. 47A shows optimization of PASTE constructs with a panel of linkers and reverse transcriptase (RT) modifications for EGFP integration at the ACTB locus, according to embodiments of the present teachings;

FIG. 47B shows the effect of cargo size on PASTE insertion efficiency at the endogenous ACTB target. Cargos were transfected with fixed molar amounts, according to embodiments of the present teachings;

FIG. 48A shows prime editing efficiency for the insertion of different length BxbINT AttB sites at ACTB, according to embodiments of the present teachings;

FIG. 48B shows prime editing efficiency for the insertion of a BxbINT AttB site at ACTB with targeting and non-targeting guides, according to embodiments of the present teachings;

FIG. 48C shows prime editing efficiency for the insertion of different integrases' (Bxb1, Tp9, and Bt1) AttB sites at ACTB. Both orientations of landing sites are profiled (F, forward; R, reverse), according to embodiments of the present teachings;

FIG. 48D shows PASTE editing efficiency for the insertion of EGFP at ACTB with and without a nicking guide, according to embodiments of the present teachings; and FIG. 49A shows optimization of PASTE editing by dosage titration and protein optimization. PASTE integration efficiency of EGFP at ACTB measured with different doses of a single-vector delivery of components.

FIG. 49B PASTE integration efficiency of EGFP at ACTB measured with different ratios of a single-vector delivery of components to the EGFP template vector.

FIG. 49C PASTE integration efficiency of EGFP at ACTB with different RT domain fusions.

FIG. 49D PASTE integration efficiency of EGFP at ACTB with different RT domain fusions and linkers.

FIG. 49E PASTE integration efficiency of EGFP at ACTB with mutant RT domains.

FIG. 49F PASTE integration efficiency of EGFP at ACTB with mutated BxbINT domains.

FIG. 50A Insertion templates delivered via AAV transduction. PASTE editing machinery was delivered via transfection, and templates were co-delivered via AAV dosing at levels indicated.

FIG. 50B Schematic of AdV delivery of the complete PASTE system with three viral vectors.

FIG. 50C Integration efficiency of AdV delivery of integrase, guides, and cargo in HEK293FT and HepG2 cells. BxbINT and guide RNAs or cargo were delivered either via plasmid transfection (P1), AdV transduction (AdV), or omitted (−). SpCas9-RT was only delivered as plasmid or omitted.

FIG. 50D AdV delivery of all PASTE components in HEK293FT and HepG2 cells.

FIG. 50E Schematic of mRNA and synthetic guide delivery of PASTE components.

FIG. 50F Delivery of PASTE system components with mRNA and synthetic guides, paired with either AdV or plasmid cargo.

FIG. 50G Delivery of circular mRNA with synthetic guides and either AdV or plasmid cargo.

FIG. 50H PASTE editing efficiency with single vector designs in primary human T cells.

FIG. 50I PASTE editing efficiency with single vector designs in primary human hepatocytes.

Figure 51A:
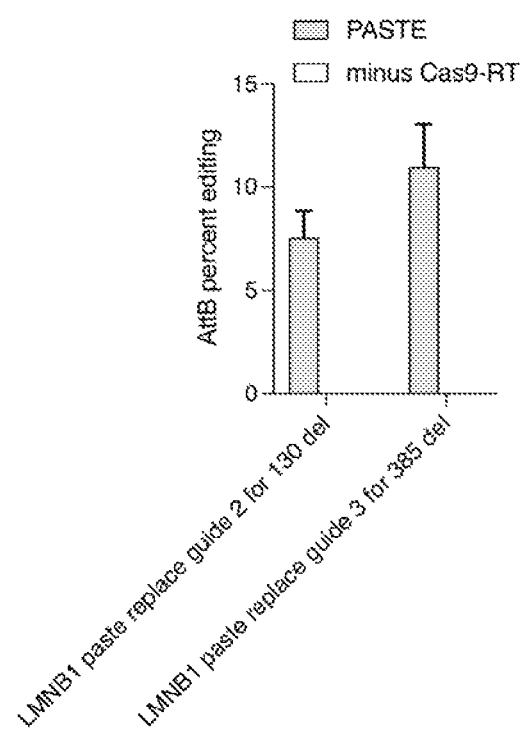

FIG. 51A PASTE editing efficiency at the LMNB1 locus with 130 bp and 385 bp deletions of the first exon of LMNB1 with combined insertion of an attB sequence.

Figure 51B:
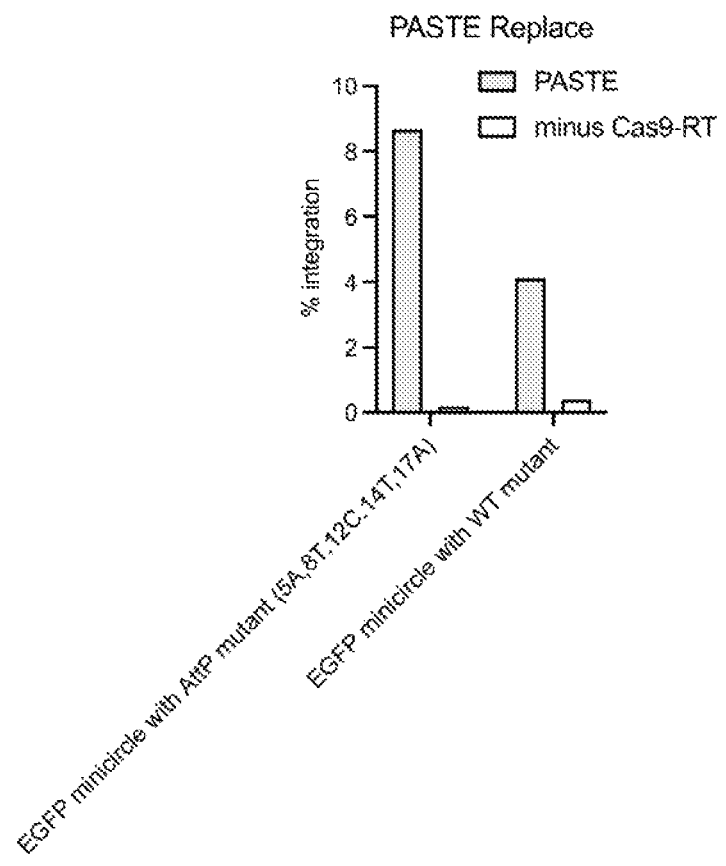

FIG. 51B PASTE editing efficiency with a 130 bp deletion of the first exon of LMNB1 with a combined insertion of a 967 bp cargo using the PASTE system.

DETAILED DESCRIPTION

It will be appreciated that for clarity, the following discussion will describe various aspects of embodiments of the applicant's teachings. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular feature, structures or characteristics may be combined in any suitable manner, as would be apparent to a person skilled in the art from this disclosure, in one or more embodiments.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise. Thus, for example, reference to "a cell" includes a plurality of such cells.

As used herein, the term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, the term "about" or "approximately" refers to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosure. It is to be understood that the value to which the modifier "about" or "approximately" refers is itself also specifically, and preferably, disclosed.

It is noted that all publications and references cited herein are expressly incorporated herein by reference in their entirety. The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

Overview

Figure 1:
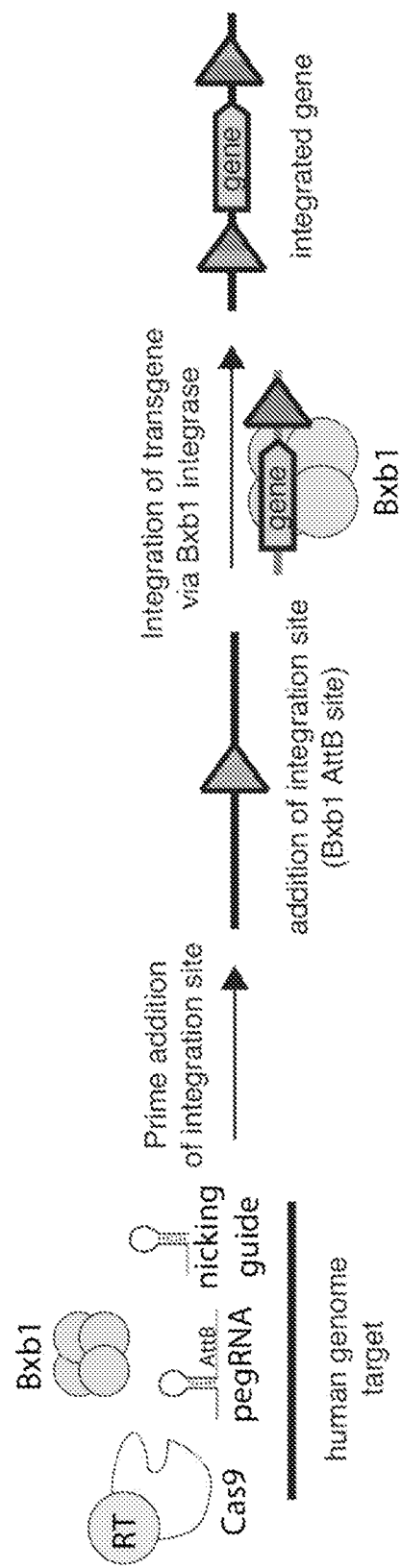
FIG. 1 shows a schematic diagram of a concept of Programmable Addition via Site-Specific Targeting Elements (PASTE) according to embodiments of the present teachings.

The embodiments disclosed herein provide non-naturally occurring or engineered systems, methods, and compositions for site-specific genetic engineering using Programmable Addition via Site-Specific Targeting Elements (PASTE). A schematic diagram illustrating the concept of PASTE is shown in FIG. 1. As discussed in more details below, PASTE comprises the addition of an integration site into a target genome followed by the insertion of one or more genes of interest or one or more nucleic acid sequences of interest at the site. This process can be done as one or more reactions in a cell. The addition of the integration site into the target genome is done using gene editing technologies that include for example, without limitation, prime editing, recombinant adeno-associated virus (rAAV)-mediated nucleic acid integration, transcription activator-like effector nucleases (TALENS), and zinc finger nucleases (ZFNs). The integration of the transgene at the integration site is done using integrase technologies that include for example, without limitation, integrases, recombinases and reverse transcriptases. The necessary components for the site-specific genetic engineering disclosed herein comprise at least one or more nucleases, one or more gRNA, one or more integration enzymes, and one or more sequences that are complementary or associated to the integration site and linked to the one or more genes of interest or one or more nucleic acid sequences of interest to be inserted into the cell genome.

An advantage of the non-naturally occurring or engineered systems, methods, and compositions for site-specific genetic engineering disclosed herein is programmable insertion of large elements without reliance on DNA damage responses.

Another advantage of the non-naturally occurring or engineered systems, methods, and compositions for site-specific genetic engineering disclosed herein is facile multiplexing, enabling programmable insertion at multiple sites.

Another advantage of the non-naturally occurring or engineered systems, methods, and compositions for site-specific genetic engineering disclosed herein is scalable production and delivery through minicircle templates.

Prime Editing

The present disclosure provides non-naturally occurring or engineered systems, methods, and compositions for site-specific genetic engineering using gene editing technologies, such as prime editing, to add an integration site into a target genome. Prime editing will be discussed in more details below.

Figure 2:
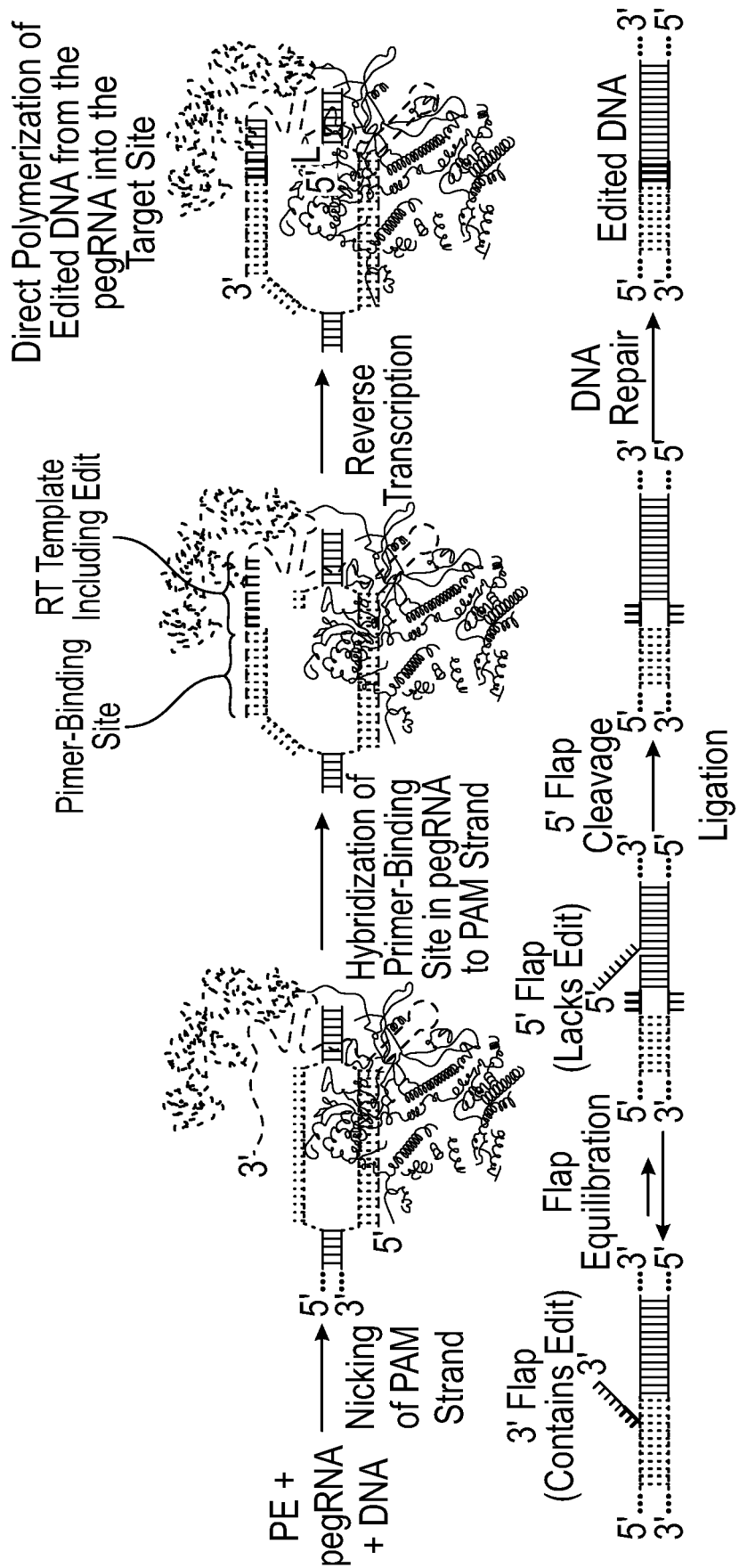
FIG. 2 shows a schematic diagram of a prime editing process according to embodiments of the present teachings.

Prime editing is a versatile and precise genome editing method that directly writes new genetic information into a specified DNA site. A schematic diagram illustrating the concept of prime editing is shown in FIG. 2. See, Anzalone, A. V., et al. "Search-and-replace genome editing without double-strand breaks or donor DNA," Nature 576, 149-157 (2019). Prime editing uses a catalytically-impaired Cas9 endonuclease that is fused to an engineered reverse transcriptase (RT) and programmed with a prime-editing guide RNA (pegRNA). The skilled person in the art would appreciate that the pegRNA both specifies the target site and encodes the desired edit. The catalytically-impaired Cas9 endonuclease also comprises a Cas9 nickase that is fused to the reverse transcriptase. During genetic editing, the Cas9 nickase part of the protein is guided to the DNA target site by the pegRNA. The reverse transcriptase domain then uses the pegRNA to template reverse transcription of the desired edit, directly polymerizing DNA onto the nicked target DNA strand. The edited DNA strand replaces the original DNA strand, creating a heteroduplex containing one edited strand and one unedited strand. Afterward, the prime editor (PE) guides resolution of the heteroduplex to favor copying the edit onto the unedited strand, completing the process.

The prime editors refer to a Moloney Murine Leukemia Virus (M-MLV) reverse transcriptase (RT) fused to a Cas9 H840A nickase. Fusing the RT to the C-terminus of the Cas9 nickase may result in higher editing efficiency. Such a complex is called PE1. The Cas9(H840A) can also be linked to a non-M-MLV reverse transcriptase such as a AMV-RT or XRT (Cas9(H840A)-AMV-RT or XRT). In some embodiments, Cas 9(H840A) can be replaced with Cas12a/b or Cas9(D10A). A Cas9 (wild type), Cas9(H840A), Cas9 (D10A) or Cas 12a/b nickase fused to a pentamutant of M-MLV RT (D200N/L603W/T330P/T306K/W313F), having up to about 45-fold higher efficiency is called PE2. In some embodiments, the M-MLV RT comprise one or more of the mutations: Y8H, P51L, S56A, S67R, E69K, V129P, L139P, T197A, H204R, V223H, T246E, N249D, E286R, Q2911, E302K, E302R, F309N, M320L, P330E, L435G, L435R, N454K, D524A, D524G, D524N, E562Q, D583N, H594Q, E607K, D653N, and L671P. In some embodiments, the reverse transcriptase can also be a wild-type or modified transcription xenopolymerase (RTX), avian myeloblastosis virus reverse transcriptase (AMV-RT), Feline Immunodeficiency Virus reverse transcriptase (FIV-RT), FeLV-RT (Feline leukemia virus reverse transcriptase), HIV-RT (Human Immunodeficiency Virus reverse transcriptase), or *Eubacterium* rectale maturase RT (MarathonRT). PE3 involves nicking the non-edited strand, potentially causing the cell to remake that strand using the edited strand as the template to induce HR. The nicking of the non-edited strand can involve the use of a nicking guide RNA (ngRNA).

Nicking the non-edited strand can increase editing efficiency. For example, nicking the non-edited strand can increase editing efficiency by about 1.1 fold, about 1.3 fold, about 1.5 fold, about 1.7 fold, about 1.9 fold, about 2.1 fold, about 2.3 fold, about 2.5 fold, about 2.7 fold, about 2.9 fold, about 3.1 fold, about 3.3 fold, about 3.5 fold, about 3.7 fold, about 3.9 fold, 4.1 fold, about 4.3 fold, about 4.5 fold, about 4.7 fold, about 4.9 fold, or any range that is formed from any two of those values as endpoints.

Although the optimal nicking position varies depending on the genomic site, nicks positioned 3' of the edit about 40-90 bp from the pegRNA-induced nick can generally increase editing efficiency without excess indel formation. The prime editing practice allows starting with non-edited strand nicks about 50 bp from the pegRNA-mediated nick, and testing alternative nick locations if indel frequencies exceed acceptable levels.

As used herein, the term "guide RNA" (gRNA) and the like refer to a RNA that guide the insertion or deletion of one or more genes of interest or one or more nucleic acid sequences of interest into a target genome. The gRNA can also refer to a prime editing guide RNA (pegRNA), a nicking guide RNA (ngRNA), and a single guide RNA (sgRNA). In some embodiments, the term "gRNA molecule" refers to a nucleic acid encoding a gRNA. In some embodiments, the gRNA molecule is naturally occurring. In some embodiments, a gRNA molecule is non-naturally occurring. In some embodiments, a gRNA molecule is a synthetic gRNA molecule. A gRNA can target a nuclease or a nickase such as Cas9, Cas 12a/b, Cas9 (H840A) or Cas9 (D10A) molecule to a target nucleic acid or sequence in a genome. In some embodiments, the gRNA can bind to a DNA nickase bound to a reverse transcriptase domain. A "modified gRNA," as used herein, refers to a gRNA molecule that has an improved half-life after being introduced into a cell as compared to a non-modified gRNA molecule after being introduced into a cell. In some embodiments, the guide RNA can facilitate the addition of the insertion site sequence for recognition by integrases, transposases, or recombinases.

Figure 24A:
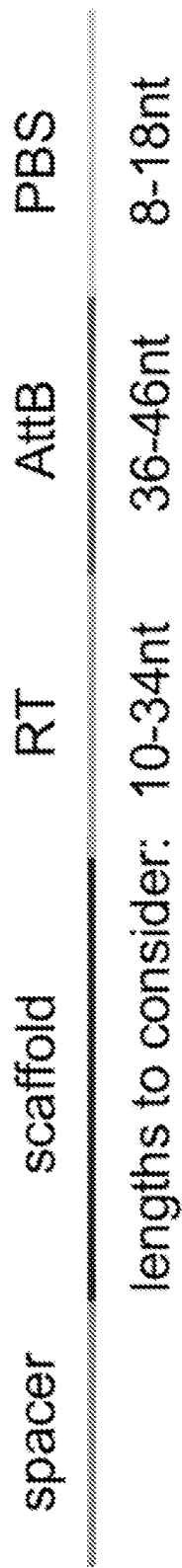
FIG. 24A shows a schematic of the design parameters for the pegRNA according to embodiments of the present teachings.

As used herein, the term "prime-editing guide RNA" (pegRNA) and the like refer to an extended single guide RNA (sgRNA) comprising a primer binding site (PBS), a reverse transcriptase (RT) template sequence, and an integration site sequence that can be recognized by recombinases, integrases, or transposases. Exemplary design parameters for pegRNA are shown in FIG. 24A. For example, the PBS can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or more nt. For example, the PBS can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or any range that is formed from any two of those values as endpoints. For example, the RT template sequence can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or more nt. For example, the RT template sequence can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or any range that is formed from any two of those values as endpoints.

During genome editing, the primer binding site allows the 3' end of the nicked DNA strand to hybridize to the pegRNA, while the RT template serves as a template for the synthesis of edited genetic information. The pegRNA is capable for instance, without limitation, of (i) identifying the target nucleotide sequence to be edited and (ii) encoding new genetic information that replaces the targeted sequence. In some embodiments, the pegRNA is capable of (i) identifying the target nucleotide sequence to be edited and (ii) encoding an integration site that replaces the targeted sequence.

Figure 24B:
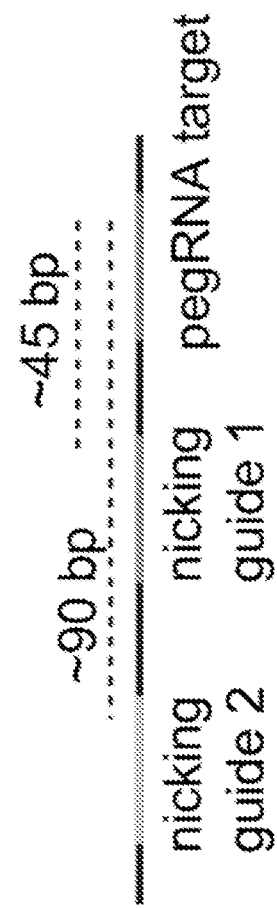
FIG. 24B shows a schematic of the design parameters for nicking guide RNA according to embodiments of the present teachings.

As used herein, the term "nicking guide RNA" (ngRNA) and the like refer to an RNA sequence that can nick a strand such as an edited strand and a non-edited strand. Exemplary design parameters for ngRNA are shown in FIG. 24B. The ngRNA can induce nicks at about 1 or more nt away from the site of the gRNA-induced nick. For example, the ngRNA can nick at least at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more nt away from the site of the gRNA induced nick. In some embodiments, the ngRNA comprises SEQ ID NO: 75 with guide sequence SEQ ID NO: 74. As used herein, the terms "reverse transcriptase" and "reverse transcriptase domain" refer to an enzyme or an enzymatically active domain that can reverse a RNA transcribe into a complementary DNA. The reverse transcriptase or reverse transcriptase domain is a RNA dependent DNA polymerase. Such reverse transcriptase domains encompass, but are not limited, to a M-MLV reverse transcriptase, or a modified reverse transcriptase such as, without limitation, Superscript® reverse transcriptase (Invitrogen; Carlsbad, Calif.), Superscript® VILO™ cDNA synthesis (Invitrogen; Carlsbad, Calif.), RTX, AMV-RT, and Quantiscript Reverse Transcriptase (Qiagen, Hilden, Germany).

The pegRNA-PE complex disclosed herein recognizes the target site in the genome and the Cas9 for example nicks a protospacer adjacent motif (PAM) strand. The primer binding site (PBS) in the pegRNA hybridizes to the PAM strand. The RT template operably linked to the PBS, containing the edit sequence, directs the reverse transcription of the RT template to DNA into the target site. Equilibration between the edited 3' flap and the unedited 5' flap, cellular 5' flap cleavage and ligation, and DNA repair results in stably edited DNA. To optimize base editing, a Cas9 nickase can be used to nick the non-edited strand, thereby directing DNA repair to that strand, using the edited strand as a template.

Integrase Technologies

The present disclosure provides non-naturally occurring or engineered systems, methods, and compositions for site-specific genetic engineering using integrase technologies. Integrase technologies will be discussed in more details below.

The integrase technologies used herein comprise proteins or nucleic acids encoding the proteins that direct integration of a gene of interest or nucleic acid sequence of interest into an integration site via a nuclease such as a prime editing nuclease. The protein directing the integration can be an enzyme such as integration enzyme. The integration enzyme can be an integrase that incorporates the genome or nucleic acid of interest into the cell genome at the integration site by integration. The integration enzyme can be a recombinase that incorporates the genome or nucleic acid of interest into the cell genome at the integration site by recombination. The integration enzyme can be a reverse transcriptase that incorporates the genome or nucleic acid of interest into the cell genome at the integration site by reverse transcription. The integration enzyme can be a retrotransposase that incorporates the genome or nucleic acid of interest into the cell genome at the integration site by retrotransposition.

As used herein, the term "integration enzyme" refers to an enzyme or protein used to integrate a gene of interest or nucleic acid sequence of interest into a desired location or at the integration site, in the genome of a cell, in a single reaction or multiple reactions. Example of integration enzymes include for example, without limitation, Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, and retrotransposases encoded by R2, L1, Tol2 Tc1, Tc3, Mariner (Himar 1), Mariner (mos 1), and Minos. In some embodiments, the term "integration enzyme" refers to a nucleic acid (DNA or RNA) encoding the above-mentioned enzymes. In some embodiments, the Cre recombinase is expressed from a Cre recombinase expression plasmid (SEQ ID NO: 71).

Mammalian expression plasmids can be found in Table 1 below.

TABLE 1

| Name | Full Description | SEQ ID NOS: |
|---|---|---|
| PE2-Bxb1 Single Vector | pCMV-PE2-P2A- Bxb1 | (SEQ ID NO: 381) |
| PE2 prime editor | pCMV-PE2/ Addgene #132775 | (SEQ ID NO: 382) |
| PE2*-Bxb1 Single Vector | New NLS pCMV- PE2-P2A-Bxb1 | (SEQ ID NO: 383) |
| PASTEv3 | pCMV-SpCas9-XTEN-RT(1-478)-Sto7d-GGGGS-BxbINT | (SEQ ID NO: 384) |
| ACTB pegRNA | ACTB N-term PBS 13 RT 29 attB 46 pegRNA | (SEQ ID NO: 385) |
| ACTB Nicking + 48 | ACTB N-term Nicking guide 1 + 48 guide | (SEQ ID NO: 386) |

TABLE 1-continued

| Name | Full Description | SEQ ID NOS: |
|---|---|---|
| Bxb1 integrase | pCAG-NLS-HA-Bxb1integrase/ Addgene #51271 | (SEQ ID NO: 387) |
| TP901-1 Integrase | TP901-1 Integrase | (SEQ ID NO: 388) |
| PhiBT Integrase | PhiBT Integrase | (SEQ ID NO: 389) |
| HDR sgRNA guide | Minicircle U6-sgRNA EFS-SpCas9 | (SEQ ID NO: 390) |
| HDR EGFP cargo | Cas9 HDR template site with EGFP | (SEQ ID NO: 391) |
| AAV helper plasmid | PDF6 AAV helper plasmid | (SEQ ID NO: 392) |
| AAV EGFP donor | GFP AAV donor plasmid | (SEQ ID NO: 393) |
| AAV2/8 | AAV2/8 capsid protein | (SEQ ID NO: 394) |

Minicircle cargo gene maps can be found in Table 2 below.

TABLE 2

| Name | Full Description | SEQ ID NOS: |
|---|---|---|
| Cargo EGFP | Parent minicircle plasmid—Cargo EGFP with attP Bxb1 site | (SEQ ID NO: 76) |
| Cargo EGFP post cleavage | Cargo EGFP with attP Bxb1 site—post minicircle cleavage | (SEQ ID NO: 395) |
| Cargo EGFP for fusion | Parent minicircle plasmid—Cargo EGFP with attP Bxb1 site for fusion | (SEQ ID NO: 396) |
| mCherry Cargo post cleavage | Cargo mCherry with attP Bxb1 site—post minicircle cleavage | (SEQ ID NO: 397) |
| YFP Cargo post cleavage | Cargo YFP with attP Bxb1 site—post minicircle cleavage | (SEQ ID NO: 398) |
| SERPINA1 Cargo post cleavage | Cargo SERPINA1 with attP Bxb1 site—post minicircle cleavage | (SEQ ID NO: 399) |
| CPS1 Cargo post cleavage | Cargo CPS1 with attP Bxb1 site—post minicircle cleavage | (SEQ ID NO: 400) |
| CFTR Cargo | Parent minicircle plasmid—Cargo CFTR with attP Bxb1 site | (SEQ ID NO: 401) |
| NYESO TCR Cargo post cleavage | Cargo NYESO TCR with attP Bxb1 site—post minicircle cleavage | (SEQ ID NO: 402) |

In some embodiments, the serine integrase φC31 from φC31 phage is use as integration enzyme. The integrase φC31 in combination with a pegRNA can be used to insert the pseudo attP integration site (SEQ ID NO: 78). A DNA minicircle containing a gene or nucleic acid of interest and attB (SEQ ID NO: 3) site can be used to integrate the gene or nucleic acid of interest into the genome of a cell. This integration can be aided by a co-transfection of an expression vector having the φC31 integrase.

As used herein, the term "integrase" refers to a bacteriophage derived integrase, including wild-type integrase and any of a variety of mutant or modified integrases. As used herein, the term "integrase complex" may refer to a complex comprising integrase and integration host factor (IF). As used herein, the term "integrase complex" and the like may also refer to a complex comprising an integrase, an integration host factor, and a bacteriophage X-derived excisionase (Xis).

As used herein, the term "recombinase" and the like refer to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R1, R2, R3, R4, R5, φRV1, φFC1, MR11, A118, U153, and gp29. Examples of serine recombinases also include, without limitation, recombinases Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, and BxZ2 from Mycobacterial phages. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange.

Recombinases have numerous applications, including the creation of gene knockouts/knock-ins and gene therapy applications. See, e.g., Brown et al., "Serine recombinases as tools for genome engineering." Methods, 2011; 53(4): 372-9; Hirano et al., "Site-specific recombinases as tools for heterologous gene integration." Appl. Microbiol. Biotechnol. 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12): 4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Creating a new biological era." *J. Zhejiang Univ. Sci. B.* 2012; 13(7):511-24; Karpenshif and Bernstein, "From yeast to mammals: recent advances in genetic control of homologous recombination." *DNA Repair (Amst).* 2012; 1; 11(10):781-8; the entire contents of each are hereby incorporated by reference in their entirety.

The recombinases provided herein are not meant to be exclusive examples of recombinases that can be used in embodiments of the disclosure. The methods and compositions of the disclosure can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety).

Other examples of recombinases that are useful in the systems, methods, and compositions described herein are known to those of skill in the art, and any new recombinase that is discovered or generated is expected to be able to be used in the different embodiments of the disclosure.

As used herein, the term "retrotransposase" and the like refer to an enzyme, or combination of one or more enzymes, wherein at least one enzyme has a reverse transcriptase domain. Retrotransposases are capable of inserting long sequences (e.g., over 3000 nucleotides) of heterologous nucleic acid into a genome. Examples of retrotransposases include for example, without limitation, retrotransposases encoded by elements such as R2, L1, Tol2 Tc1, Tc3, Mariner (Himar 1), Mariner (mos 1), Minos, and any mutants thereof.

In some embodiments, the one or more genes of interest or one or more nucleic acid sequences of interest are inserted into a desired location in a genome using a RNA fragment, such as a retrotransposon, encoding the nucleic acid linked to a complementary or associated integration site. The insertion of the nucleic acid of interest into a location in the desired location in the genome using a retrotransposon is aided by a retrotransposase.

The gene and nucleic acid sequence of interest disclosed herein can be any gene and nucleic acid sequence that are known in the art. The gene and nucleic acid sequence of interest can be for therapeutic and/or diagnostic uses. Examples of genes of interest include, without limitation, GBA, BTK, ADA, CNGB3, CNGA3, ATF6, GNAT2, ABCA1, ABCA7, APOE, CETP, LIPC, MMP9, PLTP, VTN, ABCA4, MFSD8, TLR3, TLR4, ERCC6, HMCN1, HTRA1, MCDR4, MCDR5, ARMS2, C2, C3, CFB, CFH, JAG1, NOTCH2, CACNA1F, SERPINA1, TTR, GSN, B2M, APOA2, APOA1, OSMR, ELP4, PAX6, ARG, ASL, PITX2, FOXC1, BBS1, BBS10, BBS2, BBS9, MKKS, MKS1, BBS4, BBS7, TTC8, ARL6, BBS5, BBS12, TRIM32, CEP290, ADIPOR1, BBIP1, CEP19, IFT27, LZTFL1, DMD, BEST1, HBB, CYP4V2, AMACR, CYP7B1, HSD3B7, AKR1D1, OPN1SW, NR2F1, RLBP1, RGS9, RGS9BP, PROM1, PRPH2, GUCY2D, CACD, CHM, ALAD, ASS1, SLC25A13, OTC, ACADVL, ETFDH, TMEM67, CC2D2A, RPGRIP1L, KCNV2, CRX, GUCA1A, CERKL, CDHR1, PDE6C, TTLL5, RPGR, CEP78, C21orf2, C8ORF37, RPGRIP1, ADAMS, POC1B, PITPNM3, RAB28, CACNA2D4, AIPL1, UNC119, PDE6H, OPN1LW, RIMS1, CNNM4, IFT81, RAX2, RDH5, SEMA4A, CORD17, PDE6B, GRK1, SAG, RHO, CABP4, GNB3, SLC24A1, GNAT1, GRM6, TRPM1, LRIT3, TGFBI, TACSTD2, KRT12, OVOL2, CPS1, UGT1A1, UGT1A9, UGT1A8, UGT1A7, UGT1A6, UGT1A5, UGT1A4, CFTR, DLD, EFEMP1, ABCC2, ZNF408, LRP5, FZD4, TSPAN12, EVR3, APOB, SLC2A2, LOC106627981, GBA1, NR2E3, OAT, SLC40A1, F8, F9, UROD, CPDX, HFE, JH, LDLR, EPHX1, TJP2, BAAT, NBAS, LARS1, HAMP, HJV, RS1, ADAMTS18, LRAT, RPE65, LCA5, MERTK, GDF6, RD3, CCT2, CLUAP1, DTHD1, NMNAT1, SPATA7, IFT140, IMPDH1, OTX2, RDH12, TULP1, CRB1, MT-ND4, MT-ND1, MT-ND6, BCKDHA, BCKDHB, DBT, MMAB, ARSB, GUSB, NAGS, NPC1, NPC2, NDP, OPA1, OPA3, OPA4, OPA5, RTN4IP1, TMEM126A, OPA6, OPA8, ACO2, PAH, PRKCSH, SEC63, GAA, UROS, PPDX, HPX, HMOX1, HMBS, MIR223, CYP1B1, LTBP2, AGXT, ATP8B1, ABCB11, ABCB4, FECH, ALAS2, PRPF31, RP1, EYS, TOPORS, USH2A, CNGA1, C2ORF71, RP2, KLHL7, ORF1, RP6, RP24, RP34, ROM1, ADGRA3, AGBL5, AHR, ARHGEF18, CA4, CLCC1, DHDDS, EMC1, FAM161A, HGSNAT, HK1, IDH3B, KIAA1549, KIZ, MAK, NEUROD1, NRL, PDE6A, PDE6G, PRCD, PRPF3, PRPF4, PRPF6, PRPF8, RBP3, REEP6, SAMD11, SLC7A14, SNRNP200, SPP2, ZNF513, NEK2, NEK4, NXNL1, OFD1, RP1L1, RP22, RP29, RP32, RP63, RP9, RGR, POMGNT1, DHX38, ARL3, COL2A1, SLCO1B1, SLCO1B3, KCNJ13, TIMP3, ELOVL4, TFR2, FAH, HPD, MYO7A, CDH23, PCDH15, DFNB31, GPR98, USH1C, USH1G, CIB2, CLRN1, HARS, ABHD12, ADGRV1, ARSG, CEP250, IMPG1, IMPG2, VCAN, G6PC1, ATP7B and any derivatives thereof.

As used here, the terms "retrotransposons," "jumping genes," "jumping nucleic acids," and the like refer to cellular movable genetic elements dependent on reverse transcription. The retrotransposons are of non-replication competent cellular origin, and are capable of carrying a foreign nucleic acid sequence. The retrotransposons can act as parasites of retroviruses, retaining certain classical hallmarks, such as long terminal repeats (LTR), retroviral primer binding sites, and the like. However, the naturally occurring retrotransposons usually do not contain functional retroviral structure genes, which would normally be capable of recombining to yield replication competent viruses. Some retrotransposons are examples of so-called "selfish DNA", or genetic information, which encodes nothing except the ability to replicate itself. The retrotransposon may do so by utilizing the occasional presence of a retrovirus or a retrotransposase within the host cell, efficiently packaging itself within the viral particle, which transports it to the new host genome, where it is expressed again as RNA. The information encoded within that RNA is potentially transported with the jumping gene. A retrotransposon can be a DNA transposon or a retrotransposon, including a LTR retrotransposon or a non-LTR retrotransposon.

Non-long terminal repeat (LTR) retrotransposons are a type of mobile genetic elements that are widespread in eukaryotic genomes. They include two classes: the apurinic/apyrimidinic endonuclease (APE)-type and the restriction enzyme-like endonuclease (RLE)-type. The APE class retrotransposons are comprised of two functional domains: an endonuclease/DNA binding domain, and a reverse transcriptase domain. The RLE class are comprised of three functional domains: a DNA binding domain, a reverse transcription domain, and an endonuclease domain. The reverse transcriptase domain of non-LTR retrotransposon functions by binding an RNA sequence template and reverse transcribing it into the host genome's target DNA. The RNA sequence template has a 3' untranslated region which is specifically bound to the transposase, and a variable 5' region generally having Open Reading Frame(s) ("ORF") encoding transposase proteins. The RNA sequence template may also comprise a 5' untranslated region which specifically binds the retrotransposase. In some embodiments, a non-LTR transposons can include a LINE retrotransposon, such as L1, and a SINE retrotransposon, such as an Alu sequence. Other examples include for example, without limitation, R1, R2, R3, R4, and R5 retro-transposons (Moss, W. N. et al., *RNA Biol.* 2011, 8(5), 714-718; and Burke, W. D. et al., *Molecular Biology and Evolution* 2003, 20(8), 1260-1270). The transposon can be autonomous or non-autonomous.

LTR retrotransposons, which include retroviruses, make up a significant fraction of the typical mammalian genome, comprising about 8% of the human genome and 10% of the mouse genome. Lander et al., 2001, *Nature* 409, 860-921; Waterson et al., 2002, *Nature* 420, 520-562. LTR elements include retrotransposons, endogenous retroviruses (ERVs), and repeat elements with HERV origins, such as SINE-R. LTR retrotransposons include two LTR sequences that flank a region encoding two enzymes: integrase and retrotransposase.

ERVs include human endogenous retroviruses (HERVs), the remnants of ancient germ-cell infections. While most HERV proviruses have undergone extensive deletions and mutations, some have retained ORFS coding for functional proteins, including the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, *Genome Res.* 20, 19-27. Moreover, a few families, including the HERV-K (HML-2) group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons make up about 8% of the human genome. See, e.g., Lander et al., 2001, *Nature* 409, 860-921; Hua-Van et al., 2011, Biol. Dir. 6, 19.

Integration Site

The present disclosure provides non-naturally occurring or engineered systems, methods, and compositions for site-specific genetic engineering via the addition of an integration site into a target genome. The integration site will be discussed in more details below.

As used herein, the term "integration site" refers to the site within the target genome where one or more genes of interest or one or more nucleic acid sequences of interest are inserted. Examples of integration sites include for example, without limitation, a lox71 site (SEQ ID NO: 1), attB sites (SEQ ID NO: 3 and SEQ ID NO: 43), attP sites (SEQ ID NO: 4 and SEQ ID NO: 44), an attL site (SEQ ID NO: 67), an attR site (SEQ ID NO: 68), a Vox site (SEQ ID NO: 69), a FRT site (SEQ ID NO: 70), or a pseudo attP site (SEQ ID NO: 78). The integration site can be inserted into the genome or a fragment thereof of a cell using a nuclease, a gRNA, and/or an integration enzyme. The integration site can be inserted into the genome of a cell using a prime editor such as, without limitation, PE1, PE2, and PE3, wherein the integration site is carried on a pegRNA. The pegRNA can target any site that is known in the art. Examples of cites targeted by the pegRNA include, without limitation, ACTB, SUPT16H, SRRM2, NOLC1, DEPDC4, NES, LMNB1, AAVS1 locus, CC10, CFTR, SERPINA1, ABCA4, and any derivatives thereof. The complementary integration site may be operably linked to a gene of interest or nucleic acid sequence of interest in an exogenous DNA or RNA. In some embodiments, one integration site is added to a target genome. In some embodiments, more than one integration sites are added to a target genome.

To insert multiple genes or nucleic acids of interest, two or more integration sites are added to a desired location. Multiple DNA comprising nucleic acid sequences of interest are flanked orthogonal to the integration sequences, such as, without limitation, attB and attP. An integration site is "orthogonal" when it does not significantly recognize the recognition site or nucleotide sequence of a recombinase. Thus, one attB site of a recombinase can be orthogonal to an attB site of a different recombinase. In addition, one pair of attB and attP sites of a recombinase can be orthogonal to another pair of attB and attP sites recognized by the same recombinase. A pair of recombinases are considered orthogonal to each other, as defined herein, when there is recognition of each other's attB or attP site sequences.

The lack of recognition of integration sites or pairs of sites by the same recombinase or a different recombinase can be less than about 30%. In some embodiments, the lack of recognition of integration sites or pairs of sites by the same recombinase or a different recombinase can be less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, about 1%, or any range that is formed from any two of those values as endpoints. The crosstalk can be less than about 30%. In some embodiments, the crosstalk is less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, less than about 1%, or any range that is formed from any two of those values as endpoints.

In some embodiments, the attB and/or attP site sequences comprise a central dinucleotide sequence. It has been shown that, for example, the central dinucleotide can be changed to GA from GT and that only GA containing attB/attP sites interact and will not cross react with GT containing sequences. In some embodiments, the central dinucleotide is selected from the group consisting of AG, AC, TG, TC, CA, CT, GA, AA, TT, CC, GG, AT, TA, GC, CG and GT.

As used herein, the term "pair of an attB and attP site sequences" and the like refer to attB and attP site sequences that share the same central dinucleotide and can recombine. This means that in the presence of one serine integrase as many as six pairs of these orthogonal att sites can recombine (attPTT will specifically recombine with attBTT, attPTC will specifically recombine with attBTC, and so on).

In some embodiments, the central dinucleotide is nonpalindromic. In some embodiments, the central dinucleotide is palindromic. In some embodiments, a pair of an attB site sequence and an attP site sequence are used in different DNA encoding genes of interest or nucleic acid sequences of interest for inducing directional integration of two or more different nucleic acids.

The Table 3 below shows examples of pairs of attB site sequence and attP site sequence with different central dinucleotide (CD).

TABLE 3

| Pair | attB | attP | CD |
|------|------|------|-----|
| 1 | SEQ ID NO: 5 | SEQ ID NO: 6 | TT |
| 2 | SEQ ID NO: 7 | SEQ ID NO: 8 | AA |
| 3 | SEQ ID NO: 9 | SEQ ID NO: 10 | CC |
| 4 | SEQ ID NO: 11 | SEQ ID NO: 12 | GG |
| 5 | SEQ ID NO: 13 | SEQ ID NO: 14 | TG |
| 6 | SEQ ID NO: 15 | SEQ ID NO: 16 | GT |
| 7 | SEQ ID NO: 17 | SEQ ID NO: 18 | CT |
| 8 | SEQ ID NO: 19 | SEQ ID NO: 20 | CA |
| 9 | SEQ ID NO: 21 | SEQ ID NO: 22 | TC |
| 10 | SEQ ID NO: 23 | SEQ ID NO: 24 | GA |
| 11 | SEQ ID NO: 25 | SEQ ID NO: 26 | AG |
| 12 | SEQ ID NO: 27 | SEQ ID NO: 28 | AC |
| 13 | SEQ ID NO: 29 | SEQ ID NO: 30 | AT |
| 14 | SEQ ID NO: 31 | SEQ ID NO: 32 | GC |
| 15 | SEQ ID NO: 33 | SEQ ID NO: 34 | CG |
| 16 | SEQ ID NO: 35 | SEQ ID NO: 36 | TA |

PASTE

The present disclosure provides non-naturally occurring or engineered systems, methods, and compositions for site-specific genetic engineering using PASTE. PASTE will be discussed in more details below.

The site-specific genetic engineering disclosed herein is for the insertion of one or more genes of interest or one or more nucleic acid sequences of interest into a genome of a cell. In some embodiments, the gene of interest is a mutated gene implicated in a genetic disease such as, without limitation, a metabolic disease, cystic fibrosis, muscular dystrophy, hemochromatosis, Tay-Sachs, Huntington disease, Congenital Deafness, Sickle cell anemia, Familial hypercholesterolemia, adenosine deaminase (ADA) deficiency, X-linked SCID (X-SCID), and Wiskott-Aldrich syndrome (WAS). In some embodiments, the gene of interest or nucleic acid sequence of interest can be a reporter gene upstream or downstream of a gene for genetic analyses such as, without limitation, for determining the expression of a gene. In some embodiments, the reporter gene is a GFP template (SEQ ID NO: 76) or a *Gaussia* Luciferase (G-Luciferase) template (SEQ ID NO: 77) In some embodiments, the gene of interest or nucleic acid sequence of interest can be used in plant genetics to insert genes to enhance drought tolerance, weather hardiness, and increased yield and herbicide resistance in plants. In some embodiments, the gene of interest or nucleic acid sequence of interest can be used for site-specific insertion of a protein (e.g., a lysosomal enzyme), a blood factor (e.g., Factor I, II, V, VII, X, XI, XII or XIII), a membrane protein, an exon, an intracellular protein (e.g., a cytoplasmic protein, a nuclear protein, an organellar protein such as a mitochondrial protein or lysosomal protein), an extracellular protein, a structural protein, a signaling protein, a regulatory protein, a transport protein, a sensory protein, a motor protein, a defense protein, or a storage protein, an anti-inflammatory signaling molecules into cells for treatment of immune diseases, including but not limited to arthritis, psoriasis, lupus, coeliac disease, glomerulonephritis, hepatitis, and inflammatory bowel disease.

The size of the inserted gene or nucleic acid can vary from about 1 bp to about 50,000 bp. In some embodiments, the size of the inserted gene or nucleic acid can be about 1 bp, 10 bp, 50 bp, 100 bp, 150 bp, 200 bp, 250 bp, 300 bp, 350 bp, 400 bp, 600 bp, 800 bp, 1000 bp, 1200 bp, 1400 bp, 1600 bp, 1800 bp, 2000 bp, 2200 bp, 2400 bp, 2600 bp, 2800 bp, 3000 bp, 3200 bp, 3400 bp, 3600 bp, 3800 bp, 4000 bp, 4200 bp, 4400 bp, 4600 bp, 4800 bp, 5000 bp, 5200 bp, 5400 bp, 5600 bp, 5800 bp, 6000 bp, 6200 bp, 6400 bp, 6600 bp, 6800 bp, 7000 bp, 7200 bp, 7400 bp, 7600 bp, 7800 bp, 8000 bp, 8200 bp, 8400 bp, 8600 bp, 8800 bp, 9000 bp, 9200 bp, 9400 bp, 9600 bp, 9800 bp, 10,000 bp, 10,200 bp, 10,400 bp, 10,600 bp, 10,800 bp, 11,000 bp, 11,200 bp, 11,400 bp, 11,600 bp, 11,800 bp, 12,000 bp, 14,000 bp, 16,000 bp, 18,000 bp, 20,000 bp, 30,000 bp, 40,000 bp, 50,000 bp, or any range that is formed from any two of those values as endpoints.

In some embodiments, the site-specific engineering using the gene of interest or nucleic acid sequence of interest disclosed herein is for the engineering of T cells and NKs for tumor targeting or allogeneic generation. These can involve the use of receptor or CAR for tumor specificity, anti-PD1 antibody, cytokines like IFN-gamma, TNF-alpha, IL-15, IL-12, IL-18, IL-21, and IL-10, and immune escape genes.

In the present disclosure, the site-specific insertion of the gene of interest or nucleic acid of interest is performed through Programmable Addition via Site-Specific Targeting Elements (PASTE). Components for inserting a gene of interest or a nucleic acid of interest using PASTE are for example, without limitation, a nuclease, a gRNA adding the integration site, a DNA or RNA strand comprising the gene or nucleic acid linked to a sequence that is complementary or associated to the integration site, and an integration enzyme. Components for inserting a gene of interest or a nucleic acid of interest using PASTE are for example, without limitation, a prime editor expression, pegRNA adding the integration site, nicking guide RNA, integration enzyme (Cre or serine recombinase), transgene vector comprising the gene of interest or nucleic acid sequence of interest with gene and integration signal. The nuclease and prime editor integrate the integration site into the genome. The integration enzyme integrates the gene of interest into the integration site. In some embodiments, the transgene vector comprising the gene or nucleic acid sequence of interest with gene and integration signal is a DNA minicircle devoid of bacterial DNA sequences. In some embodiments, the transgenic vector is a eukaryotic or prokaryotic vector.

As used herein, the term "vector" or "transgene vector" refers to a recombinant DNA molecule containing a desired coding sequence and appropriate nucleic acid sequences necessary for the expression of the operably linked coding sequence in a host organism. Nucleic acid sequences necessary for expression in prokaryotes usually include for example, without limitation, a promoter, an operator (optional), a ribosome binding site, and/or other sequences. Eukaryotic cells are generally known to utilize promoters (constitutive, inducible or tissue specific), enhancers, and termination and polyadenylation signals, although some elements may be deleted and other elements added without sacrificing the necessary expression. The transgenic vector may encode the PE and the integration enzyme, linked to each other via a linker. The linker can be a cleavable linker. For example, transgenic vector encoding the PE and the integration enzyme, linked to each other via a linker is pCMV PE2 P2A Cre comprises SEQ ID NO: 73. In some embodiments, the linker can be a non-cleavable linker. In some embodiments the nuclease, prime editor, and/or integration enzyme can be encoded in different vectors.

Figure 12:
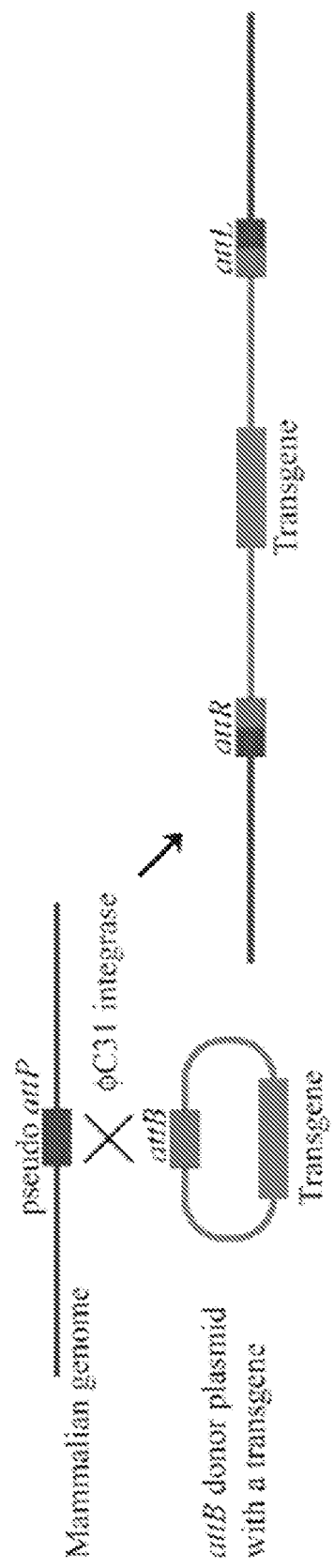
FIG. 12 shows a schematic diagram of the using φC31 as the integration enzyme, according to embodiments of the present teachings.
Figure 13:
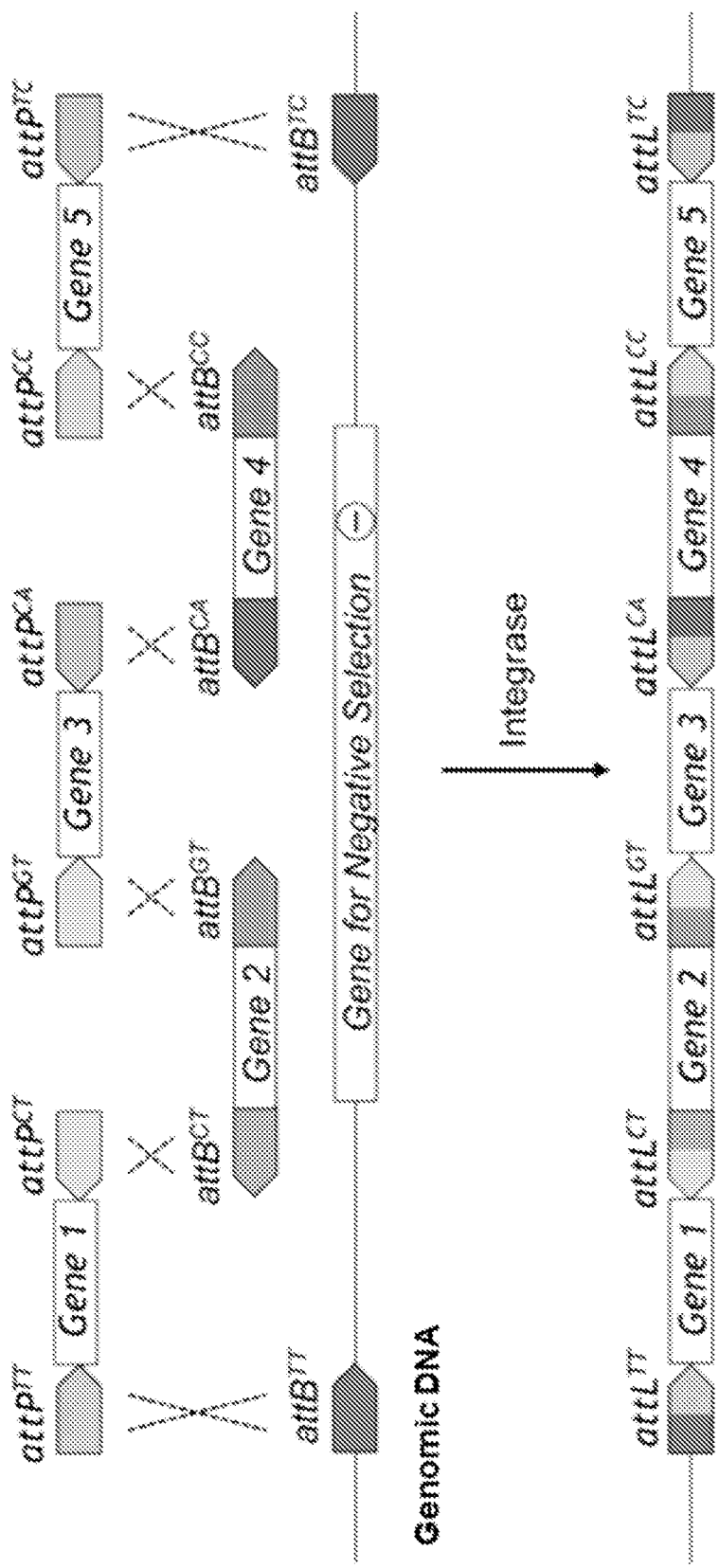
FIG. 13 shows a schematic diagram of multiplexing involving inserting multiple genes of interest in multiple loci using unique guide RNAs that incorporated exterior flanking attB sites according to embodiments of the present teachings.

A method of inserting multiple genes or nucleic acid sequences of interest into a single site according to embodiments of the present disclosure is illustrated in FIG. 12. In some embodiments, multiplexing involves inserting multiple genes of interest in multiple loci using unique pegRNA as illustrated in FIG. 13 (Merrick, C. A. et al., *ACS Synth. Biol.* 2018, 7, 299-310). The insertion of multiple genes of interest or nucleic acids of interest into a cell genome, referred herein as "multiplexing," is facilitated by incorporation of the complementary 5' integration site to the 5' end of the DNA or RNA comprising the first nucleic acid and 3' integration site to the 3' end of the DNA or RNA comprising the last nucleic acid. In some embodiments, the number of genome of interest or amino acid sequences of interest that are inserted into a cell genome using multiplexing can be about 1, 2, 3, 4, 5, 6, 7, 8, 9, 10, 11, 12, 13, 14, 15, 16, 17, 18, 19, 20, 21, 22, 23, 24, 25, or any range that is formed from any two of those values as endpoints.

In some embodiments, multiplexing allows integration of for example, signaling cascade, over-expression of a protein of interest with its cofactor, insertion of multiple genes mutated in a neoplastic condition, or insertion of multiple CARs for treatment of cancer.

In some embodiments, the integration sites may be inserted into the genome using non-prime editing methods such as rAAV mediated nucleic acid integration, TALENS and ZFNs. A number of unique properties make AAV a promising vector for human gene therapy (Muzyczka, CURRENT TOPICS IN MICROBIOLOGY AND IMMUNOLOGY, 158:97-129 (1992)). Unlike other viral vectors, AAVs have not been shown to be associated with any known human disease and are generally not considered pathogenic. Wild type AAV is capable of integrating into host chromosomes in a site-specific manner M. Kotin et al., PROC. NATL. ACAD. SCI, USA, 87:2211-2215 (1990); R. J. Samulski, EMBO 10(12):3941-3950 (1991)). Instead of creating a double-stranded DNA break, AAV stimulates endogenous homologous recombination to achieve the DNA modification. Further, transcription activator-like effector nucleases (TALENs) and Zinc-finger nucleases (ZFNs) for genome editing and introducing targeted DSBs. The specificity of TALENs arises from two polymorphic amino acids, the so-called repeat variable diresidues (RVDs) located at positions 12 and 13 of a repeated unit. TALENS are linked to FokI nucleases, which cleaves the DNA at the desired locations. ZFNs are artificial restriction enzymes for custom site-specific genome editing. Zinc fingers themselves are transcription factors, where each finger recognizes 3-4 bases. By mixing and matching these finger modules, researchers can customize which sequence to target.

As used herein, the terms "administration," "introducing," or "delivery" into a cell, a tissue, or an organ of a plasmid, nucleic acids, or proteins for modification of the host genome refers to the transport for such administration, introduction, or delivery that can occur in vivo, in vitro, or ex vivo. Plasmids, DNA, or RNA for genetic modification can be introduced into cells by transfection, which is typically accomplished by chemical means (e.g., calcium phosphate transfection, polyethyleneimine (PEI) Or lipofection), physical means (electroporation or microinjection), infection (this typically means the introduction of an infectious agent such as a virus (e.g., a baculovirus expressing the AAV Rep gene)), transduction (in microbiology, this refers to the stable infection of cells by viruses, or the transfer of genetic material from one microorganism to another by viral factors (e.g., bacteriophages)). Vectors for the expression of a recombinant polypeptide, protein or oligonucleotide may be obtained by physical means (e.g., calcium phosphate transfection, electroporation, microinjection, or lipofection) in a cell, a tissue, an organ or a subject. The vector can be delivered by preparing the vector in a pharmaceutically acceptable carrier for the in vitro, ex vivo, or in vivo delivery to the carrier.

As used herein, the term "transfection" refers to the uptake of an exogenous nucleic acid molecule by a cell. A cell is "transfected" when an exogenous nucleic acid has been introduced into the cell membrane. The transfection can be a single transfection, co-transfection, or multiple transfection. Numerous transfection techniques are generally known in the art. See, for example, Graham et al. (1973) Virology, 52: 456. Such techniques can be used to introduce one or more exogenous nucleic acid molecules into a suitable host cell.

In some embodiments, the exogenous nucleic acid molecule and/or other components for gene editing are combined and delivered in a single transfection. In other embodiments, the exogenous nucleic acid molecule and/or other components for gene editing are not combined and delivered in a single transfection. In some embodiments, exogenous nucleic acid molecule and/or other components for gene editing are combined and delivered in a single transfection to comprise for example, without limitation, a prime editing vector, a landing site such as a landing site containing pegRNA, a nicking guide such as a nicking guide for stimulating prime editing, an expression vector such as an expression vector for a corresponding integrase or recombinase, a minicircle DNA cargo such as a minicircle DNA cargo encoding for green fluorescent protein (GFP), any derivatives thereof, and any combinations thereof. In some embodiments, the gene of interest or amino acid sequence of interest can be introduced using liposomes. In some embodiments, the gene of interest or amino acid sequence of interest can be delivered using suitable vectors for instance, without limitation, plasmids and viral vectors. Examples of viral vectors include, without limitation, adeno-associated viruses (AAV), lentiviruses, adenoviruses, other viral vectors, derivatives thereof, or combinations thereof. The proteins and one or more guide RNAs can be packaged into one or more vectors, e.g., plasmids or viral vectors. In some embodiments, the delivery is via nanoparticles or exosomes. For example, exosomes can be particularly useful in delivery RNA.

In some embodiments, the prime editing inserts the landing site with efficiencies of at least about 1%, at least about 5%, at least about 10%, at least about 15%, at least about, at least about 20%, at least about 25%, at least about 30%, at least about 35%, at least about 40%, at least about 45%, or at least about 50%. In some embodiments, the prime editing inserts the landing site(s) with efficiencies of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, or any range that is formed from any two of those values as endpoints.

Sequences

Sequences of enzymes, guides, integration sites, and plasmids can be found in Table 4 below.

TABLE 4

| SEQ ID NO/ DESCRIPTION/ SOURCE | SEQUENCE |
| --- | --- |
| SEQ ID NO: 1<br>Lox71<br>(Artificial sequence) | ATAACTTCGTATAATGTATGCTATACGAACGGTA |
| SEQ ID NO: 2<br>Lox66<br>(Artificial sequence) | TACCGTTCGTATAATGTATGCTATACGAAGTTAT |
| SEQ ID NO: 3<br>attB<br>(Artificial sequence) | GGCCGGCTTGTCGACGACGGCGGTCTCCGTCGTCAGGATCATCCGG |
| SEQ ID NO: 4<br>attP<br>(Artificial Sequence) | CCGGATGATCCTGACGACGGAGACCGCCGTCGTCGACAAGCCGGCC |
| SEQ ID NO: 5<br>attB-TT<br>(Artificial Sequence) | GGCTTGTCGACGACGGCGTTCTCCGTCGTCAGGATCAT |
| SEQ ID NO: 6<br>attP-TT<br>(Artificial Sequence) | GTGGTTTGTCTGGTCAACCACCGCGTTCTCAGTGGTGTACGGTACAAACCCA |
| SEQ ID NO: 7<br>attB-AA<br>(Artificial Sequence) | GGCTTGTCGACGACGGCGAACTCCGTCGTCAGGATCAT |
| SEQ ID NO: 8<br>attP-AA<br>(Artificial Sequence) | GTGGTTTGTCTGGTCAACCACCGCGAACTCAGTGGTGTACGGTACAAACCCA |
| SEQ ID NO: 9<br>attB-CC<br>(Artificial Sequence) | GGCTTGTCGACGACGGCGCCCTCCGTCGTCAGGATCAT |
| SEQ ID NO: 10<br>attP-CC<br>(Artificial Sequence) | GTGGTTTGTCTGGTCAACCACCGCGCCCTCAGTGGTGTACGGTACAAACCCA |
| SEQ ID NO: 11<br>attB-GG<br>(Artificial Sequence) | GGCTTGTCGACGACGGCGGGCTCCGTCGTCAGGATCAT |
| SEQ ID NO: 12<br>attP-GG<br>(Artificial Sequence) | GTGGTTTGTCTGGTCAACCACCGCGGGCTCAGTGGTGTACGGTACAAACCCA |
| SEQ ID NO: 13<br>attB-TG<br>(Artificial Sequence) | GGCTTGTCGACGACGGCGTGCTCCGTCGTCAGGATCAT |
| SEQ ID NO: 14<br>attP-TG<br>(Artificial Sequence) | GTGGTTTGTCTGGTCAACCACCGCGTGCTCAGTGGTGTACGGTACAAACCCA |
| SEQ ID NO: 15<br>attB-GT<br>(Artificial Sequence) | GGCTTGTCGACGACGGCGGTCTCCGTCGTCAGGATCAT |
| SEQ ID NO: 16<br>attP-GT<br>(Artificial Sequence) | GTGGTTTGTCTGGTCAACCACCGCGGTCTCAGTGGTGTACGGTACAAACCCA |
| SEQ ID NO: 17<br>attB-CT<br>(Artificial Sequence) | GGCTTGTCGACGACGGCGCTCTCCGTCGTCAGGATCAT |
| SEQ ID NO: 18<br>attP-CT<br>(Artificial Sequence) | GTGGTTTGTCTGGTCAACCACCGCGCTCTCAGTGGTGTACGGTACAAACCCA |
| SEQ ID NO: 19<br>attB-CA<br>(Artificial Sequence) | GGCTTGTCGACGACGGCGCACTCCGTCGTCAGGATCAT |

TABLE 4-continued

| SEQ ID NO/ DESCRIPTION/ SOURCE | SEQUENCE |
| --- | --- |
| SEQ ID NO: 20 attP-CA (Artificial Sequence) | GTGGTTTGTCTGGTCAACCACCGCGCACTCAGTGGTGTACGGTACA AACCCA |
| SEQ ID NO: 21 attB-TC (Artificial Sequence) | GGCTTGTCGACGACGGCGTCCTCCGTCGTCAGGATCAT |
| SEQ ID NO: 22 attP-TC (Artificial Sequence) | GTGGTTTGTCTGGTCAACCACCGCGTCCTCAGTGGTGTACGGTACA AACCCA |
| SEQ ID NO: 23 attB-GA (Artificial Sequence) | GGCTTGTCGACGACGGCGGACTCCGTCGTCAGGATCAT |
| SEQ ID NO: 24 attP-GA (Artificial Sequence) | GTGGTTTGTCTGGTCAACCACCGCGGACTCAGTGGTGTACGGTAC AAACCCA |
| SEQ ID NO: 25 attB-AG (Artificial Sequence) | GGCTTGTCGACGACGGCGAGCTCCGTCGTCAGGATCAT |
| SEQ ID NO: 26 attP-AG (Artificial Sequence) | GTGGTTTGTCTGGTCAACCACCGCGAGCTCAGTGGTGTACGGTAC AAACCCA |
| SEQ ID NO: 27 attB-AC (Artificial Sequence) | GGCTTGTCGACGACGGCGACCTCCGTCGTCAGGATCAT |
| SEQ ID NO: 28 attP-AC (Artificial Sequence) | GTGGTTTGTCTGGTCAACCACCGCGACCTCAGTGGTGTACGGTACA AACCCA |
| SEQ ID NO: 29 attB-AT (Artificial Sequence) | GGCTTGTCGACGACGGCGATCTCCGTCGTCAGGATCAT |
| SEQ ID NO: 30 attP-AT (Artificial Sequence) | GTGGTTTGTCTGGTCAACCACCGCGATCTCAGTGGTGTACGGTACA AACCCA |
| SEQ ID NO: 31 attB-GC (Artificial Sequence | GGCTTGTCGACGACGGCGGCCTCCGTCGTCAGGATCAT |
| SEQ ID NO: 32 attP-GC (Artificial Sequence) | GTGGTTTGTCTGGTCAACCACCGCGGCCTCAGTGGTGTACGGTACA AACCCA |
| SEQ ID NO: 33 attB-CG (Artificial Sequence) | GGCTTGTCGACGACGGCGCGCTCCGTCGTCAGGATCAT |
| SEQ ID NO: 34 attP-CG (Artificial Sequence) | GTGGTTTGTCTGGTCAACCACCGCGCGCTCAGTGGTGTACGGTACA AACCCA |
| SEQ ID NO: 35 attB-TA (Artificial Sequence) | GGCTTGTCGACGACGGCGTACTCCGTCGTCAGGATCAT |
| SEQ ID NO: 36 attP-TA (Artificial Sequence) | GTGGTTTGTCTGGTCAACCACCGCGTACTCAGTGGTGTACGGTACA AACCCA |
| SEQ ID NO: 37 C31-attB (Artificial Sequence) | TGCGGGTGCCAGGGCGTGCCCTTGGGCTCCCCGGGCGCGTACTCC |
| SEQ ID NO: 38 C31-attP (Artificial Sequence) | GTGCCCCAACTGGGGTAACCTTTGAGTTCTCTCAGTTGGGGG |

TABLE 4-continued

| SEQ ID NO/<br>DESCRIPTION/<br>SOURCE | SEQUENCE |
|---|---|
| SEQ ID NO: 39<br>R4-attB<br>(Artificial Sequence) | GCGCCCAAGTTGCCCATGACCATGCCGAAGCAGTGGTAGAAGGGC<br>ACCGGCAGACAC |
| SEQ ID NO: 40<br>R4-attP<br>(Artificial Sequence) | AGGCATGTTCCCCAAAGCGATACCACTTGAAGCAGTGGTACTGCT<br>TGTGGGTACACTCTGCGGGTGATGA |
| SEQ ID NO: 41<br>BT1-attB<br>(Artificial Sequence) | GTCCTTGACCAGGTTTTTGACGAAAGTGATCCAGATGATCCAGCTC<br>CACACCCCGAACGC |
| SEQ ID NO: 42<br>BT1-attP<br>(Artificial Sequence) | GGTGCTGGGTTGTTGTCTCTGGACAGTGATCCATGGGAAACTACTC<br>AGCACCACCAATGTTCC |
| SEQ ID NO: 43<br>Bxb-attB<br>(Artificial Sequence) | TCGGCCGGCTTGTCGACGACGGCGGTCTCCGTCGTCAGGATCATCC<br>GGGC |
| SEQ ID NO: 44<br>Bxb-attP<br>(Artificial Sequence) | GTCGTGGTTTGTCTGGTCAACCACCGCGGTCTCAGTGGTGTACGGT<br>ACAAACCCCGAC |
| SEQ ID NO: 45<br>TG1-attB<br>(Artificial Sequence) | GATCAGCTCCGCGGGCAAGACCTTCTCCTTCACGGGGTGGAAGGT<br>C |
| SEQ ID NO: 46<br>TG1-attP<br>(Artificial Sequence) | TCAACCCCGTTCCAGCCCAACAGTGTTAGTCTTTGCTCTTACCCAG<br>TTGGGCGGGATAGCCTGCCCG |
| SEQ ID NO: 47<br>C1-attB<br>(Artificial Sequence) | AACGATTTTCAAAGGATCACTGAATCAAAAGTATTGCTCATCCAC<br>GCGAAATTTTTC |
| SEQ ID NO: 48<br>C1-attP<br>(Artificial Sequence) | AATATTTTAGGTATATGATTTTGTTTATTAGTGTAAATAACACTAT<br>GTACCTAAAAT |
| SEQ ID NO: 49<br>C370-attB<br>(Artificial Sequence) | TGTAAAGGAGACTGATAATGGCATGTACAACTATACTCGTCGGTA<br>AAAAGGCA |
| SEQ ID NO: 50<br>C370-attP<br>(Artificial Sequence) | TAAAAAAATACAGCGTTTTTCATGTACAACTATACTAGTTGTAGTG<br>CCTAAA |
| SEQ ID NO: 51<br>K38-attB<br>(Artificial Sequence) | GAGCGCCGGATCAGGGAGTGGACGGCCTGGGAGCGCTACACGCT<br>GTGGCTGCGGTC |
| SEQ ID NO: 52<br>K38-attP<br>(Artificial Sequence) | CCCTAATACGCAAGTCGATAACTCTCCTGGGAGCGTTGACAACTT<br>GCGCACCCTGA |
| SEQ ID NO: 53<br>RB-attB<br>(Artificial Sequence) | TCTCGTGGTGGTGGAAGGTGTTGGTGCGGGGTTGGCCGTGGTCGA<br>GGTGGGGTGGTGGTAGCCATTCG |
| SEQ ID NO: 54<br>RV-attP<br>(Artificial Sequence) | GCACAGGTGTAGTGTATCTCACAGGTCCACGGTTGGCCGTGGACT<br>GCTGAAGAACATTCCACGCCAGGA |
| SEQ ID NO: 55<br>SPBC-attB<br>(Artificial Sequence) | AGTGCAGCATGTCATTAATATCAGTACAGATAAAGCTGTATCTCCT<br>GTGAACACAATGGGTGCCA |
| SEQ ID NO: 56<br>SPBC-attP<br>(Artificial Sequence) | AAAGTAGTAAGTATCTTAAAAAACAGATAAAGCTGTATATTAAGA<br>TACTTACTAC |
| SEQ ID NO: 57<br>TP901-attB<br>(Artificial Sequence) | TGATAATTGCCAACACAATTAACATCTCAATCAAGGTAAATGCTTT<br>TTCGTTTT |

TABLE 4-continued

| SEQ ID NO/ DESCRIPTION/ SOURCE | SEQUENCE |
|---|---|
| SEQ ID NO: 58 TP901-attP (Artificial Sequence) | AATTGCGAGTTTTTATTTCGTTTATTTCAATTAAGGTAACTAAAAA ACTCCTTT |
| SEQ ID NO: 59 Wβ-attB (Artificial Sequence) | AAGGTAGCGTCAACGATAGGTGTAACTGTCGTGTTTGTAACGGTA CTTCCAACAGCTGGCGTTTCAGT |
| SEQ ID NO: 60 Wβ-attP (Artificial Sequence) | TAGTTTTAAAGTTGGTTATTAGTTACTGTGATATTTATCACGGTAC CCAATAACCAATGAATATTTGA |
| SEQ ID NO: 61 A118-attB (Artificial Sequence) | TGTAACTTTTTCGGATCAAGCTATGAAGGACGCAAAGAGGGAACT AAACACTTAATT |
| SEQ ID NO: 62 A118-attP (Artificial Sequence) | TTGTTTAGTTCCTCGTTTTCTCTCGTTGGAAGAAGAAGAAACGAGA AACTAAAATTA |
| SEQ ID NO: 63 BL3-attB (Artificial Sequence) | CAACCTGTTGACATGTTTCCACAGACAACTCACGTGGAGGTAGTC ACGGCTTTTACGTTAGTT |
| SEQ ID NO: 64 BL3-attP (Artificial Sequence) | GAGAATACTGTTGAACAATGAAAAACTAGGCATGTAGAAGTTGTT TGTGCACTAACTTTAA |
| SEQ ID NO: 65 MR11-attB (Artificial Sequence) | ACAGGTCAACACATCGCAGTTATCGAACAATCTTCGAAAATGTAT GGAGGCACTTGTATCAATATAGGATGTATACCTTCGAAGACACTT GTACATGATGGATTAGAAGGCAAATCCTTT |
| SEQ ID NO: 66 MR11-attP (Artificial Sequence) | CAAAATAAAAAACATTGATTTTTATTAACTTCTTTTGTGCGGAACT ACGAACAGTTCATTAATACGAAGTGTACAAACTTCCATACAAAAA TAACCACGACAATTAAGACGTGGTTTCTA |
| SEQ ID NO: 67 attL (Artificial Sequence) | ATTATTTCTCACCCTGA |
| SEQ ID NO: 68 attR (Artificial Sequence) | ATCATCTCCCACCCGGA |
| SEQ ID NO: 69 Vox (Artificial Sequence) | AATAGGTCTG AGAACGCCCA TTCTCAGACG TATT |
| SEQ ID NO: 70 FRT (Artificial Sequence) | GAAGTTCCTATAC TTTCTAGA GAATAGGAACTTC |
| SEQ ID NO: 71 Cre recombinase expression plasmid (Artificial Sequence) | GGTCGACATTGATTATTGACTAGTTATTAATAGTAATCAATTACGG GGTCATTAGTTCATAGCCCATATATGGAGTTCCGCGTTACATAACT TACGGTAAATGGCCCGCCTGGCTGACCGCCCAACGACCCCCGCCC ATTGACGTCAATAATGACGTATGTTCCCATAGTAACGCCAATAGG GACTTTCCATTGACGTCAATGGGTGGAGTATTTACGGTAAACTGCC CACTTGGCAGTACATCAAGTGTATCATATGCCAAGTACGCCCCCTA TTGACGTCAATGACGGTAAATGGCCCGCCTGGCATTATGCCCAGT ACATGACCTTATGGGACTTTCCTACTTGGCAGTACATCTACGTATT AGTCATCGCTATTACCATGGTCGAGGTGAGCCCCACGTTCTGCTTC ACTCTCCCCATCTCCCCCCCCTCCCCACCCCCAATTTTGTATTTATT TATTTTTTAATTATTTTGTGCAGCGATGGGGGCGGGGGGGGGGGGG GGCGCGCGCCAGGCGGGGGGGGGGGGGGGGGGGGGGGGGGGGG GGGGGGGCGGGGGGGGCGGCGGCGAGCCAATCAGAGCGGCGCGC TCCGAAAGTTTCCTTTTATGGCGAGGCGGCGGCGGCGGCGGCCCT ATAAAAAGCGAAGCGCGCGGCGGGCGGGAGTCGCTGCGCGCTGC CTTCGCCCCGTGCCCCGCTCCGCCGCCGCCTCGCGCCGCCCGCCCC GGCTCTGACTGACCGCGTTACTCCCACAGGTGAGCGGGCGGGACG GCCCTTCTCCTCCGGGCTGTAATTAGCGCTTGGTTTAATGACGGCT TGTTTCTTTTCTGTGGCTGCGTGAAAGCCTTGAGGGGCTCCGGGAG GGCCCTTTGTGCGGGGGGAGCGGCTCGGGGGGTGCGTGCGTGTGT GTGTGCGTGGGGAGCGCCGCGTGCGGCTCCGCGCTGCCCGGCGGC TGTGAGCGCTGCGGGCGCGGCGCGGGGCTTTGTGCGCTCCGCAGT GTGCGCGAGGGGAGCGCGGCCGGGGGCGGTGCCCCGCGGTGCGG GGGGGGCTGCGAGGGGAACAAAGGCTGCGTGCGGGGTGTGTGCG |

TABLE 4-continued

| SEQ ID NO/ DESCRIPTION/ SOURCE | SEQUENCE |
|---|---|
| | TGGGGGGGTGAGCAGGGGGTGTGGGCGCGTCGGTCGGGCTGCAA |
| | CCCCCCCTGCACCCCCTCCCCGAGTTGCTGAGCACGGCCCGGCTT |
| | CGGGTGCGGGGCTCCGTACGGGGCGTGGCGCGGGGCTCGCCGTGC |
| | CGGGCGGGGGGTGGCGGCAGGTGGGGGTGCCGGGCGGGGCGGGG |
| | CCGCCTCGGGCCGGGAGGGCTCGGGGGAGGGGCGCGGCGGCCC |
| | CCGGAGCGCCGGCGGCTGTCGAGGCGCGGCGAGCCGCAGCCATTG |
| | CCTTTTATGGTAATCGTGCGAGAGGGCGCAGGGACTTCCTTTGTCC |
| | CAAATCTGTGCGGAGCCGAAATCTGGGAGGCGCCGCCGCACCCCC |
| | TCTAGCGGGCGCGGGGCGAAGCGGTGCGGCGCCGGCAGGAAGGA |
| | AATGGGCGGGAGGGCCTTCGTGCGTCGCCGCGCCGCCGTCCCCT |
| | TCTCCCTCTCCAGCCTCGGGGCTGTCCGCGGGGGGACGGCTGCCTT |
| | CGGGGGGGACGGGGCAGGGCGGGGTTCGGCTTCTGGCGTGTGACC |
| | GGCGGCTCTAGAGCCTCTGCTAACCATGTTCATGCCTTCTTCTTTTT |
| | CCTACAGCTCCTGGGCAACGTGCTGGTTATTGTGCTGTCTCATCAT |
| | TTTGGCAAAGAATTCTGAGCCGCCACCATGGCCAATTTACTGACC |
| | GTACACCAAAATTTGCCTGCATTACCGGTCGATGCAACGAGTGAT |
| | GAGGTTCGCAAGAACCTGATGGACATGTTCAGGGATCGCCAGGCG |
| | TTTTTCTGAGCATACCTGGAAAATGCTTCTGTCCGTTTGCCGGTCGT |
| | GGGCGGCATGGTGCAAGTTAATAACCGGAAATGGTTTCCCGCAG |
| | AACCTGAAGATGTTCGCGATTATCTTCTATATCTTCAGGCGCGCGG |
| | TCTGGCAGTAAAAACTATCCAGCAACATTTGGGCCAGCTAAACAT |
| | GCTTCATCGTCGGTCCGGGCTGCCACGACCAAGTGACAGCAATGC |
| | TGTTTCACTGGTTATGCGGCGGATCCGAAAAGAAAACGTTGATGC |
| | CGGTGAACGTGCAAAACAGGCTCTAGCGTTCGAACGCACTGATTT |
| | CGACCAGGTTCGTTCACTCATGGAAAATAGCGATCGCTGCCAGGA |
| | TATACGTAATCTGGCATTTCTGGGGATTGCTTATAACACCCTGTTA |
| | CGTATAGCCGAAATTGCCAGGATCAGGGTTAAAGATATCTCACGT |
| | ACTGACGGTGGGAGAATGTTAATCCATATTGGCAGAACGAAAACG |
| | CTGGTTAGCACCGCAGGTGTAGAGAAGGCACTTAGCCTGGGGGTA |
| | ACTAAACTGGTCGAGCGATGGATTTCCGTCTCTGGTGTAGCTGATG |
| | ATCCGAATAACTACCTGTTTTGCCGGGTCAGAAAAAATGGTGTTG |
| | CCGCGCCATCTGCCACCAGCCAGCTATCAACTCGCGCCCTGGAAG |
| | GGATTTTTGAAGCAACTCATCGATTGATTTACGGCGCTAAGGATG |
| | ACTCTGGTCAGAGATACCTGGCCTGGTCTGGACACAGTGCCCGTG |
| | TCGGAGCCGCGCGAGATATGGCCCGCGCTGGAGTTTCAATACCGG |
| | AGATCATGCAAGCTGGTGGCTGGACCAATGTAAATATTGTCATGA |
| | ACTATATCCGTAACCTGGATAGTGAAACAGGGGCAATGGTGCGCC |
| | TGCTGGAAGATGGCGATGGACCGGTGGAACAAAAACTTATTTCTG |
| | AAGAAGATCTGTGATAGCGGCCGCACTCCTCAGGTGCAGGCTGCC |
| | TATCAGAAGGTGGTGGCTGGTGTGGCCAATGCCCTGGCTCACAAA |
| | TACCACTGAGATCTTTTTCCCTCTGCCAAAAATTATGGGGACATCA |
| | TGAAGCCCCTTGAGCATCTGACTTCTGGCTAATAAAGGAAATTTAT |
| | TTTCATTGCAATAGTGTGTTGGAATTTTTTGTGTCTCTCACTCGGAA |
| | GGACATATGGGAGGGCAAATCATTTAAAACATCAGAATGAGTATT |
| | TGGTTTAGAGTTTGGCAACATATGCCCATATGCTGGCTGCCATGAA |
| | CAAAGGTTGGCTATAAAGAGGTCATCAGTATATGAAACAGCCCCC |
| | TGCTGTCCATTCCTTATTCCATAGAAAAGCCTTGACTTGAGGTTAG |
| | ATTTTTTTTATATTTTGTTTTGTGTTATTTTTTCTTTAACATCCCTA |
| | AAATTTTCCTTACATGTTTTACTAGCCAGATTTTTCCTCCTCTCCTG |
| | ACTACTCCCAGTCATAGCTGTCCCTCTTCTCTTATGGGATCCCTC |
| | GACCTGCAGCCCAAGCTTGGCGTAATCATGGTCATAGCTGTTTCCT |
| | GTGTGAAATTGTTATCCGCTCACAATTCCACACAACATACGAGCC |
| | GGAAGCATAAAGTGTAAAGCCTGGGGTGCCTAATGAGTGAGCTAA |
| | CTCACATTAATTGCGTTGCGCTCACTGCCCGCTTTCCAGTCGGGAA |
| | ACCTGTCGTGCCAGCGGATCCGCATCTCAATTAGTCAGCAACCAT |
| | AGTCCCGCCCCTAACTCCGCCCATCCCGCCCCTAACTCCGCCCAGT |
| | TCCGCCCATTCTCCGCCCCATGGCTGACTAATTTTTTTTATTTATGC |
| | AGAGGCCGAGGCCGCCTCGGCCTCTGAGCTATTCCAGAAGTAGTG |
| | AGGAGGCTTTTTTGGAGGCCTAGGCTTTTGCAAAAAGCTAACTTGT |
| | TTATTGCAGCTTATAATGGTTACAAATAAAGCAATAGCATCACAA |
| | ATTTCACAAATAAAGCATTTTTTTCACTGCATTCTAGTTGTGTTTG |
| | TCCAAACTCATCAATGTATCTTATCATGTCTGGATCCGCTGCATTA |
| | ATGAATCGGCCAACGCGCGGGGAGAGGCGGTTTGCGTATTGGGCG |
| | CTCTTCCGCTTCCTCGCTCACTGACTCGCTGCGCTCGGTCGTTCGG |
| | CTGCGGCGAGCGGTATCAGCTCACTCAAAGGCGGTAATACGGTTA |
| | TCCACAGAATCAGGGGATAACGCAGGAAAGAACATGTGAGCAAA |
| | AGGCCAGCAAAAGGCCAGGAACCGTAAAAAGGCCGCGTTGCTGG |
| | CGTTTTTCCATAGGCTCCGCCCCCCTGACGAGCATCACAAAAATCG |
| | ACGCTCAAGTCAGAGGTGGCGAAACCCGACAGGACTATAAAGAT |
| | ACCAGGCGTTTCCCCCTGGAAGCTCCCTCGTGCGCTCTCCTGTTCC |
| | GACCCTGCCGCTTACCGGATACCTGTCCGCCTTTCTCCCTTCGGGA |
| | AGCGTGGCGCTTTCTCATAGCTCACGCTGTAGGTATCTCAGTTCGG |
| | TGTAGGTCGTTCGCTCCAAGCTGGGCTGTGTGCACGAACCCCCCGT |
| | TCAGCCCGACCGCTGCGCCTTATCCGGTAACTATCGTCTTGAGTCC |
| | AACCCGGTAAGACACGACTTATCGCCACTGGCAGCAGCCACTGGT |
| | AACAGGATTAGCAGAGCGAGGTATGTAGGCGGTGCTACAGAGTTC |

TABLE 4-continued

| SEQ ID NO/ DESCRIPTION/ SOURCE | SEQUENCE |
|---|---|
| | TTGAAGTGGTGGCCTAACTACGGCTACACTAGAAGAACAGTATTT<br>GGTATCTGCGCTCTGCTGAAGCCAGTTACCTTCGGAAAAAGAGTT<br>GGTAGCTCTTGATCCGGCAAACAAACCACCGCTGGTAGCGGTGGT<br>TTTTTTGTTTGCAAGCAGCAGATTACGCGCAGAAAAAAAGGATCT<br>CAAGAAGATCCTTTGATCTTTTCTACGGGGTCTGACGCTCAGTGGA<br>ACGAAAACTCACGTTAAGGGATTTTGGTCATGAGATTATCAAAAA<br>GGATCTTCACCTAGATCCTTTTAAATTAAAAATGAAGTTTTAAATC<br>AATCTAAAGTATATATGAGTAAACTTGGTCTGACAGTTACCAATG<br>CTTAATCAGTGAGGCACCTATCTCAGCGATCTGTCTATTTCGTTCA<br>TCCATAGTTGCCTGACTCCCCGTCGTGTAGATAACTACGATACGGG<br>AGGGCTTACCATCTGGCCCCAGTGCTGCAATGATACCGCGAGACC<br>CACGCTCACCGGCTCCAGATTTATCAGCAATAAACCAGCCAGCCG<br>GAAGGGCCGAGCGCAGAAGTGGTCCTGCAACTTTATCCGCCTCCA<br>TCCAGTCTATTAATTGTTGCCGGGAAGCTAGAGTAAGTAGTTCGCC<br>AGTTAATAGTTTGCGCAACGTTGTTGCCATTGCTACAGGCATCGTG<br>GTGTCACGCTCGTCGTTTGGTATGGCTTCATTCAGCTCCGGTTCCC<br>AACGATCAAGGCGAGTTACATGATCCCCCATGTTGTGCAAAAAAG<br>CGGTTAGCTCCTTCGGTCCTCCGATCGTTGTCAGAAGTAAGTTGGC<br>CGCAGTGTTATCACTCATGGTTATGGCAGCACTGCATAATTCTCTT<br>ACTGTCATGCCATCCGTAAGATGCTTTTCTGTGACTGGTGAGTACT<br>CAACCAAGTCATTCTGAGAATAGTGTATGCGGCGACCGAGTTGCT<br>CTTGCCCGGCGTCAATACGGGATAATACCGCGCCACATAGCAGAA<br>CTTTAAAAGTGCTCATCATTGGAAAACGTTCTTCGGGGCGAAAAC<br>TCTCAAGGATCTTACCGCTGTTGAGATCCAGTTCGATGTAACCCAC<br>TCGTGCACCCAACTGATCTTCAGCATCTTTTACTTTCACCAGCGTTT<br>CTGGGTGAGCAAAAACAGGAAGGCAAAATGCCGCAAAAAAGGGA<br>ATAAGGGCGACACGGAAATGTTGAATACTCATACTCTTCCTTTTTC<br>AATATTATTGAAGCATTTATCAGGGTTATTGTCTCATGAGCGGATA<br>CATATTTGAATGTATTTAGAAAAATAAACAAATAGGGGTTCCGCG<br>CACATTTCCCCGAAAAGTGCCACCTG |
| SEQ ID NO: 72<br>GFP-Lox66 Cre<br>expression plasmid<br>(Artificial Sequence) | AGCTCTGATCAAGAGACAGGATGAGGATCGTTTCGCATGATTGAA<br>CAAGATGGATTGCACGCAGGTTCTCCGGCCGCTTGGGTGGAGAGG<br>CTATTCGGCTATGACTGGGCACAACAGACAATCGGCTGCTCTGAT<br>GCCGCCGTGTTCCGGCTGTCAGCGCAGGGGCGCCCGGTTCTTTTTG<br>TCAAGACCGACCTGTCCGGTGCCCTGAATGAACTGCAAGACGAGG<br>CAGCGCGGCTATCGTGGCTGGCCACGACGGGCGTTCCTTGCGCAG<br>CTGTGCTCGACGTTGTCACTGAAGCGGGAAGGGACTGGCTGCTAT<br>TGGGCGAAGTGCCGGGGCAGGATCTCCATGTCATCTACACCTTGC<br>TCCTGCCGAGAAAGTATCCATCATGGCTGATGCAATGCGGCGGCT<br>GCATACGCTTGATCCGGCTACCTGCCCATTCGACCACCAAGCGAA<br>ACATCGCATCGAGCGAGCACGTACTCGGATGGAAGCCGGTCTTGT<br>CGATCAGGATGATCTGGACGAAGAGCATCAGGGGCTCGCGCCAGC<br>CGAACTGTTCGCCAGGCTCAAGGCGAGCATGCCCGACGGCGAGGA<br>TCTCGTCGTGACCCATGGCGATGCCTGCTTGCCGAATATCATGGTG<br>GAAAATGGCCGCTTTTCTGGATTCATCGACTGTGGCCGGCTGGGTG<br>TGGCGGACCGCTATCAGGACATAGCGTTGGCTACCCGTGATATTG<br>CTGAAGAGCTTGGCGGCGAATGGGCTGACCGCTTCCTCGTGCTTTA<br>CGGTATCGCCGCTCCCGATTCGCAGCGCATCGCCTTCTATCGCCTT<br>CTTGACGAGTTCTTCTGAATTATTAACTCGAGATCCACTAGAGTGT<br>GGCGGCCGCATTCTTATAATCAGCATCATGATGTGGTACCACATCA<br>TGATGCTGATTACCCCCAACTGAGAGAACTCAAAGGTTACCCCAG<br>TTGGGGCGGGCCCACAAATAAAGCAATAGCATCACAAATTTCACA<br>AATAAAGCATTTTTTTCACTGCATTCTAGTTGTGGTTTGTCCAAAC<br>TCATCGAGCTCGAGATCTGGCGAAGGCGATGGGGGTCTTGAAGGC<br>GTGCTGGTACTCCACGATGCCCAGCTCGGTGTTGCTGTGCAGCTCC<br>TCCACGCGGCGGAAGGCGAACATGGGGCCCCCGTTCTGCAGGATG<br>CTGGGGTGGATGGCGCTCTTGAAGTGCATGTGGCTGTCCACCACG<br>AAGCTGTAGTAGCCGCCGTCGCGCAGGCTGAAGGTGCGGGCGAAG<br>CTGCCCACCAGCACGTTATCGCCCATGGGGTGCAGGTGCTCCACG<br>GTGGCGTTGCTGCGGATGATCTTGTCGGTGAAGATCACGCTGTCCT<br>CGGGGAAGCCGGTGCCCACCACCTTGAAGTCGCCGATCACGCGGC<br>CGGCCTCGTAGCGGTAGCTGAAGCTCACGTGCAGCACGCCGCCGT<br>CCTCGTACTTCTCGATGCGGGTGTTGGTGTAGCCGCCGTTGTTGAT<br>GGCGTGCAGGAAGGGGTTCTCGTAGCCGCTGGGGTAGGTGCCGAA<br>GTGGTAGAAGCCGTAGCCCATCACGTGGCTCAGCAGGTAGGGGCT<br>GAAGGTCAGGGCGCCTTTGGTGCTCTTCATCTTGTTGGTCATGCGG<br>CCCTGCTCGGGGGTGCCCTCTCCGCCGCCCACCAGCTCGAACTCCA<br>CGCCGTTCAGGGTGCCGGTGATGCGGCACTCGATCTTCATGGCGG<br>GCATGGTGGCGACCGGTAGCGCTAGCGGCTTCGGATAACTTCGTA<br>TAGCATACATTATACGAACGGTAAGCGCTACCGCCGGCATACCCA<br>AGTGAAGTTGCTCGCAGCTTATAGTCGCGCCCGGGGAGCCCAAGG<br>GCACGCCCTGGCACCGCGGCCGCTGAGTCTCGACCATCATCATCA<br>TCATCATTGAGTTTATCTGGGATAACAGGGTAATGTCATCTAGGGA<br>TAACAGGGTATGTCATCTGGGATAACAGGGTAATGTATCTAGGGA<br>TAACAGGGTAATGTCATCTGGGATAACAGGGTAATGTCATCTAGG |

TABLE 4-continued

| SEQ ID NO/<br>DESCRIPTION/<br>SOURCE | SEQUENCE |
|---|---|
| | GATAACAGGGTATGTCATCTGGGATAACAGGGTAATGTATCTAGG<br>GATAACAGGGTAATGTCATCTGGGATAACAGGGTAATGTCATCTA<br>GGGATAACAGGGTATGTCATCTGGGATAACAGGGTAATGTATCTA<br>GGGATAACAGGGTAATGTCATCTGGGATAACAGGGTAATGTCATC<br>TAGGGATAACAGGGTATGTCATCTGGGATAACAGGGTAATGTATC<br>TAGGGATAACAGGGTAATGTCATCTGGGATAACAGGGTAATGTCA<br>TCTAGGGATAACAGGGTATGTCATCTGGGATAACAGGGTAATGTA<br>TCTAGGGATAACAGGGTAATGTCATCTGGGATAACAGGGTAATGT<br>CATCTAGGGATAACAGGGTATGTCATCTGGGATAACAGGGTAATG<br>TATCTAGGGATAACAGGGTAATGTCATCTGGGATAACAGGGTAAT<br>GTCATCTAGGGATAACAGGGTAAATGTCATCTAGGGATAACAGGG<br>TAATGTCATCTAGGGATAACAGGGTAATGTCATCTGGGATAACAG<br>GGTAATGTCATCTAGGGATAACAGGGTAATGTATCGCCAGCGTCG<br>CACAGCATGTTTGCTTGTCGCCGTCGCGTCTGTCACATCTTTTCCG<br>CCAGCAGTTAGGGATTAGCGTCTTAAGCTGGCGCGAGGACCAACG<br>TATCAGCCAGGCGAAGCTGCTTTTGAGCACCACCCGGATGCCTAT<br>CGCCACCGTCGGTCGCAATGTTGGTTTTGACGATCAACTCTATTTC<br>TCGCGGGTATTTAAAAAATGCACCGGGGCCAGCCCGAGCGAGTTC<br>CGTGCCGGTTGTGAAGAAAAGTGAATGATGTAGCCGTCAAGTTG<br>TCATAATTGGTAACGAATCAGACAATTGACGGCTTGACGGAGTAG<br>CATAGGGTTTGCAGAATCCCTGCTTCGTCCATTTGACAGGCACATT<br>ATGCATGCCGCTTCGCCTTCGCGCGCGAATTGATCTGCTGCCTCGC<br>GCGTTTCGGTGATGACGGTGAAAACCTCTGACACATGCAGCTCCC<br>GGAGACGGTCACAGCTTGTCTGTAAGCGGATGCCGGGAGCAGACA<br>AGCCCGTCAGGGCGCGTCAGCGGGTGTTGGCGGGTGTCGGGGCGC<br>AGCCATGACCCAGTCACGTAGCGATAGCGGAGTGTATACTGGCTT<br>AACTATGCGGCATCAGAGCAGATTGTACTGAGAGTGCACCATATG<br>CGGTGTGAAATACCGCACAGATGCGTAAGGAGAAAATACCGCATC<br>AGGCGCTCTTCCGCTTCCTCGCTCACTGACTCGCTGCGCTCGGTCG<br>TTCGGCTGCGGCGAGCGGTATCAGCTCACTCAAAGGCGGTAATAC<br>GGTTATCCACAGAATCAGGGGATAACGCAGGAAAGAACATGTGA<br>GCAAAAGGCCAGCAAAAGGCCAGGAACCGTAAAAAGGCCGCGTT<br>GCTGGCGTTTTTCCATAGGCTCCGCCCCCCTGACGAGCATCACAAA<br>AATCGACGCTCAAGTCAGAGGTGGCGAAACCCGACAGGACTATAA<br>AGATACCAGGCGTTTCCCCCTGGAAGCTCCCTCGTGCGCTCTCCTG<br>TTCCGACCCTGCCGCTTACCGGATACCTGTCCGCCTTTCTCCCTTCG<br>GGAAGCGTGGCGCTTTCTCATAGCTCACGCTGTAGGTATCTCAGTT<br>CGGTGTAGGTCGTTCGCTCCAAGCTGGGCTGTGTGCACGAACCCC<br>CCGTTCAGCCCGACCGCTGCGCCTTATCCGGTAACTATCGTCTTGA<br>GTCCAACCCGGTAAGACACGACTTATCGCCACTGGCAGCAGCCAC<br>TGGTAACAGGATTAGCAGAGCGAGGTATGTAGGCGGTGCTACAGA<br>GTTCTTGAAGTGGTGGCCTAACTACGGCTACACTAGAAGGACAGT<br>ATTTGGTATCTGCGCTCTGCTGAAGCCAGTTACCTTCGGAAAAAGA<br>GTTGGTAGCTCTTGATCCGGCAAACAAACCACCGCTGGTAGCGGT<br>GGTTTTTTTGTTTGCAAGCAGCAGATTACGCGCAGAAAAAAAGGA<br>TCTCAAGAAGATCCTTTGATCTTTTCTACGGGGTCTGACGCTCAGT<br>GGAACGAAAACTCACGTTAAGGGATTTTGGTCATGAGCGGATACA<br>TATTTGAATGTATTTAGAAAAATAAACAAAAGAGTTTGTAGAAAC<br>GCAAAAAGGCCATCCGTCAGGATGGCCTTCTGCTTAATTTGATGCC<br>TGGCAGTTTATGCGGGCGTCCTGCCCGCCACCCTCCGGGCCGTTG<br>CTTCGCAACGTTCAAATCCGCTCCCGGCGGATTTGTCCTACTCAGG<br>AGAGCGTTCACCGACAAACAACAGATAAAACGAAAGGCCCAGTC<br>TTTCGACTGAGCCTTTCGTTTTATTTGATGCCTGGCAGTTCCCTACT<br>CTCGCATGGGGAGACCCCACACTACCATCGGCGCTACGGCGTTTC<br>ACTTCTGAGTTCGGCATGGGGTCAGGTGGGACCACCGCGCTACTG<br>CCGCCAGGCAAATTCTGTTTTATCAGACCGCTTCTGCGTTCTGATT<br>TAATCTGTATCAGGCTGAAAATCTTCTCTCATCCGCCAAAACAGCC<br>AAGCTGGAGACCGTTTGGCCCCCCTCGAGCACGTAGAAAGCCAGT<br>CCGCAGAAACGGTGCTGACCCCGGATGAATGTCAGCTACTGGGCT<br>ATCTGGACAAGGGAAAACGCAAGCGCAAAGAGAAAGCAGGTAGC<br>TTGCAGTGGGCTTACATGGCGATAGCTAGACTGGGCGGTTTTATG<br>GACAGCAAGCGAACCGGAATTGCCAGCTGGGGCGCCCTCTGGTAA<br>GGTTGGGAAGCCCTGCAAAGTAAACTGGATGGCTTTCTCGCCGCC<br>AAGGATCTGATGGCGCAGGGGATCA |
| SEQ ID NO: 73<br>pCMV PE2 P2A Cre<br>plasmid<br>(Artificial Sequence) | ACGCGTTGACATTGATTATTGACTAGTTATTAATAGTAATCAATTA<br>CGGGGTCATTAGTTCATAGCCCATATATGGAGTTCCGCGTTACATA<br>ACTTACGGTAAATGGCCCGCCTGGCTGACCGCCCAACGACCCCCG<br>CCCATTGACGTCAATAATGACGTATGTTCCCATAGTAACGCCAATA<br>GGGACTTTCCATTGACGTCAATGGGTGGAGTATTTACGGTAAACT<br>GCCCACTTGGCAGTACATCAAGTGTATCATATGCCAAGTACGCCC<br>CCTATTGACGTCAATGACGGTAAATGGCCCGCCTGGCATTATGCCC<br>AGTACATGACCTTATGGGACTTTCCTACTTGGCAGTACATCTACGT<br>ATTAGTCATCGCTATTACCATGGTGATGCGGTTTTGGCAGTACATC<br>AATGGGCGTGGATAGCGGTTTGACTCACGGGGATTTCCAAGTCTC<br>CACCCCATTGACGTCAATGGGAGTTTGTTTTGGCACCAAAATCAAC |

TABLE 4-continued

| SEQ ID NO/<br>DESCRIPTION/<br>SOURCE | SEQUENCE |
|---|---|
| | GGGACTTTCCAAAATGTCGTAACAACTCCGCCCCATTGACGCAAA<br>TGGGCGGTAGGCGTGTACGGTGGGAGGTCTATATAAGCAGAGCTG<br>GTTTAGTGAACCGTCAGATCCGCTAGAGATCCGCGGCCGCTAATA<br>CGACTCACTATAGGGAGAGCCGCCACCATGAAACGGACAGCCGAC<br>GGAAGCGAGTTCGAGTCACCAAAGAAGAAGCGGAAAGTCGACAA<br>GAAGTACAGCATCGGCCTGGACATCGGCACCAACTCTGTGGGCTG<br>GGCCGTGATCACCGACGAGTACAAGGTGCCCAGCAAGAAATTCAA<br>GGTGCTGGGCAACACCGACCGGCACAGCATCAAGAAGAACCTGAT<br>CGGAGCCCTGCTGTTCGACAGCGGCGAAACAGCCGAGGCCACCCG<br>GCTGAAGAGAACCGCCAGAAGAAGATACACCAGACGGAAGAACC<br>GGATCTGCTATCTGCAAGAGATCTTCAGCAACGAGATGGCCAAGG<br>TGGACGACAGCTTCTTCCACAGACTGGAAGAGTCCTTCCTGGTGG<br>AAGAGGATAAGAAGCACGAGCGGCACCCCATCTTCGGCAACATCG<br>TGGACGAGGTGGCCTACCACGAGAAGTACCCCACCATCTACCACC<br>TGAGAAAGAAACTGGTGGACAGCACCGACAAGGCCGACCTGCGG<br>CTGATCTATCTGGCCCTGGCCCACATGATCAAGTTCCGGGGCCACT<br>TCCTGATCGAGGGCGACCTGAACCCCGACAACAGCGACGTGGACA<br>AGCTGTTCATCCAGCTGGTGCAGACCTACAACCAGCTGTTCGAGG<br>AAAACCCCATCAACGCCAGCGGCGTGGACGCCAAGGCCATCCTGT<br>CTGCCAGACTGAGCAAGAGCAGACGGCTGGAAAATCTGATCGCCC<br>AGCTGCCCGGCGAGAAGAAGAATGGCCTGTTCGGAAACCTGATTG<br>CCCTGAGCCTGGGCCTGACCCCCAACTTCAAGAGCAACTTCGACC<br>TGGCCGAGGATGCCAAACTGCAGCTGAGCAAGGACACCTACGACG<br>ACGACCTGGACAACCTGCTGGCCCAGATCGGCGACCAGTACGCCG<br>ACCTGTTTCTGGCCGCCAAGAACCTGTCCGACGCCATCCTGCTGAG<br>CGACATCCTGAGAGTGAACACCGAGATCACCAAGGCCCCCCTGAG<br>CGCCTCTATGATCAAGAGATACGACGAGCACCACCAGGACCTGAC<br>CCTGCTGAAAGCTCTCGTGCGGCAGCAGCTGCCTGAGAAGTACAA<br>AGAGATTTTCTTCGACCAGAGCAAGAACGGCTACGCCGGCTACAT<br>TGACGGCGGAGCCAGCCAGGAAGAGTTCTACAAGTTCATCAAGCC<br>CATCCTGGAAAAGATGGACGGCACCGAGGAACTGCTCGTGAAGCT<br>GAACAGAGAGGACCTGCTGCGGAAGCAGCGGACCTTCGACAACG<br>GCAGCATCCCCCACCAGATCCACCTGGGAGAGCTGCACGCCATTC<br>TGCGGCGGCAGGAAGATTTTTACCCATTCCTGAAGGACAACCGGG<br>AAAAGATCGAGAAGATCCTGACCTTCCGCATCCCCTACTACGTGG<br>GCCCTCTGGCCAGGGGAAACAGCAGATTCGCCTGGATGACCAGAA<br>AGAGCGAGGAAACCATCACCCCCTGGAACTTCGAGGAAGTGGTGG<br>ACAAGGGCGCTTCCGCCCAGAGCTTCATCGAGCGGATGACCAACT<br>TCGATAAGAACCTGCCCAACGAGAAGGTGCTGCCCAAGCACAGCC<br>TGCTGTACGAGTACTTCACCGTGTATAACGAGCTGACCAAAGTGA<br>AATACGTGACCGAGGGAATGAGAAAGCCCGCCTTCCTGAGCGGCG<br>AGCAGAAAAAGGCCATCGTGGACCTGCTGTTCAAGACCAACCGGA<br>AAGTGACCGTGAAGCAGCTGAAAGAGGACTACTTCAAGAAAATC<br>GAGTGCTTCGACTCCGTGGAAATCTCCGGCGTGGAAGATCGGTTC<br>AACGCCTCCCTGGGCACATACCACGATCTGCTGAAAATTATCAAG<br>GACAAGGACTTCCTGGACAATGAGGAAAACGAGGACATTCTGGA<br>AGATATCGTGCTGACCCTGACACTGTTTGAGGACAGAGAGATGAT<br>CGAGGAACGGCTGAAAACCTATGCCCACCTGTTCGACGACAAAGT<br>GATGAAGCAGCTGAAGCGGCGGAGATACACCGGCTGGGGCAGGC<br>TGAGCCGGAAGCTGATCAACGGCATCCGGGACAAGCAGTCCGGCA<br>AGACAATCCTGGATTTCCTGAAGTCCGACGGCTTCGCCAACAGAA<br>ACTTCATGCAGCTGATCCACGACGACAGCCTGACCTTTAAAGAGG<br>ACATCCAGAAAGCCCAGGTGTCCGGCCAGGGCGATAGCCTGCACG<br>AGCACATTGCCAATCTGGCCGGCAGCCCCGCCATTAAGAAGGGCA<br>TCCTGCAGACAGTGAAGGTGGTGGACGAGCTCGTGAAAGTGATGG<br>GCCGGCACAAGCCCGAGAACATCGTGATCGAAATGGCCAGAGAG<br>AACCAGACCACCCAGAAGGGACAGAAGAACAGCCGCGAGAGAAT<br>GAAGCGGATCGAAGAGGGCATCAAAGAGCTGGGCAGCCAGATCC<br>TGAAAGAACACCCCGTGGAAAACACCCAGCTGCAGAACGAGAAG<br>CTGTACCTGTACTACCTGCAGAATGGGCGGGATATGTACGTGGAC<br>CAGGAACTGGACATCAACCGGCTGTCCGACTACGATGTGGACGCT<br>ATCGTGCCTCAGAGCTTTCTGAAGGACGACTCCATCGACAACAAG<br>GTGCTGACCAGAAGCGACAAGAACCGGGGCAAGAGCGACAACGT<br>GCCCTCCGAAGAGGTCGTGAAGAAGATGAAGAACTACTGGCGGC<br>AGCTGCTGAACGCCAAGCTGATTACCCAGAGAAAGTTCGACAATC<br>TGACCAAGGCCGAGAGAGGCGGCCTGAGCGAACTGGATAAGGCC<br>GGCTTCATCAAGAGACAGCTGGTGGAAACCCGGCAGATCACAAAG<br>CACGTGGCACAGATCCTGGACTCCCGGATGAACACTAAGTACGAC<br>GAGAATGACAAGCTGATCCGGGAAGTGAAAGTGATCACCCTGAA<br>GTCCAAGCTGGTGTCCGATTTCCGGAAGGATTTCCAGTTTTACAAA<br>GTGCGCGAGATCAACAACTACCACCACGCCCACGACGCCTACCTG<br>AACGCCGTCGTGGGAACCGCCCTGATCAAAAAGTACCCTAAGCTG<br>GAAAGCGAGTTCGTGTACGGCGACTACAAGGTGTACGACGTGCGG<br>AAGATGATCGCCAAGAGCGAGCAGGAAATCGGCAAGGCTACCGC<br>CAAGTACTTCTTCTACAGCAACATCATGAACTTTTTCAAGACCGAG<br>ATTACCCTGGCCAACGGCGAGATCCGGAAGCGGCCTCTGATCGAG |

TABLE 4-continued

| SEQ ID NO/<br>DESCRIPTION/<br>SOURCE | SEQUENCE |
|---|---|
| | ACAAACGGCGAAACCGGGGAGATCGTGTGGGATAAGGGCCGGGA |
| | TTTTGCCACCGTGCGGAAAGTGCTGAGCATGCCCCAAGTGAATAT |
| | CGTGAAAAAGACCGAGGTGCAGACAGGCGGCTTCAGCAAAGAGT |
| | CTATCCTGCCCAAGAGGAACAGCGATAAGCTGATCGCCAGAAAGA |
| | AGGACTGGGACCCTAAGAAGTACGGCGGCTTCGACAGCCCCACCG |
| | TGGCCTATTCTGTGCTGGTGGTGGCCAAAGTGGAAAAGGGCAAGT |
| | CCAAGAAACTGAAGAGTGTGAAAGAGCTGCTGGGGATCACCATCA |
| | TGGAAAGAAGCAGCTTCGAGAAGAATCCCATCGACTTTCTGGAAG |
| | CCAAGGGCTACAAAGAAGTGAAAAAGGACCTGATCATCAAGCTG |
| | CCTAAGTACTCCCTGTTCGAGCTGGAAAACGGCCGGAAGAGAATG |
| | CTGGCCTCTGCCGGCGAACTGCAGAAGGGAAACGAACTGGCCCTG |
| | CCCTCCAAATATGTGAACTTCCTGTACCTGGCCAGCCACTATGAGA |
| | AGCTGAAGGGCTCCCCCGAGGATAATGAGCAGAAACAGCTGTTTG |
| | TGGAACAGCACAAGCACTACCTGGACGAGATCATCGAGCAGATCA |
| | GCGAGTTCTCCAAGAGAGTGATCCTGGCCGACGCTAATCTGGACA |
| | AAGTGCTGTCCGCCTACAACAAGCACCGGGATAAGCCCATCAGAG |
| | AGCAGGCCGAGAATATCATCCACCTGTTTACCCTGACCAATCTGG |
| | GAGCCCCTGCCGCCTTCAAGTACTTTGACACCACCATCGACCGGA |
| | AGAGGTACACCAGCACCAAAGAGGTGCTGGACGCCACCCTGATCC |
| | ACCAGAGCATCACCGGCCTGTACGAGACACGGATCGACCTGTCTC |
| | AGCTGGGAGGTGACTCTGGAGGATCTAGCGGAGGATCCTCTGGCA |
| | GCGAGACACCAGGAACAAGCGAGTCAGCAACACCAGAGAGCAGT |
| | GGCGGCAGCAGCGGCGGCAGCAGCACCCTAAATATAGAAGATGA |
| | GTATCGGCTACATGAGACCTCAAAAGAGCCAGATGTTTCTCTAGG |
| | GTCCACATGGCTGTCTGATTTTCCTCAGGCCTGGGCGGAAACCGG |
| | GGGCATGGGACTGGCAGTTCGCCAAGCTCCTCTGATCATACCTCTG |
| | AAAGCAACCTCTACCCCGTGTCCATAAAACAATACCCCATGTCA |
| | CAAGAAGCCAGACTGGGGATCAAGCCCCACATACAGAGACTGTTG |
| | GACCAGGGAATACTGGTACCCTGCCAGTCCCCTGGAACACGCCC |
| | CTGCTACCCGTTAAGAAACCAGGGACTAATGATTATAGGCCTGTC |
| | CAGGATCTGAGAGAAGTCAACAAGCGGGTGGAAGACATCCACCC |
| | CACCGTGCCCAACCCTTACAACCTCTTGAGCGGGCTCCCACCGTCC |
| | CACCAGTGGTACACTGTGCTTGATTTAAAGGATGCCTTTTTCTGCC |
| | TGAGACTCCACCCCACCAGTCAGCCTCTCTTCGCCTTTGAGTGGAG |
| | AGATCCAGAGATGGGAATCTCAGGACAATTGACCTGGACCAGACT |
| | CCCACAGGGTTTCAAAAACAGTCCCACCCTGTTTAATGAGGCACT |
| | GCACAGAGACCTAGCAGACTTCCGGATCCAGCACCCAGACTTGAT |
| | CCTGCTACAGTACGTGGATGACTTACTGCTGGCCGCCCACTTCTGAG |
| | CTAGACTGCCAACAAGGTACTCGGGCCCTGTTACAAACCCTAGGG |
| | AACCTCGGGTATCGOGCCTCGGCCAAGAAAGCCCAAATTTGCCAG |
| | AAACAGGTCAAGTATCTGGGGTATCTTCTAAAAGAGGGTCAGAGA |
| | TGGCTGACTGAGGCCAGAAAAGAGACTGTGATGGGGCAGCCTACT |
| | CCGAAGACCCCTCGACAACTAAGGGAGTTCCTAGGGAAGGCAGGC |
| | TTCTGTCGCCTCTTCATCCCTGGGTTTGCAGAAATGGCAGCCCCCC |
| | TGTACCCTCTCACCAAACCGGGGACTCTGTTTAATTGGGGCCCAGA |
| | CCAACAAAAGGCCTATCAAGAAATCAAGCAAGCTCTTCTAACTGC |
| | CCCAGCCCTGGGGTTGCCAGATTTGACTAAGCCCTTTGAACTCTTT |
| | GTCGACGAGAAGCAGGGCTACGCCAAAGGTGTCCTAACGCAAAA |
| | ACTGGGACCTTGGCGTCGGCCGGTGGCCTACCTGTCCAAAAAGCT |
| | AGACCCAGTAGCAGCTGGGTGGCCCCCCTTGCCTACGGATGGTAGC |
| | AGCCATTGCCGTACTGACAAAGGATGCAGGCAAGCTAACCATGGG |
| | ACAGCCACTAGTCATTCTGGCCCCCCATGCAGTAGAGGCACTAGT |
| | CAAACAACCCCCCGACCGCTGGCTTTCCAACGCCCGGATGACTCA |
| | CTATCAGGCCTTGCTTTTGGACACGGACCGGGTCCAGTTCGGACCG |
| | GTGGTAGCCCTGAACCCGGCTACGCTGCTCCCACTGCCTGAGGAA |
| | GGGCTGCAACACAACTGCCTTGATATCCTGGCCGAAGCCCACGGA |
| | ACCCGACCCGACCTAACGGACCAGCCGCTCCCAGACGCCGACCAC |
| | ACCTGGTACACGGATGGAAGCAGTCTCTTACAAGAGGGACAGCGT |
| | AAGGCGGGAGCTGCGGTGACCACCGAGACCGAGGTAATCTGGGCT |
| | AAAGCCCTGCCAGCCGGGACATCCGCTCAGCGGGCTGAACTGATA |
| | GCACTCACCCAGGCCCTAAAGATGGCAGAAGGTAAGAAGCTAAAT |
| | GTTTATACTGATAGCCGTTATGCTTTTGCTACTGCCCATATCCATG |
| | GAGAAATATACAGAAGGCGTGGGTGGCTCACATCAGAAGGCAAA |
| | GAGATCAAAAATAAAGACGAGATCTTGGCCCTACTAAAAGCCCTC |
| | TTTCTGCCCAAAAGACTTAGCATAATCCATTGTCCAGGACATCAAA |
| | AGGGACACAGCGCCGAGGCTAGAGGCAACCGGATGGCTGACCAA |
| | GCGGCCCGAAAGGCAGCCATCACAGAGACTCCAGACACCTCTACC |
| | CTCCTCATAGAAAATTCATCACCCTCTGGCGGCTCAAAAAGAACC |
| | GCCGACGGCAGCGAATTCGAGCCCAAGAAGAAGAGGAAAGTCGG |
| | AAGCGGAGCTACTAACTTCAGCCTGCTGAAGCAGGCTGGCGACGT |
| | GGAGGAGAACCCTGGACCTAATTTACTGACCGTACACCAAAATTT |
| | GCCTGCATTACCGGTCGATGCAACGAGTGATGAGGTTCGCAAGAA |
| | CCTGATGGACATGTTCAGGGATCGCCAGGCGTTTTCTGAGCATACC |
| | TGGAAAATGCTTCTGTCCGTTTGCCGGTCGTGGGCGGCATGGTGCA |
| | AGTTGAATAACCGGAAATGGTTTCCCGCAGAACCTGAAGATGTTC |
| | GCGATTATCTTCTATATCTTCAGGCGCGCGGTCTGGCAGTAAAAAC |

TABLE 4-continued

| SEQ ID NO/<br>DESCRIPTION/<br>SOURCE | SEQUENCE |
| --- | --- |
| | TATCCAGCAACATTTGGGCCAGCTAAACATGCTTCATCGTCGGTCC |
| | GGGCTGCCACGACCAAGTGACAGCAATGCTGTTTCACTGGTTATG |
| | CGGCGGATCCGAAAAGAAAACGTTGATGCCGGTGAACGTGCAAA |
| | ACAGGCTCTAGCGTTCGAACGCACTGATTTCGACCAGGTTCGTTCA |
| | CTCATGGAAAATAGCGATCGCTGCCAGGATATACGTAATCTGGCA |
| | TTTCTGGGGATTGCTTATAACACCCTGTTACGTATAGCCGAAATTG |
| | CCAGGATCAGGGTTAAAGATATCTCACGTACTGACGGTGGGAGAA |
| | TGTTAATCCATATTGGCAGAACGAAAACGCTGGTTAGCACCGCAG |
| | GTGTAGAGAAGGCACTTAGCCTGGGGGTAACTAAACTGGTCGAGC |
| | GATGGATTTCCGTCTCTGGTGTAGCTGATGATCCGAATAACTACCT |
| | GTTTTGCCGGGTCAGAAAAAATGGTGTTGCCGCGCCATCTGCCAC |
| | CAGCCAGCTATCAACTCGCGCCCTGGAAGGGATTTTTGAAGCAAC |
| | TCATCGATTGATTTACGGCGCTAAGGATGACTCTGGTCAGAGATA |
| | CCTGGCCTGGTCTGGACACAGTGCCCGTGTCGGAGCCGCGCGAGA |
| | TATGCCCGCGCTGGAGTTTCAATACCGGAGATCATGCAAGCTGG |
| | TGGCTGGACCAATGTAAATATTGTCATGAACTATATCCGTAACCTG |
| | GATAGTGAAACAGGGGCAATGGTGCGCCTGCTGGAAGATGGCGAT |
| | TAATTTAAACCCGCTGATCAGCCTCGACTGTGCCTTCAGTTGCCA |
| | GCCATCTGTTGTTTGCCCCTCCCCCGTGCCTTCCTTGACCCTGGAA |
| | GGTGCCACTCCCACTGTCCTTTCCTAATAAAATGAGAAAATTGCAT |
| | CGCATTGTCTGAGTAGGTGTCATTCTATTCTGGGGGGTGGGGTGGG |
| | GCAGGACAGCAAGGGGGAGGATTGGGAAGACAATAGCAGGCATG |
| | CTGGGGATGCGGTGGGCTCTATGGCTTCTGAGGCGGAAAGAACCA |
| | GCTGGGGCTCGATACCGTCGACCTCTAGCTAGAGCTTGGCGTAAT |
| | CATGGTCATAGCTGTTTCCTGTGTGAAATTGTTATCCGCTCACAAT |
| | TCCACACAACATACGAGCCGGAAGCATAAAGTGTAAAGCCTAGGG |
| | TGCCTAATGAGTGAGCTAACTCACATTAATTGCGTTGCGCTCACTG |
| | CCCGCTTTCCAGTCGGGAAACCTGTCGTGCCAGCTGCATTAATGAA |
| | tcggccaacgcgcgggagaggcggtttgcgtattgggcgctctt |
| | CCGCTTCCTCGCTCACTGACTCGCTGCGCTCGGTCGTTCGGCTGCG |
| | GCGAGCGGTATCAGCTCACTCAAAGGCGGTAATACGGTTATCCAC |
| | AGAATCAGGGGATAACGCAGGAAAGAACATGTGAGCAAAAGGCC |
| | AGCAAAAGGCCAGGAACCGTAAAAAGGCCGCGTTGCTGGCGTTTT |
| | TCCATAGGCTCCGCCCCCCTGACGAGCATCACAAAAATCGACGCT |
| | CAAGTCAGAGGTGGCGAAACCCGACAGGACTATAAAGATACCAG |
| | GCGTTTCCCCCTGGAAGCTCCCTCGTGCGCTCTCCTGTTCCGACCC |
| | TGCCGCTTACCGGATACCTGTCCGCCTTTCTCCCTTCGGGAAGCGT |
| | GGCGCTTTCTCATAGCTCACGCTGTAGGTATCTCAGTTCGGTGTAG |
| | GTCGTTCGCTCCAAGCTGGGCTGTGTGCACGAACCCCCCGTTCAGC |
| | CCGACCGCTGCGCCTTATCCGGTAACTATCGTCTTGAGTCCAACCC |
| | GGTAAGACACGACTTATCGCCACTGGCAGCAGCCACTGGTAACAG |
| | GATTAGCAGAGCGAGGTATGTAGGCGGTGCTACAGAGTTCTTGAA |
| | GTGGTGGCCTAACTACGGCTACACTAGAAGAACAGTATTTGGTAT |
| | CTGCGCTCTGCTGAAGCCAGTTACCTTCGGAAAAAGAGTTGGTAG |
| | CTCTTGATCCGGCAAACAAACCACCGCTGGTAGCGGTGGTTTTTTT |
| | GTTTGCAAGCAGCAGATTACGCGCAGAAAAAAAGGATCTCAAGA |
| | AGATCCTTTGATCTTTTCTACGGGGTCTGACGCTCAGTGGAACGAA |
| | AACTCACGTTAAGGGATTTTGGTCATGAGATTATCAAAAGGATC |
| | TTCACCTAGATCCTTTTAAATTAAAAATGAAGTTTTAAATCAATCT |
| | AAAGTATATATGAGTAAACTTGGTCTGACAGTTACCAATGCTTAAT |
| | CAGTGAGGCACCTATCTCAGCGATCTGTCTATTTCGTTCATCCATA |
| | GTTGCCTGACTCCCCGTCGTGTAGATAACTACGATACGGGAGGGC |
| | TTACCATCTGGCCCCAGTGCTGCAATGATACCGCGAGACCCACGC |
| | TCACCGGCTCCAGATTTATCAGCAATAAACCAGCCAGCCGGAAGG |
| | GCCGAGCGCAGAAGTGGTCCTGCAACTTTATCCGCCTCCATCCAGT |
| | CTATTAATTGTTGCCGGGAAGCTAGAGTAAGTAGTTCGCCAGTTA |
| | ATAGTTTGCGCAACGTTGTTGCCATTGCTACAGGCATCGTGGTGTC |
| | ACGCTCGTCGTTTGGTATGGCTTCATTCAGCTCCGGTTCCCAACGA |
| | TCAAGGCGAGTTACATGATCCCCCATGTTGTGCAAAAAAGCGGTT |
| | AGCTCCTTCGGTCCTCCGATCGTTGTCAGAAGTAAGTTGGCCGCAG |
| | TGTTATCACTCATGGTTATGGCAGCACTGCATAATTCTCTTACTGT |
| | CATGCCATCCGTAAGATGCTTTTCTGTGACTGGTGAGTACTCAACC |
| | AAGTCATTCTGAGAATAGTGTATGCGGCGACCGAGTTGCTCTTGCC |
| | CGGCGTCAATACGGGATAATACCGCGCCACATAGCAGAACTTTAA |
| | AAGTGCTCATCATTGGAAAACGTTCTTCGGGGCGAAAACTCTCAA |
| | GGATCTTACCGCTGTTGAGATCCAGTTCGATGTAACCCACTCGTGC |
| | ACCCAACTGATCTTCAGCATCTTTTACTTTCACCAGCGTTTCTGGG |
| | TGAGCAAAAACAGGAAGGCAAAATGCCGCAAAAAAGGGAATAAG |
| | GGCGACACGGAAATGTTGAATACTCATACTCTTCCTTTTTCAATAT |
| | TATTGAAGCATTTATCAGGGTTATTGTCTCATGAGCGGATACATAT |
| | TTGAATGTATTTAGAAAAATAAACAAATAGGGGTTCCGCGCACAT |
| | TTCCCCGAAAAGTGCCACCTGACGTCGACGGATCGGGAGATCGAT |

TABLE 4-continued

| SEQ ID NO/<br>DESCRIPTION/<br>SOURCE | SEQUENCE |
|---|---|
| | CTCCCGATCCCCTAGGGTCGACTCTCAGTACAATCTGCTCTGATGC<br>CGCATAGTTAAGCCAGTATCTGCTCCCTGCTTGTGTGTTGGAGGTC<br>GCTGAGTAGTGCGCGAGCAAAATTTAAGCTACAACAAGGCAAGGC<br>TTGACCGACAATTGCATGAAGAATCTGCTTAGGGTTAGGCGTTTTG<br>CGCTGCTTCGCGATGTACGGGCCAGATAT |
| SEQ ID NO: 74<br>+90 ngRNA guide<br>sequence<br>(Artificial Sequence) | GTCAACCAGTATCCCGGTGC |
| SEQ ID NO: 75<br>+90 ngRNA<br>(Artificial Sequence) | GTCAACCAGTATCCCGGTGCGTTTTAGAGCTAGAAATAGCAAGTT<br>AAAATAAGGCTAGTCCGTTATCAACTTGAAAAAGTGGCACCGAGT<br>CGGTGC |
| SEQ ID NO: 76<br>GFP minicircle<br>template (before<br>cleavage into a<br>minicircle)<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT<br>TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATACC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC |

TABLE 4-continued

| SEQ ID NO/ DESCRIPTION/ SOURCE | SEQUENCE |
|---|---|
| | CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCAGCTACCGG<br>TCGCCACCATGCCCGCCATGAAGATCGAGTGCCGCATCACCGGCA<br>CCCTGAACGGCGTGGAGTTCGAGCTGTGGGCGGCGGAGAGGGC<br>ACCCCCGAGCAGGGCCGCATGACCAACAAGATGAAGACCACCAA<br>AGGCGCCCTGACCTTCAGCCCCTACCTGCTGAGCCACGTGATGGG<br>CTACGGCTTCTACCACTTCGGCACCTACCCCAGCGGCTACGAGAA<br>CCCCTTCCTGCACGCCATCAACAACGGCGGCTACACCAACACCCG<br>CATCGAGAAGTACGAGGACGGCGGCGTGCTGCACGTGAGCTTCAG<br>CTACCGCTACGAGGCCGGCGCGTGATCGGCGACTTCAAGGTGGT<br>GGGCACCGGCTTCCCCGAGGACAGCGTGATCTTCACCGACAAGAT<br>CATCCGCAGCAACGCCACCGTGGAGCACCTGCACCCCATGGGCGA<br>TAACGTGCTGGTGGGCAGCTTCGCCCGCACCTTCAGCCTGCGCGA<br>CGGCGGCTACTACAGCTTCGTGGTGGACAGCCACATGCACTTCAA<br>GAGCGCCATCCACCCCAGCATCCTGCAGAACGGGGCCCCATGTT<br>CGCCTTCCGCCGCGTGGAGGAGCTGCACAGCAACACCGAGCTGGG<br>CATCGTGGAGTACCAGCACGCCTTCAAGACCCCCATCGCCTTCGCC<br>AGATCTCGAGCTCGATGAGTTTGGACAAACCACAACTAGAATGCA<br>GTGAAAAAAATGCTTTATTTGTGAAATTTGTGATGCTATTGCTTTA<br>TTTGTGGGCCCGCCCCAACTGGGGTAACCTTTGAGTTCTCTCAGTT<br>GGGGGTAATCAGCATCATGATGTGGTACCACATCATGATGCTGAT<br>TATAAGAATGCGGCCGCCACACTCTAGTGGATCTCGAGTTAATAA<br>TTCAGAAGAACTCGTCAAGAAGGCGATAGAAGGCGATGCGCTGCG<br>AATCGGGAGCGGCGATACCGTAAAGCACGAGGAAGCGGTCAGCC<br>CATTCGCCGCCAAGCTCTTCAGCAATATCACGGGTAGCCAACGCT<br>ATGTCCTGATAGCGGTCCGCCACACCCAGCCGGCCACAGTCGATG<br>AATCCAGAAAAGCGGCCATTTTCCACCATGATATTCGGCAAGCAG<br>GCATCGCCATGGGTCACGACGAGATCCTCGCCGTCGGGCATGCTC<br>GCCTTGAGCCTGGCGAACAGTTCGGCTGGCGCGAGCCCCTGATGC<br>TCTTCGTCCAGATCATCCTGATCGACAAGACCGGCTTCCATCCGAG<br>TACGTGCTCGCTCGATGCGATGTTTCGCTTGGTGGTCGAATGGGCA<br>GGTAGCCGGATCAAGCGTATGCAGCCGCCGCATTGCATCAGCCAT<br>GATGGATACTTTCTCGGCAGGAGCAAGGTGTAGATGACATGGAGA<br>TCCTGCCCCGGCACTTCGCCCAATAGCAGCCAGTCCCTTCCCGCTT<br>CAGTGACAACGTCGAGCACAGCTGCGCAAGGAACGCCCGTCGTGG<br>CCAGCCACGATAGCCGCGCTGCCTCGTCTTGCAGTTCATTCAGGGC<br>ACCGGACAGGTCGGTCTTGACAAAAAGAACCGGGCGCCCCTGCGC<br>TGACAGCCGGAACACGGCGGCATCAGAGCAGCCGATTGTCTGTTG<br>TGCCCAGTCATAGCCGAATAGCCTCTCCACCCAAGCGGCCGGAGA<br>ACCTGCGTGCAATCCATCTTGTTCAATCATGCGAAACGATCCTCAT<br>CCTGTCTCTTGATCAGAGCT |
| SEQ ID NO: 77<br>*Gaussia* Luciferase<br>minicircle template<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT |

TABLE 4-continued

| SEQ ID NO/<br>DESCRIPTION/<br>SOURCE | SEQUENCE |
|---|---|
| | TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATACATTACCCTGTTATCCCAGATGACATTAC<br>CTGTTATCCCTAGATGACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCACTACCGGT<br>CGCCACCATGGGAGTCAAAGTTCTGTTTGCCCTGATCTGCATCGCT<br>GTGGCCGAGGCCAAGCCCACCGAGAACAACGAAGACTTCAACATC<br>GTGGCCGTGGCCAGCAACTTCGCGACCACGGATCTCGATGCTGAC<br>CGCGGGAAGTTGCCCGGCAAGAAGCTGCCGCTGGAGGTGCTCAAA<br>GAGATGGAAGCCAATGCCCGGAAAGCTGGCTGCACCAGGGGCTGT<br>CTGATCTGCCTGTCCCACATCAAGTGCACGCCCAAGATGAAGAAG<br>TTCATCCCAGGACGCTGCCACACCTACGAAGGCGACAAAGAGTCC<br>GCACAGGGCGGCATAGGCGAGGCGATCGTCGACATTCCTGAGATT<br>CCTGGGTTCAAGGACTTGGAGCCCATGGAGCAGTTCATCGCACAG<br>GTCGATCTGTGTGTGGACTGCACAACTGGCTGCCTCAAAGGGCTT<br>GCCAACGTGCAGTGTTCTGACCTGCTCAAGAAGTGGCTGCCGCAA<br>CGCTGTGCGACCTTTGCCAGCAAGATCCAGGGCAGGTGGACAAG<br>ATCAAGGGGCCGGTGGTGACTAAGCGGAGCTCGATGAGTTTGGA<br>CAAACCACAACTAGAATGCAGTGAAAAAAATGCTTTATTTGTGAA<br>ATTTGTGATGCTATTGCTTTATTTGTGGGCCCGCCCCAACTGGGGT<br>AACCTTTGAGTTCTCTCAGTTGGGGGTAATCAGCATCATGATGTGG<br>TACCACATCATGATGCTGATTATAAGAATGCGGCCGCCACACTCT<br>AGTGGATCTCGAGTTAATAATTCAGAAGAACTCGTCAAGAAGGCC<br>ATAGAAGGCGATGCGCTGCGAATCGGGAGCGGCGATACCGTAAA<br>GCACGAGGAAGCGGTCAGCCCATTCGCCGCAAGCTCTTCAGCAA<br>TATCACGGGTAGCCAACGCTATGTCCTGATAGCGGTCCGCCACAC<br>CCAGCCGGCCACAGTCGATGAATCCAGAAAAGCGGCCATTTTCCA<br>CCATGATATTCGGCAAGCAGGCATCGCCATGGGTCACGACGAGAT<br>CCTCGCCGTCGGGCATGCTCGCCTTGAGCCTGGCGAACAGTTCGG<br>CTGGCGCGAGCCCTGATGCTCTTCGTCCAGATCATCCTGATCGAC<br>AAGACCGGCTTCCATCCGAGTACGTGCTCGCTCGATGCGATGTTTC<br>GCTTGGTGGTCGAATGGGCAGGTAGCCGGATCAAGCGTATGCAGC<br>CGCCGCATTGCATCAGCCATGATGGATACTTTCTCGGCAGGAGCA<br>AGGTGTAGATGACATGGAGATCCTGCCCCGGCACTTCGCCCAATA<br>GCAGCCAGTCCCTTCCCGCTTCAGTGACAACGTCGAGCACAGCTG<br>CGCAAGGAACGCCCGTCGTGGCCAGCCACGATAGCCGCGCTGCCT |

TABLE 4-continued

| SEQ ID NO/<br>DESCRIPTION/<br>SOURCE | SEQUENCE |
|---|---|
| | CGTCTTGCAGTTCATTCAGGGCACCGGACAGGTCGGTCTTGACAA<br>AAAGAACCGGGCGCCCCTGCGCTGACAGCCGGAACACGGCGGCA<br>TCAGAGCAGCCGATTGTCTGTTGTGCCCAGTCATAGCCGAATAGC<br>CTCTCCACCCAAGCGGCCGGAGAACCTGCGTGCAATCCATCTTGTT<br>CAATCATGCGAAACGATCCTCATCCTGTCTCTTGATCAGAGCT |
| SEQ ID NO: 78<br>pseudo attP site<br>(Artificial sequence) | CCCCAACTGGGGTAACCTTTGAGTTCTCTCAGTTGGGG |
| SEQ ID NO: 79<br>Albumin-pegRNA-<br>SERPIN<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTCAGTCA |
| SEQ ID NO: 80<br>Albumin-pegRNA-<br>CPS1<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTC |
| SEQ ID NO: 81<br>34 bp lox71 pegRNA<br>(Artificial Sequence) | GGCCCAGACTGAGCACGTGAGTTTTAGAGCTAGAAATAGCAAGTT<br>AAAATAAGGCTAGTCCGTTATCAACTTGAAAAAGTGGCACCGAGT<br>CGGTGCTGGAGGAAGCAGGGCTTCCTTTCCTCTGCCATCATACCGT<br>TCGTATAGCATACATTATACGAAGTTATCGTGCTCAGTCTG |
| SEQ ID NO: 82<br>34 bp lox66 pegRNA<br>(Artificial Sequence) | GGCCCAGACTGAGCACGTGAGTTTTAGAGCTAGAAATAGCAAGTT<br>AAAATAAGGCTAGTCCGTTATCAACTTGAAAAAGTGGCACCGAGT<br>CGGTGCTGGAGGAAGCAGGGCTTCCTTTCCTCTGCCATCAATAACT<br>TCGTATAGCATACATTATACGAACGGTACGTGCTCAGTCTG |
| SEQ ID NO: 83<br>gRNA<br>(Artificial Sequence) | GGCCCAGACTGAGCACGTGA |
| SEQ ID NO: 84<br>ACTB N-term PBS<br>13 RT 29 attB 46<br>(original length)<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGACCGCCGTCGTCGACAAGCCGGCCTGAGCTGCGA<br>GAA |
| SEQ ID NO: 85<br>ACTB N-term<br>PBS_13_RT_29_with<br>TP901-1 minimal<br>attB f pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCACAATTAACATCTCAATCAAGGTAAATGCTTGAGCTGCGAG<br>AA |
| SEQ ID NO: 86<br>ACTB N-term<br>PBS_13_RT_29_with<br>TP901-1 minimal<br>attB rc pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGAGCATTTACCTTGATTGAGATGTTAATTGTGTGAGCTGCGAGA<br>A |
| SEQ ID NO: 87<br>ACTB N-term<br>PBS_13_RT_29_with<br>PhiBT1 minimal<br>attB f pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCAGGTTTTTGACGAAAGTGATCCAGATGATCCAGTGAGCTGC<br>GAGAA |
| SEQ ID NO: 88<br>ACTB N-term<br>PBS 13 RT_29_with<br>PhiBT1 minimal<br>attB rc pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGAGTCGGTGCGACGAGCGCGGCGATATCATCATCCAT<br>GGCTGGATCATCTGGATCACTTTCGTCAAAAACCTGTGAGCTGCG<br>AGAA |
| SEQ ID NO: 89<br>ACTB N-term<br>Nicking guide 1 +48<br>guide<br>(Artificial Sequence) | GAAGCCGGCCTTGCACATGCGTTTTAGAGCTAGAAATAGCAAGT<br>TAAAATAAGGCTAGTCCGTTATCAACTTGAAAAAGTGGCACCGA<br>GTCGGTGC |

TABLE 4-continued

| SEQ ID NO/ DESCRIPTION/ SOURCE | SEQUENCE |
| --- | --- |
| SEQ ID NO: 90 ACTB N-term PBS_18_RT_16_with_ Lox71_Cre pegRNA (Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGCATATCATCATCCATGGTACCGTTCGTATAGCATACAT TATACGAAGTTATTGAGCTGCGAGAATAGCC |
| SEQ ID NO: 91 ACTB N-term PBS_13_RT_29_with_ Lox71_Cre pegRNA (Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGCGACGAGCGCGGCGATATCATCATCCATGGTACCGTT CGTATAGCATACATTATACGAAGTTATTGAGCTGCGAGAA |
| SEQ ID NO: 92 ACTB N-term PBS 13 RT 34 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCGACGACGAGCGCGGCGATATCATCATCCATGGCCGGAT GATCCTGACGACGGAGACCGCCGTCGTCGACAAGCCGGCCTGAGC TGCGAGAA |
| SEQ ID NO: 93 ACTB N-term PBS 13 RT 26 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGAGCGCGGCGATATCATCATCCATGGCCGGATGATCCTGA CGACGGAGACCGCCGTCGTCGACAAGCCGGCCTGAGCTGCGAGAA |
| SEQ ID NO: 94 ACTB N-term PBS 13 RT 23 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCCGCGGCGATATCATCATCCATGGCCGGATGATCCTGACGAC GGAGACCGCCGTCGTCGACAAGCCGGCCTGAGCTGCGAGAA |
| SEQ ID NO: 95 ACTB N-term PBS 13 RT 20 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGGCGATATCATCATCCATGGCCGGATGATCCTGACGACGG AGACCGCCGTCGTCGACAAGCCGGCCTGAGCTGCGAGAA |
| SEQ ID NO: 96 ACTB N-term PBS 13 RT 16 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCATATCATCATCCATGGCCGGATGATCCTGACGACGGAGAC CGCCGTCGTCGACAAGCCGGCCTGAGCTGCGAGAA |
| SEQ ID NO: 97 ACTB N-term PBS 18 RT 34 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCGACGACGAGCGCGGCGATATCATCATCCATGGCCGGAT GATCCTGACGACGGAGACCGCCGTCGTCGACAAGCCGGCCTGAGC TGCGAGAATAGCC |
| SEQ ID NO: 98 ACTB N-term PBS 18 RT 29 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAGACCGCCGTCGTCGACAAGCCGGCCTGAGCTGCGA GAATAGCC |
| SEQ ID NO: 99 ACTB N-term PBS 18 RT 16 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCATATCATCATCCATGGCCGGATGATCCTGACGACGGAGAC CGCCGTCGTCGACAAGCCGGCCTGAGCTGCGAGAATAGCC |
| SEQ ID NO: 100 LMNB1 N-term PBS 13 RT 39 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCTGCCCATCCGCGGCGGCACGGGGGTCGCAGTCGCCA TGCCGGATGATCCTGACGACGGAGACCGCCGTCGTCGACAAGCC GGCCCGGGCGGCGGAGA |
| SEQ ID NO: 101 LMNB1 N-term PBS 13 RT 34 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCATCCGCGGCGGCACGGGGGTCGCAGTCGCCATGCCG GATGATCCTGACGACGGAGACCGCCGTCGTCGACAAGCCGGCCC GGGCGGCGGAGA |
| SEQ ID NO: 102 LMNB1 N-term PBS 13 RT 29 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGCGGCGGCACGGGGGTCGCAGTCGCCATGCCGGATGA TCCTGACGACGGAGACCGCCGTCGTCGACAAGCCGGCCCGGGCG GCGGAGA |

TABLE 4-continued

| SEQ ID NO/<br>DESCRIPTION/<br>SOURCE | SEQUENCE |
|---|---|
| SEQ ID NO: 103<br>LMNB1 N-term PBS<br>13 RT 24 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGCACGGGGGTCGCAGTCGCCATGCCGGATGATCCTG<br>ACGACGGAGACCGCCGTCGTCGACAAGCCGGCCCGGGCGGCGGA<br>GA |
| SEQ ID NO: 104<br>LMNB1 N-term PBS<br>13 RT 19 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGGGGTCGCAGTCGCCATGCCGGATGATCCTGACGAC<br>GGAGACCGCCGTCGTCGACAAGCCGGCCCGGGCGGCGGAGA |
| SEQ ID NO: 105<br>LMNB1 N-term PBS<br>18 RT 39 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCTGCCCATCCGCGGCGGCACGGGGGTCGCAGTCGCCA<br>TGCCGGATGATCCTGACGACGGAGACCGCCGTCGTCGACAAGCC<br>GGCCCGGGCGGCGGAGACAGCG |
| SEQ ID NO: 106<br>LMNB1 N-term PBS<br>18 RT 34 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCATCCGCGGCGGCACGGGGGTCGCAGTCGCCATGCCG<br>GATGATCCTGACGACGGAGACCGCCGTCGTCGACAAGCCGGCCC<br>GGGCGGCGGAGACAGCG |
| SEQ ID NO: 107<br>LMNB1 N-term PBS<br>18 RT 29 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCCGGATGATC<br>CTGACGACGGAGACCGCCGTCGTCGACAAGCCGGCCCGGGCGGCG<br>GAGACAGCG |
| SEQ ID NO: 108<br>LMNB1 N-term PBS<br>18 RT 24 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGCACGGGGGTCGCAGTCGCCATGCCGGATGATCCTG<br>ACGACGGAGACCGCCGTCGTCGACAAGCCGGCCCGGGCGGCGGA<br>GACAGCG |
| SEQ ID NO: 109<br>LMNB1 N-term PBS<br>18 RT 19 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGGGGTCGCAGTCGCCATGCCGGATGATCCTGACGAC<br>GGAGACCGCCGTCGTCGACAAGCCGGCCCGGGCGGCGGAGACAG<br>CG |
| SEQ ID NO: 110<br>LMNB1 N-term<br>Nicking guide 1 +46<br>(Artificial Sequence) | GCGTGGTGGGCCGCCAGCGGTTTTAGAGCTAGAAATAGCAAGT<br>TAAAATAAGGCTAGTCCGTTATCAACTTGAAAAAGTGGCACCGA<br>GTCGGTGC |
| SEQ ID NO: 111<br>ACTB N-term PBS<br>13 RT 29 attB 42<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGGATGATCCTG<br>ACGACGGAGACCGCCGTCGTCGACAAGCCGGTGAGCTGCGAGAA |
| SEQ ID NO: 112<br>ACTB N-term PBS<br>13 RT 29 attB 40<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATGATCCTGA<br>CGACGGAGACCGCCGTCGTCGACAAGCCGTGAGCTGCGAGAA |
| SEQ ID NO: 113<br>ACTB N-term PBS<br>13 RT 29 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATGATCCTGAC<br>GACGGAGACCGCCGTCGTCGACAAGCCTGAGCTGCGAGAA |
| SEQ ID NO: 114<br>ACTB N-term PBS<br>13 RT 29 attB 36<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGATCCTGACG<br>ACGGAGACCGCCGTCGTCGACAAGCTGAGCTGCGAGAA |
| SEQ ID NO: 115<br>LMNB1 N-term PBS<br>13 RT 29 attB 44<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGTCGCAGTCGCCATGCGGATGATCC<br>TGACGACGGAGACCGCCGTCGTCGACAAGCCGGCCGGGCGGCGG<br>AGA |

TABLE 4-continued

| SEQ ID NO/ DESCRIPTION/ SOURCE | SEQUENCE |
| --- | --- |
| SEQ ID NO: 116 LMNB1 N-term PBS 13 RT 29 attB 42 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGGGATGATCCT GACGACGGAGACCGCCGTCGTCGACAAGCCGGCGGGCGGCGGAG A |
| SEQ ID NO: 117 LMNB1 N-term PBS 13 RT 29 attB 40 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGGATGATCCTG ACGACGGAGACCGCCGTCGTCGACAAGCCGCGGGCGGCGGAGA |
| SEQ ID NO: 118 LMNB1 N-term PBS 13 RT 29 attB 38 pegRNA v2 (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGATGATCCTGA CGACGGAGACCGCCGTCGTCGACAAGCCCGGGCGGCGGAGA |
| SEQ ID NO: 119 NOLC1 N-term PBS 18 RT 29 attB 46 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCCCGGATG ATCCTGACGACGGAGACCGCCGTCGTCGACAAGCCGGCCTCCTC CAGGCAATACGCG |
| SEQ ID NO: 120 NOLC1 N-term PBS 13 RT 29 attB 46 pegRNA (Artificial Sequence) | GCGTATTGCCTGGAGGATGGGTTTTAGAGCTAGAAATAGCAAGTT AAAATAAGGCTAGTCCGTTATCAACTTGAAAAAGTGGCACCGAGT CGGTGCGAACCACGCGGCGAATGCCGGCGTCCGCCCCGGATGATC CTGACGACGGAGACCGCCGTCGTCGACAAGCCGGCCTCCTCCAGG CAAT |
| SEQ ID NO: 121 NOLC1 N-term PBS 13 RT 29 attB 44 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCCGGATGA TCCTGACGACGGAGACCGCCGTCGTCGACAAGCCGGCTCCTCCA GGCAAT |
| SEQ ID NO: 122 NOLC1 N-term PBS 13 RT 29 attB 42 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCGGATGAT CCTGACGACGGAGACCGCCGTCGTCGACAAGCCGGTCCTCCAGG CAAT |
| SEQ ID NO: 123 NOLC1 N-term PBS 13 RT 29 attB 40 pegRNA (Artificial Sequence) | GCGTATTGCCTGGAGGATGGGTTTTAGAGCTAGAAATAGCAAGT TAAAATAAGGCTAGTCCGTTATCAACTTGAAAAAGTGGCACCGA GTCGGTGCGAACCACGCGGCGAATGCCGGCGTCCGCCGATGATC CTGACGACGGAGACCGCCGTCGTCGACAAGCCGTCCTCCAGGCA AT |
| SEQ ID NO: 124 NOLC1 N-term PBS 13 RT 29 attB 38 pegRNA (Artificial Sequence) | GCGTATTGCCTGGAGGATGGGTTTTAGAGCTAGAAATAGCAAGTT AAAATAAGGCTAGTCCGTTATCAACTTGAAAAAGTGGCACCGAGT CGGTGCGAACCACGCGGCGAATGCCGGCGTCCGCCATGATCCT GACGACGGAGACCGCCGTCGTCGACAAGCCTCCTCCAGGCAAT |
| SEQ ID NO: 125 NOLC1 nicking guide-43 (Artificial Sequence) | GAGCCGAGCACGAGGGGATACGTTTTAGAGCTAGAAATAGCAAGT TAAAATAAGGCTAGTCCGTTATCAACTTGAAAAAGTGGCACCGAG TCGGTGC |
| SEQ ID NO: 126 ACTB N-term PBS 13 RT 20 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGGCGATATCATCATCCATGGATGATCCTGACGACGGAGAC CGCCGTCGTCGACAAGCCTGAGCTGCGAGAA |
| SEQ ID NO: 127 ACTB N-term PBS 13 RT 15 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTATCATCATCCATGGATGATCCTGACGACGGAGACCGCCG TCGTCGACAAGCCTGAGCTGCGAGAA |
| SEQ ID NO: 128 ACTB N-term PBS 13 RT 10 attB 38 pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCATCCATGGATGATCCTGACGACGGAGACCGCCGTCGTC GACAAGCCTGAGCTGCGAGAA |

TABLE 4-continued

| SEQ ID NO/<br>DESCRIPTION/<br>SOURCE | SEQUENCE |
|---|---|
| SEQ ID NO: 129<br>ACTB N-term PBS 9<br>RT 20 attB 38<br>pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGGCGATATCATCATCCATGGATGATCCTGACGACGGAG<br>ACCGCCGTCGTCGACAAGCCTGAGCTGCG |
| SEQ ID NO: 130<br>ACTB N-term PBS 9<br>RT 15 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTATCATCATCCATGGATGATCCTGACGACGGAGACCGCCG<br>TCGTCGACAAGCCTGAGCTGCG |
| SEQ ID NO: 131<br>ACTB N-term PBS 9<br>RT 10 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCATCCATGGATGATCCTGACGACGGAGACCGCCGTCGTC<br>GACAAGCCTGAGCTGCG |
| SEQ ID NO: 132<br>LMNB1 N-term PBS<br>13 RT 20 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCGGGGGTCGCAGTCGCCATGATGATCCTGACGACGGA<br>GACCGCCGTCGTCGACAAGCCCGGGCGGCGGAGA |
| SEQ ID NO: 133<br>LMNB1 N-term PBS<br>13 RT 15 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGTCGCAGTCGCCATGATGATCCTGACGACGGAGACCG<br>CCGTCGTCGACAAGCCCGGGCGGCGGAGA |
| SEQ ID NO: 134<br>LMNB1 N-term PBS<br>13 RT 10 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCAGTCGCCATGATGATCCTGACGACGGAGACCGCCGTC<br>GTCGACAAGCCCGGGCGGCGGAGA |
| SEQ ID NO: 135<br>LMNB1 N-term PBS<br>9 RT 20 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCCGGGGGTCGCAGTCGCCATGATGATCCTGACGACGGAGA<br>CCGCCGTCGTCGACAAGCCCGGGCGGCG |
| SEQ ID NO: 136<br>LMNB1 N-term PBS<br>9 RT 15 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGTCGCAGTCGCCATGATGATCCTGACGACGGAGACCG<br>CCGTCGTCGACAAGCCCGGGCGGCG |
| SEQ ID NO: 137<br>LMNB1 N-term PBS<br>9 RT 10 attB 38<br>pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCAGTCGCCATGATGATCCTGACGACGGAGACCGCCGTCGT<br>CGACAAGCCCGGGCGGCG |
| SEQ ID NO: 138<br>SUPT16H N-term<br>PBS 13 RT 24 Bxb1-<br>GT_Initial length<br>(Artificial Sequence) | GAGAAGCGGCGTCCGGGGCTAGTTTTAGAGCTAGAAATAGCAAGT<br>TAAAATAAGGCTAGTCCGTTATCAACTTGAAAAAGTGGCACCGA<br>TCGGTGCTCTTTGTCCAGAGTCACAGCCATACCGGATGATCCTGAC<br>GACGGAGACCGCCGTCGTCGACAAGCCGGCCCCCCGGACGCCGC |
| SEQ ID NO: 139<br>SRRM2 N-term PBS<br>13 RT 24 Bxb1<br>Initial length<br>(Artificial Sequence) | GGGCACGGGGCCATGTACAAGTTTTAGAGCTAGAAATAGCAAGT<br>TAAAATAAGGCTAGTCCGTTATCAACTTGAAAAAGTGGCACCGA<br>GTCGGTGCGGCGTCGGCAGCCCGATCCCGTTGCCGGATGATCCT<br>GACGACGGAGACCGCCGTCGTCGACAAGCCGGCCTACATGGCCC<br>CGT |
| SEQ ID NO: 140<br>DEPDC4 N-term<br>PBS 18 RT 24 Bxb1<br>Initial length<br>(Artificial Sequence) | GTGTCAGGTGGGGCGGGCTAGTTTTAGAGCTAGAAATAGCAAG<br>TTAAAATAAGGCTAGTCCGTTATCAACTTGAAAAAGTGGCACCG<br>AGTCGGTGCGCTGGCTCCTCCCCTGGCACCATACCGGATGATCCT<br>GACGACGGAGACCGCCGTCGTCGACAAGCCGGCCCCCCGCCCCA<br>CCTGACAC |

TABLE 4-continued

| SEQ ID NO/ DESCRIPTION/ SOURCE | SEQUENCE |
|---|---|
| SEQ ID NO: 141 NES N-term PBS 13 RT 29 Bxb1 Initial length (Artificial Sequence) | GAGTGGGTCAGACGAGCAGGAGTTTTAGAGCTAGAAATAGCAAGT TAAAATAAGGCTAGTCCGTTATCAACTTGAAAAAGTGGCACCGAG TCGGTGCGATGGAGGGCTGCATGGGGGAGGAGTCGCCGGATGATC CTGACGACGGAGACCGCCGTCGTCGACAAGCCGGCCTGCTCGTCT GACC |
| SEQ ID NO: 142 SUPT16H nicking guide-53 (Artificial Sequence) | GCAGCCACCCGCTCTCGGCCCGTTTTAGAGCTAGAAATAGCAAG TTAAAATAAGGCTAGTCCGTTATCAACTTGAAAAAGTGGCACCG AGTCGGTGC |
| SEQ ID NO: 143 SRRM2 N-term nicking guide 1 +87 (Artificial Sequence) | GTGTAGTCAGGCCGCTCACCCGTTTTAGAGCTAGAAATAGCAAG TTAAAATAAGGCTAGTCCGTTATCAACTTGAAAAAGTGGCACCG AGTCGGTGC |
| SEQ ID NO: 144 DEPDC4 N-term Nicking guide 1 +59 (Artificial Sequence) | GCTGACAAGTCTACGGAACCTGTTTTAGAGCTAGAAATAGCAAG TTAAAATAAGGCTAGTCCGTTATCAACTTGAAAAAGTGGCACCG AGTCGGTGC |
| SEQ ID NO: 145 NES N-term Nicking guide 2 + 9 (Artificial Sequence) | GCTCCTCCAGCGCCTTGACCGTTTTAGAGCTAGAAATAGCAAGTTA AAATAAGGCTAGTCCGTTATCAACTTGAAAAAGTGGCACCGAGTC GGTGC |
| SEQ ID NO: 146 HITI_ACTB_guide (Artificial Sequence) | GCTATTCTCGCAGCTCACCA |
| SEQ ID NO: 147 HITI_SUPTH16_guide (Artificial Sequence) | AGAAGCGGCGTCCGGGGCTA |
| SEQ ID NO: 148 HITI_SRRM2_guide (Artificial Sequence) | GGGCACGGGGCCATGTACAA |
| SEQ ID NO: 149 HITI_NOLC1_guide (Artificial Sequence) | GCGTATTGCCTGGAGGATGG |
| SEQ ID NO: 150 HITI_DEPDC4_guide (Artificial Sequence) | TGTCAGGTGGGGCGGGGCTA |
| SEQ ID NO: 151 HITI_NES_guide (Artificial Sequence) | AGTGGGTCAGACGAGCAGGA |
| SEQ ID NO: 152 HITI_LMNB1_guide (Artificial Sequence) | GCTGTCTCCGCCGCCCGCCA |
| SEQ ID NO: 153 HDR Cas9 ACTB guide (Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGC |
| SEQ ID NO: 154 ACTB N-term PBS 13 RT 29 attB original length pegRNAs for dinucleotides (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACAGAGCGCGGCGATATCATCATCCATGGCCGGATGATCC TGACGACGGAGXXCGCCGTCGTCGACAAGCCGGCCTGAGCTGCGA GAA XX: CG, GC, AT, TA, GG, TT, GA, AG, CC, TC, CT, AA, TG, GT, CA, or AC |
| SEQ ID NO: 155 ACTB N-term PBS 13 RT 29 pegRNA with attB 46 GT for fusion (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGCCGGATGATCCT GACGACGGAGACCGCCGTCGTCGACAAGCCGGCCTGAGCTGCGAG AA |

TABLE 4-continued

| SEQ ID NO/ DESCRIPTION/ SOURCE | SEQUENCE |
| --- | --- |
| SEQ ID NO: 156 ACTB N-term PBS 13 RT 29 pegRNA with attB 46 CT for multiplexing (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGCCGGATGATCCT GACGACGGAGAGCGCCGTCGTCGACAAGCCGGCCTGAGCTGCGA GAA |
| SEQ ID NO: 157 NOLC1 N-term PBS 18 RT 29 pegRNA with attB 46 GA for multiplexing (Artificial Sequence) | GCGTATTGCCTGGAGGATGGGTTTTAGAGCTAGAAATAGCAAGTT AAAATAAGGCTAGTCCGTTATCAACTTGAAAAAGTGGCACCGAGT CGGTGCGAACCACGCGGCGAATGCCGGCGTCCGCCCCGGATGATC CTGACGACGGAGTCCGCCGTCGTCGACAAGCCGGCCTCCTCCAGG CAATACGCG |
| SEQ ID NO: 158 LMNB1 N-term PBS 18 RT 29 pegRNA with attB 46 AG for multiplexing (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCGCGGCGGCACGGGGGTCGCAGTCGCCATGCCGGATGATC CTGACGACGGAGCTCGCCGTCGTCGACAAGCCGGCCCGGGCGGCG GAGACAGCG |
| SEQ ID NO: 159 EMX1 Cas9 guide 1 (Artificial Sequence) | GTCACCTCCAATGACTAGGG |
| SEQ ID NO: 160 EMX1 Cas9 guide 2 (Artificial Sequence) | GGGCAACCACAAACCCACGA |
| SEQ ID NO: 161 ACTB N-term PBS 13 RT 29 attB 56 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCTATGCCGGAT GATCCTGACGACGGAGTCCGCCGTCGTCGACAAGCCGGCCCTAGC TGAGCTGCGAGAA |
| SEQ ID NO: 162 ACTB N-term PBS 13 RT 29 attB 51 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGCCGGATGAT CCTGACGACGGAGTCCGCCGTCGTCGACAAGCCGGCCCTATGAGC TGCGAGAA |
| SEQ ID NO: 163 ACTB N-term PBS 13 RT 29 attB 46 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAGTCCGCCGTCGTCGACAAGCCGGCCTGAGCTGCGA GAA |
| SEQ ID NO: 164 ACTB N-term PBS 13 RT 29 attB 41 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGGATGATCCTG ACGACGGAGTCCGCCGTCGTCGACAAGCCGTGAGCTGCGAGAA |
| SEQ ID NO: 165 ACTB N-term PBS 13 RT 29 attB 36 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGATCCTGACG ACGGAGTCCGCCGTCGTCGACAAGCTGAGCTGCGAGAA |
| SEQ ID NO: 166 ACTB N-term PBS 13 RT 29 attB 31 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGATCCTGACGAC GGAGTCCGCCGTCGTCGACATGAGCTGCGAGAA |
| SEQ ID NO: 167 ACTB N-term PBS 13 RT 29 attB 26 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCTGACGACGG AGTCCGCCGTCGTCGTGAGCTGCGAGAA |
| SEQ ID NO: 168 ACTB N-term PBS 13 RT 29 attB 21 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGTGACGACGGAG TCCGCCGTCGTGAGCTGCGAGAA |

TABLE 4-continued

| SEQ ID NO/ DESCRIPTION/ SOURCE | SEQUENCE |
|---|---|
| SEQ ID NO: 169 ACTB N-term PBS 13 RT 29 attB 16 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGACGACGGAGTC CGCCGTGAGCTGCGAGAA |
| SEQ ID NO: 170 ACTB N-term PBS 13 RT 29 attB 11 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGGACGGAGTCCG TGAGCTGCGAGAA |
| SEQ ID NO: 171 ACTB N-term PBS 13 RT 29 attB 6 GA pegRNA (Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCGGAGTTGAGC TGCGAGAA |
| SEQ ID NO: 172 ACTB N-term PBS_18_RT_34_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAATAG CC |
| SEQ ID NO: 173 ACTB N-term PBS_18_RT_29_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCGACGAGCGCGGCGATATCATCATCCATGGTACCGTTCGT ATAGCATACATTATACGAAGTTATTGAGCTGCGAGAATAGCC |
| SEQ ID NO: 174 ACTB N-term PBS_13_RT_34_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAA |
| SEQ ID NO: 175 ACTB N-term PBS_13_RT_16_with_ Lox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCATATCATCATCCATGGTACCGTTCGTATAGCATACATTAT ACGAAGTTATTGAGCTGCGAGAA |
| SEQ ID NO: 176 ACTB N-term Nicking guide 2 +93 guide (Artificial Sequence) | CCCCACGATGGAGGGGAAGAGTTTTAGAGCTAGAAATAGCAAGTT AAAATAAGGCTAGTCCGTTATCAACTTGAAAAAGTGGCACCGAGT CGGTGC |
| SEQ ID NO: 177 LMNB1 N-term Nicking guide 2 +87 guide (Artificial Sequence) | CCTTCTCCTGGAGCCGCGACGTTTTAGAGCTAGAAATAGCAAGTT AAAATAAGGCTAGTCCGTTATCAACTTGAAAAAGTGGCACCGAGT CGGTGC |

Sequences of insertion sites can be found in Table 4 below.

TABLE 4

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attP_GT_ original_site (Artificial Sequence) | 178 | GTGGTTTGTCTGGTC AACCACCGCGGTCT CAGTGGTGTACGGT ACAAACCCA | 179 | TGGGTTTGTACCGTA CACCACTGAGACCG CGGTGGTTGACCAG ACAAACCAC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attP_CG_ site (Artificial Sequence) | 180 | GTGGTTTGTCTGGTC AACCACCGCGCGCT CAGTGGTGTACGGT ACAAACCCA | 181 | TGGGTTTGTACCGTA CACCACTGAGCGCG CGGTGGTTGACCAG ACAAACCAC |
| Bxb1_attP_GC_ site (Artificial Sequence) | 182 | GTGGTTTGTCTGGTC AACCACCGCGGCCT CAGTGGTGTACGGT ACAAACCCA | 183 | TGGGTTTGTACCGTA CACCACTGAGGCCG CGGTGGTTGACCAG ACAAACCAC |
| Bxb1_attP_AT_ site (Artificial Sequence) | 184 | GTGGTTTGTCTGGTC AACCACCGCGATCT CAGTGGTGTACGGT ACAAACCCA | 185 | TGGGTTTGTACCGTA CACCACTGAGATCG CGGTGGTTGACCAG ACAAACCAC |
| Bxb1_attP_TA_ site (Artificial Sequence) | 186 | GTGGTTTGTCTGGTC AACCACCGCGTACT CAGTGGTGTACGGT ACAAACCCA | 187 | TGGGTTTGTACCGTA CACCACTGAGTACG CGGTGGTTGACCAG ACAAACCAC |
| Bxb1_attP_GG_ site (Artificial Sequence) | 188 | GTGGTTTGTCTGGTC AACCACCGCGGGCT CAGTGGTGTACGGT ACAAACCCA | 189 | TGGGTTTGTACCGTA CACCACTGAGCCCG CGGTGGTTGACCAG ACAAACCAC |
| Bxb1_attP_TT_ site (Artificial Sequence) | 190 | GTGGTTTGTCTGGTC AACCACCGCGTTCTC AGTGGTGTACGGTA CAAACCCA | 191 | TGGGTTTGTACCGTA CACCACTGAGAACG CGGTGGTTGACCAG ACAAACCAC |
| Bxb1_attP_GA_ site (Artificial Sequence) | 192 | GTGGTTTGTCTGGTC AACCACCGCGGACT CAGTGGTGTACGGT ACAAACCCA | 193 | TGGGTTTGTACCGTA CACCACTGAGTCCG CGGTGGTTGACCAG ACAAACCAC |
| Bxb1_attP_AG_ site (Artificial Sequence) | 194 | GTGGTTTGTCTGGTC AACCACCGCGAGCT CAGTGGTGTACGGT ACAAACCCA | 195 | TGGGTTTGTACCGTA CACCACTGAGCTCG CGGTGGTTGACCAG ACAAACCAC |
| Bxb1_attP_CC_ site (Artificial Sequence) | 196 | GTGGTTTGTCTGGTC AACCACCGCGCCCT CAGTGGTGTACGGT ACAAACCCA | 197 | TGGGTTTGTACCGTA CACCACTGAGGGCG CGGTGGTTGACCAG ACAAACCAC |
| Bxb1_attP_TC_ site (Artificial Sequence) | 198 | GTGGTTTGTCTGGTC AACCACCGCGTCCTC AGTGGTGTACGGTA CAAACCCA | 199 | TGGGTTTGTACCGTA CACCACTGAGGACG CGGTGGTTGACCAG ACAAACCAC |
| Bxb1_attP_CT_ site (Artificial Sequence) | 200 | GTGGTTTGTCTGGTC AACCACCGCGCTCTC AGTGGTGTACGGTA CAAACCCA | 201 | TGGGTTTGTACCGTA CACCACTGAGAGCG CGGTGGTTGACCAG ACAAACCAC |
| Bxb1_attP_AA_ site (Artificial Sequence) | 202 | GTGGTTTGTCTGGTC AACCACCGCGAACT CAGTGGTGTACGGT ACAAACCCA | 203 | TGGGTTTGTACCGTA CACCACTGAGTTCGC GGTGGTTGACCAGA CAAACCAC |
| Bxb1_attP_CA_site (Artificial Sequence) | 204 | GTGGTTTGTCTGGTC AACCACCGCGCACT CAGTGGTGTACGGT ACAAACCCA | 205 | TGGGTTTGTACCGTA CACCACTGAGTGCG CGGTGGTTGACCAG ACAAACCAC |
| Bxb1_attP_AC_ site (Artificial Sequence) | 206 | GTGGTTTGTCTGGTC AACCACCGCGACCT CAGTGGTGTACGGT ACAAACCCA | 207 | TGGGTTTGTACCGTA CACCACTGAGGTCG CGGTGGTTGACCAG ACAAACCAC |
| Bxb1_attP_TG_ site (Artificial Sequence) | 208 | GTGGTTTGTCTGGTC AACCACCGCGTGCT CAGTGGTGTACGGT ACAAACCCA | 209 | TGGGTTTGTACCGTA CACCACTGAGCACG CGGTGGTTGACCAG ACAAACCAC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_46_ GT_original_ site (Artificial Sequence) | 210 | GGCCGGCTTGTCGA CGACGGCGGTCTCC GTCGTCAGGATCATC CGG | 211 | CCGGATGATCCTGA CGACGGAGACCGCC GTCGTCGACAAGCC GGCC |
| Bxb1_attB_46_ AA_site (Artificial Sequence) | 212 | GGCCGGCTTGTCGA CGACGGCGAACTCC GTCGTCAGGATCATC CGG | 213 | CCGGATGATCCTGA CGACGGAGTTCGCC GTCGTCGACAAGCC GGCC |
| Bxb1_attB_46_ GA_site (Artificial Sequence) | 214 | GGCCGGCTTGTCGA CGACGGCGGACTCC GTCGTCAGGATCATC CGG | 215 | CCGGATGATCCTGA CGACGGAGTCCGCC GTCGTCGACAAGCC GGCC |
| Bxb1_attB_46_ CA_site (Artificial Sequence) | 216 | GGCCGGCTTGTCGA CGACGGCGCACTCC GTCGTCAGGATCATC CGG | 217 | CCGGATGATCCTGA CGACGGAGTGCGCC GTCGTCGACAAGCC GGCC |
| Bxb1_attB_46_ TA_site (Artificial Sequence) | 218 | GGCCGGCTTGTCGA CGACGGCGTACTCC GTCGTCAGGATCATC CGG | 219 | CCGGATGATCCTGA CGACGGAGTACGCC GTCGTCGACAAGCC GGCC |
| Bxb1_attB_46_ AG_site (Artificial Sequence) | 220 | GGCCGGCTTGTCGA CGACGGCGAGCTCC GTCGTCAGGATCATC CGG | 221 | CCGGATGATCCTGA CGACGGAGCTCGCC GTCGTCGACAAGCC GGCC |
| Bxb1_attB_46_ GG_site (Artificial Sequence) | 222 | GGCCGGCTTGTCGA CGACGGCGGGCTCC GTCGTCAGGATCATC CGG | 223 | CCGGATGATCCTGA CGACGGAGCCCGCC GTCGTCGACAAGCC GGCC |
| Bxb1_attB_46_ CG_site (Artificial Sequence) | 224 | GGCCGGCTTGTCGA CGACGGCGCGCTCC GTCGTCAGGATCATC CGG | 225 | CCGGATGATCCTGA CGACGGAGCGCGCC GTCGTCGACAAGCC GGCC |
| Bxb1_attB_46_ TG_site (Artificial Sequence) | 226 | GGCCGGCTTGTCGA CGACGGCGTGCTCC GTCGTCAGGATCATC CGG | 227 | CCGGATGATCCTGA CGACGGAGCACGCC GTCGTCGACAAGCC GGCC |
| Bxb1_attB_46_ AC_site (Artificial Sequence) | 228 | GGCCGGCTTGTCGA CGACGGCGACCTCC GTCGTCAGGATCATC CGG | 229 | CCGGATGATCCTGA CGACGGAGGTCGCC GTCGTCGACAAGCC GGCC |
| Bxb1_attB_46_ GC_site (Artificial Sequence) | 230 | GGCCGGCTTGTCGA CGACGGCGGCCTCC GTCGTCAGGATCATC CGG | 231 | CCGGATGATCCTGA CGACGGAGGCCGCC GTCGTCGACAAGCC GGCC |
| Bxb1_attB_46_ CC_site (Artificial Sequence) | 232 | GGCCGGCTTGTCGA CGACGGCGCCCTCC GTCGTCAGGATCATC CGG | 233 | CCGGATGATCCTGA CGACGGAGGGCGCC GTCGTCGACAAGCC GGCC |
| Bxb1_attB_46_ TC_site (Artificial Sequence) | 234 | GGCCGGCTTGTCGA CGACGGCGTCCTCC GTCGTCAGGATCATC CGG | 235 | CCGGATGATCCTGA CGACGGAGGACGCC GTCGTCGACAAGCC GGCC |
| Bxb1_attB_46_ AT_site (Artificial Sequence) | 236 | GGCCGGCTTGTCGA CGACGGCGATCTCC GTCGTCAGGATCATC CGG | 237 | CCGGATGATCCTGA CGACGGAGATCGCC GTCGTCGACAAGCC GGCC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_46_ CT_site (Artificial Sequence) | 238 | GGCCGGCTTGTCGA CGACGGCGCTCTCC GTCGTCAGGATCATC CGG | 239 | CCGGATGATCCTGA CGACGGAGAGCGCC GTCGTCGACAAGCC GGCC |
| Bxb1_attB_46_ TT_site (Artificial Sequence) | 240 | GGCCGGCTTGTCGA CGACGGCGTTCTCCG TCGTCAGGATCATCC GG | 241 | CCGGATGATCCTGA CGACGGAGAACGCC GTCGTCGACAAGCC GGCC |
| Bxb1_attB_38_ GT_site (Artificial Sequence) | 242 | GGCTTGTCGACGAC GGCGGTCTCCGTCGT CAGGATCAT | 243 | ATGATCCTGACGAC GGAGACCGCCGTCG TCGACAAGCC |
| Bxb1_attB_38_ AA_site (Artificial Sequence) | 244 | GGCTTGTCGACGAC GGCGAACTCCGTCG TCAGGATCAT | 245 | ATGATCCTGACGAC GGAGTTCGCCGTCGT CGACAAGCC |
| Bxb1_attB_38_ GA_site (Artificial Sequence) | 246 | GGCTTGTCGACGAC GGCGGACTCCGTCG TCAGGATCAT | 247 | ATGATCCTGACGAC GGAGTCCGCCGTCG TCGACAAGCC |
| Bxb1_attB_38_ CA_site (Artificial Sequence) | 248 | GGCTTGTCGACGAC GGCGCACTCCGTCGT CAGGATCAT | 249 | ATGATCCTGACGAC GGAGTGCGCCGTCG TCGACAAGCC |
| Bxb1_attB_38_ TA_site (Artificial Sequence) | 250 | GGCTTGTCGACGAC GGCGTACTCCGTCGT CAGGATCAT | 251 | ATGATCCTGACGAC GGAGTACGCCGTCG TCGACAAGCC |
| Bxb1_attB_38_ AG_site (Artificial Sequence) | 252 | GGCTTGTCGACGAC GGCGAGCTCCGTCG TCAGGATCAT | 253 | ATGATCCTGACGAC GGAGCTCGCCGTCG TCGACAAGCC |
| Bxb1_attB_38_ GG_site (Artificial Sequence) | 254 | GGCTTGTCGACGAC GGCGGGCTCCGTCG TCAGGATCAT | 255 | ATGATCCTGACGAC GGAGCCCGCCGTCG TCGACAAGCC |
| Bxb1_attB_38_ CG_site (Artificial Sequence) | 256 | GGCTTGTCGACGAC GGCGCGCTCCGTCGT CAGGATCAT | 257 | ATGATCCTGACGAC GGAGCGCGCCGTCG TCGACAAGCC |
| Bxb1_attB_38_ TG_site (Artificial Sequence) | 258 | GGCTTGTCGACGAC GGCGTGCTCCGTCGT CAGGATCAT | 259 | ATGATCCTGACGAC GGAGCACGCCGTCG TCGACAAGCC |
| Bxb1_attB_38_ AC_site (Artificial Sequence) | 260 | GGCTTGTCGACGAC GGCGACCTCCGTCGT CAGGATCAT | 261 | ATGATCCTGACGAC GGAGGTCGCCGTCG TCGACAAGCC |
| Bxb1_attB_38_ GC_site (Artificial Sequence) | 262 | GGCTTGTCGACGAC GGCGGCCTCCGTCGT CAGGATCAT | 263 | ATGATCCTGACGAC GGAGGCCGCCGTCG TCGACAAGCC |
| Bxb1_attB_38_ CC_site (Artificial Sequence) | 264 | GGCTTGTCGACGAC GGCGCCCTCCGTCGT CAGGATCAT | 265 | ATGATCCTGACGAC GGAGGGCGCCGTCG TCGACAAGCC |
| Bxb1_attB_38_ TC_site (Artificial Sequence) | 266 | GGCTTGTCGACGAC GGCGTCCTCCGTCGT CAGGATCAT | 267 | ATGATCCTGACGAC GGAGGACGCCGTCG TCGACAAGCC |

TABLE 4-continued

| DESCRIPTION/SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_38_AT_site (Artificial Sequence) | 268 | GGCTTGTCGACGACGGCGATCTCCGTCGTCAGGATCAT | 269 | ATGATCCTGACGACGGAGATCGCCGTCGTCGACAAGCC |
| Bxb1_attB_38_CT_site (Artificial Sequence) | 270 | GGCTTGTCGACGACGGCGCTCTCCGTCGTCAGGATCAT | 271 | ATGATCCTGACGACGGAGAGCGCCGTCGTCGACAAGCC |
| Bxb1_attB_38_TT_site (Artificial Sequence) | 272 | GGCTTGTCGACGACGGCGTTCTCCGTCGTCAGGATCAT | 273 | ATGATCCTGACGACGGAGAACGCCGTCGTCGACAAGCC |
| Cre Lox 66 site (Artificial Sequence) | 274 | TACCGTTCGTATAATGTATGCTATACGAAGTTAT | 275 | ATAACTTCGTATAGCATACATTATACGAACGGTA |
| Cre Lox 71 site (Artificial Sequence) | 276 | ATAACTTCGTATAATGTATGCTATACGAACGGTA | 277 | TACCGTTCGTATAGCATACATTATACGAAGTTAT |
| TP901-1 minimal attB site (Artificial Sequence) | 278 | TTTACCTTGATTGAGATGTTAATTGTG | 279 | CACAATTAACATCTCAATCAAGGTAAA |
| TP901-1 minimal attP site (Artificial Sequence) | 280 | GCGAGTTTTTATTTCGTTTATTTCAATTAAGGTAACTAAAAAACTCCTTT | 281 | AAAGGAGTTTTTTAGTTACCTTAATTGAAATAAACGAAATAAAAACTCGC |
| PhiBT1 minimal attB site (Artificial Sequence) | 282 | CTGGATCATCTGGATCACTTTCGTCAAAAACCTG | 283 | CAGGTTTTTGACGAAAGTGATCCAGATGATCCAG |
| PhiBT1 minimal attP site (Artificial Sequence) | 284 | TTCGGGTGCTGGGTTGTTGTCTCTGGACAGTGATCCATGGGAAACTACTCAGCACCA | 285 | TGGTGCTGAGTAGTTTCCCATGGATCACTGTCCAGAGACAACAACCCAGCACCCGAA |

Sequences of Bxb1 and RT mutants can be found in Table 6 below.

TABLE 6

| SEQ ID NO/DESCRIPTION/SOURCE | FORWARD SEQUENCE (5'-3') |
|---|---|
| SEQ ID NO: 286 Bxb1_mut_V368A (Artificial Sequence) | AAAAGTGTGGGCTGCAGGATCTGA |
| SEQ ID NO: 287 Bxb1_mut_E379A (Artificial Sequence) | GGAGCTGGCAGCTGTCAATGCC |
| SEQ ID NO: 288 Bxb1_mut_E383A (Artificial Sequence) | AGTCAATGCCGCTCTCGTGGA |

TABLE 6-continued

| SEQ ID NO/ DESCRIPTION/ SOURCE | FORWARD SEQUENCE (5'-3') |
|---|---|
| SEQ ID NO: 403 RT_mut_L139P (Artificial Sequence) | TTGAGCGGGCCCCCACCGT |
| SEQ ID NO: 289 RT_mut_E562Q (Artificial Sequence) | CAGCGGGCTCAGCTGATAGCA |
| SEQ ID NO: 290 RT_mut_D653N (Artificial Sequence) | CGGATGGCTAACCAAGCGGCC |
| SEQ ID NO: 404 RT(1-478)_Sto7d fusion | atgactcactatcaggccttgcttaggacacggacccgggtccagttcggaccggtggtagccctgaaccc ggctacgctgctcccactgcctgaggaagggctgcaacacaactgccttgatGGGACAGGTGG CGGTGGTGTCACCGTCAAGTTCAAGTACAAGGGTGAGGAACTT GAAGTTGATATTAGCAAAATCAAGAAGGTTTGGCGCGTTGGTA AAATGATATCTTTTACTTATGACGACAACGGCAAGACAGGTAG AGGGGCAGTGTCTGAGAAAGACGCCCCCAAGGAGCTGTTGCAA ATGTTGGAAAAGTCTGGGAAAAAGTctggcggctcaaaaagaaccgccgacgg cagcgaattcgagcccaagaagaagaggaaagtc |

Sequences of primers, probes and restriction enzymes used in ddPCR readout can be found in Table 7 below.

TABLE 7

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | GFP (pDY0186) | 291 | CCCG GCTTC CTTTG TCC | 292 | GAAC TCCAC GCCG TTCA | /56-FAM/C C GGC TTG T/ZEN/ C GAC GAC GGC G/3IAB kFQ/ | 405 | Eco91I, HindIII |
| ACTB | TP90-1 GFP (pDY0333) | 293 | CCCG GCTTC CTTTG TCC | 294 | AACC ACAA CTAG AATG CAGT GA | /56-FAM/T G CTA TTG C/ZEN/ T TTA TTT GTG GGC CCG /3IABk FQ/ | 406 | None |
| ACTB | TP90-1 rc GFP (pDY0334) | 295 | CCCG GCTTC CTTTG TCC | 296 | GAAC TCCAC GCCG TTCA | /56-FAM/ CC ATG AAG A/ZEN/ T CGA GTG CCG CAT CA/3I ABkF Q/ | 407 | None |
| ACTB | PhiBT1 GFP (pDY0367) | 297 | CCCG GCTTC CTTTG TCC | 298 | AACC ACAA CTAG AATG CAGT | /56-FAM/T G CTA TTG C/ZEN/ | 406 | None |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | GA | T TTA TTT GTG GGC CCG /3IABkFQ/ | | |
| ACTB | PhiBT1 rc GFP (pDY0368) | 299 | CCCG GCTTC CTTTG TCC | 300 | GAAC TCCAC GCCG TTCA | /56-FAM/ CC ATG AAG A/ZEN/ T CGA GTG CCG CAT CA/3I ABkF Q/ | 407 | None |
| LMNB1 | GFP (pDY0186) | 301 | TCCTT ATCA CGGT CCCG CTCG | 302 | GAAC TCCAC GCCG TTCA | /56-FAM/ CC ATG AAG A/ZEN/ T CGA GTG CCG CAT CA/3I ABkF Q/ | 407 | Eco91I, HindIII |
| NOLC1 | GFP (pDY0186) | 303 | CGTC GACA ACGG TAGT G | 304 | GAAC TCCAC GCCG TTCA | /56-FAM/ CC ATG AAG A/ZEN/ T CGA GTG CCG CAT CA/3I ABkF Q/ | 407 | Eco91I, HindIII |
| SUPT1 6 H | GFP pDY0186) | 305 | TCGC GTGA TTCTC GGAA C | 306 | GAAC TCCA CGCC GTTC A | /56-FAM/C C ATG AAG A/ZEN/ T CGA GTG CCG CAT CA/3IA BkFQ/ | 407 | Eco91I, HindIII |
| SRRM2 | GFP (pDY0186) | 307 | GGGC GGTA AGTG GTTA GTTT | 308 | GAAC TCCAC GCCG TTCA | /56-FAM/ CC ATG AAG A/ZEN/ T CGA GTG | 407 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | CCG CAT CA/3I ABkFQ/ | | |
| DEPDC4 | GFP (pDY0186) | 309 | AAGA GGCG GAGC CAGT A | 310 | GAAC TCCAC GCCG TTCA | /56-FAM/CC ATG AAG A/ZEN/T CGA GTG CCG CAT CA/3I ABkFQ/ | 407 | Eco91I, HindIII |
| NES | GFP (pDY0186) | 311 | CTCCC TTCTC CCGG TGCCC | 312 | GAAC TCCAC GCCG TTCA | /56-FAM/C C GGC TTG T/ZEN/C GAC GAC GGC G/3IABkFQ/ | 405 | Eco91I, HindIII |
| ACTB | ACTB HITI template GFP (pDY0219) | 313 | CCCG GCTTC CTTTG TCC | 314 | GAAC TCCAC GCCG TTCA | /56-FAM/CC ATG AAG A/ZEN/T CGA GTG CCG CAT CA/3I ABkFQ/ | 407 | Eco91I |
| SRRM2 | SRRM2 HITI template GFP (aRY0182_A2) | 315 | GGGC GGTA AGTG GTTA GTTT | 316 | GAAC TCCAC GCCG TTCA | /56-FAM/CC ATG AAG A/ZEN/T CGA GTG CCG CAT CA/3I ABkFQ/ | 407 | Eco91I |
| NOLC1 | NOLC1 HITI template GFP (aRY0182_A3) | 317 | CGTC GACA ACGG TAGT G | 318 | GAAC TCCAC GCCG TTCA | /56-FAM/CC ATG AAG A/ZEN/T CGA GTG CCG CAT CA/3I ABkFQ/ | 407 | Eco91I |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| DEPDC4 | DEPDC4 HITI template GFP (aRY0182_A5) | 319 | AAGAGGCGGAGCCAGTA | 320 | GAACTCCACGCCGTTCA | /56-FAM/CCATGAAGA/ZEN/TCGAGTGCCGCATCA/3IABkFQ/ | 407 | Eco91I |
| NES | NES HITI template GFP (aRY0182_A7) | 321 | CTCCCTTCTCCCGGTGCCC | 322 | GAACTCCACGCCGTTCA | /56-FAM/CCATGAAGA/ZEN/TCGAGTGCCGCATCA/3IABkFQ/ | 407 | Eco91I |
| LMNB1 | LMNB1 HITI template GFP (aRY0182_A4) | 323 | TCCTTATCACGGTCCCGCTCG | 324 | GAACTCCACGCCGTTCA | /56-FAM/CCATGAAGA/ZEN/TCGAGTGCCGCATCA/3IABkFQ/ | 407 | Eco91I |
| ACTB | SERPINA (pDY0298) | 325 | CCCGGCTTCCTTTGTCC | 326 | GGCCTGCCAGCAGGGAGGA | /56-FAM/CCGGCTTGT/ZEN/CGACGACGGCG/3IABkFQ/ | 405 | EcoRI, XhoI, HindIII |
| ACTB | CPS1 (pDY299) | 327 | CCCGGCTTCCTTTGTCC | 328 | GGTGTGCAGTCACATTGGTAAAGCC | /56-FAM/ACAGCTTTC/ZEN/AAAGTGGTGAGGACACT/3IABkFQ/ | 408 | XhoI, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| ACTB | CFTR (pDY0373) | 329 | CCCGGCTTCCTTTGTCC | 330 | GATGGGTCTAGTCCAGCTAAAG | /56-FAM/TACGGTACA/ZEN/AACCCACCCGAGAGA/3IABkFQ/ | 409 | Eco91I, HindIII |
| ACTB | NYESO TRAC (pDY0318) | 331 | CCCGGCTTCCTTTGTCC | 332 | GAGAGACAAGGCTGCACA | /56-FAM/TACGGTACA/ZEN/AACCCACCCGAGAGA/3IABkFQ/ | 409 | Eco47III, HindIII |
| NC_000003 | GFP (pDY0186) | 333 | CCAGGTGAGAGTCAGGGTAGTGTTCA | 334 | GAACTCCACGCCGTTCA | /56-FAM/CCGGCTTGT/ZEN/CGACGACGGCG/3IABkFQ/ | 405 | Eco91I, HindIII |
| NC_000002 | GFP (pDY0186) | 335 | AGGGACCTTTGCCTGTGTGAGTC | 336 | GAACTCCACGCCGTTCA | /56-FAM/CCGGCTTGT/ZEN/CGACGACGGCG/3IABkFQ/ | 405 | Eco91I, HindIII |
| NC_000009 | GFP (pDY0186) | 337 | TCAGCTCTGTGCTGAGGCGAA | 338 | GAACTCCACGCCGTTCA | /56-FAM/CCGGCTTGT/ZEN/CGACGACGGCG/3IABkFQ/ | 405 | Eco91I, HindIII |
| chr6: 149045959 | GFP (pDY0186) | 339 | AAGCCATCTCCCAGAATATCTG | 340 | GAACTCCACGCCGTTCA | /56-FAM/CCGGCTTG | 405 | Eco91I, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | CTTAG AAAT G | | | T/ZE N/C GAC GAC GGC G/3I ABkF Q/ | | |
| chr16: 18607730 | GFP (pDY0186) | 341 | GAGA GGAG CAAC AGTG AGCA TGAT G | 342 | GAAC TCCAC GCCG TTCA | /56- FAM/ CC GGC TTG T/ZE N/C GAC GAC GGC G/3I ABkF Q/ | 405 | Eco91I, HindIII |
| chr6: 149045959 | ACTB HITI template GFP (pDY0219) | 343 | AAGC CATCT CCCA GAAT ATCTG CTTAG AAAT G | 344 | GAAC TCCAC GCCG TTCA | /56- FAM/ CC GGC TTG T/ZE N/C GAC GAC GGC G/3I ABkF Q/ | 405 | Eco91I |
| chr16: 18607730 | ACTB HITI template GFP (pDY0219) | 345 | GAGA GGAG CAAC AGTG AGCA TGAT G | 346 | GAAC TCCAC GCCG TTCA | /56- FAM/ CC GGC TTG T/ZE N/C GAC GAC GGC G/3I ABkF Q/ | 405 | Eco91I |
| ACTB | CAG_ Kozak_ bGH_ thera- peutic_ genes generic minicircle | 347 | CCCG GCTTC CTTTG TCC | 348 | GGCT ATGA ACTA ATGA CCCC GT | /56- FAM/ CC GGC TTG T/ZE N/C GAC GAC GGC G/3I ABkF Q/ | 405 | Eco91I, HindIII |
| ACTB | Hibit- SERPINA (pDY045) | 349 | CCCG GCTTC CTTTG TCC | 350 | GGCC TGCC AGCA GGAG GA | /56- FAM/ CC GGC TTG T/ZE N/C GAC GAC | 405 | EcoRI, XhoI, HindIII |

TABLE 7-continued

| Locus | Cargo | SEQ ID NO: | Forward Primer | SEQ ID NO: | Reverse Primer | Probe | SEQ ID NO: | Restriction Enzymes |
|---|---|---|---|---|---|---|---|---|
| | | | | | | GGC G/3I ABkF Q/ | | |
| ACTB | Hibit-CPS1 (pDY406) | 351 | CCCG GCTTC CTTTG TCC | 352 | GGTG TGCA GTCA CATTG GTAA AGCC | /56-FAM/ AC AGC TTT C/ZE N/A AAG TGG TGA GGA CAC T/3IA BkFQ/ | 408 | XhoI, HindIII |

Sequences of primers used for NGS readout can be found in Table 8 below.

TABLE 8

| SEQ ID NO/ DESCRIPTION/ SOURCE | ID | SEQUENCE (5'-3') |
|---|---|---|
| SEQ ID NO: 353 N-term ACTB Tn5 readout F 1 (Artificial Sequence) | PD0966 | ACACTCTTTCCCTACACGACGCTCTTCCGATCTCCGAC CTCGGC TCACAGCG |
| SEQ ID NO: 354 N-term ACTB Tn5 readout F 2 (Artificial Sequence) | PD0967 | ACACTCTTTCCCTACACGACGCTCTTCCGATCTACCGA CCTCGG CTCACAGCG |
| SEQ ID NO: 355 N-term ACTB Tn5 readout F 3 (Artificial Sequence) | PD0968 | ACACTCTTTCCCTACACGACGCTCTTCCGATCTGACCG ACCTCG GCTCACAGCG |
| SEQ ID NO: 356 N-term ACTB Tn5 readout F 4 (Artificial Sequence) | PD0969 | ACACTCTTTCCCTACACGACGCTCTTCCGATCTTGACC GACCTC GGCTCACAGCG |
| SEQ ID NO: 357 N-term ACTB Tn5 readout F 5 (Artificial Sequence) | PD0970 | ACACTCTTTCCCTACACGACGCTCTTCCGATCTCTGAC CGACCT CGGCTCACAGCG |
| SEQ ID NO: 358 N-term ACTB Tn5 readout F 6 (Artificial Sequence) | PD0971 | ACACTCTTTCCCTACACGACGCTCTTCCGATCTACTGA CCGACC TCGGCTCACAGCG |
| SEQ ID NO: 359 N-term ACTB Tn5 readout F 7 (Artificial Sequence) | PD0972 | ACACTCTTTCCCTACACGACGCTCTTCCGATCTTACTG ACCGAC CTCGGCTCACAGCG |
| SEQ ID NO: 360 N-term ACTB Tn5 readout F 8 (Artificial Sequence) | PD0973 | ACACTCTTTCCCTACACGACGCTCTTCCGATCTGTACT GACCGA CCTCGGCTCACAGCG |
| SEQ ID NO: 361 ACTB N-term NGS R for Cas14 indels (Artificial Sequence) | FP0952 | GTGACTGGAGTTCAGACGTGTGCTCTTCCGATCTCCAC CCAGCC AGCTCCC |

TABLE 8-continued

| SEQ ID NO/<br>DESCRIPTION/<br>SOURCE | ID | SEQUENCE (5'-3') |
|---|---|---|
| SEQ ID NO: 362<br>NGS EMX1<br>Forward 1<br>(Artificial Sequence) | PD0313 | ACACTCTTTCCCTACACGACGCTCTTCCGATCTCCGGT GGCGCAT TGCCAC |
| SEQ ID NO: 363<br>NGS EMX1<br>Forward 2<br>(Artificial Sequence) | PD0314 | ACACTCTTTCCCTACACGACGCTCTTCCGATCTACCGG TGGCGCA TTGCCAC |
| SEQ ID NO: 364<br>NGS EMX1<br>Forward 3<br>(Artificial Sequence) | PD0315 | ACACTCTTTCCCTACACGACGCTCTTCCGATCTGACCG GTGGCGC ATTGCCAC |
| SEQ ID NO: 365<br>NGS EMX1<br>Forward 4<br>(Artificial Sequence) | PD0316 | ACACTCTTTCCCTACACGACGCTCTTCCGATCTTGACC GGTGGCG CATTGCCAC |
| SEQ ID NO: 366<br>NGS EMX1<br>Forward 5<br>(Artificial Sequence) | PD0317 | ACACTCTTTCCCTACACGACGCTCTTCCGATCTCTGAC CGGTGGC GCATTGCCAC |
| SEQ ID NO: 367<br>NGS EMX1<br>Forward 6<br>(Artificial Sequence) | PD0318 | ACACTCTTTCCCTACACGACGCTCTTCCGATCTACTGA CCGGTGG CGCATTGCCAC |
| SEQ ID NO: 368<br>NGS EMX1<br>Forward 7<br>(Artificial Sequence) | PD0319 | ACACTCTTTCCCTACACGACGCTCTTCCGATCTTACTG ACCGGTG GCGCATTGCCAC |
| SEQ ID NO: 369<br>NGS EMX1<br>Forward 8<br>(Artificial Sequence) | PD0320 | ACACTCTTTCCCTACACGACGCTCTTCCGATCTGTACT GACCGG GGCGCATTGCCAC |
| SEQ ID NO: 370<br>NGS EMX1 Reverse<br>(Artificial Sequence) | PD0321 | GTGACTGGAGTTCAGACGTGTGCTCTTCCGATCTCAGA GTCCAGC TTGGGCCCA |

Sequences of off-target sites can be found in Table 9 below.

TABLE 9

| SEQ ID NO/<br>DESCRIPTION/<br>SOURCE | SEQUENCE (5'-3') |
|---|---|
| SEQ ID NO: 371<br>Cas9_chr6:149045959<br>(Artificial Sequence) | GATATTTTCCCAGCTCACCA |
| SEQ ID NO: 372<br>Cas9_chr16:18607730<br>(Artificial Sequence) | TCTATTCTCCCAGCTCCCCA |
| SEQ ID NO: 373<br>Bxb1_NC_000002<br>(Artificial Sequence) | AGCGGCTTCTGTCTCTGTGAGTGAGCTGGCGGTCTCCGTC |
| SEQ ID NO: 374<br>Bxb1_NC_000003<br>(Artificial Sequence) | GACTAGCCCACGCTCCGGTTCTGAGCCGCGACGGCGGTCTCCG |

TABLE 9-continued

| SEQ ID NO/<br>DESCRIPTION/<br>SOURCE | SEQUENCE (5'-3') |
|---|---|
| SEQ ID NO: 375<br>Bxb1_NC_000009<br>(Artificial<br>Sequence) | CCCAGGGTCCCATGCGCTCCCCGGCCCTGACGGCGGTCTCC |

Linker sequences in Table 10 below.

TABLE 10

| Description | Sequence (5'-3') | Amino acid sequence |
|---|---|---|
| A-P2A | GGAAGCGGAGCTACTAACTTCAGCCT<br>GCTGAAGCAGGCTGGCGACGTGGAGG<br>AGAACCCTGGACCT (SEQ ID NO: 410) | GSGATNFSLLKQAGDVEENPGP (SEQ ID<br>NO: 418) |
| B-(GGGS)3 | GGGGGAGGAGGTTCTGGAGGCGGAGG<br>CTCCGGAGGCGGAGGGTCA (SEQ ID<br>NO: 411) | GGGGSGGGSGGGGS (SEQ ID NO: 419) |
| C-GGGGS | GGAGGTGGCGGGAGC (SEQ ID NO:<br>412) | GGGGS (SEQ ID NO: 420) |
| D-PAPAP | CCCGCACCAGCGCCT (SEQ ID NO:<br>413) | PAPAP (SEQ ID NO: 421) |
| E-(EAAAK)3 | GAGGCAGCTGCCAAGGAAGCCGCT<br>GCCAAGGAGGCGGCCGCAAAG<br>(SEQ ID NO: 414) | EAAAKEAAAKEAAAK (SEQ ID NO:<br>422) |
| F-XTEN | AGTGGGAGCGAGACCCCTGGGACT<br>AGCGAGTCAGCTACACCCGAAAGC<br>(SEQ ID NO: 415) | SGSETPGTSESATPES (SEQ ID NO: 423) |
| G-(GGS)6 | GGGGGGTCAGGTGGATCCGGCGG<br>AAGTGGCGGATCCGGTGGATCTGG<br>CGGCAGT (SEQ ID NO: 416) | GGSGGSGGSGGSGGSGGS (SEQ ID NO<br>424) |
| H-EAAAK | GAAGCTGCTGCTAAG (SEQ ID NO:<br>417) | EAAAK (SEQ ID NO: 425) |

Exemplary fusion sequences in Table 11 below.

| Description | Sequence |
|---|---|
| SpCas9-XTEN-<br>RT(1-478)-Sto7d-<br>GGGGS-BxbINT<br>Amino acid<br>SEQ ID NO: 376 | MKRTADGSEFESPKKKRKVDKKYSIGLDIGTNSVGWAVITDEYKVPS<br>KKFKVLGNTDRHSIKKNLIGALLFDSGETAEATRLKRTARRRYTRR<br>KNRICYLQEIFSNEMAKVDDSFFHRLEESFLVEEDKKHERHPIFGNI<br>VDEVAYHEKYPTIYHLRKKLVDSTDKADLRLIYLALAHMIKFRGHF<br>LIEGDLNPDNSDVDKLFIQLVQTYNQLFEENPINASGVDAKAILSAR<br>LSKSRRLENLIAQLPGEKKNGLFGNLIALSLGLTPNFKSNFDLAEDA<br>KLQLSKDTYDDDLDNLLAQIGDQYADLFLAAKNLSDAILLSDILRVN<br>TEITKAPLSASMIKRYDEHHQDLTLLKALVRQQLPEKYKEIFFDQS<br>KNGYAGYIDGGASQEEFYKFIKPILEKMDGTEELLVKLNREDLLRK<br>QRTFDNGSIPHQIHLGELHAILRRQEDFYPFLKDNREKIEKILTFRIP<br>YYVGPLARGNSRFAWMTRKSEETITPWNFEEVVDKGASAQSFIER<br>MTNFDKNLPNEKVLPKIISLLYEYFTVYNELTKVKYVTEGMRKPAF<br>LSGEQKKAIVDLLFKTNRKVTVKQLKEDYFKKIECFDSVEISGVED<br>RFNASLGTYHDLLKIIKDKDFLDNEENEDILEDIVLTLTLFEDREMIE<br>ERLKTYAHLFDDKVMKQLICRRRYTGWGRLSRKLINGIRDKQSGK<br>TILDFLKSDGFANRNFMQLIHDDSLTFKEDIQKAQVSGQGDSLHEHI<br>ANLAGSPAIKKGILQTVKVVDELVKVMGRHKPENIVIEMARENQTT<br>QKGQKNSRERMKRIEEGIKELGSQILKEHPVENTQLQNEKLYLYYL<br>QNGRDMYVDQELDINRLSDYDVDAIVPQSFLKDDSIDNKVLTRSDK<br>NRGKSDNVPSEEVVKKMKNYWRQLLNAKLITQRKFDNLTKAERG<br>GLSELDKAGFIKRQLVETRQITKHVAQILDSRMNTKYDENDKLIRE<br>VKVITLKSKLVSDFRKDFQFYKVREINNYHHAHDAYLNAVVGTALI<br>KKYPKLESEFVYGDYKVYDVRKMIAKSEQEIGKATAKYFFYSNIMN<br>FFKTEITLANGEIRKRPLIETNGETGEIVWDKGRDFATVRKVLSMP<br>QVNIVKKTEVQTGGFSKESILPKRNSDKLIARKKDWDPKKYGGFDS |

| Description | Sequence |
|---|---|
| | PTVAYSVLVVAKVEKGKSKKLKSVKELLGITIMERSSFEKNPIDFLE |
| | AKGYKEVKKDLIIKLPKYSLFELENGRKRMLASAGELQKGNELAL |
| | PSKYVNFLYLASHYEKLKGSPEDNEQKQLFVEQHKHYLDEHEQISE |
| | FSKRVILADANLDKVLSAYNKHRDKPIREQAENIIHLFTLTNLGAPA |
| | AFKYFDTTIDRKRYTSTKEVLDATLIHQSITGLYETRIDLSQLGGDS |
| | GGSSGGSSGSETPGTSESATPESSGSETPGTSESATPESSGSETPGTSESAT |
| | PESSGGSSGGSSTLNIEDEYRLHETSKEPDVSLGSTWLSDFPQAWAET |
| | GGMGLAVRQAPLIIPLKATSTPVSIKQVPMSQEARLGIKPHIQRLLD |
| | QGILVPCQSPWNTPLLPVKKPGTNDYRPVQDLREVNKRVEDIHPTV |
| | PNPYNLLSGPPPSHQWYTVLDLKDAFFCLRLHPTSQPLFAFEWRDP |
| | EMGISGQLTWTRLPQGFKNSPTLFNEALHRDLADFRIQHPDLILLQ |
| | YVDDLLLAATSELDCQQGTRALLQTLGNLGYRASAKKAQKQKQV |
| | KYLGYLLKEGQRWLTEARKETVMGQPTPKTPRQLREFLGKAGFC |
| | RLFIPGFAEMAAPLYPLTKPGTLFNWGPDQQKAYQEIKQALLTAPA |
| | LGLPDLTKPFELFVDEKQGYAKGVLTQKLGPWRRPVAYLSKKLDP |
| | VAAGWPPCLRMVAAIAVLTKDAGKLTMGQPLVILAPHAVEALVK |
| | QPPDRWLSNARNITHYQALLLDTDRVQFGPVVALNPATLLPLPEEG |
| | LQIINCLDGTGGGGVTVKFKYKGEELEVDISKIKKVWRVGKNIISFT |
| | YDDNGKTGRGAVSEKDAPKELLQMLEKSGKKSGGSKRTADGSEFE |
| | PKKKRKVGGGGSPKKKRKVYPYDVPDYAGSRALVVIRLSRVTDATTS |
| | PERQLESCQQLCAQRGWDVVGVAEDLDVSGAVDPFDRKRRPNLAR |
| | WLAFEEQPFDVIVAYRVDRLTRSIRHLQQLVHWAEDHKKLVVSAT |
| | EAHFDTTTPFAAVVIALMGTVAQMELEAIKERNRSAAHFNIRAGKY |
| | RGSLPPWGYLPTRVDGEWRLVPDPVQRERILEVYHRVVDNHEPLH |
| | LVAHDLNRRGVLSPKDYFAQLGREPQGREWSATALKRSMISEAM |
| | LGYATLNGKTVRDDDGAPLVRAEPILTREQLEALRAELVKTSRAKP |
| | AVSTPSLLLRVLFCAVCGEPAYKFAGGGRKHPRYRCRSMGFPKHC |
| | GNGTVAMAEWDAFCEEQVLDLLGDAERLEKVWVAGSDSAVELAE |
| | VNAELVDLTSLIGSPAYRAGSPQREALDARIAALAARQEELEGLEAR |
| | PSGWEWRETGQRFGDWWREQDTAAKNTWLRSMNVRLTFDVRGG |
| | LTRTIDFGDLQEYEQHLRLGSVVERLHTGMS |
| SpCas9-XTEN-<br>RT(1-478)-Sto7d-<br>GGGGS-BxbINT<br>Nucleic acid<br>SEQ ID NO: 377 | ATGAAACGGACAGCCGACGGAAGCGAGTTCGAGTCACCAAAGAAG<br>AAGCGGAAAGTCGACAAGAAGTACAGCATCGGCCTGGACATCGGCA<br>CCAACTCTGTGGGCTGGGCCGTGATCACCGACGAGTACAAGGTGCC<br>CAGCAAGAAATTCAAGGTGCTGGGCAACACCGACCGGCACAGCATC<br>AAGAAGAACCTGATCGGAGCCCTGCTGTTCGACAGCGGCGAAACAG<br>CCGAGGCCACCCGGCTGAAGAGAACCGCCAGAAGAAGATACACCA<br>GACGGAAGAACCGGATCTGCTATCTGCAAGAGATCTTCAGCAACGA<br>GATGGCCAAGGTGGACGACAGCTTCTTCCACAGACTGGAAGAGTCC<br>TTCCTGGTGGAAGAGGATAAGAAGCACGAGCGGCACCCCATCTTCG<br>GCAACATCGTGGACGAGGTGGCCTACCACGAGAAGTACCCCACCAT<br>CTACCACCTGAGAAAGAAACTGGTGGACAGCACCGACAAGGCCGAC<br>CTGCGGCTGATCTATCTGGCCCTGGCCCACATGATCAAGTTCCGGGG<br>CCACTTCCTGATCGAGGGCGACCTGAACCCCGACAACAGCGACGTG<br>GACAAGCTGTTCATCCAGCTGGTGCAGACCTACAACCAGCTGTTCGA<br>GGAAAACCCCATCAACGCCAGCGGCGTGGACGCCAAGGCCATCCTG<br>TCTGCCAGACTGAGCAAGAGCAGACGGCTGGAAAATCTGATCGCCC<br>AGCTGCCCGGCGAGAAGAAGAATGGCCTGTTCGGAAACCTGATTGC<br>CCTGAGCCTGGGCCTGACCCCCAACTTCAAGAGCAACTTCGACCTGG<br>CCGAGGATGCCAAACTGCAGCTGAGCAAGGACACCTACGACGACGA<br>CCTGGACAACCTGCTGGCCCAGATCGGCGACCAGTACGCCGACCTG<br>TTTCTGGCCGCCAAGAACCTGTCCGACGCCATCCTGCTGAGCGACAT<br>CCTGAGAGTGAACACCGAGATCACCAAGGCCCCCCTGAGCGCCTCT<br>ATGATCAAGAGATACGACGAGCACCACCAGGACCTGACCCTGCTGA<br>AAGCTCTCGTGCGGCAGCAGCTGCCTGAGAAGTACAAAGAGATTTT<br>CTTCGACCAGAGCAAGAACGGCTACGCCGGCTACATTGACGGCGGA<br>GCCAGCCAGGAAGAGTTCTACAAGTTCATCAAGCCCATCCTGGAAA<br>AGATGGACGGCACCGAGGAACTGCTCGTGAAGCTGAACAGAGAGG<br>ACCTGCTGCGGAAGCAGCGGACCTTCGACAACGGCAGCATCCCCCA<br>CCAGATCCACCTGGGAGAGCTGCACGCCATTCTGCGGCGGCAGGAA<br>GATTTTTACCCATTCCTGAAGGACAACCGGGAAAAGATCGAGAAGA<br>TCCTGACCTTCCGCATCCCCTACTACGTGGGCCCTCTGGCCAGGGGA<br>AACAGCAGATTCGCCTGGATGACCAGAAAGAGCGAGGAAACCATCA<br>CCCCCTGGAACTTCGAGGAAGTGGTGGACAAGGGCGCTTCCGCCCA<br>GAGCTTCATCGAGCGGATGACCAACTTCGATAAGAACCTGCCCAAC<br>GAGAAGGTGCTGCCCAAGCACAGCCTGCTGTACGAGTACTTCACCG<br>TGTATAACGAGCTGACCAAAGTGAAATACGTGACCGAGGGAATGAG<br>AAAGCCCGCCTTCCTGAGCGGCGAGCAGAAAAAGGCCATCGTGGAC<br>CTGCTGTTCAAGACCAACCGGAAAGTGACCGTGAAGCAGCTGAAAG<br>AGGACTACTTCAAGAAAATCGAGTGCTTCGACTCCGTGGAAATCTCC<br>GGCGTGGAAGATCGGTTCAACGCCTCCCTGGGCACATACCACGATC<br>TGCTGAAAATTATCAAGGACAAGGACTTCCTGGACAATGAGGAAAA<br>CGAGGACATTCTGGAAGATATCGTGCTGACCCTGACACTGTTTGAGG<br>ACAGAGAGATGATCGAGGAACGGCTGAAAACCTATGCCCACCTGTT<br>CGACGACAAAGTGATGAAGCAGCTGAAGCGGCGGAGATACACCGG<br>CTGGGGCAGGCTGAGCCGGAAGCTGATCAACGGCATCCGGGACAAG |

| Description | Sequence |
|---|---|
| | CAGTCCGGCAAGACAATCCTGGATTTCCTGAAGTCCGACGGCTTCGC |
| | CAACAGAAACTTCATGCAGCTGATCCACGACGACAGCCTGACCTTT |
| | AAAGAGGACATCCAGAAAGCCCAGGTGTCCGGCCAGGGCGATAGCC |
| | TGCACGAGCACATTGCCAATCTGGCCGGCAGCCCCGCCATTAAGAA |
| | GGGCATCCTGCAGACAGTGAAGGTGGTGGACGAGCTCGTGAAAGTG |
| | ATGGGCCGGCACAAGCCCGAGAACATCGTGATCGAAATGGCCAGAG |
| | AGAACCAGACCCACCCAGAAGGGACAGAAGAACAGCCGCGAGAGAA |
| | TGAAGCGGATCGAAGAGGGCATCAAAGAGCTGGGCAGCCAGATCCT |
| | GAAAGAACACCCCGTGGAAAACACCCAGCTGCAGAACGAGAAGCT |
| | GTACCTGTACTACCTGCAGAATGGGCGGGATATGTACGTGGACCAG |
| | GAACTGGACATCAACCGGCTGTCCGACTACGATGTGGACGCTATCG |
| | TGCCTCAGAGCTTTCTGAAGGACGACTCCATCGACAACAAGGTGCT |
| | GACCAGAAGCGACAAGAACCGGGGCAAGAGCGACAACGTGCCCTC |
| | CGAAGAGGTCGTGAAGAAGATGAAGAACTACTGGCGGCAGCTGCTG |
| | AACGCCAAGCTGATTACCCAGAGAAAGTTCGACAATCTGACCAAGG |
| | CCGAGAGAGGCGGCCTGAGCGAACTGGATAAGGCCGGCTTCATCAA |
| | GAGACAGCTGGTGGAAACCCGGCAGATCACAAAGCACGTGGCACA |
| | GATCCTGGACTCCCGGATGAACACTAAGTACGACGAGAATGACAAG |
| | CTGATCCGGGAAGTGAAAGTGATCACCCTGAAGTCCAAGCTGGTGT |
| | CCGATTTCCGGAAGGATTTCCAGTTTTACAAAGTGCGCGAGATCAAC |
| | AACTACCACCACGCCCACGACGCCTACCTGAACGCCGTCGTGGGAA |
| | CCGCCCTGATCAAAAAGTACCCTAAGCTGGAAAGCGAGTTCGTGTA |
| | CGGCGACTACAAGGTGTACGACGTGCGGAAGATGATCGCCAAGAGC |
| | GAGCAGGAAATCGGCAAGGCTACCGCCAAGTACTTCTTCTACAGCA |
| | ACATCATGAACTTTTTCAAGACCGAGATTACCCTGGCCAACGGCGA |
| | GATCCGGAAGCGGCCTCTGATCGAGACAAACGGCGAAACCGGGGA |
| | GATCGTGTGGGATAAGGGCCGGGATTTTGCCACCGTGCGGAAAGTG |
| | CTGAGCATGCCCCAAGTGAATATCGTGAAAAAGACCGAGGTGCAGA |
| | CAGGCGGCTTCAGCAAAGAGTCTATCCTGCCCAAGAGGAACAGCGA |
| | TAAGCTGATCGCCAGAAAGAAGGACTGGGACCCTAAGAAGTACGGC |
| | GGCTTCGACAGCCCCACCGTGGCCTATTCTGTGCTGGTGGTGGCCAA |
| | AGTGGAAAAGGGCAAGTCCAAGAAACTGAAGAGTGTGAAAGAGCT |
| | GCTGGGGATCACCATCATGGAAAGAAGCAGCTTCGAGAAGAATCCC |
| | ATCGACTTTCTGGAAGCCAAGGGCTACAAAGAAGTGAAAAAGGACC |
| | TGATCATCAAGCTGCCTAAGTACTCCCTGTTCGAGCTGGAAAACGGC |
| | CGGAAGAGAATGCTGGCCTCTGCCGGCGAACTGCAGAAGGGAAACG |
| | AACTGGCCCTGCCCTCCAAATATGTGAACTTCCTGTACCTGGCCAGC |
| | CACTATGAGAAGCTGAAGGGCTCCCCCGAGGATAATGAGCAGAAAC |
| | AGCTGTTTGTGGAACAGCACAAGCACTACCTGGACGAGATCATCGA |
| | GCAGATCAGCGAGTTCTCCAAGAGAGTGATCCTGGCCGACGCTAAT |
| | CTGGACAAAGTGCTGTCCGCCTACAACAAGCACCGGGATAAGCCCA |
| | TCAGAGAGCAGGCCGAGAATATCATCCACCTGTTTACCCTGACCAAT |
| | CTGGGAGCCCCTGCCGCCTTCAAGTACTTTGACACCACCATCGACCG |
| | GAAGAGGTACACCAGCACCAAAGAGGTGCTGGACGCCACCCTGATC |
| | CACCAGAGCATCACCGGCCTGTACGAGACACGGATCGACCTGTCTC |
| | AGCTGGGAGGTGACTCTGGAGGATCTAGCGGAGGATCCTCTGGCAG |
| | CGAGACACCAGGAACAAGCGAGTCAGCAACACCAGAGAGCTCTGGT |
| | AGCGAGACACCCGGTACCAGTGAAAGCGCCACGCCAGAAAGCAGT |
| | GGGAGTGAGACTCCGGGTACATCTGAATCAGCGACACCGGAATCAA |
| | GTGGCGGCAGCAGCGGCGGCAGCAGCACCCTAAATATAGAAGATGA |
| | GTATCGGCTACATGAGACCTCAAAAGAGCCAGATGTTTCTCTAGGGT |
| | CCACATGGCTGTCTGATTTTCCTCAGGCCTGGGCGGAAACCGGGGGC |
| | ATGGGACTGGCAGTTCGCCAAGCTCCTCTGATCATACCTCTGAAAGC |
| | AACCTCTACCCCCGTGTCCATAAAACAATACCCCATGTCACAAGAA |
| | GCCAGACTGGGGATCAAGCCCCACATACAGAGACTGTTGGACCAGG |
| | GAATACTGGTACCCTGCCAGTCCCCCTGGAACACGCCCCTGCTACCC |
| | GTTAAGAAACCAGGGACTAATGATTATAGGCCTGTCCAGGATCTGA |
| | GAGAAGTCAACAAGCGGGTGGAAGACATCCACCCCACCGTGCCCAA |
| | CCCTTACAACCTCTTGAGCGGGCCCCACCGTCCCACCAGTGGTACA |
| | CTGTGCTTGATTTAAAGGATGCCTTTTTCTGCCTGAGACTCCACCCC |
| | ACCAGTCAGCCTCTCTTCGCCTTTGAGTGGAGAGATCCAGAGATGGG |
| | AATCTCAGGACAATTGACCTGGACCAGACTCCCACAGGGTTTCAAA |
| | AACAGTCCCACCCTGTTTAATGAGGCACTGCACAGAGACCTAGCAG |
| | ACTTCCGGATCCAGCACCCAGACTTGATCCTGCTACAGTACGTGGAT |
| | GACTTACTGCTGGCCGCCACTTCTGAGCTAGACTGCCAACAAGGTAC |
| | TCGGGCCCTGTTACAAACCCTAGGGAACCTCGGGTATCGGGCCTCG |
| | GCCAAGAAAGCCCAAATTTGCCAGAAACAGGTCAAGTATCTGGGGT |
| | ATCTTCTAAAAGAGGGTCAGAGATGGCTGACTGAGGCCAGAAAAGA |
| | GACTGTGATGGGGCAGCCTACTCCGAAGACCCCTCGACAACTAAGG |
| | GAGTTCCTAGGGAAGGCAGGCTTCTGTCGCCTCTTCATCCCTGGGTT |
| | TGCAGAAATGGCAGCCCCCCTGTACCCTCTCACCAAACCGGGGACT |
| | CTGTTTAATTGGGGCCCAGACCAACAAAAGGCCTATCAAGAAATCA |
| | AGCAAGCTCTTCTAACTGCCCCAGCCCTGGGGTTGCCAGATTTGACT |
| | AAGCCCTTTGAACTCTTTGTCGACGAGAAGCAGGGCTACGCCAAAG |
| | GTGTCCTAACGCAAAAACTGGGACCTTGGCGTCGGCCGGTGGCCTA |
| | CCTGTCCAAAAAGCTAGACCCAGTAGCAGCTGGGTGGCCCCCTTGC |
| | CTACGGATGGTAGCAGCCATTGCCGTACTGACAAAGGATGCAGGCA |

-continued

| Description | Sequence |
|---|---|
| | AGCTAACCATGGGACAGCCACTAGTCATTCTGGCCCCCCATGCAGTA<br>GAGGCACTAGTCAAACAACCCCCGACCGCTGGCTTTCCAACGCCC<br>GGATGACTCACTATCAGGCCTTGCTTTTGGACACGGACCGGGTCCAG<br>TTCGGACCGGTGGTAGCCCTGAACCCGGCTACGCTGCTCCCACTGCC<br>TGAGGAAGGGCTGCAACACAACTGCCTTGATGGGACAGGTGGCGGT<br>GGTGTCACCGTCAAGTTCAAGTACAAGGGTGAGGAACTTGAAGTTG<br>ATATTAGCAAAATCAAGAAGGTTTGGCGCGTTGGTAAAATGATATC<br>TTTTACTTATGACGACAACGGCAAGACAGGTAGAGGGGCAGTGTCT<br>GAGAAAGACGCCCCCAAGGAGCTGTTGCAAATGTTGGAAAAGTCTG<br>GGAAAAAGTCTGGCGGCTCAAAAAGAACCGCCGACGGCAGCGAATT<br>CGAGCCCAAGAAGAAGAGGAAAGTCGGAGGTGGCGGGAGCCCAAA<br>AAAGAAAAGAAAAGTGTATCCCTATGATGTCCCCGATTATGCCGGT<br>TCAAGAGCCCTGGTCGTGATTAGACTGAGCCGAGTGACAGACGCCA<br>CCACAAGTCCCGAGAGACAGCTGGAATCATGCCAGCAGCTCTGTGC<br>TCAGCGGGGTTGGGATGTGGTCGGCGTGGCAGAGGATCTGGACGTG<br>AGCGGGGCCGTCGATCCATTCGACAGAAAGAGGAGGCCCAACCTGG<br>CAAGATGGCTCGCTTTCGAGGAACAGCCCTTTGATGTGATCGTCGCC<br>TACAGAGTGGACCGGCTGACCCGCTCAATTCGACATCTCCAGCAGCT<br>GGTGCATTGGGCTGAGGACCACAAGAAACTGGTGGTCAGCGCAACA<br>GAAGCCCACTTCGATACTACCACACCTTTTGCCGCTGTGGTCATCGC<br>ACTGATGGGCACTGTGGCCCAGATGGAGCTCGAAGCTATCAAGGAG<br>CGAAACAGGAGCGCAGCCCATTTCAATATTAGGGCCGGTAAATACA<br>GAGGCTCCCTGCCCCCTTGGGGATATCTCCCTACCAGGGTGGATGGG<br>GAGTGGAGACTGGTGCCAGACCCCGTCCAGAGAGAGCGGATTCTGG<br>AAGTGTACCACAGAGTGGTCGATAACCACGAACCACTCCATCTGGT<br>GGCACACGACCTGAATAGACGCGGCGTGCTCTCTCCAAAGGATTAT<br>TTTGCTCAGCTGCAGGGAAGAGAGCCACAGGGAAGAGAATGGAGTG<br>CTACTGCACTGAAGAGATCTATGATCAGTGAGGCTATGCTGGGTTAC<br>GCAACACTCAATGGCAAAACTGTCCGGGACGATGACGGAGCCCCTC<br>TGGTGAGGGCTGAGCCTATTCTCACCAGAGAGCAGCTCGAAGCTCT<br>GCGGGCAGAACTGGTCAAGACTAGTCGCGCCAAACCTGCCGTGAGC<br>ACCCCCAAGCCTGCTCCTGAGGGTGCTGTTCTGCGCCGTCTGTGAGA<br>GCCAGCATACAAGTTTGCCGGCGGAGGGCGCAAACATCCCCGCTAT<br>CGATGCAGGAGCATGGGGTTCCCTAAGCACTGTGGAAACGGGACAG<br>TGGCCATGGCTGAGTGGGACGCCTTTTGCGAGGAACAGGTGCTGGA<br>TCTCCTGGGTGACGCTGAGCGGCTGGAAAAAGTGTGGGTGGCAGGA<br>TCTGACTCCGCTGTGGAGCTGGCAGAAGTCAATGCCGAGCTCGTGG<br>ATCTGACTTCCCTCATCGGATCTCCTGCATATAGAGCTGGGTCCCCA<br>CAGAGAGAAGCTCTGGACGCACGAATTGCTGCACTCGCTGCTAGAC<br>AGGAGGAACTGGAGGGCTGGAGGCCAGGCCCTCTGGATGGGAGTG<br>GCGAGAAACCGGACAGAGGTTTGGGGATTGGTGGAGGGAGCAGGA<br>CACCGCAGCCAAGAACACATGGCTGAGATCCATGAATGTCCGGCTC<br>ACATTCGACGTGCGCGGTGGCCTGACTCGAACCATCGATTTTGGCGA<br>CCTGCAGGAGTATGAACAGCACCTGAGACTGGGGTCCGTGGTCGAA<br>AGACTGCACACTGGGATGTCC |
| SpCas9<br>Amino acid<br>SEQ ID NO: 378 | DKKYSIGLDIGTNSVGWAVITDEYKVPSKKFKVLGNTDRHSIKKNLIGA<br>LLFDSGETAEATRLKRTARRRYTRRKNRICYLQEIFSNEMAKVDDSFFH<br>RLEESFLVEEDKKHERHPIFGNIVDEVAYHEKYPTIYHLRKKLVDSTDK<br>ADLRLIYLALAHMIKFRGHFLIEGDLNPDNSDVDKLFIQLVQTYNQLFE<br>ENPINASGVDAKAILSARLSKSRRLENLIAQLPGEKKNGLFGNLIALSLG<br>LTPNFKSNFDLAEDAKLQLSKDTYDDDLDNLLAQIGDQYADLFLAAKN<br>LSDAILLSDILRVNTEITKAPLSASMIKRYDEHHQDLTLLKALVRQQLPE<br>KYKEIFFDQSKNGYAGYIDGGASQEEFYKFIKPILEKMDGTEELLVKLN<br>REDLLRKQRTFDNGSIPHQIHLGELHAILRRQEDFYPFLKDNREKIEKILT<br>FRIPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASL<br>GTYHDLLKIIKDKDFLDNEENEDILEDIVLTLTLFEDREMIEERLKTYAH<br>LFDDKVMKQLKRRRYTGWGRLSRKLINGIRDKQSGKTILDFLKSDGFA<br>NRNFMQLIHDDSLTFKEDIQKAQVSGQGDSLHEHIANLAGSPAIKKGIL<br>QTVKVVDELVKVMGRHKPENIVIEMARENQTTQKGQKNSRERMKRIE<br>EGIKELGSQILKEHPVENTQLQNEKLYLYYLQNGRDMYVDQELDINRL<br>SDYDVDAIVPQSFLKDDSIDNKVLTRSDKNRGKSDNVPSEEVVKKMKN<br>YWRQLLNAKLITQRKFDNLTKAERGGLSELDKAGFIKRQLVETRQITK<br>HVAQILDSRMNTKYDENDKLIREVKVITLKSKLVSDFRKDFQFYKVREI<br>NNYHHAHDAYLNAVVGTALIKKYPKLESEFVYGDYKVYDVRKMIAKS<br>EQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKK<br>DWDPKKYGGFDSPTVAYSVLVVAKVEKGKSKKLKSVKELLGITIMERS<br>SFEKNPIDFLEAKGYKEVKKDLIIKLPKYSLFELENGRKRMLASAGELQ<br>KGNELALPSKYVNFLYLASHYEKLKGSPEDNEQKQLFVEQHKYLDEII<br>EQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD |
| RT(1-478)-Sto7d<br>Amino acid | LNIEDEYRLHETSKEPDVSLGSTWLSDFPQAWAETGGMGLAVRQAPLII<br>PLKATSTPVSIKQYPMSQEARLGIKPHIQRLLDQGILVPCQSPWNTPLLP |

-continued

| Description | Sequence |
|---|---|
| SEQ ID NO: 379 | VKKPGTNDYRPVQDLREVNKRVEDIHPTVPNPYNLLSGPPPSHQWYTV<br>LDLKDAFFCLRLHPTSQPLFAFEWRDPEMGISGQLTWTRLPQGFKNSPT<br>LFNEALHRDLADFRIQHPDLILLQYVDDLLLAATSELDCQQGTRALLQT<br>LGNLGYRASAKKAQICQKQVKYLGYLLKEGQRWLTEARKETVMGQPT<br>PKTPRQLREFLGKAGFCRLFIPGFAEMAAPLYPLTKPGTLFNWGPDQQK<br>AYQEIKQALLTAPALGLPDLTKPFELFVDEKQGYAKGVLTQKLGPWRR<br>PVAYLSKKLDPVAAGWPPCLRMVAAIAVLTKDAGKLTMGQPLVILAP<br>HAVEALVKQPPDRWLSNARMTHYQALLLDTDRVQFGPVVALNPATLL<br>PLPEEGLQHNCLDGTGGGGVTVKFKYKGEELEVDISKIKKVWRVGKMI<br>SFTYDDNGKTGRGAVSEKDAPKELLQMLEKSGKKSGGSKRTADGS |
| BxbINT<br>Amino acid<br>SEQ ID NO: 380 | SRALVVIRLSRVTDATTSPERQLESCQQLCAQRGWDVVGVAEDLDVSG<br>AVDPFDRKRRPNLARWLAFEEQPFDVIVAYRVDRLTRSIRHLQQLVHW<br>AEDHKKLVVSATEAHFDTTTPFAAVVIALMGTVAQMELEAIKERNRSA<br>AHFNIRAGKYRGSLPPWGYLPTRVDGEWRLVPDPVQRERILEVYHRVV<br>DNHEPLHLVAHDLNRRGVLSPKDYFAQLQGREPQGREWSATALKRSM<br>ISEAMLGYATLNGKTVRDDDGAPLVRAEPILTREQLEALRAELVKTSRA<br>KPAVSTPSLLLRVLFCAVCGEPAYKFAGGGRKHPRYRCRSMGFPKHCG<br>NGTVAMAEWDAFCEEQVLDLLGDAERLEKVWVAGSDSAVELAEVNA<br>ELVDLTSLIGSPAYRAGSPQREALDARIAALAARQEELEGLEARPSGWE<br>WRETGQRFGDWWREQDTAAKNTWLRSMNVRLTFDVRGGLTRTIDFG<br>DLQEYEQHLRLGSVVERLHTGMS |

EXAMPLES

While several experimental Examples are contemplated, these Examples are intended to be non-limiting.

Example 1

CRE Integration Efficiency

Figure 3:
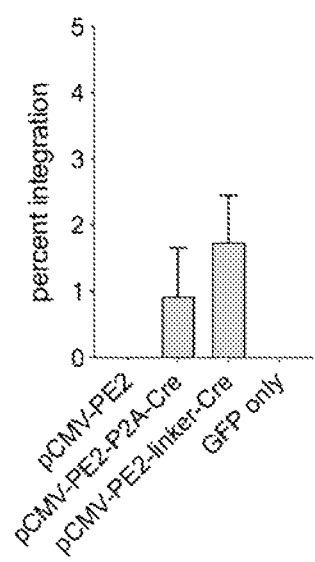
FIG. 3 shows the percent integration of green fluorescent protein (GFP) in the lentiviral integrated lox71 site in HEK293FT cell line in the presence of various plasmids according to embodiments of the present teachings.

The efficiency of the CRE integration was tested. In order to test the efficacy of PASTE with GFP using lox71/lox66/Cre recombinase system, a clonal HEK293FT cell line with lox71 sequence (SEQ ID NO: 1) integrated into the genome using lentivirus was developed. The integration of GFP was tested by transfection of modified HEK293FT cell line with: (1) plus/minus SEQ ID NO: 71 comprising a Cre recombinase expression plasmid, and (2) SEQ ID NO: 72 comprising a GFP template and a lox 66 Cre site of SEQ ID NO: 2. After 72 hours, the percent integration of GFP into the lox71 site was probed. FIG. 3 shows the percent integration of GFP in the lentiviral integrated lox71 site in HEK293FT cell line in the presence of various plasmids. It was observed that pCMV PE2 P2A Cre (SEQ ID NO: 73), a mammalian expression vector with prime editing complex and Cre recombinase linked to PE2 via a cleavable linker or a non-cleavable linker, shows integration of GFP.

Example 2

Figure 4:
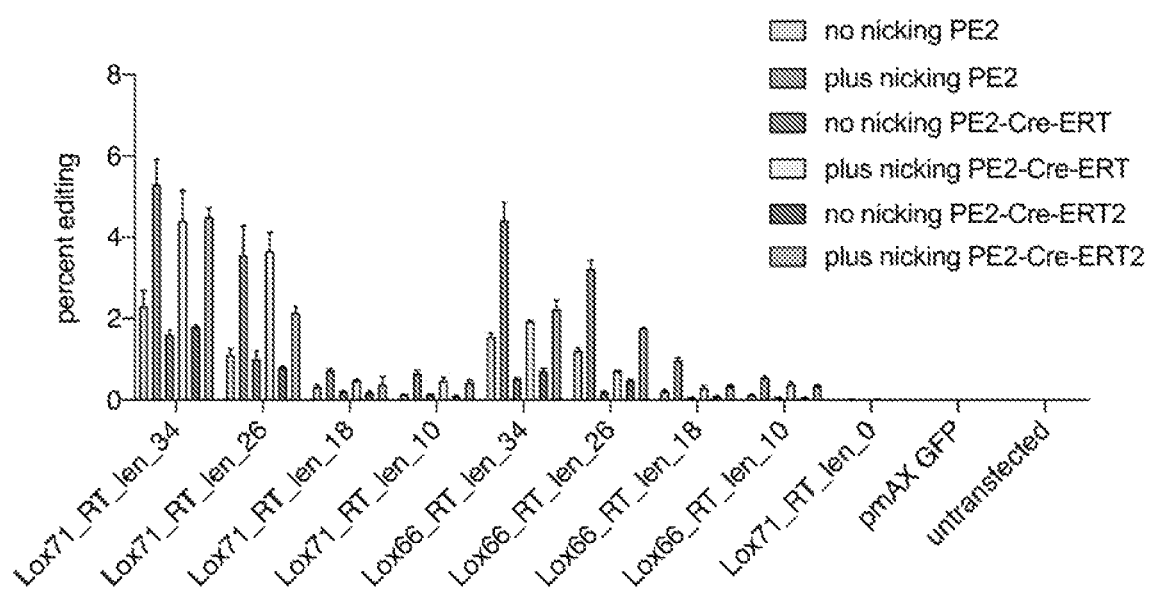
FIG. 4 shows the percent editing of the HEK293FT genome for incorporation of various lengths of lox71 or lox66 according to embodiments of the present teachings.

Programmable Addition Via Site-Specific Targeting Elements (PASTE) with Cre Recombinase—Addition of Lox Site The lox71 (SEQ ID NO: 1) or lox66 (SEQ ID NO: 2) sequence was inserted into the HEK293FT cell genome using prime editing to test integration of GFP into the HEK293FT genome. In order to insert lox71 or lox66 sequence into HEK293FT cell genome, a pegRNA with PBS length of 13 base pairs operably linked to RT region of varying lengths was used. The following plasmids were used in the transfection of HEK293FT cells. The cells were transfected with (1) prime editing construct (PE2) or PE2 with conditional Cre expression, (2) Lox71 or Lox66 pegRNA targeting the HEK3 locus, and (3) plus/minus+90 HEK3 nicking second guide RNA targeting the HEK3 locus (+90 ngRNA). After 72 hours, the percent editing of the HEK293FT genome at the HEK3 locus was probed for incorporation of various lengths of lox71 or lox66 (see FIG. 4). It was observed that 34 base pair lox71 (HEK3 locus guide, SEQ ID NO: 83; and Lox71 pegRNA with RT 34 and PBS 13, SEQ ID NO: 81) with +90 ngRNA (SEQ ID NO: 75) and 34 base pair lox66 (HEK3 locus guide, SEQ ID NO: 83; and Lox66 pegRNA with RT 34 and PBS 13, SEQ ID NO: 82) with +90 ngRNA (SEQ ID NO: 75) had the highest percent editing.

Example 3

PASTE with Cre Recombinase—Integration of Gene

Figure 5A:
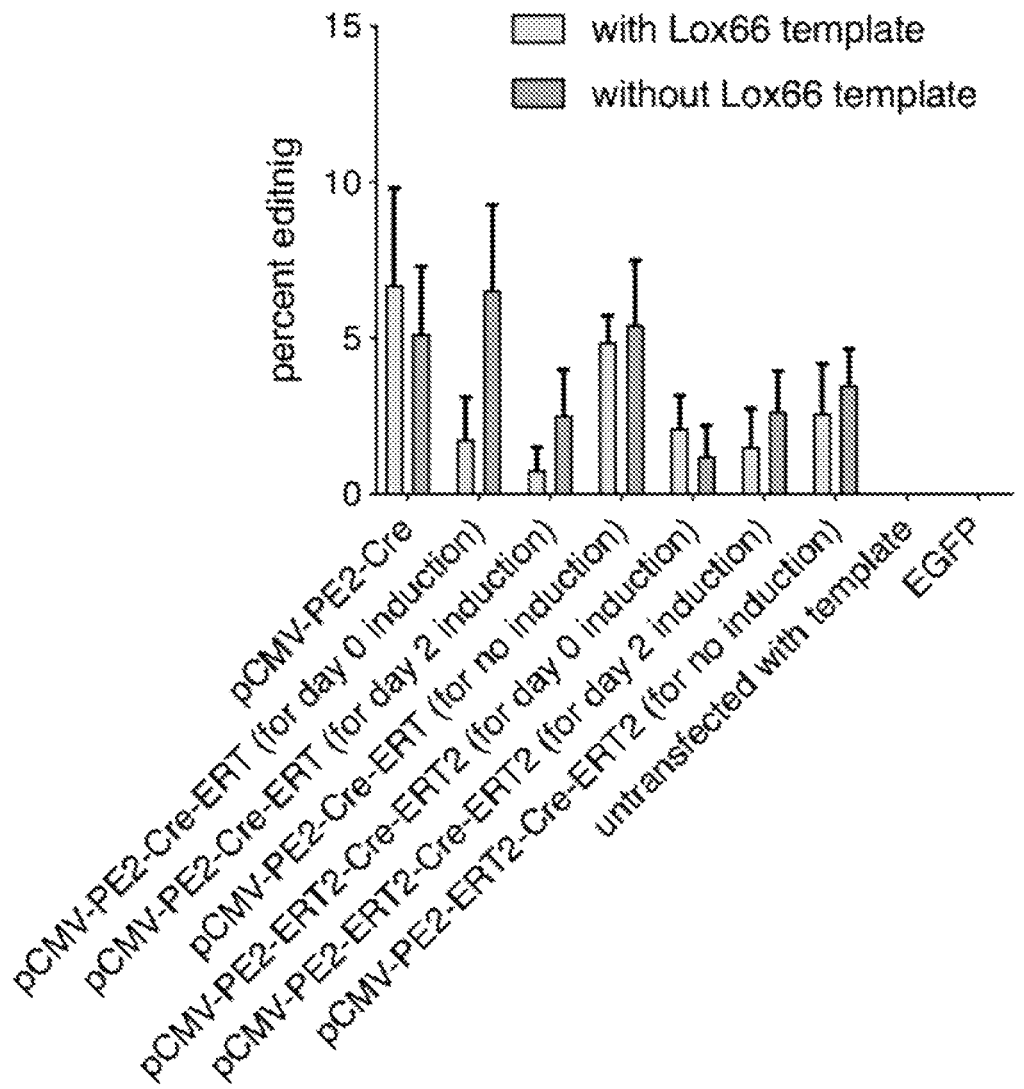
FIG. 5A shows the percent editing of lox71 site with different PE/Cre vectors according to embodiments of the present teachings.
Figure 5B:
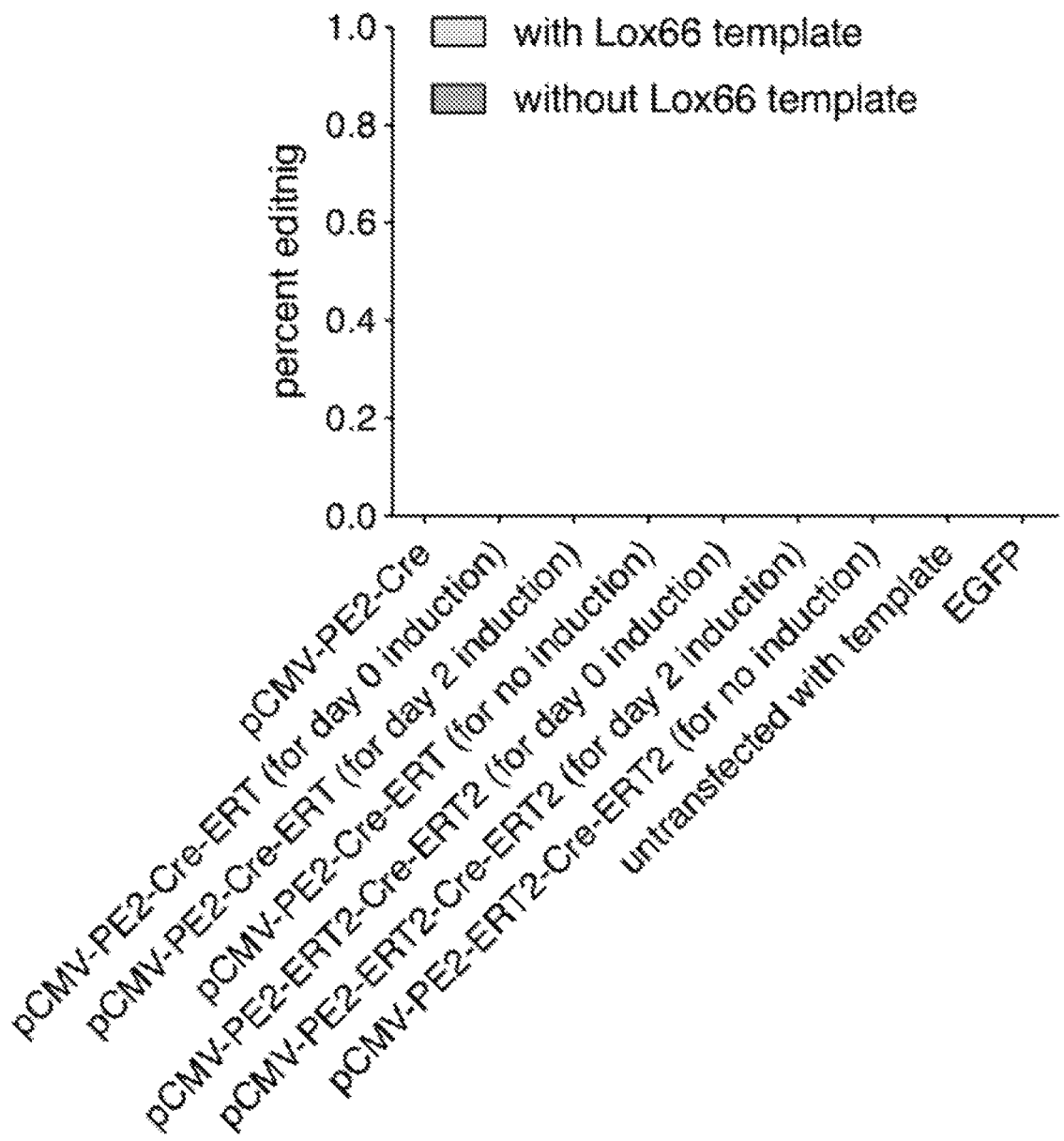
FIG. 5B shows the percent integration of GFP at the lox71 site in HEK293FT cell genome according to embodiments of the present teachings.

The lox71 or lox66 pegRNAs having PBS length of 13 base pairs and insert length of 34 base pairs were used to probe integration of GFP in the HEK293F genome. The PE and Cre were delivered in an inducible expression vectors and induced at day 2. The HEK293FT cells were transfected with the following plasmids: (1) prime editing construct (PE2 or PE2 with conditional Cre expression); (2) Lox71 pegRNA; (3) plus/minus+90 HEK3 nicking guide RNA; and (4) EGFP template with Lox66 site. After 72 hours, the percent editing of lox71 site and percent integration of GFP was probed with or without lox66 site in the presence of various PE/Cre constructs. FIG. 5A summarizes the percent editing of lox71 site with different PE/Cre vectors. FIG. 5B summarizes the percent integration of GFP at the lox71 site in HEK293FT cell genome. It was observed that although the lox71 site was edited in the presence of inducible or non-inducible PE/Cre expression system, there was no GFP integration.

Example 4

Bxb1 Integration Data *Lenti* Reporter

Figure 6:
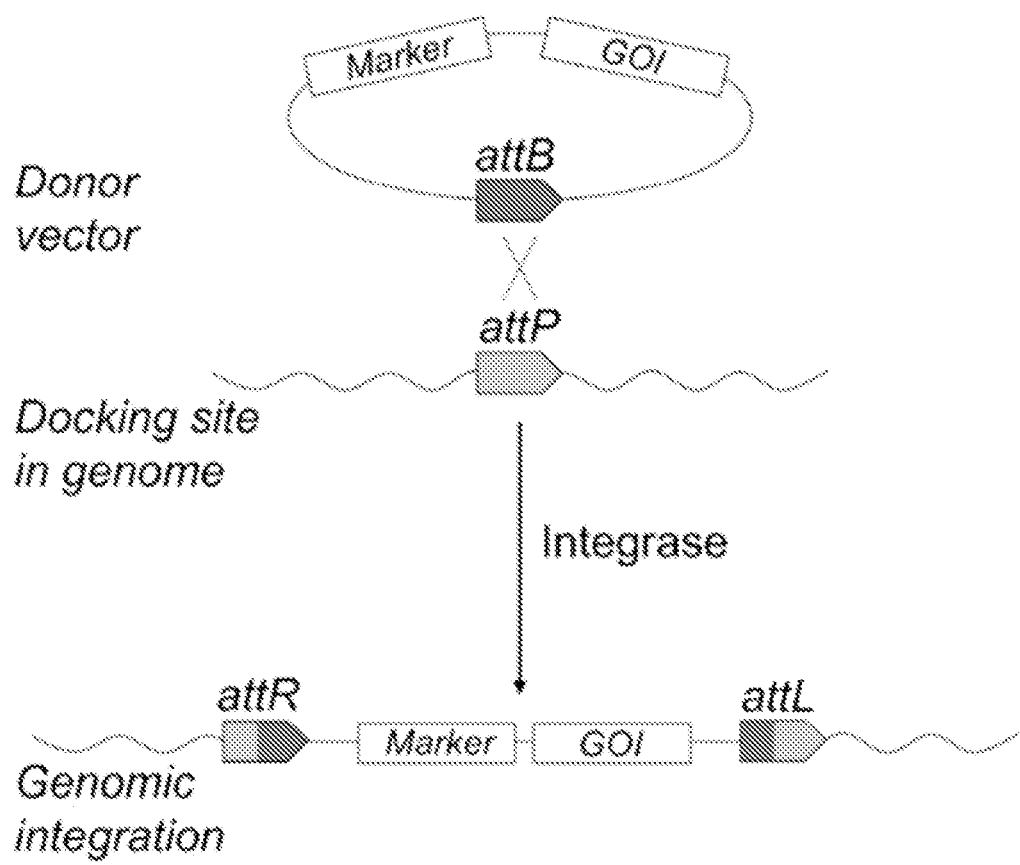
FIG. 6 shows a schematic representation of using Bxb1 to integrate a nucleic acid into the genome according to embodiments of the present teachings.

The integration system was switched to an integrase system that could result in an integration of target genes into a genome with higher efficiency. Serine integrase Bxb1 has been shown to be more active than Cre recombinase and highly efficient in bacteria and mammalian cells for irreversible integration of target genes. FIG. 6 shows a schematic of PASTE methodology using Bxb1 (Merrick, C. A. et al., ACS Synth. Biol. 2018, 7, 299-310).

Figure 7:
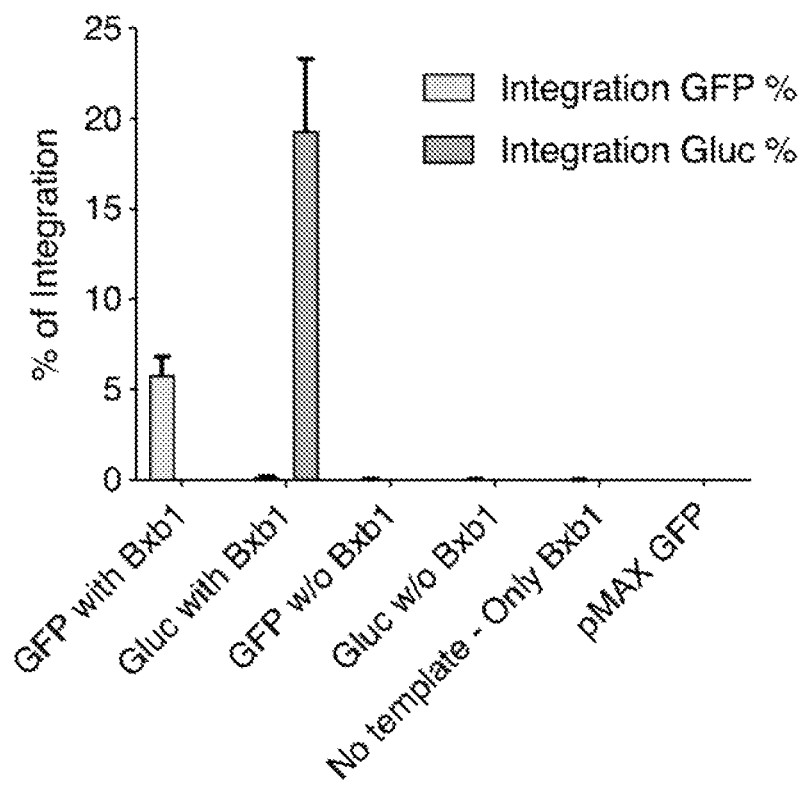
FIG. 7 shows the percent integration of GFP or Gluc into the attB locus using Bxb1 Programmable Addition via Site-Specific Targeting Elements (PASTE) according to embodiments of the present teachings.

To probe the efficiency of the Bxb1 integration system, a clonal HEK293FT cell line with attB Bxb1 site (SEQ ID NO: 3) integrated using lentivirus was developed. The modified HEK293FT cell line was then transferred with the following plasmids: (1) plus/minus Bxb1 expression plasmid and (2) plus/minus GFP (SEQ ID NO: 76) or G-Luc (SEQ ID NO: 77) minicircle template with attP Bxb1 site. After 72 hours, the integration of GFP or Gluc into the attB site in the HEK293FT genome was probed. The percent integrations of GFP or Gluc into the attB locus are shown in FIG. 7. It was observed that GFP and Gluc showed efficient integration into the attB site in HEK293FT cells.

Example 5

Addition of Bxb1 Site to Human Genome Using PRIME

Figure 8:
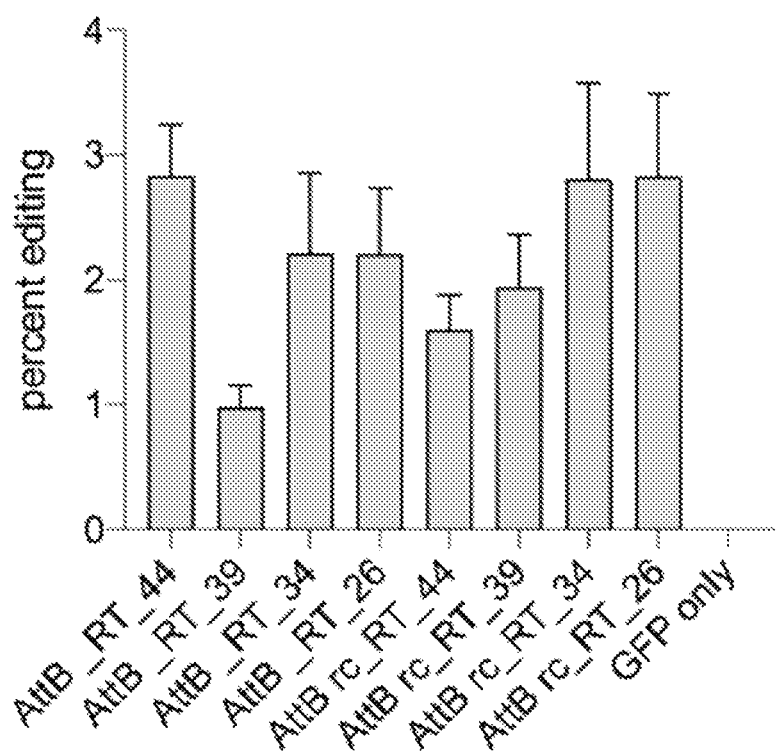
FIG. 8 shows the percent editing of various HEK3 targeting pegRNA Programmable Addition via Site-Specific Targeting Elements (PASTE) according to embodiments of the present teachings.
Figure 9A:
FIG. 9A shows a fluorescent image of cells wherein the SUPT16H marker is tagged with EGFP using PASTE according to embodiments of the present teachings.
Figure 9B:
FIG. 9B shows a fluorescent image of cells wherein the SRRM2 marker is tagged with EGFP using Programmable Addition via Site-Specific Targeting Elements (PASTE) according to embodiments of the present teachings.
Figure 9C:
FIG. 9C shows a fluorescent image of cells wherein the LAMNB1 marker is tagged with EGFP using Programmable Addition via Site-Specific Targeting Elements (PASTE) according to embodiments of the present teachings.
Figure 9D:
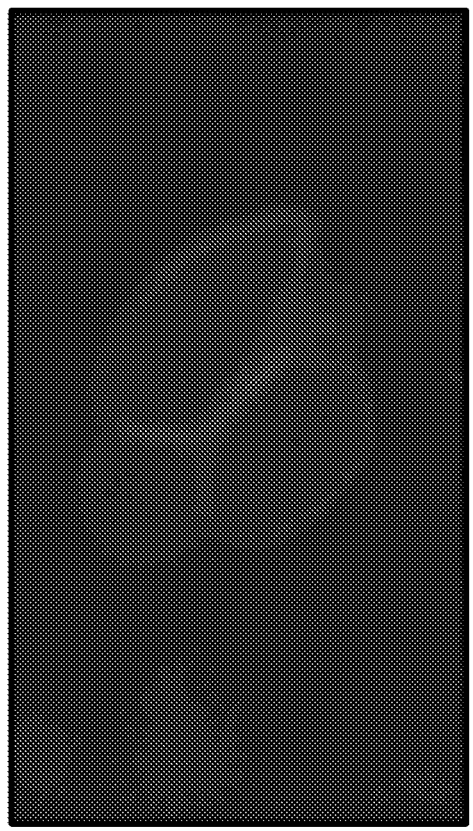
FIG. 9D shows a fluorescent image of cells wherein the NOLC1 marker is tagged with EGFP using Programmable Addition via Site-Specific Targeting Elements (PASTE) according to embodiments of the present teachings.
Figure 9E:
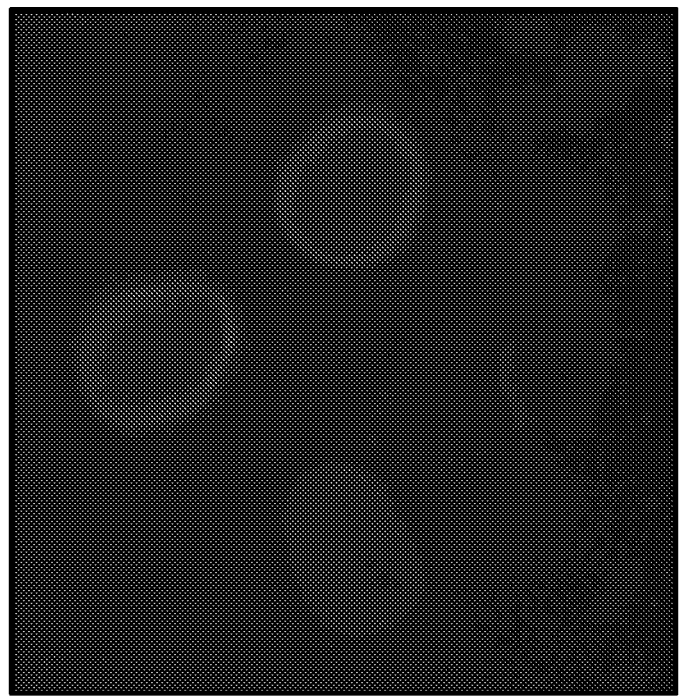
FIG. 9E shows a fluorescent image of cells wherein the NOLC1 marker is tagged with EGFP using Programmable Addition via Site-Specific Targeting Elements (PASTE) according to embodiments of the present teachings.
Figure 9F:
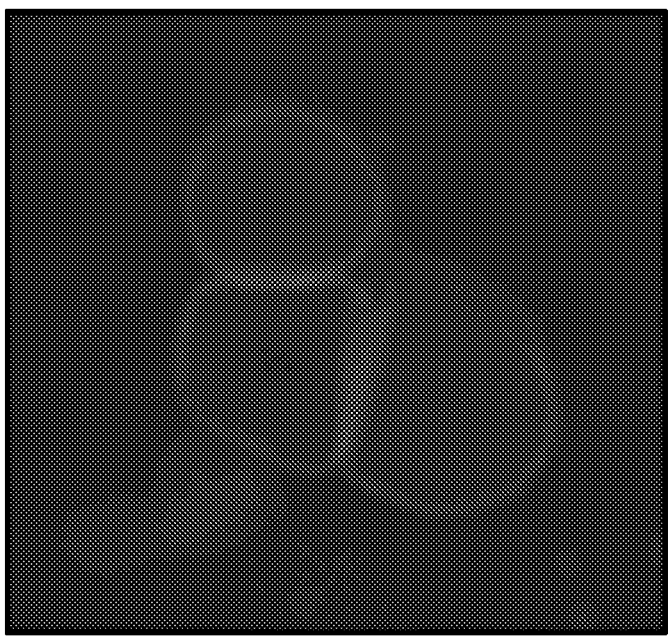
FIG. 9F shows a fluorescent image of cells wherein the NOLC1 marker is tagged with EGFP using Programmable Addition via Site-Specific Targeting Elements (PASTE) according to embodiments of the present teachings.
Figure 9G:
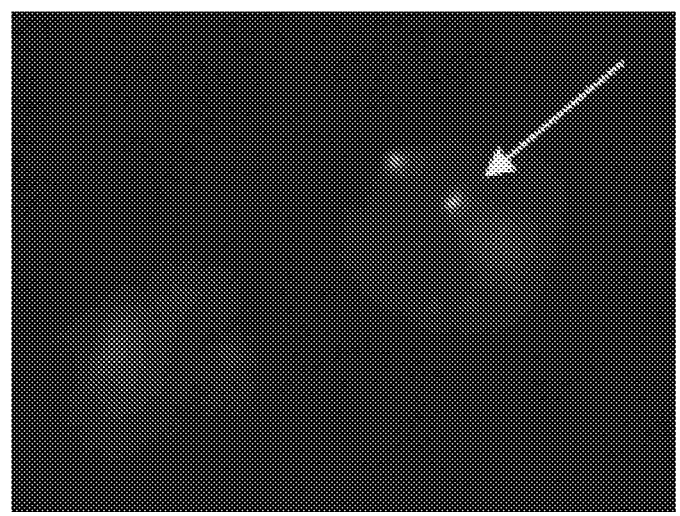
FIG. 9G shows a fluorescent image of cells wherein the DEPDC4 marker is tagged with EGFP using Programmable Addition via Site-Specific Targeting Elements (PASTE) according to embodiments of the present teachings.

The maximum length of attB that can be integrated into a HEK293FT cell line with the best efficiency was probed. To probe the best length of attB (SEQ ID NO: 3) or its reverse complement attP (SEQ ID NO: 4) for prime editing, pegRNAs having PBS length of 13 nt with varying RT homology length were used. The following plasmids were transfected in HEK293FT: (1) prime expression plasmid; (2) HEK3 targeting pegRNA design; and (3) HEK3 +90 nicking guide. After 72 hours, the percent integration of each of the attB construct was probed. FIG. 8 shows the percent editing in each HEK3 targeting pegRNA. It was observed that attB with 44, 34 and 26 base pairs and attB reverse complement with 34 and 26 base pairs showed the highest percent editing.

Integration PASTE was then tested with tagging cell-organelle marker proteins with GFP in HEK29FT cells. PASTE was used to tag SUPT16H, SRRM2, LAMNB1, NOLC1 and DEPDC4 with GFP in different cell-culture wells and to test the usefulness of PASTE in tracking protein localization within the cells using microscopy. FIGS. 9A-9G shows the fluorescent microscopy results for each of the organelles. SUPT16H-GFP was observed to be enriched in the nucleus, SRRM2-GFP was observed to be enriched in the nuclear speckles, LAMNB1-GFP was observed to be enriched in the nuclear membrane, NOLC1-GFP was observed to be enriched in the fibrillar center, and DEPDC4-GFP was observed to be enriched in the aggresome.

Figure 10A:
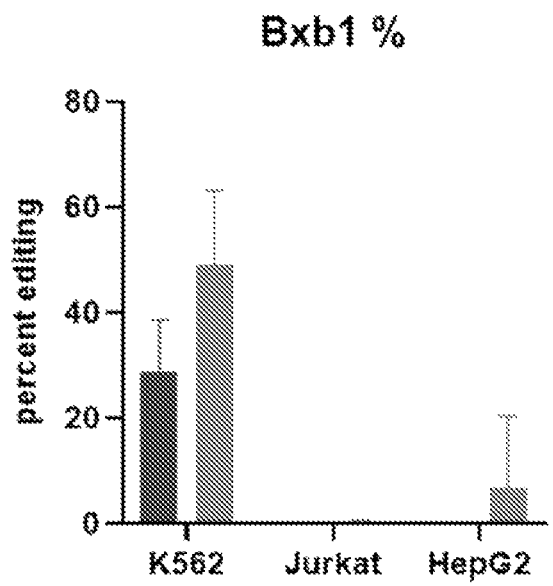
FIG. 10A shows comparisons of lipofectamine aided transfection in blue with electroporation aided transfection in red for the addition of the Bxb1 attB site at the ACTB N-terminal site in the genome using PASTE according to embodiments of the present teachings.
Figure 10B:
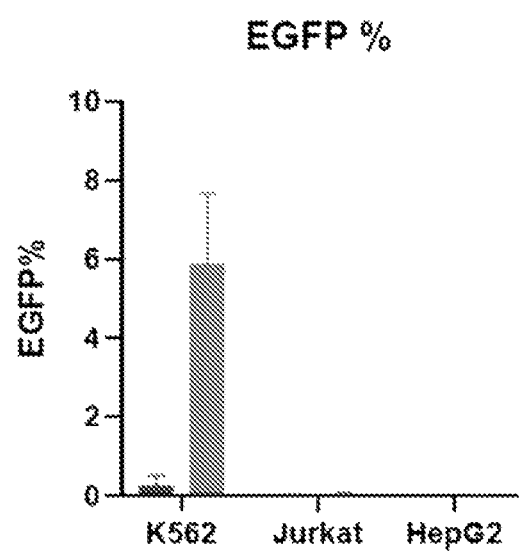
FIG. 10B shows comparisons of lipofectamine aided transfection in blue with electroporation aided transfection in red for EGFP integration at the ACTB N-terminal site in the genome using PASTE according to embodiments of the present teachings.

The transfection of the plasmids can be achieved using electroporation as illustrated in FIGS. 10A-10B.

Example 6

Programmable Integration of Genes with PASTE

The efficiency of gene integration of Gluc or EGFP with PASTE was tested. To enable gene integration with PASTE, the following HEK3 targeting pegRNAs were used: (1) 44 pegRNA: PBS of 13nt and RT homology of 44nt; (2) 34 pegRNA: PBS of 13nt and RT homology of 34nt; and (3) 26 pegRNA: PBS of 13nt and RT homology of 26nt.

Figure 11:
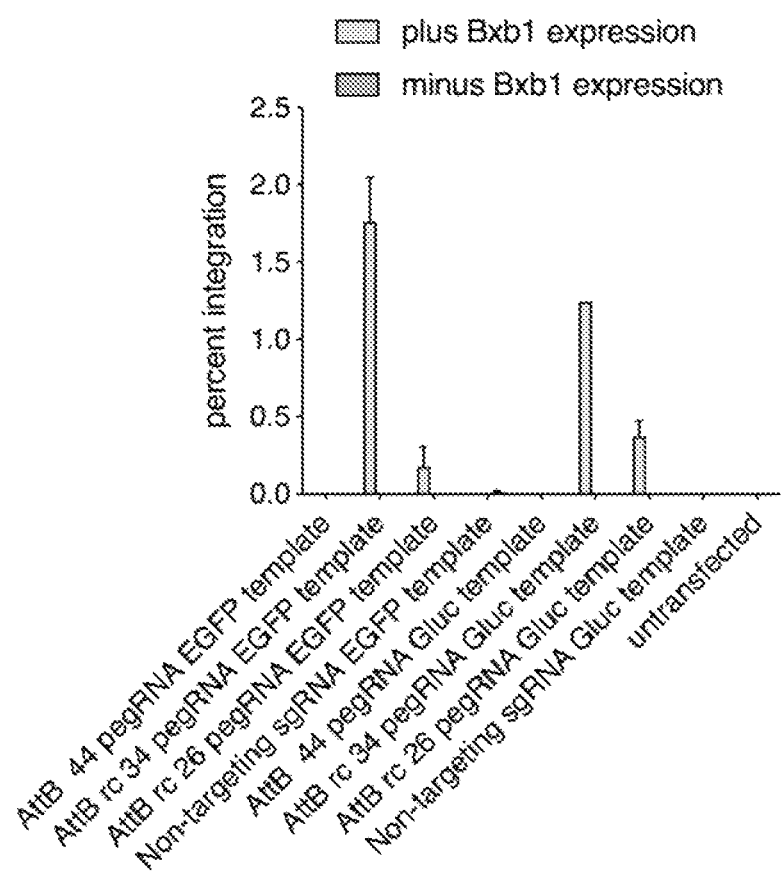
FIG. 11 shows a diagram of the integration of EGFP and Gluc with various HEK3 targeting pegRNAs according to embodiments of the present teachings.

A HEK293 cell line was transfected with following plasmids HEK293FT: (1) Prime expression plasmid; (2) Bxb1 expression plasmid; (3) HEK3 targeting pegRNA design; (4) HEK3 +90 nicking guide; and (5) EGFP or Gluc minicircle. After 72 hours, the percent integration of Gluc or EGFP was observed. FIG. 11 shows integration of EGFP and Gluc with each of the tested HEK3 targeting pegRNAs. It was observed that EGFP and Gluc were efficiently integrated using PASTE.

Example 7

PASTE for Integration of Multiple Genes

The PASTE technique for site-specific integration of multiple genes into a cell is facilitated with the use of orthogonal attB and attP sites. Central dinucleotide can be changed to GA from GT, and only GA containing attB/attP sites can interact and do not cross react with GT containing sequences. A screen of dinucleotide combinations to find orthogonal attB/attP pairs for multiplexed PASTE editing can be performed. It has been shown that many orthogonal dinucleotide combinations can be found using a Bxb1 reporter system.

Figure 14A:
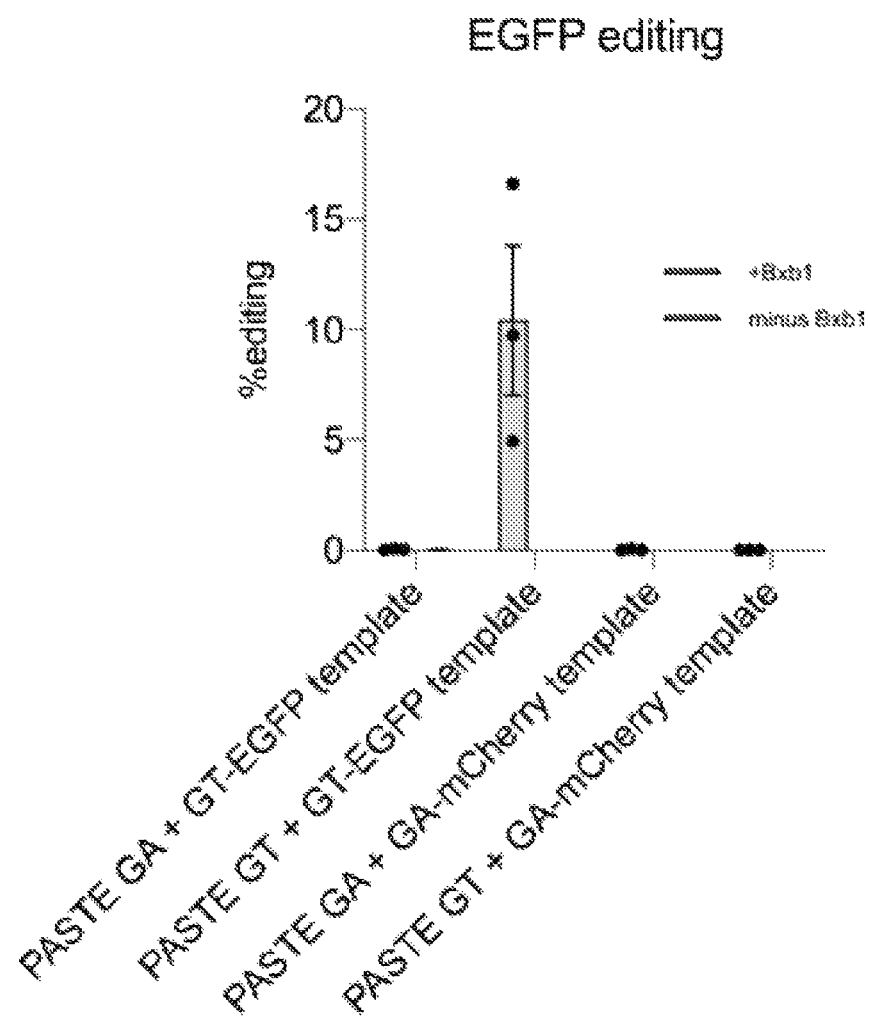
FIG. 14A shows a diagram of the orthogonal editing with the right GT-EGFP according to embodiments of the present teachings.
Figure 14B:
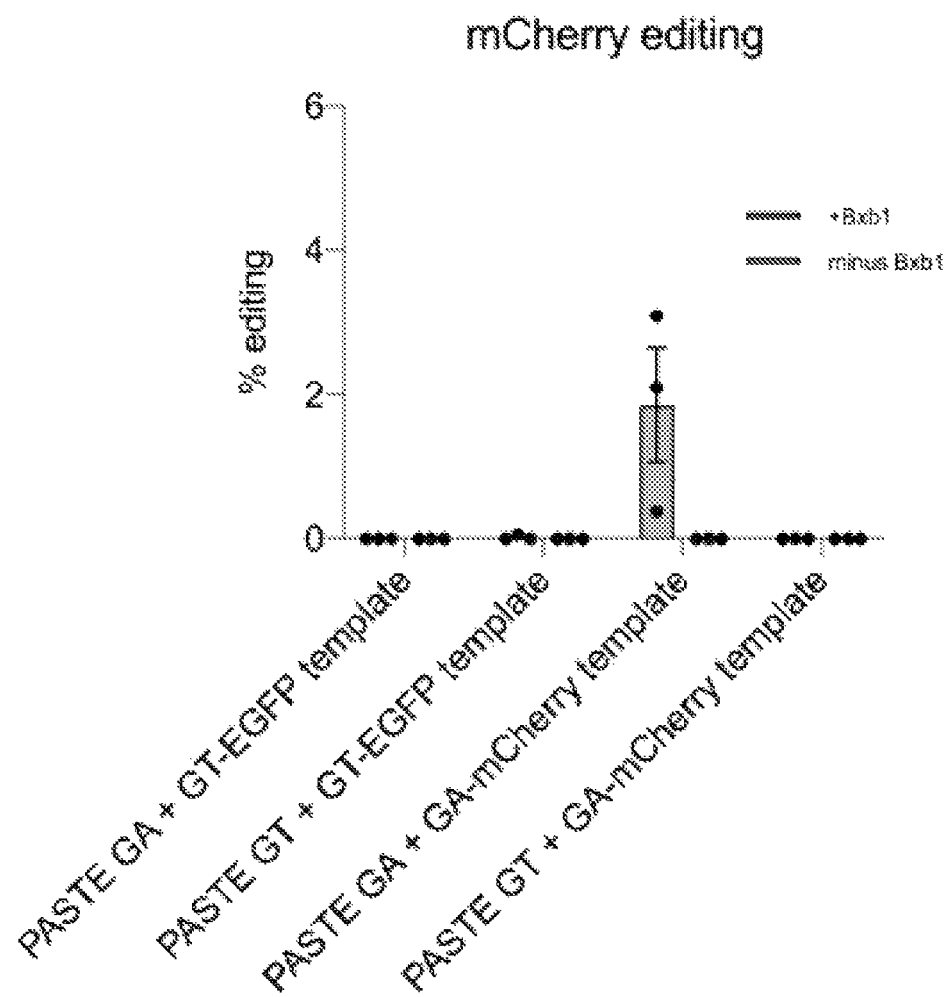
FIG. 14B shows a diagram of the orthogonal editing with the right GA-mCherry according to embodiments of the present teachings.

To test this, attB$^{GT}$ and attB$^{GA}$ dinucleotides for Bxb1 was added at a ACTB site by prime editing. A EGFP—attP$^{GT}$ DNA minicircle and a mCherry—attP$^{GA}$ DNA minicircle was introduced to test the percent EGFP and mCherry editing in the presence or absence of Bxb1. The results of EGFP and mCherry editing are shown in FIGS. 14A-14B.

Orthogonal editing with the right GT-EGFP and GA-mCherry pairs was achieved demonstrating the ability for multiplexed PASTE editing in cells.

Figure 15A:
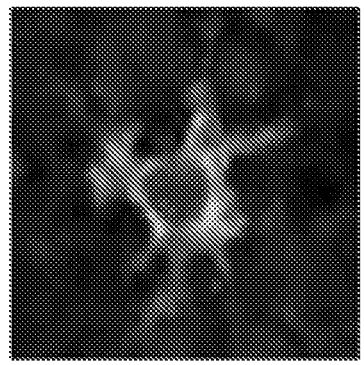
FIG. 15A shows a fluorescent image of a multiplexing of ACTB-EGFP and NOLC1-mCherry according to embodiments of the present teachings
Figure 15B:
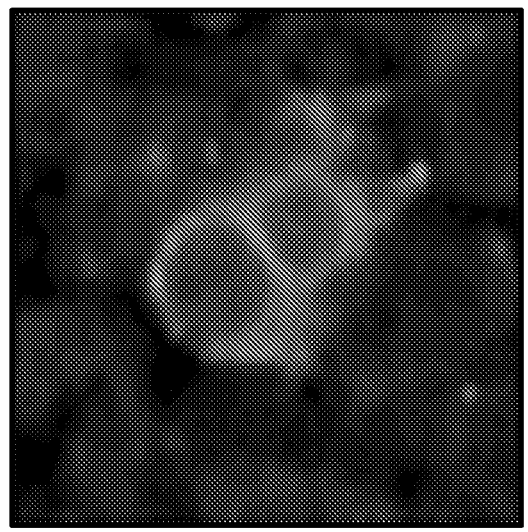
FIG. 15B shows a fluorescent image of a multiplexing of ACTB-EGFP and LAMNB1-mCherry according to embodiments of the present teachings.

Two genes were introduced in the same cell using multiplexed PASTE to tag two different genes in a single reaction. EGFP and mCherry were tagged into the loci of ACTB and NOLC1 in a x cell line, in a single reaction. Further, EGFP and mCherry were tagged into the loci of ACTB and LAMNB1. The cells were visualized using fluorescence microscopy. FIGS. 15A-15B show the results of fluorescent microscopy for multiplexed PASTE.

Figure 16A:
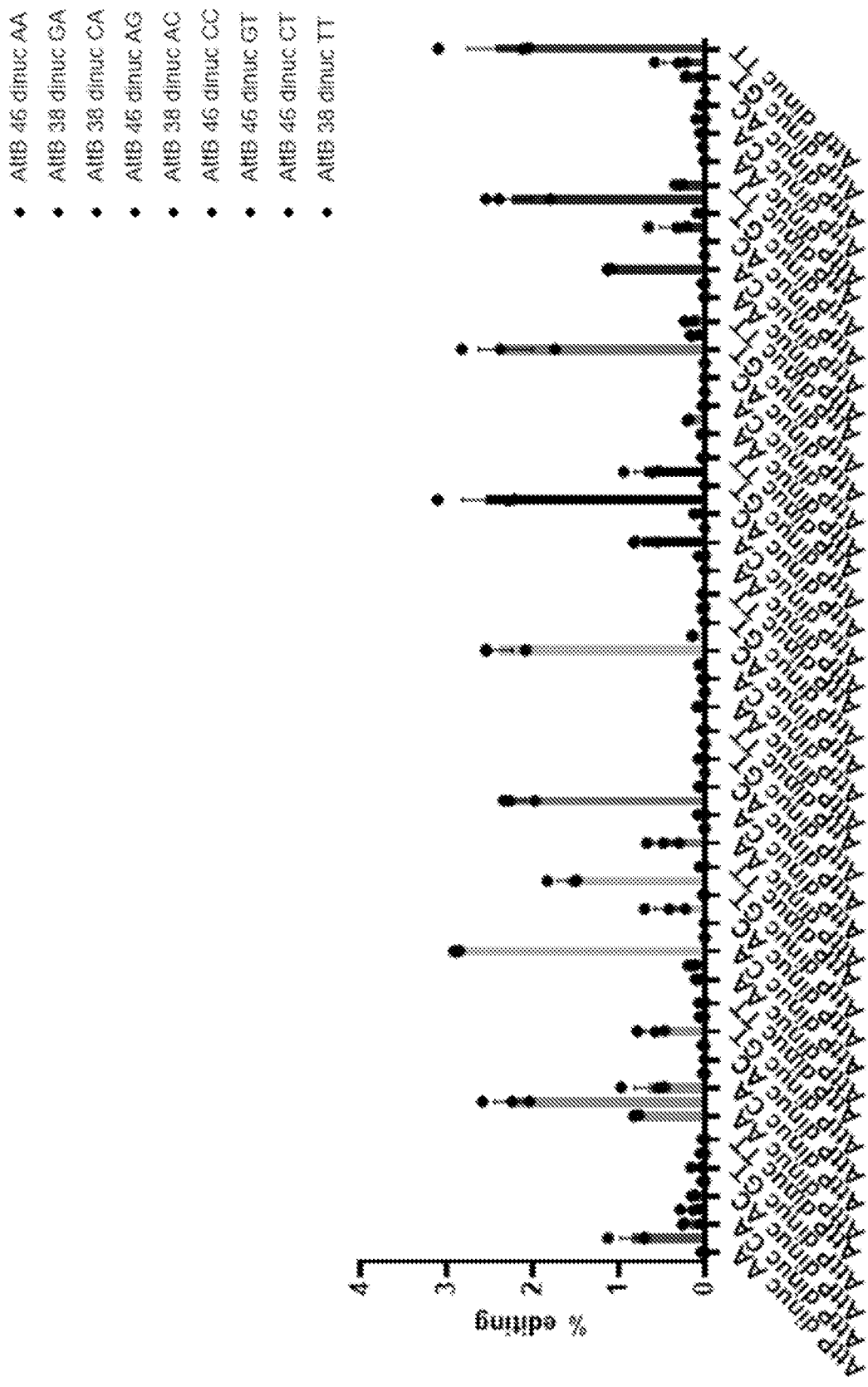
FIG. 16A shows next generation sequencing results of 9×9 attP and attB central dinucleotide variants and their edit percentage wherein the orthogonality of attB/attP combinations for potential multiplexing applications is shown according to embodiments of the present teachings.
Figure 16B:
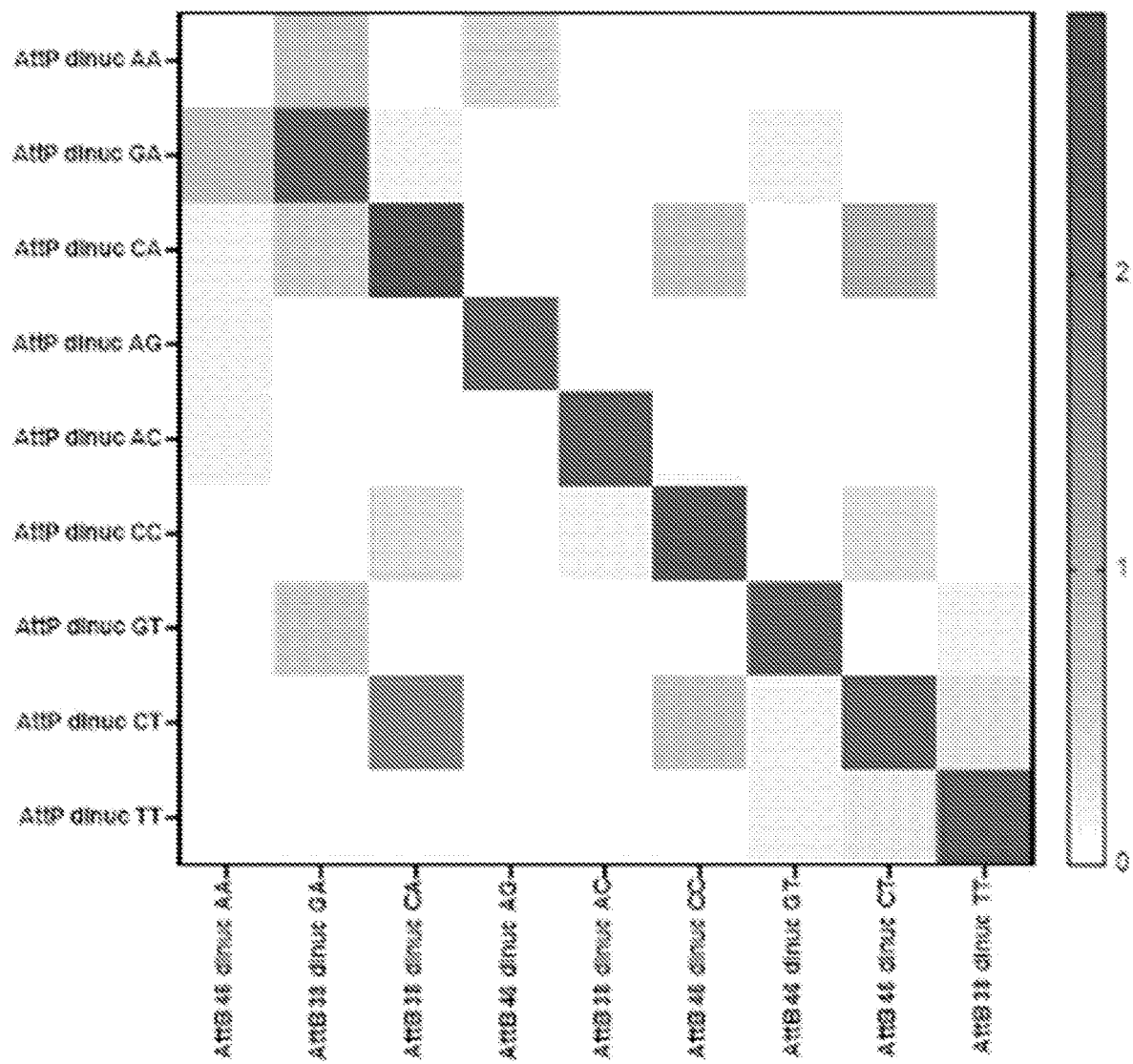
FIG. 16B shows an heatmap of 9×9 attP and attB central dinucleotide variants and their edit percentage according to embodiments of the present teachings.

The ability of multiplexing with 9-different attB and attP central dinucleotides—AA, GA, CA, AG, AC, CC, GT, CT and TT (SEQ ID NOs: 7, 8, 23, 24, 19, 20, 25, 26, 27, 28, 9, 10, 15, 16, 17, 18, 5 and 6)— in a 9×9 cross of attB and attP was tested. The edits were probed using next-generation sequencing. The results of the 9×9 cross of attB and attP central dinucleotides— AA, GA, CA, AG, AC, CC, GT, CT and TT— are shown in FIG. 16A. Only orthogonal pairs of attB and attP show the highest edit percentage. This result is also shown in the heat-map of FIG. 16B.

Example 8

Figure 17:
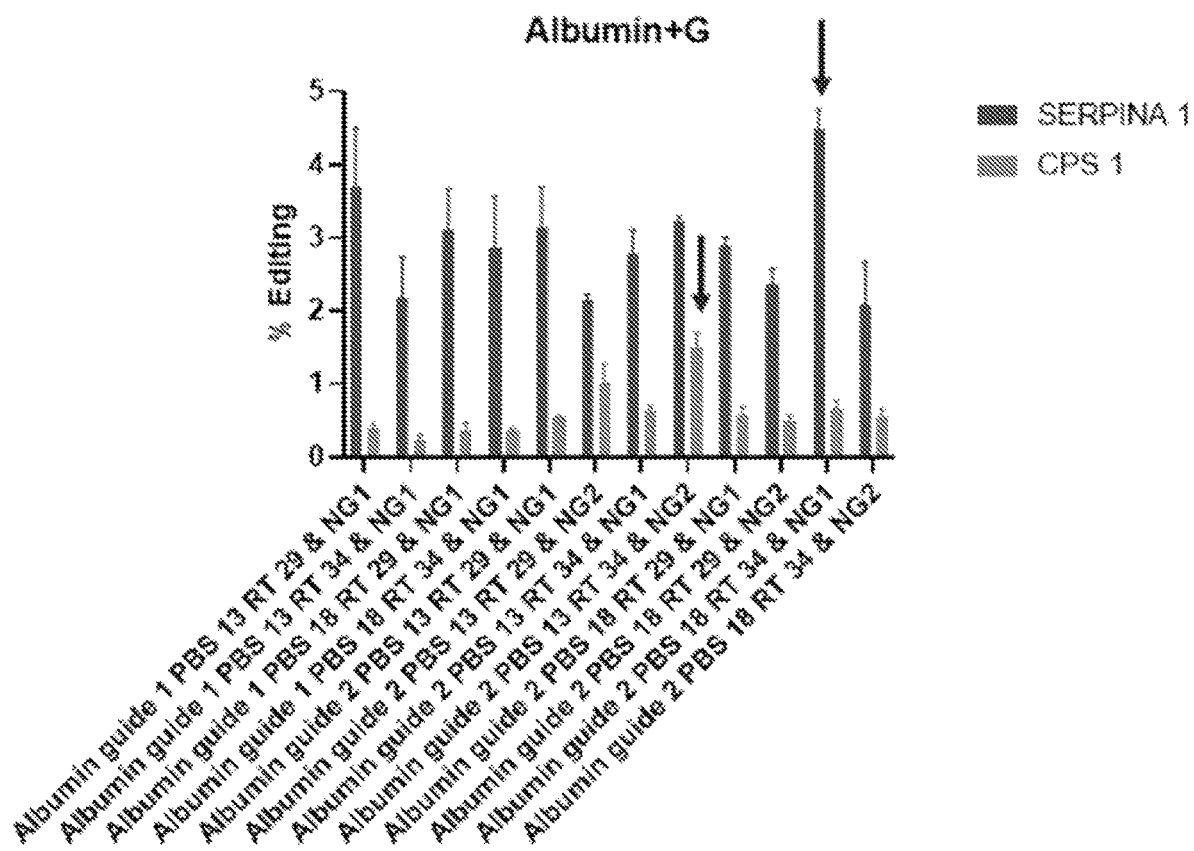
FIG. 17 shows integration of SERPINA and CPS1 into Albumin loci using Albumin guide-pegRNA in HEK293FT cells according to embodiments of the present teachings.

Integration of Albumin and CPS1 Into Albumin Locus 12 pegRNAs with albumin guide were linked to PBS and reverse transcriptase sequence of variable length, and different nicking guide RNAs were used to transfect HEK293FT cells. The percent editing in the albumin was probed using next-generation sequencing. The results of prime editing at the albumin locus are shown in FIG. 17. It was observed that SEQ ID NO: 79 showed the highest percent edits with SERPINA1 and SEQ ID NO: 80 showed the highest percent edits with CPS1.

Example 9

Engineering T-cells

Figure 18:
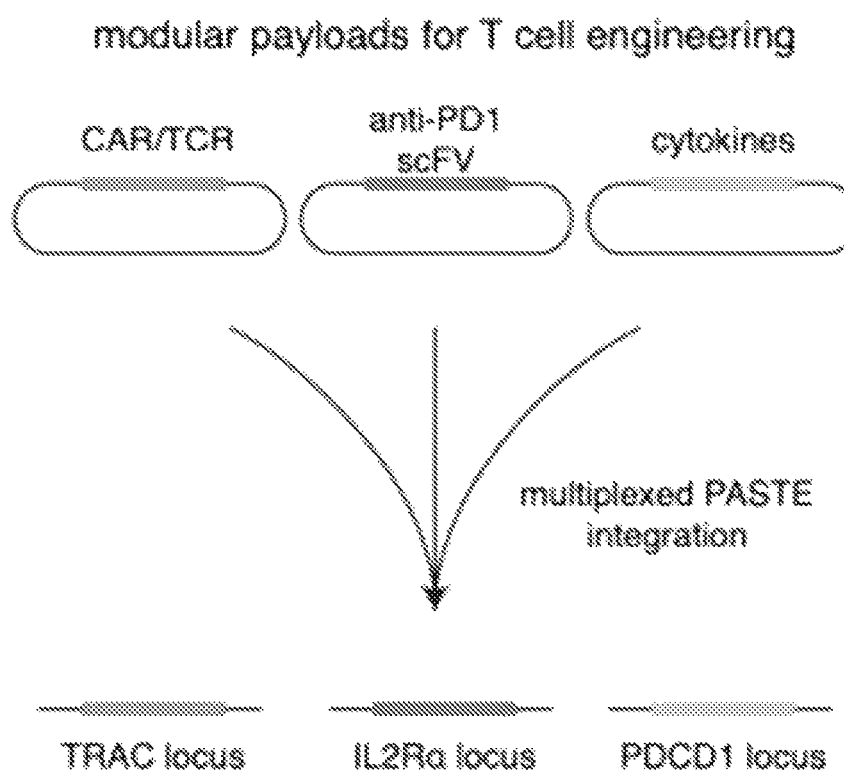
FIG. 18 shows schematics for different nucleic acids for engineering T-cells according to embodiments of the present teachings.

In order to engineer CD8+ T-cells, the efficiency of PASTE delivery and editing in T-cells can be evaluated (FIG. 18). ACTB targeting pegRNA can be used to insert an integration site with an EGFP insertion template. To deliver the PASTE components to CD8+ T-cells, electroporation can be used along with an optimized electroporation protocol for unstimulated T-cells. As multiple plasmids may reduce the efficiency of electroporation, the consolidated PASTE components that use fewer vectors can be applied.

Figure 19:
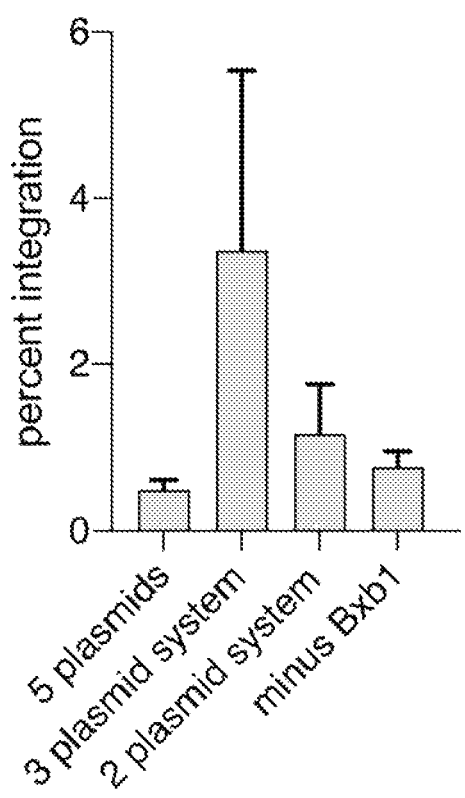
FIG. 19 shows the editing efficiency for EGFP integration at the ACTB locus in primary T-cells according to embodiments of the present teachings.
Figure 20:
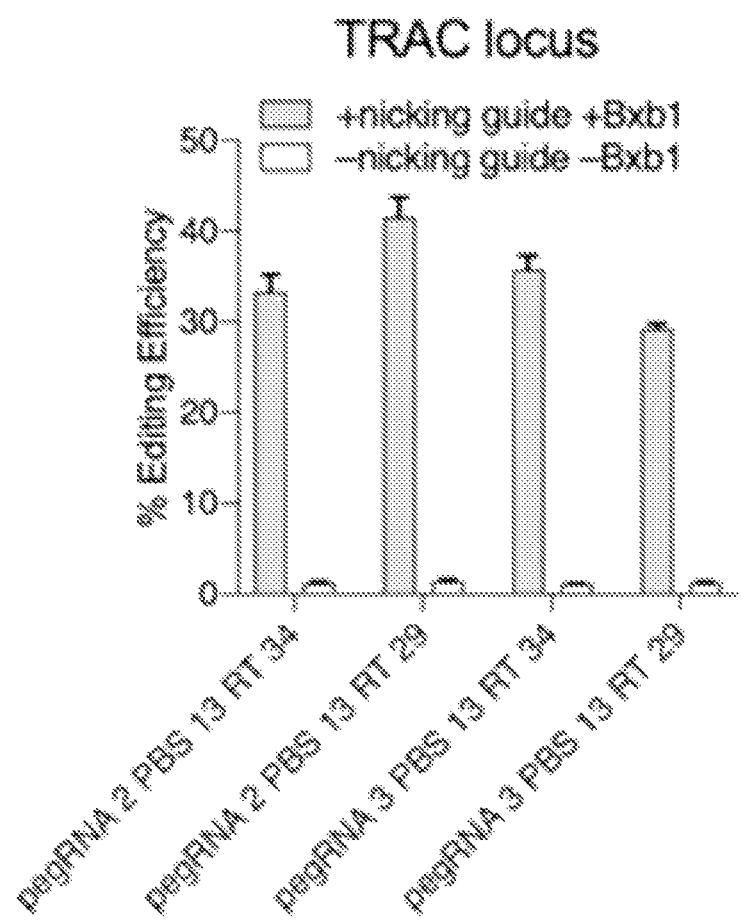
FIG. 20 shows editing in TRAC locus in HEK293FT with different pegRNA according to embodiments of the present teachings.

Five vectors, three vectors, and two vectors PASTE systems show that robust T-cell editing can be achieved with maximal editing using the three-vector approach (FIG. 19). Further, expanded sets of electroporation conditions, including the overall plasmid amounts, cell numbers, and voltage/amperage protocol can be tested. In addition, stimulation of T-cells may influence the efficiency of transduction and PASTE efficiency. Further, CD4+/CD8+ T cell mixtures stimulated with T-Activator CD3/CD28 ligands can have higher PASTE editing efficiency versus unstimulated cells. In order to separate efficiency of PASTE from the overall delivery rate, an mCherry expression cassette on PASTE vectors can be evaluated in order to sort successfully transfected T cells. Once optimized parameters are achieved, a panel of 10 insertion sites with PASTE in T cells, including the TRAC, IL2Rα, and PDCD1 loci, can be evaluated, using different insertions (e.g. EGFP, BFP, and YFP), both in single and multiplexed editing contexts. A tested subset of relevant sites in HEK293FT achieved greater than 40% editing for EGFP insertion (FIG. 20). The PASTE efficiency at TRAC locus with different TCR and CAR constructs can be evaluated. The T-cells can successfully be transfected to achieve insertion of CARs or TCRs.

Example 10

PASTE for CFTR

PASTE for the CFTR locus can be tested in HEK293FT cells to identify top performing pegRNA and nicking designs for human cells. Neuro-2A cells can also be tested to identify top performing pegRNA and nicking designs for mouse cells. The best constructs can be applied for testing in mouse air lung interface (ALI) organoids in vitro or for delivery in pre-clinical models of cystic fibrosis in mice. Table 12 shows the pegRNA, nicking guide and minicircle DNA characteristics for the CFTR gene modulation.

TABLE 12

| Variables | Characteristics |
|---|---|
| pegRNA | 38 bp shortened minimal attB and normal 46 bp attB sequence with: <br> a. PBS of 17, 13, and 9 nt length, and <br> b. RT of 20, 15, and 10 nt in length |
| Nicking guides | Nicking guide 1 +64 bp Nicking guide 2 +23 bp Nicking guide 3 −60 bp Nicking guide 4 −78 bp (distance is calculated from cut site of pegRNA) |
| Minicircle template | A. CFTR coding sequence alone (~4,454 pb in size) <br> B. CFTR coding sequence plus 5' and 3' UTRs (~6,011 bp in size) <br> (Both minicircles have attP site on them for integration by Bxb1 and a bGH poly A signal) |

Example 11

AttB and EGPF Integration Using PASTE

Figure 21A:
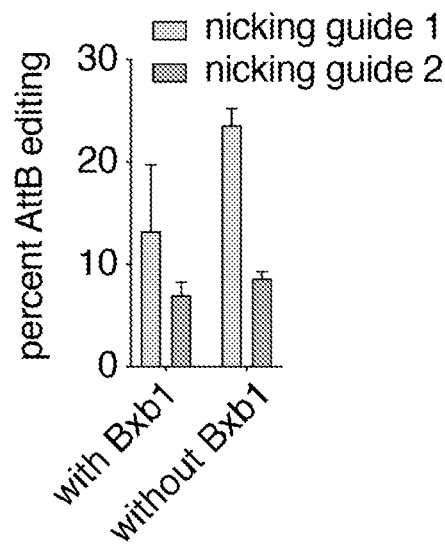
FIG. 21A shows the attB integration at the ACTB locus using nicking guides 1 and 2 according to embodiments of the present teachings.
Figure 21B:
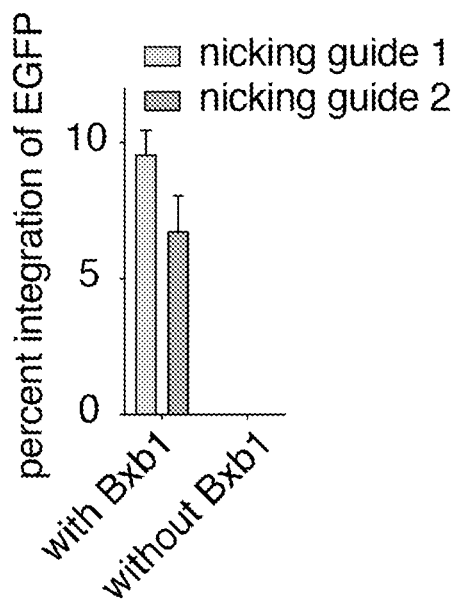
FIG. 21B shows the EGFP integration at the ACTB locus using nicking guides 1 and 2 according to embodiments of the present teachings.
Figure 21C:
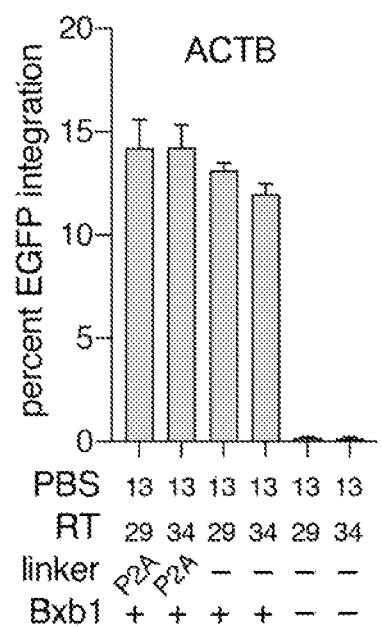
FIG. 21C shows the EGFP integration at an ACTB site according to embodiments of the present teachings.

The efficiency of the integration of attB and EGPF at the ACTB locus was evaluated (FIGS. 21A-21C). To investigate whether Bxb1 can add an EGFP template into this site, a delivery approach using a 5 plasmid system expressing each of the following component was deployed: 1) pegRNA expression, 2) nicking guide expression, 3) Prime expression (Cas9-RT), 4) Bxb1 expression and 5) the insertion template (in this case EGFP). This approach was found to yield editing efficiency of the attB site up to 24% and integration of EGFP ~10% in HEK293FT cells as measured by sequencing (FIGS. 21A-21B). Optimal activity is achieved in 3-4 days and can be performed as a single step transfection or electroporation of all components. Because the EGFP plasmid is designed as a minicircle, allowing removal of all undesired bacterial components, only the desired gene is inserted along with minimal scars from the Bxb1 recombined sites.

To make the tool simpler to use, the Bxb1 can be linked to Prime via a P2A linker to the Cas9-RT fusion, allowing for only a single plasmid to be used for PASTE protein expression rather than two. This optimization can maintain the same level of editing, making it easier to use the tool and deliver it (FIG. 21C).

Example 12

Programmable EGFP Integrations in Different Cell Types

Figure 22A:
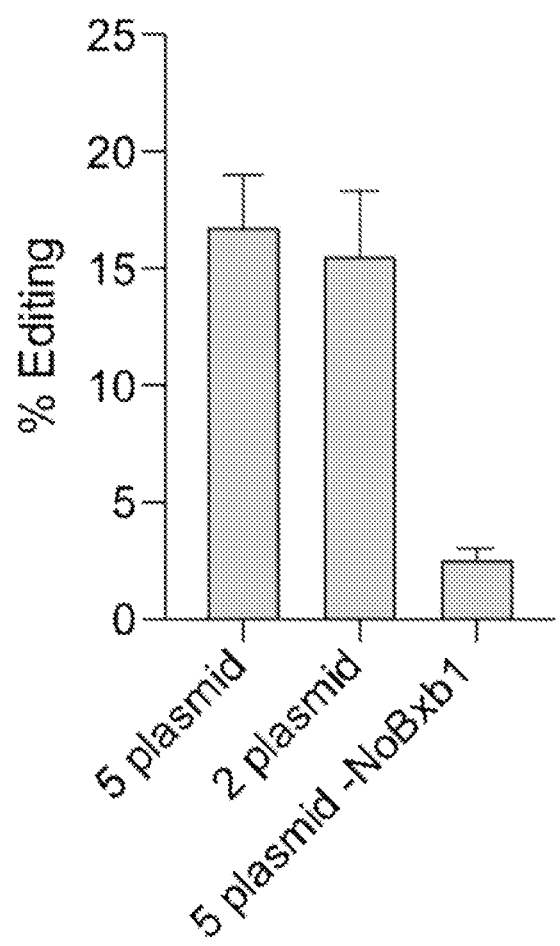
FIG. 22A shows PASTE editing in liver hepatocellular carcinoma cell line HEPG2 according to embodiments of the present teachings.
Figure 22B:
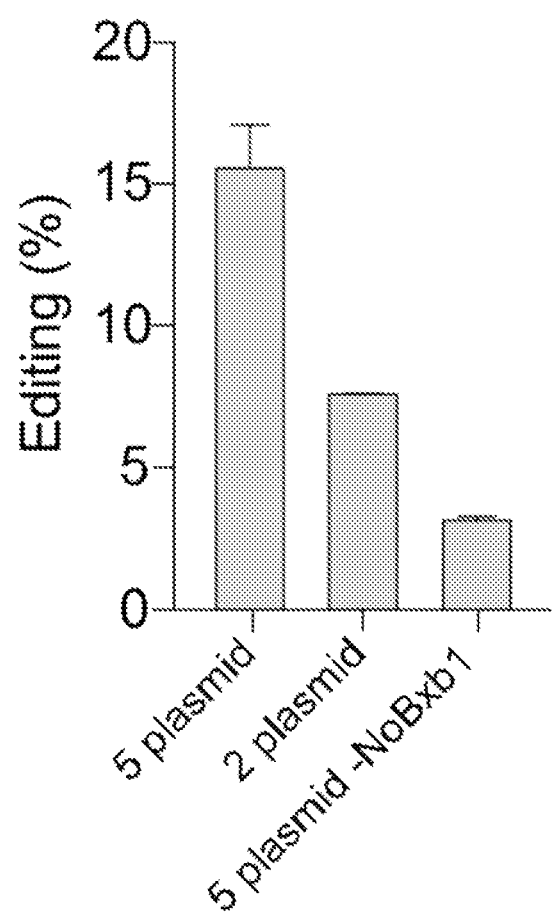
FIG. 22B shows PASTE editing of chronic myelogenous leukemia cell line K562 according to embodiments of the present teachings.

The programmable EGFP integration in liver hepatocellular carcinoma cell line HEPG2 (FIG. 22A) and chronic myelogenous leukemia cell line K562 (FIG. 22B) was evaluated. EGFP integration at the ACTB locus in K562 and HEPG2 cells of about 15% was observed, demonstrating robustness of the platform across cell types.

Example 13

Mutagenesis of Bxb1 for Enhanced PASTE Activity

Figure 23A:
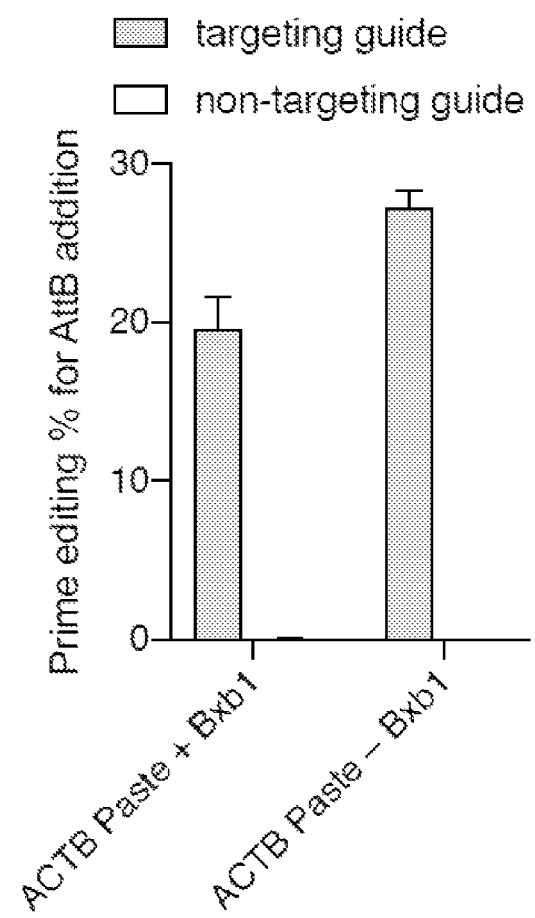
FIG. 23A shows the attB addition with targeting and non-targeting guides according to embodiments of the present teachings.
Figure 23B:
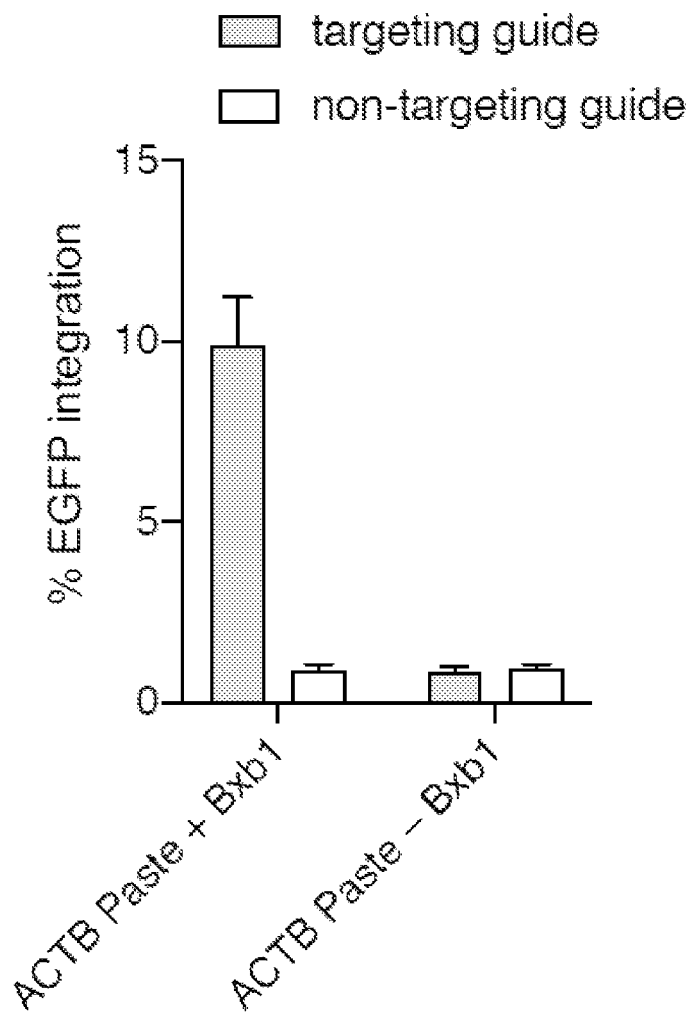
FIG. 23B shows the EGFP integration with targeting and non-targeting guides according to embodiments of the present teachings.
Figure 23C:
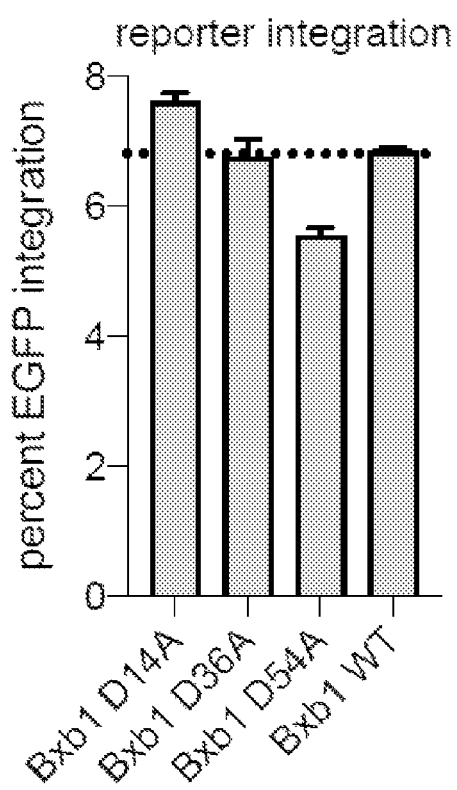
FIG. 23C shows the EGFP integration for mutagenized Bxb1 according to embodiments of the present teachings.

The mutagenesis of Bxb1 for enhanced PASTE activity was evaluated (FIGS. 23A-23C). Two levers for optimizing PASTE activity exist: 1) improving the activity of the integrase and 2) enhancing the Prime addition of the integration sequence. As illustrated in FIGS. 23A-23B, Bxb1 activity can be improved as only about 30% of Bxb1 attB sites that are added by PASTE are integrated into by Bxb1. This illustrates that if the Bxb1 efficiency can be improved, the PASTE can be improved. Furthermore, catalytic residues in the Bxb1 integrase were identified via conservation and structural analyses and Bxb1 mutants were generated to test as part of PASTE. As illustrated in FIG. 23B, the mutations can improve integration by about 20-30%.

Example 14

Figure 25A:
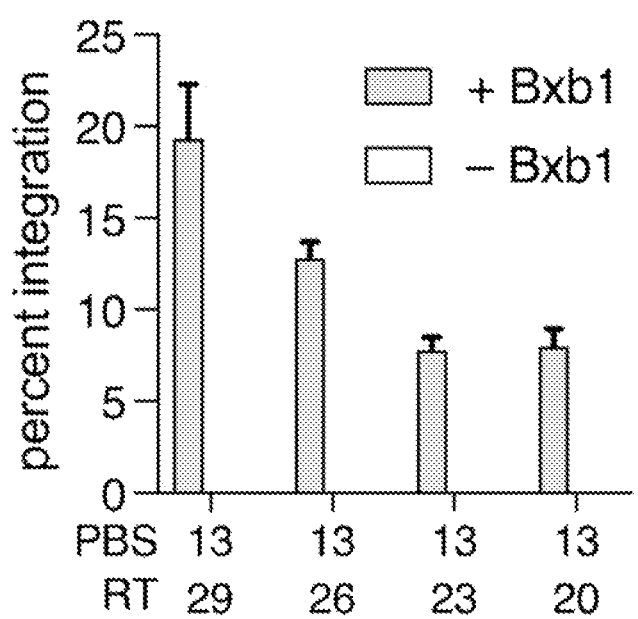
FIG. 25A shows the integration of EGFP at the ACTD locus with different PBS and RT lengths according to embodiments of the present teachings.
Figure 25B:
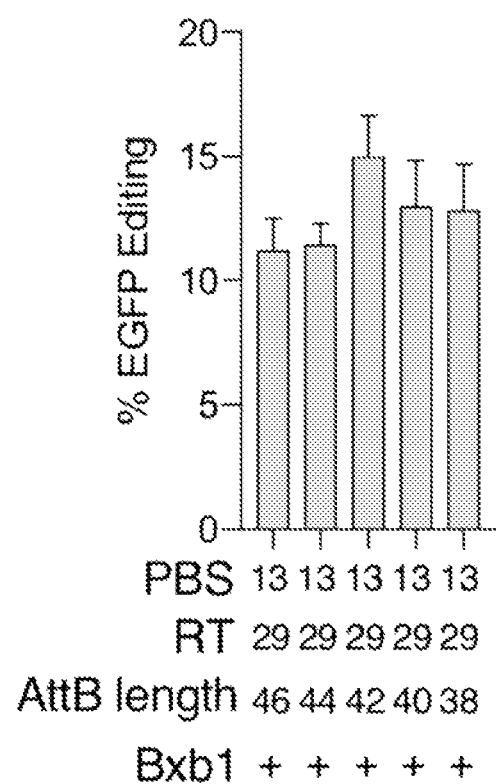
FIG. 25B shows the integration of EGFP at the LMNB1 loci with different PBS and RT lengths according to embodiments of the present teachings.
Figure 25C:
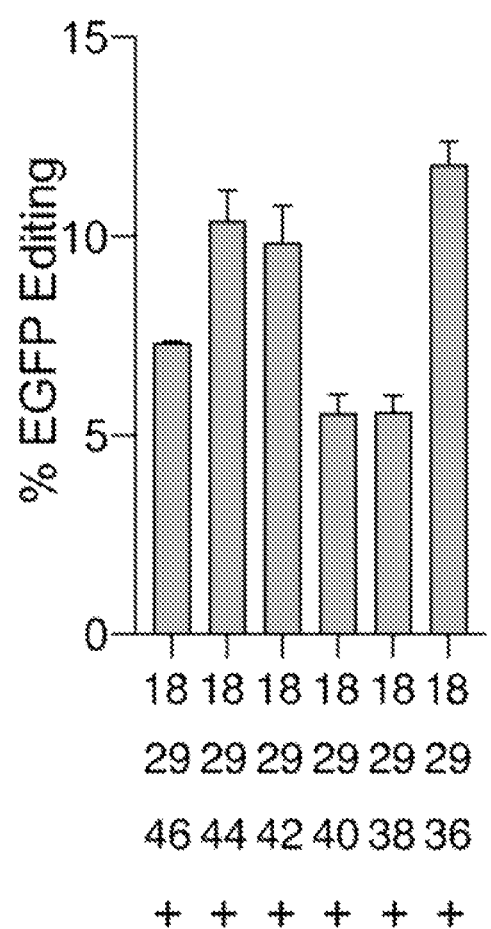
FIG. 25C shows the integration of EGFP at the NOLC1 loci with different PBS and RT lengths according to embodiments of the present teachings.
Figure 25D:
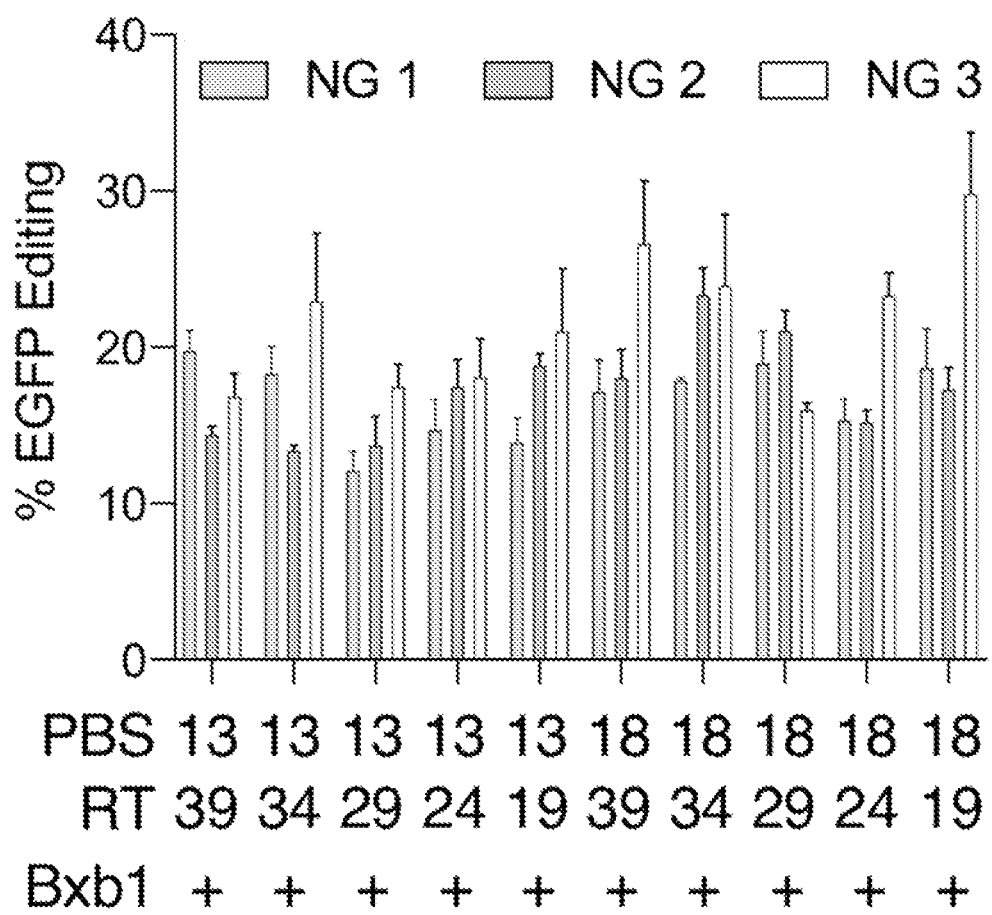
FIG. 25D shows the integration of EGFP at the GRSF1 locus with different PBS and RT lengths and different nicking guides according to embodiments of the present teachings.
Figure 25E:
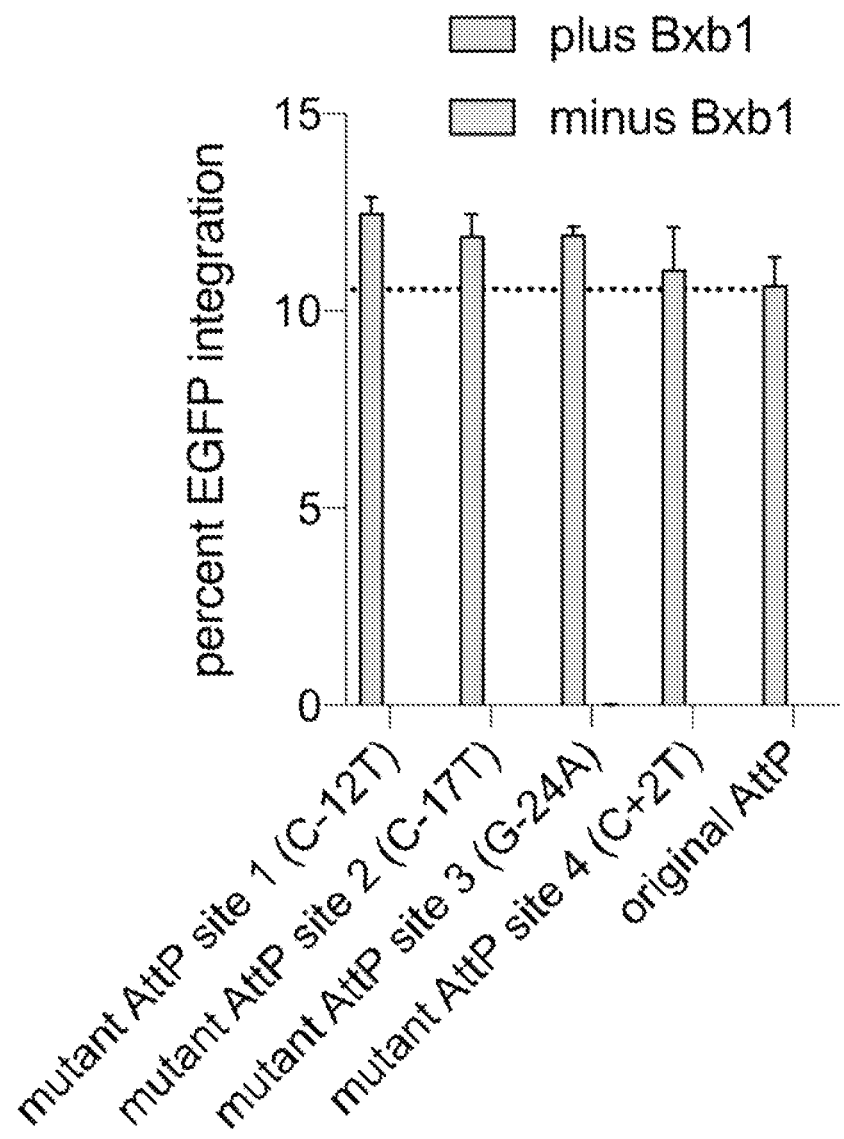
FIG. 25E shows EGFP integration with mutant attP sites according to embodiments of the present teachings.
Figure 25F:
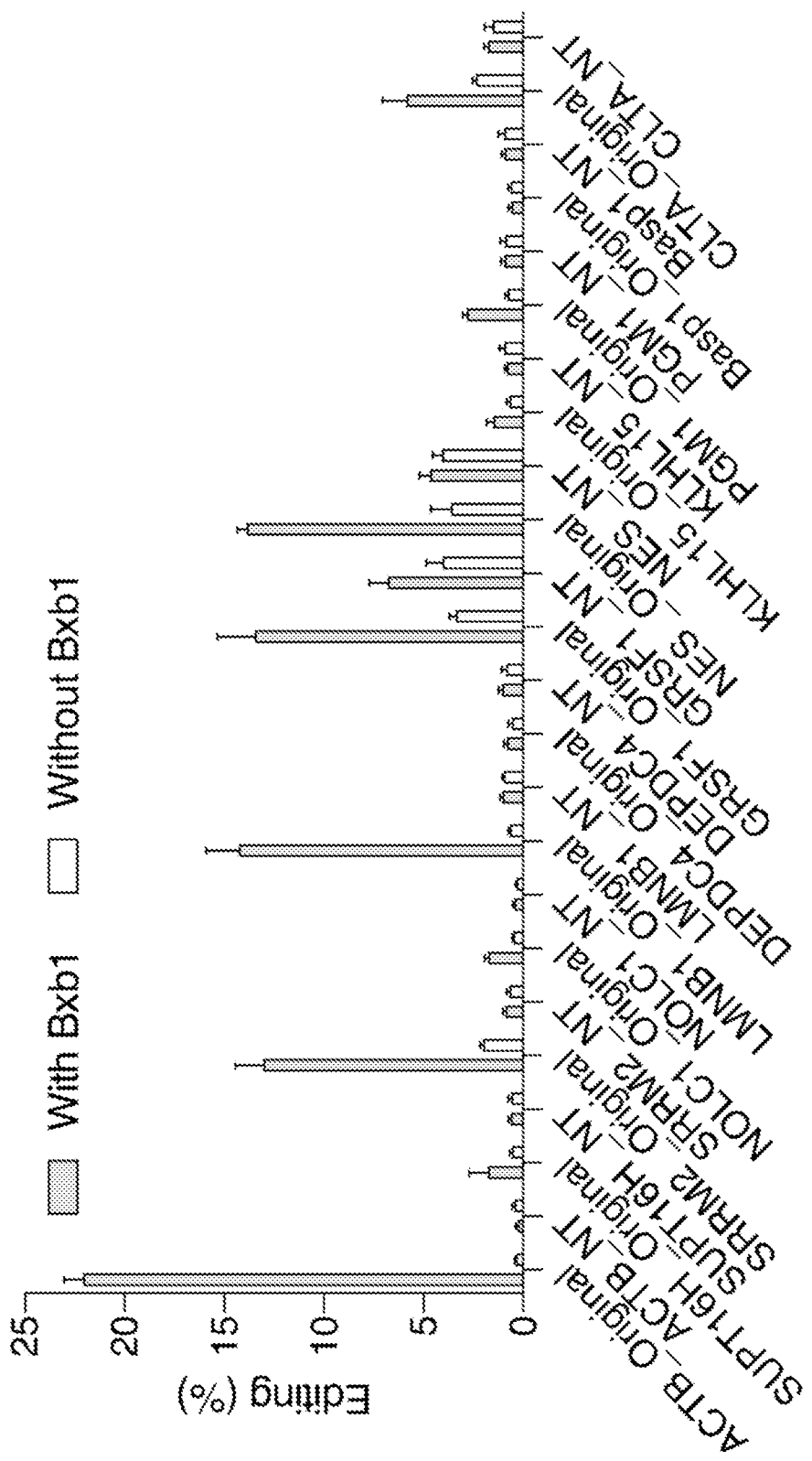
FIG. 25F shows the PASTE editing of an expanded panel of genes according to embodiments of the present teachings.

Effect of the pegRNA PBS and RT Lengths on the Prime Editing Integration Efficiency The effect of the pegRNA PBS and RT lengths on the prime editing integration efficiency was evaluated (FIGS. 25A-25F). It was found that PASTE can be optimized by tuning the PBS and RT lengths at the ACTB locus to achieve editing rates up to about 20% (FIG. 25A). It was found that shortening the attB site can help improve PASTE function as Prime is better at inserting shorter sequences. Further optimization of PBS, RT, and attB lengths showed that optimal designs can be found for insertion upstream of the LMNB1, NOLC1, and GRSF1 loci (FIGS. 25B, 25C, and 25D). Lengths as short as 36nt for attB were found to be still functional for integration into a reporter plasmid (FIGS. 25B and 25C). It was found that the reverse complemented version of the attB sequence was better integrated via Prime editing, suggesting that the sequence of what Prime is inserting matters. EGFP integrations with attP site mutants showed that certain mutants can improve integration efficiency significantly (FIG. 25E). PASTE was also performed with a large panel of genes, inserting EGFP at the N-terminus of ACTB, LMNB1, SUPT16H, SRRM2, NOLC1, KLHL15, GRSF1, DEPDC4, NES, PGM1, CLTA, BASP1, and DNAJC18 (FIG. 25F). Editing rates that are about 5%-40% were found using digital droplet PCR (ddPCR).

Example 15

Comparison of PASTE and HITI On-target and Off-target Activities

Figure 26A:
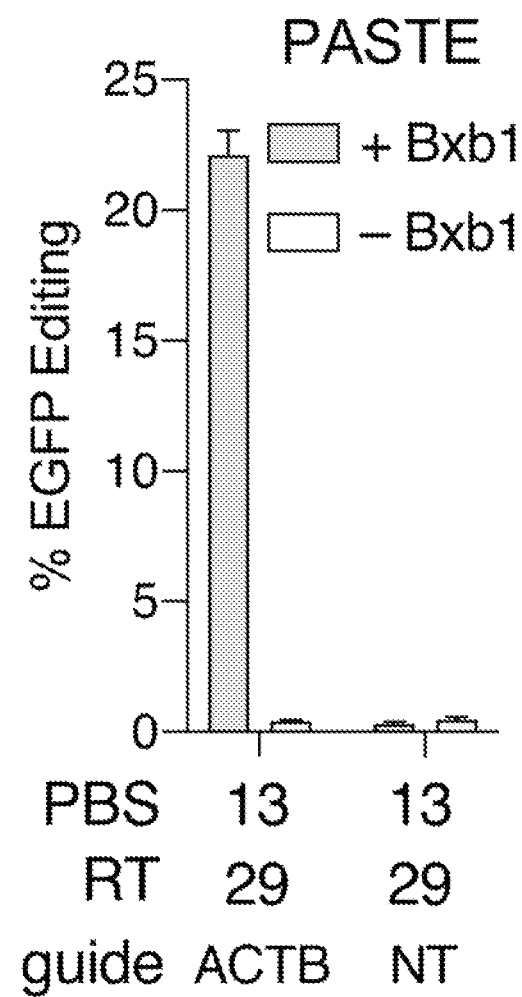
FIG. 26A shows the PASTE EGPF editing at the ACTB locus according to embodiments of the present teachings.
Figure 26B:
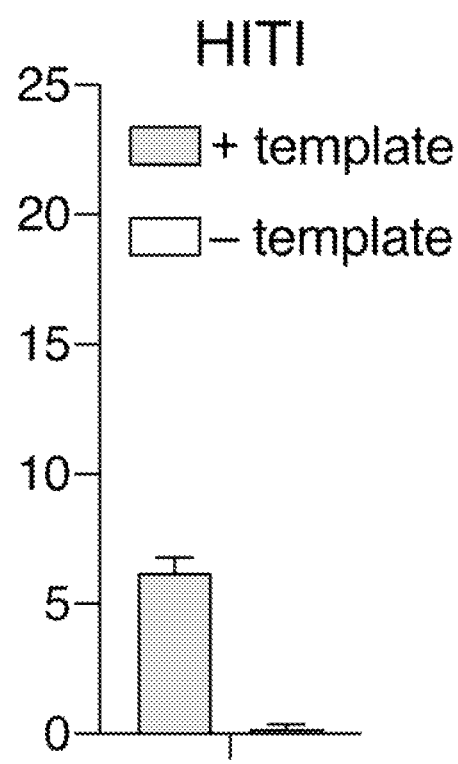
FIG. 26B shows the HITI EGPF editing at the ACTB locus according to embodiments of the present teachings.
Figure 26C:
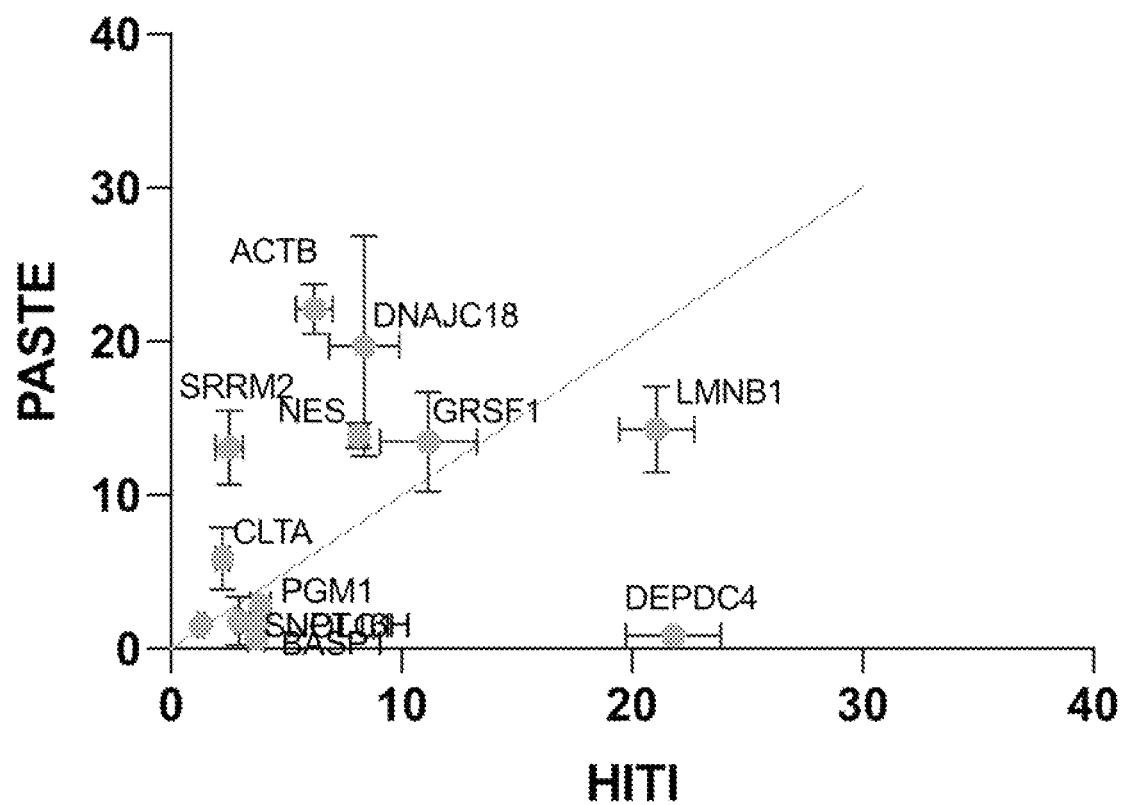
FIG. 26C shows the comparison between the PASTE and HITI editing a panel of 14 genes according to embodiments of the present teachings.
Figure 26D:
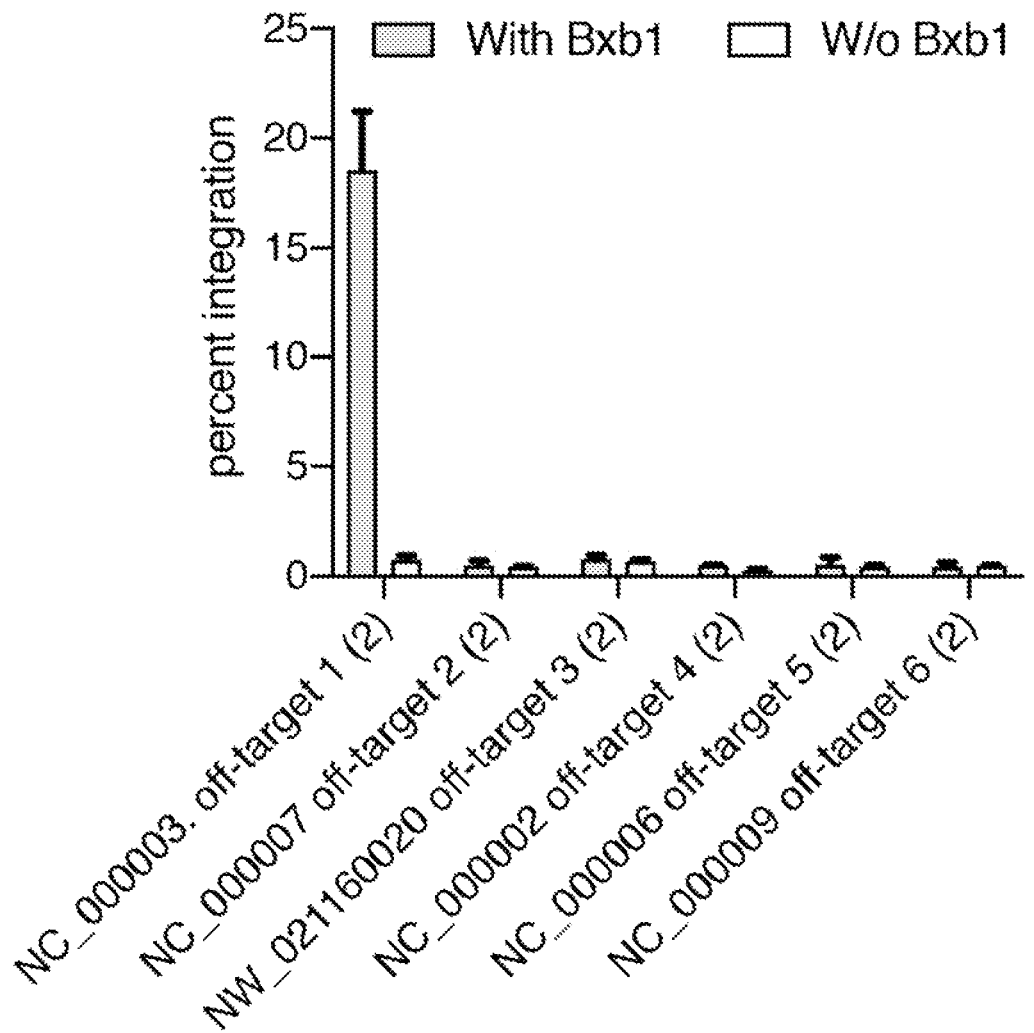
FIG. 26D shows PASTE Bxb1 off-target integrations according to embodiments of the present teachings.
Figure 26E:
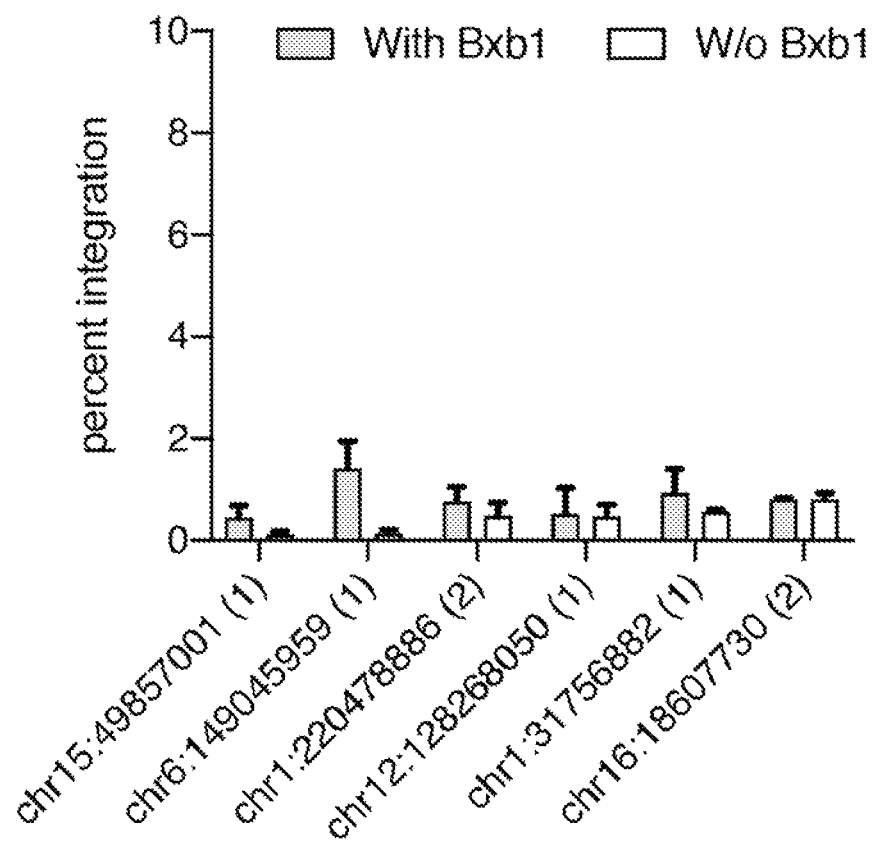
FIG. 26E shows PASTE Cas9 off-target integrations according to embodiments of the present teachings.
Figure 26F:
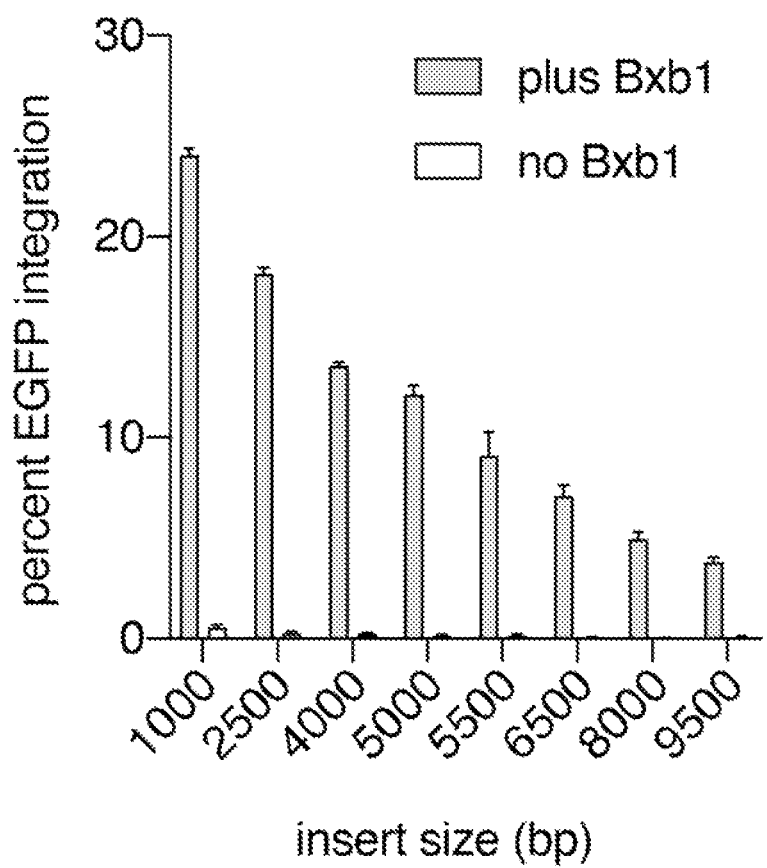
FIG. 26F shows the EGFP integration for gene inserts of different sizes according to embodiments of the present teachings.
Figure 27A:
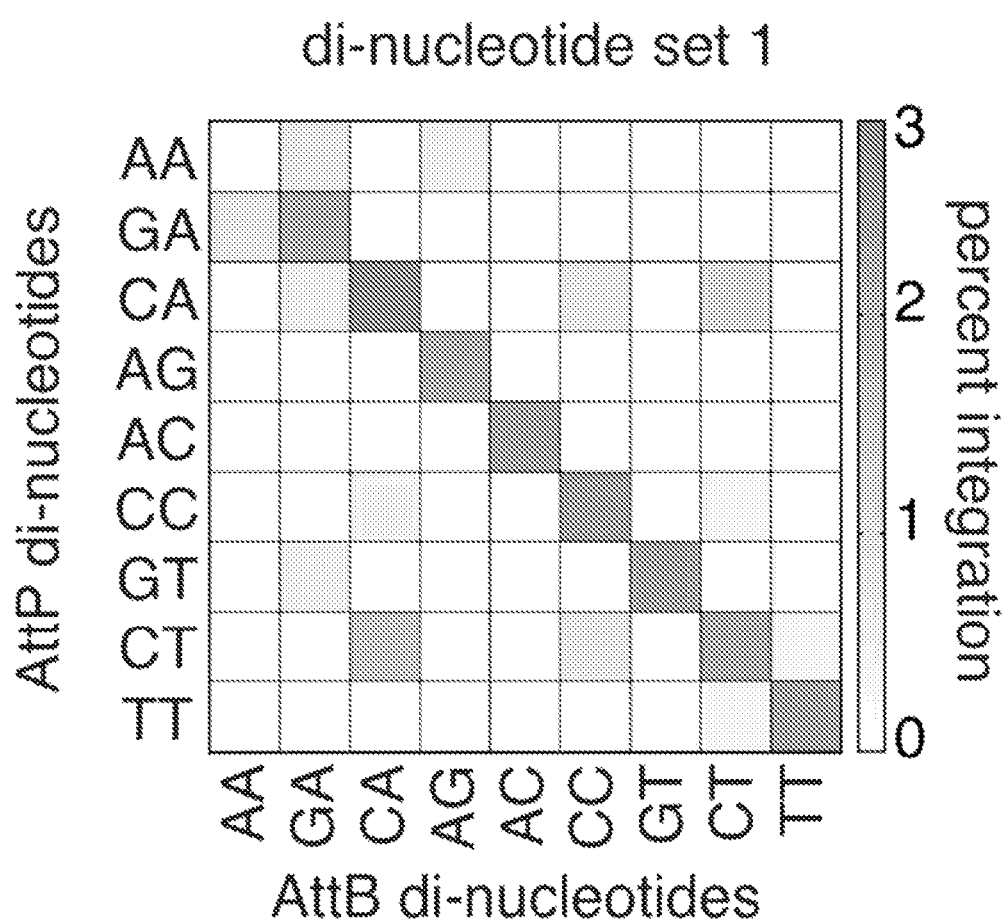
FIG. 27A shows the orthogonality between selected sets of attB and attP sites according to embodiments of the present teachings.
Figure 27B:
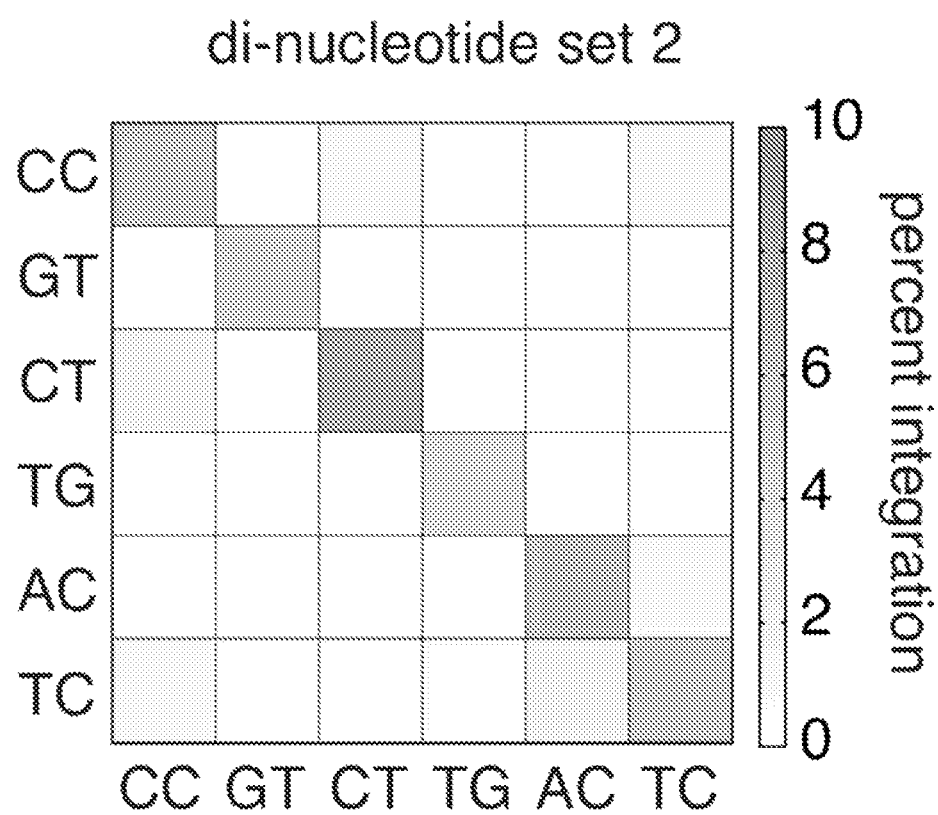
FIG. 27B shows the orthogonality between selected sets of attB and attP sites according to embodiments of the present teachings.
Figure 27C:
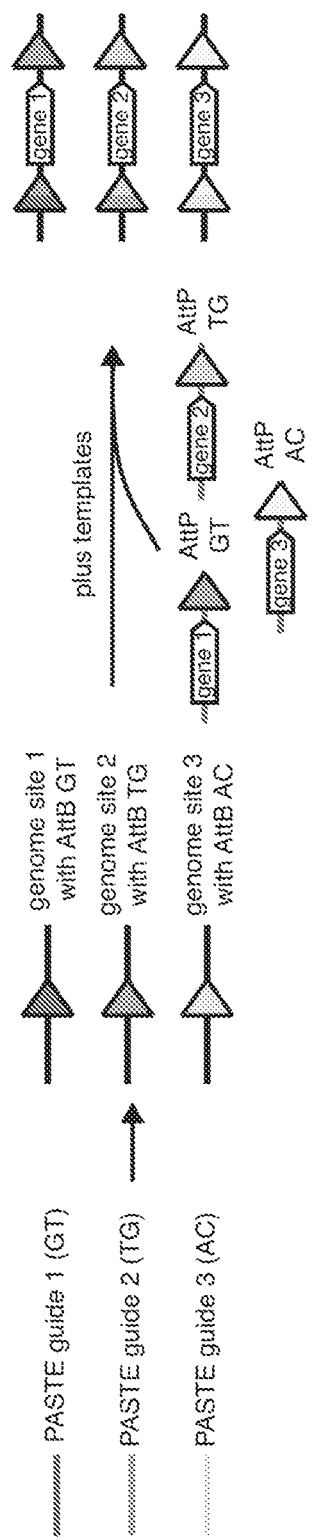
FIG. 27C shows a schematic for the orthogonal PASTE editing using engineered di-nucleotide combinations according to embodiments of the present teachings.

The PASTE and HITI on-target and off-target activities were compared (FIGS. 26A-26F). PASTE and HITI were found to have about 22% and 5% integration efficiencies respectively when using the same guide sequence (FIGS. 26A and 26B). PASTE was found to outperform HITI at most sites when analyzing the editing of 14 genes (FIG. 26C). Using a ddPCR based approach, it was found that PASTE was very specific with minimal off-target activity for Bxb1 off-targets integrations (FIG. 26D) and Cas9 off-targets integrations (FIG. 26E). The analysis of inserts of different sizes showed that PASTE can reliably insert sequences 1 kb-10 kb in size (FIG. 26F), revealing the wide range of sequence sizes PASTE is capable of working with. A decrease in insertion efficiency at larger sizes was also observed, which was likely due to the reduction in plasmid delivery to HEK293FT cells at larger plasmid sizes.

Example 16

Multiplexing with PASTE and Orthogonal Di-nucleotide attB and attP Sites

Multiplexing with PASTE and orthogonal di-nucleotide attB and attP sites was evaluated (FIGS. 28A-28C). Multiple orthogonal combinations were found for mutants of the central di-nucleotide motif (FIGS. 28A and 28B). As illustrated in FIG. 28C, programmable multiplexed gene insertion can be achieved by using these orthogonal combinations with PASTE only delivering different pegRNAs and gene inserts while keeping the protein components the same (FIG. 8C).

Example 17

PASTE Multiplexed Integrations at Endogenous Sites

Figure 28D:
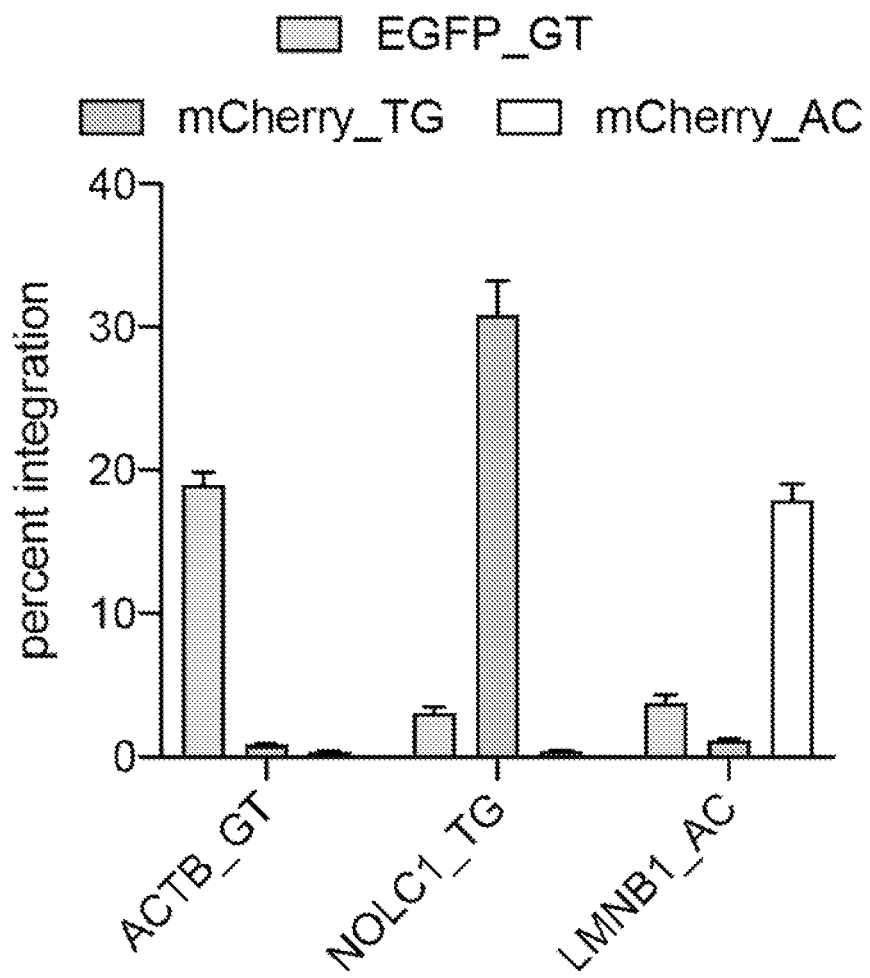
FIG. 28D shows the orthogonal gene integration at three endogenous sites with PASTE according to embodiments of the present teachings.
Figure 28E:
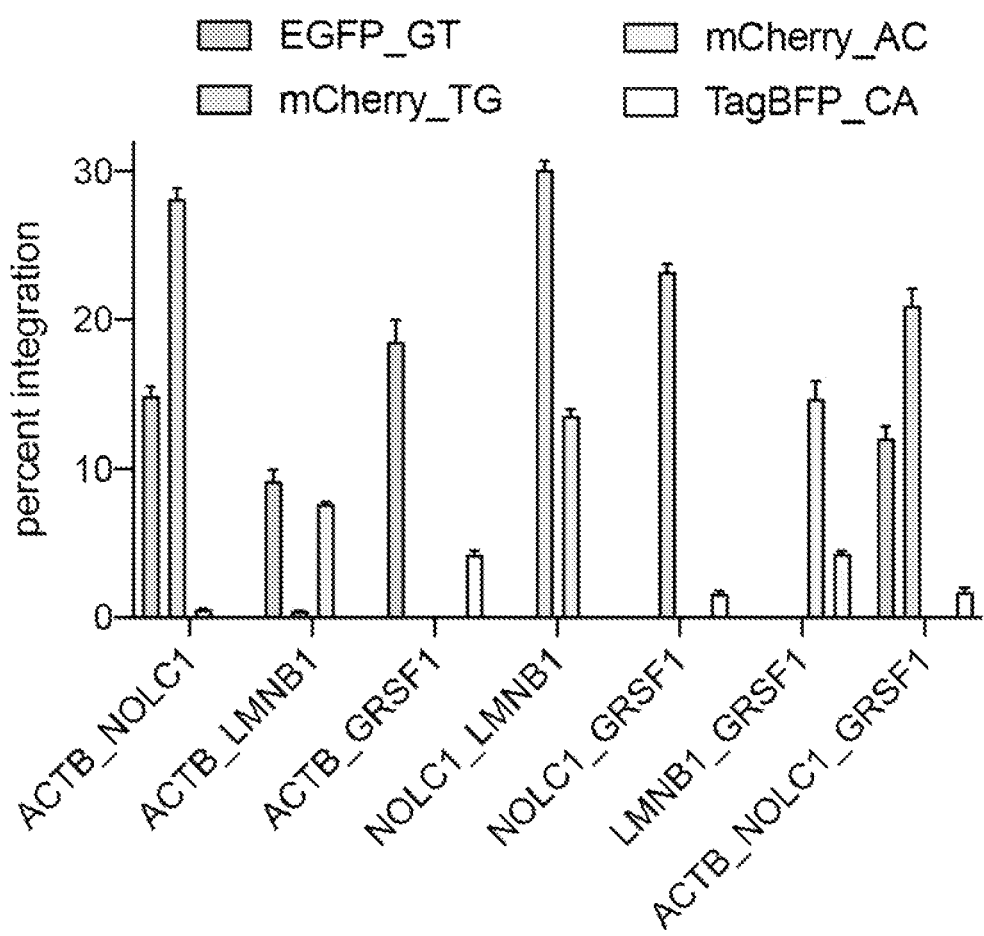
FIG. 28E shows the multiplexed insertion via one-plex, two-plex, and three-plex gene insertion at three endogenous sites via PASTE according to embodiments of the present teachings.
Figure 28G:
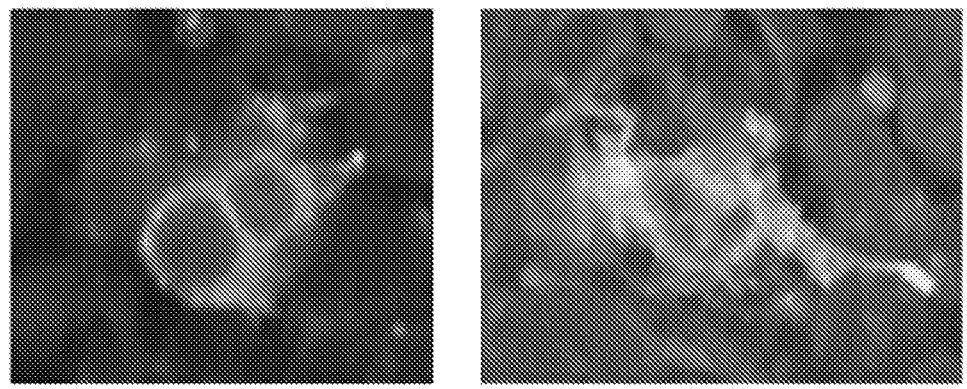
FIG. 28G shows fluorescent images two single cells with multiplexed gene tagging of ACTB (EGFP) and LMNB1 (mCherry) using PASTE according to embodiments of the present teachings.

PASTE multiplexed integrations at endogenous sites were evaluated (FIGS. 28A-28G). A reading frame for the attR scar that is left post-integration by Bxb1 that is ideal for a protein linker due to the enrichment of glycines, serines, and prolines in the sequence (GLSGQPPRSPSSGSSG (SEQ ID NO: 426)) was identified. PegRNAs were designed using this linker frame for the resolution of the attR for tagging a number of genes at the N-terminus with EGFP (ACTB, NOLC1, LMNB1, SUPT16H, SRRM2, and DEPDC4). As these genes all have distinct protein localization appearances, microscopy can be used for ascertaining proper gene tagging. PASTE was found to be capable of high-efficiency gene tagging with protein localizations that match the reference images and expected localization of the proteins in the cells (FIGS. 28A-28C). Genes were also tagged in multiplexed fashion to demonstrate the orthogonality of the engineered integration sites. ACTB, LMNB1, NOLC1, and GRSF were targeted with orthogonal pegRNAs carrying GT, TG, AC, and CA, respectively in HEK293FT in groups of single, dual-plexing, and triple-plexing (FIGS. 28D-28E). These dinucleotides were paired with templates carrying EGFP, BFP, and mCherry to allow for multicolor imaging of these labeled genes. The efficiencies of integration for these multiplexing experiments were found to range from about 5%-32%, revealing efficient multiplex integration with PASTE. Using confocal microscopy of these multiplexed integration experiments, cells were found with simultaneous labeling of these different proteins (FIGS. 28F-28G).

Example 18

Combination of CRISPR-Based Genome Editing and Site-Specific Integration

The combination of CRISPR-based genome editing and site-specific integration was evaluated.

Figure 29A:
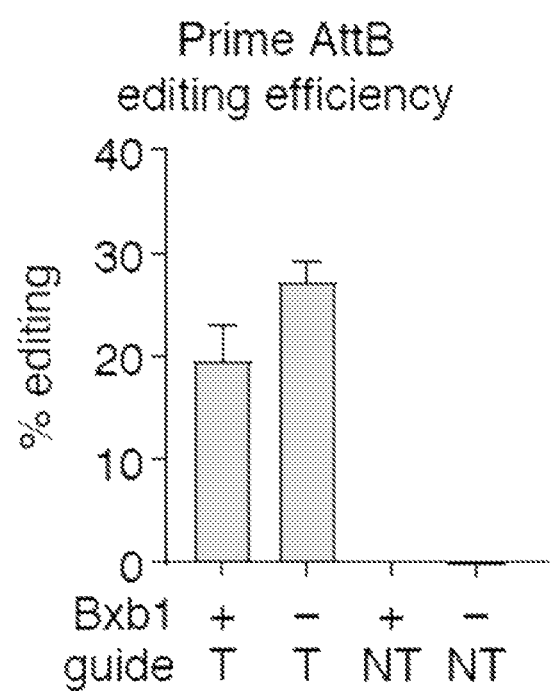
FIG. 29A shows the prime editing efficiency of Bxb1 attB site insertion at the ACTB locus according to embodiments of the present teachings.
Figure 29B:
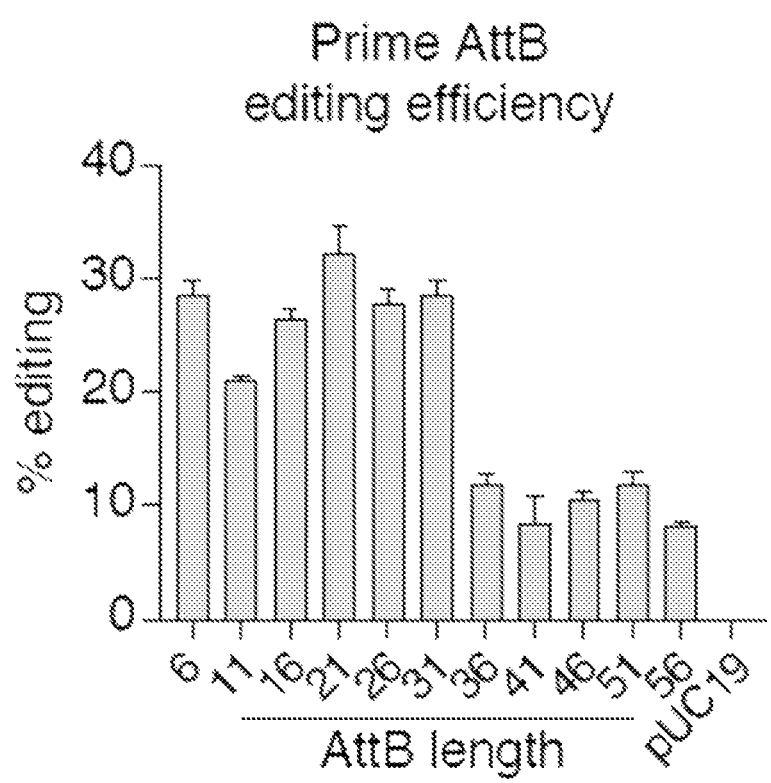
FIG. 29B shows the prime editing efficiency at inserting Bxb1 attB sites of different lengths at the ACTB locus according to embodiments of the present teachings.
Figure 29C:
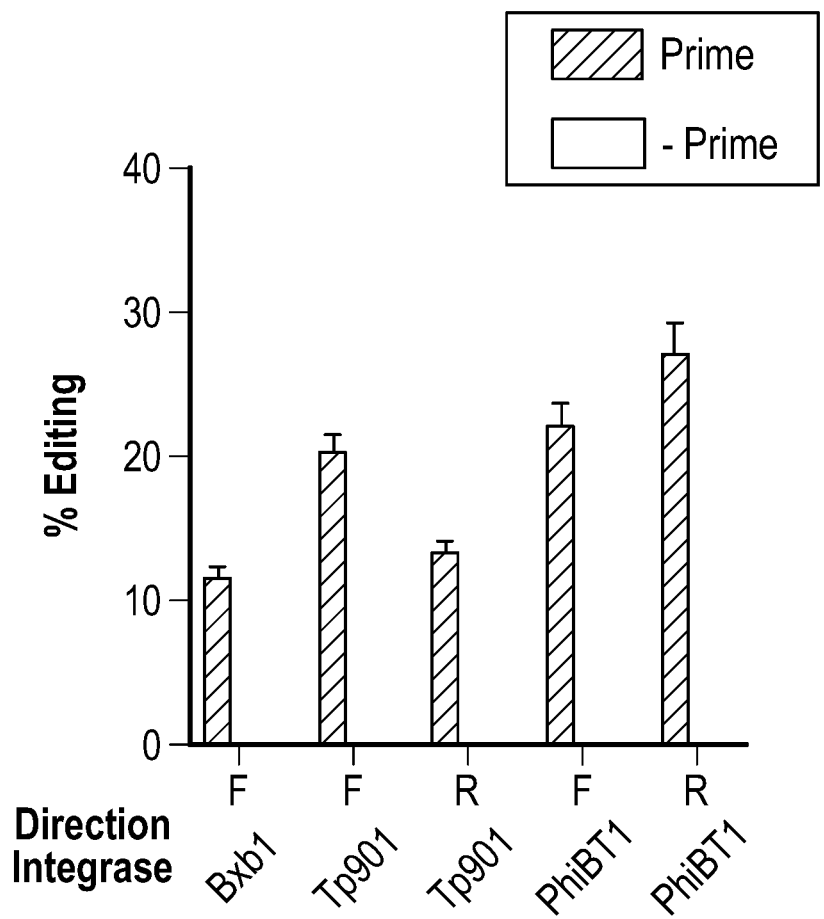
FIG. 29C shows the prime editing efficiency of inserting attB sequences from different integrases, wherein both orientations of landing sites are profiled (F, forward; and R, reverse) according to embodiments of the present teachings.
Figure 29D:
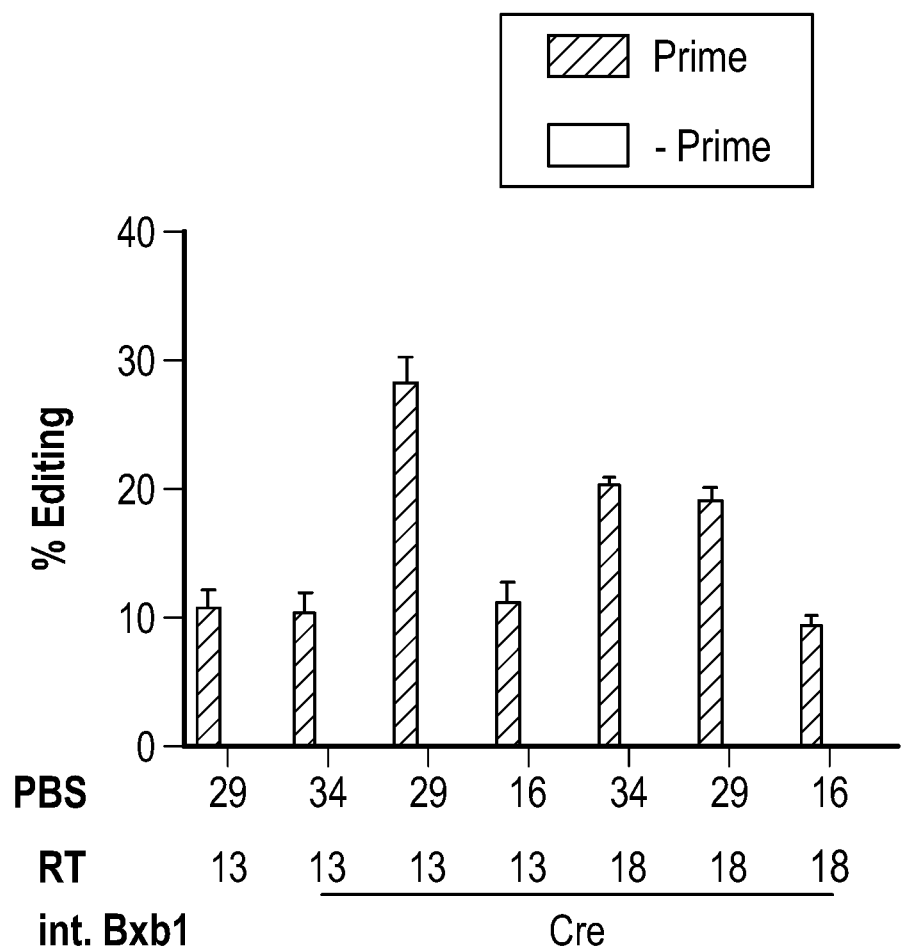
FIG. 29D shows the prime editing efficiency of inserting attB sequences from Bxb1 integrase and Cre recombinase, wherein both orientations of landing sites are profiled (F, forward; and R, reverse) according to embodiments of the present teachings.
Figure 29E:
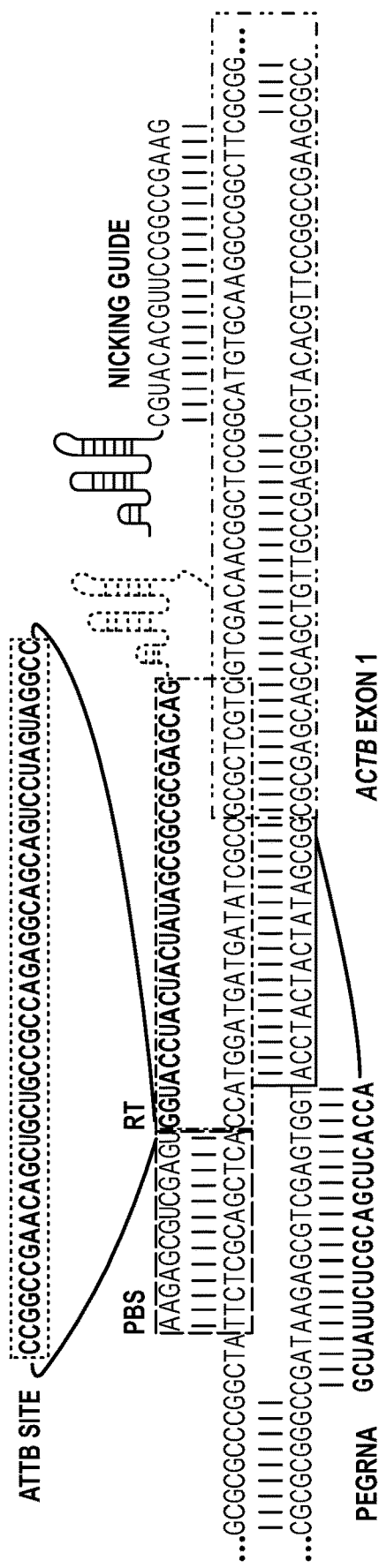
FIG. 29E shows a schematic of PASTE insertion at the ACTB locus showing guide and target sequences according to embodiments of the present teachings.
Figure 29F:
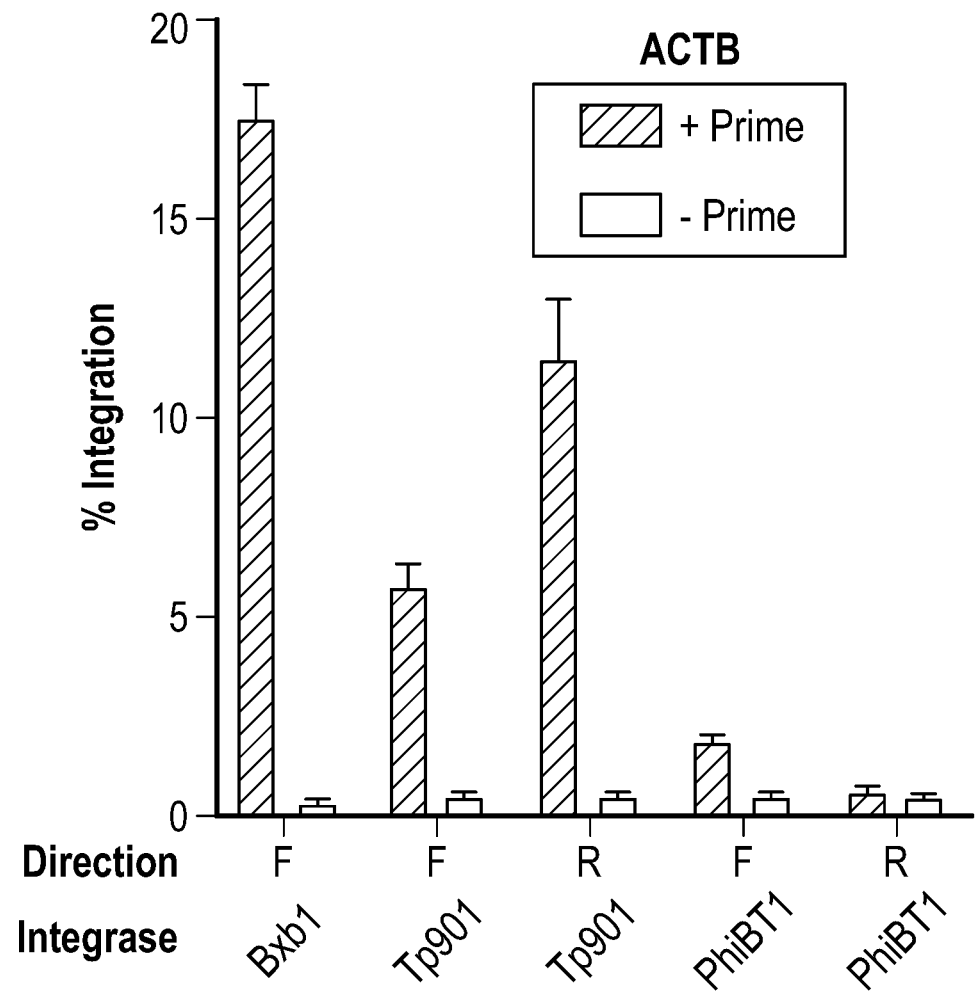
FIG. 29F shows a comparison of PASTE integration efficiency of GFP with a panel of integrases targeting the 5' end of the ACTB locus, wherein both orientations of landing sites are profiled (F, forward; and R, reverse) according to embodiments of the present teachings.
Figure 29G:
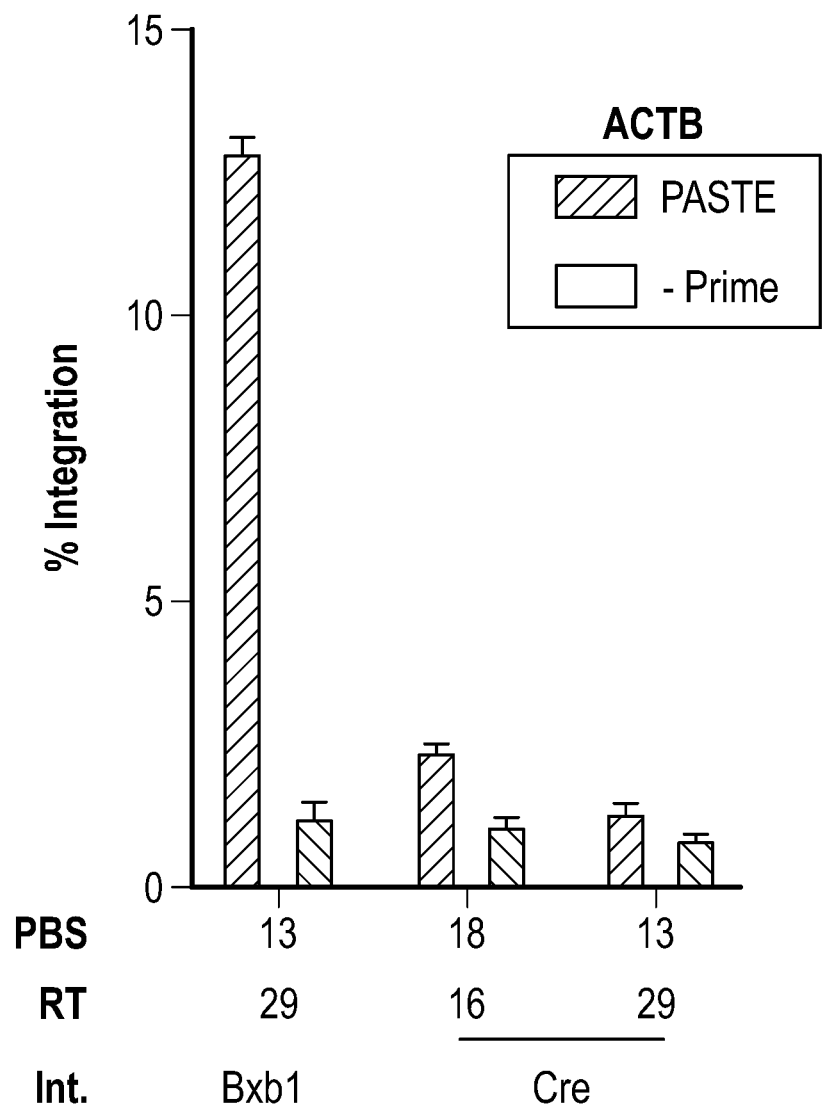
FIG. 29G shows a comparison of GFP cargo integration efficiency between Bxb1 integrases and Cre recombinase according to embodiments of the present teachings.
Figure 29H:
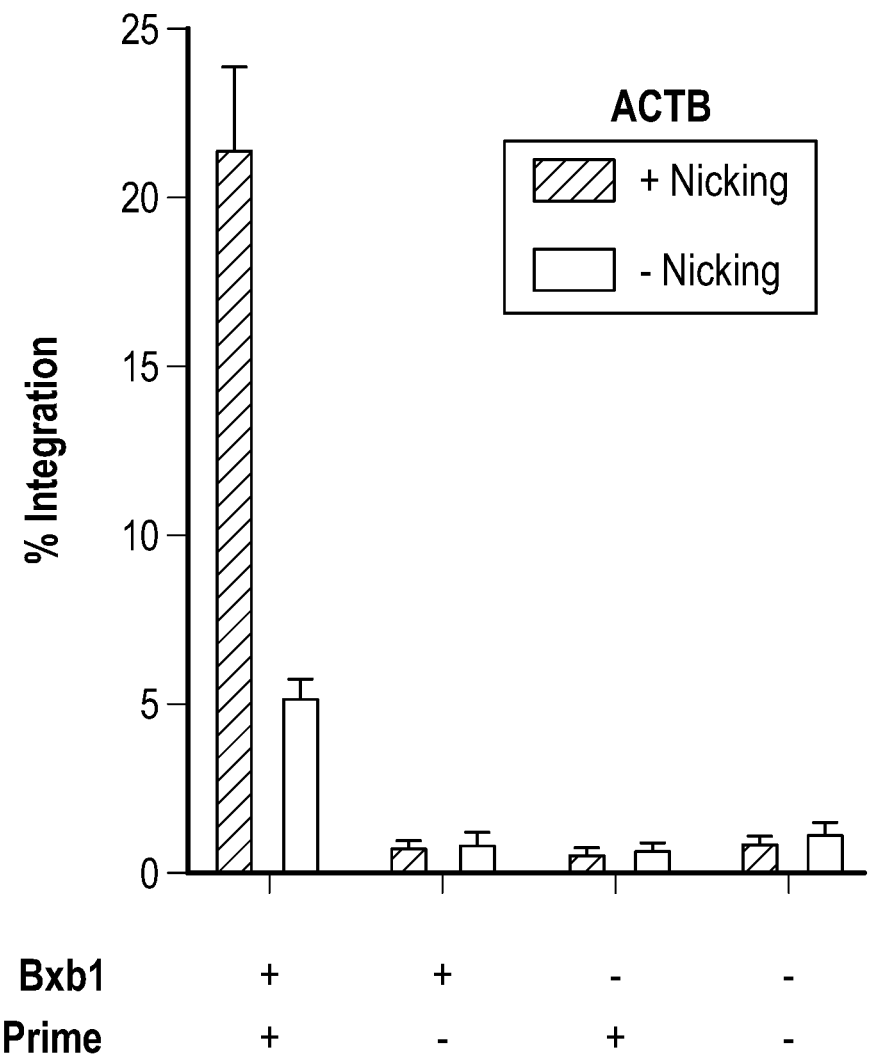
FIG. 29H shows the dependence of PASTE editing activity on different prime and integrase components according to embodiments of the present teachings.
Figure 29I:
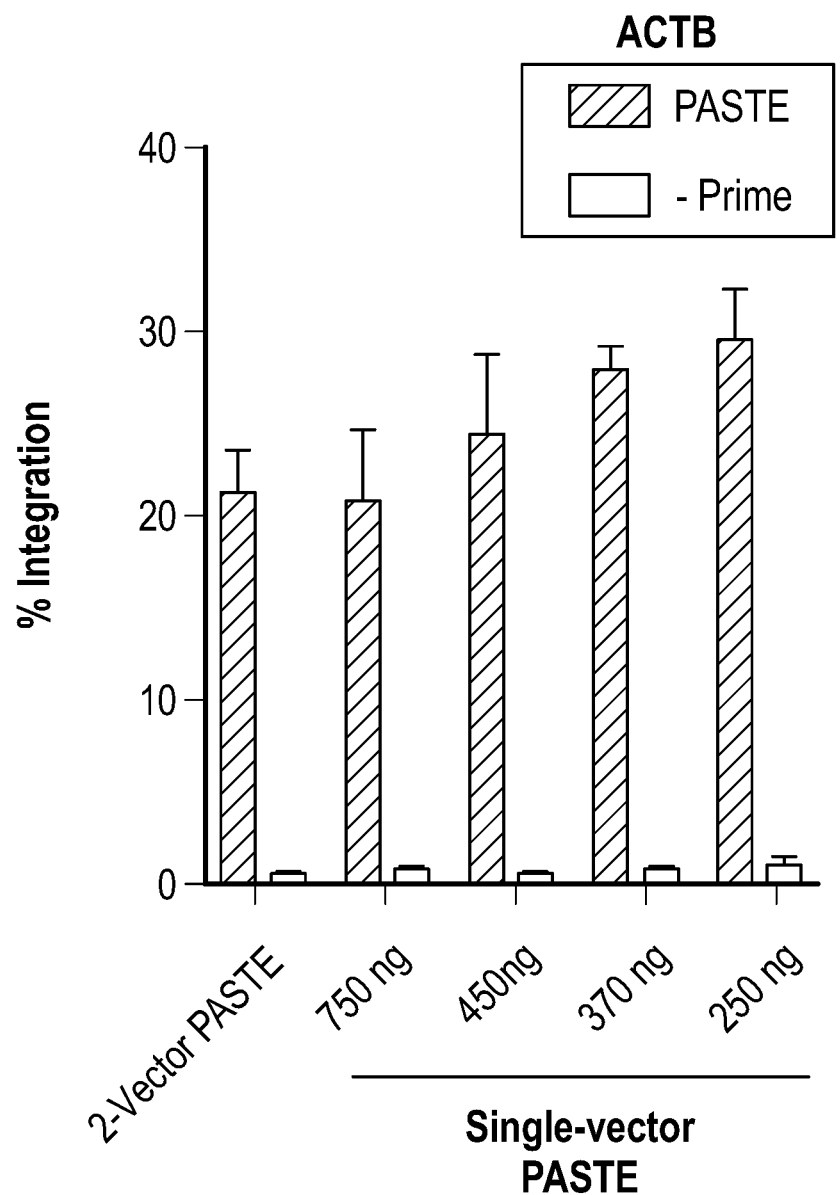
FIG. 29I shows a titration of a single vector PASTE system (SpCas9-RT-P2A-Bxb1) on integrase efficiency according to embodiments of the present teachings.
Figure 29J:
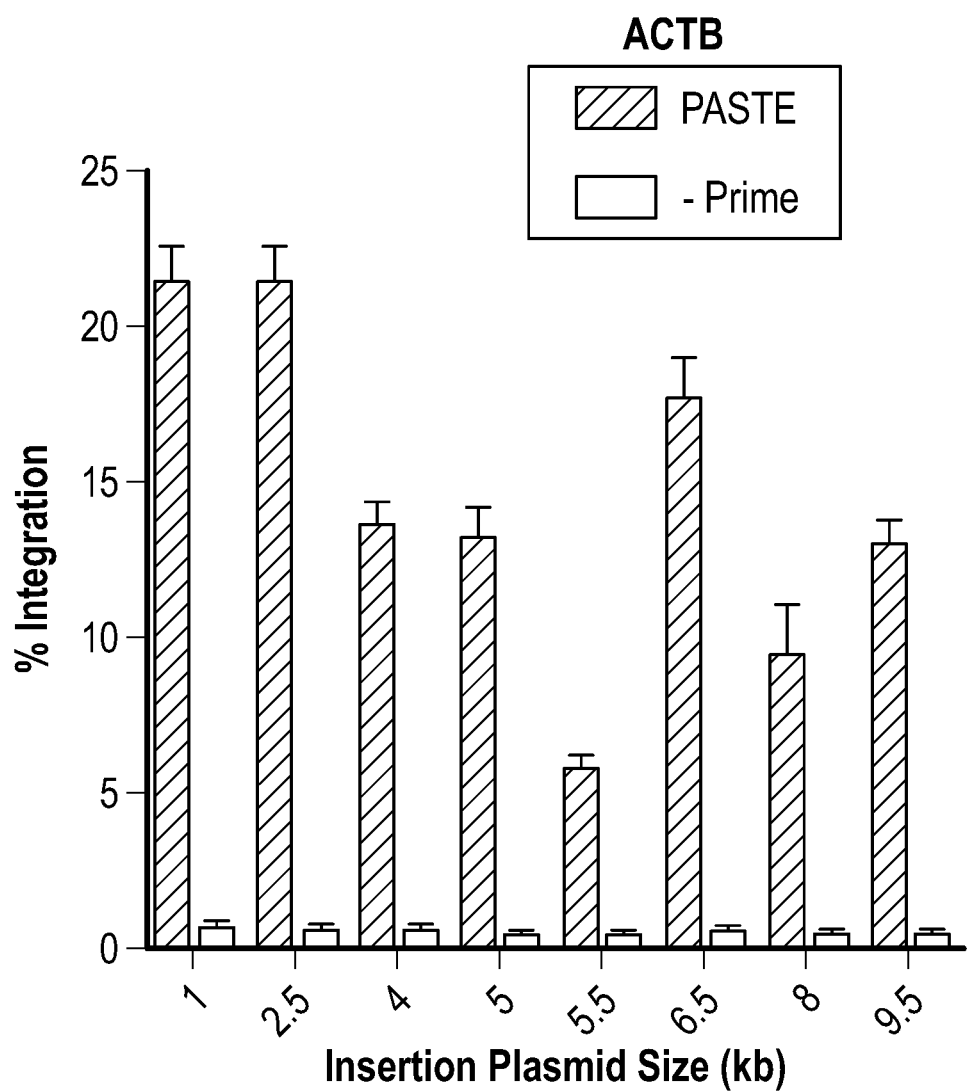
FIG. 29J shows the effect of cargo size on PASTE insertion efficiency at the endogenous ACTB target according to embodiments of the present teachings.
Figure 29K:
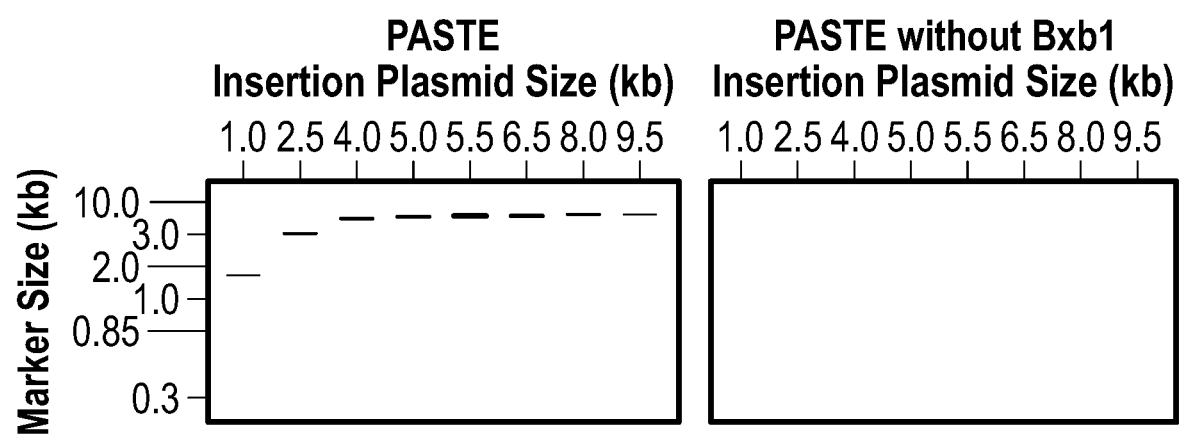
FIG. 29K shows a gel electrophoresis showing complete insertion by PASTE for multiple cargo sizes according to embodiments of the present teachings.
Figure 30A:
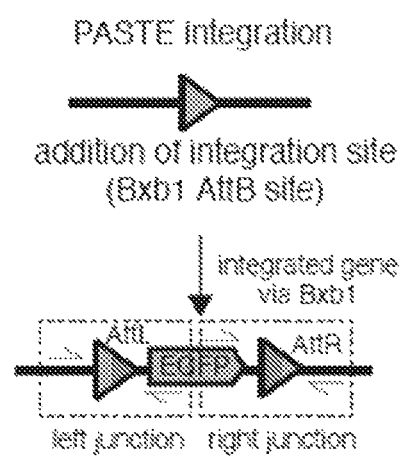
FIG. 30A shows a schematic of PASTE integration, including resulting attR and attL sites that are generated and PCR primers for assaying the integration junctions according to embodiments of the present teachings.
Figure 30B:
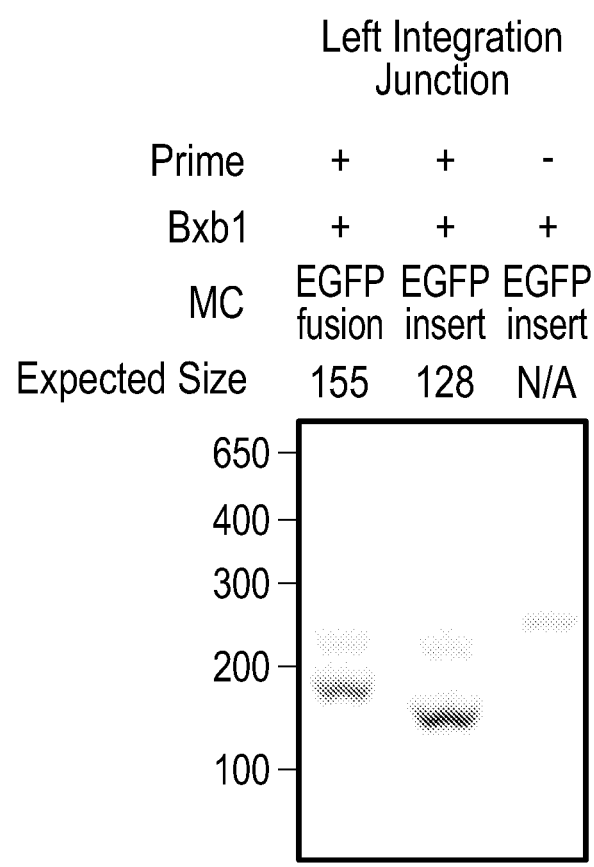
FIG. 30B shows a PCR and gel electrophoresis readout of left integration junction from PASTE insertion of GFP at the ACTB locus, wherein the insertion is analyzed for in-frame and out-of-frame GFP integration experiments as well as for a no prime control and expected sizes of the PCR fragments are shown using the primers shown in the schematic in subpanel FIG. 30A according to embodiments of the present teachings.
Figure 30C:
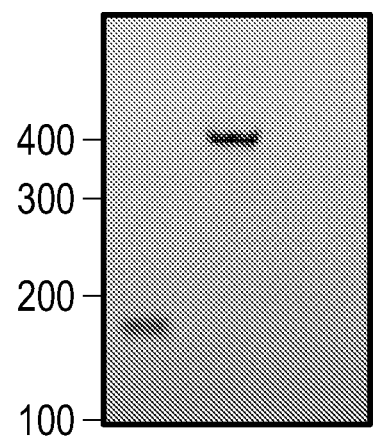
FIG. 30C shows a PCR and gel electrophoresis readout of right integration junction from PASTE insertion of GFP at the ACTB locus, wherein the insertion is analyzed for in-frame and out-of-frame GFP integration experiments as well as for a no prime control and the expected sizes of the PCR fragments are shown using the primers shown in the schematic in subpanel FIG. 30A according to embodiments of the present teachings.
Figure 30D:
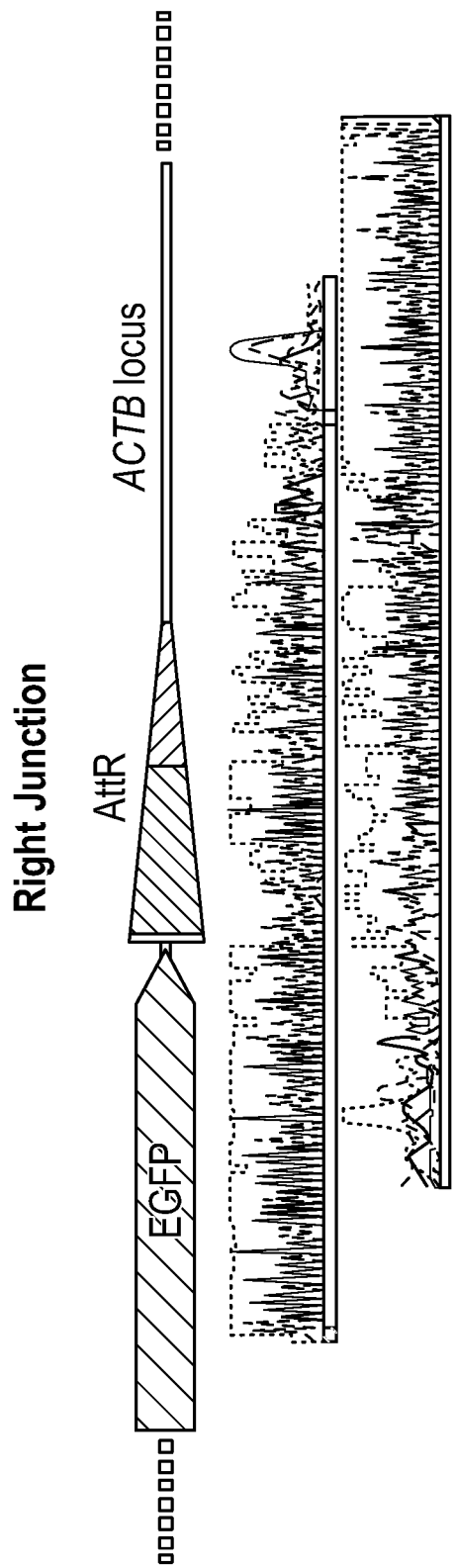
FIG. 30D shows a Sanger sequencing shown for the right integration junction for an in-frame fusion of GFP via PASTE to the N-terminus of ACTB according to embodiments of the present teachings.
Figure 30E:
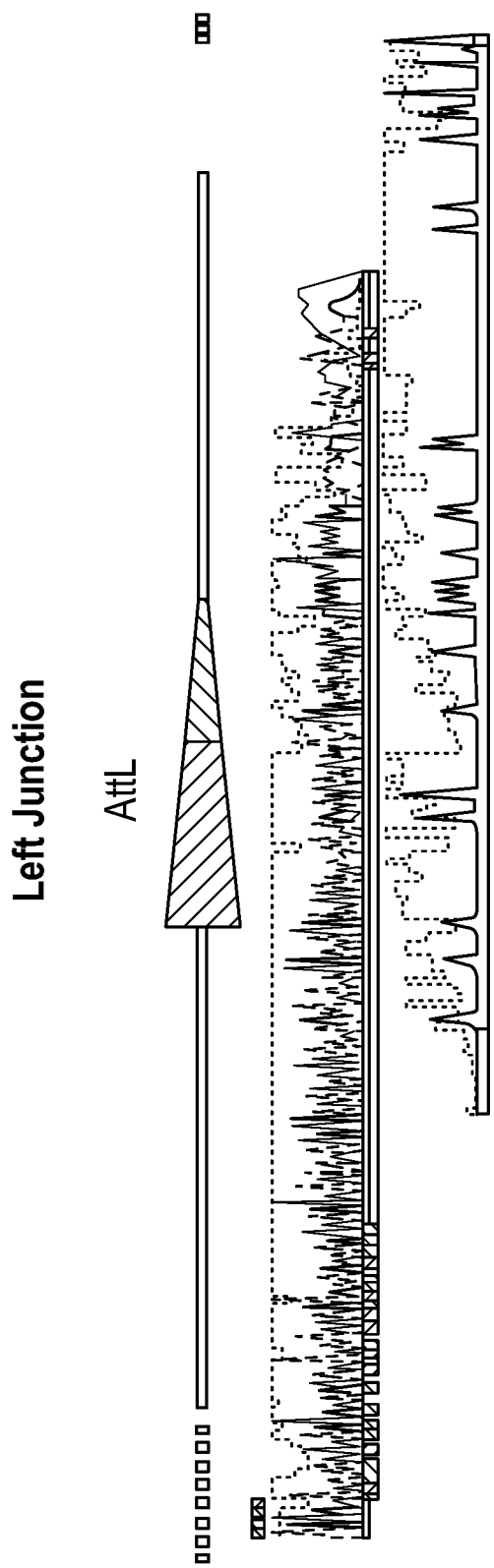
FIG. 30E shows a Sanger sequencing shown for the left integration junction for an in-frame fusion of GFP via PASTE to the N-terminus of ACTB according to embodiments of the present teachings.

PegRNAs containing different attB length truncations were assessed (FIG. 29A). Prime editing was found to be capable of inserting sequences up to 56 bp at the beta-actin (ACTB) gene locus, with higher efficiency at lengths below 31 bp (FIGS. 29A-B) The integration of cognate landing sites was tested for multiple insertion enzymes: Bxb1, TP901, and phiBT1 phage serine integrases and Cre recombinase. Prime editing successfully inserted all landing sites tested, with efficiencies between 10-30% (FIGS. 29C-D). To test the complete system, all components were combined and delivered in a single transfection: the prime editing vector, the landing site containing pegRNA, a nicking guide for stimulating prime editing, a mammalian expression vector for the corresponding integrase or recombinase and a 969 bp minicircle DNA cargo encoding green fluorescent protein (GFP) (FIG. 29E). GFP integration rates among the four integrases and recombinases were compared and Bxb1 integrase was found to have the highest integration rate (~20%) at the targeted ACTB locus and require the prime editing nicking guide for optimal performance (FIGS. 29F-H). Finally, to reduce the number of transfected components, Bxb1 was co-expressed with the SpCas9-M-MLV reverse transcriptase (PE2) fusion protein via a P2A protein cleavage site. This combination maintained high GFP insertion efficiency, up to 30% (FIG. 29E). The complete system, PASTE, achieved precise integration of templates as large as 9,500 bp with greater than 10% integration efficiency (FIGS. 29J-K and 26E), with complete integration of the full-length cargo confirmed by Sanger sequencing (FIG. 30A-E).

Example 19

Impact of Prime Editing and Integrase Parameters on PRIME Editing

The impact of prime editing and integrase parameters on the integration efficiency of PRIME editing was assessed.

Relevant pegRNA parameters for PASTE include the primer binding site (PBS), reverse transcription template (RT), and attB site lengths, as well as the relative locations and efficacy of the pegRNA spacer and nicking guide (FIG.

Figure 31B:
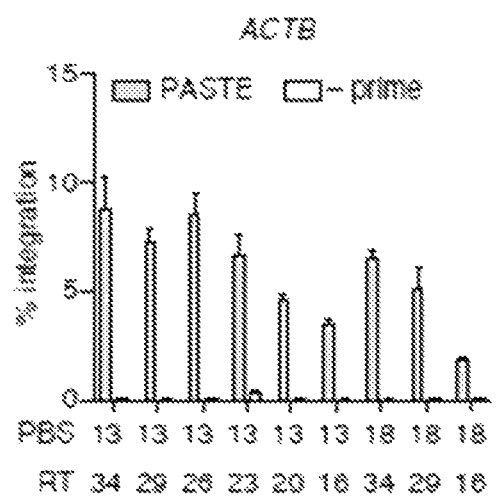
FIG. 31B shows the impact of PBS and RT length on PASTE integration of GFP at the ACTB locus according to embodiments of the present teachings.
Figure 31C:
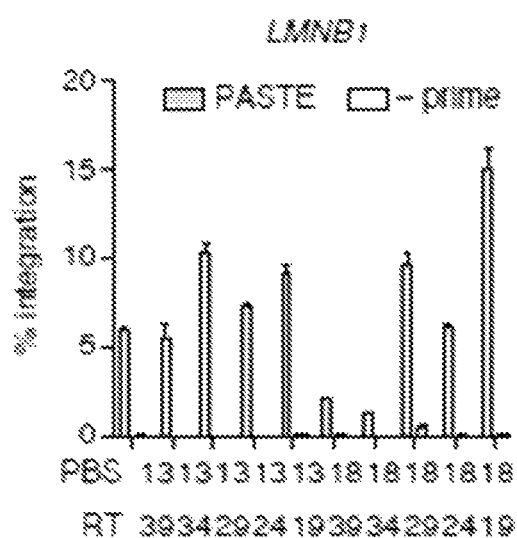
FIG. 31C shows the impact of PBS and RT length on PASTE integration of GFP at the LMNB1 locus according to embodiments of the present teachings.

31A). A range of PBS and RT lengths were tested at two loci, ACTB and lamin B1 (LMNB1), and rules governing efficiency were found to vary between loci, with shorter PBS lengths and longer RT designs having higher editing at the ACTB locus (FIG. 31B) and longer PBS and shorter RT designs performing better at LMNB1 (FIG. 31C).

Figure 31D:
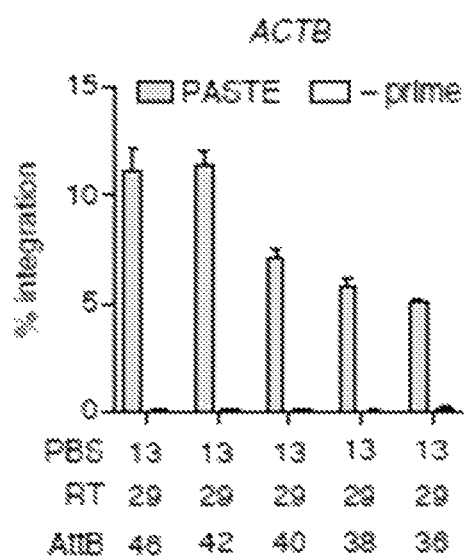
FIG. 31D shows the impact of attB length on PASTE integration of GFP at the ACTB locus according to embodiments of the present teachings.
Figure 31E:
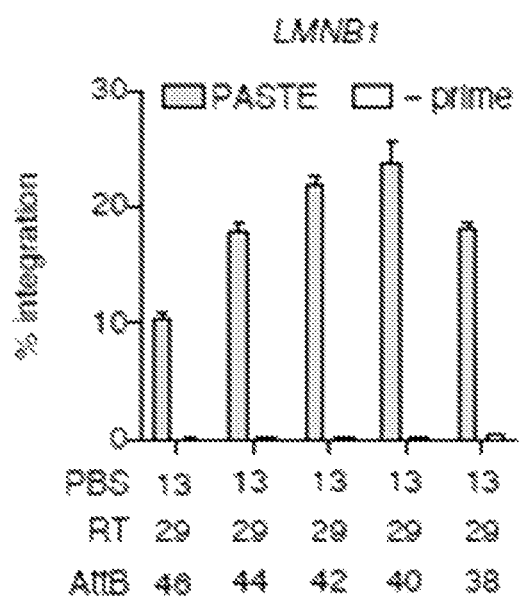
FIG. 31E shows the impact of attB length on PASTE integration of GFP at the LMNB1 locus according to embodiments of the present teachings.
Figure 31F:
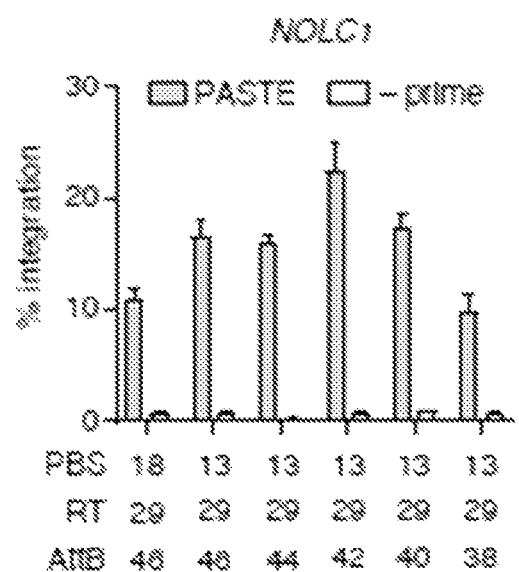
FIG. 31F shows the impact of attB length on PASTE integration of GFP at the NOLC1 locus according to embodiments of the present teachings.

The length of the attB landing site must balance two conflicting factors: the higher efficiency of prime editing for smaller inserts and reduced efficiency of Bxb1 integration at shorter attB lengths. AttB lengths were evaluated at ACTB, LMNB1, and nucleolar phosphoprotein p130 (NOLC1), and the optimal attB length was found to be locus dependent. At the ACTB locus, long attB lengths could be inserted by prime editing (FIG. 29B) and overall PASTE efficiencies for the insertion of GFP were highest for long attB lengths (FIG. 31d). In contrast, intermediate attB lengths had higher overall integration efficiencies (>20%) at LMNB1 (FIG. 31E) and NOLC1 (FIG. 31F), indicating that the increased efficiency of installing shorter attB sequences overcame the reduction of Bxb1 integration at these sites.

Figure 32A:
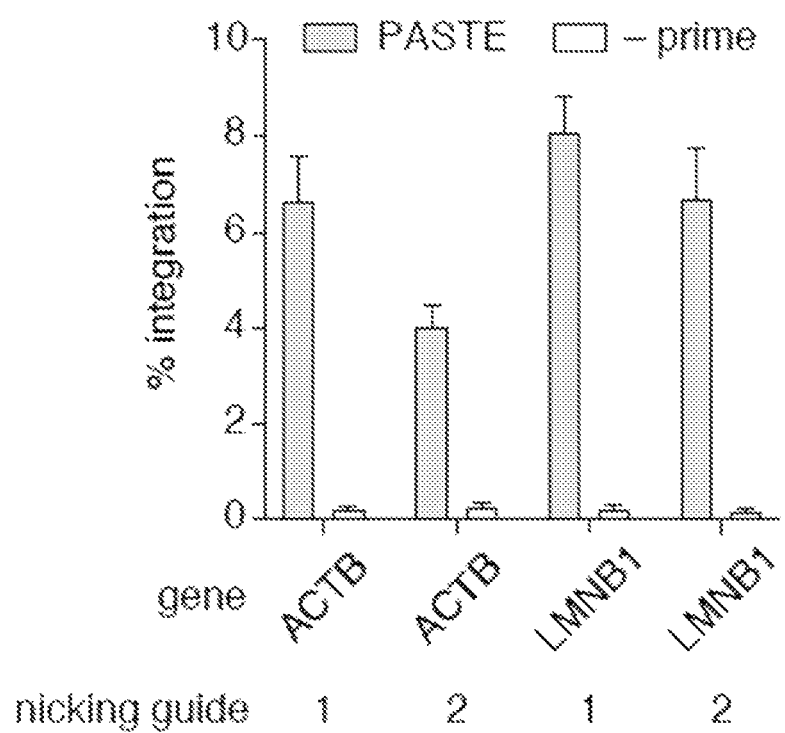
FIG. 32A shows the PASTE insertion efficiency at ACTB and LMNB1 loci with two different nicking guide designs according to embodiments of the present teachings.
Figure 32B:
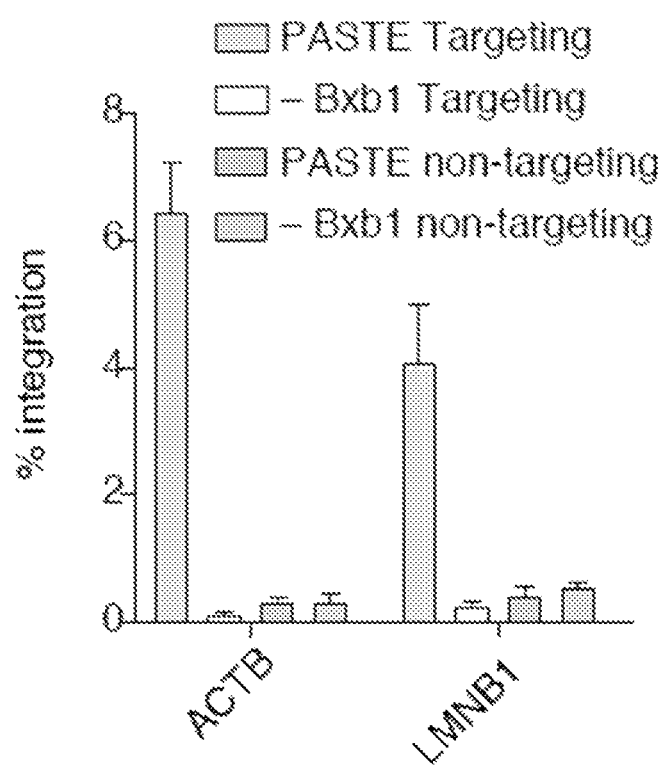
FIG. 32B shows the PASTE editing efficiency at ACTB and LMNB1 with target and non-targeting spacers and matched pegRNAs with and without Bxb1 expression according to embodiments of the present teachings.

The PE3 version of prime editing combines PE2 and an additional nicking guide to bias resolution of the flap intermediate towards insertion. To test the importance of nicking guide selection on PASTE editing, editing at ACTB and LMNB1 loci was tested with two nicking guide positions. Suboptimal nicking guide positions were found to reduce the PASTE efficiency up to 30% (FIG. 32A) in agreement with the 75% reduction of PASTE efficiency in the absence of nicking guide (FIG. 29G). The pegRNA spacer sequence was found to be necessary for PASTE editing, and substitution of the spacer sequence with a non-targeting guide was found to eliminate editing (FIG. 32B).

Figure 33A:
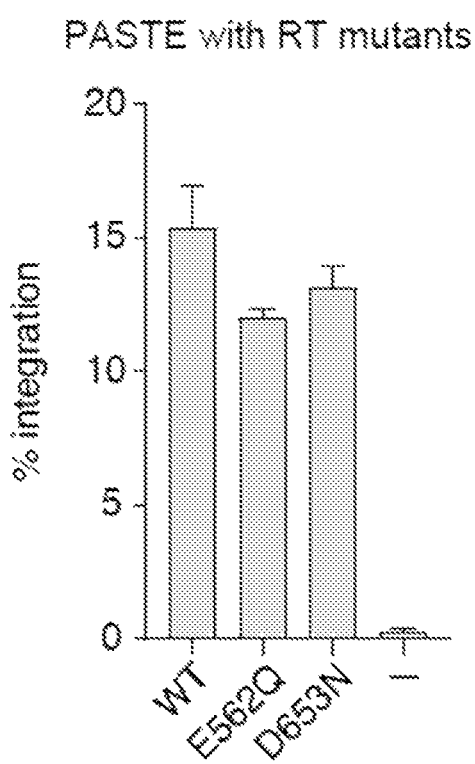
FIG. 33A shows the PASTE integration of GFP at the ACTB locus with different Bxb1 catalytic mutants according to embodiments of the present teachings.
Figure 33B:
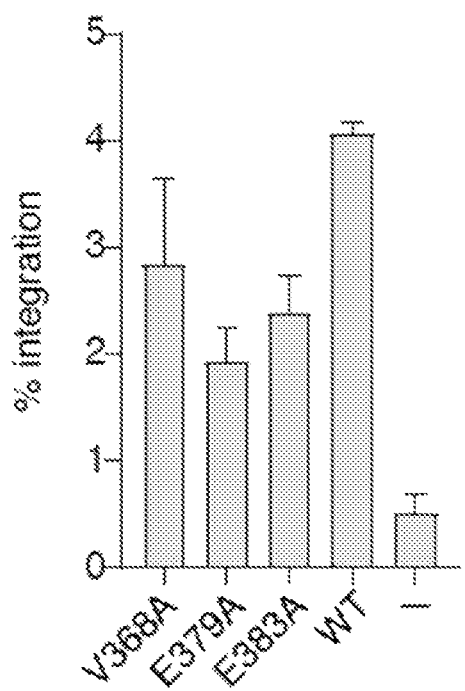
FIG. 33B shows the PASTE integration of GFP at the ACTB locus with different RT catalytic mutants according to embodiments of the present teachings.

Rational mutations were also introduced in both the Bxb1 integrase and reverse transcriptase domain of the PE2 construct to optimize PASTE further. While some of these mutations were well tolerated by PASTE (FIGS. 33A-B), none of them improved PASTE editing efficiency.

Figure 31G:
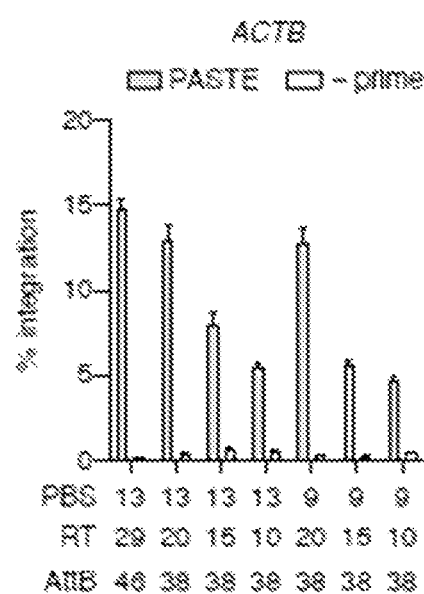
FIG. 31G shows the impact of minimal PBS, RT, and attB lengths on PASTE integration efficiency of GFP at the ACTB locus according to embodiments of the present teachings.
Figure 31H:
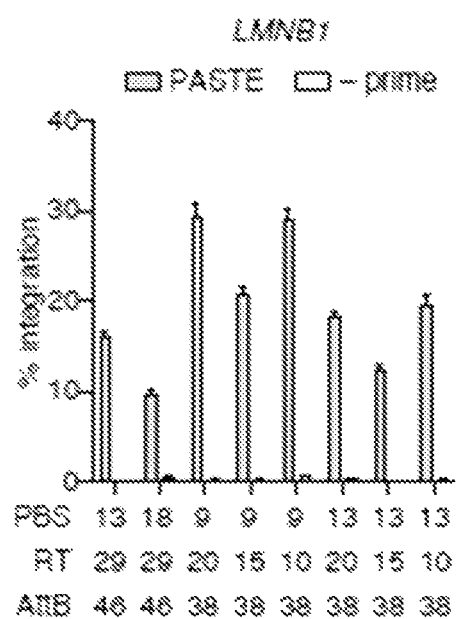
FIG. 31H shows the impact of minimal PBS, RT, and attB lengths on PASTE integration efficiency of GFP at the LMNB1 locus according to embodiments of the present teachings.
Figure 31I:
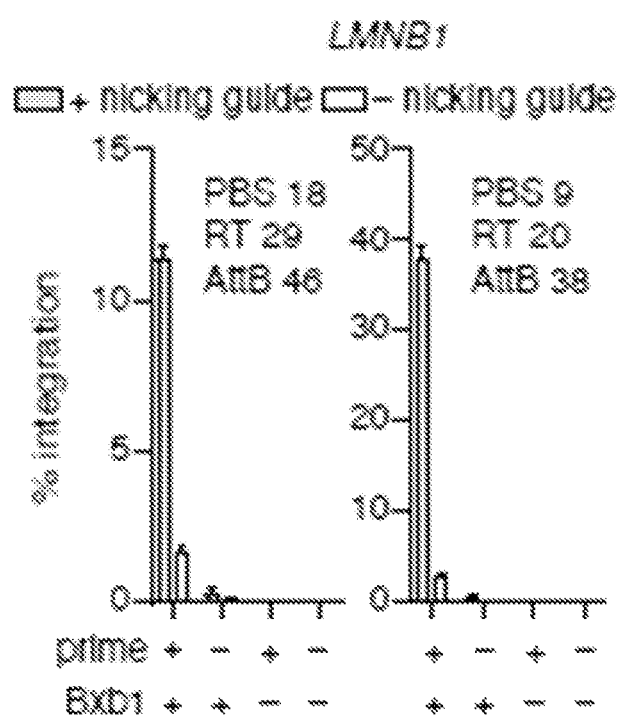
FIG. 31I shows the PASTE integration of GFP at the LMNB1 locus in the presence and absence of nicking guide, prime, and Bxb1 with a minimally compact pegRNA containing a 38 bp attB compared to a longer pegRNA design according to embodiments of the present teachings.

Short RT and PBS lengths can offer additional improvements for editing. A panel of shorter RT and PBS guides were tested at ACTB and LMNB1 loci and while shorter RT and PBS sequences did not increase editing at ACTB (FIG. 31G), it was found that they had improved editing at LMNB1 (FIG. 31H) with best performing guides reaching GFP insertion rates of ~40% (FIG. 31I).

Example 20

PASTE Tagging at Multiple Endogenous Genes

Figure 34A:
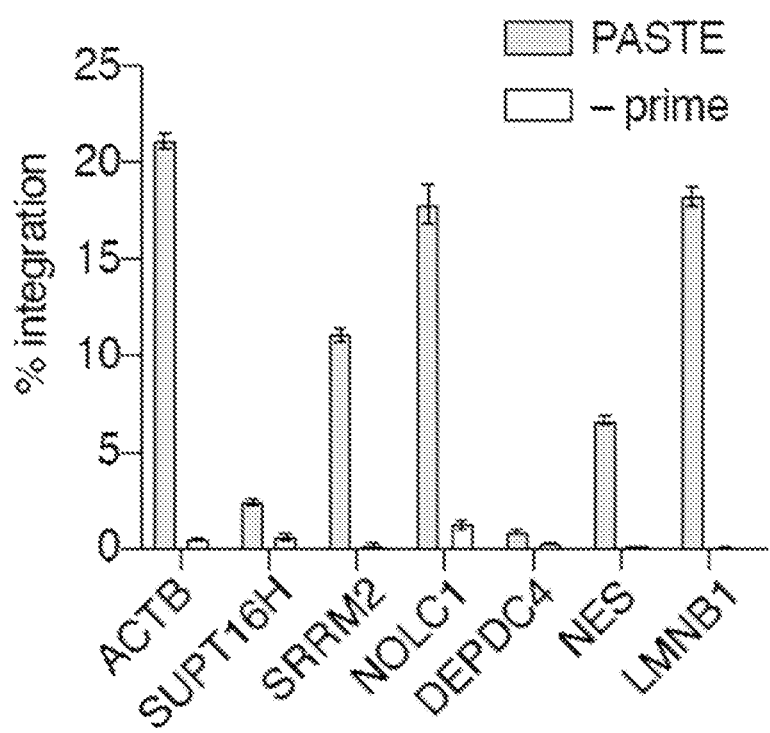
FIG. 34A shows the GFP integration by PASTE at a panel of endogenous genomic loci according to embodiments of the present teachings.
Figure 34B:
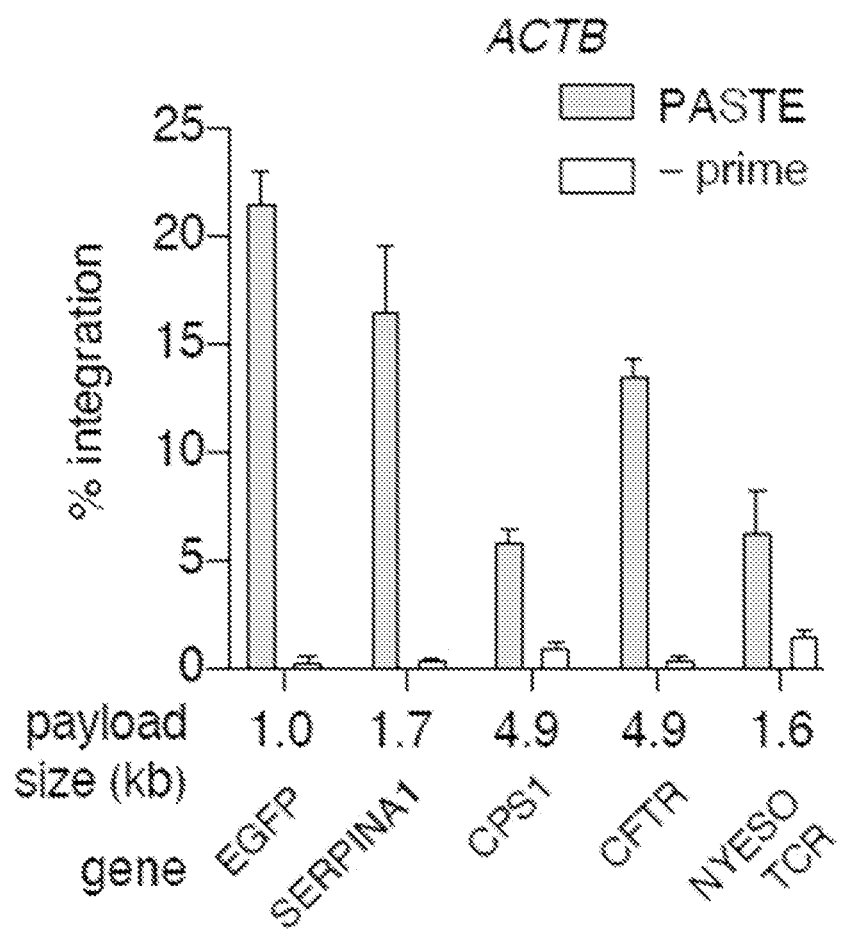
FIG. 34B shows the integration of a panel of different gene cargo at ACTB locus via PASTE according to embodiments of the present teachings.
Figure 34C:
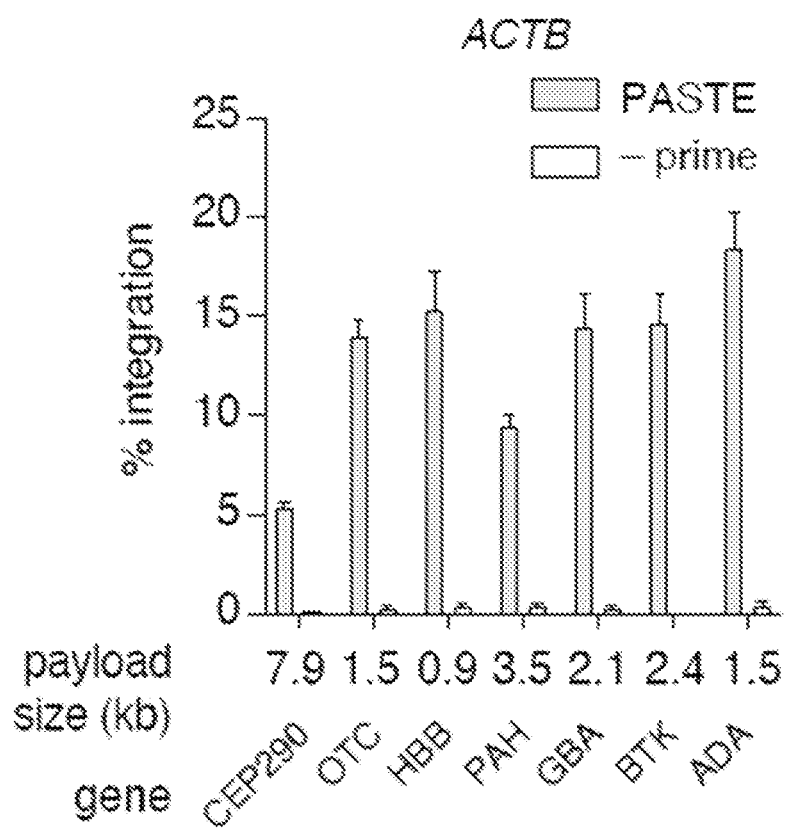
FIG. 34C shows the integration efficiency of therapeutically relevant genes at the ACTB locus according to embodiments of the present teachings.
Figure 35:
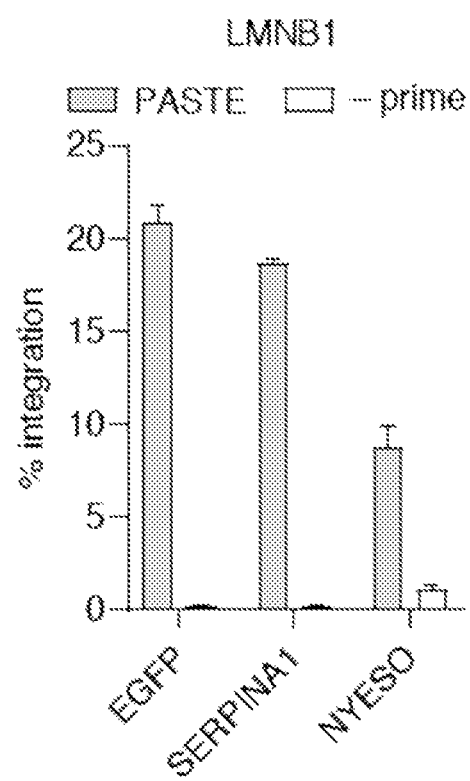
FIG. 35 shows the integration of a panel of different gene cargo at LMNB1 locus via PASTE according to embodiments of the present teachings.

GFP insertion efficiency was measured at seven different gene loci—ACTB, SUP T16H, SRM2, NOLC1, DEPDC4, NES, and LMNB1—to test the versatility of the PASTE programming. A range of integration rates up to 22% was found (FIG. 34A). Because PASTE does not require homology or sequence similarity on cargo plasmids, integration of diverse cargo sequences is modular and easily scaled across different loci. Six different gene cargos, varying in size from 969 bp to 4906 bp, were tested for insertion at ACTB and LMNB1 loci with PASTE. Integration frequencies between 5% and 22% depending on the gene and insertion locus were found (FIGS. 34B and 35). Additionally, a panel of seven common therapeutic genes, CEP290, OTC, HBB, PAH, GBA, BTK, and ADA was evaluated for insertion at the ACTB locus, and the efficient integration of these cargos were found between 5%-20% (FIG. 34C).

Figure 34D:
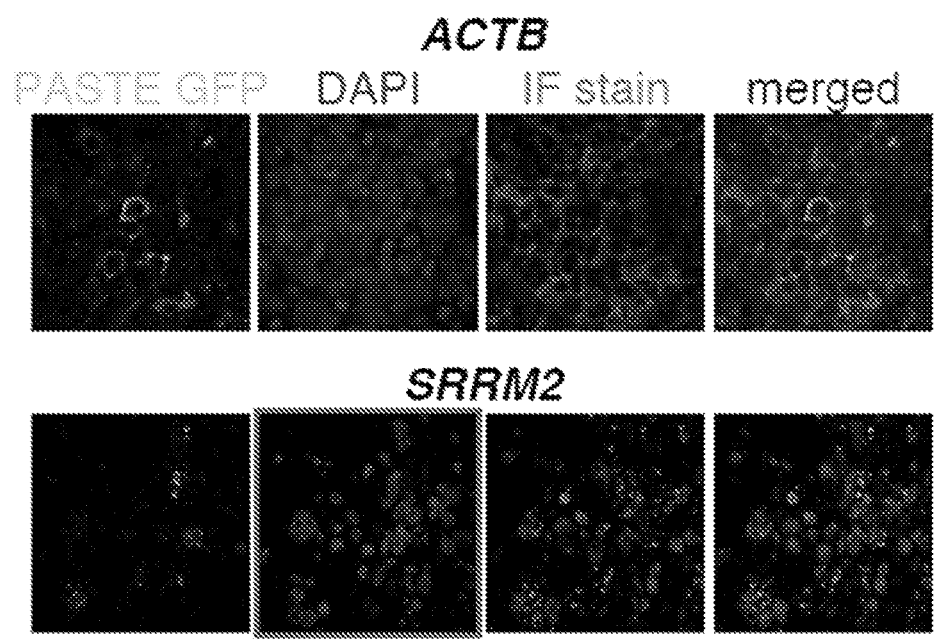
FIG. 34D shows the endogenous protein tagging with GFP via PASTE by in-frame endogenous gene tagging at the ACTB loci and SRRM2 loci according to embodiments of the present teachings.
Figure 34E:
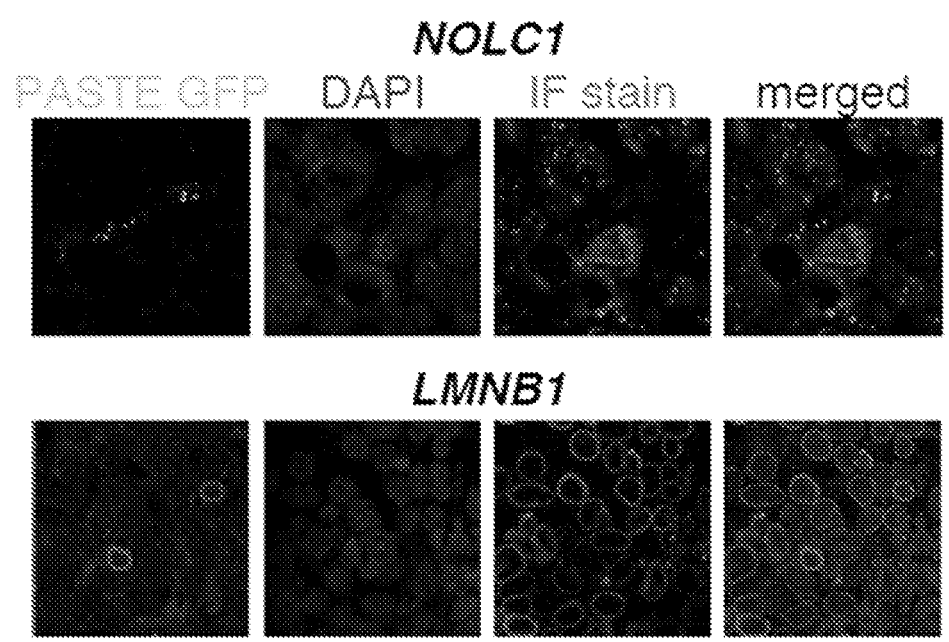
FIG. 34E shows the endogenous protein tagging with GFP via PASTE by in-frame endogenous gene tagging at the NOLC1 loci and LMNB1 loci according to embodiments of the present teachings.

The precise insertions of PASTE for in-frame protein tagging or expressing cargo without disruption of endogenous gene expression was assessed. As Bxb1 leaves residual sequences in the genome (termed attL and attR) after cargo integration, these genomic scars can serve as protein linkers. The frame of the attR sequence was positioned through strategic placement of the attP on the minicircle cargo, achieving a suitable protein linker, GGLSGQPPRSPSSGSSG (SEQ ID NO: 427). Using this linker, four genes (ACTB, SRRM2, NOLC1, and LMNB1) were tagged with GFP using PASTE. To assess correct gene tagging, the subcellular location of GFP was compared with the tagged gene product by immunofluorescence. For all four targeted loci, GFP co-localized with the tagged gene product, indicating successful tagging (FIGS. 34D-E).

Example 21

Orthogonal Sequence Preferences for Bxb1 Integration

Figure 36A:
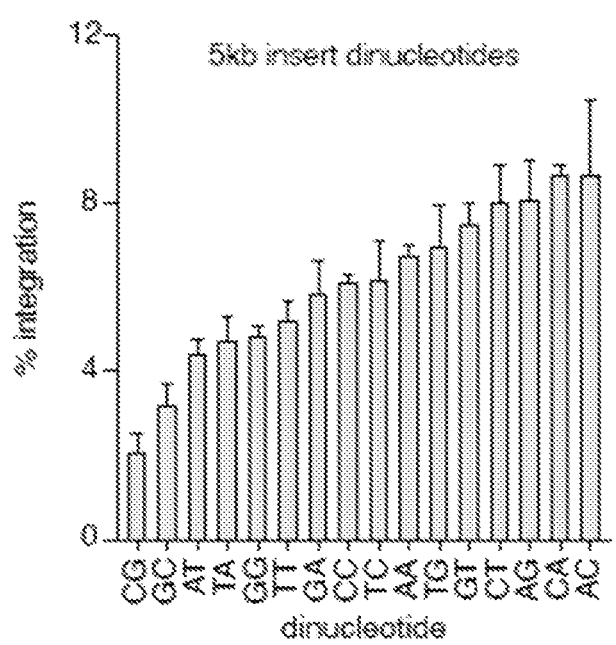
FIG. 36A shows the PASTE integration efficiency for all 16 central dinucleotide attB/attP sequence pairs with a 5 kb GFP template at the ACTB locus according to embodiments of the present teachings.

The central dinucleotide of Bxb1 is involved in the association of attB and attP sites for integration, and changing the matched central dinucleotide sequences can modify integrase activity and provide orthogonality for insertion of two genes. Expanding the set of attB/attP dinucleotides can enable multiplexed gene insertion with PASTE. The efficiency of GFP integration at the ACTB locus with PASTE across all 16 dinucleotide attB/attP sequence pairs was profiled to find optimal attB/attP dinucleotides for PASTE insertion. Several dinucleotides with integration efficiencies greater than the wild-type GT sequence were found (FIG. 36A). A majority of dinucleotides had 75% editing efficiency or greater compared to wild-type attB/attP efficiency, implying that these dinucleotides can be orthogonal channels for multiplexed gene insertion with PASTE.

Figure 36B:
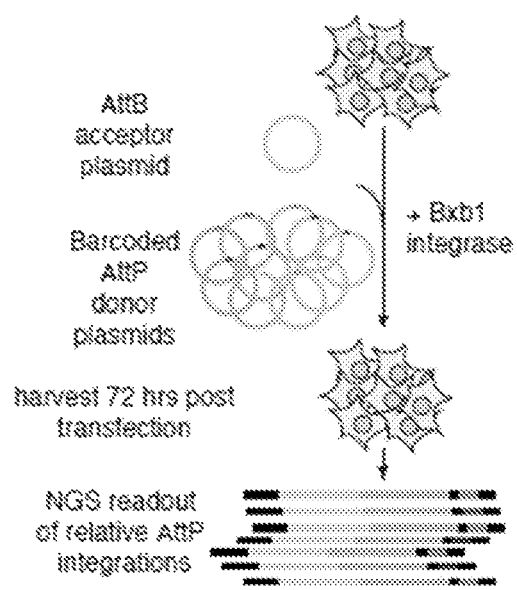
FIG. 36B shows a schematic of the pooled attB/attP dinucleotide orthogonality assay, wherein each attB dinucleotide sequence is co-transfected with a barcoded pool of all 16 attP dinucleotide sequences and Bxb1 integrase, relative integration efficiencies are determined by next generation sequencing of barcodes, and all 16 attB dinucleotides are profiled in an arrayed format with attP pools according to embodiments of the present teachings.
Figure 36C:
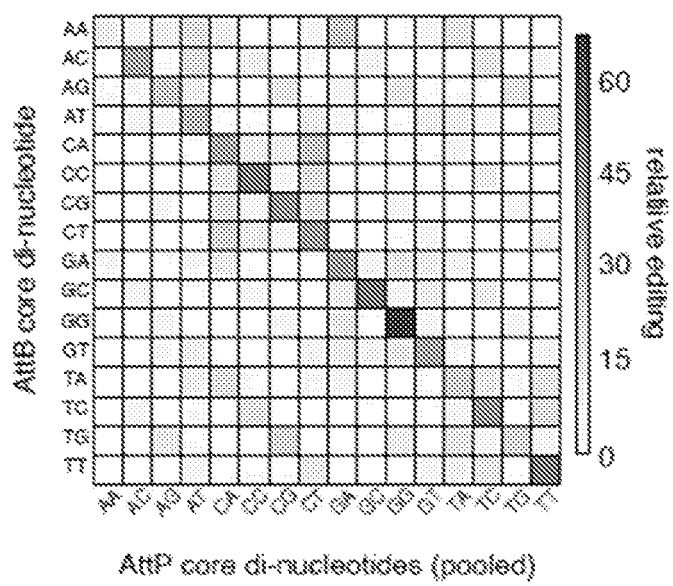
FIG. 36C shows the relative insertion preferences for all possible attB/attP dinucleotide pairs determined by the pooled orthogonality assay according to embodiments of the present teachings.
Figure 37:
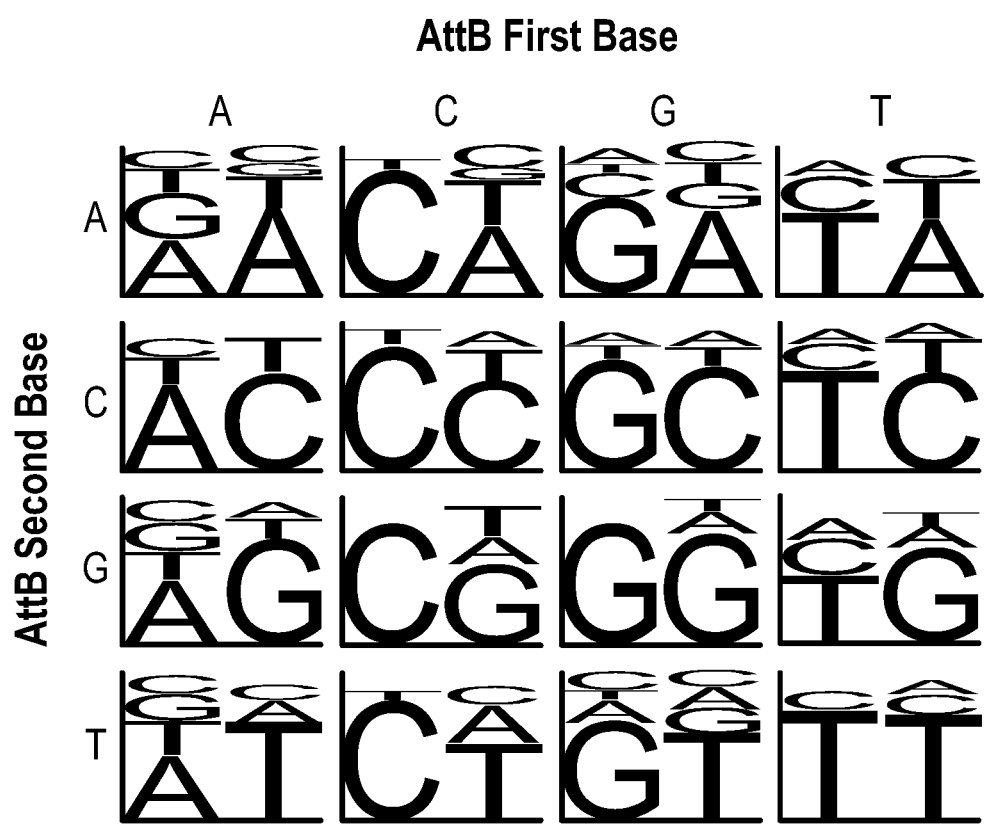
FIG. 37 shows the orthogonality of Bxb1 dinucleotides as measured by a pooled reporter assay, wherein each web logo motif shows the relative integration of different attP sequences in a pool at a denoted attB sequence with the listed dinucleotide according to embodiments of the present teachings.

The specificity of matched and unmatched attB/attP dinucleotide interactions was then assessed. The interactions between all dinucleotide combinations in a scalable fashion using a pooled assay to compare attB/attP integration were profiled (FIG. 36B). By barcoding 16 attP dinucleotide plasmids with unique identifiers, co-transfecting this attP pool with the Bxb1 integrase expression vector and a single attB dinucleotide acceptor plasmid, and sequencing the resulting integration products, the relative integration efficiencies of all possible attB/attP pairs were measured (FIG. 36C). Dinucleotide specificity was found to vary, with some dinucleotides (GG) exhibiting strong self-interaction with negligible crosstalk, and others (AA) showing minimal self-preference. Sequence logos of attP preferences (FIG. 37) revealed that dinucleotides with C or G in the first position have stronger preferences for attB dinucleotide sequences with shared first bases, while other attP dinucleotides, especially those with an A in the first position, have reduced specificity for the first attB base.

Figure 36D:
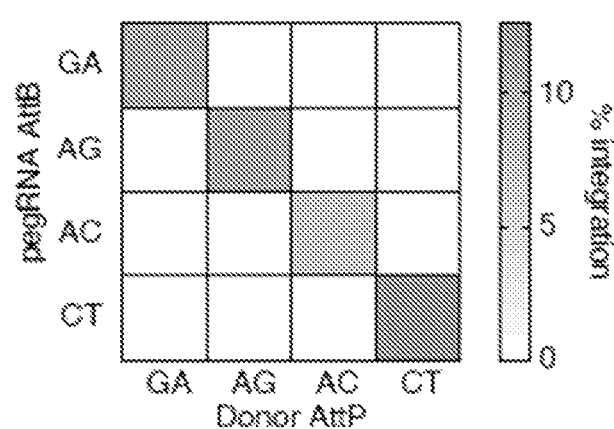
FIG. 36D shows the orthogonality of top 4 attB/attP dinucleotide pairs evaluated for GFP integration with PASTE at the ACTB locus according to embodiments of the present teachings.

GA, AG, AC, and CT dinucleotide pegRNAs were then tested for GFP integration at ACTB, either paired with their corresponding attP cargo or mispaired with the other three dinucleotide attP sequences. All four of the tested dinucleotides efficiently were found to integrate cargo only when paired with the corresponding attB/attP pair, with no detectable integration across mispaired combinations (FIG. 36D).

Example 22

Multiplex Gene Integration with PASTE

Figure 38A:
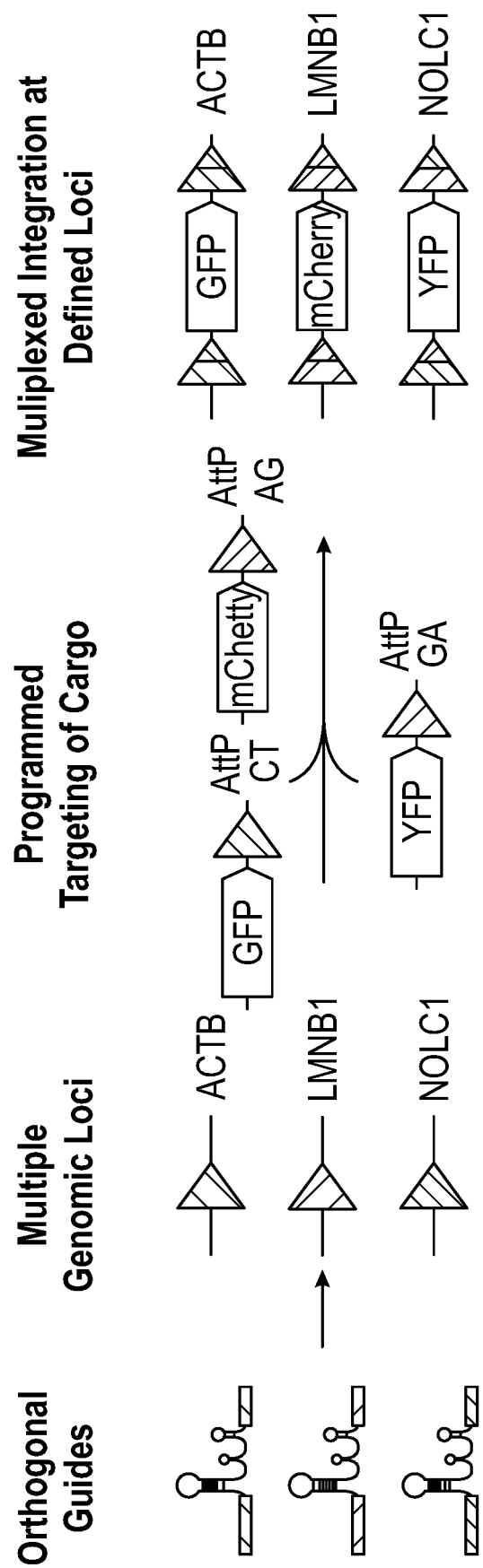
FIG. 38A shows a schematic of multiplexed integration of different cargo sets at specific genomic loci, wherein three fluorescent cargos (GFP, mCherry, and YFP) are inserted orthogonally at three different loci (ACTB, LMNB1, NOLC1) for in-frame gene tagging according to embodiments of the present teachings.
Figure 38B:
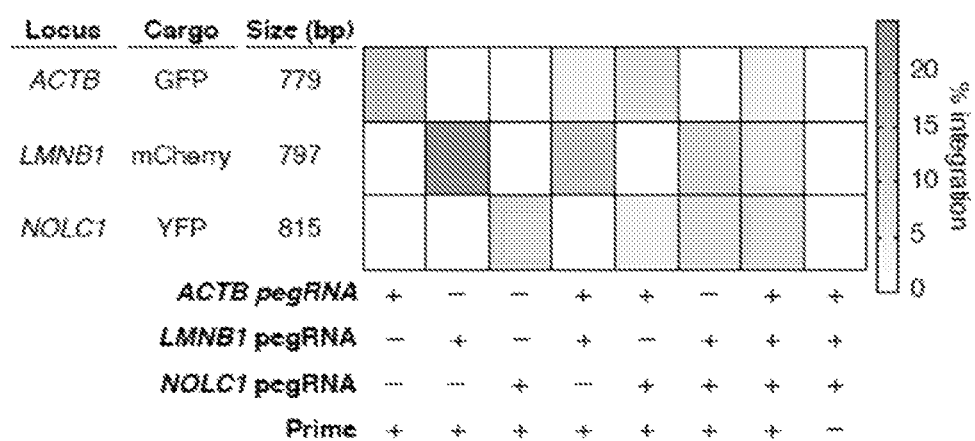
FIG. 38B shows the efficiency of multiplexed PASTE insertion of combinations of fluorophores at ACTB, LMNB1, and NOLC1 loci according to embodiments of the present teachings.

Multiplexing in cells by using orthogonal pegRNAs that direct a matched attP cargo to a specific site in the genome was assessed (FIG. 38A). Selecting the three top dinucleotide attachment site pairs (CT, AG, and GA), pegRNAs that target ACTB (CT), LMNB1 (AG), and NOLC1 (GA) and corresponding minicircle cargo containing GFP (CT), mCherry (AG), and YFP (GA) were designed. Upon co-delivering these reagents to cells, single-plex, dual-plex, and trip-plex editing of all possible combinations of these pegRNAs and cargo in the range of 5%-25% integration was found to be achieved (FIG. 38B).

An application for multiplexed gene integration is for labeling different proteins to visualize intracellular localization and interactions within the same cell. PASTE was used to simultaneously tag ACTB (GFP) and NOLC1 (mCherry) or ACTB (GFP) and LMNB1 (mCherry) in the same cell. No overlap of GFP and mCherry fluorescence was observed and tagged genes were confirmed to be visible in their appropriate cellular compartments, based on the known subcellular localizations of the ACTB, NOLC1 and LMNB1 protein products (FIGS. 15A-B).

Example 23

PASTE Efficiencies Compared with DSB-Based Insertion Methods

PASTE efficiencies were found to exceed comparable DSB-based insertion methods.

Figure 39A:
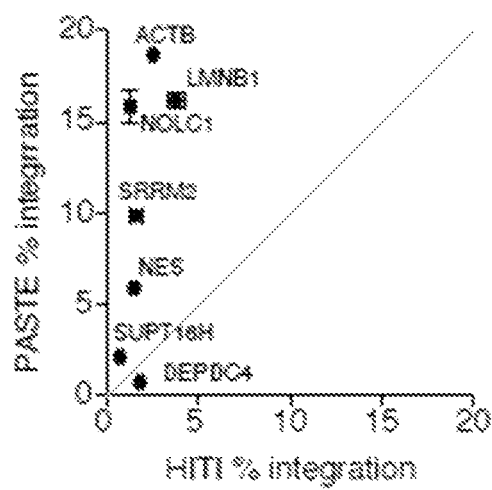
FIG. 39A shows the GFP integration efficiency at a panel of genomic loci by PASTE compared to insertion rates by homology-independent targeted integration (HITI) according to embodiments of the present teachings.
Figure 39B:
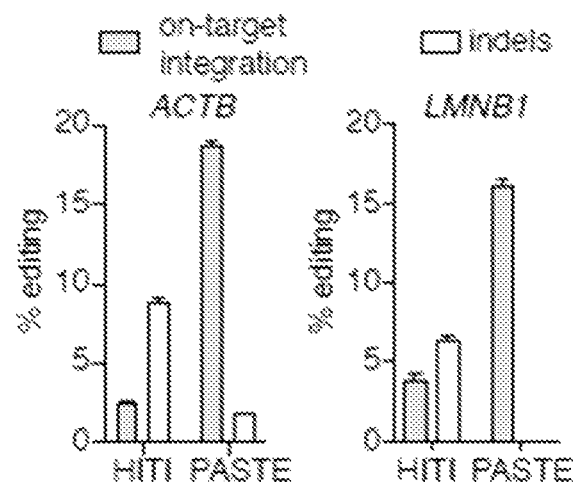
FIG. 39B shows a comparison of unintended indel generation by PASTE and HITI at the ACTB and LMNB1 target sites, wherein the on-target EGFP integration rate observed compared to unintended indels is shown according to embodiments of the present teachings.
Figure 39C:
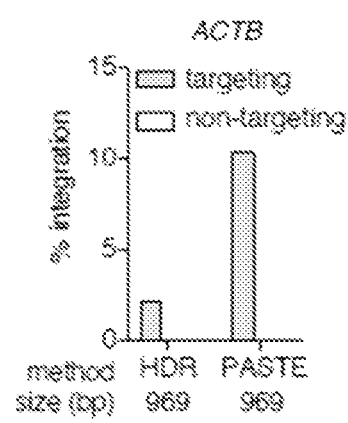
FIG. 39C shows the integration of a GFP template by PASTE at the ACTB locus compared to homology-directed repair (HDR) at the same target, wherein the quantification is by single-cell clone counting, wherein targeting and non-targeting guides were used for HDR insertion, and wherein for PASTE targeting and non-targeting refers to the presence or absence of the SpCas9-RT protein respectively according to embodiments of the present teachings.
Figure 39D:
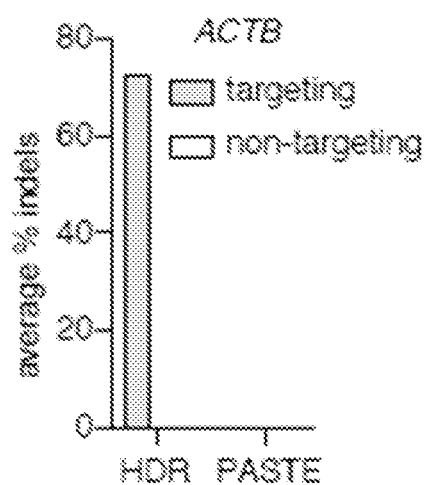
FIG. 39D shows the comparison of unintended indel generation by PASTE and HDR based EGFP insertion at the ACTB target site, wherein the average indel rate measured across all single-cell clones generated is showed according to embodiments of the present teachings.
Figure 40A:
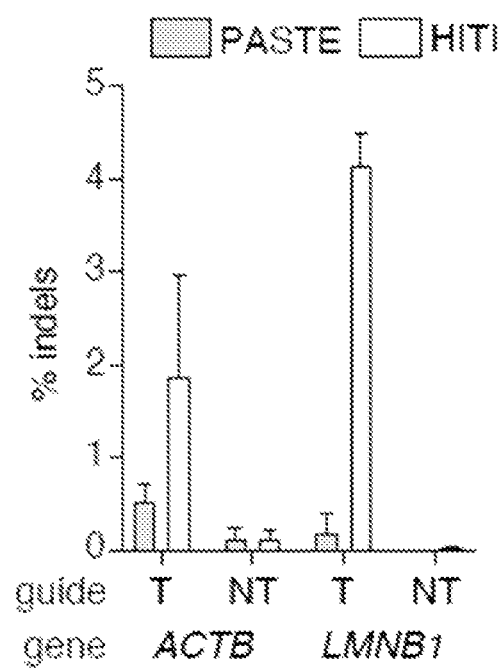
FIG. 40A shows a comparison of indel rates generated by PASTE and HITI mediated insertion of EGFP at the ACTB and LMNB1 loci in HepG2 cells according to embodiments of the present teachings.
Figure 40B:
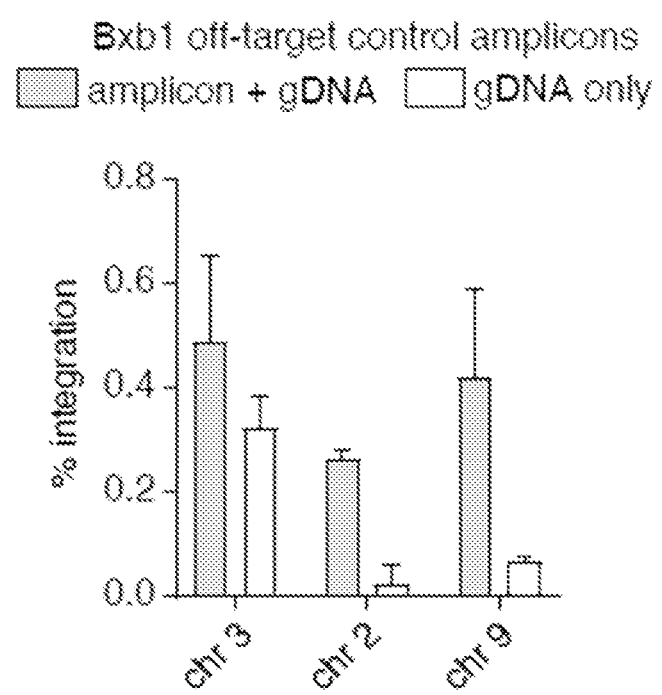
FIG. 40B shows the validation of ddPCR assays for detecting editing at predicted Bxb1 offtarget sites using synthetic amplicons according to embodiments of the present teachings.
Figure 40C:
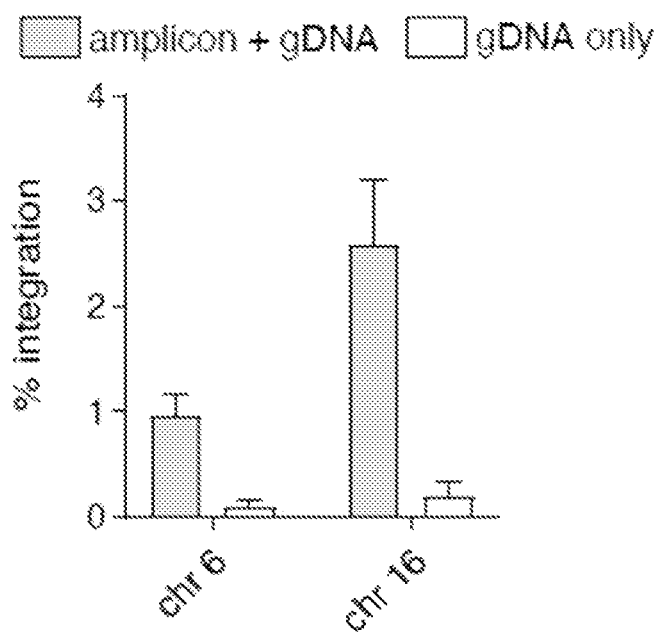
Figure 40D:
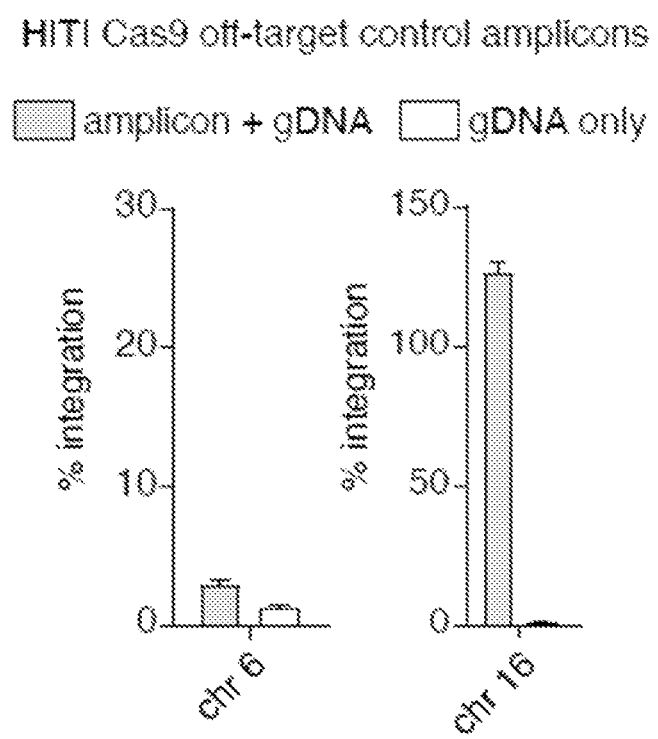

PASTE editing was assessed alongside DSB-dependent gene integration using either NHEJ (i.e., homology-independent targeted integration, HITI) or HDR pathways. PASTE had equivalent or better gene insertion efficiencies than either HITI (FIG. 39A-B) or HDR (FIGS. 39C-D). On a panel of 7 different endogenous targets, PASTE exceeded HITI editing at 6 out of 7 genes, with similar efficiency for the 7th gene (FIG. 39A). As DSB generation can lead to insertions or deletions (indels) as an alternative and undesired editing outcome, the indel frequency of all three methods was assessed by next-generation sequencing, finding significantly fewer indels generated with PASTE than either HDR or HITI in both HEK293FT and HepG2 cells (FIGS. 39B, 39D and 40A), showcasing the high purity of gene integration outcomes with PASTE.

Example 24

Off-target Characterization of PASTE and HITI Gene Integration

Figure 39E:
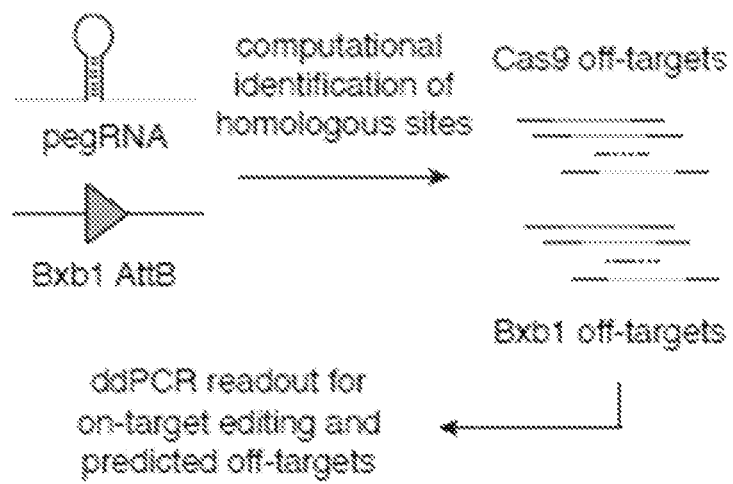
FIG. 39E shows a schematic for Bxb1 and Cas9 off-target identification and a detection assay according to embodiments of the present teachings.
Figure 39F:
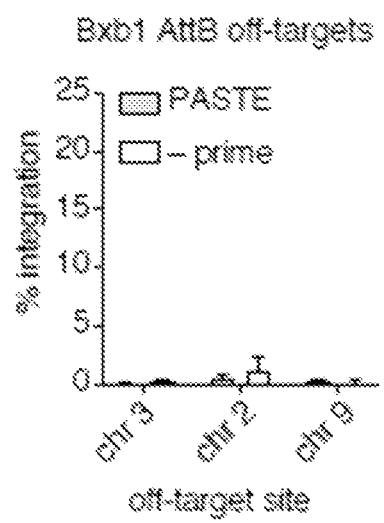
FIG. 39F shows the GFP integration activity at predicted Bxb1 off-target sites in the human genome according to embodiments of the present teachings.
Figure 39G:
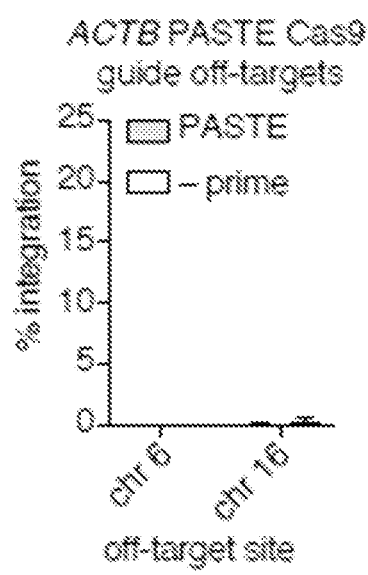
FIG. 39G shows the GFP integrations activity at predicted PASTE ACTB Cas9 guide off target sites according to embodiments of the present teachings.
Figure 39H:
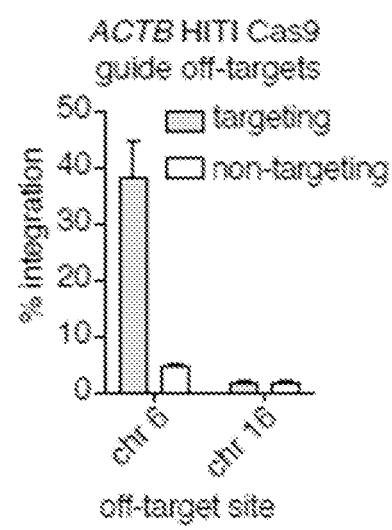
FIG. 39H shows the GFP integration activity at predicted HITI ACTB Cas9 guide off-target sites according to embodiments of the present teachings.

Off-target editing can be used in genome editing technologies. The specificity of PASTE at specific sites was assessed based on off-targets generated by Bxb1 integration into pseudo-attB sites in the human genome and off-targets generated via guide- and Cas9-dependent editing in the human genome (FIG. 39E). While Bxb1 lacks documented integration into the human genome at pseudo-attachment sites, potential sites with partial similarity to the natural Bxb1 attB core sequence were computationally identified. Bxb1 integration by ddPCR across these sites was tested and no off-target activity was found (FIGS. 39F and 40B-D). To assay Cas9 off-targets for the ACTB pegRNA, two potential off-target sites were identified via computational prediction and no off-target integration for PASTE was found (FIGS. 39G and 40A-D), but substantial off-target activity by HITI at one of the sites was found (FIGS. 39H and 40A-D).

Figure 39I:
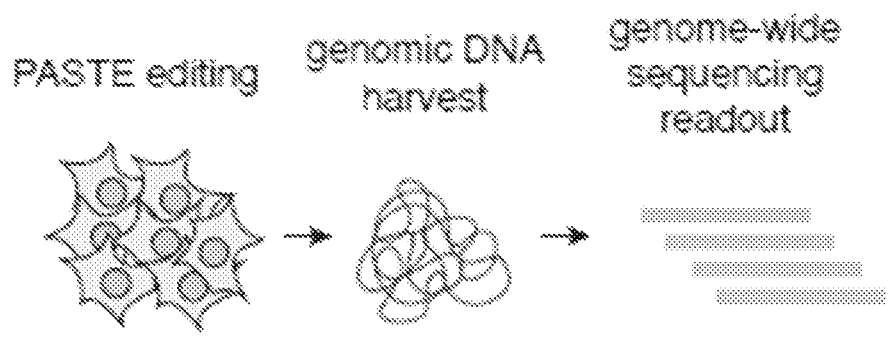
FIG. 39I shows a schematic of next-generation sequencing method to assay genome-wide off-target integration sites by PASTE according to embodiments of the present teachings.
Figure 39J:
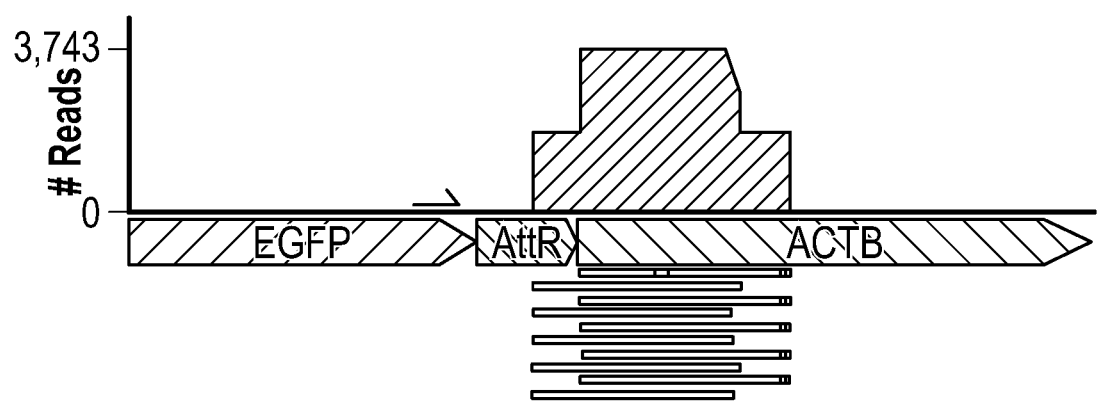
FIG. 39J shows the alignment of reads at the on-target ACTB site using a genome-wide integration assay, wherein expected on-target integration outcomes are shown according to embodiments of the present teachings.
Figure 39K:
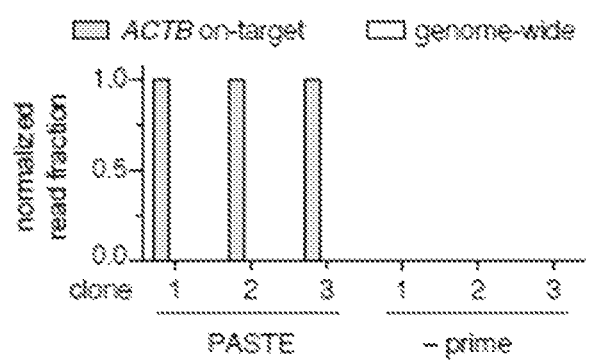
FIG. 39K shows the analysis of on-target and off-target integration events across 3 single-cell clones for PASTE and 3 single-cell clones for no prime condition according to embodiments of the present teachings.
Figure 39L:
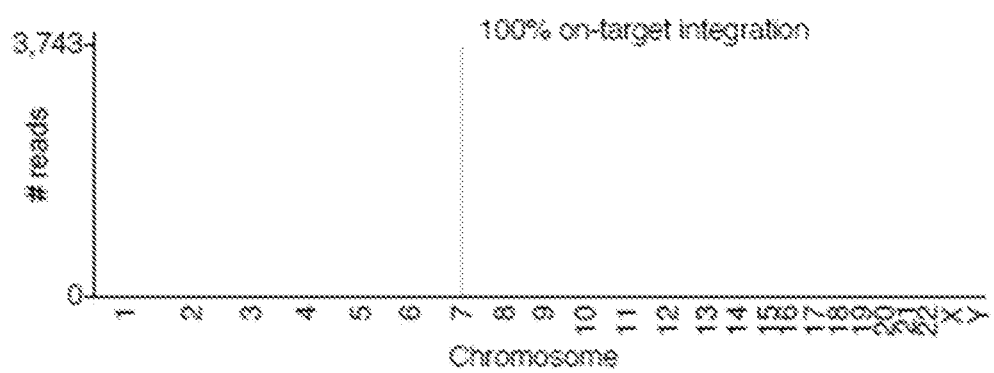
FIG. 39L shows a Manhattan plot of integration events for a representative single-cell clone with PASTE editing, wherein the on-target site is at the ACTB gene on chromosome 7 according to embodiments of the present teachings.

Genome-wide off-targets due to either Cas9 or Bxb1 through tagging and PCR amplification of insert-genomic junctions were additionally assessed (FIG. 39I). Single cell clones were isolated for conditions with PASTE editing and negative controls missing PE2, and deep sequencing of insert genomic junctions from these clones showed all reads aligning to the on-target ACTB site, confirming no off-target genomic insertions (FIGS. 39J-L).

Expression of reverse transcriptases and integrases involved in PASTE can have detrimental effects on cellular health. The complete PASTE system, the corresponding guides and cargo with only PE2, and the corresponding guides and cargo with only Bxb1 were transfected and compared to both GFP control transfections and guides without protein expression via transcriptome-wide RNA sequencing to determine the extent of these effects. While Bxb1 expression in the absence of Prime editing was found to have several significant off targets, the complete PASTE system had only one differentially regulated gene with more than a 1.5-fold change (FIGS. 41A-B). Genes upregulated by Bxb1 overexpression included stress response genes, such as TENT5C and DDIT3, but these changes were not seen in the expression of the PASTE system (FIG. 41C), potentially due to the decreased expression of Bxb1 from the P2A linker on the PASTE construct.

Example 25

PASTE Efficiency in Non-Dividing Cell

PASTE activity in non-dividing cells was assessed. Cas9 and HDR templates or PASTE were transfected into HEK293FT cells and cell division was arrested via aphidicolin treatment (FIG. 42A). In this model of blocked cell division, PASTE was found to maintain a GFP gene integration activity greater than 20% at the ACTB locus whereas HDR-mediated integration was abolished (FIGS. 42B and 43A).

Example 26

Production and Secretion of Therapeutic Transgene

PASTE with larger transgenes and in additional cell lines were assessed.

To evaluate the size limits for therapeutic transgenes, insertion of cargos up to 13.3 kb in length in both dividing and aphidicolin treated cells was assessed. Insertion efficiency greater than 10% was found (FIG. 42C), enabling insertion of ~99.7% of all full-length human cDNA transgenes. To overcome reduction of large insert delivery to cells because of delivery inefficiencies, delivering larger DNA amounts of insert was found to significantly improve gene integration efficiency (FIG. 43B). PASTE editing to additional cell types such as PASTE in the K562 lymphoblast line and in primary human T cells were also assessed. Both PE2-P2A-Bxb1 (PASTE) and separate delivery of PE2 and Bxb1 were found to result in efficient editing in both cell types (FIGS. 42D-E). Lastly, as therapeutic delivery of PASTE in vivo might require viral delivery of the DNA cargo, whether AAV could deliver an attP containing payload that could be integrated into the genome via Bxb1 was evaluated. Targeting the ACTB locus, AAV was found to be capable of delivering the appropriate template for integrase mediated insertion with rates up to 4% in a dose dependent fashion (FIGS. 42F and 43C).

To improve the efficiency of PASTE, PE2* NLS was incorporated for prime editing and improved PASTE integration at multiple loci was found (FIG. 44A). Furthermore, PE2* resulted in more robust integration at lower titrations of cargo plasmid, demonstrating integration at amounts as low as 8 ng of plasmid (FIG. 44B). To combat reductions in PASTE efficiency due to incomplete plasmid delivery, a puromycin resistance gene was co-delivered and found to increase the PASTE efficiency in the presence of drug selection (FIG. 45).

Programmable gene integration provides a modality for expression of therapeutic protein products, and protein production was assessed for therapeutically relevant proteins Alpha-1 antitrypsin (encoded by SERPINA1) and Carbamoyl phosphate synthetase I (encoded by CPS1), involved in the diseases Alpha-1 antitrypsin deficiency and CPS1 deficiency, respectively. By tagging gene products with the luminescent protein subunit HiBiT, the transgene production and secretion were assessed independently in response to PASTE treatment (FIG. 42G). PASTE was transfected with SERPINA1 or CPS1 cargo in HEK293FT cells and a human hepatocellular carcinoma cell line (HepG2) and efficient integration at the ACTB locus was found (FIG. 42H-I). This integration resulted in robust protein expression, intracellular accumulation of transgene products (FIGS. 42J and 46A-B), and secretion of proteins into the media (FIG. 42K).

Example 27

Optimized PASTE Constructs

To optimize complex activity, a panel of protein modifications were screened, including alternative reverse transcriptase fusions and mutations, various linkers between the reverse transcriptase domain and integrase and between the Cas9 and reverse transcriptase domain, and reverse transcriptase and BxbINT domain mutants (FIG. 47A and FIG. 49C-FIG. 49F). A number of protein modifications, including a 48 residue XTEN linker between the Cas9 and reverse transcriptase and the fusion of MMuLV to the Sto7d DNA binding domain (Oscorbin et al. FEBS Lett. 594. 4338-4356. 2020) improved editing efficiency (FIG. 47A and FIG. 49C-FIG. 49D). When these top modifications were combined with a GGGGS linker (SEQ ID NO: 420) between the reverse transcriptase-Sto7d domain and the BxbINT, they produced—55% gene integration, highlighting the importance of directly recruiting the integrase to the target site (FIG. 47A). This optimized construct was referred to as SpCas9-(XTEN-48)-RT-Sto7d-(GGGGS)-BxbINT. The optimized contruct achieved precise integration of templates as large as ~36,000 bp with ~20% integration efficiency (FIG. 47A), with complete integration of the full-length cargo confirmed by Sanger sequencing.

Additionally, pegRNAs containing different AttB length truncations were tested and found that prime editing was capable of inserting sequences up to 56 bp at the beta-actin (ACTB) gene locus, with higher efficiency at lengths below 31 bp (FIG. 48A-FIG. 48B). A panel of multiple enzymes was evaluated, including Bxb1 (i.e., BxbINT), TP901 (i.e., Tp9INT), and phiBT1 (i.e., Bt1INT) phage serine integrases. Prime editing successfully inserted all landing sites tested, with efficiencies between 10-30% (FIG. 48C-FIG. 48D)

Example 28

Viral Delivery & In Vivo Editing

In order to package the complete PASTE system in viral vectors, an AdV vector was utilized (FIG. 50B). Adenovirus was evaluated for if it could deliver a suitable template for BxbINT-mediated insertion along with plasmids for SpCas9-RT-BxbINT and guide expression, or AdV delivery of guides and BxbINT with plasmid delivery of SpCas9-RT, finding that 10-20% integration of the ~36 kb adenovirus genome carrying EGFP in HEK293FT and HepG2 cells was achieved (FIG. 50C). Upon packaging and delivering the cargo and PASTE system components across 3 AdV vectors, the complete PASTE system (Cas9-reverse transcriptase, integrase and guide RNAs, or cargo) could be substituted by adenoviral delivery, with integration of up to ~50-60% with viral-only delivery in HEK293FT and HepG2 cells (FIG. 50D).

To further demonstrate PASTE would be amenable for in vivo delivery, an mRNA version of the PASTE protein components was developed as well as chemically-modified synthetic atgRNA and nicking guide against the LMNB1 target (FIG. 50E). Electroporation of the mRNA and guides along with delivery of the template via adenovirus or plasmid yielded high efficiency integration up to ~23% (FIG. 50E-FIG. 50F). More sustained BxbINT expression could allow for integration into newly placed AttB sites in the genome, so circular mRNA expression was tested and found to boost the efficiency of integration to ~30% (FIG. 50G-FIG. 50I).

Example 29

Simultaneous Deletion & Insertion With PASTE

The PASTE system was used to simultaneously delete one sequence and insert another. 130 bp and 385 bp deletions of first exon of LMNB1 with combined insertion of AttB nucleic acid sequence was performed (FIG. 51A). This data shows that it is possible to replace DNA sequence using the PASTE system.

A130 bp deletion of the first exon of LMNB1 with combined insertion of a 967 bp cargo using the PASTE system was also performed.

One of two attP sequences were inserted using the mini circle template that has mutated AttP, as described above. This AttP mutants shows better integration kinetics and efficiency, especially for the shorter AttBs (38-44 bp). The LMNB1 AttB used in this experiment is 38 bp (FIG. 51B).

What is claimed is:

1. A method of site-specifically integrating an exogenous nucleic acid sequence into a mammalian cell genome or intracellular target nucleic acid, the method comprising:
(a) incorporating at least one integration sequence at a specific target site in the cell genome or intracellular target nucleic acid by introducing ex vivo into a mammalian cell:
(i) an expressible polynucleotide construct encoding an editing polypeptide, wherein the editing polypeptide comprises a DNA binding nuclease domain linked via a linker to a reverse transcriptase domain, wherein the DNA binding nuclease domain comprises a nickase activity; and
(ii) at least two guide RNAs (gRNAs), each comprising a targeting sequence, a primer binding sequence, and a complement of the at least one integration sequence,
wherein each of the at least two gRNAs interacts with the expressed editing polypeptide to direct the editing polypeptide to the specific target site of the cell genome or intracellular target nucleic acid,
wherein the DNA binding nuclease domain nicks a strand of the cell genome or intracellular target nucleic acid to form a nicked site, and
wherein the reverse transcriptase domain reverse transcribes the complement of the at least one integration sequence within each of the gRNAs and thereby incorporates the at least one integration sequence into the nicked site, thereby incorporating the at least one integration sequence at the specific target site of the cell genome or intracellular target nucleic acid; and
(b) integrating an exogenous nucleic acid sequence into the cell genome or intracellular target nucleic acid by introducing into the cell:
(i) the exogenous nucleic acid sequence linked to a sequence that is an integration cognate to the at least one site-specifically incorporated-integration sequence; and
(ii) an expressible polynucleotide construct encoding an integration enzyme, wherein the integration enzyme integrates the exogenous nucleic acid sequence into the cell genome or the intracellular target nucleic acid at the at least one site-specifically incorporated integration sequence, thereby site-specifically integrating the exogenous nucleic acid sequence into the cell genome or the intracellular target nucleic acid,
wherein the expressible polynucleotide encoding the editing polypeptide, the at least two gRNAs, the expressible polynucleotide construct encoding the integration enzyme, and the exogenous nucleic acid sequence are introduced into the mammalian cell concurrently.

2. The method of claim 1, wherein the at least two gRNAs, the expressible polynucleotide construct encoding the editing polypeptide, and the expressible polynucleotide construct encoding the integration enzyme are introduced into the mammalian cell using a virus, a RNP, an mRNA, a lipid, or a polymeric nanoparticle.

3. The method of claim 1, wherein the at least two gRNAs hybridizes to a strand of the mammalian cell genome.

4. The method of claim 1, wherein the exogenous nucleic acid is introduced into the mammalian cell as an adeno-associated virus (AAV) or an adenovirus (AdV).

5. The method of claim 1, wherein the exogenous nucleic acid is introduced into the mammalian cell as a minicircle, a plasmid, mRNA, or a linear DNA.

6. The method of claim 5, wherein the minicircle does not comprise a sequence of a bacterial origin.

7. The method of claim 1, wherein the linker is cleavable.

8. The method of claim 1, wherein the linker is non-cleavable.

9. The method of claim 1, wherein the linker is two associating binding domains of the DNA binding nuclease linked to a reverse transcriptase.

10. The method of claim 1, wherein the integration enzyme is selected from the group consisting of Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptlI, Museum, Severus, Airmid, Benedict, Hinder, ICleared, Sheen, Mundrea, BxZ2, φRV, retrotransposases encoded by R2, L1, Tol2 Tc1, Tc3, Mariner Himar 1, Mariner mos-1, and Minos, and any mutants thereof.

11. The method of claim 1, wherein the integration sequence is an attB sequence, an attP sequence, an attL sequence, an attR sequence, a Vox sequence, or a FRT sequence.

12. The method of claim 1, wherein the DNA binding nuclease domain comprising a nickase activity is selected from Cas9-D10A, Cas9-H840A, and Cas12a/b nickase.

13. The method of claim 1, wherein the reverse transcriptase domain comprises a mutation relative to a wild-type sequence.

14. The method of claim 1, wherein the reverse transcriptase domain is selected from the group consisting of Moloney Murine Leukemia Virus (M-MLV) reverse transcriptase domain, transcription xenopolymerase (RTX), avian myeloblastosis virus reverse transcriptase (AMV-RT), and *Eubacterium* rectale maturase RT.

15. The method of claim 14, wherein the M-MLV reverse transcriptase domain comprises one or more mutations selected from the group consisting of D200N, T306K, W313F, T330P, and L603W.

16. The method of claim 1, wherein:
the exogenous nucleic acid is a reporter gene;
the exogenous nucleic acid is a degradation tag for programmable knockdown of proteins in the presence of small molecules;
the exogenous nucleic acid is a T-cell receptor (TCR), a chimeric antigen receptor (CAR), an interleukin, a cytokine, or an immune checkpoint gene and the mammalian cell is a T-cell or natural killer (NK) cell;
the exogenous nucleic acid is a beta hemoglobin (HBB) gene and the cell is a hematopoietic stem cell (HSC;
the exogenous nucleic acid is a metabolic gene; or
the exogenous nucleic acid is a gene involved in an inherited disease or an inherited syndrome.

17. The method of claim 16, wherein the reporter gene is a fluorescent protein.

18. The method of claim 1, wherein the mammalian cell is a dividing cell or a non-dividing cell.

19. The method of claim 1, wherein:
the exogenous nucleic acid is between 1000 bp and 36,000 bp;
the exogenous nucleic acid is more than 36,000 bp; or
the exogenous nucleic acid is less than 1000 bp.

20. The method of claim 16 wherein the inherited disease is cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

21. A method of site-specifically integrating an exogenous nucleic acid sequence into a mammalian cell genome or intracellular target nucleic acid, the method comprising:

(a) incorporating at least one integration sequence at a specific target site in the cell genome or intracellular target nucleic acid by introducing ex vivo into a mammalian cell:
   (i) an expressible polynucleotide construct encoding an editing polypeptide, wherein the editing polypeptide comprises a DNA-binding nuclease domain linked via a linker to a reverse transcriptase domain, wherein the DNA-binding nuclease domain comprises a nickase activity; and
   (ii) an expressible polynucleotide construct encoding at least two guide RNAs (gRNAs) comprising a targeting sequence, a primer binding sequence, and a complement of the at least one integration sequence,
wherein the at least two gRNAs interacts with the expressed editing polypeptide to direct the editing polypeptide to the specific target site of the cell genome or intracellular target nucleic acid,
wherein the DNA-binding nuclease domain nicks a strand of the cell genome or intracellular target nucleic acid to form a nicked site, and
wherein the reverse transcriptase domain reverse transcribes the complement of the at least one integration sequence and thereby incorporates the at least one integration sequence into the nicked site, thereby incorporating the at least one integration sequence at the specific target site of the cell genome or intracellular target nucleic acid; and (b) integrating the exogenous nucleic acid sequence into the cell genome or intracellular target nucleic acid by introducing into the mammalian cell:
   (i) an exogenous nucleic acid sequence linked to a sequence that is an integration cognate to the site-specifically incorporated integration sequence; and
   (ii) an expressible polynucleotide construct encoding an integration enzyme, wherein the integration enzyme integrates the exogenous nucleic acid into the cell genome or intracellular target nucleic acid at the at least one site-specifically incorporated integration sequence, thereby site-specifically integrating the exogenous nucleic acid into the cell genome or the intracellular target nucleic acid,
wherein the integration sequence is an attB sequence, an attP sequence, an attL sequence, an attR sequence, a lox71 sequence, a Vox sequence, or a FRT sequence,
wherein the integration sequence is longer than 38 basepairs, and
wherein the expressible polynucleotide constructs encoding the editing polypeptide, the at least two gRNAs, and the integration enzyme, and the exogenous nucleic acid, are introduced into the mammalian cell concurrently.

22. The method of claim 21, wherein the integration sequence is 40, 42, 44, or 46 base pairs.

* * * * *

SEQUENCE LISTING

```
Sequence total quantity: 431
SEQ ID NO: 1            moltype = DNA  length = 34
FEATURE                 Location/Qualifiers
misc_feature            1..34
                        note = Description of Artificial Sequence: Synthetic
                        oligonucleotide
misc_feature            1..34
                        note = Lox71
```

```
source                  1..34
                        mol_type = other DNA
                        organism = synthetic construct
SEQUENCE: 1
ataacttcgt ataatgtatg ctatacgaac ggta                                     34

SEQ ID NO: 2            moltype = DNA   length = 34
FEATURE                 Location/Qualifiers
misc_feature            1..34
                        note = Description of Artificial Sequence: Synthetic
                        oligonucleotide
misc_feature            1..34
                        note = Lox66
source                  1..34
                        mol_type = other DNA
                        organism = synthetic construct
SEQUENCE: 2
taccgttcgt ataatgtatg ctatacgaag ttat                                     34

SEQ ID NO: 3            moltype = DNA   length = 46
FEATURE                 Location/Qualifiers
misc_feature            1..46
                        note = Description of Artificial Sequence: Synthetic
                        oligonucleotide
misc_feature            1..46
                        note = AttB
source                  1..46
                        mol_type = other DNA
                        organism = synthetic construct
SEQUENCE: 3
ggccggcttg tcgacgacgg cggtctccgt cgtcaggatc atccgg                        46

SEQ ID NO: 4            moltype = DNA   length = 46
FEATURE                 Location/Qualifiers
misc_feature            1..46
                        note = Description of Artificial Sequence: Synthetic
                        oligonucleotide
misc_feature            1..46
                        note = AttP
source                  1..46
                        mol_type = other DNA
                        organism = synthetic construct
SEQUENCE: 4
ccggatgatc ctgacgacgg agaccgccgt cgtcgacaag ccggcc                        46

SEQ ID NO: 5            moltype = DNA   length = 38
FEATURE                 Location/Qualifiers
misc_feature            1..38
                        note = Description of Artificial Sequence: Synthetic
                        oligonucleotide
misc_feature            1..38
                        note = AttB-TT
source                  1..38
                        mol_type = other DNA
                        organism = synthetic construct
SEQUENCE: 5
ggcttgtcga cgacggcgtt ctccgtcgtc aggatcat                                 38

SEQ ID NO: 6            moltype = DNA   length = 52
FEATURE                 Location/Qualifiers
misc_feature            1..52
                        note = Description of Artificial Sequence: Synthetic
                        oligonucleotide
misc_feature            1..52
                        note = AttP-TT
source                  1..52
                        mol_type = other DNA
                        organism = synthetic construct
SEQUENCE: 6
gtggtttgtc tggtcaacca ccgcgttctc agtggtgtac ggtacaaacc ca                 52

SEQ ID NO: 7            moltype = DNA   length = 38
FEATURE                 Location/Qualifiers
misc_feature            1..38
                        note = Description of Artificial Sequence: Synthetic
                        oligonucleotide
misc_feature            1..38
                        note = AttB-AA
source                  1..38
```

```
                          mol_type = other DNA
                          organism = synthetic construct
SEQUENCE: 7
ggcttgtcga cgacggcgaa ctccgtcgtc aggatcat                              38

SEQ ID NO: 8              moltype = DNA  length = 52
FEATURE                   Location/Qualifiers
misc_feature              1..52
                          note = Description of Artificial Sequence: Synthetic
                            oligonucleotide
misc_feature              1..52
                          note = AttP-AA
source                    1..52
                          mol_type = other DNA
                          organism = synthetic construct
SEQUENCE: 8
gtggtttgtc tggtcaacca ccgcgaactc agtggtgtac ggtacaaacc ca              52

SEQ ID NO: 9              moltype = DNA  length = 38
FEATURE                   Location/Qualifiers
misc_feature              1..38
                          note = Description of Artificial Sequence: Synthetic
                            oligonucleotide
misc_feature              1..38
                          note = AttB-CC
source                    1..38
                          mol_type = other DNA
                          organism = synthetic construct
SEQUENCE: 9
ggcttgtcga cgacggcgcc ctccgtcgtc aggatcat                              38

SEQ ID NO: 10             moltype = DNA  length = 52
FEATURE                   Location/Qualifiers
misc_feature              1..52
                          note = Description of Artificial Sequence: Synthetic
                            oligonucleotide
misc_feature              1..52
                          note = AttP-CC
source                    1..52
                          mol_type = other DNA
                          organism = synthetic construct
SEQUENCE: 10
gtggtttgtc tggtcaacca ccgcgccctc agtggtgtac ggtacaaacc ca              52

SEQ ID NO: 11             moltype = DNA  length = 38
FEATURE                   Location/Qualifiers
misc_feature              1..38
                          note = Description of Artificial Sequence: Synthetic
                            oligonucleotide
misc_feature              1..38
                          note = AttB-GG
source                    1..38
                          mol_type = other DNA
                          organism = synthetic construct
SEQUENCE: 11
ggcttgtcga cgacggcggg ctccgtcgtc aggatcat                              38

SEQ ID NO: 12             moltype = DNA  length = 52
FEATURE                   Location/Qualifiers
misc_feature              1..52
                          note = Description of Artificial Sequence: Synthetic
                            oligonucleotide
misc_feature              1..52
                          note = AttP-GG
source                    1..52
                          mol_type = other DNA
                          organism = synthetic construct
SEQUENCE: 12
gtggtttgtc tggtcaacca ccgcgggctc agtggtgtac ggtacaaacc ca              52

SEQ ID NO: 13             moltype = DNA  length = 38
FEATURE                   Location/Qualifiers
misc_feature              1..38
                          note = Description of Artificial Sequence: Synthetic
                            oligonucleotide
misc_feature              1..38
                          note = AttB-TG
source                    1..38
                          mol_type = other DNA
```

```
                        organism = synthetic construct
SEQUENCE: 13
ggcttgtcga cgacggcgtg ctccgtcgtc aggatcat                           38

SEQ ID NO: 14           moltype = DNA   length = 52
FEATURE                 Location/Qualifiers
misc_feature            1..52
                        note = Description of Artificial Sequence: Synthetic
                          oligonucleotide
misc_feature            1..52
                        note = AttP-TG
source                  1..52
                        mol_type = other DNA
                        organism = synthetic construct
SEQUENCE: 14
gtggtttgtc tggtcaacca ccgcgtgctc agtggtgtac ggtacaaacc ca          52

SEQ ID NO: 15           moltype = DNA   length = 38
FEATURE                 Location/Qualifiers
misc_feature            1..38
                        note = Description of Artificial Sequence: Synthetic
                          oligonucleotide
misc_feature            1..38
                        note = AttB-GT
source                  1..38
                        mol_type = other DNA
                        organism = synthetic construct
SEQUENCE: 15
ggcttgtcga cgacggcggt ctccgtcgtc aggatcat                           38

SEQ ID NO: 16           moltype = DNA   length = 52
FEATURE                 Location/Qualifiers
misc_feature            1..52
                        note = Description of Artificial Sequence: Synthetic
                          oligonucleotide
misc_feature            1..52
                        note = AttP-GT
source                  1..52
                        mol_type = other DNA
                        organism = synthetic construct
SEQUENCE: 16
gtggtttgtc tggtcaacca ccgcggtctc agtggtgtac ggtacaaacc ca          52

SEQ ID NO: 17           moltype = DNA   length = 38
FEATURE                 Location/Qualifiers
misc_feature            1..38
                        note = Description of Artificial Sequence: Synthetic
                          oligonucleotide
misc_feature            1..38
                        note = AttB-CT
source                  1..38
                        mol_type = other DNA
                        organism = synthetic construct
SEQUENCE: 17
ggcttgtcga cgacggcgct ctccgtcgtc aggatcat                           38

SEQ ID NO: 18           moltype = DNA   length = 52
FEATURE                 Location/Qualifiers
misc_feature            1..52
                        note = Description of Artificial Sequence: Synthetic
                          oligonucleotide
misc_feature            1..52
                        note = AttP-CT
source                  1..52
                        mol_type = other DNA
                        organism = synthetic construct
SEQUENCE: 18
gtggtttgtc tggtcaacca ccgcgctctc agtggtgtac ggtacaaacc ca          52

SEQ ID NO: 19           moltype = DNA   length = 38
FEATURE                 Location/Qualifiers
misc_feature            1..38
                        note = Description of Artificial Sequence: Synthetic
                          oligonucleotide
misc_feature            1..38
                        note = AttB-CA
source                  1..38
                        mol_type = other DNA
                        organism = synthetic construct
```

```
SEQUENCE: 19
ggcttgtcga cgacggcgca ctccgtcgtc aggatcat                             38

SEQ ID NO: 20           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-CA
source                  1..52
                        mol_type = other DNA
                        organism = synthetic construct
SEQUENCE: 20
gtggtttgtc tggtcaacca ccgcgcactc agtggtgtac ggtacaaacc ca             52

SEQ ID NO: 21           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-TC
source                  1..38
                        mol_type = other DNA
                        organism = synthetic construct
SEQUENCE: 21
ggcttgtcga cgacggcgtc ctccgtcgtc aggatcat                             38

SEQ ID NO: 22           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-TC
source                  1..52
                        mol_type = other DNA
                        organism = synthetic construct
SEQUENCE: 22
gtggtttgtc tggtcaacca ccgcgtcctc agtggtgtac ggtacaaacc ca             52

SEQ ID NO: 23           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-GA
source                  1..38
                        mol_type = other DNA
                        organism = synthetic construct
SEQUENCE: 23
ggcttgtcga cgacggcgga ctccgtcgtc aggatcat                             38

SEQ ID NO: 24           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-GA
source                  1..52
                        mol_type = other DNA
                        organism = synthetic construct
SEQUENCE: 24
gtggtttgtc tggtcaacca ccgcggactc agtggtgtac ggtacaaacc ca             52

SEQ ID NO: 25           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-AG
source                  1..38
                        mol_type = other DNA
                        organism = synthetic construct
SEQUENCE: 25
```

```
ggcttgtcga cgacggcgag ctccgtcgtc aggatcat                             38

SEQ ID NO: 26           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-AG
source                  1..52
                        mol_type = other DNA
                        organism = synthetic construct
SEQUENCE: 26
gtggtttgtc tggtcaacca ccgcgagctc agtggtgtac ggtacaaacc ca             52

SEQ ID NO: 27           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-AC
source                  1..38
                        mol_type = other DNA
                        organism = synthetic construct
SEQUENCE: 27
ggcttgtcga cgacggcgac ctccgtcgtc aggatcat                             38

SEQ ID NO: 28           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-AC
source                  1..52
                        mol_type = other DNA
                        organism = synthetic construct
SEQUENCE: 28
gtggtttgtc tggtcaacca ccgcgacctc agtggtgtac ggtacaaacc ca             52

SEQ ID NO: 29           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-AT
source                  1..38
                        mol_type = other DNA
                        organism = synthetic construct
SEQUENCE: 29
ggcttgtcga cgacggcgat ctccgtcgtc aggatcat                             38

SEQ ID NO: 30           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-AT
source                  1..52
                        mol_type = other DNA
                        organism = synthetic construct
SEQUENCE: 30
gtggtttgtc tggtcaacca ccgcgatctc agtggtgtac ggtacaaacc ca             52

SEQ ID NO: 31           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-GC
source                  1..38
                        mol_type = other DNA
                        organism = synthetic construct
SEQUENCE: 31
ggcttgtcga cgacggcggc ctccgtcgtc aggatcat                             38
```

```
SEQ ID NO: 32          moltype = DNA  length = 52
FEATURE                Location/Qualifiers
misc_feature           1..52
                       note = Description of Artificial Sequence: Synthetic
                         oligonucleotide
misc_feature           1..52
                       note = AttP-GC
source                 1..52
                       mol_type = other DNA
                       organism = synthetic construct
SEQUENCE: 32
gtggtttgtc tggtcaacca ccgcggcctc agtggtgtac ggtacaaacc ca          52

SEQ ID NO: 33          moltype = DNA  length = 38
FEATURE                Location/Qualifiers
misc_feature           1..38
                       note = Description of Artificial Sequence: Synthetic
                         oligonucleotide
misc_feature           1..38
                       note = AttB-CG
source                 1..38
                       mol_type = other DNA
                       organism = synthetic construct
SEQUENCE: 33
ggcttgtcga cgacggcgcg ctccgtcgtc aggatcat                          38

SEQ ID NO: 34          moltype = DNA  length = 52
FEATURE                Location/Qualifiers
misc_feature           1..52
                       note = Description of Artificial Sequence: Synthetic
                         oligonucleotide
misc_feature           1..52
                       note = AttB-CG
source                 1..52
                       mol_type = other DNA
                       organism = synthetic construct
SEQUENCE: 34
gtggtttgtc tggtcaacca ccgcgcgctc agtggtgtac ggtacaaacc ca          52

SEQ ID NO: 35          moltype = DNA  length = 38
FEATURE                Location/Qualifiers
misc_feature           1..38
                       note = Description of Artificial Sequence: Synthetic
                         oligonucleotide
misc_feature           1..38
                       note = AttB-TA
source                 1..38
                       mol_type = other DNA
                       organism = synthetic construct
SEQUENCE: 35
ggcttgtcga cgacggcgta ctccgtcgtc aggatcat                          38

SEQ ID NO: 36          moltype = DNA  length = 52
FEATURE                Location/Qualifiers
misc_feature           1..52
                       note = Description of Artificial Sequence: Synthetic
                         oligonucleotide
misc_feature           1..52
                       note = AttP-TA
source                 1..52
                       mol_type = other DNA
                       organism = synthetic construct
SEQUENCE: 36
gtggtttgtc tggtcaacca ccgcgtactc agtggtgtac ggtacaaacc ca          52

SEQ ID NO: 37          moltype = DNA  length = 45
FEATURE                Location/Qualifiers
misc_feature           1..45
                       note = Description of Artificial Sequence: Synthetic
                         oligonucleotide
misc_feature           1..45
                       note = C-31-B
source                 1..45
                       mol_type = other DNA
                       organism = synthetic construct
SEQUENCE: 37
tgcgggtgcc agggcgtgcc cttgggctcc ccgggcgcgt actcc                  45
```

```
SEQ ID NO: 38           moltype = DNA  length = 42
FEATURE                 Location/Qualifiers
misc_feature            1..42
                        note = Description of Artificial Sequence: Synthetic
                        oligonucleotide
misc_feature            1..42
                        note = C31-P
source                  1..42
                        mol_type = other DNA
                        organism = synthetic construct
SEQUENCE: 38
gtgcccaac tggggtaacc tttgagttct ctcagttggg gg                             42

SEQ ID NO: 39           moltype = DNA  length = 57
FEATURE                 Location/Qualifiers
misc_feature            1..57
                        note = Description of Artificial Sequence: Synthetic
                        oligonucleotide
misc_feature            1..57
                        note = R4-B
source                  1..57
                        mol_type = other DNA
                        organism = synthetic construct
SEQUENCE: 39
gcgcccaagt tgcccatgac catgccgaag cagtggtaga agggcaccgg cagacac           57

SEQ ID NO: 40           moltype = DNA  length = 70
FEATURE                 Location/Qualifiers
misc_feature            1..70
                        note = Description of Artificial Sequence: Synthetic
                        oligonucleotide
misc_feature            1..70
                        note = R4-P
source                  1..70
                        mol_type = other DNA
                        organism = synthetic construct
SEQUENCE: 40
aggcatgttc cccaaagcga taccacttga agcagtggta ctgcttgtgg gtacactctg        60
cgggtgatga                                                                70

SEQ ID NO: 41           moltype = DNA  length = 60
FEATURE                 Location/Qualifiers
misc_feature            1..60
                        note = Description of Artificial Sequence: Synthetic
                        oligonucleotide
misc_feature            1..60
                        note = BT1-B
source                  1..60
                        mol_type = other DNA
                        organism = synthetic construct
SEQUENCE: 41
gtccttgacc aggtttttga cgaaagtgat ccagatgatc cagctccaca ccccgaacgc        60

SEQ ID NO: 42           moltype = DNA  length = 63
FEATURE                 Location/Qualifiers
misc_feature            1..63
                        note = Description of Artificial Sequence: Synthetic
                        oligonucleotide
misc_feature            1..63
                        note = BT1-P
source                  1..63
                        mol_type = other DNA
                        organism = synthetic construct
SEQUENCE: 42
ggtgctgggt tgttgtctct ggacagtgat ccatgggaaa ctactcagca ccaccaatgt        60
tcc                                                                       63

SEQ ID NO: 43           moltype = DNA  length = 50
FEATURE                 Location/Qualifiers
misc_feature            1..50
                        note = Description of Artificial Sequence: Synthetic
                        oligonucleotide
misc_feature            1..50
                        note = Bxb-B
source                  1..50
                        mol_type = other DNA
                        organism = synthetic construct
SEQUENCE: 43
tcggccggct tgtcgacgac ggcggtctcc gtcgtcagga tcatccgggc                   50
```

```
SEQ ID NO: 44            moltype = DNA  length = 58
FEATURE                  Location/Qualifiers
misc_feature             1..58
                         note = Description of Artificial Sequence: Synthetic
                         oligonucleotide
misc_feature             1..58
                         note = Bxb-P
source                   1..58
                         mol_type = other DNA
                         organism = synthetic construct
SEQUENCE: 44
gtcgtggttt gtctggtcaa ccaccgcggt ctcagtggtg tacggtacaa accccgac      58

SEQ ID NO: 45            moltype = DNA  length = 46
FEATURE                  Location/Qualifiers
misc_feature             1..46
                         note = Description of Artificial Sequence: Synthetic
                         oligonucleotide
misc_feature             1..46
                         note = TG1-B
source                   1..46
                         mol_type = other DNA
                         organism = synthetic construct
SEQUENCE: 45
gatcagctcc gcgggcaaga ccttctcctt cacggggtgg aaggtc                   46

SEQ ID NO: 46            moltype = DNA  length = 67
FEATURE                  Location/Qualifiers
misc_feature             1..67
                         note = Description of Artificial Sequence: Synthetic
                         oligonucleotide
misc_feature             1..67
                         note = TG1-P
source                   1..67
                         mol_type = other DNA
                         organism = synthetic construct
SEQUENCE: 46
tcaaccccgt tccagcccaa cagtgttagt ctttgctctt acccagttgg gcgggatagc    60
ctgcccg                                                              67

SEQ ID NO: 47            moltype = DNA  length = 57
FEATURE                  Location/Qualifiers
misc_feature             1..57
                         note = Description of Artificial Sequence: Synthetic
                         oligonucleotide
misc_feature             1..57
                         note = C1-B
source                   1..57
                         mol_type = other DNA
                         organism = synthetic construct
SEQUENCE: 47
aacgattttc aaaggatcac tgaatcaaaa gtattgctca tccacgcgaa attttc        57

SEQ ID NO: 48            moltype = DNA  length = 57
FEATURE                  Location/Qualifiers
misc_feature             1..57
                         note = Description of Artificial Sequence: Synthetic
                         oligonucleotide
misc_feature             1..57
                         note = C1-P
source                   1..57
                         mol_type = other DNA
                         organism = synthetic construct
SEQUENCE: 48
aatattttag gtatatgatt ttgtttatta gtgtaaataa cactatgtac ctaaaat       57

SEQ ID NO: 49            moltype = DNA  length = 53
FEATURE                  Location/Qualifiers
misc_feature             1..53
                         note = Description of Artificial Sequence: Synthetic
                         oligonucleotide
misc_feature             1..53
                         note = C370-B
source                   1..53
                         mol_type = other DNA
                         organism = synthetic construct
SEQUENCE: 49
tgtaaaggag actgataatg gcatgtacaa ctatactcgt cggtaaaaag gca           53
```

```
SEQ ID NO: 50              moltype = DNA  length = 52
FEATURE                    Location/Qualifiers
misc_feature               1..52
                           note = Description of Artificial Sequence: Synthetic
                             oligonucleotide
misc_feature               1..52
                           note = C370-P
source                     1..52
                           mol_type = other DNA
                           organism = synthetic construct
SEQUENCE: 50
taaaaaaata cagcgttttt catgtacaac tatactagtt gtagtgccta aa           52

SEQ ID NO: 51              moltype = DNA  length = 56
FEATURE                    Location/Qualifiers
misc_feature               1..56
                           note = Description of Artificial Sequence: Synthetic
                             oligonucleotide
misc_feature               1..56
                           note = K38-B
source                     1..56
                           mol_type = other DNA
                           organism = synthetic construct
SEQUENCE: 51
gagcgccgga tcagggagtg gacggcctgg gagcgctaca cgctgtggct gcggtc       56

SEQ ID NO: 52              moltype = DNA  length = 56
FEATURE                    Location/Qualifiers
misc_feature               1..56
                           note = Description of Artificial Sequence: Synthetic
                             oligonucleotide
misc_feature               1..56
                           note = K38-P
source                     1..56
                           mol_type = other DNA
                           organism = synthetic construct
SEQUENCE: 52
ccctaatacg caagtcgata actctcctgg gagcgttgac aacttgcgca ccctga       56

SEQ ID NO: 53              moltype = DNA  length = 68
FEATURE                    Location/Qualifiers
misc_feature               1..68
                           note = Description of Artificial Sequence: Synthetic
                             oligonucleotide
misc_feature               1..68
                           note = RB-B
source                     1..68
                           mol_type = other DNA
                           organism = synthetic construct
SEQUENCE: 53
tctcgtggtg gtggaaggtg ttggtgcggg gttggccgtg gtcgaggtgg ggtggtggta   60
gccattcg                                                            68

SEQ ID NO: 54              moltype = DNA  length = 69
FEATURE                    Location/Qualifiers
misc_feature               1..69
                           note = Description of Artificial Sequence: Synthetic
                             oligonucleotide
misc_feature               1..69
                           note = RV-P
source                     1..69
                           mol_type = other DNA
                           organism = synthetic construct
SEQUENCE: 54
gcacaggtgt agtgtatctc acaggtccac ggttggccgt ggactgctga agaacattcc   60
acgccagga                                                           69

SEQ ID NO: 55              moltype = DNA  length = 65
FEATURE                    Location/Qualifiers
misc_feature               1..65
                           note = Description of Artificial Sequence: Synthetic
                             oligonucleotide
misc_feature               1..65
                           note = SPBC-B
source                     1..65
                           mol_type = other DNA
                           organism = synthetic construct
SEQUENCE: 55
```

```
agtgcagcat gtcattaata tcagtacaga taaagctgta tctcctgtga acacaatggg   60
tgcca                                                               65

SEQ ID NO: 56           moltype = DNA   length = 55
FEATURE                 Location/Qualifiers
misc_feature            1..55
                        note = Description of Artificial Sequence: Synthetic
                        oligonucleotide
misc_feature            1..55
                        note = SPBC-P
source                  1..55
                        mol_type = other DNA
                        organism = synthetic construct
SEQUENCE: 56
aaagtagtaa gtatcttaaa aaacagataa agctgtatat taagatactt actac         55

SEQ ID NO: 57           moltype = DNA   length = 54
FEATURE                 Location/Qualifiers
misc_feature            1..54
                        note = Description of Artificial Sequence: Synthetic
                        oligonucleotide
misc_feature            1..54
                        note = TP901-B
source                  1..54
                        mol_type = other DNA
                        organism = synthetic construct
SEQUENCE: 57
tgataattgc caacacaatt aacatctcaa tcaaggtaaa tgcttttcg tttt            54

SEQ ID NO: 58           moltype = DNA   length = 54
FEATURE                 Location/Qualifiers
misc_feature            1..54
                        note = Description of Artificial Sequence: Synthetic
                        oligonucleotide
misc_feature            1..54
                        note = TP901-P
source                  1..54
                        mol_type = other DNA
                        organism = synthetic construct
SEQUENCE: 58
aattgcgagt ttttatttcg tttatttcaa ttaaggtaac taaaaaactc cttt           54

SEQ ID NO: 59           moltype = DNA   length = 68
FEATURE                 Location/Qualifiers
misc_feature            1..68
                        note = Description of Artificial Sequence: Synthetic
                        oligonucleotide
misc_feature            1..68
                        note = Wbeta-B
source                  1..68
                        mol_type = other DNA
                        organism = synthetic construct
SEQUENCE: 59
aaggtagcgt caacgatagg tgtaactgtc gtgtttgtaa cggtacttcc aacagctggc    60
gtttcagt                                                             68

SEQ ID NO: 60           moltype = DNA   length = 68
FEATURE                 Location/Qualifiers
misc_feature            1..68
                        note = Description of Artificial Sequence: Synthetic
                        oligonucleotide
misc_feature            1..68
                        note = Wbeta-P
source                  1..68
                        mol_type = other DNA
                        organism = synthetic construct
SEQUENCE: 60
tagtttaaa gttggttatt agttactgtg atatttatca cggtacccaa taaccaatga    60
atatttga                                                             68

SEQ ID NO: 61           moltype = DNA   length = 57
FEATURE                 Location/Qualifiers
misc_feature            1..57
                        note = Description of Artificial Sequence: Synthetic
                        oligonucleotide
misc_feature            1..57
                        note = A118-B
source                  1..57
                        mol_type = other DNA
```

```
                        organism = synthetic construct
SEQUENCE: 61
tgtaactttt tcggatcaag ctatgaagga cgcaagagg gaactaaaca cttaatt         57

SEQ ID NO: 62           moltype = DNA  length = 57
FEATURE                 Location/Qualifiers
misc_feature            1..57
                        note = Description of Artificial Sequence: Synthetic
                        oligonucleotide
misc_feature            1..57
                        note = A118-P
source                  1..57
                        mol_type = other DNA
                        organism = synthetic construct
SEQUENCE: 62
ttgtttagtt cctcgttttc tctcgttgga agaagaagaa acgagaaact aaaatta         57

SEQ ID NO: 63           moltype = DNA  length = 63
FEATURE                 Location/Qualifiers
misc_feature            1..63
                        note = Description of Artificial Sequence: Synthetic
                        oligonucleotide
misc_feature            1..63
                        note = BL3-B
source                  1..63
                        mol_type = other DNA
                        organism = synthetic construct
SEQUENCE: 63
caacctgttg acatgtttcc acagacaact cacgtggagg tagtcacggc ttttacgtta     60
gtt                                                                    63

SEQ ID NO: 64           moltype = DNA  length = 61
FEATURE                 Location/Qualifiers
misc_feature            1..61
                        note = Description of Artificial Sequence: Synthetic
                        oligonucleotide
misc_feature            1..61
                        note = BL3-P
source                  1..61
                        mol_type = other DNA
                        organism = synthetic construct
SEQUENCE: 64
gagaatactg ttgaacaatg aaaaactagg catgtagaag ttgtttgtgc actaacttta     60
a                                                                     61

SEQ ID NO: 65           moltype = DNA  length = 120
FEATURE                 Location/Qualifiers
misc_feature            1..120
                        note = Description of Artificial Sequence: Synthetic
                        polynucleotide
misc_feature            1..120
                        note = MR11-B
source                  1..120
                        mol_type = other DNA
                        organism = synthetic construct
SEQUENCE: 65
acaggtcaac acatcgcagt tatcgaacaa tcttcgaaaa tgtatggagg cacttgtatc     60
aatataggat gtataccttc gaagacactt gtacatgatg gattagaagg caaatccttt    120

SEQ ID NO: 66           moltype = DNA  length = 120
FEATURE                 Location/Qualifiers
misc_feature            1..120
                        note = Description of Artificial Sequence: Synthetic
                        polynucleotide
misc_feature            1..120
                        note = MR11-P
source                  1..120
                        mol_type = other DNA
                        organism = synthetic construct
SEQUENCE: 66
caaaataaaa aacattgatt tttattaact tcttttgtgc ggaactacga acagttcatt     60
aatacgaagt gtacaaactt ccatacaaaa ataaccacga caattaagac gtggtttcta   120

SEQ ID NO: 67           moltype = DNA  length = 17
FEATURE                 Location/Qualifiers
misc_feature            1..17
                        note = Description of Artificial Sequence: Synthetic
                        oligonucleotide
misc_feature            1..17
```

```
                        note = AttL
source                  1..17
                        mol_type = other DNA
                        organism = synthetic construct
SEQUENCE: 67
attatttctc accctga                                                        17

SEQ ID NO: 68           moltype = DNA  length = 17
FEATURE                 Location/Qualifiers
misc_feature            1..17
                        note = Description of Artificial Sequence: Synthetic
                         oligonucleotide
misc_feature            1..17
                        note = AttR
source                  1..17
                        mol_type = other DNA
                        organism = synthetic construct
SEQUENCE: 68
atcatctccc acccgga                                                        17

SEQ ID NO: 69           moltype = DNA  length = 34
FEATURE                 Location/Qualifiers
misc_feature            1..34
                        note = Description of Artificial Sequence: Synthetic
                         oligonucleotide
misc_feature            1..34
                        note = Vox
source                  1..34
                        mol_type = other DNA
                        organism = synthetic construct
SEQUENCE: 69
aataggtctg agaacgccca ttctcagacg tatt                                     34

SEQ ID NO: 70           moltype = DNA  length = 34
FEATURE                 Location/Qualifiers
misc_feature            1..34
                        note = Description of Artificial Sequence: Synthetic
                         oligonucleotide
misc_feature            1..34
                        note = FRT
source                  1..34
                        mol_type = other DNA
                        organism = synthetic construct
SEQUENCE: 70
gaagttccta tactttctag agaataggaa cttc                                     34

SEQ ID NO: 71           moltype = DNA  length = 5881
FEATURE                 Location/Qualifiers
misc_feature            1..5881
                        note = Description of Artificial Sequence: Synthetic
                         polynucleotide
misc_feature            1..5881
                        note = Cre Recombinase Expression Plasmid
source                  1..5881
                        mol_type = other DNA
                        organism = synthetic construct
SEQUENCE: 71
ggtcgacatt gattattgac tagttattaa tagtaatcaa ttacgggtc attagttcat          60
agcccatata tggagttccg cgttacataa cttacggtaa atggcccgcc tggctgaccg        120
cccaacgacc cccgcccatt gacgtcaata atgacgtatg ttcccatagt aacgccaata        180
gggactttcc attgacgtca atgggtggag tatttacggt aaactgccca cttggcagta        240
catcaagtgt atcatatgcc aagtacgccc cctattgacg tcaatgacgg taaatggccc        300
gcctggcatt atgcccagta catgacctta tgggactttc ctacttggca gtacatctac        360
gtattagtca tcgctattac catggtcgag gtgagcccca cgttctgctt cactctcccc        420
atctccccc cctccccacc cccaattttg tatttattta ttttttaatt attttgtgca         480
gcgatggggg cggggggggg gggggcgcgc gccaggcggg gggggggggg gggggggggg        540
gggggggggg gggcggggg gggcggcggc agcaatcag agcggcgcgc tccgaaagtt         600
tccttttatg gcgaggcggc ggcggcggcg gccctataaa aagcgaagcg cgcggcgggc        660
gggagtcgct gcgcgctgcc ttcgccccgt gccccgctcc gccgccgcct cgcgccgccc       720
gccccggctc tgactgaccg cgttactccc acaggtgagc gggcgggacg gcccttctcc        780
tccgggctgt aattagcgct tggtttaatg acggcttgtt tcttttctgt ggctgcgtga       840
aagccttgag gggctccggg agggcccttt gtgcgggggg agcggctcgg gggtgcgtg        900
cgtgtgtgtg tgcgtgggga cgccgcgtg cggctccgcg ctgcccggcg gctgtgagcg        960
ctgcgggcgc ggcgcgggc tttgtgcgct ccgcagtgtg cgcagggga gcgcggccgg       1020
gggcggtgcc ccgcggtgcg ggggggctg cgagggaac aaaggctgcg tgcgggtgt        1080
gtgcgtgggg gggtgagcag ggggtgtggg cgcgtcggtc gggctgcaac ccccctgca       1140
cccccctccc cgagttgctg agcacggccc ggcttcgggt gcggggctcc gtacggggcg       1200
tggcgcgggg ctcgccgtgc cgggcggggg gtggcggcag gtggggtgc cgggcgggc        1260
gggccgcct cgggccgggg agggctcggg ggaggggcgc ggcggccccc ggagcgccgg       1320
```

```
cggctgtcga ggcgcggcga gccgcagcca ttgcctttta tggtaatcgt gcgagagggc   1380
gcagggactt cctttgtccc aaatctgtgc ggagccgaaa tctgggaggc gccgccgcac   1440
cccctctagc gggcgcgggg cgaagcggtg cggcgccggc aggaaggaaa tgggcgggga   1500
gggccttcgt gcgtcgccgc gccgccgtcc ccttctccct ctccagcctc ggggctgtcc   1560
gcgggggggac ggctgccttc gggggggacg gggcagggcg gggttcggct tctggcgtgt   1620
gaccggcggc tctagagcct ctgctaacca tgttcatgcc ttcttctttt tcctacagct   1680
cctgggcaac gtgctggtta ttgtgctgtc tcatcatttt ggcaaagaat tctgagccgc   1740
caccatggcc aatttactga ccgtacacca aaatttgcct gcattaccgg tcgatgcaac   1800
gagtgatgag gttcgcaaga acctgatgga catgttcagg gatcgccagg cgttttctga   1860
gcatacctgg aaaatgcttc tgtccgtttg ccggtcgtgg gcggcatggt gcaagttgaa   1920
taaccggaaa tggtttcccg cagaacctga agatgttcgc gattatcttc tatatcttca   1980
ggcgcgcggt ctggcagtaa aaactatcca gcaacatttg ggccagctaa acatgcttca   2040
tcgtcggtcc gggctgccac gaccaagtga cagcaatgct gtttcactgg ttatgcggcg   2100
gatccgaaaa gaaaacgttg atgccggtga acgtgcaaga caggctctag cgttcgaacg   2160
cactgatttc gaccaggttc gttcactcat ggaaaatagc gatcgctgcc aggatatacg   2220
taatctggca tttctgggga ttgcttataa caccctgtta cgtatagccg aaattgccag   2280
gatcagggtt aaagatatct cacgtactga cggtgggaga atgttaatcc atattggcag   2340
aacgaaaacg ctggttagca ccgcaggtgt agagaaggca cttagcctgg gggtaactaa   2400
actggtcgag cgatggattt ccgtctctgg tgtagctgat gatccgaata actacctgtt   2460
ttgccgggtc agaaaaaatg gtgttgccgg gccatctgcc accagccagc tatcaactcg   2520
cgccctggaa gggattttg aagcaactca tcgattgatt tacggcgcta aggatgactc   2580
tggtcagaga tacctggcct ggtctggaca cagtgcccgt gtcggagccg cgcgagatat   2640
ggcccgcgct ggagtttcaa taccggagat catgcaagct ggtggctgga ccaatgtaaa   2700
tattgtcatg aactatatcc gtaacctgga tagtgaaaca ggggcaatgg tgcgcctgct   2760
ggaagatggc gatggaccgg tggaacaaaa acttattttct gaagaagatc tgtgatagcg   2820
gccgcactcc tcaggtgcag gctgcctatc agaaggtggt ggctggtgtg gccaatgccc   2880
tggctcacaa ataccactga gatctttttc cctctgccaa aaattatgg gacatcatga   2940
agccccttga gcatctgact tctggctaat aaaggaaatt tattttcatt gcaatagtgt   3000
gttgaatttt tttgtgtctc tcactcggaa ggacatatgg gagggcaaat catttaaaac   3060
atcagaatga gtatttggtt tagagtttgg caacatatgc ccatatgctg gctgccatga   3120
acaaaggttg gctataaaga ggtcatcagt atatgaaaca gccccctgct gtccattcct   3180
tattccatag aaaagccttg acttgaggtt agatttttttt tatatttgt tttgtgttat   3240
ttttttcttt aacatcccta aaattttcct tacatgtttt actagccaga ttttcctcc     3300
tctcctgact actcccagtc atagctgtcc ctcttctctt attggagatcc ctcgacctgc   3360
agcccaagct tggcgtaatc atggtcatag ctgtttcctg tgtgaaattg ttatccgctc   3420
acaattccac acaacatacg agccggaagc ataaagtgta aagcctgggg tgcctaatga   3480
gtgagctaac tcacattaat tgcgttcgc tcactgcccg ctttccagtc gggaaacctg    3540
tcgtgccagc ggatccgcat ctcaattagt cagcaaccat agtcccgccc ctaactccgc    3600
ccatccgccc cctaactccg cccagttccg cccattctcc gccccatggc tgactaattt    3660
ttttttattta tgcagaggcc gaggccgcct cggcctctga gctattccag aagtagtgag    3720
gaggcttttt tggaggccta ggcttttgca aaaagctaac ttgtttattg cagcttataa   3780
tggttacaaa taaagcaata gcatcacaaa tttcacaaat aaagcatttt ttcactgca    3840
ttctagttgt ggtttgtcca aactcatcaa tgtatcttat catgtctgga tccgctgcat    3900
taatgaatcg gccaacgcgc ggggagaggc ggtttgcgta ttgggcgctc ttccgcttcc   3960
tcgctcactg actcgctgcg ctcggtcgtt cggctgcggc gagcggtatc agctcactca    4020
aaggcggtaa tacggttatc cacagaatca ggggataacg caggaaagaa catgtgagca    4080
aaaggccagc aaaaggccag gaaccgtaaa aaggccgcgt tgctggcgtt tttccatagg    4140
ctccgccccc ctgacgagca tcacaaaaat cgacgctcaa gtcagaggtg gcgaaacccg    4200
acaggactat aaagatacca ggcgtttccc cctggaagct ccctcgtgcg ctctcctgtt   4260
ccgaccctgc cgcttaccgg atacctgtcc gcctttctcc cttcgggaag cgtggcgctt    4320
tctcatagct cacgctgtag gtatctcagt tcggtgtagg tcgttcgctc caagctgggc    4380
tgtgtgcacg aaccccccgt tcagcccgac cgctgcgcct tatccggtaa ctatcgtctt    4440
gagtccaacc cggtaagaca cgacttatcg ccactggcag cagccactgg taacaggatt    4500
agcagagcga ggtatgtagg cggtgctaca gagttcttga agtggtggcc taactacggc    4560
tacactagaa gaacagtatt tggtatctgc gctctgctga agccagttac cttcggaaaa    4620
agagttggta gctcttgatc cggcaaacaa accaccgctg gtagcggtgg tttttttgtt    4680
tgcaagcagc agattacgcg cagaaaaaaa ggatctcaag aagatccttt gatcttttct    4740
acggggtctg acgctcagtg gaacgaaaac tcacgttaag ggattttggt catgagatta    4800
tcaaaaagga tcttcaccta gatccttttta aattaaaaat gaagttttaa atcaatctaa    4860
agtatatatg agtaaacttg gtctgacagt taccaatgct taatcagtga ggcacctatc    4920
tcagcgatct gtctatttcg ttcatccata gttgcctgac tccccgtcgt gtagataact    4980
acgatacggg agggcttacc atctggcccc agtgctgcaa tgataccgcg agacccacgc    5040
tcaccggctc cagatttatc agcaataaac cagccagccg aagggccga gcgcagaagt    5100
ggtcctgcaa ctttatccgc ctccatccag tctattaatt gttgccggga agctagagta    5160
agtagttcgc cagttaatag tttgcgcaac gttgttgcca ttgctacagg catcgtggtg    5220
tcacgctcgt cgtttggtat ggcttcattc agctccggtt cccaacgatc aaggcgagtt    5280
acatgatccc ccatgttgtg caaaaaagcg gttagctcct tcggtcctcc gatcgttgtc    5340
agaagtaagt tggccgcagt gttatcactc atggttatgg cagcactgca taattctcttc    5400
actgtcatgc catccgtaag atgcttttct gtgactgagt agtactcaac caagtcattc    5460
tgagaatagt gtatgcggcg accgagttgc tcttgcccgg cgtcaatacg ggataatacc    5520
gcgccacata gcagaacttt aaaagtgctc atcattggaa aacgttcttc ggggcgaaaa    5580
ctctcaagga tcttaccgct gttgagatcc agttcgatgt aacccactcg tgcacccaac    5640
tgatcttcag catctttac tttcaccagc gtttctgggt gagcaaaaac aggaaggcaa    5700
aatgccgcaa aaaagggaat aagggcgaca cggaaatgtt gaatactcat actcttcctt    5760
tttcaatatt attgaagcat ttatcagggt tattgtctca tgagcggata catatttgaa    5820
tgtatttaga aaaataaaca aataggggtt ccgcgcacat ttccccgaaa agtgccacct    5880
g                                                                    5881

SEQ ID NO: 72          moltype = DNA   length = 4915
```

| FEATURE | Location/Qualifiers |
|---|---|
| misc_feature | 1..4915 |
| | note = Description of Artificial Sequence: Synthetic polynucleotide |
| misc_feature | 1..4915 |
| | note = GFP-Lox66-Cre expression plasmid |
| source | 1..4915 |
| | mol_type = other DNA |
| | organism = synthetic construct |

SEQUENCE: 72

```
agctctgatc aagagacagg atgaggatcg tttcgcatga ttgaacaaga tggattgcac   60
gcaggttctc cggccgcttg ggtggagagg ctattcggct atgactgggc acaacagaca  120
atcggctgct ctgatgccgc cgtgttccgg ctgtcagcgc aggggcgccc ggttcttttt  180
gtcaagaccg acctgtccgg tgccctgaat gaactgcaag acgaggcagc gcggctatcg  240
tggctggcca cgacgggcgt tccttgcgca gctgtgctcg acgttgtcac tgaagcggga  300
agggactggc tgctattggg cgaagtgccg gggcaggatc tcctgtcat ctacaccttg  360
ctcctgccga gaaagtatcc atcatggctg atgcaatgcg gcggctgcat acgcttgatc  420
cggctacctg cccattcgac caccaagcga aacatcgcat cgagcgagca cgtactcgga  480
tggaagccgg tcttgtcgat caggatgatc tggacgaaga gcatcagggg ctcgcgccag  540
ccgaactgtt cgccaggctc aaggcgagca tgcccgacgg cgaggatctc gtcgtgaccc  600
atggcgatgc ctgcttgccg aatatcatgg tggaaaatgg ccgcttttct ggattcatcg  660
actgtggccg gctgggtgtg gcggaccgct atcaggacat agcgttggct acccgtgata  720
ttgctgaaga gcttggcggc gaatgggctg accgcttcct cgtgctttac ggtatcgccg  780
ctcccgattc gcagcgcatc gccttctatc gccttcttga cgagttcttc tgaattatta  840
actcgagatc cactagagtg tggcggccgc attcttataa tcagcatcat gatgtggtac  900
cacatcatga tgctgattac ccccaactga gagaactcaa aggttacccc agttggggca  960
ggcccacaaa taaagcaata gcatcacaaa tttcacaaat aaagcatttt tttcactgca 1020
ttctagttgt ggtttgtcca aactcatcga gctcgagatc tggcgaaggc gatggggtc 1080
ttgaaggcgt gctggtactc cacgatgccc agctcggtgt tgctgtgcag ctcctccacg 1140
cggcgaagg cgaacatggg gccccgttc tgcaggatgc tggggtggat ggcgctcttg 1200
aagtgcatgt ggctgtccac cacgaagctg tagtagccgc cgtcgcgcag gctgaaggtg 1260
cgggcgaagc tgcccaccag cacgttatcg cccatgggt gcaggtgctc cacggtggcg 1320
ttgctgcgga tgatcttgtc ggtgaagatc acgctgtcct cggggaagcc ggtgcccacc 1380
accttgaagt cgccgatcac gcggccggcc tcgtagcggt agctgaagtc cacgtgcagc 1440
acgccgccgt cctcgtactt ctcgatgcgg tgttggtgt agccgccgtt gttgatgccg 1500
tgcaggaagg ggttctcgta gccgctgggg taggtgccga agtggtagaa gccgtagccc 1560
atcacgtggc tcagcaggta ggggctgaag gtcagggcgc ctttggtgct cttcatcttg 1620
ttggtcatgc ggccctgctc gggggtgccc tctccgccgc ccaccagctc gaactccacg 1680
ccgttcaggg tgccggtgat gcggcactcg atcttcatgg cgggcatggt ggcgaccggt 1740
agcgctagcg cgttcggata acttcgtata gcatacatta tacgaacggt aagcgctacc 1800
gccggcatac ccaagtgaag ttgctcgcag ctttatagtcg cgcccgggga gcccaagggc 1860
acgccctggc accgcggccg ctgagtctcg accatcatca tcatcatcat tgagtttatc 1920
tgggataaca gggtaatgtc atctagggat aacagggtaa tgtcatctagg ataacagggt 1980
aatgtatcta gggataacag ggtaatgtca tctgggataa cagggtaatg tcatctaggg 2040
ataacagggt atgtcatctg ggataacagg gtaatgtatc tagggataac agggtaatgt 2100
catctggat aacagggtaa tgtcatctag ggataacagg gtatgtcatc tgggataaca 2160
gggtaatgta tctagggata acagggtaat gtcatctggg ataacagggt aatgtcatct 2220
agggataaca gggtatgtca tctgggataa cagggtaatg tatctaggga taacagggta 2280
atgtcatctg ggataacagg gtaatgtcat ctagggataa cagggtatgt catctgggat 2340
aacagggtaa tgtatctagg gataacaggg taatgtcatc tgggataaca gggtaatgtc 2400
atctagggat aacagggtat gtcatctggg ataacaggt aatgtatcta gggataacag 2460
ggtaatgtca tctgggataa cagggtaatg tcatctaggg ataacagggt aaatgtcatc 2520
tagggataac agggtaatgt catctaggga taacagggta atgtcatctg gataacagg 2580
gtaatgtcat ctagggataa cagggtaatg tatcgccagc gtcgcacagc atgtttgctt 2640
gtcgccgtcg cgtctgtcac atcttttccg ccagcagtta gggattagcg tcttaagctg 2700
gcgcgaggac caacgtatca gccaggcgaa gctgcttttg agcaccaccc ggatgcctat 2760
cgccaccgtc ggtcgcaatg ttggttttga cgatcaactc tatttctcgc gggtatttaa 2820
aaaatgcacc ggggccagcc cgagcgagtt ccgtgccggt tgtgaagaaa agtgaatga 2880
tgtagccgtc aagttgtcat aattggtaac gaatcagaca attgacggct tgacggagta 2940
gcatagggtt tgcagaatcc ctgcttcgtc catttgacag gcacattatg catgccgctt 3000
cgccttcgcg cgcgaattga tctgctgcct cgcgcgtttc ggtgatgacg tgaaaacct 3060
ctgacacatg cagctcccgg agacggtcac agcttgtctg taagcggatg ccgggagcag 3120
acaagcccgt cagggcgcgt cagcgggtgt tggcgggtgt cggggcgcag ccatgaccca 3180
gtcacgtagc gatagcggag tgtatactgg cttaactatg cggcatcaga gcagattgta 3240
ctgagagtgc accatatgcg gtgtgaaata ccgcacagat gcgtaaggag aaaataccgc 3300
atcaggcgct cttccgcttc ctcgctcact gactcgctgc gctcggtcgt tcggctgcgg 3360
cgagcggtat cagctcactc aaaggcggta atacggttat ccacagaatc aggggataac 3420
gcaggaaaga acatgtgagc aaaaggccag caaaaggcca ggaaccgtaa aaaggccgcg 3480
ttgctggcgt ttttccatag gctccgcccc cctgacgagc atcacaaaaa tcgacgctca 3540
agtcagaggt ggcgaaaccc gacaggacta taaagatacc aggcgtttcc cctggaagc 3600
tccctcgtgc gctctcctgt tccgaccctg ccgcttaccg gatacctgtc cgcctttctc 3660
ccttcgggaa gcgtggcgct ttctcatagc tcacgctgta ggtatctcag ttcggtgtag 3720
gtcgttcgct ccaagctggg ctgtgtgcac gaaccccccg ttcagcccga ccgctgcgcc 3780
ttatccggta actatcgtct tgagtccaac ccggtaagac acgacttatc gccactggca 3840
gcagccactg gtaacaggat tagcagagcg aggtatgtag gcggtgctac agagttcttg 3900
aagtggtggc ctaactacgg ctacactaga aggacagtat ttggtatctg cgctctgctg 3960
aagccagtta ccttcggaaa aagagttggt agctcttgat ccggcaaaca aaccaccgct 4020
ggtagcggtg gtttttttgt ttgcaagcag cagattacgc gcagaaaaaa aggatctcaa 4080
gaagatcctt tgatcttttc tacggggtct gacgctcagt ggaacgaaaa ctcacgttaa 4140
```

```
gggattttgg tcatgagcgg atacatattt gaatgtattt agaaaaataa acaaaagagt    4200
ttgtagaaac gcaaaaggcc catccgtcag gatggccttc tgcttaattt gatgcctggc    4260
agtttatggc gggcgtcctg cccgccaccc tccgggccgt tgcttcgcaa cgttcaaatc    4320
cgctcccggc ggatttgtcc tactcaggag agcgttcacc gacaaacaac agataaaacg    4380
aaaggcccag tctttcgact gagccttttcg ttttatttga tgcctggcag ttccctactc    4440
tcgcatgggg agaccccaca ctaccatcgg cgctacggcg tttcacttct gagttcggca    4500
tggggtcagg tgggaccacc gcgctactgc cgccaggcaa attctgtttt atcagaccgc    4560
ttctgcgttc tgatttaatc tgtatcaggc tgaaaatctt ctctcatccg ccaaaacagc    4620
caagctggag accgtttggc cccctcgag cacgtagaaa gccagtccgc agaaacggtg    4680
ctgaccccgg atgaatgtca gctactgggc tatctggaca agggaaaacg caagcgcaaa    4740
gagaaagcag gtagcttgca gtgggcttac atggcgatag ctagactggg cggttttatg    4800
gacagcaagc gaaccggaat tgccagctgg ggcgccctct ggtaaggttg ggaagccctg    4860
caaagtaaac tggatggctt tctcgccgcc aaggatctga tggcgcaggg gatca         4915
```

SEQ ID NO: 73          moltype = DNA   length = 10815
FEATURE                Location/Qualifiers
misc_feature           1..10815
                       note = Description of Artificial Sequence: Synthetic
                       polynucleotide
misc_feature           1..10815
                       note = pCMV-PE2-P2A-Cre
source                 1..10815
                       mol_type = other DNA
                       organism = synthetic construct
SEQUENCE: 73

```
acgcgttgac attgattatt gactagttat taatagtaat caattacggg gtcattagtt      60
catagcccat atatggagtt ccgcgttaca taacttacgg taaatggccc gcctggctga     120
ccgcccaacg acccccgccc attgacgtca ataatgacgt atgttcccat agtaacgcca     180
atagggactt tccattgacg tcaatgggtg gagtatttac ggtaaactgc ccacttggca     240
gtacatcaag tgtatcatat gccaagtacg cccctattg acgtcaatga cggtaaatgg     300
cccgcctggc attatgccca gtacatgacc ttatgggact ttcctacttg gcagtacatc     360
tacgtattag tcatcgctat taccatggtg atgcggtttt ggcagtacat caatgggcgt     420
ggatagcggt ttgactcacg gggatttcca agtctccacc ccattgacgt caatgggagt     480
ttgttttggc accaaaatca acgggacttt ccaaaatgtc gtaacaactc cgccccattg     540
acgcaaatgg gcggtaggcg tgtacggtgg gaggtctata taagcagagc tggtttagtg     600
aaccgtcaga tccgctagag atccgcggcc gctaatacga ctcactatag ggagagccgc     660
caccatgaaa cggacagccg acggaagcga gttcgagtca ccaaagaaga gcggaaagt     720
cgacaagaag tacagcatcg gcctggacat cggcaccaac tctgtgggct gggccgtgat     780
caccgacgag tacaaggtgc ccagcaagaa attcaaggtg ctgggcaaca ccgaccggca     840
cagcatcaag aagaacctga tcggagccct gctgttcgac agcggcgaaa cagccgaggc     900
cacccggctg aagagaaccg ccagaagaag atacaccaga cggaagaacc ggatctgcta     960
tctgcaagag atcttcagca acgagatggc caaggtggac gacagcttct tccacagact    1020
ggaagagtcc ttcctggtgg aagaggataa gaagcacgag cggcacccca tcttcggcaa    1080
catcgtggac gaggtggcct accacgagaa gtacccacc atctaccacc tgagaaagaa    1140
actggtggac agcaccgaca aggccgacct gcggctgatc tatctggccc tggcccacat    1200
gatcaagttc cggggccact tcctgatcga gggcgacctg aaccccgaca cagcgacgt    1260
ggacaagctg ttcatccagc tggtgcagac ctacaaccag ctgttcgagg aaaacccccat    1320
caacgccagc ggcgtggacg ccaaggccat cctgtctgcc agactgagca gagcagacg    1380
gctgaaaat ctgatcgccc agctgcccgg cgagaagaag aatggcctgt tcggaaacct    1440
gattgccctg agcctgggcc tgaccccaa cttcaagagc aacttcgacc tggccgagga    1500
tgccaaactg cagctgagca aggacaccta cgacgacgac ctggacaacc tgctggccca    1560
gatcggcgac cagtacgccg acctgttcct ggccgccaag aacctgtccg acgccatcct    1620
gctgagcgac atcctgagag tgaacaccga gatcaccaag gcccccctga gcgcctctat    1680
gatcaagaga tacgacgagc accaccagga cctgaccctg ctgaaagctc tcgtgcggca    1740
gcagctgcct gagaagtaca aagagatttt cttcgaccag agcaagaacg gctacgccgg    1800
ctacattgac ggcggagcca gccaggaaga gttctacaag ttcatcaagc ccatcctgga    1860
aaagatggac ggcaccgagg aactgctcgt gaagctgaac agagaggacc tgctgcggaa    1920
gcagcggacc ttcgacaacg gcagcatccc ccaccagatc cacctgggag agctgcacgc    1980
cattctgcgg cggcaggaag attttaccc attcctgaag gacaaccggg aaaagatcga    2040
gaagatcctg accttccgca tcccctacta cgtgggccct ctggccaggg gaaacagcag    2100
attcgcctgg atgaccagaa agagcgagga accatcacc cctggaact tcgaggaagt    2160
ggtggacaag ggcgcttccg cccagagctt catcgagcgg atgaccaact tcgataagaa    2220
cctgcccaac gagaaggtgc tgcccaagca gcctgctg tacgagtact tcaccgtgta    2280
taacgagctg accaaagtga atacgacgc cgagggaacg agaaagcccg ccttcctgag    2340
cggcgagcag aaaaaggcca tcgtggacct gctgttcaag accaaccgga aagtgaccgt    2400
gaagcagctg aagagactc ttcaagaa atcgagtgc ttcgactccg tggaaatctc    2460
cggcgtggaa gatcggttca acgcctccct gggcacatac cacgatctgc tgaaaattat    2520
caaggacaag gacttcctgg acaatgagga aaacgaggac attctggaag atatcgtgct    2580
gaccctgaca ctgtttgagg acagagagat gatcgaggaa cgcctgaaaa cctatgccca    2640
cctgttcgac gacaaagtga tgaagcagct gaagcggcgg agatacaccg gctgggcag    2700
gctgagccgg aagctgatca acggcatccg ggacaagcag tccggcaaga caatcctgga    2760
tttcctgaag tccgacggct cgccaacag aaacttcatg cagctgatcc acgacgacag    2820
cctgaccttt aaagaggaca tccagaaagc ccaggtgtcc ggccagggcg atagcctgca    2880
cgagcacatt gccaatctgg ccggcagccc cgccattaag aagggcatcc tgcagacagt    2940
gaaggttgtg gacgagctcg tgaaagtgat gggccggcac aagcccgaga acatcgtgat    3000
cgaaatggcc agagagaacc agaccaccca aagggacag aagaacagcc gcgagagaat    3060
gaagcggatc gaagagggca tcaaagagct gggcagccag atcctgaaag aacacccgt    3120
ggaaaacacc cagctgcaga acgagaagct gtacctgtac tacctgcaga atgggcggga    3180
tatgtacgtg gaccaggaac tggacatcaa ccggctgtcc gactacgatg tggacgctat    3240
```

```
cgtgcctcag agctttctga aggacgactc catcgacaac aaggtgctga ccagaagcga  3300
caagaaccgg ggcaagagcg acaacgtgcc ctccgaagag gtcgtgaaga agatgaagaa  3360
ctactggcgg cagctgctga acgccaagct gattacccag agaaagttcg acaatctgac  3420
caaggccgag agaggcggcc tgagcgaact ggataaggcc ggcttcatca agagacagct  3480
ggtggaaacc cggcagatca caaagcacgt ggcacagatc ctggactccc ggatgaacac  3540
taagtacgac gagaatgaca agctgatccg ggaagtgaaa gtgatcaccc tgaagtccaa  3600
gctggtgtcc gatttccgga aggatttcca gttttacaaa gtgcgcgaga tcaacaacta  3660
ccaccacgcc cacgacgcct acctgaacgc cgtcgtggga accgccctga tcaaaaagta  3720
ccctaagctg gaaagcgagt tcgtgtacgg cgactacaag gtgtacgacg tgcggaagat  3780
gatcgccaag agcgagcagg aaatcggcaa ggctaccgcc aagtacttct tctacagcaa  3840
catcatgaac ttttcaaga ccgagattac cctggccaac ggcgagatcc ggaagcggcc  3900
tctgatcgag acaaacggcg aaaccgggga gatcgtgtgg gataagggcc gggattttgc  3960
caccgtgcgg aaagtgctga gcatgcccca agtgaatatc gtgaaaaaga ccgaggtgca  4020
gacaggcggc ttcagcaaag agtctatcct gcccaagagg aacagcgata gctgatcgc  4080
cagaaagaag gactgggacc ctaagaagta cggcggcttc gacagcccca ccgtggccta  4140
ttctgtgctg gtggtggcca agtggaaaa gggcaagtcc aagaaactga agagtgtgaa  4200
agagctgctg gggatcacca tcatggaaag aagcagcttc gagaagaatc catcgactt  4260
tctggaagcc aagggctaca aagaagtgaa aaaggacctg atcatcaagc tgcctaagta  4320
ctccctgttc gagctggaaa acggccgaa gagaatgctg gcctctgccg gcgaactgca  4380
gaagggaaac gaactggccc tgccctccaa atatgtgaac ttcctgtacc tggcagcca  4440
ctatgagaag ctgaagggct cccccgagga taatgagcag aaacagctgt tgtggaaca  4500
gcacaagcac tacctggacg agatcatcga gcagatcagc gagttctcca agagagtgat  4560
cctggccgac gctaatctgg acaaagtgct gtccgcctac aacaagcacc gggataagcc  4620
catcagagag caggccgaga atatcatcca cctgtttacc ctgaccaatc tgggagccc  4680
tgccgccttc aagtactttg acaccaccat cgaccggaag aggtacacca gcaccaaga  4740
ggtgctggac gccaccctga tccaccagag catcaccggc ctgtacgaga cacggatcga  4800
cctgtctcag ctgggaggtg actctggagg atctagcgga ggatcctctg gcagcgagac  4860
accaggaaca agcgagtcag caacaccaga gagcagtggc ggcagcagcg gcggcagcag  4920
caccctaaat atagaagatg agtatcggct acatgagacc tcaaaagagc cagatgttc  4980
tctagggtcc acatgctgt ctgattttcc tcaggcctgg gcggaaaccg gggcatggg  5040
actggcagtt cgccaagctc ctctgatcat acctctgaaa gcaacctcta cccccgtgtc  5100
cataaaacaa taccccatgt cacaagaagc cagactgggg atcaagcccc acatacagag  5160
actgttggac cagggaatac tggtaccctg ccagtccccc tggaacacgc ccctgctacc  5220
cgttaagaaa ccagggacta atgattatag gcctgtccag gatctgagag aagtcaacaa  5280
gcgggtggaa gacatccacc ccaccgtgcc caacccttac aacctcttga gcgggctccc  5340
accgtcccac cagtggtaca ctgtgcttga tttaaaggat gccttttctc gcctgagact  5400
ccaccccacc agtcagcctc tcttcgcctt tgagtggaga gatccagaga tgggaatctc  5460
aggacaattg acctggacca gactcccaca gggtttcaaa aacagtccca ccctgtttaa  5520
tgaggcactg cacagagacc tagcagactt ccggatccag cacccagact tgatcctgct  5580
acagtacgtg gatgacttac tgctggccgc cacttctgag ctagactgcc aacaaggtac  5640
tcgggccctg ttacaaaccc tagggaacct cgggtatcgg gcctcggcca agaaagccca  5700
aatttgccag aaacaggtca gtatctgggg tatcttcta aaagagggtc agagatggct  5760
gactgaggcc agaaaagaga ctgtgatggg gcagcctact ccgaagaccc ctcgacaact  5820
aagggagttc ctagggaagg caggcttctg tcgcctcttc atccctgggt ttgcagaaat  5880
ggcagccccc ctgtaccctc tcaccaaacc ggggactctg tttaattggg cccagacca  5940
acaaaaggcc tatcaagaaa tcaagcaagc tcttctaact gccccagccc tggggttgcc  6000
agatttgact aagccctttg aactctttgt cgacgagaag cagggctacg ccaaaggtgt  6060
cctaacgcaa aaactgggac cttggcgtcg gccggtggcc tacctgtcca aaaagctaga  6120
cccagtagca gctgggtggc cccttgcct acggatggta gcagccattg ccgtactgac  6180
aaaggatgca ggcaagctaa ccatgggaca gccactagtc attctggccc ccatgcagt  6240
agaggcacta gtcaaacaac ccccgaccg ctggctttcc aacgcccgga tgactcacta  6300
tcaggccttg ctttggaca cggaccgggt ccagttcgga ccggtggtag ccctgaaccc  6360
ggctacgctg ctcccactgc tgaggaagg gctgcaacac aactgccttg atatcctggc  6420
cgaagcccac ggaacccgac ccgacctaac ggaccagccg ctcccagacg ccgaccacac  6480
ctggtacacg gatggaagca gtctcttaca agagggacag cgtaaggcgg gagctgcggt  6540
gaccaccgag accgaggtaa tctgggctaa agccctgcca gccgggacat ccgctcagcg  6600
ggctgaactg atagcactca cccaggcct aaagatggca gaaggtaaga gctaaatgt  6660
ttatactgat agccgttatg cttttgctac tgcccatatc catggagaaa tatacagaag  6720
gcgtgggtgg ctcacatcag aaggcaaaga gatcaaaaat aaagacgaga tcttggccct  6780
actaaaagcc ctctttctgc ccaaaagact tagcataatc cattgtccag gacatcaaa  6840
gggacacagc gccgaggcta gaggcaaccg gatggctgac caagcggccc gaaaggcagc  6900
catcacagag actccagaca cctctaccct cctcatagaa aattcatcac cctctggcgg  6960
ctcaaaaaga accgccgacg gcagcgaatt cgagcccaag aagaagagga aagtcggaag  7020
cggagctact aacttcagcc tgctgaagca ggctggcgac gtggaggaa accggaacc  7080
taatttactg accgtacacc aaaatttgcc tgcattaccg gtcgatgcaa cgagtgatga  7140
ggttcgcaag aacctgatgg acatgttcag ggatcgccag gcgttttctg agcatacctg  7200
gaaaatgctt ctgtccgttt gccggtcgtg gcggcatgg tgcaagttga ataaccggaa  7260
atggtttccc gcagaacctg aagatgttcg cgattatctt ctatatcttc aggcgcgcgg  7320
tctggcagta aaaactatcc agcaacattt gggccagcta aatatcttc atcgtcggtc  7380
cgggctgcca cgaccaagtg acagcaatgc tgttcactg gttatgcggc ggatccgaaa  7440
agaaaacgtt gatgccggtg aacgtgcaaa acaggctcta gcgttcgaac gcactgattt  7500
cgaccaggtt cgttcactca tggaaaatag cgatcgctgc caggatatac gtaatctggc  7560
atttctgggg attgcttata cacccctgtt acgtatagcc gaaattgcca ggatcaggt  7620
taaagatatc tcacgtactg ggactgggag aatgttaatc catattggca gaacgaaaac  7680
gctggttagc accgcaggtg tagagaaggc acttagcctg ggggtaacta aactggtcga  7740
gcgatggatt tccgtctctg gtgtagctga tgatccgaat aactaccgt tttgccgggt  7800
cagaaaaaat ggtgttgccg cgccatctgc caccagccag ctatcaactc gcgccctgga  7860
agggattttt gaagcaactc atcgattgat ttacggcgct aaggatgact ctggtcagag  7920
ataccctggc tggtctggac acagtgcccg tgtcggagcc gcgcgagata tggcccgcgc  7980
```

```
tggagtttca ataccggaga tcatgcaagc tggtggctgg accaatgtaa atattgtcat   8040
gaactatatc cgtaacctgg atagtgaaac aggggcaatg gtgcgcctgc tggaagatgg   8100
cgattaattt aaacccgctg atcagcctcg actgtgcctt ctagttgcca gccatctgtt   8160
gtttgcccct cccccgtgcc ttccttgacc ctggaaggtg ccactccac  tgtcctttcc   8220
taataaaatg agaaaattgc atcgcattgt ctgagtaggt gtcattctat tctgggggat   8280
ggggtggggc aggacagcaa gggggaggat tgggaagaca atagcaggca tgctggggat   8340
gcggtgggct ctatgcttc  tgaggcggaa agaaccagct ggggctcgat accgtcgacc   8400
tctagctaga gcttggcgta atcatggtca tagctgtttc ctgtgtgaaa ttgttatccg   8460
ctcacaattc cacacaacat acgagccgga agcataaagt gtaaagccta gggtgcctaa   8520
tgagtgagct aactcacatt aattgcgttg cgctcactgc ccgctttcca gtcgggaaac   8580
ctgtcgtgcc agctgcatta atgaatcggc caacgcgcgg ggagaggcgg tttgcgtatt   8640
gggcgctctt ccgcttcctc gctcactgac tcgctgcgct cggtcgttcg gctgcggcga   8700
gcggtatcag ctcactcaaa ggcggtaata cggttatcca cagaatcagg gataacgcag   8760
ggaaagaaca tgtgagcaaa aggccagcaa aaggccagga accgtaaaaa ggccgcgttg   8820
ctggcgtttt tccataggct ccgcccccct gacgagcatc acaaaaatcg acgctcaagt   8880
cagaggtggc gaaacccgac aggactataa agataccagg cgtttccccc tggaagctcc   8940
ctcgtgcgct ctcctgttcc gaccctgccg cttaccggat acctgtccgc ctttctccct   9000
tcgggaagcg tggcgctttc tcatagctca cgctgtaggt atctcagttc ggtgtaggtc   9060
gttcgctcca agctgggctg tgtgcacgaa ccccccgttc agcccgaccg ctgcgcctta   9120
tccggtaact atcgtcttga gtccaacccg gtaagacacg acttatcgcc actggcagca   9180
gccactggta acaggattag cagagcgagg tatgtaggcg gtgctacaga gttcttgaag   9240
tggtggccta actacggcta cactagaaga acagtatttg gtatctgcgc tctgctgaag   9300
ccagttacct tcggaaaaag agttggtagc tcttgatccg gcaaacaaac caccgctggt   9360
agcggtggtt tttttgtttg caagcagcag attacgcgca gaaaaaaagg atctcaagaa   9420
gatcctttga tcttttctac ggggtctgac gctcagtgga acgaaaactc acgttaaggg   9480
attttggtca tgagattatc aaaaaggatc ttcacctaga tccttttaaa ttaaaaatga   9540
agttttaaat caatctaaag tatatatgag taaacttggt ctgacagtta ccaatgctta   9600
atcagtgagg cacctatctc agcgatctgt ctatttcgtt catccatagt tgcctgactc   9660
cccgtcgtgt agataactac gatacgggag ggcttaccat ctggccccag tgctgcaatg   9720
ataccgcgag acccacgctc accggctcca gatttatcag caataaacca gccagccgga   9780
agggccgagc gcagaagtgg tcctgcaact ttatccgcct ccatccagtc tattaattgt   9840
tgccgggaag ctagagtaag tagttcgcca gttaatagtt tgcgcaacgt tgttgccatt   9900
gctacaggca tcgtggtgtc acgctcgtcg tttggtatgg cttcattcag ctccggttcc   9960
caacgatcaa ggcgagttac atgatccccc atgttgtgca aaaaagcggt tagctccttc  10020
ggtcctccga tcgttgtcag aagtaagttg gccgcagtgt tatcactcat ggttatgcca  10080
gcactgcata attctcttac tgtcatgcca tccgtaagat gcttttctgt gactggtgag  10140
tactcaacca agtcattctg agaatagtgt atgcggcgac cgagttgctc ttgcccggcg  10200
tcaatacggg ataataccgc gccacatagc agaactttaa aagtgctcat cattggaaaa  10260
cgttcttcgg ggcgaaaact ctcaaggatc ttaccgctgt tgagatccag ttcgatgtaa  10320
cccactcgtg cacccaactg atcttcagca tcttttactt tcaccagcgt ttctgggtga  10380
gcaaaaacag gaaggcaaaa tgccgcaaaa aagggaataa gggcgacacg gaaatgttga  10440
atactcatac tcttcctttt tcaatattat tgaagcattt atcagggtta ttgtctcatg  10500
agcggataca tatttgaatg tatttagaaa aataaacaaa taggggttcc gcgcacattt  10560
ccccgaaaag tgccacctga cgtcgacgga tcgggagatc gatctcccga tcccctaggg  10620
tcgactctca gtacaatctg ctctgatgcc gcatagttaa gccagtatct gctccctgct  10680
tgtgtgttgg aggtcgctga gtagtgcgcg agcaaaattt aagctacaac aaggcaaggc  10740
ttgaccgaca attgcatgaa gaatctgctt agggttaggc gttttgcgct gcttcgcgat  10800
gtacgggcca gatat                                                   10815
```

| | | |
|---|---|---|
| SEQ ID NO: 74 | moltype = DNA  length = 20 | |
| FEATURE | Location/Qualifiers | |
| misc_feature | 1..20 | |
| | note = Description of Artificial Sequence: Synthetic oligonucleotide | |
| misc_feature | 1..20 | |
| | note = +90ngRNA guide sequence | |
| source | 1..20 | |
| | mol_type = other DNA | |
| | organism = synthetic construct | |
| SEQUENCE: 74 | | |
| gtcaaccagt atcccggtgc | | 20 |

| | | |
|---|---|---|
| SEQ ID NO: 75 | moltype = DNA  length = 96 | |
| FEATURE | Location/Qualifiers | |
| misc_feature | 1..96 | |
| | note = Description of Artificial Sequence: Synthetic oligonucleotide | |
| misc_feature | 1..96 | |
| | note = +90ngRNA | |
| source | 1..96 | |
| | mol_type = other DNA | |
| | organism = synthetic construct | |
| SEQUENCE: 75 | | |
| gtcaaccagt atcccggtgc gttttagagc tagaaatagc aagttaaaat aaggctagtc | | 60 |
| cgttatcaac ttgaaaaagt ggcaccgagt cggtgc | | 96 |

| | |
|---|---|
| SEQ ID NO: 76 | moltype = DNA  length = 4968 |
| FEATURE | Location/Qualifiers |
| misc_feature | 1..4968 |

|  | note = Description of Artificial Sequence: Synthetic polynucleotide |
|---|---|
| misc_feature | 1..4968 |
|  | note = GFP minicircle template (before cleavage) |
| source | 1..4968 |
|  | mol_type = other DNA |
|  | organism = synthetic construct |

SEQUENCE: 76

```
tgatcccctg cgccatcaga tccttggcgg cgagaaagcc atccagttta ctttgcaggg   60
cttcccaacc ttaccagagg gcgcccccagc tggcaattcc ggttcgcttg ctgtccataa  120
aaccgcccag tctagctatc gccatgtaag cccactgcaa gctacctgct ttctctttgc  180
gcttgcgttt tccttgtcc agatagccca gtagctgaca ttcatccggg gtcagcaccg   240
tttctgcgga ctggctttct acgtgctcga gggggggccaa acggtctcca gcttggctgt  300
tttggcggat gagagaagat tttcagcctg atacagatta aatcagaacg cagaagcgt   360
ctgataaaac agaatttgcc tggcggcagt agcgcggtgg tcccacctga ccccatgccg  420
aactcagaag tgaaacgccg tagcgccgat ggtagtgtgg ggtctcccca tgcgagagta  480
gggaactgcc aggcatcaaa taaaacgaaa ggctcagtcg aaagactggg cctttcgttt  540
tatctgttgt ttgtcggtga acgctctcct gagtaggaca aatccgccgg gagcggattt  600
gaacgttgcg aagcaacggc ccggagggtg gcgggcagga cgcccgccat aaactgccag  660
gcatcaaatt aagcagaagg ccatcctgac ggatggcctt tttgcgtttc tacaaactct  720
tttgtttatt tttctaaata cattcaaata tgtatccgct catgaccaaa atcccttaac  780
gtgagttttc gttccactga gcgtcagacc ccgtagaaaa gatcaaagga tcttcttgag  840
atccttttt tctgcgcgta atctgctgct tgcaaacaaa aaaaccaccg ctaccagcgg  900
tggtttgttt gccggatcaa gagctaccaa ctctttttcc gaaggtaact ggcttcagca  960
gagcgcagat accaaatact gtccttctag tgtagccgta gttaggccac cacttcaaga 1020
actctgtagc accgcctaca tacctcgctc tgctaatcct gttaccagtg gctgctgcca 1080
gtggcgataa gtcgtgtctt accgggttgg actcaagacg atagttaccg gataaggcgc 1140
agcggtcggg ctgaacgggg ggttcgtgca cacagcccag cttggagcga acgacctaca 1200
ccgaactgag atacctacag cgtgagctat gagaaagcgc cacgcttccc gaagggagaa 1260
aggcggacag gtatccggta agcggcaggg tcggaacagg agagcgcacg agggagcttc 1320
cagggggaaa cgcctggtat ctttatagtc ctgtcgggtt tcgccacctc tgacttgagc 1380
gtcgattttt gtgatgctcg tcaggggggc ggagcctatg gaaaaacgcc agcaacgcgg 1440
cctttttacg gttcctggcc ttttgctggc cttttgctca catgttcttt cctgcgttat 1500
cccctgattc tgtggataac cgtattaccg cctttgagtg agctgatacc gctgccgca  1560
gccgaacgac cgagcgcagc gagtcagtga gcgaggaagc ggaagagcgc ctgatgcggt 1620
attttctcct tacgcatctg tgcggtattt cacaccgcat atggtgcact ctcagtacaa 1680
tctgctctga tgccgcatag ttaagccagt atacactccg ctatcgctac gtgactgggt 1740
catggctgcg ccccgacacc cgccaacacc cgctgacgcg ccctgacggg cttgtctgct 1800
cccggcatcc gcttacagac aagctgtgac cgtctccggg agctgcatgt gtcagaggtt 1860
ttcaccgtca tcaccgaaac gcgcgaggca gcagatcaat tcgcgcgcga aggcgaagcg 1920
gcatgcataa tgtgcctgtc aaatggacga agcagggatt ctgcaaaccc tatgctactc 1980
cgtcaagccg tcaattgtct gattcgttac caattatgac aacttgacgg ctacatcatt 2040
cacttttttct tcacaaccgg cacggaactc gctcgggctg gccccggtgc attttttaaa 2100
tacccgcgag aaatagagtt gatcgtcaaa accaacattg cgaccgacgg tggcgatagg 2160
catccgggtg tgtgctcaaaa gcagcttcgc ctggctgata cgttggtcct cgcgccagct 2220
taagacgcta atccctaact gctggcggaa aagatgtgac agacgcgacg gcgacaagca 2280
aacatgctgt gcgacgctgg cgatacatta ccctgttatc cctagatgac attaccctgt 2340
tatcccagat gacattaccc tgttatcctt agatgacatt accctgttat ccctagtga   2400
catttaccct gttatccta gatgacatta ccctgttatc cagatgaca ttaccctgtt  2460
atccctagat acattaccct gttatcccag atgacatacc ctgttatccc tagatgacat  2520
taccctgtta tcccagatga cattaccctg ttatccctag atacattacc ctgttatccc  2580
agatgacata ccctgttatc cctagatgac attaccctgt tatcccagat gacattaccc  2640
tgttatccct agatacatta ccctgttatc cagatgaca taccctgtta tccctagatg   2700
acattaccct gttatcccag atgacattac cctgttatcc ctagatacat taccctgtta  2760
tcccagatga cataccctgt tatccctaga tgacattacc ctgttatccc agatgacatt  2820
accctgttat cccagatac attaccctgt tatcccagat gacataccct gttatcccta  2880
gatgacatta ccctgttatc cagatgaca ttaccctgtt atcccctagat acattaccct  2940
gttatcccag atgacatacc ctgttatccc tagatgacat taccctgtta tcccagataa  3000
actcaatgat gatgatgatg atggtcgaga ctcagcggcc gcggtgccag ggcgtgccct  3060
tgggctcccc gggcgcgact ataagctgcg agcaacttca cttgggtatg ctcggcggtag  3120
cgcttaccgt tcgtataatg tatgctatac gaagttatcc gaagccgcta gcggtggttt  3180
gtctggtcaa ccaccgcggt ctcagtggtg tacggtacaa acccagctac cggtcgccac  3240
catgcccgcc atgaagatcg agtgccgcat caccggcacc ctgaacgcgg tggagttcga  3300
gctggtgggc ggcggagagg gcaccccccga gcagggccgc atgaccaaca agtgaagag  3360
caccaaaggc gccctgacct tcagccccta cctgctgagc cacgtgatgg gctacggctt  3420
ctaccacttc ggcacctacc cagcggcta cgagaacccc ttcctgcacg ccatcaacaa  3480
cggcggctac accaacaccc gcatcgagaa gtacgaggac ggcggcgtgc tgcacgtgag  3540
cttcagctac cgctacgagg ccggccgcgt gatcggcgac ttcaaggtgg tgggcaccgg  3600
cttccccgag cacagcgtga tcttcaccga caagatcatc cgcagcaacg ccaccgtgga  3660
gcacctgcac cccatgggcg ataacgtgct ggtgggcagc ttcgcccgca ccttcagcct  3720
gcgcgacggc ggctactaca gcttcgtggt ggacagccac atgcacttca aagagcgcat  3780
ccaccccagc atcctgcaga acgggggccc catgttcgcc ttcgccgcg tggaggagct  3840
gcacagcaac accgagctgg gcatcgtgga gtaccagcac gccttcaaga ccccccatcgc  3900
cttccagaga tctcgagctc gatgagtttg gacaaaccac aactagaatg cagtgaaaaa  3960
aatgctttat ttgtgaaatt tgtgatgcta ttgctttatt tgtgggcccg cccaactgg  4020
ggtaaccttt gagttctctc agttgggggt aatcagcatc atgatgtggt accacatcat  4080
gatgctgatt ataagaatgc ggccgccaca ctcagtggaa tctcgagtta ataattcaga  4140
agaactcgtc aagaaggcga taaggcga tgcgctgcga atcgggagcg gcgataccgt  4200
aaagcacgag gaagcggtca gcccattcgc cgccaagctc ttcagcaata tcacgggtag  4260
```

```
ccaacgctat gtcctgatag cggtccgcca cacccagccg gccacagtcg atgaatccag    4320
aaaagcggcc attttccacc atgatattcg gcaagcaggc atcgccatgg gtcacgacga    4380
gatcctcgcc gtcgggcatg ctcgccttga gcctggcgaa cagttcggct ggcgcgagcc    4440
cctgatgctc ttcgtccaga tcatcctgat cgacaagacc ggcttccatc cgagtacgtg    4500
ctcgctcgat gcgatgtttc gcttggtggt cgaatggcga ggtagccgga tcaagcgtat    4560
gcagccgccg cattgcatca gccatgatgg atactttctc ggcaggagca aggtgtagat    4620
gacatggaga tcctgccccg gcacttcgcc caatagcagc cagtcccttc ccgcttcagt    4680
gacaacgtcg agcacagctg cgcaaggaac gcccgtcgtg gccagccacg atagccgcgc    4740
tgcctcgtct tgcagttcat tcagggcacc ggacaggtcg gtcttgacaa aaagaaccgg    4800
gcgcccctgc gctgacagcc ggaacacggc ggcatcagag cagccgattg tctgttgtgc    4860
ccagtcatag ccgaatagcc tctccaccca agcggccgga gaacctgcgt gcaatccatc    4920
ttgttcaatc atgcgaaacg atcctcatcc tgtctcttga tcagagct                4968
```

| SEQ ID NO: 77 | moltype = DNA  length = 4855 |
|---|---|
| FEATURE | Location/Qualifiers |
| misc_feature | 1..4855 |
| | note = Description of Artificial Sequence: Synthetic polynucleotide |
| misc_feature | 1..4855 |
| | note = GLuc minicircle template |
| source | 1..4855 |
| | mol_type = other DNA |
| | organism = synthetic construct |

```
SEQUENCE: 77
tgatcccctg cgccatcaga tccttggcgg cgagaaagcc atccagttta ctttgcaggg      60
cttcccaacc ttaccagagg gcgccccagc tggcaattcc ggttcgcttg ctgtccataa     120
aaccgcccag tctagctatc gccatgtaag cccactgcaa gctacctgct ttctctttgc     180
gcttgcgttt tcccttgtcc agatagccca gtagctgaca ttcatccggg gtcagcaccg     240
tttctgcgga ctggctttct acgtgctcga gggggggccaa acggtctcca gcttggctgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggagggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atcctttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaagggagaa   1260
aggcggacag gtatccggta agcggcaggg tcggaacagg agagcgcacg agggagcttc   1320
caggggggaaa cgcctggtat ctttatagtc ctgtcgggtt tcgccacctc tgacttgagc   1380
gtcgattttt gtgatgctcg tcagggggggc ggagcctatg gaaaaacgcc agcaacgcgg   1440
cctttttacg gttcctggcc ttttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cacttttttct tcacaaccgg cacggaactc gctcgggctg gccccggtgc atttttaaa   2100
tacccgcgag aaatagagtt gatcgtcaaa accaacattg cgaccgacgg tggcgatagg   2160
catccggggtg gtgctcaaaa gcagcttcgc ctggctgata cgttggtcct cgcgccagct   2220
taagacgcta atccctaact gctggcgaaa agatgtgac agacgcgacg gcgacaagca   2280
aacatgctgt gcgacgctgg cgatacatta ccctgttatc cctagatgac attacccgtt   2340
tatcccagat gacattaccc tgttatccct agatgacatt accctgttat ccctagatga   2400
catttaccct gttatcccta gatgacatta ccctgttatc cagatgaca ttaccctgtt   2460
atccctagat acattaccct gttatcccag atgacatacc ctgttatccc tagatgacat   2520
taccctgtta tcccagatga cattacccctg ttatccctag acattacc ctgttatccc   2580
agatgacata ccctgttatc cctagatgac attaccctgt tatcccagat gacattaccc   2640
tgttatccct agatacatta ccctgttatc cagatgacata taccctgtta tcccctagatg   2700
acattaccct gttatcccag atgacattac cctgttatcc ctagatacat taccctgtta   2760
tcccagatga cataccctgt tatccctaga tgacattacc ctgttatccc agatgacatt   2820
accctgttat ccctagatac attaccctgt tatcccagat gacataccct gttatcccta   2880
gatgacatta ccctgttatc ccagatgaca ttaccctgtt atccctagat acattaccct   2940
gttatcccag atgacatacc ctgttatcct tagatgacat taccctgtta tcccagataa   3000
actcaatgat gatgatgatg atggtcgaga ctcagcggcc gcggtgccag ggcgtgccct   3060
tgggctcccc gggcgcgact ataagctgcg agcaacttca cttgggtatg ccggcggtag   3120
cgcttaccgt tcgtataatg tatgctatac gaagttatcc gaagccgcta gcggtggttt   3180
gtctggtcaa ccaccgcggt ctcagtgtgt acggtacaaa cccactacc ggtcgccacc   3240
atgggagtca aagttctgtt tgccctgatc tgcatcgctg tggccgaggc caagcccacc   3300
```

```
gagaacaacg aagacttcaa catcgtggcc gtggccagca acttcgcgac cacggatctc  3360
gatgctgacc gcgggaagtt gcccggcaag aagctgccgc tggaggtgct caaagagatg  3420
gaagccaatg cccggaaagc tggctgcacc aggggctgtc tgatctgcct gtcccacatc  3480
aagtgcacgc caagatgaa gaagttcatc caggacgct gccacaccta cgaaggcgac    3540
aaagagtccg cacagggcgg cataggcgag gcgatcgtcg acattcctga gattcctggg  3600
ttcaaggact tggagcccat ggagcagttc atcgcacagg tcgatctgtg tgtggactgc  3660
acaactggct gcctcaaagg gcttgccaac gtgcagtgtt ctgacctgct caagaagtgg  3720
ctgccgcaac gctgtgcgac ctttgccagc aagatccagg gccaggtgga caagatcaag  3780
ggggccggtg gtgactaagc ggagctcgat gagtttggac aaaccacaac tagaatgcag  3840
tgaaaaaaat gctttatttg tgaaatttgt gatgctattg ctttatttgt ggggcccgcc  3900
caactggggt aacctttgag ttctctcagt tgggggtaat cagcatcatg atgtggtacc  3960
acatcatgat gctgattata agaatgcggc cgccacactc tagtggatct cgagttaata  4020
attcagaaga actcgtcaag aaggcgatag aaggcgatgc gctgcgaatc gggagcggcg  4080
ataccgtaaa gcacgaggaa gcggtcagcc cattcgccgc caagctcttc agcaatatca  4140
cgggtagcca acgctatgtc ctgatagcgg tccgccacac ccagccggcc acagtcgatg  4200
aatccagaaa agcggccatt ttccaccatg atattcggca agcaggcatc gccatgggtc  4260
acgacgagat cctcgccgtc gggcatgctc gccttgagct ggcgaacag ttcggctggc   4320
gcgagcccct gatgctcttc gtccagatca tcctgatcga caagaccggc ttccatccga  4380
gtacgtgctc gctcgatgcg atgtttcgct tggtggtcga atgggcaggt agccggatca  4440
agcgtatgca gccgccgcat tgcatcagcc atgatggata ctttctcggc aggagcaagg  4500
tgtagatgac atggagatcc tgccccggca cttcgcccaa tagcagccag tcccttcccg  4560
cttcagtgac aacgtcgagc acagcgtgcg aaggaacgcc cgtcgtggcc agccacgata  4620
gccgcgctgc ctcgtcttgc agttcattca gggcaccgga caggtcggtc ttgacaaaaa  4680
gaaccgggcg cccctgcgct gacagccgga acacggcggc atcagagcag ccgattgtct  4740
gttgtgccca gtcatagccg aatagcctct cacccaagc ggccgagaa cctgcgtgca    4800
atccatcttg ttcaatcatg cgaaacgatc ctcatcctgt ctcttgatca gagct        4855

SEQ ID NO: 78          moltype = DNA   length = 38
FEATURE                Location/Qualifiers
misc_feature           1..38
                       note = Description of Artificial Sequence: Synthetic
                       oligonucleotide
misc_feature           1..38
                       note = pseudo-attP
source                 1..38
                       mol_type = other DNA
                       organism = synthetic construct
SEQUENCE: 78
ccccaactgg ggtaaccttt gagttctctc agttggggg                              38

SEQ ID NO: 79          moltype = DNA   length = 194
FEATURE                Location/Qualifiers
misc_feature           1..194
                       note = Description of Artificial Sequence: Synthetic
                       polynucleotide
misc_feature           1..194
                       note = Albumin-pegRNA-SERPIN
source                 1..194
                       mol_type = other DNA
                       organism = synthetic construct
SEQUENCE: 79
gactgaaact tcacagaata gttttagagc tagaaatagc aagttaaaat aaggctagtc     60
cgttatcaac ttgaaaaagt ggcaccgagt cggtgcttgg gatagttatg aattcaatct    120
tcaaccctat ccggatgatc ctgacgacgg agaccgccgt cgtcgacaag ccggcctctg    180
tgaagtttca gtca                                                      194

SEQ ID NO: 80          moltype = DNA   length = 189
FEATURE                Location/Qualifiers
misc_feature           1..189
                       note = Description of Artificial Sequence: Synthetic
                       polynucleotide
misc_feature           1..189
                       note = Albumin-pegRNA-CPS1
source                 1..189
                       mol_type = other DNA
                       organism = synthetic construct
SEQUENCE: 80
gactgaaact tcacagaata gttttagagc tagaaatagc aagttaaaat aaggctagtc     60
cgttatcaac ttgaaaaagt ggcaccgagt cggtgcttgg gatagttatg aattcaatct    120
tcaaccctat ccggatgatc ctgacgacgg agaccgccgt cgtcgacaag ccggcctctg    180
tgaagtttc                                                            189

SEQ ID NO: 81          moltype = DNA   length = 177
FEATURE                Location/Qualifiers
misc_feature           1..177
                       note = Description of Artificial Sequence: Synthetic
                       polynucleotide
misc_feature           1..177
                       note = 34bp lox71 pegRNA
```

```
source                          1..177
                                mol_type = other DNA
                                organism = synthetic construct
SEQUENCE: 81
ggcccagact gagcacgtga gttttagagc tagaaatagc aagttaaaat aaggctagtc    60
cgttatcaac ttgaaaaagt ggcaccgagt cggtgctgga ggaagcaggg cttcctttcc   120
tctgccatca taccgttcgt atagcataca ttatacgaag ttatcgtgct cagtctg      177

SEQ ID NO: 82                   moltype = DNA  length = 177
FEATURE                         Location/Qualifiers
misc_feature                    1..177
                                note = Description of Artificial Sequence: Synthetic
                                polynucleotide
misc_feature                    1..177
                                note = 34bp lox66 pegRNA
source                          1..177
                                mol_type = other DNA
                                organism = synthetic construct
SEQUENCE: 82
ggcccagact gagcacgtga gttttagagc tagaaatagc aagttaaaat aaggctagtc    60
cgttatcaac ttgaaaaagt ggcaccgagt cggtgctgga ggaagcaggg cttcctttcc   120
tctgccatca ataacttcgt atagcataca ttatacgaac ggtacgtgct cagtctg      177

SEQ ID NO: 83                   moltype = DNA  length = 20
FEATURE                         Location/Qualifiers
misc_feature                    1..20
                                note = Description of Artificial Sequence: Synthetic
                                oligonucleotide
misc_feature                    1..20
                                note = gRNA2
source                          1..20
                                mol_type = other DNA
                                organism = synthetic construct
SEQUENCE: 83
ggcccagact gagcacgtga                                                20

SEQ ID NO: 84                   moltype = DNA  length = 184
FEATURE                         Location/Qualifiers
misc_feature                    1..184
                                note = Description of Artificial Sequence: Synthetic
                                polynucleotide
source                          1..184
                                mol_type = other DNA
                                organism = synthetic construct
SEQUENCE: 84
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggccgga tgatcctgac gacggagacc gccgtcgtcg acaagccggc ctgagctgcg   180
agaa                                                                184

SEQ ID NO: 85                   moltype = DNA  length = 179
FEATURE                         Location/Qualifiers
misc_feature                    1..179
                                note = Description of Artificial Sequence: Synthetic
                                polynucleotide
source                          1..179
                                mol_type = other DNA
                                organism = synthetic construct
SEQUENCE: 85
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggcacaa ttaacatctc aatcaaggta aatgcttgag ctgcgagaa    179

SEQ ID NO: 86                   moltype = DNA  length = 179
FEATURE                         Location/Qualifiers
misc_feature                    1..179
                                note = Description of Artificial Sequence: Synthetic
                                polynucleotide
source                          1..179
                                mol_type = other DNA
                                organism = synthetic construct
SEQUENCE: 86
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggagcat ttaccttgat tgagatgtta attgtgtgag ctgcgagaa    179

SEQ ID NO: 87                   moltype = DNA  length = 182
FEATURE                         Location/Qualifiers
misc_feature                    1..182
```

```
                        note = Description of Artificial Sequence: Synthetic
                            polynucleotide
source                  1..182
                        mol_type = other DNA
                        organism = synthetic construct
SEQUENCE: 87
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggcaggt ttttgacgaa agtgatccag atgatccagt gagctgcgag   180
aa                                                                  182

SEQ ID NO: 88           moltype = DNA  length = 182
FEATURE                 Location/Qualifiers
misc_feature            1..182
                        note = Description of Artificial Sequence: Synthetic
                            polynucleotide
source                  1..182
                        mol_type = other DNA
                        organism = synthetic construct
SEQUENCE: 88
gctattctcg cagctcacca gttttagagc tagaaatagc aagttaaaat aaggctagtc    60
cgttatcaac ttgaaaaagt ggcaccgagt cggtgcgagt cggtgcgacg agcgcggcga   120
tatcatcatc catggctgga tcatctggat cactttcgtc aaaaacctgt gagctgcgag   180
aa                                                                  182

SEQ ID NO: 89           moltype = DNA  length = 96
FEATURE                 Location/Qualifiers
misc_feature            1..96
                        note = Description of Artificial Sequence: Synthetic
                            oligonucleotide
source                  1..96
                        mol_type = other DNA
                        organism = synthetic construct
SEQUENCE: 89
gaagccggcc ttgcacatgc gttttagagc tagaaatagc aagttaaaat aaggctagtc    60
cgttatcaac ttgaaaaagt ggcaccgagt cggtgc                              96

SEQ ID NO: 90           moltype = DNA  length = 164
FEATURE                 Location/Qualifiers
misc_feature            1..164
                        note = Description of Artificial Sequence: Synthetic
                            polynucleotide
source                  1..164
                        mol_type = other DNA
                        organism = synthetic construct
SEQUENCE: 90
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaat agcc                    164

SEQ ID NO: 91           moltype = DNA  length = 172
FEATURE                 Location/Qualifiers
misc_feature            1..172
                        note = Description of Artificial Sequence: Synthetic
                            polynucleotide
source                  1..172
                        mol_type = other DNA
                        organism = synthetic construct
SEQUENCE: 91
gaagccggcc ttgcacatgc gttttagagc tagaaatagc aagttaaaat aaggctagtc    60
cgttatcaac ttgaaaaagt ggcaccgagt cggtgcgacg agcgcggcga tatcatcatc   120
catggtaccg ttcgtatagc atacattata cgaagttatt gagctgcgag aa           172

SEQ ID NO: 92           moltype = DNA  length = 189
FEATURE                 Location/Qualifiers
misc_feature            1..189
                        note = Description of Artificial Sequence: Synthetic
                            polynucleotide
source                  1..189
                        mol_type = other DNA
                        organism = synthetic construct
SEQUENCE: 92
gctattctcg cagctcacca gttttagagc tagaaatagc aagttaaaat aaggctagtc    60
cgttatcaac ttgaaaaagt ggcaccgagt cggtgctcga cgacgagcgc ggcgatatca   120
tcatccatgg cccggatgatc ctgacgacgg agaccgccgt cgtcgacaag ccggcctgag  180
ctgcgagaa                                                           189

SEQ ID NO: 93           moltype = DNA  length = 181
FEATURE                 Location/Qualifiers
```

```
misc_feature            1..181
                        note = Description of Artificial Sequence: Synthetic
                         polynucleotide
source                  1..181
                        mol_type = other DNA
                        organism = synthetic construct
SEQUENCE: 93
gctattctcg cagctcacca gttttagagc tagaaatagc aagttaaaat aaggctagtc   60
cgttatcaac ttgaaaaagt ggcaccgagt cggtgcgagc gcggcgatat catcatccat  120
ggccggatga tcctgacgac ggagaccgcc gtcgtcgaca agccggcctg agctgcgaga  180
a                                                                  181

SEQ ID NO: 94           moltype = DNA  length = 178
FEATURE                 Location/Qualifiers
misc_feature            1..178
                        note = Description of Artificial Sequence: Synthetic
                         polynucleotide
source                  1..178
                        mol_type = other DNA
                        organism = synthetic construct
SEQUENCE: 94
gctattctcg cagctcacca gttttagagc tagaaatagc aagttaaaat aaggctagtc   60
cgttatcaac ttgaaaaagt ggcaccgagt cggtgccgcg gcgatatcat catccatggc  120
cggatgatcc tgacgacgga gaccgccgtc gtcgacaagc cggcctgagc tgcgagaa    178

SEQ ID NO: 95           moltype = DNA  length = 175
FEATURE                 Location/Qualifiers
misc_feature            1..175
                        note = Description of Artificial Sequence: Synthetic
                         polynucleotide
source                  1..175
                        mol_type = other DNA
                        organism = synthetic construct
SEQUENCE: 95
gctattctcg cagctcacca gttttagagc tagaaatagc aagttaaaat aaggctagtc   60
cgttatcaac ttgaaaaagt ggcaccgagt cggtgcggcg atatcatcat ccatggccgg  120
atgatcctga cgacggagac cgccgtcgtc gacaagccgg cctgagctgc gagaa       175

SEQ ID NO: 96           moltype = DNA  length = 171
FEATURE                 Location/Qualifiers
misc_feature            1..171
                        note = Description of Artificial Sequence: Synthetic
                         polynucleotide
source                  1..171
                        mol_type = other DNA
                        organism = synthetic construct
SEQUENCE: 96
gctattctcg cagctcacca gttttagagc tagaaatagc aagttaaaat aaggctagtc   60
cgttatcaac ttgaaaaagt ggcaccgagt cggtgcatat catcatccat ggccggatga  120
tcctgacgac ggagaccgcc gtcgtcgaca agccggcctg agctgcgaga a            171

SEQ ID NO: 97           moltype = DNA  length = 194
FEATURE                 Location/Qualifiers
misc_feature            1..194
                        note = Description of Artificial Sequence: Synthetic
                         polynucleotide
source                  1..194
                        mol_type = other DNA
                        organism = synthetic construct
SEQUENCE: 97
gctattctcg cagctcacca gttttagagc tagaaatagc aagttaaaat aaggctagtc   60
cgttatcaac ttgaaaaagt ggcaccgagt cggtgctcga cgacgagcgc ggcgatatca  120
tcatccatgg ccggatgatc ctgacgacgg agaccgccgt cgtcgacaag ccggcctgag  180
ctgcgagaat agcc                                                    194

SEQ ID NO: 98           moltype = DNA  length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 98
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggccgga tgatcctgac gacggagacc gccgtcgtcg acaagccggc ctgagctgcg  180
agaatagcc                                                          189
```

```
SEQ ID NO: 99            moltype = DNA   length = 176
FEATURE                  Location/Qualifiers
misc_feature             1..176
                         note = Description of Artificial Sequence: Synthetic
                         polynucleotide
source                   1..176
                         mol_type = other DNA
                         organism = synthetic construct
SEQUENCE: 99
gctattctcg cagctcacca gttttagagc tagaaatagc aagttaaaat aaggctagtc    60
cgttatcaac ttgaaaaagt ggcaccgagt cggtgcatat catcatccat ggccggatga   120
tcctgacgac ggagaccgcc gtcgtcgaca agccggcctg agctgcgaga atagcc       176

SEQ ID NO: 100           moltype = DNA   length = 194
FEATURE                  Location/Qualifiers
misc_feature             1..194
                         note = Description of Artificial Sequence: Synthetic
                         polynucleotide
source                   1..194
                         mol_type = other DNA
                         organism = synthetic construct
SEQUENCE: 100
gctgtctccg ccgcccgcca gttttagagc tagaaatagc aagttaaaat aaggctagtc    60
cgttatcaac ttgaaaaagt ggcaccgagt cggtgcctgc ccatccgcgg cggcacgggg   120
gtcgcagtcg ccatgccgga tgatcctgac gacggagacc gccgtcgtcg acaagccggc   180
ccgggcggcg gaga                                                     194

SEQ ID NO: 101           moltype = DNA   length = 189
FEATURE                  Location/Qualifiers
misc_feature             1..189
                         note = Description of Artificial Sequence: Synthetic
                         polynucleotide
source                   1..189
                         mol_type = other DNA
                         organism = synthetic construct
SEQUENCE: 101
gctgtctccg ccgcccgcca gttttagagc tagaaatagc aagttaaaat aaggctagtc    60
cgttatcaac ttgaaaaagt ggcaccgagt cggtgccatc cgcggcggca cggggtcgc    120
agtcgccatg ccggatgatc ctgacgacgg agaccgccgt cgtcgacaag ccggcccggg   180
cggcggaga                                                           189

SEQ ID NO: 102           moltype = DNA   length = 184
FEATURE                  Location/Qualifiers
misc_feature             1..184
                         note = Description of Artificial Sequence: Synthetic
                         polynucleotide
source                   1..184
                         mol_type = other DNA
                         organism = synthetic construct
SEQUENCE: 102
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagacc gccgtcgtcg acaagccggc ccgggcggcg   180
gaga                                                                184

SEQ ID NO: 103           moltype = DNA   length = 179
FEATURE                  Location/Qualifiers
misc_feature             1..179
                         note = Description of Artificial Sequence: Synthetic
                         polynucleotide
source                   1..179
                         mol_type = other DNA
                         organism = synthetic construct
SEQUENCE: 103
gctgtctccg ccgcccgcca gttttagagc tagaaatagc aagttaaaat aaggctagtc    60
cgttatcaac ttgaaaaagt ggcaccgagt cggtgcggca cggggqtcgc agtcgccatg   120
ccggatgatc ctgacgacgg agaccgccgt cgtcgacaag ccggcccggg cggcggaga    179

SEQ ID NO: 104           moltype = DNA   length = 174
FEATURE                  Location/Qualifiers
misc_feature             1..174
                         note = Description of Artificial Sequence: Synthetic
                         polynucleotide
source                   1..174
                         mol_type = other DNA
                         organism = synthetic construct
SEQUENCE: 104
gctgtctccg ccgcccgcca gttttagagc tagaaatagc aagttaaaat aaggctagtc    60
cgttatcaac ttgaaaaagt ggcaccgagt cggtgcgggg gtcgcagtcg ccatgccgga   120
```

```
tgatcctgac gacggagacc gccgtcgtcg acaagccggc ccgggcggcg gaga        174

SEQ ID NO: 105              moltype = DNA   length = 199
FEATURE                     Location/Qualifiers
misc_feature                1..199
                            note = Description of Artificial Sequence: Synthetic
                            polynucleotide
source                      1..199
                            mol_type = other DNA
                            organism = synthetic construct
SEQUENCE: 105
gctgtctccg ccgcccgcca gttttagagc tagaaatagc aagttaaaat aaggctagtc   60
cgttatcaac ttgaaaaagt ggcaccgagt cggtgcctgc ccatccgcgg cggcacgggg  120
gtcgcagtcg ccatgccgga tgatcctgac gacggagacc gccgtcgtcg acaagccggc  180
ccgggcggcg gagacagcg                                               199

SEQ ID NO: 106              moltype = DNA   length = 194
FEATURE                     Location/Qualifiers
misc_feature                1..194
                            note = Description of Artificial Sequence: Synthetic
                            polynucleotide
source                      1..194
                            mol_type = other DNA
                            organism = synthetic construct
SEQUENCE: 106
gctgtctccg ccgcccgcca gttttagagc tagaaatagc aagttaaaat aaggctagtc   60
cgttatcaac ttgaaaaagt ggcaccgagt cggtgccatc cgcggcggca cggggggtcgc 120
agtcgccatg ccggatgatc ctgacgacgg agaccgccgt cgtcgacaag ccggcccggg  180
cggcggagac agcg                                                    194

SEQ ID NO: 107              moltype = DNA   length = 189
FEATURE                     Location/Qualifiers
misc_feature                1..189
                            note = Description of Artificial Sequence: Synthetic
                            polynucleotide
source                      1..189
                            mol_type = other DNA
                            organism = synthetic construct
SEQUENCE: 107
gctgtctccg ccgcccgcca gttttagagc tagaaatagc aagttaaaat aaggctagtc   60
cgttatcaac ttgaaaaagt ggcaccgagt cggtgcgcgg cggcacgggg gtcgcagtcg  120
ccatgccgga tgatcctgac gacggagacc gccgtcgtcg acaagccggc ccgggcggcg  180
gagacagcg                                                          189

SEQ ID NO: 108              moltype = DNA   length = 184
FEATURE                     Location/Qualifiers
misc_feature                1..184
                            note = Description of Artificial Sequence: Synthetic
                            polynucleotide
source                      1..184
                            mol_type = other DNA
                            organism = synthetic construct
SEQUENCE: 108
gctgtctccg ccgcccgcca gttttagagc tagaaatagc aagttaaaat aaggctagtc   60
cgttatcaac ttgaaaaagt ggcaccgagt cggtgcggca cggggggtcgc agtcgccatg  120
ccggatgatc ctgacgacgg agaccgccgt cgtcgacaag ccggcccggg cggcggagac  180
agcg                                                               184

SEQ ID NO: 109              moltype = DNA   length = 179
FEATURE                     Location/Qualifiers
misc_feature                1..179
                            note = Description of Artificial Sequence: Synthetic
                            polynucleotide
source                      1..179
                            mol_type = other DNA
                            organism = synthetic construct
SEQUENCE: 109
gctgtctccg ccgcccgcca gttttagagc tagaaatagc aagttaaaat aaggctagtc   60
cgttatcaac ttgaaaaagt ggcaccgagt cggtgcgggg gtcgcagtcg ccatgccgga  120
tgatcctgac gacggagacc gccgtcgtcg acaagccggc ccgggcggcg gagacagcg   179

SEQ ID NO: 110              moltype = DNA   length = 96
FEATURE                     Location/Qualifiers
misc_feature                1..96
                            note = Description of Artificial Sequence: Synthetic
                            oligonucleotide
source                      1..96
                            mol_type = other DNA
                            organism = synthetic construct
```

```
SEQUENCE: 110
gcgtggtggg gccgccagcg gttttagagc tagaaatagc aagttaaaat aaggctagtc    60
cgttatcaac ttgaaaaagt ggcaccgagt cggtgc                              96

SEQ ID NO: 111          moltype = DNA   length = 180
FEATURE                 Location/Qualifiers
misc_feature            1..180
                        note = Description of Artificial Sequence: Synthetic
                          polynucleotide
source                  1..180
                        mol_type = other DNA
                        organism = synthetic construct
SEQUENCE: 111
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggggatg atcctgacga cggagaccgc cgtcgtcgac aagccggtga gctgcgagaa   180

SEQ ID NO: 112          moltype = DNA   length = 178
FEATURE                 Location/Qualifiers
misc_feature            1..178
                        note = Description of Artificial Sequence: Synthetic
                          polynucleotide
source                  1..178
                        mol_type = other DNA
                        organism = synthetic construct
SEQUENCE: 112
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catgggatga tcctgacgac ggagaccgcc gtcgtcgaca agccgtgagc tgcgagaa     178

SEQ ID NO: 113          moltype = DNA   length = 176
FEATURE                 Location/Qualifiers
misc_feature            1..176
                        note = Description of Artificial Sequence: Synthetic
                          polynucleotide
source                  1..176
                        mol_type = other DNA
                        organism = synthetic construct
SEQUENCE: 113
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggatgat cctgacgacg gagaccgccg tcgtcgacaa gcctgagctg cgagaa       176

SEQ ID NO: 114          moltype = DNA   length = 174
FEATURE                 Location/Qualifiers
misc_feature            1..174
                        note = Description of Artificial Sequence: Synthetic
                          polynucleotide
source                  1..174
                        mol_type = other DNA
                        organism = synthetic construct
SEQUENCE: 114
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgatc ctgacgacgg agaccgccgt cgtcgacaag ctgagctgcg agaa         174

SEQ ID NO: 115          moltype = DNA   length = 182
FEATURE                 Location/Qualifiers
misc_feature            1..182
                        note = Description of Artificial Sequence: Synthetic
                          polynucleotide
source                  1..182
                        mol_type = other DNA
                        organism = synthetic construct
SEQUENCE: 115
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgcggat gatcctgacg acggagaccc cgtcgtcga caagccggcc gggcggcgga   180
ga                                                                  182

SEQ ID NO: 116          moltype = DNA   length = 180
FEATURE                 Location/Qualifiers
misc_feature            1..180
                        note = Description of Artificial Sequence: Synthetic
                          polynucleotide
source                  1..180
                        mol_type = other DNA
                        organism = synthetic construct
SEQUENCE: 116
```

```
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgggatg atcctgacga cggagaccgc cgtcgtcgac aagccggcgg gcggcggaga   180

SEQ ID NO: 117         moltype = DNA   length = 178
FEATURE                Location/Qualifiers
misc_feature           1..178
                       note = Description of Artificial Sequence: Synthetic
                       polynucleotide
source                 1..178
                       mol_type = other DNA
                       organism = synthetic construct
SEQUENCE: 117
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatggatga tcctgacgac ggagaccgcc gtcgtcgaca agccgcgggc ggcggaga     178

SEQ ID NO: 118         moltype = DNA   length = 176
FEATURE                Location/Qualifiers
misc_feature           1..176
                       note = Description of Artificial Sequence: Synthetic
                       polynucleotide
source                 1..176
                       mol_type = other DNA
                       organism = synthetic construct
SEQUENCE: 118
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgatgat cctgacgacg gagaccgccg tcgtcgacaa gcccgggcgg cggaga       176

SEQ ID NO: 119         moltype = DNA   length = 189
FEATURE                Location/Qualifiers
misc_feature           1..189
                       note = Description of Artificial Sequence: Synthetic
                       polynucleotide
source                 1..189
                       mol_type = other DNA
                       organism = synthetic construct
SEQUENCE: 119
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccggga tgatcctgac gacggagacc gccgtcgtcg acaagccggc ctcctccagg   180
caatacgcg                                                            189

SEQ ID NO: 120         moltype = DNA   length = 184
FEATURE                Location/Qualifiers
misc_feature           1..184
                       note = Description of Artificial Sequence: Synthetic
                       polynucleotide
source                 1..184
                       mol_type = other DNA
                       organism = synthetic construct
SEQUENCE: 120
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccgga tgatcctgac gacggagacc gccgtcgtcg acaagccggc ctcctccagg    180
caat                                                                184

SEQ ID NO: 121         moltype = DNA   length = 182
FEATURE                Location/Qualifiers
misc_feature           1..182
                       note = Description of Artificial Sequence: Synthetic
                       polynucleotide
source                 1..182
                       mol_type = other DNA
                       organism = synthetic construct
SEQUENCE: 121
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccggat gatcctgacg acggagaccg ccgtcgtcga caagccggct cctccaggca   180
at                                                                  182

SEQ ID NO: 122         moltype = DNA   length = 180
FEATURE                Location/Qualifiers
misc_feature           1..180
                       note = Description of Artificial Sequence: Synthetic
                       polynucleotide
source                 1..180
                       mol_type = other DNA
```

```
                        organism = synthetic construct
SEQUENCE: 122
gcgtattgcc tggaggatgg gttttagagc tagaaatagc aagttaaaat aaggctagtc   60
cgttatcaac ttgaaaaagt ggcaccgagt cggtgcgaac cacgcggcga atgccggcgt  120
ccgccggatg atcctgacga cggagaccgc cgtcgtcgca aagccggtcc tccaggcaat  180

SEQ ID NO: 123          moltype = DNA   length = 178
FEATURE                 Location/Qualifiers
misc_feature            1..178
                        note = Description of Artificial Sequence: Synthetic
                          polynucleotide
source                  1..178
                        mol_type = other DNA
                        organism = synthetic construct
SEQUENCE: 123
gcgtattgcc tggaggatgg gttttagagc tagaaatagc aagttaaaat aaggctagtc   60
cgttatcaac ttgaaaaagt ggcaccgagt cggtgcgaac cacgcggcga atgccggcgt  120
ccgccgatga tcctgacgac ggagaccgcc gtcgtcgaca agccgtcctc caggcaat    178

SEQ ID NO: 124          moltype = DNA   length = 176
FEATURE                 Location/Qualifiers
misc_feature            1..176
                        note = Description of Artificial Sequence: Synthetic
                          polynucleotide
source                  1..176
                        mol_type = other DNA
                        organism = synthetic construct
SEQUENCE: 124
gcgtattgcc tggaggatgg gttttagagc tagaaatagc aagttaaaat aaggctagtc   60
cgttatcaac ttgaaaaagt ggcaccgagt cggtgcgaac cacgcggcga atgccggcgt  120
ccgccatgat cctgacgacg gagaccgccg tcgtcgacaa gcctcctcca ggcaat      176

SEQ ID NO: 125          moltype = DNA   length = 97
FEATURE                 Location/Qualifiers
misc_feature            1..97
                        note = Description of Artificial Sequence: Synthetic
                          oligonucleotide
source                  1..97
                        mol_type = other DNA
                        organism = synthetic construct
SEQUENCE: 125
gagccgagca cgaggggata cgttttagag ctagaaatag caagttaaaa taaggctagt   60
ccgttatcaa cttgaaaaag tggcaccgag tcggtgc                            97

SEQ ID NO: 126          moltype = DNA   length = 167
FEATURE                 Location/Qualifiers
misc_feature            1..167
                        note = Description of Artificial Sequence: Synthetic
                          polynucleotide
source                  1..167
                        mol_type = other DNA
                        organism = synthetic construct
SEQUENCE: 126
gctattctcg cagctcacca gttttagagc tagaaatagc aagttaaaat aaggctagtc   60
cgttatcaac ttgaaaaagt ggcaccgagt cggtgcggcg atatcatcat ccatggatga  120
tcctgacgac ggagaccgcc gtcgtcgaca agcctgagct gcgagaa                167

SEQ ID NO: 127          moltype = DNA   length = 162
FEATURE                 Location/Qualifiers
misc_feature            1..162
                        note = Description of Artificial Sequence: Synthetic
                          polynucleotide
source                  1..162
                        mol_type = other DNA
                        organism = synthetic construct
SEQUENCE: 127
gctattctcg cagctcacca gttttagagc tagaaatagc aagttaaaat aaggctagtc   60
cgttatcaac ttgaaaaagt ggcaccgagt cggtgctatc atcatccatg gatgatcctg  120
acgacggaga ccgccgtcgt cgacaagcct gagctgcgag aa                     162

SEQ ID NO: 128          moltype = DNA   length = 157
FEATURE                 Location/Qualifiers
misc_feature            1..157
                        note = Description of Artificial Sequence: Synthetic
                          polynucleotide
source                  1..157
                        mol_type = other DNA
                        organism = synthetic construct
SEQUENCE: 128
```

```
gctattctcg cagctcacca gttttagagc tagaaatagc aagttaaaat aaggctagtc   60
cgttatcaac ttgaaaaagt ggcaccgagt cggtgctcat ccatggatga tcctgacgac  120
ggagaccgcc gtcgtcgaca agcctgagct gcgagaa                           157

SEQ ID NO: 129            moltype = DNA   length = 163
FEATURE                   Location/Qualifiers
misc_feature              1..163
                          note = Description of Artificial Sequence: Synthetic
                          polynucleotide
source                    1..163
                          mol_type = other DNA
                          organism = synthetic construct
SEQUENCE: 129
gctattctcg cagctcacca gttttagagc tagaaatagc aagttaaaat aaggctagtc   60
cgttatcaac ttgaaaaagt ggcaccgagt cggtgcggcg atatcatcat ccatggatga  120
tcctgacgac ggagaccgcc gtcgtcgaca agcctgagct gcg                    163

SEQ ID NO: 130            moltype = DNA   length = 158
FEATURE                   Location/Qualifiers
misc_feature              1..158
                          note = Description of Artificial Sequence: Synthetic
                          polynucleotide
source                    1..158
                          mol_type = other DNA
                          organism = synthetic construct
SEQUENCE: 130
gctattctcg cagctcacca gttttagagc tagaaatagc aagttaaaat aaggctagtc   60
cgttatcaac ttgaaaaagt ggcaccgagt cggtgctatc atcatccatg gatgatcctg  120
acgacggaga ccgccgtcgt cgacaagcct gagctgcg                          158

SEQ ID NO: 131            moltype = DNA   length = 153
FEATURE                   Location/Qualifiers
misc_feature              1..153
                          note = Description of Artificial Sequence: Synthetic
                          polynucleotide
source                    1..153
                          mol_type = other DNA
                          organism = synthetic construct
SEQUENCE: 131
gctattctcg cagctcacca gttttagagc tagaaatagc aagttaaaat aaggctagtc   60
cgttatcaac ttgaaaaagt ggcaccgagt cggtgctcat ccatggatga tcctgacgac  120
ggagaccgcc gtcgtcgaca agcctgagct gcg                               153

SEQ ID NO: 132            moltype = DNA   length = 167
FEATURE                   Location/Qualifiers
misc_feature              1..167
                          note = Description of Artificial Sequence: Synthetic
                          polynucleotide
source                    1..167
                          mol_type = other DNA
                          organism = synthetic construct
SEQUENCE: 132
gctgtctccg ccgcccgcca gttttagagc tagaaatagc aagttaaaat aaggctagtc   60
cgttatcaac ttgaaaaagt ggcaccgagt cggtgccggg ggtcgcagtc gccatgatga  120
tcctgacgac ggagaccgcc gtcgtcgaca agcccgggcg gcggaga              167

SEQ ID NO: 133            moltype = DNA   length = 162
FEATURE                   Location/Qualifiers
misc_feature              1..162
                          note = Description of Artificial Sequence: Synthetic
                          polynucleotide
source                    1..162
                          mol_type = other DNA
                          organism = synthetic construct
SEQUENCE: 133
gctgtctccg ccgcccgcca gttttagagc tagaaatagc aagttaaaat aaggctagtc   60
cgttatcaac ttgaaaaagt ggcaccgagt cggtgcgtcg cagtcgccat gatgatcctg  120
acgacggaga ccgccgtcgt cgacaagccc gggcggcgga ga                     162

SEQ ID NO: 134            moltype = DNA   length = 157
FEATURE                   Location/Qualifiers
misc_feature              1..157
                          note = Description of Artificial Sequence: Synthetic
                          polynucleotide
source                    1..157
                          mol_type = other DNA
                          organism = synthetic construct
SEQUENCE: 134
gctgtctccg ccgcccgcca gttttagagc tagaaatagc aagttaaaat aaggctagtc   60
```

```
cgttatcaac ttgaaaaagt ggcaccgagt cggtgcagtc gccatgatga tcctgacgac  120
ggagaccgcc gtcgtcgaca agcccgggcg gcggaga                            157

SEQ ID NO: 135         moltype = DNA   length = 163
FEATURE                Location/Qualifiers
misc_feature           1..163
                       note = Description of Artificial Sequence: Synthetic
                       polynucleotide
source                 1..163
                       mol_type = other DNA
                       organism = synthetic construct
SEQUENCE: 135
gctgtctccg ccgcccgcca gttttagagc tagaaatagc aagttaaaat aaggctagtc   60
cgttatcaac ttgaaaaagt ggcaccgagt cggtgccggg ggtcgcagtc gccatgatga  120
tcctgacgac ggagaccgcc gtcgtcgaca agcccgggcg gcg                    163

SEQ ID NO: 136         moltype = DNA   length = 158
FEATURE                Location/Qualifiers
misc_feature           1..158
                       note = Description of Artificial Sequence: Synthetic
                       polynucleotide
source                 1..158
                       mol_type = other DNA
                       organism = synthetic construct
SEQUENCE: 136
gctgtctccg ccgcccgcca gttttagagc tagaaatagc aagttaaaat aaggctagtc   60
cgttatcaac ttgaaaaagt ggcaccgagt cggtgcgtcg cagtcgccat gatgatcctg  120
acgacggaga ccgccgtcgt cgacaagccc gggcggcg                          158

SEQ ID NO: 137         moltype = DNA   length = 153
FEATURE                Location/Qualifiers
misc_feature           1..153
                       note = Description of Artificial Sequence: Synthetic
                       polynucleotide
source                 1..153
                       mol_type = other DNA
                       organism = synthetic construct
SEQUENCE: 137
gctgtctccg ccgcccgcca gttttagagc tagaaatagc aagttaaaat aaggctagtc   60
cgttatcaac ttgaaaaagt ggcaccgagt cggtgcagtc gccatgatga tcctgacgac  120
ggagaccgcc gtcgtcgaca agcccgggcg gcg                               153

SEQ ID NO: 138         moltype = DNA   length = 180
FEATURE                Location/Qualifiers
misc_feature           1..180
                       note = Description of Artificial Sequence: Synthetic
                       polynucleotide
source                 1..180
                       mol_type = other DNA
                       organism = synthetic construct
SEQUENCE: 138
gagaagcggc gtccggggct agttttagag ctagaaatag caagttaaaa taaggctagt   60
ccgttatcaa cttgaaaaag tggcaccgag tcggtgctct tgtccagag tcacagccat   120
accggatgat cctgacgacg gagaccgccg tcgtcgacaa gccggcccc cggacgccgc   180

SEQ ID NO: 139         moltype = DNA   length = 179
FEATURE                Location/Qualifiers
misc_feature           1..179
                       note = Description of Artificial Sequence: Synthetic
                       polynucleotide
source                 1..179
                       mol_type = other DNA
                       organism = synthetic construct
SEQUENCE: 139
gggcacgggg ccatgtacaa gttttagagc tagaaatagc aagttaaaat aaggctagtc   60
cgttatcaac ttgaaaaagt ggcaccgagt cggtgcggcg tcggcagccc gatcccgttg  120
ccggatgatc ctgacgacgg agaccgccgt cgtcgacaag ccggcctaca tggcccgt    179

SEQ ID NO: 140         moltype = DNA   length = 185
FEATURE                Location/Qualifiers
misc_feature           1..185
                       note = Description of Artificial Sequence: Synthetic
                       polynucleotide
source                 1..185
                       mol_type = other DNA
                       organism = synthetic construct
SEQUENCE: 140
gtgtcaggtg gggcggggct agttttagag ctagaaatag caagttaaaa taaggctagt   60
ccgttatcaa cttgaaaaag tggcaccgag tcggtgcgct ggctcctccc ctggcaccat  120
```

```
accggatgat cctgacgacg gagaccgccg tcgtcgacaa gccggcccc cgccccacct    180
gacac                                                              185

SEQ ID NO: 141         moltype = DNA   length = 184
FEATURE                Location/Qualifiers
misc_feature           1..184
                       note = Description of Artificial Sequence: Synthetic
                       polynucleotide
source                 1..184
                       mol_type = other DNA
                       organism = synthetic construct
SEQUENCE: 141
gagtgggtca gacgagcagg agttttagag ctagaaatag caagttaaaa taaggctagt    60
ccgttatcaa cttgaaaaag tggcaccgag tcggtgcgat ggagggctgc atgggggagg   120
agtcgccgga tgatcctgac gacggagacc gccgtcgtcg acaagccggc ctgctcgtct   180
gacc                                                               184

SEQ ID NO: 142         moltype = DNA   length = 97
FEATURE                Location/Qualifiers
misc_feature           1..97
                       note = Description of Artificial Sequence: Synthetic
                       oligonucleotide
source                 1..97
                       mol_type = other DNA
                       organism = synthetic construct
SEQUENCE: 142
gcagccaccc gctctcggcc cgttttagag ctagaaatag caagttaaaa taaggctagt    60
ccgttatcaa cttgaaaaag tggcaccgag tcggtgc                            97

SEQ ID NO: 143         moltype = DNA   length = 97
FEATURE                Location/Qualifiers
misc_feature           1..97
                       note = Description of Artificial Sequence: Synthetic
                       oligonucleotide
source                 1..97
                       mol_type = other DNA
                       organism = synthetic construct
SEQUENCE: 143
gtgtagtcag gccgctcacc cgttttagag ctagaaatag caagttaaaa taaggctagt    60
ccgttatcaa cttgaaaaag tggcaccgag tcggtgc                            97

SEQ ID NO: 144         moltype = DNA   length = 97
FEATURE                Location/Qualifiers
misc_feature           1..97
                       note = Description of Artificial Sequence: Synthetic
                       oligonucleotide
source                 1..97
                       mol_type = other DNA
                       organism = synthetic construct
SEQUENCE: 144
gctgacaagt ctacggaacc tgttttagag ctagaaatag caagttaaaa taaggctagt    60
ccgttatcaa cttgaaaaag tggcaccgag tcggtgc                            97

SEQ ID NO: 145         moltype = DNA   length = 96
FEATURE                Location/Qualifiers
misc_feature           1..96
                       note = Description of Artificial Sequence: Synthetic
                       oligonucleotide
source                 1..96
                       mol_type = other DNA
                       organism = synthetic construct
SEQUENCE: 145
gctcctccag cgccttgacc gttttagagc tagaaatagc aagttaaaat aaggctagtc    60
cgttatcaac ttgaaaaagt ggcaccgagt cggtgc                             96

SEQ ID NO: 146         moltype = DNA   length = 20
FEATURE                Location/Qualifiers
misc_feature           1..20
                       note = Description of Artificial Sequence: Synthetic
                       oligonucleotide
source                 1..20
                       mol_type = other DNA
                       organism = synthetic construct
SEQUENCE: 146
gctattctcg cagctcacca                                               20

SEQ ID NO: 147         moltype = DNA   length = 20
FEATURE                Location/Qualifiers
misc_feature           1..20
```

```
                        note = Description of Artificial Sequence: Synthetic
                            oligonucleotide
source                  1..20
                        mol_type = other DNA
                        organism = synthetic construct
SEQUENCE: 147
agaagcggcg tccggggcta                                                  20

SEQ ID NO: 148          moltype = DNA  length = 20
FEATURE                 Location/Qualifiers
misc_feature            1..20
                        note = Description of Artificial Sequence: Synthetic
                            oligonucleotide
source                  1..20
                        mol_type = other DNA
                        organism = synthetic construct
SEQUENCE: 148
gggcacgggg ccatgtacaa                                                  20

SEQ ID NO: 149          moltype = DNA  length = 20
FEATURE                 Location/Qualifiers
misc_feature            1..20
                        note = Description of Artificial Sequence: Synthetic
                            oligonucleotide
source                  1..20
                        mol_type = other DNA
                        organism = synthetic construct
SEQUENCE: 149
gcgtattgcc tggaggatgg                                                  20

SEQ ID NO: 150          moltype = DNA  length = 20
FEATURE                 Location/Qualifiers
misc_feature            1..20
                        note = Description of Artificial Sequence: Synthetic
                            oligonucleotide
source                  1..20
                        mol_type = other DNA
                        organism = synthetic construct
SEQUENCE: 150
tgtcaggtgg ggcggggcta                                                  20

SEQ ID NO: 151          moltype = DNA  length = 20
FEATURE                 Location/Qualifiers
misc_feature            1..20
                        note = Description of Artificial Sequence: Synthetic
                            oligonucleotide
source                  1..20
                        mol_type = other DNA
                        organism = synthetic construct
SEQUENCE: 151
agtgggtcag acgagcagga                                                  20

SEQ ID NO: 152          moltype = DNA  length = 20
FEATURE                 Location/Qualifiers
misc_feature            1..20
                        note = Description of Artificial Sequence: Synthetic
                            oligonucleotide
source                  1..20
                        mol_type = other DNA
                        organism = synthetic construct
SEQUENCE: 152
gctgtctccg ccgcccgcca                                                  20

SEQ ID NO: 153          moltype = DNA  length = 96
FEATURE                 Location/Qualifiers
misc_feature            1..96
                        note = Description of Artificial Sequence: Synthetic
                            oligonucleotide
source                  1..96
                        mol_type = other DNA
                        organism = synthetic construct
SEQUENCE: 153
gctattctcg cagctcacca gttttagagc tagaaatagc aagttaaaat aaggctagtc      60
cgttatcaac ttgaaaaagt ggcaccgagt cggtgc                                96

SEQ ID NO: 154          moltype = DNA  length = 184
FEATURE                 Location/Qualifiers
misc_feature            1..184
                        note = Description of Artificial Sequence: Synthetic
```

```
                        polynucleotide
misc_difference         148..149
                        note = CG, GC, AT, TA, GG, TT, GA, AG, CC, TC, CT, AA, TG,
                        GT, CA, or AC
source                  1..184
                        mol_type = other DNA
                        organism = synthetic construct
SEQUENCE: 154
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggccgga tgatcctgac gacggagnnc gccgtcgtcg acaagccggc ctgagctgcg  180
agaa                                                               184

SEQ ID NO: 155          moltype = DNA   length = 183
FEATURE                 Location/Qualifiers
misc_feature            1..183
                        note = Description of Artificial Sequence: Synthetic
                        polynucleotide
source                  1..183
                        mol_type = other DNA
                        organism = synthetic construct
SEQUENCE: 155
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catgccggat gatcctgacg acggagaccg ccgtcgtcga caagccggcc tgagctgcga  180
gaa                                                                183

SEQ ID NO: 156          moltype = DNA   length = 183
FEATURE                 Location/Qualifiers
misc_feature            1..183
                        note = Description of Artificial Sequence: Synthetic
                        polynucleotide
source                  1..183
                        mol_type = other DNA
                        organism = synthetic construct
SEQUENCE: 156
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catgccggat gatcctgacg acggagagcg ccgtcgtcga caagccggcc tgagctgcga  180
gaa                                                                183

SEQ ID NO: 157          moltype = DNA   length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 157
gcgtattgcc tggaggatgg gttttagagc tagaaatagc aagttaaaat aaggctagtc   60
cgttatcaac ttgaaaaagt ggcaccgagt cggtgcgaac cacgcggcga atgccggcgt  120
ccgccccgga tgatcctgac gacggagtcc gccgtcgtcg acaagccggc ctcctccagg  180
caatacgcg                                                          189

SEQ ID NO: 158          moltype = DNA   length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 158
gctgtctccg ccgcccgcca gttttagagc tagaaatagc aagttaaaat aaggctagtc   60
cgttatcaac ttgaaaaagt ggcaccgagt cggtgcgcgg cggcacgggg gtcgcagtcg  120
ccatgccgga tgatcctgac gacggagctc gccgtcgtcg acaagccggc ccgggcggcg  180
gagacagcg                                                          189

SEQ ID NO: 159          moltype = DNA   length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 159
gtcacctcca atgactaggg                                               20
```

```
SEQ ID NO: 160          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 160
gggcaaccac aaacccacga                                                  20

SEQ ID NO: 161          moltype = DNA  length = 194
FEATURE                 Location/Qualifiers
misc_feature            1..194
                        note = Description of Artificial Sequence: Synthetic
                         polynucleotide
source                  1..194
                        mol_type = other DNA
                        organism = synthetic construct
SEQUENCE: 161
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catggctatg ccggatgatc ctgacgacgg agtccgccgt cgtcgacaag ccggccctag      180
ctgagctgcg agaa                                                       194

SEQ ID NO: 162          moltype = DNA  length = 189
FEATURE                 Location/Qualifiers
misc_feature            1..189
                        note = Description of Artificial Sequence: Synthetic
                         polynucleotide
source                  1..189
                        mol_type = other DNA
                        organism = synthetic construct
SEQUENCE: 162
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catggtgccg gatgatcctg acgacggagt ccgccgtcgt cgacaagccg gccctatgag      180
ctgcgagaa                                                             189

SEQ ID NO: 163          moltype = DNA  length = 184
FEATURE                 Location/Qualifiers
misc_feature            1..184
                        note = Description of Artificial Sequence: Synthetic
                         polynucleotide
source                  1..184
                        mol_type = other DNA
                        organism = synthetic construct
SEQUENCE: 163
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catggccgga tgatcctgac gacggagtcc gccgtcgtc acaagccggc ctgagctgcg       180
agaa                                                                  184

SEQ ID NO: 164          moltype = DNA  length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 164
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catggggatg atcctgacga cggagtccgc cgtcgtcgac aagccgtgag ctgcgagaa       179

SEQ ID NO: 165          moltype = DNA  length = 174
FEATURE                 Location/Qualifiers
misc_feature            1..174
                        note = Description of Artificial Sequence: Synthetic
                         polynucleotide
source                  1..174
                        mol_type = other DNA
                        organism = synthetic construct
SEQUENCE: 165
gctattctcg cagctcacca gttttagagc tagaaatagc aagttaaaat aaggctagtc       60
cgttatcaac ttgaaaaagt ggcaccgagt cggtgcgacg agcgcggcga tatcatcatc      120
catggtgatc ctgacgacgg agtccgccgt cgtcgacaag ctgagctgcg agaa           174
```

```
SEQ ID NO: 166          moltype = DNA   length = 169
FEATURE                 Location/Qualifiers
misc_feature            1..169
                        note = Description of Artificial Sequence: Synthetic
                         polynucleotide
source                  1..169
                        mol_type = other DNA
                        organism = synthetic construct
SEQUENCE: 166
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggatcct gacgacggag tccgccgtcg tcgacatgag ctgcgagaa              169

SEQ ID NO: 167          moltype = DNA   length = 164
FEATURE                 Location/Qualifiers
misc_feature            1..164
                        note = Description of Artificial Sequence: Synthetic
                         polynucleotide
source                  1..164
                        mol_type = other DNA
                        organism = synthetic construct
SEQUENCE: 167
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggcctga cgacggagtc cgccgtcgtc gtgagctgcg agaa                   164

SEQ ID NO: 168          moltype = DNA   length = 159
FEATURE                 Location/Qualifiers
misc_feature            1..159
                        note = Description of Artificial Sequence: Synthetic
                         polynucleotide
source                  1..159
                        mol_type = other DNA
                        organism = synthetic construct
SEQUENCE: 168
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggtgacg acggagtccg ccgtcgtgag ctgcgagaa                         159

SEQ ID NO: 169          moltype = DNA   length = 154
FEATURE                 Location/Qualifiers
misc_feature            1..154
                        note = Description of Artificial Sequence: Synthetic
                         polynucleotide
source                  1..154
                        mol_type = other DNA
                        organism = synthetic construct
SEQUENCE: 169
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggacgac ggagtccgcc gtgagctgcg agaa                              154

SEQ ID NO: 170          moltype = DNA   length = 149
FEATURE                 Location/Qualifiers
misc_feature            1..149
                        note = Description of Artificial Sequence: Synthetic
                         polynucleotide
source                  1..149
                        mol_type = other DNA
                        organism = synthetic construct
SEQUENCE: 170
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catgggacgg agtccgtgag ctgcgagaa                                    149

SEQ ID NO: 171          moltype = DNA   length = 144
FEATURE                 Location/Qualifiers
misc_feature            1..144
                        note = Description of Artificial Sequence: Synthetic
                         polynucleotide
source                  1..144
                        mol_type = other DNA
                        organism = synthetic construct
SEQUENCE: 171
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggcggag ttgagctgcg agaa                                         144
```

-continued

```
SEQ ID NO: 172          moltype = DNA   length = 182
FEATURE                 Location/Qualifiers
misc_feature            1..182
                        note = Description of Artificial Sequence: Synthetic
                        polynucleotide
source                  1..182
                        mol_type = other DNA
                        organism = synthetic construct
SEQUENCE: 172
gaagccggcc ttgcacatgc gttttagagc tagaaatagc aagttaaaat aaggctagtc    60
cgttatcaac ttgaaaaagt ggaccgagt cggtgctcga cgacgagcgc ggcgatatca   120
tcatccatgg taccgttcgt atagcataca ttatacgaag ttattgagct gcgagaatag   180
cc                                                                  182

SEQ ID NO: 173          moltype = DNA   length = 177
FEATURE                 Location/Qualifiers
misc_feature            1..177
                        note = Description of Artificial Sequence: Synthetic
                        polynucleotide
source                  1..177
                        mol_type = other DNA
                        organism = synthetic construct
SEQUENCE: 173
gaagccggcc ttgcacatgc gttttagagc tagaaatagc aagttaaaat aaggctagtc    60
cgttatcaac ttgaaaaagt ggcaccgagt cggtgcgacg agcgcggcga tatcatcatc   120
catggtaccg ttcgtatagc atacattata cgaagttatt gagctgcgag aatagcc      177

SEQ ID NO: 174          moltype = DNA   length = 177
FEATURE                 Location/Qualifiers
misc_feature            1..177
                        note = Description of Artificial Sequence: Synthetic
                        polynucleotide
source                  1..177
                        mol_type = other DNA
                        organism = synthetic construct
SEQUENCE: 174
gaagccggcc ttgcacatgc gttttagagc tagaaatagc aagttaaaat aaggctagtc    60
cgttatcaac ttgaaaaagt ggcaccgagt cggtgctcga cgacgagcgc ggcgatatca   120
tcatccatgg taccgttcgt atagcataca ttatacgaag ttattgagct gcgagaa      177

SEQ ID NO: 175          moltype = DNA   length = 159
FEATURE                 Location/Qualifiers
misc_feature            1..159
                        note = Description of Artificial Sequence: Synthetic
                        polynucleotide
source                  1..159
                        mol_type = other DNA
                        organism = synthetic construct
SEQUENCE: 175
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaa                          159

SEQ ID NO: 176          moltype = DNA   length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 176
ccccacgatg gaggggaaga gttttagagc tagaaatagc aagttaaaat aaggctagtc    60
cgttatcaac ttgaaaaagt ggcaccgagt cggtgc                              96

SEQ ID NO: 177          moltype = DNA   length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 177
ccttctcctg gagccgcgac gttttagagc tagaaatagc aagttaaaat aaggctagtc    60
cgttatcaac ttgaaaaagt ggcaccgagt cggtgc                              96

SEQ ID NO: 178          moltype = DNA   length = 52
FEATURE                 Location/Qualifiers
```

```
misc_feature            1..52
                        note = Description of Artificial Sequence: Synthetic
                           oligonucleotide
source                  1..52
                        mol_type = other DNA
                        organism = synthetic construct
SEQUENCE: 178
gtggtttgtc tggtcaacca ccgcggtctc agtggtgtac ggtacaaacc ca            52

SEQ ID NO: 179          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 179
tgggtttgta ccgtacacca ctgagaccgc ggtggttgac cagacaaacc ac            52

SEQ ID NO: 180          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 180
gtggtttgtc tggtcaacca ccgcgcgctc agtggtgtac ggtacaaacc ca            52

SEQ ID NO: 181          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 181
tgggtttgta ccgtacacca ctgagcgcgc ggtggttgac cagacaaacc ac            52

SEQ ID NO: 182          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 182
gtggtttgtc tggtcaacca ccgcggcctc agtggtgtac ggtacaaacc ca            52

SEQ ID NO: 183          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 183
tgggtttgta ccgtacacca ctgaggccgc ggtggttgac cagacaaacc ac            52

SEQ ID NO: 184          moltype = DNA  length = 52
FEATURE                 Location/Qualifiers
misc_feature            1..52
                        note = Description of Artificial Sequence: Synthetic
                           oligonucleotide
source                  1..52
                        mol_type = other DNA
                        organism = synthetic construct
SEQUENCE: 184
gtggtttgtc tggtcaacca ccgcgatctc agtggtgtac ggtacaaacc ca            52

SEQ ID NO: 185          moltype = DNA  length = 52
FEATURE                 Location/Qualifiers
misc_feature            1..52
                        note = Description of Artificial Sequence: Synthetic
```

```
                        oligonucleotide
source                  1..52
                        mol_type = other DNA
                        organism = synthetic construct
SEQUENCE: 185
tgggtttgta ccgtacacca ctgagatcgc ggtggttgac cagacaaacc ac          52

SEQ ID NO: 186          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 186
gtggtttgtc tggtcaacca ccgcgtactc agtggtgtac ggtacaaacc ca          52

SEQ ID NO: 187          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 187
tgggtttgta ccgtacacca ctgagtacgc ggtggttgac cagacaaacc ac          52

SEQ ID NO: 188          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 188
gtggtttgtc tggtcaacca ccgcgggctc agtggtgtac ggtacaaacc ca          52

SEQ ID NO: 189          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 189
tgggtttgta ccgtacacca ctgagcccgc ggtggttgac cagacaaacc ac          52

SEQ ID NO: 190          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 190
gtggtttgtc tggtcaacca ccgcgttctc agtggtgtac ggtacaaacc ca          52

SEQ ID NO: 191          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 191
tgggtttgta ccgtacacca ctgagaacgc ggtggttgac cagacaaacc ac          52

SEQ ID NO: 192          moltype = DNA  length = 52
FEATURE                 Location/Qualifiers
misc_feature            1..52
                        note = Description of Artificial Sequence: Synthetic
                        oligonucleotide
source                  1..52
```

```
                        mol_type = other DNA
                        organism = synthetic construct
SEQUENCE: 192
gtggtttgtc tggtcaacca ccgcggactc agtggtgtac ggtacaaacc ca         52

SEQ ID NO: 193          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 193
tgggtttgta ccgtacacca ctgagtccgc ggtggttgac cagacaaacc ac         52

SEQ ID NO: 194          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 194
gtggtttgtc tggtcaacca ccgcgagctc agtggtgtac ggtacaaacc ca         52

SEQ ID NO: 195          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 195
tgggtttgta ccgtacacca ctgagctcgc ggtggttgac cagacaaacc ac         52

SEQ ID NO: 196          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 196
gtggtttgtc tggtcaacca ccgcgccctc agtggtgtac ggtacaaacc ca         52

SEQ ID NO: 197          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 197
tgggtttgta ccgtacacca ctgagggcgc ggtggttgac cagacaaacc ac         52

SEQ ID NO: 198          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 198
gtggtttgtc tggtcaacca ccgcgtcctc agtggtgtac ggtacaaacc ca         52

SEQ ID NO: 199          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
```

```
SEQUENCE: 199
tgggtttgta ccgtacacca ctgaggacgc ggtggttgac cagacaaacc ac            52

SEQ ID NO: 200           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 200
gtggtttgtc tggtcaacca ccgcgctctc agtggtgtac ggtacaaacc ca            52

SEQ ID NO: 201           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 201
tgggtttgta ccgtacacca ctgagagcgc ggtggttgac cagacaaacc ac            52

SEQ ID NO: 202           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 202
gtggtttgtc tggtcaacca ccgcgaactc agtggtgtac ggtacaaacc ca            52

SEQ ID NO: 203           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 203
tgggtttgta ccgtacacca ctgagttcgc ggtggttgac cagacaaacc ac            52

SEQ ID NO: 204           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 204
gtggtttgtc tggtcaacca ccgcgcactc agtggtgtac ggtacaaacc ca            52

SEQ ID NO: 205           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 205
tgggtttgta ccgtacacca ctgagtgcgc ggtggttgac cagacaaacc ac            52

SEQ ID NO: 206           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 206
gtggtttgtc tggtcaacca ccgcgacctc agtggtgtac ggtacaaacc ca            52
```

```
SEQ ID NO: 207         moltype = DNA  length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 207
tgggtttgta ccgtacacca ctgaggtcgc ggtggttgac cagacaaacc ac         52

SEQ ID NO: 208         moltype = DNA  length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 208
gtggtttgtc tggtcaacca ccgcgtgctc agtggtgtac ggtacaaacc ca         52

SEQ ID NO: 209         moltype = DNA  length = 52
FEATURE                Location/Qualifiers
misc_feature           1..52
                       note = Description of Artificial Sequence: Synthetic
                         oligonucleotide
source                 1..52
                       mol_type = other DNA
                       organism = synthetic construct
SEQUENCE: 209
tgggtttgta ccgtacacca ctgagcacgc ggtggttgac cagacaaacc ac         52

SEQ ID NO: 210         moltype = DNA  length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 210
ggccggcttg tcgacgacgg cggtctccgt cgtcaggatc atccgg              46

SEQ ID NO: 211         moltype = DNA  length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 211
ccggatgatc ctgacgacgg agaccgccgt cgtcgacaag ccggcc              46

SEQ ID NO: 212         moltype = DNA  length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 212
ggccggcttg tcgacgacgg cgaactccgt cgtcaggatc atccgg              46

SEQ ID NO: 213         moltype = DNA  length = 46
FEATURE                Location/Qualifiers
misc_feature           1..46
                       note = Description of Artificial Sequence: Synthetic
                         oligonucleotide
source                 1..46
                       mol_type = other DNA
                       organism = synthetic construct
SEQUENCE: 213
ccggatgatc ctgacgacgg agttcgccgt cgtcgacaag ccggcc              46

SEQ ID NO: 214         moltype = DNA  length = 46
```

```
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 214
ggccggcttg tcgacgacgg cggactccgt cgtcaggatc atccgg            46

SEQ ID NO: 215          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 215
ccggatgatc ctgacgacgg agtccgccgt cgtcgacaag ccggcc            46

SEQ ID NO: 216          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 216
ggccggcttg tcgacgacgg cgcactccgt cgtcaggatc atccgg            46

SEQ ID NO: 217          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 217
ccggatgatc ctgacgacgg agtgcgccgt cgtcgacaag ccggcc            46

SEQ ID NO: 218          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 218
ggccggcttg tcgacgacgg cgtactccgt cgtcaggatc atccgg            46

SEQ ID NO: 219          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 219
ccggatgatc ctgacgacgg agtacgccgt cgtcgacaag ccggcc            46

SEQ ID NO: 220          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 220
ggccggcttg tcgacgacgg cgagctccgt cgtcaggatc atccgg            46

SEQ ID NO: 221          moltype = DNA  length = 46
FEATURE                 Location/Qualifiers
misc_feature            1..46
```

```
                    note = Description of Artificial Sequence: Synthetic
                        oligonucleotide
source              1..46
                    mol_type = other DNA
                    organism = synthetic construct
SEQUENCE: 221
ccggatgatc ctgacgacgg agctcgccgt cgtcgacaag ccggcc              46

SEQ ID NO: 222      moltype = DNA   length = 46
FEATURE             Location/Qualifiers
misc_feature        1..46
                    note = Description of Artificial Sequence: Synthetic
                        oligonucleotide
source              1..46
                    mol_type = other DNA
                    organism = synthetic construct
SEQUENCE: 222
ggccggcttg tcgacgacgg cgggctccgt cgtcaggatc atccgg              46

SEQ ID NO: 223      moltype = DNA   length = 46
FEATURE             Location/Qualifiers
misc_feature        1..46
                    note = Description of Artificial Sequence: Synthetic
                        oligonucleotide
source              1..46
                    mol_type = other DNA
                    organism = synthetic construct
SEQUENCE: 223
ccggatgatc ctgacgacgg agcccgccgt cgtcgacaag ccggcc              46

SEQ ID NO: 224      moltype = DNA   length = 46
FEATURE             Location/Qualifiers
misc_feature        1..46
                    note = Description of Artificial Sequence: Synthetic
                        oligonucleotide
source              1..46
                    mol_type = other DNA
                    organism = synthetic construct
SEQUENCE: 224
ggccggcttg tcgacgacgg cgcgctccgt cgtcaggatc atccgg              46

SEQ ID NO: 225      moltype = DNA   length = 46
FEATURE             Location/Qualifiers
misc_feature        1..46
                    note = Description of Artificial Sequence: Synthetic
                        oligonucleotide
source              1..46
                    mol_type = other DNA
                    organism = synthetic construct
SEQUENCE: 225
ccggatgatc ctgacgacgg agcgcgccgt cgtcgacaag ccggcc              46

SEQ ID NO: 226      moltype = DNA   length = 46
FEATURE             Location/Qualifiers
misc_feature        1..46
                    note = Description of Artificial Sequence: Synthetic
                        oligonucleotide
source              1..46
                    mol_type = other DNA
                    organism = synthetic construct
SEQUENCE: 226
ggccggcttg tcgacgacgg cgtgctccgt cgtcaggatc atccgg              46

SEQ ID NO: 227      moltype = DNA   length = 46
FEATURE             Location/Qualifiers
misc_feature        1..46
                    note = Description of Artificial Sequence: Synthetic
                        oligonucleotide
source              1..46
                    mol_type = other DNA
                    organism = synthetic construct
SEQUENCE: 227
ccggatgatc ctgacgacgg agcacgccgt cgtcgacaag ccggcc              46

SEQ ID NO: 228      moltype = DNA   length = 46
FEATURE             Location/Qualifiers
misc_feature        1..46
                    note = Description of Artificial Sequence: Synthetic
                        oligonucleotide
```

```
source                  1..46
                        mol_type = other DNA
                        organism = synthetic construct
SEQUENCE: 228
ggccggcttg tcgacgacgg cgacctccgt cgtcaggatc atccgg            46

SEQ ID NO: 229          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 229
ccggatgatc ctgacgacgg aggtcgccgt cgtcgacaag ccggcc            46

SEQ ID NO: 230          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 230
ggccggcttg tcgacgacgg cggcctccgt cgtcaggatc atccgg            46

SEQ ID NO: 231          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 231
ccggatgatc ctgacgacgg aggccgccgt cgtcgacaag ccggcc            46

SEQ ID NO: 232          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 232
ggccggcttg tcgacgacgg cgccctccgt cgtcaggatc atccgg            46

SEQ ID NO: 233          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 233
ccggatgatc ctgacgacgg agggcgccgt cgtcgacaag ccggcc            46

SEQ ID NO: 234          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 234
ggccggcttg tcgacgacgg cgtcctccgt cgtcaggatc atccgg            46

SEQ ID NO: 235          moltype = DNA  length = 46
FEATURE                 Location/Qualifiers
misc_feature            1..46
                        note = Description of Artificial Sequence: Synthetic
                        oligonucleotide
source                  1..46
                        mol_type = other DNA
```

```
                        organism = synthetic construct
SEQUENCE: 235
ccggatgatc ctgacgacgg aggacgccgt cgtcgacaag ccggcc            46

SEQ ID NO: 236          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 236
ggccggcttg tcgacgacgg cgatctccgt cgtcaggatc atccgg            46

SEQ ID NO: 237          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 237
ccggatgatc ctgacgacgg agatcgccgt cgtcgacaag ccggcc            46

SEQ ID NO: 238          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 238
ggccggcttg tcgacgacgg cgctctccgt cgtcaggatc atccgg            46

SEQ ID NO: 239          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 239
ccggatgatc ctgacgacgg agagcgccgt cgtcgacaag ccggcc            46

SEQ ID NO: 240          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 240
ggccggcttg tcgacgacgg cgttctccgt cgtcaggatc atccgg            46

SEQ ID NO: 241          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 241
ccggatgatc ctgacgacgg agaacgccgt cgtcgacaag ccggcc            46

SEQ ID NO: 242          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 242
```

```
ggcttgtcga cgacggcggt ctccgtcgtc aggatcat                              38

SEQ ID NO: 243          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 243
atgatcctga cgacggagac cgccgtcgtc gacaagcc                              38

SEQ ID NO: 244          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 244
ggcttgtcga cgacggcgaa ctccgtcgtc aggatcat                              38

SEQ ID NO: 245          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 245
atgatcctga cgacggagtt cgccgtcgtc gacaagcc                              38

SEQ ID NO: 246          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 246
ggcttgtcga cgacggcgga ctccgtcgtc aggatcat                              38

SEQ ID NO: 247          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 247
atgatcctga cgacggagtc cgccgtcgtc gacaagcc                              38

SEQ ID NO: 248          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 248
ggcttgtcga cgacggcgca ctccgtcgtc aggatcat                              38

SEQ ID NO: 249          moltype = DNA  length = 38
FEATURE                 Location/Qualifiers
misc_feature            1..38
                        note = Description of Artificial Sequence: Synthetic
                          oligonucleotide
source                  1..38
                        mol_type = other DNA
                        organism = synthetic construct
SEQUENCE: 249
atgatcctga cgacggagtg cgccgtcgtc gacaagcc                              38
```

```
SEQ ID NO: 250          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 250
ggcttgtcga cgacggcgta ctccgtcgtc aggatcat                              38

SEQ ID NO: 251          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 251
atgatcctga cgacggagta cgccgtcgtc gacaagcc                              38

SEQ ID NO: 252          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 252
ggcttgtcga cgacggcgag ctccgtcgtc aggatcat                              38

SEQ ID NO: 253          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 253
atgatcctga cgacggagct cgccgtcgtc gacaagcc                              38

SEQ ID NO: 254          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 254
ggcttgtcga cgacggcggg ctccgtcgtc aggatcat                              38

SEQ ID NO: 255          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 255
atgatcctga cgacggagcc cgccgtcgtc gacaagcc                              38

SEQ ID NO: 256          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 256
ggcttgtcga cgacggcgcg ctccgtcgtc aggatcat                              38

SEQ ID NO: 257          moltype = DNA   length = 38
FEATURE                 Location/Qualifiers
```

```
misc_feature            1..38
                        note = Description of Artificial Sequence: Synthetic
                            oligonucleotide
source                  1..38
                        mol_type = other DNA
                        organism = synthetic construct
SEQUENCE: 257
atgatcctga cgacggagcg cgccgtcgtc gacaagcc                         38

SEQ ID NO: 258          moltype = DNA   length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 258
ggcttgtcga cgacggcgtg ctccgtcgtc aggatcat                         38

SEQ ID NO: 259          moltype = DNA   length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 259
atgatcctga cgacggagca cgccgtcgtc gacaagcc                         38

SEQ ID NO: 260          moltype = DNA   length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 260
ggcttgtcga cgacggcgac ctccgtcgtc aggatcat                         38

SEQ ID NO: 261          moltype = DNA   length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 261
atgatcctga cgacggaggt cgccgtcgtc gacaagcc                         38

SEQ ID NO: 262          moltype = DNA   length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 262
ggcttgtcga cgacggcggc ctccgtcgtc aggatcat                         38

SEQ ID NO: 263          moltype = DNA   length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 263
atgatcctga cgacggaggc cgccgtcgtc gacaagcc                         38

SEQ ID NO: 264          moltype = DNA   length = 38
FEATURE                 Location/Qualifiers
misc_feature            1..38
                        note = Description of Artificial Sequence: Synthetic
```

-continued

```
                        oligonucleotide
source                  1..38
                        mol_type = other DNA
                        organism = synthetic construct
SEQUENCE: 264
ggcttgtcga cgacggcgcc ctccgtcgtc aggatcat                              38

SEQ ID NO: 265          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 265
atgatcctga cgacggaggg cgccgtcgtc gacaagcc                              38

SEQ ID NO: 266          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 266
ggcttgtcga cgacggcgtc ctccgtcgtc aggatcat                              38

SEQ ID NO: 267          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 267
atgatcctga cgacggagga cgccgtcgtc gacaagcc                              38

SEQ ID NO: 268          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 268
ggcttgtcga cgacggcgat ctccgtcgtc aggatcat                              38

SEQ ID NO: 269          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 269
atgatcctga cgacggagat cgccgtcgtc gacaagcc                              38

SEQ ID NO: 270          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 270
ggcttgtcga cgacggcgct ctccgtcgtc aggatcat                              38

SEQ ID NO: 271          moltype = DNA   length = 38
FEATURE                 Location/Qualifiers
misc_feature            1..38
                        note = Description of Artificial Sequence: Synthetic
                        oligonucleotide
source                  1..38
```

```
                              mol_type = other DNA
                              organism = synthetic construct
SEQUENCE: 271
atgatcctga cgacggagag cgccgtcgtc gacaagcc                                  38

SEQ ID NO: 272           moltype = DNA   length = 38
FEATURE                  Location/Qualifiers
misc_feature             1..38
                         note = Description of Artificial Sequence: Synthetic
                              oligonucleotide
source                   1..38
                         mol_type = other DNA
                         organism = synthetic construct
SEQUENCE: 272
ggcttgtcga cgacggcgtt ctccgtcgtc aggatcat                                  38

SEQ ID NO: 273           moltype = DNA   length = 38
FEATURE                  Location/Qualifiers
misc_feature             1..38
                         note = Description of Artificial Sequence: Synthetic
                              oligonucleotide
source                   1..38
                         mol_type = other DNA
                         organism = synthetic construct
SEQUENCE: 273
atgatcctga cgacggagaa cgccgtcgtc gacaagcc                                  38

SEQ ID NO: 274           moltype = DNA   length = 34
FEATURE                  Location/Qualifiers
misc_feature             1..34
                         note = Description of Artificial Sequence: Synthetic
                              oligonucleotide
source                   1..34
                         mol_type = other DNA
                         organism = synthetic construct
SEQUENCE: 274
taccgttcgt ataatgtatg ctatacgaag ttat                                      34

SEQ ID NO: 275           moltype = DNA   length = 34
FEATURE                  Location/Qualifiers
misc_feature             1..34
                         note = Description of Artificial Sequence: Synthetic
                              oligonucleotide
source                   1..34
                         mol_type = other DNA
                         organism = synthetic construct
SEQUENCE: 275
ataacttcgt atagcataca ttatacgaac ggta                                      34

SEQ ID NO: 276           moltype = DNA   length = 34
FEATURE                  Location/Qualifiers
misc_feature             1..34
                         note = Description of Artificial Sequence: Synthetic
                              oligonucleotide
source                   1..34
                         mol_type = other DNA
                         organism = synthetic construct
SEQUENCE: 276
ataacttcgt ataatgtatg ctatacgaac ggta                                      34

SEQ ID NO: 277           moltype = DNA   length = 34
FEATURE                  Location/Qualifiers
misc_feature             1..34
                         note = Description of Artificial Sequence: Synthetic
                              oligonucleotide
source                   1..34
                         mol_type = other DNA
                         organism = synthetic construct
SEQUENCE: 277
taccgttcgt atagcataca ttatacgaag ttat                                      34

SEQ ID NO: 278           moltype = DNA   length = 27
FEATURE                  Location/Qualifiers
misc_feature             1..27
                         note = Description of Artificial Sequence: Synthetic
                              oligonucleotide
source                   1..27
                         mol_type = other DNA
                         organism = synthetic construct
```

```
SEQUENCE: 278
tttaccttga ttgagatgtt aattgtg                                            27

SEQ ID NO: 279          moltype = DNA   length = 27
FEATURE                 Location/Qualifiers
misc_feature            1..27
                        note = Description of Artificial Sequence: Synthetic
                        oligonucleotide
source                  1..27
                        mol_type = other DNA
                        organism = synthetic construct
SEQUENCE: 279
cacaattaac atctcaatca aggtaaa                                            27

SEQ ID NO: 280          moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
SEQUENCE: 280
gcgagttttt atttcgttta tttcaattaa ggtaactaaa aaactccttt                   50

SEQ ID NO: 281          moltype = DNA   length = 50
FEATURE                 Location/Qualifiers
misc_feature            1..50
                        note = Description of Artificial Sequence: Synthetic
                        oligonucleotide
source                  1..50
                        mol_type = other DNA
                        organism = synthetic construct
SEQUENCE: 281
aaaggagttt tttagttacc ttaattgaaa taaacgaaat aaaaactcgc                   50

SEQ ID NO: 282          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 282
ctggatcatc tggatcactt tcgtcaaaaa cctg                                    34

SEQ ID NO: 283          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 283
caggttttg acgaaagtga tccagatgat ccag                                     34

SEQ ID NO: 284          moltype = DNA   length = 57
FEATURE                 Location/Qualifiers
misc_feature            1..57
                        note = Description of Artificial Sequence: Synthetic
                        oligonucleotide
source                  1..57
                        mol_type = other DNA
                        organism = synthetic construct
SEQUENCE: 284
ttcgggtgct gggttgttgt ctctggacag tgatccatgg gaaactactc agcacca          57

SEQ ID NO: 285          moltype = DNA   length = 57
FEATURE                 Location/Qualifiers
misc_feature            1..57
                        note = Description of Artificial Sequence: Synthetic
                        oligonucleotide
source                  1..57
                        mol_type = other DNA
                        organism = synthetic construct
SEQUENCE: 285
tggtgctgag tagtttccca tggatcactg tccagagaca acaacccagc acccgaa          57
```

| | |
|---|---|
| SEQ ID NO: 286 | moltype = DNA   length = 24 |
| FEATURE | Location/Qualifiers |
| misc_feature | 1..24 |
| | note = Description of Artificial Sequence: Synthetic oligonucleotide |
| source | 1..24 |
| | mol_type = other DNA |
| | organism = synthetic construct |

SEQUENCE: 286
aaaagtgtgg gctgcaggat ctga                                          24

| | |
|---|---|
| SEQ ID NO: 287 | moltype = DNA   length = 22 |
| FEATURE | Location/Qualifiers |
| misc_feature | 1..22 |
| | note = Description of Artificial Sequence: Synthetic oligonucleotide |
| source | 1..22 |
| | mol_type = other DNA |
| | organism = synthetic construct |

SEQUENCE: 287
ggagctggca gctgtcaatg cc                                            22

| | |
|---|---|
| SEQ ID NO: 288 | moltype = DNA   length = 21 |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |

SEQUENCE: 288
agtcaatgcc gctctcgtgg a                                             21

| | |
|---|---|
| SEQ ID NO: 289 | moltype = DNA   length = 21 |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |

SEQUENCE: 289
cagcgggctc agctgatagc a                                             21

| | |
|---|---|
| SEQ ID NO: 290 | moltype = DNA   length = 21 |
| FEATURE | Location/Qualifiers |
| misc_feature | 1..21 |
| | note = Description of Artificial Sequence: Synthetic oligonucleotide |
| source | 1..21 |
| | mol_type = other DNA |
| | organism = synthetic construct |

SEQUENCE: 290
cggatggcta accaagcggc c                                             21

| | |
|---|---|
| SEQ ID NO: 291 | moltype = DNA   length = 17 |
| FEATURE | Location/Qualifiers |
| misc_feature | 1..17 |
| | note = Description of Artificial Sequence: Synthetic primer |
| source | 1..17 |
| | mol_type = other DNA |
| | organism = synthetic construct |

SEQUENCE: 291
cccggcttcc tttgtcc                                                  17

| | |
|---|---|
| SEQ ID NO: 292 | moltype = DNA   length = 17 |
| FEATURE | Location/Qualifiers |
| misc_feature | 1..17 |
| | note = Description of Artificial Sequence: Synthetic primer |
| source | 1..17 |
| | mol_type = other DNA |
| | organism = synthetic construct |

SEQUENCE: 292
gaactccacg ccgttca                                                  17

| | |
|---|---|
| SEQ ID NO: 293 | moltype = DNA   length = 17 |
| FEATURE | Location/Qualifiers |
| misc_feature | 1..17 |

```
                    note = Description of Artificial Sequence: Synthetic primer
source              1..17
                    mol_type = other DNA
                    organism = synthetic construct
SEQUENCE: 293
cccggcttcc tttgtcc                                                        17

SEQ ID NO: 294      moltype = DNA  length = 22
FEATURE             Location/Qualifiers
misc_feature        1..22
                    note = Description of Artificial Sequence: Synthetic primer
source              1..22
                    mol_type = other DNA
                    organism = synthetic construct
SEQUENCE: 294
aaccacaact agaatgcagt ga                                                  22

SEQ ID NO: 295      moltype = DNA  length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 295
cccggcttcc tttgtcc                                                        17

SEQ ID NO: 296      moltype = DNA  length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 296
gaactccacg ccgttca                                                        17

SEQ ID NO: 297      moltype = DNA  length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 297
cccggcttcc tttgtcc                                                        17

SEQ ID NO: 298      moltype = DNA  length = 22
FEATURE             Location/Qualifiers
misc_feature        1..22
                    note = Description of Artificial Sequence: Synthetic primer
source              1..22
                    mol_type = other DNA
                    organism = synthetic construct
SEQUENCE: 298
aaccacaact agaatgcagt ga                                                  22

SEQ ID NO: 299      moltype = DNA  length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 299
cccggcttcc tttgtcc                                                        17

SEQ ID NO: 300      moltype = DNA  length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 300
gaactccacg ccgttca                                                        17

SEQ ID NO: 301      moltype = DNA  length = 21
FEATURE             Location/Qualifiers
```

```
misc_feature              1..21
                          note = Description of Artificial Sequence: Synthetic primer
source                    1..21
                          mol_type = other DNA
                          organism = synthetic construct
SEQUENCE: 301
tccttatcac ggtcccgctc g                                                 21

SEQ ID NO: 302            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 302
gaactccacg ccgttca                                                      17

SEQ ID NO: 303            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 303
cgtcgacaac ggtagtg                                                      17

SEQ ID NO: 304            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 304
gaactccacg ccgttca                                                      17

SEQ ID NO: 305            moltype = DNA  length = 18
FEATURE                   Location/Qualifiers
misc_feature              1..18
                          note = Description of Artificial Sequence: Synthetic primer
source                    1..18
                          mol_type = other DNA
                          organism = synthetic construct
SEQUENCE: 305
tcgcgtgatt ctcggaac                                                     18

SEQ ID NO: 306            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 306
gaactccacg ccgttca                                                      17

SEQ ID NO: 307            moltype = DNA  length = 20
FEATURE                   Location/Qualifiers
misc_feature              1..20
                          note = Description of Artificial Sequence: Synthetic primer
source                    1..20
                          mol_type = other DNA
                          organism = synthetic construct
SEQUENCE: 307
gggcggtaag tggttagttt                                                   20

SEQ ID NO: 308            moltype = DNA  length = 17
FEATURE                   Location/Qualifiers
misc_feature              1..17
                          note = Description of Artificial Sequence: Synthetic primer
source                    1..17
                          mol_type = other DNA
                          organism = synthetic construct
SEQUENCE: 308
gaactccacg ccgttca                                                      17

SEQ ID NO: 309            moltype = DNA  length = 17
```

```
                            -continued

FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 309
aagaggcgga gccagta                                                    17

SEQ ID NO: 310          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 310
gaactccacg ccgttca                                                    17

SEQ ID NO: 311          moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 311
ctcccttctc ccggtgccc                                                  19

SEQ ID NO: 312          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 312
gaactccacg ccgttca                                                    17

SEQ ID NO: 313          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 313
cccggcttcc tttgtcc                                                    17

SEQ ID NO: 314          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 314
gaactccacg ccgttca                                                    17

SEQ ID NO: 315          moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 315
gggcggtaag tggttagttt                                                 20

SEQ ID NO: 316          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 316
gaactccacg ccgttca                                                    17
```

| | | |
|---|---|---|
| SEQ ID NO: 317<br>FEATURE<br>misc_feature<br><br>source | moltype = DNA length = 17<br>Location/Qualifiers<br>1..17<br>note = Description of Artificial Sequence: Synthetic primer<br>1..17<br>mol_type = other DNA<br>organism = synthetic construct | |
| SEQUENCE: 317<br>cgtcgacaac ggtagtg | | 17 |
| SEQ ID NO: 318<br>FEATURE<br>misc_feature<br><br>source | moltype = DNA length = 17<br>Location/Qualifiers<br>1..17<br>note = Description of Artificial Sequence: Synthetic primer<br>1..17<br>mol_type = other DNA<br>organism = synthetic construct | |
| SEQUENCE: 318<br>gaactccacg ccgttca | | 17 |
| SEQ ID NO: 319<br>FEATURE<br>misc_feature<br><br>source | moltype = DNA length = 17<br>Location/Qualifiers<br>1..17<br>note = Description of Artificial Sequence: Synthetic primer<br>1..17<br>mol_type = other DNA<br>organism = synthetic construct | |
| SEQUENCE: 319<br>aagaggcgga gccagta | | 17 |
| SEQ ID NO: 320<br>FEATURE<br>misc_feature<br><br>source | moltype = DNA length = 17<br>Location/Qualifiers<br>1..17<br>note = Description of Artificial Sequence: Synthetic primer<br>1..17<br>mol_type = other DNA<br>organism = synthetic construct | |
| SEQUENCE: 320<br>gaactccacg ccgttca | | 17 |
| SEQ ID NO: 321<br>FEATURE<br>misc_feature<br><br>source | moltype = DNA length = 19<br>Location/Qualifiers<br>1..19<br>note = Description of Artificial Sequence: Synthetic primer<br>1..19<br>mol_type = other DNA<br>organism = synthetic construct | |
| SEQUENCE: 321<br>ctcccttctc ccggtgccc | | 19 |
| SEQ ID NO: 322<br>FEATURE<br>misc_feature<br><br>source | moltype = DNA length = 17<br>Location/Qualifiers<br>1..17<br>note = Description of Artificial Sequence: Synthetic primer<br>1..17<br>mol_type = other DNA<br>organism = synthetic construct | |
| SEQUENCE: 322<br>gaactccacg ccgttca | | 17 |
| SEQ ID NO: 323<br>FEATURE<br>misc_feature<br><br>source | moltype = DNA length = 21<br>Location/Qualifiers<br>1..21<br>note = Description of Artificial Sequence: Synthetic primer<br>1..21<br>mol_type = other DNA<br>organism = synthetic construct | |
| SEQUENCE: 323<br>tccttatcac ggtcccgctc g | | 21 |
| SEQ ID NO: 324<br>FEATURE<br>misc_feature<br><br>source | moltype = DNA length = 17<br>Location/Qualifiers<br>1..17<br>note = Description of Artificial Sequence: Synthetic primer<br>1..17<br>mol_type = other DNA<br>organism = synthetic construct | |
| SEQUENCE: 324<br>gaactccacg ccgttca | | 17 |

```
SEQ ID NO: 325          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 325
cccggcttcc tttgtcc                                                          17

SEQ ID NO: 326          moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 326
ggcctgccag caggagga                                                         18

SEQ ID NO: 327          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 327
cccggcttcc tttgtcc                                                          17

SEQ ID NO: 328          moltype = DNA   length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 328
ggtgtgcagt cacattggta aagcc                                                 25

SEQ ID NO: 329          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 329
cccggcttcc tttgtcc                                                          17

SEQ ID NO: 330          moltype = DNA   length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 330
gatgggtcta gtccagctaa ag                                                    22

SEQ ID NO: 331          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 331
cccggcttcc tttgtcc                                                          17

SEQ ID NO: 332          moltype = DNA   length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 332
```

```
gagagacaag gctgcaca                                                 18

SEQ ID NO: 333          moltype = DNA   length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 333
ccaggtgaga gtcagggtag tgttca                                        26

SEQ ID NO: 334          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 334
gaactccacg ccgttca                                                  17

SEQ ID NO: 335          moltype = DNA   length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 335
agggaccttt gcctgtgtga gtc                                           23

SEQ ID NO: 336          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 336
gaactccacg ccgttca                                                  17

SEQ ID NO: 337          moltype = DNA   length = 21
FEATURE                 Location/Qualifiers
misc_feature            1..21
                        note = Description of Artificial Sequence: Synthetic primer
source                  1..21
                        mol_type = other DNA
                        organism = synthetic construct
SEQUENCE: 337
tcagctctgt gctgaggcga a                                             21

SEQ ID NO: 338          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 338
gaactccacg ccgttca                                                  17

SEQ ID NO: 339          moltype = DNA   length = 32
FEATURE                 Location/Qualifiers
misc_feature            1..32
                        note = Description of Artificial Sequence: Synthetic primer
source                  1..32
                        mol_type = other DNA
                        organism = synthetic construct
SEQUENCE: 339
aagccatctc ccagaatatc tgcttagaaa tg                                 32

SEQ ID NO: 340          moltype = DNA   length = 17
FEATURE                 Location/Qualifiers
misc_feature            1..17
                        note = Description of Artificial Sequence: Synthetic primer
source                  1..17
                        mol_type = other DNA
                        organism = synthetic construct
```

```
SEQUENCE: 340
gaactccacg ccgttca                                                  17

SEQ ID NO: 341         moltype = DNA   length = 25
FEATURE                Location/Qualifiers
misc_feature           1..25
                       note = Description of Artificial Sequence: Synthetic primer
source                 1..25
                       mol_type = other DNA
                       organism = synthetic construct
SEQUENCE: 341
gagaggagca acagtgagca tgatg                                         25

SEQ ID NO: 342         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 342
gaactccacg ccgttca                                                  17

SEQ ID NO: 343         moltype = DNA   length = 32
FEATURE                Location/Qualifiers
misc_feature           1..32
                       note = Description of Artificial Sequence: Synthetic primer
source                 1..32
                       mol_type = other DNA
                       organism = synthetic construct
SEQUENCE: 343
aagccatctc ccagaatatc tgcttagaaa tg                                 32

SEQ ID NO: 344         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 344
gaactccacg ccgttca                                                  17

SEQ ID NO: 345         moltype = DNA   length = 25
FEATURE                Location/Qualifiers
misc_feature           1..25
                       note = Description of Artificial Sequence: Synthetic primer
source                 1..25
                       mol_type = other DNA
                       organism = synthetic construct
SEQUENCE: 345
gagaggagca acagtgagca tgatg                                         25

SEQ ID NO: 346         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 346
gaactccacg ccgttca                                                  17

SEQ ID NO: 347         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 347
cccggcttcc tttgtcc                                                  17

SEQ ID NO: 348         moltype = DNA   length = 22
FEATURE                Location/Qualifiers
misc_feature           1..22
                       note = Description of Artificial Sequence: Synthetic primer
source                 1..22
                       mol_type = other DNA
```

```
                        organism = synthetic construct
SEQUENCE: 348
ggctatgaac taatgacccc gt                                              22

SEQ ID NO: 349          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 349
cccggcttcc tttgtcc                                                    17

SEQ ID NO: 350          moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 350
ggcctgccag caggagga                                                   18

SEQ ID NO: 351          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 351
cccggcttcc tttgtcc                                                    17

SEQ ID NO: 352          moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 352
ggtgtgcagt cacattggta aagcc                                           25

SEQ ID NO: 353          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 353
acactctttc cctacacgac gctcttccga tctccgacct cggctcacag cg             52

SEQ ID NO: 354          moltype = DNA  length = 53
FEATURE                 Location/Qualifiers
misc_feature            1..53
                        note = Description of Artificial Sequence: Synthetic
                          oligonucleotide
source                  1..53
                        mol_type = other DNA
                        organism = synthetic construct
SEQUENCE: 354
acactctttc cctacacgac gctcttccga tctaccgacc tcggctcaca gcg            53

SEQ ID NO: 355          moltype = DNA  length = 54
FEATURE                 Location/Qualifiers
misc_feature            1..54
                        note = Description of Artificial Sequence: Synthetic
                          oligonucleotide
source                  1..54
                        mol_type = other DNA
                        organism = synthetic construct
SEQUENCE: 355
acactctttc cctacacgac gctcttccga tctgaccgac ctcggctcac agcg           54

SEQ ID NO: 356          moltype = DNA  length = 55
FEATURE                 Location/Qualifiers
```

```
misc_feature              1..55
                          note = Description of Artificial Sequence: Synthetic
                             oligonucleotide
source                    1..55
                          mol_type = other DNA
                          organism = synthetic construct
SEQUENCE: 356
acactctttc cctacacgac gctcttccga tcttgaccga cctcggctca cagcg          55

SEQ ID NO: 357            moltype = DNA  length = 56
FEATURE                   Location/Qualifiers
misc_feature              1..56
                          note = Description of Artificial Sequence: Synthetic
                             oligonucleotide
source                    1..56
                          mol_type = other DNA
                          organism = synthetic construct
SEQUENCE: 357
acactctttc cctacacgac gctcttccga tctctgaccg acctcggctc acagcg         56

SEQ ID NO: 358            moltype = DNA  length = 57
FEATURE                   Location/Qualifiers
misc_feature              1..57
                          note = Description of Artificial Sequence: Synthetic
                             oligonucleotide
source                    1..57
                          mol_type = other DNA
                          organism = synthetic construct
SEQUENCE: 358
acactctttc cctacacgac gctcttccga tctactgacc gacctcggct cacagcg        57

SEQ ID NO: 359            moltype = DNA  length = 58
FEATURE                   Location/Qualifiers
misc_feature              1..58
                          note = Description of Artificial Sequence: Synthetic
                             oligonucleotide
source                    1..58
                          mol_type = other DNA
                          organism = synthetic construct
SEQUENCE: 359
acactctttc cctacacgac gctcttccga tcttactgac cgacctcggc tcacagcg       58

SEQ ID NO: 360            moltype = DNA  length = 59
FEATURE                   Location/Qualifiers
misc_feature              1..59
                          note = Description of Artificial Sequence: Synthetic
                             oligonucleotide
source                    1..59
                          mol_type = other DNA
                          organism = synthetic construct
SEQUENCE: 360
acactctttc cctacacgac gctcttccga tctgtactga ccgacctcgg ctcacagcg      59

SEQ ID NO: 361            moltype = DNA  length = 51
FEATURE                   Location/Qualifiers
misc_feature              1..51
                          note = Description of Artificial Sequence: Synthetic
                             oligonucleotide
source                    1..51
                          mol_type = other DNA
                          organism = synthetic construct
SEQUENCE: 361
gtgactggag ttcagacgtg tgctcttccg atctccaccc agccagctcc c              51

SEQ ID NO: 362            moltype = DNA  length = 51
FEATURE                   Location/Qualifiers
misc_feature              1..51
                          note = Description of Artificial Sequence: Synthetic
                             oligonucleotide
source                    1..51
                          mol_type = other DNA
                          organism = synthetic construct
SEQUENCE: 362
acactctttc cctacacgac gctcttccga tctccggtgg cgcattgcca c              51

SEQ ID NO: 363            moltype = DNA  length = 52
FEATURE                   Location/Qualifiers
misc_feature              1..52
                          note = Description of Artificial Sequence: Synthetic
```

```
                              oligonucleotide
source                        1..52
                              mol_type = other DNA
                              organism = synthetic construct
SEQUENCE: 363
acactctttc cctacacgac gctcttccga tctaccggtg gcgcattgcc ac           52

SEQ ID NO: 364                moltype = DNA  length = 53
FEATURE                       Location/Qualifiers
misc_feature                  1..53
                              note = Description of Artificial Sequence: Synthetic
                              oligonucleotide
source                        1..53
                              mol_type = other DNA
                              organism = synthetic construct
SEQUENCE: 364
acactctttc cctacacgac gctcttccga tctgaccggt ggcgcattgc cac          53

SEQ ID NO: 365                moltype = DNA  length = 54
FEATURE                       Location/Qualifiers
misc_feature                  1..54
                              note = Description of Artificial Sequence: Synthetic
                              oligonucleotide
source                        1..54
                              mol_type = other DNA
                              organism = synthetic construct
SEQUENCE: 365
acactctttc cctacacgac gctcttccga tcttgaccgg tggcgcattg ccac         54

SEQ ID NO: 366                moltype = DNA  length = 55
FEATURE                       Location/Qualifiers
misc_feature                  1..55
                              note = Description of Artificial Sequence: Synthetic
                              oligonucleotide
source                        1..55
                              mol_type = other DNA
                              organism = synthetic construct
SEQUENCE: 366
acactctttc cctacacgac gctcttccga tctctgaccg gtggcgcatt gccac        55

SEQ ID NO: 367                moltype = DNA  length = 56
FEATURE                       Location/Qualifiers
misc_feature                  1..56
                              note = Description of Artificial Sequence: Synthetic
                              oligonucleotide
source                        1..56
                              mol_type = other DNA
                              organism = synthetic construct
SEQUENCE: 367
acactctttc cctacacgac gctcttccga tctactgacc ggtggcgcat tgccac       56

SEQ ID NO: 368                moltype = DNA  length = 57
FEATURE                       Location/Qualifiers
misc_feature                  1..57
                              note = Description of Artificial Sequence: Synthetic
                              oligonucleotide
source                        1..57
                              mol_type = other DNA
                              organism = synthetic construct
SEQUENCE: 368
acactctttc cctacacgac gctcttccga tcttactgac cggtggcgca ttgccac      57

SEQ ID NO: 369                moltype = DNA  length = 58
FEATURE                       Location/Qualifiers
misc_feature                  1..58
                              note = Description of Artificial Sequence: Synthetic
                              oligonucleotide
source                        1..58
                              mol_type = other DNA
                              organism = synthetic construct
SEQUENCE: 369
acactctttc cctacacgac gctcttccga tctgtactga ccggtggcgc attgccac     58

SEQ ID NO: 370                moltype = DNA  length = 54
FEATURE                       Location/Qualifiers
misc_feature                  1..54
                              note = Description of Artificial Sequence: Synthetic
                              oligonucleotide
source                        1..54
```

```
                        mol_type = other DNA
                        organism = synthetic construct
SEQUENCE: 370
gtgactggag ttcagacgtg tgctcttccg atctcagagt ccagcttggg ccca        54

SEQ ID NO: 371          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 371
gatattttcc cagctcacca                                              20

SEQ ID NO: 372          moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 372
tctattctcc cagctcccca                                              20

SEQ ID NO: 373          moltype = DNA  length = 40
FEATURE                 Location/Qualifiers
misc_feature            1..40
                        note = Description of Artificial Sequence: Synthetic
                         oligonucleotide
source                  1..40
                        mol_type = other DNA
                        organism = synthetic construct
SEQUENCE: 373
agcggcttct gtctctgtga gtgagctggc ggtctccgtc                        40

SEQ ID NO: 374          moltype = DNA  length = 43
FEATURE                 Location/Qualifiers
misc_feature            1..43
                        note = Description of Artificial Sequence: Synthetic
                         oligonucleotide
source                  1..43
                        mol_type = other DNA
                        organism = synthetic construct
SEQUENCE: 374
gactagccca cgctccggtt ctgagccgcg acggcggtct ccg                    43

SEQ ID NO: 375          moltype = DNA  length = 41
FEATURE                 Location/Qualifiers
misc_feature            1..41
                        note = Description of Artificial Sequence: Synthetic
                         oligonucleotide
source                  1..41
                        mol_type = other DNA
                        organism = synthetic construct
SEQUENCE: 375
cccagggtcc catgcgctcc ccggccctga cggcggtctc c                      41

SEQ ID NO: 376          moltype = AA  length = 2560
FEATURE                 Location/Qualifiers
REGION                  1..2560
                        note = Description of Artificial Sequence: Synthetic
                         polypeptide
source                  1..2560
                        mol_type = protein
                        organism = synthetic construct
SEQUENCE: 376
MKRTADGSEF ESPKKKRKVD KKYSIGLDIG TNSVGWAVIT DEYKVPSKKF KVLGNTDRHS   60
IKKNLIGALL FDSGETAEAT RLKRTARRRY TRRKNRICYL QEIFSNEMAK VDDSFFHRLE  120
ESFLVEEDKK HERHPIFGNI VDEVAYHEKY PTIYHLRKKL VDSTDKADLR LIYLALAHMI  180
KFRGHFLIEG DLNPDNSDVD KLFIQLVQTY NQLFEENPIN ASGVDAKAIL SARLSKSRRL  240
ENLIAQLPGE KKNGLFGNLI ALSLGLTPNF KSNFDLAEDA KLQLSKDTYD DDLDNLLAQI  300
GDQYADLFLA AKNLSDAILL SDILRVNTEI TKAPLSASMI KRYDEHHQDL TLLKALVRQQ  360
LPEKYKEIFF DQSKNGYAGY IDGGASQEEF YKFIKPILEK MDGTEELLVK LNREDLLRKQ  420
RTFDNGSIPH QIHLGELHAI LRRQEDFYPF LKDNREKIEK ILTFRIPYYV GPLARGNSRF  480
AWMTRKSEET ITPWNFEEVV DKGASAQSFI ERMTNFDKNL PNEKVLPKHS LLYEYFTVYN  540
ELTKVKYVTE GMRKPAFLSG EQKKAIVDLL FKTNRKVTVK QLKEDYFKKI ECFDSVEISG  600
```

```
VEDRFNASLG TYHDLLKIIK DKDFLDNEEN EDILEDIVLT LTLFEDREMI EERLKTYAHL    660
FDDKVMKQLK RRRYTGWGRL SRKLINGIRD KQSGKTILDF LKSDGFANRN FMQLIHDDSL    720
TFKEDIQKAQ VSGQGDSLHE HIANLAGSPA IKKGILQTVK VVDELVKVMG RHKPENIVIE    780
MARENQTTQK GQKNSRERMK RIEEGIKELG SQILKEHPVE NTQLQNEKLY LYYLQNGRDM    840
YVDQELDINR LSDYDVDAIV PQSFLKDDSI DNKVLTRSDK NRGKSDNVPS EEVVKKMKNY    900
WRQLLNAKLI TQRKFDNLTK AERGGLSELD KAGFIKRQLV ETRQITKHVA QILDSRMNTK    960
YDENDKLIRE VKVITLKSKL VSDFRKDFQF YKVREINNYH HAHDAYLNAV VGTALIKKYP   1020
KLESEFVYGD YKVYDVRKMI AKSEQEIGKA TAKYFFYSNI MNFFKTEITL ANGEIRKRPL   1080
IETNGETGEI VWDKGRDFAT VRKVLSMPQV NIVKKTEVQT GGFSKESILP KRNSDKLIAR   1140
KKDWDPKKYG GFDSPTVAYS VLVVAKVEKG KSKKLKSVKE LLGITIMERS SFEKNPIDFL   1200
EAKGYKEVKK DLIIKLPKYS LFELENGRKR MLASAGELQK GNELALPSKY VNFLYLASHY   1260
EKLKGSPEDN EQKQLFVEQH KHYLDEIIEQ ISEFSKRVIL ADANLDKVLS AYNKHRDKPI   1320
REQAENIIHL FTLTNLGAPA AFKYFDTTID RKRYTSTKEV LDATLIHQSI TGLYETRIDL   1380
SQLGGDSGGS SGGSSGSETP GTSESATPES SGSETPGTSE SATPESSGSE TPGTSESATP   1440
ESSGGSSGGS STLNIEDEYR LHETSKEPDV SLGSTWLSDF PQAWAETGGM GLAVRQAPLI   1500
IPLKATSTPV SIKQYPMSQE ARLGIKPHIQ RLLDQGILVP CQSPWNTPLL PVKKPGTNDY   1560
RPVQDLREVN KRVEDIHPTV PNPYNLLSGP PPSHQWYTVL DLKDAFFCLR LHPTSQPLFA   1620
FEWRDPEMGI SGQLTWTRLP QGFKNSPTLF NEALHRDLAD FRIQHPDLIL LQYVDDLLLA   1680
ATSELDCQQG TRALLQTLGN LGYRASAKKA QICQKQVKYL GYLLKEGQRW LTEARKETVM   1740
GQPTPKTPRQ LREFLGKAGF CRLFIPGFAE MAAPLYPLTK PGTLFNWGPD QQKAYQEIKQ   1800
ALLTAPALGL PDLTKPFELF VDEKQGYAKG VLTQKLGPWR RPVAYLSKKL DPVAAGWPPC   1860
LRMVAAIAVL TKDAGKLTMG QPLVILAPHA VEALVKQPPD RWLSNARMTH YQALLLDTDR   1920
VQFGPVVALN PATLLPLPEE GLQHNCLDGT GGGGVTVKFK YKGEELEVDI SKIKKVWRVG   1980
KMISFTYDDN GKTGRGAVSE KDAPKELLQM LEKSGKKSGG SKRTADGSEF EPKKKRKVGG   2040
GGSPKKKRKV YPYDVPDYAG SRALVVIRLS RVTDATTSPE RQLESCQQLC AQRGWDVVGV   2100
AEDLDVSGAV DPFDRKRRPN LARWLAFEEQ PFDVIVAYRV DRLTRSIRHL QQLVHWAEDH   2160
KKLVVSATEA HFDTTTPFAA VVIALMGTVA QMELEAIKER NRSAAHFNIR AGKYRGSLPP   2220
WGYLPTRVDG EWRLVPDPVQ RERILEVYHR VVDNHEPLHL VAHDLNRRGV LSPKDYFAQL   2280
QGREPQGREW SATALKRSMI SEAMLGYATL NGKTVRDDDG APLVRAEPIL TREQLEALRA   2340
ELVKTSRAKP AVSTPSLLLR VLFCAVCGEP AYKFAGGGRK HPRYRCRSMG FPKHCGNGTV   2400
AMAEWDAFCE EQVLDLLGDA ERLEKVWVAG SDSAVELAEV NAELVDLTSL IGSPAYRAGS   2460
PQREALDARI AALAARQEEL EGLEARPSGW EWRETGQRFG DWWREQDTAA KNTWLRSMNV   2520
RLTFDVRGGL TRTIDFGDLQ EYEQHLRLGS VVERLHTGMS                        2560

SEQ ID NO: 377         moltype = DNA   length = 7680
FEATURE                Location/Qualifiers
misc_feature           1..7680
                       note = Description of Artificial Sequence: Synthetic
                        polynucleotide
source                 1..7680
                       mol_type = other DNA
                       organism = synthetic construct
SEQUENCE: 377
atgaaacgga cagccgacgg aagcgagttc gagtcaccaa agaagaagcg gaaagtcgac     60
aagaagtaca gcatcggcct ggacatcggc accaactctg tgggctgggc cgtgatcacc    120
gacgagtaca aggtgcccag caagaaattc aaggtgctgg gcaacaccga ccggcacagc    180
atcaagagaa acctgatcgg agcccctgct ttcgacagcg gcgaggccat cggcctgaag    240
cggctgaaga gaaccgccag aaagaagtac accagacgga gaaccggat ctgctatctg     300
caagagatct tcagcaacga gatggccaag gtggacgaca gcttcttcca cagactggaa    360
gagtccttcc tggtggaaga ggataagaag cacgagcggc accccatctt cggcaacatc    420
gtggcagagg tggcctacca cgagaagtac cccaccatct accacctgag aaagaaactg    480
gtggacagca ccgacaaggc cgacctgcgc ctgatctatc tggccctggc ccacatgatc    540
aagttccggg gccacttcct gatcgagggc gacctgaacc ccgacaacag cgacgtggac    600
aagctgttca tccagctggt gcagacctac aaccagctgt tcgaggaaaa ccccatcaac    660
gccagcggcg tggacgccaa ggccatcctg tctgccagac tgagcaagag cagacggctg    720
gaaaatctga tcgcccagct gcccggcgag aagaagaatg gcctgttcgg aaacctgatt    780
gccctgagcc tgggcctgac ccccaacttc aagagcaact tcgacctggc cgaggatgcc    840
aaactgcagc tgagcaagga cacctacgac gacgacctgg acaacctgct ggcccagatc    900
ggcgaccagt acgccgacct gtttctggcc gccaagaacc tgtccgacgc catcctgctg    960
agcgacatcc tgagagtgaa caccgagatc accaaggccc ccctgagcgc ctctatgatc   1020
aagagatacg acgagcacca ccaggacctg accctgctga agctctcgt gcggcagcag   1080
ctgcctgaga agtacaaaga gattttcttc gaccagagca gaacggcta cgccggctac   1140
attgacggcg gagccagcca ggaagagttc tacaagttca tcaagcccat cctggaaaag   1200
atggacggca ccgaggaact gctcgtgaag ctgaacagag aggacctgct gcggaagcag   1260
cggaccttcg acaacggcag catccccac cagatccacc tgggagagct gcacgccatt   1320
ctgcggcggc aggaagattt tacccattc tgaaggaca accgggaaaa gatcgagaag   1380
atcctgacct tccgcatccc ctactacgtg ggccctctgg ccaggggaaa cagcagattc   1440
gcctggatga ccagaaagag cgaggaaaca atcaccccct ggaacttcga ggaagtggtg   1500
gacaagggcg cttccgccca gagcttcatc gagcggatga ccaacttcga taagaacctg   1560
cccaacgaga aggtgctgcc caagcacagc ctgctgtacg agtacttcac cgtgtataac   1620
gagctgacca agtgaaata cgtgaccgag ggaatgagaa agcccgcctt cctgagcggc   1680
gagcagaaaa aggccatcgt ggacctgctg ttcaagacca ccggaaagt gaccgtgaag   1740
cagctgaaag aggactactt caagaaaatc gagtgcttcg actccgtgga aatttccggc   1800
gtggaagatc ggttcaacgc ctccctgggc acataccacg atctgctgaa aattatcaag   1860
gacaaggact ccctggacaa tgaggaaaac gaggacattc tggaagatat cgtgctgacc   1920
ctgacactgt ttgaggacag agagatgatc gaggaacggc tgaaaccta tgcccacctg   1980
ttcgacgaca aagtgatgaa gcagctgaag cggcggagat acaccggctg gggcaggctg   2040
agccggaagc tgatcaacgg catccgggac aagcagtccg gcaagacaat cctggatttc   2100
ctgaagtccg acggcttcgc caacagaaac ttcatgcagc tgatccacga cgacagcctg   2160
```

```
acctttaaag aggacatcca gaaagcccag gtgtccggcc agggcgatag ccctgcacgag  2220
cacattgcca atctggccgg cagccccgcc attaagaagg gcatcctgca gacagtgaag  2280
gtggtggacg agctcgtgaa agtgatgggc cggcacaagc ccgagaacat cgtgatcgaa  2340
atggccagag agaaccagac cacccagaag ggacagaaga acagccgcga gagaatgaag  2400
cggatcggaa agggcatcaa agagctgggc agccagatcc tgaaagaaca ccccgtggaa  2460
aacacccagc tgcagaacga gaagctgtac ctgtactacc tgcagaatgg gcgggatatg  2520
tacgtggacc aggaactgga catcaaccgg ctgtccgact acgatgtgga cgctatcgtg  2580
cctcagagct ttctgaagga cgactccatc gacaacaagg tgctgaccag aagcgacaag  2640
aaccggggca gagcgacaa cgtgccctcc gaagaggtcg tgaagaagat gaagaactac  2700
tggcggcagc tgctgaacgc caagctgatt acccagagaa agttcgacaa tctgaccaag  2760
gccgagagag cgggcctgag cgaactggat aaggccggct tcatcaagag acagctggtg  2820
gaaacccggc agatcacaaa gcacgtggca cagatcctgg actcccggat gaacactaag  2880
tacgacgaga atgacaagct gatccgggaa gtgaaagtga tcaccctgaa gtccaagctg  2940
gtgtccgatt tccggaagga tttccagttt tacaaagtgc gcgagatcaa caactaccac  3000
cacgcccacg acgcctacct gaacgccgtc gtgggaaccg ccctgatcaa aaagtaccct  3060
aagctggaaa gcgagttcgt gtacggcgac tacaaggtgt acgacgtgcg gaagatgatc  3120
gccaagagcg agcaggaaat cggcaaggct accgccaagt acttcttcta cagcaacatc  3180
atgaacttt tcaagaccga gattaccctg gccaacggcg agatccggaa gcggcctctg  3240
atcgagacaa acggcgaaac cggggagatc gtgtgggata agggccggga ttttgccacc  3300
gtgcggaaag tgctgagcat gccccaagtg aatatcgtga aaaagaccga ggtgcagaca  3360
ggcggcttca gcaaagagtc tatcctgccc aagaggaaca gcgataagct gatcgccaga  3420
aagaaggact gggaccctaa gaagtacggc ggcttcgaca gccccaccgt ggcctattct  3480
gtgctggtgg tggccaaagt ggaaaagggc aagtccaaga aactgaagag tgtgaaagag  3540
ctgctgggga tcaccatcat ggaaagaagc agcttcgaga agaatcccat cgactttctg  3600
gaagccaagg gctacaaaga agtgaaaaag gacctgatca tcaagctgcc taagtactcc  3660
ctgttcgagc tggaaaacgg ccggaagaga atgctggcct ctgccggcga actgcagaag  3720
ggaaacgaac tggccctgcc ctccaaatat gtgaacttcc tgtacctggc cagccactat  3780
gagaagctga agggctcccc cgaggataat gagcagaaac agctgtttgt ggaacagcac  3840
aagcactacc tggacgagat catcgagcag atcagcgagt tctccaagag agtgatcctg  3900
gccgacgcta atctggacaa agtgctgtcc gcctacaaca agcaccggaa taagcccatc  3960
agagacgcagg ccgagaatat catccacctg tttaccctga ccaatctggg agcccctgcc  4020
gccttcaagt actttgacac caccatcgac cggaagaggt acaccagcac caaagaggtg  4080
ctggacgcca ccctgatcca ccagagcatc accggcctgt acgagacacg gatcgacctg  4140
tctcagctga gaggtgactc tggagatct agcggaggat cctctggcg cgagacacca  4200
ggaacaagcg agtcagcaac accagagagc tctggtacgg agacaccgg taccagtgaa  4260
agcgccacgc cagaaagcag tgggagtgag actccgggta catctgaatc agcgacaccg  4320
gaatcaagtg cgggcagcag cggcggcagc agcacccctaa atatagaaga tgagtatcgg  4380
ctacatgaga cctcaaaaga gccagatgtt tctctagggt ccacatggct gtctgattt  4440
cctcaggcct gggcggaaac cggggcatg ggactggcga ttcgccaagc tcctctgatc  4500
ataccctga aagcaacctc tacccccgtg tccataaaac aataccccat gtcacaagaa  4560
gccagactgg ggatcaagcc ccacatacag agactgttgg accagggaat actggtaccc  4620
tgccagtccc cctggaacac gccctgcta cccgttaaga aaccagggac taatgattat  4680
aggcctgtcc aggatctgag agaagtcaac aagcgggtgg agacatcca ccccaccgtg  4740
cccaaccctt acaacctctt gagcgggccc ccaccgtccc accagtggta cactgtgctt  4800
gatttaaagg atgccttttt ctgcctgaga ctccaccca ccagtcagcc tctcttcgcc  4860
tttgagtgga gagatccaga gatgggaatc tcaggacaat tgacctggac cagactccca  4920
caggtttca aaaacagtcc caccctgttt aatgaggcac tgcacagaga cctagcagac  4980
ttccggatcc agcacccaga cttgatcctg ctacagtacg tggatgactt actgctggcc  5040
gccacttctg agctagactg ccaacaaggt actcgggccc tgttacaaac cctagggaac  5100
ctcgggtatc gggcctcggc caagaaagcc caaatttgcc agaaacaggt caagtatctg  5160
gggtatcttc taaaagaggg tcagagatgg ctgactgagg ccagaaaaga gactgtgatg  5220
gggcagccta ctccgaagac ccctcgacaa ctaagggagt tcctagggaa ggcaggcttc  5280
tgtcgcctct tcatccctgg gtttgcagaa atggcagccc cctgtacccc tctcaccaaa  5340
ccggggactc tgtttaattg gggcccagac caacaaagg cctatcaaga aatcaagcaa  5400
gctcttctaa ctgccccagc cctggggttg ccagatttga ctaagcccct tgaactcttt  5460
gtcgacgaga agcagggcta cgccaaaggt gtcctaacgc aaaaactggg accttggcgt  5520
cggccggtgg cctacctgtc caaaaagcta gacccagtag cagctgggtg gccccttgc  5580
ctacggatgt tagcagccat tgccgtactg acaaggatg caggcaagct aaccatggga  5640
cagccactag tcattctggc ccccatgca gtagaggcac tagtcaaaca accccccgag  5700
cgctggcttt ccaacgcccg gatgactcac tatcaggcct tgcttttgga cacggaccgg  5760
gtccagttcg gaccggtggt agccctgaac ccggctacgc tgctcccact gcctgaggaa  5820
gggctgcaac acaactgcct tgatgggaca ggtggcggtg tgtcaccgt caagttcaag  5880
tacaaggggt aggaacttga agttgatatt agcaaaatca gaaggtttg gcgcgttggt  5940
aaaatgatat cttttactta tgacgacaac ggcaagacag gtagagggcc agtgtcgag  6000
aaagacgccc caaggagct gttgcaaatg ttggaaaagt ctgggaaaaa gtctggcggc  6060
tcaaaaagaa ccgccgacgg cagcgaattc gagcccaaga agaagaggaa agtcggaggt  6120
ggcgggagcc caaaaagaa aagaaaagtg tatcccctatg atgtccccga ttatgccggt  6180
tcaagagccc tggtcgtgat tagactgagc cgagtgacag acgccaccac aagtcccgag  6240
agacagtgga aatcatgcca gcagctctgt gctcagcggg gttggatgt ggtcggctga  6300
gcagaggatc tggacgtgag cggggccgtc gatccattcg acagaaagag gaggccaac  6360
ctggcaagat ggctcgcttt cgaggaacag cccttgatg tgatcgtcgc ctacagagtg  6420
gaccggctga cccgctcaat tcgacatctc cagcagctgg tgcattgggc tgaggaccac  6480
aagaaactgg tggtcagcgc aacagaagcc cacttcgata ctaccacacc ttttgccgct  6540
gtgctacgg cactgatggg cactgtggcc cagatggagc tgaagctat caaggagcga  6600
aacaggagcg cagcccattt caatattagg gccggtaaat acagaggctc cctgcccct  6660
tggggatatc tccctaccag ggtgatggg gagtggagac tggtgccaga ccccgtccag  6720
agagagcgga ttctggaagt gtaccacaga gtggtcgata ccacgaacc actccatctg  6780
gtggcacacg acctgaatag acgcggcgtg ctctctccaa aggattattt tgctcagctg  6840
cagggaagag agccacaggg aagagaatgg agtgctactg cactgaagag atctatgatc  6900
```

```
agtgaggcta tgctgggtta cgcaacactc aatggcaaaa ctgtccggga cgatgacgga 6960
gccctctgg tgaggctga gcctattctc accagagagc agctcgaagc tctgcgggca 7020
gaactggtca agactagtcg cgccaaacct gccgtgagca ccccaagcct gctcctgagg 7080
gtgctgttct gcgccgtctg tggagagcca gcatacaagt tgccggcgg agggcgcaaa 7140
catcccgct atcgatgcag gagcatgggg ttccctaagc actgtggaaa cgggacagtg 7200
gccatggctc agtgggacgc cttttgcgag gaacaggtgc tggatctcct gggtgacgct 7260
gagcggctgg aaaaagtgtg ggtggcagga tctgactccg ctgtggagct ggcagaagtc 7320
aatgccgagc tcgtggatct gacttccctc atcggatctc ctgcatatag agctgggtcc 7380
ccacagagag aagctctgga cgcacgaatt gctgcactcg ctgctagaca gggaggaactg 7440
gagggctgg aggccaggcc ctctggatgg gagtggcgag aaaccggaca gaggtttgga 7500
gattggtgga gggagcagga caccgcagcc aagaacacat ggctgagatc catgaatgtc 7560
cggctcacat tcgacgtgcg cggtggcctg actcgaacca tcgatttttgg cgacctgcag 7620
gagtatgaac agcacctgag actggggtcc gtggtcgaaa gactgcacac tgggatgtcc 7680
```

```
SEQ ID NO: 378          moltype = AA  length = 1367
FEATURE                 Location/Qualifiers
REGION                  1..1367
                        note = Description of Artificial Sequence: Synthetic
                        polypeptide
source                  1..1367
                        mol_type = protein
                        organism = synthetic construct
SEQUENCE: 378
DKKYSIGLDI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDAI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD                1367

SEQ ID NO: 379          moltype = AA  length = 576
FEATURE                 Location/Qualifiers
REGION                  1..576
                        note = Description of Artificial Sequence: Synthetic
                        polypeptide
source                  1..576
                        mol_type = protein
                        organism = synthetic construct
SEQUENCE: 379
LNIEDEYRLH ETSKEPDVSL GSTWLSDFPQ AWAETGGMGL AVRQAPLIIP LKATSTPVSI   60
KQYPMSQEAR LGIKPHIQRL LDQGILVPCQ SPWNTPLLPV KKPGTNDYRP VQDLREVNKR  120
VEDIHPTVPN PYNLLSGPPP SHQWYTVLDL KDAFFCLRLH PTSQPLFAFE WRDPEMGISG  180
QLTWTRLPQG FKNSPTLFNE ALHRDLADFR IQHPDLILLQ YVDDLLLAAT SELDCQQGTR  240
ALLQTLGNLG YRASAKKAQI CQKQVKYLGY LLKEGQRWLT EARKETVMGQ PTPKTPRQLR  300
EFLGKAGFCR LFIPGFAEMA APLYPLTKPG TLFNWGPDQQ KAYQEIKQAL LTAPALGLPD  360
LTKPFELFVD EKQGYAKGVL TQKLGPWRRP VAYLSKKLDP VAAGWPPCLR MVAAIAVLTK  420
DAGKLTMGQP LVILAPHAVE ALVKQPPDRW LSNARMTHYQ ALLLDTDRVQ FGPVVALNPA  480
TLLPLPEEGL QHNCLDGTGG GGVTVKFKYK GEELEVDISK IKKVWRVGKM ISFTYDDNGK  540
TGRGAVSEKD APKELLQMLE KSGKKSGGSK RTADGS                             576

SEQ ID NO: 380          moltype = AA  length = 500
FEATURE                 Location/Qualifiers
REGION                  1..500
                        note = Description of Artificial Sequence: Synthetic
                        polypeptide
source                  1..500
                        mol_type = protein
                        organism = synthetic construct
SEQUENCE: 380
SRALVVIRLS RVTDATTSPE RQLESCQQLC AQRGWDVVGV AEDLDVSGAV DPFDRKRRPN   60
LARWLAFEEQ PFDVIVAYRV DRLTRSIRHL QQLVHWAEDH KKLVVSATEA HFDTTTPFAA  120
VVIALMGTVA QMELEAIKER NRSAAHFNIR AGKYRGSLPP WGYLPTRVDG EWRLVPDPVQ  180
```

```
RERILEVYHR VVDNHEPLHL VAHDLNRRGV LSPKDYFAQL QGREPQGREW SATALKRSMI    240
SEAMLGYATL NGKTVRDDDG APLVRAEPIL TREQLEALRA ELVKTSRAKP AVSTPSLLLR    300
VLFCAVCGEP AYKFAGGGRK HPRYRCRSMG FPKHCGNGTV AMAEWDAFCE EQVLDLLGDA    360
ERLEKVWVAG SDSAVELAEV NAELVDLTSL IGSPAYRAGS PQREALDARI AALAARQEEL    420
EGLEARPSGW EWRETGQRFG DWWREQDTAA KNTWLRSMNV RLTFDVRGGL TRTIDFGDLQ    480
EYEQHLRLGS VVERLHTGMS                                                500

SEQ ID NO: 381        moltype = DNA   length = 11344
FEATURE               Location/Qualifiers
misc_feature          1..11344
                      note = Description of Artificial Sequence: Synthetic
                      polynucleotide
source                1..11344
                      mol_type = other DNA
                      organism = synthetic construct
SEQUENCE: 381
ccgaaaagtg ccacctgacg tcgacggatc gggagatcga tctcccgatc ccctagggtc    60
gactctcagt acaatctgct ctgatgccgc atagttaagc cagtatctgc tccctgcttg    120
tgtgttggag gtcgctgagt agtgcgcgag caaaatttaa gctacaacaa ggcaaggctt    180
gaccgacaat tgcatgaaga atctgcttag ggttaggcgt tttgcgctgc ttcgcgatgt    240
acgggccaga tatacgcgtt gacattgatt attgactagt tattaatagt aatcaattac    300
ggggtcatta gttcatagcc catatatgga gttccgcgtt acataactta cggtaaatgg    360
cccgcctggc tgaccgccca acgaccccgc ccattgacg tcaataatga cgtatgttcc    420
catagtaacg ccaatagggg cttt ccattg acgtcaatgg gtggagtatt tacggtaaac    480
tgcccacttg gcagtacatc aagtgtatca tatgccaagt acgcccccta ttgacgtcaa    540
tgacggtaaa tggcccgcct ggcattatgc ccagtacatg accttatggg actttcctac    600
ttggcagtac atctacgtat tagtcatcgc tattaccatg gtgatgcggt tttggcagta    660
catcaatggg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg gccgctaata cgactcacta    900
tagggagagc cgccaccatg aaacggacac ccgacggaag cgagttcgag tcaccaaaga    960
agaagcggaa agtcgacaag aagtacagca tcggcctgga catcggcacc aactctgtgg    1020
gctgggccgt gatcaccgac gagtacaagg tgcccgacaa gaaattcaag gtgctgggca    1080
acaccgaccg gcacagcatc aagaagaacc tgatcggagc cctgctgttc gacagcgggg    1140
aaacagccga ggccacccgg ctgaagagaa ccgccagaag aagatacacc agacggaaga    1200
accggatctg ctatctgcaa gagatcttca gcaacgagat ggccaaggtg gacgacagct    1260
tcttccacag actggaagag tccttcctgg tggaagagga taagaagcac gagcggcacc    1320
ccatcttcgg caacatcgtg gacgaggtgg cctaccacga gaagtacccc accatctacc    1380
acctgagaaa gaaactggtg gacagcaccg acaaggccga cctgcggctg atctatctgg    1440
ccctggccca catgatcaag ttccggggcc acttcctgat cgaggcggac ctgaaccccg    1500
acaacagcga cgtggacaag ctgttcatcc agctggtgca gacctacaac cagctgttcg    1560
aggaaaaccc catcaacgcc agcggcgtgg acgccaaggc catcctgtct gccagactga    1620
gcaagagcag acggctggaa aatctgatcg cccagctgcc cggcgagaag aagaatggcc    1680
tgttcggaaa cctgattgcc ctgagcctgg gcctgacccc caacttcaag agcaacttcg    1740
acctggccga ggatgccaaa ctgcagctga gcaaggacac ctacgacgac gacctggaca    1800
acctgctggc ccagatcggc gaccagtacg ccgacctgtt tctggccgcc aagaacctgt    1860
ccgacgccat cctgctgagc gacatcctga gagtgaacac cgagatcacc aaggcccccc    1920
tgagcgcctc tatgatcaag agatacgacg agcaccacca ggacctgacc ctgctgaaag    1980
ctctcgtgcg gcagcagctg cctgagaagt acaaagagat tttcttcgac cagagcaaga    2040
acggctacgc cggctacatt gacggcggag ccagccagga agattctac agttcatca    2100
agcccatcct ggaaaagatg gacggcaccg aggaactgct cgtgaagctg aacagagagg    2160
acctgctgcg gaagcagcgg accttcgaca acggcagcat ccccaccag atccacctgg    2220
gagagctgca cgccattctg cggcggcagg aagatttta cccattcctg aaggacaacc    2280
gggaaaagat cgagaagatc ctgaccttcc gcatccccta ctacgtgggc cctctggcca    2340
ggggaaacag cagattcgcc tggatgacca gaaagagcga ggaaaccatc accccctgga    2400
acttcgagga agtggtggac aagggcgctt ccgcccagag cttcatcgag cggatgacca    2460
acttcgataa gaacctgccc aacgagaagg tgctgcccaa gcacagcctg ctgtacgagt    2520
acttcaccgt gtataacgag ctgaccaaag tgaaatatgt gaccgaggga atgagaaagc    2580
ccgccttcct gagcggcgag cagaaaaagg ccatcgtgga cctgctgttc aagaccaacc    2640
ggaaagtgac cgtgaagcag ctgaaagagg actacttcaa gaaaatcgag tgcttcgact    2700
ccgtggaaat ctccggcgtg gaagatcggt tcaacgcctc cctgggcaca taccacgatc    2760
tgctgaaaat tatcaaggac aaggacttcc tggacaatga ggaaaacgag gacattctgg    2820
aagatatcgt gctgaccctg acactgtttg aggacagaga gatgatcgaa gagcggctga    2880
aaacctatgc ccacctgttc gacgacaaag tgatgaagca gctgaagcgg cggagataca    2940
ccggctgggg caggctgagc cggaagctga tcaacggcat ccgggacaag cagtccggca    3000
agacaatcct ggatttcctg aagtccgacg gcttcgccaa cagaaacttc atgcagctga    3060
tccacgacga cagcctgacc tttaagagg acatccagaa agcccaggtg tccggccagg    3120
gcgatagcct gcacgagcac attgccaatc tggccggacg ccccgccatt aagaagggca    3180
tcctgcagac agtgaaggtg gtggacgagc tcgtgaaagt gatgggccgg cacaagcccg    3240
agaacatcgt gatcgaaatg gccagagaga accagaccac ccagaaggga cagaagaaca    3300
gccgcgagag aatgaagcgg atcgaagagg gcatcaaaga gctgggcagc cagatcctga    3360
aagaacaccc cgtggaaaac acccagctgc agaacgagaa gctgtacctg tactacctgc    3420
agaatgggcg ggatatgtac gtggaccagg aactggacat caaccggctg tccgactacg    3480
atgtggacgc tatcgtgcct cagagctttc tgaaggacga ctccatcgac aacaaggtgc    3540
tgaccagaag cgacaagaac cggggcaaga gcgacaacgt gccctccgaa gaggtcgtga    3600
agaagatgaa gaactactgg cggcagctgc tgaacgccaa gctgattacc cagagaaagt    3660
tcgacaatct gaccaaggcc gagagaggcg gcctgagcga actggataag gccggcttca    3720
tcaagagaca gctggtggaa acccggcaga tcacaaagca cgtggcacag atcctggact    3780
```

```
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aagtgtacg    4020
acgtgcggaa gatgatcgcc aagagcgagc aggaaatcgg caaggctacc gccaagtact   4080
tcttctacag caacatcatg aacttttca agaccgagat taccctggcc aacggcgaga    4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga agaagcagc ttcgagaaga    4500
atcccatcga ctttctggaa gccaagggct acaaagaagt gaaaaaggac ctgatcatca   4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccag ccactatgag aagctgaagg gctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctgg ggaggatcct    5100
ctggcagcga gacaccagga acaagcgagt cagcaacacc agagagcagt ggcggcagca   5160
gcggcggcag cagcacccta aatatagaag atgagtatcg gctacatgag acctcaaaag   5220
agccagatgt ttctctaggg tccacatggc tgtctgattt tcctcaggcc tgggcggaaa   5280
ccggggggcat gggactggca gttcgccaag ctcctctgat catacctctg aaagcaacct   5340
ctaccccggt gtccataaaa caataccccca tgtcacaaga agccagactg ggatcaagc    5400
cccacataca gagactgttg gaccaggaaa tactggtacc ctgccagtcc ccctggaaca   5460
cgccctgct acccgttaag aaaccaggga ctaatgatta taggcctgtc caggatctga   5520
gagaagtcaa caagcgggtg gaagacatcc accccaccgt gcccaaccct tacaacctct   5580
tgagcgggct cccaccgtcc caccagtggt acactgtgct tgatttaaag gatgccttt    5640
tctgcctgag actccacccc accagtcagc ctctcttcgc ctttgagtgg agagatccag   5700
agatgggaat ctcaggacaa ttgacctgga ccagactccc acagggtttc aaaaacagtc   5760
ccaccctgtt taatgaggca ctgcacagag acctagcaga cttccggata cagcacccag   5820
acttgatcct gctacagtac gtggatgact tactgctggc cgccacttct gagctagact   5880
gccaacaagg tactcgggcc ctgttacaaa ccctagggaa cctcgggtat cgggcctcgg   5940
ccaagaaagc ccaaatttgc cagaaacagg tcaagtatct ggggtatctt ctaaaagagg   6000
gtcagagatg gctgactgag gccagaaaag agactgtgat ggggcagcct actccgaaga   6060
ccccctgaca actaagggag ttcctaggga aggcaggctt ctgtcgcctc ttcatccttg   6120
ggtttgcaga aatggcagcc ccccgtacc ctctccaccaa accggggact ctgtttaatt    6180
ggggcccaga ccaacaaaag gcctatcaag aaatcaagca agctcttcta actgcccag    6240
ccctgggggtt gccagatttg actaagccct ttgaactctt tgtcgacgag aagcagggct   6300
acgccaaagg tgtcctaacg caaaaactgg gacctggccg gcctacctgt                6360
ccaaaaagct agaccagta gcagctgggt ggccccctgg cctacggatg gtagcagcca     6420
ttgccgtact gacaaaggat gcaggcaagc taaccatggg acagccacta gtcattctgg     6480
cccccccatgc agtagaggca ctagtcaaac aaccccccga ccgctggctt tccaacgccc     6540
ggatgactca ctatcaggcc ttgcttttgg acacggacg ggtccagttc ggaccggtgg      6600
tagccctgaa cccggctacg ctgctcccac tgcctgagga agggctgcaa cacaactgcc     6660
ttgatatcct ggccgaagcc cacggaaccc gaccccgaccct aacggaccag ccgctcccag    6720
acgccgacca cacctggtac acggatgaa gcagtctctt acaagaggga cagcgtaagg     6780
cgggagctgc ggtgaccacc gagaccgagg taatctggc taaagccctg ccagcgtga     6840
catccgctca gcgggctgaa ctgatagcac tcacccaggc cctaaagatg gcagaaggta    6900
agaagctaaa tgtttatact gatagccgtt atgcttttgc tactgcccat atccatggag     6960
aaatatacag aaggcgtggg tggctcacat cagaaggcaa agagatcaaa aataaagacg     7020
agatcttggc cctactaaaa gccctctttc tgcccaaaag acttagcata atccattgtc     7080
caggacatca aaagggacac agcgccgagg ctagaggcaa ccggatggct gaccaagcgg     7140
cccgaaaggc agccatcaca gagactccag acacctctac cctcctcata gaaaattcat     7200
caccctctgg cggctcaaaa agaaccgcgc acggcagcga attcgagccc aagaagaaga     7260
ggaaagtcgg aagcggagct actaacttca gcctgctgaa gcaggctggc gacgtggagg     7320
agaaccctgg acctccaaaa aagaaagaga agtgtatcc ctatgatgtc cccgattatg     7380
ccggttcaag agccctggtc gtgattagac tgagccgagt gacagacgcc accacaagtc     7440
ccgagagaca gctggaatca tgccagcagc tctgtgctca gcggggttgg gatgtggtcg     7500
gcgtggcaga ggatctggac gtgagcgggg ccgtcgatcc attcgacaga aagaggaggc     7560
ccaacctggc aagatggctc gctttgagg aacagccctt tgatgtgatc gtcgcctaca     7620
gagtggaccg gctgacccgc tcaattcgac atctccagca gctgtcat gggctgagg       7680
accacaagaa actggtggtc agcgcaacag aagcccactt cgatactacc acaccttttg    7740
ccgctgtggt catcgcactg atgggcactg tggcccagat ggagctcgaa gctatcaagg    7800
agcgaaacag gagcgcagcc catttcaata ttagggccgg taaatacaga ggctccctgc    7860
cccctggggg atatctcct accagggtgg atggggagtg cgataccggt ccagacccg     7920
tccagagaga gcggattctg gaagtgtacc acagagtgac cgataaccac gaaccactcc    7980
atctggtggc acacgacctg aatagacgcg cgtgctctc tccaaggat tatttttgctc     8040
agctgcaggg aagagagcca cagggaagag aatggagtgc tactgcactg aagagatcta    8100
tgatcagtga ggctatgctg gttacgcaa cactcaatgg caaaactgtc cggacgatg     8160
acggagcccc tctggtgagg gctgagctta tttctaccag agacgagtgc gaagctctgc    8220
gggcagaact ggtcaagact agtcgcgcca aacctgccgt gagcacccca gcctgctcc    8280
tgagggtgct gttctgcgcc gtctgtggag accagcata caagttttgcc ggcggagggc   8340
gcaaacatcc ccgctatcga tgcaggagca tgggttccc taagcactgt ggaaacggga   8400
cagtggccat ggctgagtgg gacgccttt gcgaggaaca ggtgctggat ctcctgggtg     8460
acgctgagcg gctggaaaaa gtgtgggtgg caggatctga ctccgctgtg gagctggcag    8520
```

```
aagtcaatgc cgagctcgtg gatctgactt ccctcatcgg atctcctgca tatagagctg    8580
ggtccccaca gagagaagct ctggacgcac gaattgctgc actcgctgct agacaggagg    8640
aactggaggg cctggaggcc aggccctctg gatgggagtg gcgagaaacc ggacagaggt    8700
ttggggattg gtgagggag caggacaccg cagccaagaa cacatggctg agatccatga    8760
atgtccggct cacattcgac gtgcgcggtg gcctgactcg aaccatcgat tttggcgacc    8820
tgcaggagta tgaacagcac ctgagactgg ggtccgtggt cgaaagactg cacactggga    8880
tgtcctaggt ttaaacccgc tgatcagcct cgactgtgcc ttctagttgc cagccatctg    8940
ttgtttgccc ctccccgtg ccttccttga ccctggaagg tgccactccc actgtccttt     9000
cctaataaaa tgagaaaatt gcatcgcatt gtctgagtag gtgtcattct attctggggg    9060
gtggggtggg gcaggacagc aagggggagg attgggaaga caatagcagg catgctgggg    9120
atgcggtggg ctctatggct tctgaggcgg aaagaaccag ctggggctcg ataccgtcga    9180
cctctagcta gagcttggcg taatcatggt catagctgtt tcctgtgtga aattgttatc    9240
cgctcacaat tccacacaac atacgagccg gaagcataaa gtgtaaagcc tagggtgcct    9300
aatgagtgag ctaactcaca ttaattgcgt tgcgctcact gcccgctttc cagtcgggaa    9360
acctgtcgtg ccagctgcat taatgaatcg gccaacgcgc ggggagaggc ggtttgcgta    9420
ttgggcgctc ttccgcttcc tcgctcactg actcgctgcg ctcggtcgtt cggctgcggc    9480
gagcggtatc agctcactca aaggcggtaa tacggttatc cacagaatca ggggataacg    9540
caggaaagaa catgtgagca aaaggccagc aaaaggccag gaaccgtaaa aaggccgcgt    9600
tgctggcgtt tttccatagg ctccgccccc ctgacgagca tcacaaaaat cgacgctcaa    9660
gtcagaggtg gcgaaacccg acaggactat aaagatacca ggcgtttccc cctggaagct    9720
ccctcgtgcg ctctcctgtt ccgaccctgc cgcttaccgg atacctgtcc gcctttctcc    9780
cttcggaag cgtggcgctt tctcatagct cacgctgtag gtatctcagt tcggtgtagg    9840
tcgttcgctc caagctgggc tgtgtgcacg aaccccccgt tcagcccgac cgctgcgcct    9900
tatccggtaa ctatcgtctt gagtccaacc cggtaagaca cgacttatcg ccactggcag    9960
cagccactgg taacaggatt agcagagcga ggtatgtagg cggtgctaca gagttcttga   10020
agtggtggcc taactacggc tacactagaa gaacagtatt tggtatctgc gctctgctga   10080
agccagttac cttcggaaaa agagttggta gctcttgatc cggcaaacaa accaccgctg   10140
gtagcggtgg ttttttttgtt tgcaagcagc agattacgcg cagaaaaaaa ggatctcaag   10200
aagatccttt gatcttttct acggggtctg acgctcagtg gaacgaaaac tcacgttaag   10260
ggattttggt catgagatta tcaaaaagga tcttcaccta gatccttta aattaaaaat    10320
gaagttttaa atcaatctaa agtatatatg agtaaacttg gtctgacagt taccaatgct   10380
taatcagtga ggcacctatc tcagcgatct gtctatttcg ttcatccata gttgcctgac   10440
tccccgtcgt gtagataact acgatacggg agggcttacc atctggcccc agtgctgcaa   10500
tgataccgcg agaccacgc tcaccggctc cagatttatc agcaataaac cagccagccg   10560
gaagggccga gcgcagaagt ggtcctgcaa ctttatccgc ctccatccag tctattaatt   10620
gttgccggga agctagagta agtagttcgc cagttaatag tttgcgcaac gttgttgcca   10680
ttgctacagg catcgtggtg tcacgctcgt cgtttggtat ggcttcattc agctccggtt   10740
cccaacgatc aaggcgagtt acatgatccc ccatgttgtg caaaaaagcg gttagctcct   10800
tcggtcctcc gatcgttgtc agaagtaagt tggccgcagt gttatcactc atggttatgg   10860
cagcactgca taattctctt actgtcatgc catccgtaag atgcttttct gtgactggtg   10920
agtactcaac caagtcattc tgagaatagt gtatgcggcg accgagttgc tcttgcccgg   10980
cgtcaatacg ggataaatacc gcgccacata gcagaacttt aaaagtgctc atcattggaa   11040
aacgttcttc ggggcgaaaa ctctcaagga tcttaccgct gttgagatcc agttcgatgt   11100
aaccactcg tgcacccaac tgatcttcag catctttta tttcaccagc gtttctgggt      11160
gagcaaaaac aggaaggcaa aatgccgcaa aaaagggaat aagggcgaca cggaaatgtt    11220
gaatactcat actcttcctt tttcaatatt attgaagcat ttatcagggt tattgtctca    11280
tgagcggata catatttgaa tgtatttaga aaaataaaca aataggggtt ccgcgcacat    11340
ttcc                                                                 11344
```

| SEQ ID NO: 382 | moltype = DNA   length = 9753 |
|---|---|
| FEATURE | Location/Qualifiers |
| misc_feature | 1..9753 |
| | note = Description of Artificial Sequence: Synthetic polynucleotide |
| source | 1..9753 |
| | mol_type = other DNA |
| | organism = synthetic construct |

SEQUENCE: 382

```
ccgaaaagtg ccacctgacg tcgacggatc gggagatcga tctcccgatc ccctagggtc    60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat tgcatgaaga atctgcttag ggttaggcgt tttgcgctgc ttcgcgatgt   240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgacccccg cccattgacg tcaataatga cgtatgttcc   420
catagtaacg ccaatagga cttttccattg acgtcaatgg gtggagtatt tacggtaaac    480
tgcccacttg gcagtacatc aagtgtatca tatgccaagt acgccccta ttgacgtcaa    540
tgacggtaaa tggcccgcct ggcattatgc ccagtacatg accttatggg actttcctac   600
ttggcagtac atctacgtat tagtcatcgc tattaccatg gtgatgcggt tttggcagta   660
catcaatggg cgtggatagc ggtttgactc acggggattt ccaagtctcc accccattga   720
cgtcaatggg agtttgtttt ggcaccaaaa tcaacgggac tttccaaaat gtcgtaacaa   780
ctccgcccca ttgacgcaaa tgggcggtag gcgtgtacgg tgggaggtct atataagcag   840
agctggttta gtgaaccgtc agatccgcta gagatccgcg gccgctaata cgactcacta   900
tagggagagc cgccaccatg aaacggacag cggttctgag tcaccaaaga                 960
agaagcggaa agtcgacaag aagtacagca tcggcctgga catcggcacc aactctgtgg   1020
gctgggcgt gatcaccgac gagtacaagg tgcccagcaa gaaattcaag gtgctgggca   1080
acaccgaccg gcacagcatc aagaagaacc tgatcggagc cctgctgttc gacagcgcg    1140
aaacagccga ggccacccgg ctgaagagaa ccgccagaag aagatacacc agacggaaga   1200
accggatctg ctatctgcaa gagatcttca gcaacgagat ggccaaggtg gacgacagct   1260
```

```
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggccga cctgcggctg atctatctgg   1440
ccctggccca catgatcaag ttccggggcc acttcctgat cgaggcgac ctgaaccccg    1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg gcctgacccc caacttcaag agcaacttcg   1740
acctggccga ggatgccaaa ctgcagctga gcaaggacac ctacgacgac gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgagaagt acaaagagat tttcttcgac cagagcaaga   2040
acggctacgc cggctacatt gacggcggag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat cccccaccag atccacctgg   2220
gagagctgca cgccattctg cggcggcagg aagattttta cccattcctg aaggacaacc   2280
gggaaaagat cgagaagatc ctgaccttcc gcatccccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga ggaaaacgag gacattctgg   2820
aagatatcgt gctgaccctg acactgtttg aggacagaga gatgatcgag gaacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac cagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagctttc tgaaggacga ctccatcgac aacaaggtgc   3540
tgaccagaag cgacaagaac cggggcaaga gcgacaacgt ccctcccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttttca agaccgagat taccctggcc aacggcgaga   4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga gaagcagc ttcgagaaga    4500
atcccatcga ctttctggaa gccaaggct acaaagagt gaaaaaggac ctgatcatca    4560
agctgcctaa gtactccctg ttcgagctgg aaaacggccg gaagagaatg ctggcctctg   4620
ccggcgaact gcagaaggga acgaactggg ccctgccctc caaatatgtg aacttcctgt   4680
acctggccag ccactatgag aagctgaagg ctcccccga ggataatgag cagaaacagc    4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctggag gtgatctag gaggatctgt                5100
ctggcagcga gacaccagga acaagcgagt cagcaacacc agagagcagt ggcggcagca   5160
gcggcggcag cagcaccct aatatagag atgagtatcg gctacatgag acctcaaaag    5220
agccagatgt ttctctaggg tccacatggc tgtctgattt tcctcaggcc tgggcggaaa   5280
ccggggggcat gggactggca gttcgccaag ctcctctgat catacctctg aaagcaacct   5340
ctaccccgt gtccataaaa caatacccca tgtcacaaga agccagactg gggatcaagc   5400
cccacataca gagactgttg gaccaggaa tactggtacc ctgccagtcc cctggaaca    5460
cgcccctgct acccgttaag aaaccaggga ctaatgatta taggcctgtc caggatctga   5520
gagaagtcaa caagcgggtg gaagcatcc accccaccgt gcccaacct acaacctct     5580
tgagcgggct cccaccgtcc caccagtggt acactgtgct tgatttaaag gatgccttt    5640
tctgcctgag actccacccc accgtcagc ctcttcgc ctttgagtgg agagatccag      5700
agatgggaat ctcaggacaa ttgacctgga ccagactccc acaggggttc aaaaacagtc   5760
ccaccctgtt taatgaggca ctgcacagag acctagcaga cttccggatc cagcacccag   5820
acttgatcct gctacagtac gtggatgact tactgctggc cgccacttct gagctagact   5880
gccaacaagg tactcgggcc ctgttacaaa ccctaggaa cctcgggtat cgggcctcgg   5940
ccaagaaagc ccaaatttgc cagaaacagg tcaagtatct ggggtatctt ctaaaagagg   6000
```

```
gtcagagatg gctgactgag gccagaaaag agactgtgat ggggcagcct actccgaaga  6060
cccctcgaca actaagggag ttcctaggga aggcaggctt ctgtcgcctc ttcatccctg  6120
ggtttgcaga aatggcagcc cccctgtacc ctctcaccaa accggggact ctgtttaatt  6180
ggggcccaga ccaacaaaag gcctatcaag aaatcaagca agctcttcta actgcccccag 6240
ccctgggtt gccagatttg actaagccct ttgaactctt tgtcgacgag aagcagggct  6300
acgccaaagg tgtcctaacg caaaaactgg gaccttggcg tcggccggtg gcctacctgt  6360
ccaaaaagct agacccagta gcagctgggg ggcccccttg cctacggatg gtagcagcca  6420
ttgccgtact gacaaaggat gcaggcaagc taaccatggg acagccacta gtcattctgg  6480
cccccatgc agtagaggca ctagtcaaac aacccccga ccgctggctt tccaacgcc  6540
ggatgactca ctatcaggcc ttgcttttgg acacggaccg ggtccagttc ggaccggtgg  6600
tagccctgaa cccggctacg ctgctcccac tgcctgagga agggctgcaa cacaactgcc  6660
ttgatatcct ggccgaagcc cacggaaccc gacccgacct aacggaccag ccgctcccag  6720
acgccgacca cacctggtac acggatggaa gcagtctctt acaagaggga cagcgtaagg  6780
cgggagctgc ggtgaccacc gagaccgagg taatcgtggc taaagccctg ccagccgggg  6840
catccgctca gcgggctgaa ctgatagcac tcacccaggc cctaaagatg cagaaaggta  6900
agaagctaaa tgtttatact gatagccgtt atgcttttgc tactgcccat atccatggag  6960
aaatatacag aaggcgtggg tggctcacat cagaaggcaa agagatcaaa aataaagacg  7020
agatcttggc cctactaaaa gccctctttc tgcccaaaag acttagcata atccattgtc  7080
caggacatca aaagggacac agcgccgagg ctagaggcaa ccggatggct gaccaagcgg  7140
cccgaaaggc agccatcaca gagactccag acacctctac cctcctcata gaaaattcat  7200
caccctctgg cggctcaaaa agaaccgccg acggcagcga attcgagccc aagaagaaga  7260
ggaaagtcta accggtcatc accaccatca ccattagcat taaaccccgct gatcagcctc  7320
gactgtgcct tctagttgcc agccatctgt tgtttgcccc tccccgtgc cttccttgac  7380
cctgaaggt gccactccca ctgtcctttc ctaataaaat gagaaaattg catcgcattg  7440
tctgagtagg tgtcattcta ttctgggggg tggggtgggg caggacagca agggggagga  7500
tgggaagac aatagcagge atgctgggga tgcggtgggc tctatggctt ctgaggcgga  7560
aagaaccagc tggggctcga taccgtcgac ctctagctag agcttggcgt aatcatggtc  7620
atagctgttt cctgtgtgaa attgttatcc gctcacaatt ccacacaaca tacgagccgg  7680
aagcataaag tgtaaagcct agggtgccta atgagtgagc taactcacat taattgcgtt  7740
gcgctcactg cccgctttcc agtcgggaaa cctgtcgtgc cagctgcatt aatgaatcgg  7800
ccaacgcgcg gggagaggcg gtttgcgtat tgggcgctct tccgcttcct cgctcactga  7860
ctcgctgcgc tcggtcgttc ggctgcggcg agcggtatca gctcactcaa aggcggtaat  7920
acggttatcc acagaatcag gggataacgc aggaaagaac atgtgagcaa aaggccagca  7980
aaaggccagg aaccgtaaaa aggccgcgtt gctggcgttt ttccataggc tccgcccccc  8040
tgacgagcat cacaaaaatc gacgctcaag tcagaggtgg cgaaacccga caggactata  8100
aagataccag gcgtttcccc ctggaagctc cctcgtgcgc tctcctgttc cgaccctgcc  8160
gcttaccgga tacctgtccg cctttctccc ttcgggaagc gtggcgcttt ctcatagctc  8220
acgctgtagg tatctcagtt cggtgtaggt cgttcgctcc aagctgggct gtgtgcacga  8280
accccccgtt cagcccgacc gctgcgcctt atccggtaac tatcgtcttg agtccaaccc  8340
ggtaagacac gacttatcgc cactggcagc agccactggt aacaggatta gcagagcgag  8400
gtatgtaggc ggtgctacag agttcttgaa gtggtggcct aactacggct acactagaag  8460
aacagtattt ggtatctgcg ctctgctgaa gccagttacc ttcggaaaaa gagttggtag  8520
ctcttgatcc ggcaaacaaa ccaccgctgg tagcggtggt ttttttgttt gcaagcagca  8580
gattacgcgc agaaaaaaag gatctcaaga agatcctttg atcttttcta cggggtctga  8640
cgctcagtgg aacgaaaact cacgttaagg gattttggtc atgagattat caaaaaggat  8700
cttcacctag atccttttaa attaaaaatg aagttttaaa tcaatctaaa gtatatatga  8760
gtaaacttgg tctgacagtt accaatgctt aatcagtgag gcacctatct cagcgatctg  8820
tctatttcgt tcatccatag ttgcctgact ccccgtcgtg tagataacta cgatacggga  8880
gggcttacca tctggcccca gtgctgcaat gataccgcga gacccacgct caccggctcc  8940
agatttatca gcaataaacc agccagccgg aagggccgag cgcagaagtg gtcctgcaac  9000
tttatcgcc tccatccagt ctattaattg ttgccggaa gctagagtaa gtagttcgcc  9060
agttaatagt ttgcgcaacg ttgttgccat tgctacagge atcgtggtgt cacgctcgtc  9120
gtttggtatg gcttcattca gctccggttc ccaacgatca aggcgagtta catgatcccc  9180
catgttgtgc aaaaaagcgg ttagctcctt cggtcctccg atcgttgtca gaagtaagtt  9240
ggccgcagtg ttatcactca tggttatggc agcactgcat aattctctta ctgtcatgcc  9300
atccgtaaga tgcttttctg tgactggtga gtactcaacc aagtcattct gagaatagtg  9360
tatgcggcga ccgagttgct cttgcccggc gtcaatacgg gataataccg cgccacatag  9420
cagaacttta aaagtgctca tcattggaaa acgttcttcg gggcgaaaac tctcaaggat  9480
cttaccgctg ttgagatcca gttcgatgta acccactcgt gcacccaact gatcttcagc  9540
atcttttact ttcaccagcg tttctgggtg agcaaaaaca ggaaggcaaa atgccgcaaa  9600
aaagggaata agggcgacac ggaaatgttg aatactcata ctcttccttt ttcaatatta  9660
ttgaagcatt tatcagggtt attgtctcat gagcggatac atatttgaat gtatttagaa  9720
aaataaacaa ataggggttc cgcgcacatt tcc                               9753
```

```
SEQ ID NO: 383        moltype = DNA   length = 11433
FEATURE               Location/Qualifiers
misc_feature          1..11433
                      note = Description of Artificial Sequence: Synthetic
                      polynucleotide
source                1..11433
                      mol_type = other DNA
                      organism = synthetic construct
SEQUENCE: 383
ccgaaaagtg ccacctgacg tcgacggatc gggagatcga tctcccgatc ccctagggtc  60
gactctcagt acaatctgct ctgatgccgc atagttaagc cagtatctgc tccctgcttg  120
tgtgttggag gtcgctgagt agtgcgcgag caaaatttaa gctacaacaa ggcaaggctt  180
gaccgacaat gcatgaagaa atctgcttag ggttaggcgt tttgcgctgc ttcgcgatgt  240
acgggccaga tatacgcgtt gacattgatt attgactagt tattaatagt aatcaattac  300
ggggtcatta gttcatagcc catatatgga gttccgcgtt acataactta cggtaaatgg  360
```

```
cccgcctggc tgaccgccca acgaccccg cccattgacg tcaataatga cgtatgttcc    420
catagtaacg ccaataggga ctttccattg acgtcaatgg gtggagtatt tacggtaaac    480
tgcccacttg gcagtacatc aagtgtatca tatgccaagt acgccccta ttgacgtcaa    540
tgacggtaaa tggcccgcct ggcattatgc ccagtacatg accttatggg actttcctac    600
ttggcagtac atctacgtat tagtcatcgc tattaccatg gtgatgcggt tttggcagta    660
catcaatggg cgtggatagc ggtttgactc acggggattt ccaagtctcc accccattga    720
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcta gccgctaata cgactcacta    900
tagggagagc cgccaccatg cccgcggcta agagggtgaa gcttgacggt ggaaaacgga    960
cagccgacgg aagcgagttc gagtcaccaa agaagaagcg gaaagtcgac aagaagtaca   1020
gcatcggcct ggacatcggc accaactctg tgggctgggc cgtgatcacc gacgagtaca   1080
aggtgcccag caagaaattc aaggtgctgg gcaacaccga ccggcacagc atcaagaaga   1140
acctgatcgg agccctgctg ttcgacagcg gcgaaacagc cggccccta cggctgaaga   1200
gaaccgccag aagaagatac accagacgga agaaccggat ctgctatctg caagagatct   1260
tcagcaacga gatggccaag gtggacgaca gcttcttcca cagactggaa gagtccttcc   1320
tggtggaaga ggataagaag cacgagcggc acccatctt cggcaacatc gtggacgagg   1380
tggcctacca cgagaagtac cccaccatct accacctgag aaagaaactg gtggacagca   1440
ccgacaaggc cgacctgcgg ctgatctatc tggccctggc ccacatgatc aagttccggg   1500
gccacttcct gatcgagggc gacctgaacc ccgacaacag cgacgtggac aagctgttca   1560
tccagctggt gcagacctac aaccagctgt tcgaggaaaa ccccatcaac gccagcggcg   1620
tggacgccaa ggccatcctg tctgccgagac tgagcaagag cagacggctg gaaaatctga   1680
tcgcccagct gcccggcgag aagaagaatg gcctgttcgg aaacctgatt gccctgagcc   1740
tgggcctgac cccaacttc aagagcaact tcgacctggc cgaggatgcc aaactgcagc   1800
tgagcaagga cacctacgac gacgacctgg acaacctgct ggcccagatc ggcgaccagt   1860
acgccgacct gtttctggcc gccaagaacc tgtccgacgc catcctgctg agcgacatcc   1920
tgagagtgaa caccgagatc accaaggccc cctgagcgc ctctatgatc aagagatacg   1980
acgagcacca ccaggacctg accctgctga aagctctcgt gcggcagcag ctgcctgaga   2040
agtacaaaga gattttcttc gaccagagca agaacggcta cgccggctac attgacggcg   2100
gagccagcca ggaagagttc tacaagttca tcaagcccat cctggaaaag atggacggca   2160
ccgaggaact gctcgtgaag ctgaacagag gaggacctgct gcggaagcag cggaccttcg   2220
acaacggcag catcccccac cagatccacc tgggagagct gcacgccatt ctgcggcggc   2280
aggaagattt tacccattc ctgaaggaca accgggaaaa gatcgagaag atcctgacct   2340
tccgcatccc ctactacgtg ggccctctgg ccaggggaaa cagcagattc gcctggatga   2400
ccagaaagag cgaggaaacc atcacccct ggaacttcga ggaagtggtg gacaagggcc   2460
cttccgccca gagcttcatc gagcggatga ccaacttcga taagaacctg cccaacgaga   2520
aggtgctgcc caagcacagc ctgctgtacg agtacttcac cgtgtataac gagctgacca   2580
aagtgaaata cgtgaccgag ggaatgagaa agcccgcctc cctgagcggc gagcagaaaa   2640
aggccatcgt ggacctgctg ttcaagacca accggaaagt gaccgtgaag cagctgaaag   2700
aggactactt caagaaaatc gagtgcttcg actccgtgga aatctccggc gtggaagatc   2760
ggttcaacgc ctcccctggc acataccacg atctgctgaa aattatcaag gacaaggact   2820
tcctggacaa tgaggaaaac gaggacattc tggaagatat cgtgctgacc ctgacactgt   2880
ttgaggacag agagatgatc gaggaacggc tgaaaaccta tgcccacctg ttcgacgaca   2940
aagtgatgaa gcagctgaag cggcggagat acaccggctg gggcaggctg agccggaagc   3000
tgatcaacgg catccgggac aagcagtccg gcaagacaat cctggatttc ctgaagtccg   3060
acggcttcgc caacagaaac ttcatgcagc tgatccacga cgacagcctg accttttaaag   3120
aggacatcca gaaagcccga gtgtccggcc agggcgacag cctgcacgag cacattgcca   3180
atctggccgg cagccccgcc attaagaagg gcatcctgca gacagtgaag gtggtggacg   3240
agctcgtgaa agtgatgggc cggcacaagc ccgagaacat cgtgatcgaa atggccagag   3300
agaaccagac cacccagaag ggacagaaga cagccgcgca gagaatgaag cggatcgaag   3360
agggcataag agagctgggc agccagatcc tgaaagaaca ccccgtggaa aacacccagc   3420
tgcagaacga gaagctgtac ctgtactacc tgcagaatgg gcgggatatg tacgtggacc   3480
aggaactgga catcaaccgg ctgtccgact acgatgtgga cgctatcgtg cctcagagct   3540
ttctgaagga cgactccatc gacaacaagg tgctgaccag aagcgacaag aaccggggca   3600
agagcgacaa cgtgccctcc gaagaggtcg tgaagaagat gaagaactac tggcggcaac   3660
tgctgaacgc caagctgatt acccagagaa agttcgacaa tctgaccaag gccgagagag   3720
gcggcctgag cgaactggat aaggccggct tcatcaagag acagctggtg gaaacccggc   3780
agatcacaaa gcacgtggca cagatcctgg actcccggat gaacactaag tacgacgaga   3840
atgacaagct gatccgggaa gtgaaagtga tcaccctgaa gtccaagctg gtgtccgatt   3900
tccggaagga tttccagttt tacaaagtgc gcgagatcaa caactaccac cacgcccacg   3960
acgcctacct gaacgccgtc gtgggaaccg cctgatcaa aaagtacccct aagctggaaa   4020
gcgagttcgt gtacggcgac tacaaggtgt acgacgtgcg gaagatgatc gccaagagcg   4080
agcaggaaat cggcaaggct accgccaagt acttcttcta cagcaacatc atgaactttt   4140
tcaagaccga gattaccctg gccaacgcg agatccggaa gcggcctctg atcgagacaa   4200
acggcgaaac cggggagatc gtgtgggata agggccggga ttttgccacc gtgcggaaag   4260
tgctgagcat gccccaagtg aatatcgtga aaaagaccga ggtgcagaca ggcggcttca   4320
gcaaagagtc tatcctgccc aagaggaaca gcgataagct gatcgccaga aagaaggact   4380
gggaccctaa gaagtacggc ggcttcgaca gccccaccgt ggcctattct gtgctggtgg   4440
tggccaaagt ggaaaagggc aagtccaaga aactgaagag tgtgaaagag ctgctgggga   4500
tcaccatcat ggaaagaagc agcttcgaga agaatcccat cgactttctg gaagccaagg   4560
gctacaaaga agtgaaaaag gacctgatca tcaagctgcc taagtactcc ctgttcgagc   4620
tggaaaacgg ccggaagaga atgctggcct ctgccggcga actgcagaag ggaaacgaac   4680
tggccctgcc ctccaaatat gtgaacttcc tgtacctggc cagccactat gagaagctga   4740
agggctcccc cgaggataat gagcagaaac agctgtttgt ggaacagcac aagcactacc   4800
tggacgagat catcgagcag atcagcgagt ctccaagag agtgatcctg gccgacgcta   4860
atctggacaa agtgctgtcc gcctacaaca agcacgga taagcccatc agagagcagg   4920
ccgagaatat catccacctg tttacctga ccaatctggg agccctgcc gcttcaagt   4980
actttgcac caccatcgac cggaagaggt acaccagcac caaagaggtg ctggacgcca   5040
ccctgatcca ccagagcatc accggcctgt acgagacacg gatcgacctg tctcagctgg   5100
```

```
gaggtgactc tggaggatct agcggaggat cctctggcag cgagacacca ggaacaagcg   5160
agtcagcaac accagagagc agtggcggca gcagcggcgg cagcagcacc ctaaatatag   5220
aagatgagta tcggctacat gagacctcaa aagagccaga tgtttctcta gggtccacat   5280
ggctgtctga ttttcctcag gcctgggcgg aaaccggggg catgggactg gcagttcgcc   5340
aagctcctct gatcatacct ctgaaagcaa cctctacccc cgtgtccata aaacaataac   5400
ccatgtcaca agaagccaga ctggggatca agcccacat acagagactg ttggaccagg    5460
gaatatggta ccctgccagt cccctggaa cacgccctg ctacccgtta agaaaccagg     5520
gactaatgat tataggcctg tccaggatct gagagaagtc aacaagcggg tggaagacat   5580
ccaccccacc gtgcccaacc cttacaacct cttgagcggg ctcccaccgt cccaccagtg   5640
gtacactgtg cttgatttaa aggatgcctt tttctgcctg agactccacc ccaccagtca   5700
gcctctcttc gcctttgagt ggagagatcc agagatggga atctcaggac aattgacctg   5760
gaccagactc ccacagggtt tcaaaaacag tcccaccctg tttaatgagg cactgcacag   5820
agacctagca gacttccgga tccagcaccc agacttgatc ctgctacagt acgtggatga   5880
cttactgctg gccgccactt ctgagctaga ctgccaacaa ggtactcggg ccctgttaca   5940
aaccctaggg aacctcgggt atcgggcctc ggccaagaaa gcccaaattt gccagaaaca   6000
ggtcaagtat ctggggtatc ttctaaaaga gggtcagaga tggctgactg aggccagaaa   6060
agagactgtg atggggcagc ctactccgaa gaccctcga caactaaggg agttcctagg    6120
gaaggcaggc ttctgtcgcc tcttcatccc tgggtttgca gaaatggcag ccccccgta    6180
ccctctcacc aaaccgggga ctctgtttaa ttggggccca gaccaacaaa aggcctatca   6240
agaaatcaag caagctcttc taactgcccc agccctgggg ttgccagatt tgactaagcc   6300
cttTgaactc tttgtcgacg agaagcaggg ctacgccaaa ggtgtcctaa cgcaaaaact   6360
gggaccttgg cgtcggccgg tggcctacct gtccaaaaag ctagaccag tagcagctgg   6420
gtggcccct tgcctacgga tggtagcagc cattgccgta ctgacaaaag atgcaggcaa    6480
gctaaccatg ggacagccac tagtcattct ggccccccat gcagtagagg cactagtcaa   6540
acaacccccc gaccgctggc tttccaacgc ccggatgact cactatcagg ccttgctttt   6600
ggacacggac cgggtccagt tcggaccggt ggtagccgta aacccggcta cgctgctccc   6660
actgctgag aaggctgc aacacaactg ccttgatatc ctggccgaag cccacggaac     6720
ccgacccgac ctaacggacc agccgctccc agacgccgac cacacctggt acacggatgg   6780
aagcagtctc ttacaagagg gacagcgtaa ggcgggagct gcggtgacca ccgagaccga   6840
ggtaatctgg gctaaagccc tgccagccgg gacatccgct cagcgggctg aactgatagc   6900
actcacccag gccctaaaga tggcagaagg taagaagcta aatgtttata ctgatagccc   6960
ttatgctttt gctactgccc atatccatgg agaaatatac agaaggcgtg ggtggctcac   7020
atcagaaggc aaagagatca aaaataaaga cgagatcttg gccctactaa agccctctt    7080
tctgcccaaa agacttagca taatccattg tccaggacat caaaagggac acagcgccga   7140
ggctagaggc aaccgatgg ctgaccaagc ggcccgaaag gcagccatca cagagactcc    7200
agacacctct accctcctca tagaaaattc atcaccctct ggcggctcaa aaagaaccgc   7260
cgacggcagc gaaaaaagaa ccgctgactc tcaacattcc acacctccaa aaaccaagcg   7320
aaaagtggaa ttcgagccca agaagaagag gaaagtcgga agcggagcta ctaacttcag   7380
cctgctgaag caggctggcg acgtggagga gaaccctgga cctccaaaaa agaaaagaa    7440
agtgtatccc tatgatgtcc ccgattatgc cggttcaaga gccctggtcg tgattagact   7500
gagccgagtg acagacgcca ccacaagtcc cgagagacag ctggaatcat gccagcagct   7560
ctgtgctcag cggggttggg atgtggtcgg cgtggcagag atctggacg tgagcggggc    7620
cgtcgatcca ttcgacagaa agaggaggcc caacctgcag agatggctcg cttTcgagga   7680
acagccctTT gatgtgatcg tcgcctacag agtggaccgg ctgacccgct caattcgaca   7740
tctccagcag ctggtgcatt gggctgagga ccacaagaaa ctggtggtca gcgcaacaga   7800
agcccacttc gatactacca caccttttgc cgctgtggtc atcgcactga tgggcactgt   7860
ggcccagatg gagctgaag ctatcaagga gcgaaacagg agcgcagccc attTcaatat    7920
tagggccggt aaatacagag gctccctgcc cccttgggga tatctcccta ccagggtgga   7980
tgggagtgg agactggtgc cagaccccgt ccagagagag cggattctgg aagtgtacca    8040
cagagtggtc gataaccacg aaccactcca tctggtggca cacgacctga atagacgcgg   8100
cgtgctctct ccaaaggatt attTtgctca gctgcaggga agagcagcca agggaagaga   8160
atggagtgct actgcactga agagatctat gatcagtgag gctatgctgg gttacgcaac   8220
actcaatggc aaaactgtcc gggacgatga cggagcccct ctggtgagg ctgagcctat    8280
tctcaccaga gagcagctcg aagctctgcg ggcagaactg gtcaagacta gtcgcgccaa   8340
acctgccgtg agcaccccaa gcctgctcct gagggtgctg ttctgcgccg tctgtgagga   8400
gccagcatac aagtttgccg gcggagggc caaacatccc cgctatcgat gcagagcat    8460
ggggttccct aagcactgtg aaacgggac agtggccatg gctgagtggg acgccttttg   8520
cgaggaacag gtgctggatc tcctgggtga cgctgagcgg ctggaaaag tgtgggtggc    8580
aggatctgac tccgctgtgg agtcggcaga agtcaatgcc gagtcgtgg atctgacttc    8640
cctcatcgga tctcctgcat atagagctgg gtccccacag agagaagctc tggacgcacg   8700
aattgctgca ctcgctgcta acaggagga actggagggc ctggaggcca ggccctctgg    8760
atgggagtgg cgagaaaccg gacagaggtt tggggattgg tggagggagc aggacaccgc   8820
agccaagaac acatggctga gatccatgaa tgtccggctc acattcgacg tgcgcggtgg   8880
cctgactcga accatcgatt ttgcgaccct gcaggagtat gaacagcact tgaactgagg   8940
gtccgtggtc gaaagactgc acactgggat gtcctaggtt taaacccgct gatcagcctc   9000
gactgtgcct tctagttgcc agccatctgt tgtttgcccc tcccccgtgc cttccttgac   9060
cctgaaggt gccactccca ctgtcctttc ctaataaaat gagaaattg catcgcattg    9120
tctgagtagg tgtcattcta ttctggggg tggggtgggg caggacagca agggggagga   9180
ttgggaagac aatagcaggc atgctgggga tgcggtgggc tctatggctt ctgaggcgga   9240
aagaaccagc tggggctcga taccgtcgac ctctagctag agcttggcgt aatcatggtc   9300
atagctgttt cctgtgtgaa attgttatcc gctcacaatt ccacacaaca tacgagccgg   9360
aagcataaag tgtaaagcct agggtgccta atgagtgagc taactcacat taattgcgtt   9420
gcgctcactg cccgctttcc agtcgggaaa cctgtcgtgc cagctgcatt aatgaatcgg   9480
ccaacgcgg ggagaggcg gttTgcgtat tgggcgctct tccgcttcct cgctcactga    9540
ctcgctgcgc tcggtcgttc ggctgcggcg agcggtatca gctcactcaa aggcggtaat   9600
acggttatcc acagaatcag gggataacgc aggaaagaac atgtgagcaa aaggccagca   9660
aaaggccagg aaccgtaaaa aggccgcgtt gctggcgttt ttccataggc tccgcccccc   9720
tgacgagcat cacaaaaatc gacgctcaag tcagaggtgg cgaaacccga caggactata   9780
aagataccag gcgtttcccc ctggaagctc cctcgtgcgc tctcctgttc cgaccctgcc   9840
```

```
gcttaccgga taccgtccg cctttctccc ttcgggaagc gtggcgcttt ctcatagctc  9900
acgctgtagg tatctcagtt cggtgtaggt cgttcgctcc aagctgggct gtgtgcacga  9960
accccccgtt cagcccgacc gctgcgcctt atccggtaac tatcgtcttg agtccaaccc 10020
ggtaagacac gacttatcgc cactggcagc agccactggt aacaggatta gcagagcgag 10080
gtatgtaggc ggtgctacag agttcttgaa gtggtggcct aactacggct acactgaaag 10140
aacagtattt ggtatctgcg ctctgctgaa gccagttacc ttcggaaaaa gagttggtag 10200
ctcttgatcc ggcaaacaaa ccaccgctgg tagcggtggt ttttttgttt gcaagcagca 10260
gattacgcgc agaaaaaaag gatctcaaga agatcctttg atcttttcta cggggtctga 10320
cgctcagtgg aacgaaaact cacgttaagg gattttggtc atgagattat caaaaaggat 10380
cttcacctag atccttttaa attaaaaatg aagttttaaa tcaatctaaa gtatatatga 10440
gtaaacttgg tctgacagtt accaatgctt aatcagtgag gcacctatct cagcgatctg 10500
tctatttcgt tcatccatag ttgcctgact ccccgtcgtg tagataacta cgatacggga 10560
gggcttacca tctggcccca gtgctgcaat gataccgcga gacccacgct caccggctcc 10620
agatttatca gcaataaacc agccagccgg aagggccgag cgcagaagtg gtcctgcaac 10680
tttatccgcc tccatccagt ctattaattg ttgccgggaa gctagagtaa gtagttcgcc 10740
agttaatagt ttgcgcaacg ttgttgccat tgctacaggc atcgtggtgt cacgctcgtc 10800
gtttggtatg gcttcattca gctccggttc caacgatca aggcgagtta catgatcccc 10860
catgttgtgc aaaaaagcgg ttagctcctt cggtcctccg atcgttgtca gaagtaagtt 10920
ggccgcagtg ttatcactca tggttatggc agcactgcat aattctctta ctgtcatgcc 10980
atccgtaaga tgcttttctg tgactggtga gtactcaacc aagtcattct gagaatagtg 11040
tatgcggcga ccgagttgct cttgcccggc gtcaatacgg gataataccg cgccacatag 11100
cagaacttta aaagtgctca tcattggaaa acgttcttcg gggcgaaaac tctcaaggat 11160
cttaccgctg ttgagatcca gttcgatgta acccactcgt gcacccaact gatcttcagc 11220
atcttttact tcaccagcg tttctgggtg agcaaaaaca ggaaggcaaa atgccgcaaa 11280
aaagggaata agggcgacac ggaaatgttg aatactcata ctcttccttt ttcaatatta 11340
ttgaagcatt tatcagggtt attgtctcat gagcggatac atatttgaat gtatttagaa 11400
aaataaacaa atagggggttc cgcgcacatt tcc                             11433

SEQ ID NO: 384         moltype = DNA  length = 11056
FEATURE                Location/Qualifiers
misc_feature           1..11056
                       note = Description of Artificial Sequence: Synthetic
                       polynucleotide
source                 1..11056
                       mol_type = other DNA
                       organism = synthetic construct
SEQUENCE: 384
ccgaaaagtg ccacctgacg tcgacggatc gggagatcga tctcccgatc ccctagggtc   60
gactctcagt acaatctgct ctgatgccgc atagttaagc cagtactctg tccctgcttg  120
tgtgttggag gtcgctgagt agtgcgcgag caaaatttaa gctacaacaa ggcaaggctt  180
gaccgacaat tgcatgaaga atctgcttag ggttaggcgt tttgcgctgc ttcgcgatgt  240
acgggccaga tatacgcgtt gacattgatt attgactagt tattaatagt aatcaattac  300
ggggtcatta gttcatagcc catatatgga gttccgcgtt acataactta cggtaaatgg  360
cccgcctggc tgaccgccca acgacccccg cccattgacg tcaataatga cgtatgttcc  420
catagtaacg ccaatagggga cttttccattg acgtcaatgg gtggagtatt tacggtaaac  480
tgcccacttg gcagtacatc aagtgtatca tatgccaagt acgccccta ttgacgtcaa  540
tgacggtaaa tggcccgcct ggcattatgc ccagtacatg accttatggg actttcctac  600
ttggcagtac atctacgtat tagtcatcgc tattaccatg gtgatgcggt tttggcagta  660
catcaatggg cgtggatagc ggtttgactc acggggattt ccaagtctcc accccattga  720
cgtcaatggg agtttgtttt ggcaccaaaa tcaacgggac tttccaaaat gtcgtaacaa  780
ctccgcccca ttgacgcaaa tgggcggtag gcgtgtacgg tgggaggtct atataagcag  840
agctggttta gtgaaccgtc agatccgcta gagatccgcg gccgctaata cgactcacta  900
tagggagagc cgccaccatg aaacggacag ccgacgaaag cgagttcgag tcaccaaaga  960
agaagcggaa agtcgacaag aagtacagca tcggcctgga catcggcacc aactctgtgg 1020
gctgggccgt gatcacggac gagtacaagg tgcccgcaa gaaattcaag gtgctgggca 1080
acaccgaccg gcacagcatc aagaagaacc tgatcggagc cctgctgttc gacagcggcg 1140
aaacagccga ggcaccccgg ctgaagagaa ccgccgaaag aagataccc agacggaaga 1200
accggatctg ctatctgcaa gagatcttca gcaacgagat ggccaaggtg gacgacagct 1260
tcttccacag actggaagag tccttcctgg tggaagagga taagaagcac gagcggcca 1320
ccatcttcgg caacatcgtg gacgaggtgg cctaccacga gaagtaccc accatctacc 1380
acctgagaaa gaaactggtg gacagcaccg acaaggccga cctgcggctg atctatctgg 1440
ccctggccca catgatcaag ttccggggcc acttcctgat cgaggcgac ctgaaccccg 1500
acaacagcga cgtggacaag ctgttcatcc agctggtgca gacctacaac cagctgttcg 1560
aggaaaaccc catcaacgcc agcggcgtgg acgccaaggc catcctgtct gccagactga 1620
gcaagagcag acggctggaa aatctgatcg cccagctgcc cggcgagaag aagaatggcc 1680
tgttcggaaa cctgattgcc ctgagcctgg gcctgacccc caacttcaag agcaacttcg 1740
acctggccga ggatgccaaa ctgcagctga gcaaggacac ctacgacgac gacctggaca 1800
acctgctggc ccagatcggc gaccagtacg ccgacctgtt tctggccgcc aagaacctgt 1860
ccgacgccat cctgctgagc gacatcctga gagtgaacac cgaatccacc aaggcccccc 1920
tgagcgcctc tatgatcaag agatacgacg agcaccacca ggacctgacc ctgctgaaag 1980
ctctcgtgcg gcagcagctg cctgagaagt acaaagagat tttcttcgac cagagcaaga 2040
acggctacgc cggctacatt gacggcggag ccagccagga agagttctac aagttcatca 2100
agccatcct ggaaaagatg gacggcaccg aggaactgct cgtgaagctg aacagagagg 2160
acctgctgcg gaagcagcgg accttcgaca acggcagcat ccccaccag atccacgtgg 2220
gagagctgca cgccattctg cggcggcagg aagatttta ccccattctg aaggacaacc 2280
gggaaaagat cgagaagatc ctgaccttcc gcatccccta ctacgtgggc cctctggcca 2340
ggggaaacag cagattcgcc tggatgacca gaaagagcga ggaaaccatc accccctgga 2400
acttcgagga agtggtggac aagggcgctt ccgcccagag cttcatcgag cggatgacca 2460
acttcgataa gaacctgccc aacgagaagg tgctgccaa gcacagcctg ctgtacgagt 2520
```

```
acttcaccgt gtataacgag ctgaccaaag tgaaatacgt gaccgaggga atgagaaagc  2580
ccgccttcct gagcggcgag cagaaaaagg ccatcgtgga cctgctgttc aagaccaacc  2640
ggaaagtgac cgtgaagcag ctgaaagagg actacttcaa gaaaatcgag tgcttcgact  2700
ccgtggaaat ctccggcgtg gaagatcggt tcaacgcctc cctgggcaca taccacgatc  2760
tgctgaaaat tatcaaggac aaggacttcc tggacaatga ggaaaacgag gacattctgg  2820
aagatatcgt gctgaccctg acactgtttg aggacagaga gatgatcgag aacggctga  2880
aaacctatgc ccacctgttc gacgacaaag tgatgaagca gctgaagcgg cggagataca  2940
ccggctgggg caggctgagc cggaagctga tcaacggcat ccgggacaag cagtccggca  3000
agacaatcct ggatttcctg aagtccgacg gcttcgccaa cagaaacttc atgcagctga  3060
tccacgacga cagcctgacc tttaaagagg acatccagaa agcccaggtg tccggccagg  3120
gcgatagcct gcacgagcac attgccaatc tggccggcag ccccgccatt aagaagggca  3180
tcctgcagac agtgaaggtg gtggacgagc tcgtgaaagt gatgggccgg cacaagcccg  3240
agaacatcgt gatcgaaatg gccagagaga accagaccac ccagaaggga cagaagaaca  3300
gccgcgaggg aatgaagcgg atcgaagagg gcatcaaaga gctgggcagc cagatcctga  3360
aagaacaccc cgtggaaaac acccagctgc agaacgagaa gctgtacctg tactacctgc  3420
agaatgggcg ggatatgtac gtggaccagg aactggacat caaccggctg tccgactacg  3480
atgtggacgc tatcgtgcct cagagctttc tgaaggacga ctccatcgac aacaaggtgc  3540
tgaccagaag cgacaagaac cggggcaaga gcgacaacgt gcccteegaa gaggtcgtga  3600
agaagatgaa gaactactgg cggcagctgc tgaacgccaa gctgattacc cagagaaagt  3660
tcgacaatct gaccaaggcc gagagaggcg gcctgagcga actggataag gccggcttca  3720
tcaagagaca gctggtggaa acccggcaga tcacaaagca cgtggcacag atcctggact  3780
cccggataaa cactaagtac gacgaaatg acaagctgat ccgggaagtg aaagtgatca  3840
ccctgaagtc caagctggtg tccgatttcc ggaaggattt ccagttttac aaagtgcgcg  3900
agatcaacaa ctaccaccac gcccacgacg cctacctgaa cgccgtcgtg gaaccgccc  3960
tgatcaaaaa gtaccctaag ctggaaagcg agttcgtgta cggcgactac aagtgtacg  4020
acgtgcggaa gatgatcgcc aagagcgagc aggaaatcgg caaggctacc gccaagtact  4080
tcttctacag caacatcatg aacttttca agaccgagat taccctggcc aacggcgaga  4140
tccggaagcg gcctctgatc gagacaaacg gcgaaaccgg ggagatcgtg tgggataagg  4200
gccgggattt tgccaccgtg cggaaagtgc tgagcatgcc ccaagtgaat atcgtgaaaa  4260
agaccgaggt gcagacaggc ggcttcagca aagtctat cctgcccaag aggaacagcg  4320
ataagctgat cgccagaaaa aaggactggg accctaagaa gtacggcggc ttcgacagcc  4380
ccaccgtggc ctattctgtg ctggtggtgg ccaaagtgga aaagggcaag tccaagaaac  4440
tgaagagtgt gaaagagctg ctggggatca ccatcatgga aagaagcagc ttcgagaaga  4500
atcccatcga cttttctggaa gccaagggct acaaagaagt gaaaaaggac ctgatcatca  4560
agctgcctaa gtactccctg ttcgagctgg aaaacggccg gaagaatg ctggcctctg  4620
ccggcgaact gcagaaggga acgaactggg ccctgcccte caaatatgtg aacttcctgt  4680
acctggccag ccactatgag aagctgaagg ctccccga ggataatgag cagaaacagc  4740
tgtttgtgga acagcacaag cactacctgg acgagatcat cgagcagatc agcgagttct  4800
ccaagagagt gatcctggcc gacgctaatc tggacaaagt gctgtccgcc tacaacaagc  4860
accgggataa gcccatcaga gagcaggccg agaatatcat ccacctgttt accctgacca  4920
atctgggagc ccctgccgcc ttcaagtact ttgacaccac catcgaccgg aagaggtaca  4980
ccagcaccaa agaggtgctg gacgccaccc tgatccacca gagcatcacc ggcctgtacg  5040
agacacggat cgacctgtct cagctgggag gtgactctgg aggatcgctg ggaggatcct  5100
ctggcagcga gacaccagga acaagcgagt cagcaacacc agagagctct ggtagcgaga  5160
cacccggtac cagtgaaagc gccacgccag aaagcagtgg gagtgagact ccgggtacat  5220
ctgaatcagc gacaccggaa tcaagtgcg gcagcagcgg cggcagcagc ccctaaata  5280
tagaagatga gtatcggcta catgagacct caaaagagcc agatgttct ctagggtcca  5340
catggctgtc tgattttcct caggcctggg cggaaaccgg gggcatggga ctggcagttc  5400
gccaagctcc tctgatcata cctctgaaag caacctctac cccgtgtcc ataaaacaat  5460
accccatgtc acaagaagcc agactgggga tcaagccca catacagaga ctgttggacc  5520
agggaatact ggtaccctgc cagtcccct ggaacacgcc cctgctaccc gttaagaaac  5580
cagggactaa tgattatagg cctgtccagg atctgagaga agtcaacaag cgggtggaag  5640
acatccaccc caccgtgccc aaccttaca acctcttgag cgggcccca ccgtcccacc  5700
agtggtacac tgtgcttgat ttaaaggatg cctttttctg cctgagactc caccccacca  5760
gtcagcctct cttcgccttt gagtcggaag atccagagat gggaatctca ggacaattga  5820
cctggaccag actcccacag ggtttcaaaa acagtcccac cctgtttaat gaggcactga  5880
acagagacct agcagacttc cggatccagc acccagactt gatcctgcta cagtacgtgg  5940
atgacttact gctggccgcc acttctgagc tagactgcca acaaggtact cgggccctgt  6000
tacaaaccct agggaacctc gggtatcggg cctcggccaa gaaagcccaa atttgccaga  6060
aacaggtcaa gtatctgggg tatcttctaa aagagggtca gagatggctg actgaggcca  6120
gaaaagagac tgtgatgggg cagcctactc gaagaccc tcgacaacta agggagttcc  6180
tagggaaggc aggcttctgt cgcctcttca tccctgggtt tgcagaaatg gcagccccc  6240
tgtaccctct caccaaaccg gggactctgt ttaattgggg cccagaccaa caaaggcct  6300
atcaagaaat caagcaagct cttctaactg ccccagccct ggggttgcca gatttgacta  6360
agccctttga actctttgtc gacgagaagc agggctacgc caaaggtgtc ctaacgcaaa  6420
aactgggacc ttggcgtcgg ccggtggcct acctgtccaa aaagctagac ccagtagcag  6480
ctgggtggcc cccttgccta cggatggtag cagccattgc cgtactgaca aaggatgcag  6540
gcaagctaac catgggacag ccactagtca ttctggccc ccatgcagta gaggcactag  6600
tcaaacaacc ccccgaccgc tggcttttcca acgcccgat gactcactat caggccttgc  6660
ttttggacac ggaccgggtc cagttcggac cggtggtagc cctgaaccg gctacgctgc  6720
tcccactgcc tgaggaaggg ctgcaacaca actgccttga tgggacaggt ggcggtggtg  6780
tcaccgtcaa gttcaagtac aagggtgagg aacttgaagt tgatattagc aaaatcaaga  6840
aggtttggcg cgttggtaaa atgatatctt ttacttatga cgacaacggc aagacaggta  6900
gagggcagt gtctgagaaa gacgccccca aggagctgtt ccaaagttg gaaaagtctg  6960
ggaaaaagtc tggcggctca aaaagaaccg ccgacggcag cgaattcgag cccaagaaga  7020
agaggaaagt cggaggtgc gggagcccaa aaaagaaaag aaaagtgtat ccctatgatg  7080
tccccgatta tgccggttca agagccctgg tcgtgattag actgagccga gtgacagacg  7140
ccaccacaag tcccgagaga cagctggaat catgccagca gctctgtgct cagcgggttt  7200
gggatgtggt cggcgtggca gaggatctgg acgtgagcgg ggccgtcgat ccattcgaca  7260
```

```
gaaagaggag gcccaacctg gcaagatggc tcgctttcga ggaacagccc tttgatgtga   7320
tcgtcgccta cagagtggac cggctgaccc gctcaattcg acatctccag cagctggtgc   7380
attgggctga ggaccacaag aaactggtgg tcagcgcaac agaagcccac ttcgatacta   7440
ccacacctt  tgccgctgtg gtcatcgcac tgatgggcac tgtggcccag atggagctcg   7500
aagctatcaa ggagcgaaac aggagcgcag cccatttcaa tattagggcc ggtaaataca   7560
gaggctccct gccccttgg  ggatatctcc ctaccagggt ggatgggag tggagactgg    7620
tgccagaccc cgtccagaga gagcggattc tggaagtgta ccacagagtg gtcgataacc   7680
acgaaccact ccatctggtg gcacacgacc tgaatagacg cggcgtgctc tctccaaagg   7740
attattttgc tcagctgcag ggaagagagc cacagggaag agaatggagt gctactgcac   7800
tgaagagatc tatgatcagt gaggctatgc tgggttacgc aacactcaat ggcaaaactg   7860
tccgggacga tgacggagcc cctctggtga gggctgagcc tattctcacc agagagcagc   7920
tcgaagctct gcgggcagaa ctggtcaaga ctagtcgcgc caaacctgcc gtgagcaccc   7980
caagcctgct cctgagggtg ctgttctgcg ccgtctgtgg agagccagca tacaagtttg   8040
ccggcggagg gcgcaaacat ccccgctatc gatgcaggag catgggttc  cctaagcact   8100
gtggaaacgg gacagtggcc atggctgagt gggacgcctt ttgcgaggaa caggtgctgg   8160
atctcctggg tgacgctgag cggctggaaa aagtgtgggt ggcaggatct gactccgctg   8220
tggagctggc agaagtcaat gccgagctcg tggatctgac ttccctcatc ggatctcctg   8280
catatagac  tgggtcccca cagagagaag ctctcgacgc acgaattgct gcactcgccg   8340
ctagacagga ggaactggag ggcctggagg ccaggccctc tggatgggag tggcgagaaa   8400
ccggacagag gtttggggat tggtggaggg agcaggacac cgcagccaag aacacatggc   8460
tgagatccat gaatgtccgg ctcacattcg acgtgcgcg  tggcctgact cgaaccatcg   8520
attttggcga cctgcaggag tatgaacagc acctgagact tgggttccgtg gtcgaaagac   8580
tgcacactgg gatgtcctag gtttaaaccc gctgatcagc ctcgactgtg ccttctagtt   8640
gccagccatc tgttgtttgc ccctcccccg tgccttcctt gaccctgaa  ggtgccactc    8700
ccactgtcct ttcctaataa aatgagaaaa ttgcatcgca ttgtctgagt aggtgtcatt   8760
ctattctggg gggtggggtg gggcaggaca gcaagggga  ggattgggaa gacaatagca    8820
ggcatgctgg ggatgcggtg ggctctatgg cttctgaggc ggaaagaacc agctgggggct  8880
cgataccgtc gacctctagc tagagcttgg cgtaatcatg gtcatagctg tttcctgtgt   8940
gaaattgtta tccgctcaca attccacaca acatacgagc cggaagcata aagtgtaaag   9000
cctagggtgc ctaatgagtg agctaactca cattaattgc gttgcgctca ctgcccgctt   9060
tccagtcggg aaacctgtcg tgccagctgc attaatgaat cggccaacgc gcggggagag   9120
gcggtttgcg tattgggcgc tcttccgctt cctcgctcac tgactcgctg cgctcggtcg   9180
ttcggctgcg gcgagcggta tcagctcact caaaggcggt aatacggtta tccacagaat   9240
caggggataa cgcaggaaag aacatgtgag caaaaggcca gcaaaaggcc aggaaccgta   9300
aaaaggccgc gttgctggcg tttttccata ggctccgccc ccctgacgag catcacaaaa   9360
atcgacgctc aagtcagagg tggcgaaacc cgacaggact ataaagatac caggcgtttc   9420
cccctggaag ctccctcgtg cgctctcctg ttccgaccct gccgcttacc ggatacctgt   9480
ccgcctttct cccttcggga agcgtggcgc tttctcatag ctcacgctgt aggtatctca   9540
gttcggtgta ggtcgttcgc tccaagctgg gctgtgtgca cgaaccccc  gttcagccg    9600
accgctgcgc cttatccggt aactatcgtc ttgagtccaa cccggtaaga cacgacttat   9660
cgccactggc agcagccact ggtaacagga ttagcagagc gaggtatgta ggcggtgcta   9720
cagagttctt gaagtggtgg cctaactacg gctacactag aagaacagta tttggtatct   9780
gcgctctgct gaagccagtt accttcggaa aaagagttgg tagtcttga tccggcaaac    9840
aaaccaccgc tggtagcggt ggtttttttg tttgcaagca gcagattacg cgcagaaaaa   9900
aaggatctca agaagatcct ttgatctttt ctacggggtc tgacgctcag tggaacgaaa   9960
actcacgtta agggattttg gtcatgagat tatcaaaaag gatcttcacc tagatccttt  10020
taaattaaaa atgaagtttt aaatcaatct aaagtatata tgagtaaact tggtctgaca  10080
gttaccaatg cttaatcagt gaggcaccta tctcagcgat ctgtctattt cgttcatcca  10140
tagttgcctg actccccgtc gtgtagataa ctacgatacg gagggctta  ccatctggcc   10200
ccagtgctga atgataccg cgagacccac gctcaccggc tccagattta tcagcaataa    10260
accagccagc cggaagggcc gagcgcagaa gtggtcctgc aactttatcc gcctccatcc  10320
agtctattaa ttgttgccgg gaagctagag taagtagttc gccagttaat agtttgcgca  10380
acgttgttgc cattgctaca ggcatcgtgg tgtcacgctc gtcgtttggt atggcttcat  10440
tcagctccgg ttcccaacga tcaaggcgag ttacatgatc cccatgttg  tgcaaaaaag   10500
cggttagctc cttcggtcct ccgatcgttg tcagaagtaa gttggccgca gtgttatcac  10560
tcatggttat ggcagcactg cataattctc ttactgtcat gccatccgta agatgctttt  10620
ctgtgactgt tgagtactca accaagtcat tctgagaata gtgtatgcgg cgaccgagtt  10680
gctcttgccc ggcgtcaata cgggataata ccgcgccaca tagcagaact ttaaaagtgc  10740
tcatcattgg aaaacgttct cggggcgaa  aactctcaag gatcttaccg ctgttgagat   10800
ccagttcgat gtaacccact cgtgcaccca actgatcttc agcatctttt actttcacca  10860
gcgtttctgg gtgagcaaaa acaggaaggc aaaatgccgc aaaaaaggga ataagggcga  10920
cacgaaatg  ttgaatactc atactcttcc ttttcaata ttattgaagc atttatcagg   10980
gttattgtct catgagcgga tacatatttg aatgtattta gaaaaataaa caaatagggg  11040
ttccgcgcac atttcc                                                 11056
```

SEQ ID NO: 385      moltype = DNA  length = 2367
FEATURE               Location/Qualifiers
misc_feature      1..2367
                     note = Description of Artificial Sequence: Synthetic
                     polynucleotide
source                 1..2367
                     mol_type = other DNA
                     organism = synthetic construct
SEQUENCE: 385

```
tgttgagatc cagttcgatg taacccactc gtgcacccaa ctgatcttca gcatctttta    60
ctttcaccag cgtttctggg tgagcaaaaa caggaaggca aaatgccgca aaaaaggaa   120
taagggcgac acgaaatgt  tgaatactca tactcttcct tttcaatat tattgaagca   180
tttatcaggg ttattgtctc atgagcggat acatatttga atgtattag  aaaaataaac   240
aaatagggt  tccgcgcaca tttccccgaa aagtgccacc tgacgtcgct agctgtacaa   300
```

```
aaaagcaggc tttaaaggaa ccaattcagt cgactggatc cggtaccaag gtcgggcagg    360
aagagggcct atttcccatg attccttcat atttgcatat acgatacaag gctgttagag    420
agataattag aattaatttg actgtaaaca caaagatatt agtacaaaat acgtgacgta    480
gaaagtaata atttcttggg tagtttgcag ttttaaaatt atgttttaaa atggactatc    540
atatgcttac cgtaacttga aagtatttcg atttcttggc tttatatatc ttgtggaaag    600
gacgaaacac cgctattctc gcagctcacc agttttagag ctagaaatag caagttaaaa    660
taaggctagt ccgttatcaa cttgaaaaag tggcaccgag tcggtgcgac gagcgcggcg    720
atatcatcat ccatggccgg atgatcctga cgacggagac cgccgtcgtc gacaagccgg    780
cctgagctgc gagaattttt ttaagcttgg gccgctcgag gtacctctct acatatgaca    840
tgtgagcaaa aggccagcaa aaggccagga accgtaaaaa ggccgcgttg ctggcgtttt    900
tccataggct ccgcccccct gacgagcatc acaaaaatcg acgctcaagt cagaggtggc    960
gaaacccgac aggactataa agataccagg cgtttccccc tggaagctcc ctcgtgcgct   1020
ctcctgttcc gaccctgccg cttaccggat acctgtccgc ctttctccct tcgggaagcg   1080
tggcgcttc tcatagctca cgctgtaggt atctcagttc ggtgtaggtc gttcgctcca   1140
agctgggctg tgtgcacgaa ccccccgttc agcccgaccg ctgcgcctta tccggtaact   1200
atcgtcttga gtccaacccg gtaagacacg acttatcgcc actggcagca gccactggta   1260
acaggattag cagagcgagg tatgtaggcg gtgctacaga gttcttgaag tggtggccta   1320
actacggcta cactagaaga acagtatttg gtatctgcgc tctgctgaag ccagttacct   1380
tcggaaaaag agttggtagc tcttgatccg gcaaacaaac caccgctggt agcggtggtt   1440
tttttgtttg caagcagcag attacgcgca gaaaaaaagg atctcaagaa gatcctttga   1500
tcttttctac ggggtctgac gctcagtgga acgaaaactc acgttaaggg attttggtca   1560
tgagattatc aaaaaggatc ttcacctaga tccttttaaa ttaaaaatga agttttaaat   1620
caatctaaag tatatatgag taaacttggt ctgacagtta ccaatgctta atcagtgagg   1680
cacctatctc agcgatctgt ctatttcgtt catccatagt tgcctgactc cccgtcgtgt   1740
agataactac gatacgggag ggcttaccat ctggccccag tgctgcaatg ataccgcgag   1800
atccacgctc accggctcca gatttatcag caataaacca gccagccgga agggccgagc   1860
gcagaagtgg tcctgcaact ttatccgcct ccatccagtc tattaattgt tgccgggaag   1920
ctagagtaag tagttcgcca gttaatagtt tgcgcaacgt tgttgccatt gctacaggca   1980
tcgtggtgtc acgctcgtcg tttggtatgg cttcattcag ctccggttcc caacgatcaa   2040
ggcgagttac atgatccccc atgttgtgca aaaaagcggt tagctccttc ggtcctccga   2100
tcgttgtcag aagtaagttg gccgcagtgt tatcactcat ggttatggca gcactgcata   2160
attctcttac tgtcatgcca tccgtaagat gcttttctgt gactggtgag tactcaacca   2220
agtcattctg agaatagtgt atgcggcgac cgagttgctc ttgcccggcg tcaatacggg   2280
ataataccgc gccacatagc agaactttaa aagtgctcat cattggaaaa cgttcttcgg   2340
ggcgaaaact ctcaaggatc ttaccgc                                       2367

SEQ ID NO: 386         moltype = DNA  length = 2280
FEATURE                Location/Qualifiers
misc_feature           1..2280
                       note = Description of Artificial Sequence: Synthetic
                       polynucleotide
source                 1..2280
                       mol_type = other DNA
                       organism = synthetic construct
SEQUENCE: 386
ctccatccag tctattaatt gttgccggga agctagagta agtagttcgc cagttaatag     60
tttgcgcaac gttgttgcca ttgctacagg catcgtggtg tcacgctcgt cgtttggtat    120
ggcttcattc agctccggtt cccaacgatc aaggcgagtt acatgatccc catgttgtg    180
caaaaaagcg gttagctcct tcggtcctcc gatcgttgtc agaagtaagt tggccgcagt    240
gttatcactc atggttatgg cagcactgca taattctctt actgtcatgc catccgtaag    300
atgcttttct gtgactggtg agtactcaac caagtcattc tgagaatagt gtatgcggcg    360
accgagttgc tcttgcccgg cgtcaatacg ggataatacc gcgccacata gcagaacttt    420
aaaagtgctc atcattggaa aacgttcttc ggggcgaaaa ctctcaagga tcttaccgct    480
gttgagatcc agttcgatgt aacccactcg tgcacccaac tgatcttcag catctttac    540
tttcaccagc gtttctgggt gagcaaaaac aggaaggcaa aatgccgcaa aaaagggaat    600
aagggcgaca cggaaatgtt gaatactcat actcttcctt tttcaatatt attgaagcat    660
ttatcagggt tattgtctca tgagcggata catatttgaa tgtatttaga aaataaaca    720
aataggggtt ccgcgcacat ttccccgaaa agtgccacct gacgtcgcta gctgtacaaa    780
aaagcaggct ttaaaggaac caattcagtc gactggatcc ggtaccaagg tcgggcagga    840
agagggccta tttcccatga ttccttcata tttgcatata cgatacaagg ctgttagaga    900
gataattaga attaatttga ctgtaaacac aaagatatta gtacaaaata cgtgacgtag    960
aaagtaataa tttcttgggt agtttgcagt tttaaaatta tgttttaaaa tggactatca   1020
tatgcttacc gtaacttgaa agtatttcga tttcttggct ttatatatct tgtggaaagg   1080
acgaaacacc gaagccggcc ttgcacatgc gtttagaga tagaaatagc aagttaaaat   1140
aaggctagtc cgttatcaac ttgaaaaagt ggcaccgagt cggtgcgttt ttaagcttgg   1200
gggccgctcg aggtacctct ctacatatga catgtgagca aaaggccagc aaaaggccag   1260
gaaccgtaaa aaggccgcgt tgctggcgtt tttccatagg ctccgccccc tgacgagca   1320
tcacaaaaat cgacgctcaa gtcagaggtg gcgaaacccg acaggactat aaagatacca   1380
ggcgtttccc cctggaagct ccctcgtgcg ctctcctgcg ccgctgccg cttaccgga    1440
tacctgtccg cctttctccc ttcgggaagc gtggcgcttt tcatagctc acgctgtag    1500
gtatctcagt tcggtgtagg tcgttcgctc caagctgggc tgtgtgcacg aaccccccgt   1560
tcagcccgac cgctgcgcct tatccggtaa ctatcgtctt gagtccaacc cggtaagaca   1620
cgacttatcg ccactggcag cagccactgg taacaggatt agcagagcga ggtatgtagg   1680
cggtgctaca gagttcttga agtggtggcc taactacggc tacactagaa gaacagtatt   1740
tggtatctgc gctctgctga agccagttac cttcggaaaa agagtggta gctcttgatc   1800
cggcaaacaa accaccgctg gtagcggtgg tttttttgtt tgcaagcagc agattacgcg   1860
cagaaaaaaa ggatctcaag aagatccttt gatcttttct acggggtctg acgctcagtg   1920
gaacgaaaac tcacgttaag ggattttggt catgagatta tcaaaaagga tcttcaccta   1980
gatcctttta aattaaaaat gaagttttaa atcaatctaa agtatatatg agtaaacttg   2040
```

-continued

```
gtctgacagt taccaatgct taatcagtga ggcacctatc tcagcgatct gtctatttcg  2100
ttcatccata gttgcctgac tccccgtcgt gtagataact acgatacggg agggcttacc  2160
atctggcccc agtgctgcaa tgataccgcg agatccacgc tcaccggctc cagatttatc  2220
agcaataaac cagccagccg aagggccga gcgcagaagt ggtcctgcaa ctttatccgc   2280
```

SEQ ID NO: 387        moltype = DNA   length = 6386
FEATURE               Location/Qualifiers
misc_feature          1..6386
                      note = Description of Artificial Sequence: Synthetic
                      polynucleotide
source                1..6386
                      mol_type = other DNA
                      organism = synthetic construct
SEQUENCE: 387

```
tgagcgcaac gcaattaatg tgagttagct cactcattag gcaccccagg ctttacactt  60
tatgcttccg gctcgtatgt tgtgtggaat tgtgagcgga taacaatttc acacaggaaa  120
cagctatgac catgaggcgc gccggattcg acattgatta ttgactagtt attaatagta  180
atcaattacg gggtcattag ttcatagccc atatatggag ttccgcgtta cataacttac  240
ggtaaatggc ccgcctggct gaccgcccaa cgacccccgc ccattgacgt caataatgac  300
gtatgttccc atagtaacgc caatagggac tttccattga cgtcaatggg tggagtattt  360
acggtaaact gcccacttgg cagtacatca agtgtatcat atgccaagta cgcccccat   420
tgacgtcaat gacggtaaat ggcccgcctg gcattatgcc cagtacatga cctatgggga  480
ctttcctact tggcagtaca tctacgtatt agtcatcgct attaccatgg tcgaggtgag  540
ccccacgttc tgcttcactc tccccatctc ccccccctcc caccccaa ttttgtattt    600
atttatttt taattatttt gtgcagcgat ggggcggggg gggggggggg ggcgcgcgcc   660
rggsgggsg gggsggggsg rgggsgggg sgggsgagg cggagggcgg cggcgcagc     720
caatcagagc ggcgcgctcc gaaagtttcc ttttatgcg aggcggccggc gcgcggcc    780
ctataaaag cgaagcgcgc ggcgggcggg agtcgctgcg cgctgccttc gccccgtgcc   840
ccgctccgcc gccgctcgc gccgcccgcc ccggctctga ctgaccgcgt tactcccaca   900
ggtgagcggg cgggacggcc cttctcctcc gggctgtaat tagcgcttgg tttaatgacg   960
gcttgtttct tttctgtggc tgcgtgaaag ccttgagggg ctccggggagg gccctttgtg  1020
cggggggagc ggctcggggg gtgcgtgcgt gtgtgtgtgc gtggggagcg ccgcgtgcgg  1080
ctccgcgctg cccggcggct gtgagcgctg cgggcgcggc gcggggcttt gtgcgctccg  1140
cagtgtgcgc gaggggagcg cggcccgggg cggtgccccg cggtgcgggg ggggctgcga  1200
ggggaacaaa ggctgcgtgc ggggtgtgtg cgtggggggga tgagcagggg gtgtgggcgc  1260
gtcggtcggg ctgcaacccc ccctgcaccc ccctcccga gttgctgagc acggcccggc   1320
ttcgggtgcg gggctccgta cggggcgtgg cgcggggctc gccgtgccgg gcggggggtg  1380
gcggcaggtg ggggtgccgg gcgggcggg gccgcctcgg gccgggaagg gctcggggga   1440
ggggcggcc ggcccccgga gcgccggcgg ctgtcgagcg gcgcgagcc gcagccattg   1500
ccttttatgg taatcgtgcg agagggcgca gggacttcct ttgtcccaaa tctgtgcgga  1560
gccgaaatct gggaggcgcc gccgcacccc tctagcgggg cgcggggcga agcggtgcgg  1620
cgccggcagg aaggaaatgg gcgggagggg ccttcgtgcg tcgccgcgcc gccgtcccct   1680
tctccctctc cagcctcggg gctgtccgcg ggggacggc tgccttcggg gggacggggg  1740
cagggcgggg ttcggcttct ggcgtgtgac cggcggctct agagcctctg ctaaccatgt   1800
tcatgccttc ttctttttcc tacagatcct taattaataa tacgactcac tataggggt   1860
cgacccgcca ccatgccaaa aagaaaaga aagtgtatc cctatgatgt ccccgattat   1920
gccggttcaa gagccctggt cgtgattaga ctgagccggg tgacagacgc caccacaagt  1980
cccgagagac agctgaatc atgccagcag ctctgtgctc agcggggttg ggatgtggtc   2040
ggcgtggcag aggatctgga cgtgagcggg gccgtcgatc cattcgacag aaagaggagg   2100
cccaacctgg caagatggct cgcttcgag gaacagccct ttgatgtgat cgtcgcctac   2160
agagtggacc ggctgacccg ctcaattcga catctccaga agctggtgca ttgggctgga   2220
gaccacaaga aactggtggt cagcgcaaca gaagcccact tcgatactac cacacctttt  2280
gccgctgtgg tcatcgcact gatgggcact gtgcccaga tggagctcga agctataagg    2340
gagcgaaaca ggagcgcagc ccatttcaat attagggccg gtaaatacag agctccctg   2400
cccccttggg gatatctccc taccaggggt gatgggagt ggagactggt gccagacccc  2460
gtccagagag agcggattct ggaagtgtac cacagagtgg tcgataacca cgaaccactc   2520
catctggtgg cacacgacct gaatagacgc ggcgtgctct ctccaaagga ttattttgct   2580
cagctgcagg aagagagcc acagggaaga gaatggagtg ctactgcact gaagagatcc   2640
atgatcagtg aggctatgct gggttacgca cactcaatg gcaaaactgt ccgggacgat   2700
gacggagccc ctctggtgag ggctgagcct attctcacca gagagcagct cgaagtctg   2760
cgggcagaac tggtcaagac tagtcgcgcc aaacctgccg tgagcacccc aagcctgctc   2820
ctgagggtgc tgttctgcgc cgtctgtgga gagccagcat acaagtttgc cggcggagg   2880
cgcaaacatc cccgctatcg atgcaggagc atggggttcc ctaagcactg tggaaacggg   2940
acagtggcca tggctgagtg ggacgccttt gcgaggaag atgctggga tctcgttgga    3000
gacgctgagc ggctggaaaa agtgtgggtg gcaggatctg actccgctgt ggagctggca   3060
gaagtcaatg ccgagctgt ggatctgact tccctcatcg gatctcctgc atatagagct   3120
gggtccccac agagagaagc tctggacgca cgaattgctg cactcgctgc tagacaggag  3180
gaactggagg gcctggaggc caggccctct ggatgggagt ggcgagaaac cggacagagg   3240
tttgggatt ggtggaggga gcaggacacc gcagccaaga acatggct gagatccatg    3300
aatgtccggc tcacattcga cgtgcgcggt ggcctgactc gaaccatcga ttttggcgac  3360
ctgcaggagt atgaacagca cctgagactg ggtccgtgg tcgaaagact gcacactggg  3420
atgtcctagg tcagagctcg ctgatcagcc tcgactgtgc cttctagttg ccagccatct  3480
gttgtttgcc cctcccccgt gccttccttg acccctggaag gtgccactcc cactgtcctt   3540
tcctaataaa atgaggaaat tgcatcgcat tgtctgagta ggtgtcattc tattctgggg   3600
ggtggggtgg ggcaggacag caaggggag gattgggaag acaatagcag gcatgctggg   3660
gatgcggtgg gctctatggc ttctgaggcg aaagaaccca gctgggctc gagatccact   3720
agttctagcc tcgaggctag agcggccgcc actggccgtc gttttacaac gtcgtgactg   3780
ggaaaaccct ggcgttaccc aacttaatcg ccttgcagca catccccctt tcgccagctg   3840
gcgtaatagc gaagaggccc gcaccgatcg cccttcccaa cagttgcgca gcctgaatgg   3900
```

```
cgaatgggac gcgccctgta gcggcgcatt aagcgcggcg ggtgtggtgg ttacgcgcag   3960
cgtgaccgct acacttgcca gcgccctagc gcccgctcct ttcgctttct tcccttcctt   4020
tctcgccacg ttcgccggct ttccccgtca agctctaaat cggggggctcc ctttagggtt   4080
ccgatttagt gctttacggc acctcgaccc caaaaaactt gattagggtg atggttcacg   4140
tagtgggcca tcgccctgat agacggtttt tcgccctttg acgttggagt ccacgttctt   4200
taatagtgga ctcttgttcc aaactgaac aacactcaac cctatctcgg tctattcttt   4260
tgatttataa gggattttgc cgatttcggc ctattggtta aaaatgagc tgatttaaca   4320
aaaatttaac gcgaatttta acaaaatatt aacgcttacr mktymsrtks smcwttymgg   4380
sgaaatgtgc gcggaacccc tatttgttta tttttctaaa tacattcaaa tatgtatccg   4440
ctcatgagac aataaccctg ataaatgctt caataatatt gaaaaaggaa gagtatgagt   4500
attcaacatt tccgtgtcgc ccttattccc ttttttgcgg catttgcct tcctgttttt   4560
gctcacccag aaacgctggt gaaagtaaaa gatgctgaag atcagttggg tgcacgagtg   4620
ggttacatcg aactggatct caacagcggt aagatccttg agagttttcg ccccgaagaa   4680
cgttttccaa tgatgagcac ttttaaagtt ctgctatgtg gcgcggtatt atcccgtatt   4740
gacgccgggc aagagcaact cggtcgccgc atacactatt ctcagaatga cttggttgag   4800
tactcaccag tcacagaaaa gcatcttacg gatggcatga cagtaagaga attatgcagt   4860
gctgccataa ccatgagtga taacactgcg gccaacttac ttctgacaac gatcggagga   4920
ccgaaggagc taaccgcttt tttgcacaac atgggggatc atgtaactcg ccttgatcgt   4980
tgggaaccgg agctgaatga agccatacca aacgacgagc gtgacaccac gatgcctgta   5040
gcaatggcaa caacgttgcg caaactatta actggcgaac tacttactct agcttcccgg   5100
caacaattaa tagactggat ggaggcggat aaagttgcag gaccacttct gcgctcggcc   5160
cttccggctg gctggtttat tgctgataaa tctggagccg gtgagcgtgg gtctcgcggt   5220
atcattgcag cactgggcc agatggtaag ccctcccgta tcgtagttat ctacacgacg   5280
gggagtcagg caactatgga tgaacgaaat agacagatcg ctgagatagg tgcctcactg   5340
attaagcatt ggtaactgtc agaccaagtt tactcatata cttagat tgatttaaaa   5400
cttcattttt aatttaaaag gatctaggtg aagatccttt ttgataatct catgaccaaa   5460
atcccttaac gtgagttttc gttccactga gcgtcagacc ccgtagaaaa gatcaaagga   5520
tcttcttgag atcctttttt tctgcgcgta atctgctgct tgcaaacaaa aaaaccaccg   5580
ctaccagcgg tggtttgttt gccggatcaa gagctaccaa ctcttttcc gaaggtaact   5640
ggcttcagca gagcgcagat accaaatact gttcttctag tgtagccgta gttaggccac   5700
cacttcaaga actctgtagc accgcctaca tacctcgctc tgctaatcct gttaccagtg   5760
gctgctgcca gtggcgataa gtcgtgtctt accgggttgg actcaagacg atagttaccg   5820
gataaggcgc agcggtcggg ctgaacgggg gttcgtgca cacagcccag cttggagcga   5880
acgacctaca ccgaactgag atacctacag cgtgagctat gagaaagcgc cacgcttccc   5940
gaagggagaa aggcggacag gtatccggta agcggcaggg tcggaacagg agagcgcacg   6000
agggagcttc caggggaaa cgcctggtat ctttatagtc ctgtcgggtt tcgccacctc   6060
tgacttgagc gtcgatttt gtgatgctcg tcaggggggc ggagcctatg gaaaaacgcc   6120
agcaacgcgg ccttttacg gttcctggcc ttttgctggc cttttgctca catgttcttt   6180
cctgcgttat cccctgattc tgtggataac cgtattaccg cctttgagtg agctgatacc   6240
gctcgccgca gccgaacgac cgagcgcagc gagtcagtga gcgaggaagc ggaagagcgc   6300
ccaatacgca aaccgcctct ccccgcgcgt tggccgattc attaatgcag ctggcacgac   6360
aggtttcccg actggaaagc gggcag                                         6386
```

```
SEQ ID NO: 388          moltype = DNA   length = 6317
FEATURE                 Location/Qualifiers
misc_feature            1..6317
                        note = Description of Artificial Sequence: Synthetic
                         polynucleotide
source                  1..6317
                        mol_type = other DNA
                        organism = synthetic construct
SEQUENCE: 388
gattcgacat tgattattga ctagttatta atagtaatca attacggggt cattagttca   60
tagcccatat atggagttcc gcgttacata acttacggta aatggcccgc ctggctgacc   120
gcccaacgac ccccgcccat tgacgtcaat aatgacgtat gttcccatag taacgccaat   180
agggactttc cattgacgtc aatgggtgga gtatttacgg taaactgccc acttggcagt   240
acatcaagtg tatcatatgc caagtacgcc ccctattgac gtcaatgacg gtaaatggcc   300
cgcctggcat tatgcccagt acatgacctt atgggacttt cctacttggc agtacatcta   360
cgtattagtc atcgctatta ccatggtcga ggtgagcccc acgttctgct tcactctccc   420
catctccccc cctccccac cccaatttt gtattttaat tatttttgtg   480
agcgatgggg gcgggggggg gggggggcg cgcgccrggs ggggsgggs ggggsgrggg   540
gsggggsggg gsgaggcgga gaggtgcggc ggcagccaat cagagcggcg cgctccgaaa   600
gtttccttt atggcgaggc ggcggcgcg gcggccctat aaaaagcgaa gcgcgcggcg   660
ggcggagtc gctgcgcgct gccttcgcc cgtgccccgc tccgccgccg cctcgcccgg   720
cccgcccgcg ctctgactga ccgcgttact cccacaggtg agcggcggg acggccttc   780
tcctccggc tgtaattagc gcttggttta atgacggctt gtttctttc tgtggctgcg   840
tgaaagcctt gaggggctcc gggaggcc tttgtgcggg ggagcggct cgggggtgc   900
gtgcgtgtgt gtgtgcgtgg ggagcgccgc gtgcggctcc gcgctgcccg gcggctgtga   960
gcgctgcggg cgcggcgcgg ggctttgtgc gctccgcagt gtgcgcgagg gagcgcggcc   1020
cggggcggt gccccgcggt gcgggggggg ctgcgaggg aacaaaggct gcgtgcgggg   1080
tgtgtgcgtg ggggggtgag caggggtgt gggcgcgtcg gtcgggctgc aaccccccct   1140
gcacccccct cccgagttg ctgagcacgg cccggctcg ggtgcgggc tccgtacggg   1200
gcgtggcgcg ggctcgccg tgccgggcgg ggggtggcg caggtggggg tgccgggcgg   1260
gcggggcggg cctcgggcg ggggaggggctc ggggagggg cgcgccgccg cccggagccg   1320
ccgcggctgt cgaggcgcgg cgagccgcag ccattgcctt ttatggtaat cgtgcgagag   1380
ggcgcaggga cttcctttgt cccaaatctg tgcggagccg aaatctggga ggcgccgccg   1440
cacccccctct agcgggcgcg gggcgaagcg gtgcggcgcc gcaggaagg aaatgggcgg   1500
ggagggcctt cgtgcgtcgc cgcgccgccg tcccctctc cctctccagc ctcggggctg   1560
tccgcggggg gacggctgcc ttcgggggg acggggcagg gcggggttcg gcttctggcg   1620
```

```
tgtgaccggc ggctctagag cctctgctaa ccatgttcat gccttcttct tttttcctaca   1680
gatccttaat taataatacg actcactata ggggtcgac ccgccaccat gacagcgcca     1740
aagaaaaaga ggaaggtcat gaccaagaaa gtggccatct atactagagt gagcacaacg    1800
aatcaggccg aggaggggtt ctctattgac gagcaaatcg atcgtctgac caagtacgcg    1860
gaagcaatgg gctggcaagt cagcgacact tacaccgatg ctgggttctc cggcgccaaa    1920
ctggaaaggc ctgccatgca gcggctgatt aacgacattg agaacaaggc ctttgataca    1980
gtgctcgtat acaagctcga caggctcagc cgatctgtgc gggacacgct ttacctcgta    2040
aaggatgttt tcactaagaa taaaatcgac ttcattagcc tgaacgaatc cattgacacc    2100
agctcagcta tgggctctct gttcctgacc atcctgagcg ctatcaatga gtttgagagg    2160
gagaatataa aggagcgcat gacaatggga aagctgggta gagcgaagtc cgggaaatct    2220
atgatgtgga ccaagaccgc ttttggatac taccacaata ggaagacggg cattctggag    2280
atcgtgccct gcaggcaac catcgttgag cagatcttca ccgactacct gagcggaata     2340
tctctcacga agttgcgaga taagctgaat gagagcggac acattggcaa ggatattcct    2400
tggtcatata gaaccctccg ccaaactctg gataatccgg tgtactgcgg ttacatcaag    2460
ttcaaagaca gcctcttcga gggaatgcat aaacctatca ttccatacga gacatacctg    2520
aaaagtccaaa aggaactcga agagcgccag caacagactt acgaacgaa taataatccc     2580
aggccttttcc aggccaaata tatgctgtcc ggcatggcaa gatgcggata ctgcggggca    2640
ccactcaaga ttgtgcttgg ccataaacgg aaggatgaa gcagaaccat gaaatatcac     2700
tgcgcaaacc gctttccaag gaaaacgaag gggattaccg tgtacaatga caacaaaaaa    2760
tgtgatagcg gaacctacga tctgtccaac ttggaaaaca ccgtcattga caatttaatt    2820
ggattcagg aaaataatga cagccttctg aagattatca cgggaacaa tcagccgatt      2880
ctggacactt catctttcaa aaaacagatc tctcagattg ataagaaaat tcagaaaaat    2940
tccgatttat accctcaatga tttcataacg atggatgagc tgaaggaccg gaccgacagt   3000
ttgcaggccg agaagaaact gctgaaagca aagatctccg agaacaagtt caatgacagt    3060
accgatgtct tcgagttggt gaagacccag ctgggtagta tcccaatcaa cgagttgagc    3120
tatgacaata agaagaagat tgttaataac ctggtgacga aagtggacgt gaccgctgat    3180
aacgtggata ttatcttcaa gttccagctg gcctgagtca gagctcgctg atcagcctcg    3240
actgtgcctt ctagttgcca gccatctgtt gtttgcccct cccccgtgcc ttccttgacc    3300
ctggaaggtg ccactcccac tgtcctttcc taataaaatg aggaaattgc atcgcattgt    3360
ctgagtaggt gtcattctat tctgaggggt ggggtgggggg aggacagca gggggaggat    3420
tgggaagaca atagcaggca tgctggggat gcggtgggct ctatggcttc tgaggcggaa    3480
agaaccagct ggggctcgag atccactagt tctagcctcg aggctagagc ggccgccact    3540
ggccgtcgtt ttacaacgtc gtgactggga aaaccctggc gttacccaac ttaatcgcct    3600
tgcagcacat ccccctttcg ccagctggcg taatagcgaa gaggcccgca ccgatcgccc    3660
ttcccaacag ttgcgcagcc tgaatggcga atgggacgcg ccctgtagcg cgcattaag    3720
cgcggcgggt gtggtggtta cgcgcagcgt gaccgctaca cttgccagcg ccctagcgcc    3780
cgctcctttc gctttcttcc cttcctttct cgccacgttc gccggctttc cccgtcaagc    3840
tctaaatcgg gggctccctt tagggttccg atttagtgct ttacggcacc tcgaccccaa    3900
aaaacttgat tagggtgatg gttcacgtag tgggccatcg cccctgataga cggttttcg    3960
cccttttgacg ttggagtcca cgttcttaa tagtggactc ttgttccaaa ctggaacaac    4020
actcaaccct atctcggtct attcttttga tttataaggg attttgccga tttcggccta    4080
ttggttaaaa aatgagctga tttaacaaaa atttaacgcg aattttaaca aaatattaac    4140
gcttacrmkt ymsrtkssmc wttymggsga aatgtgcgcg gaacccctat ttgttttattt    4200
ttctaaaatac attcaaatat gtatccgctc atgagacaat aaccctgata aatgcttcaa    4260
taatattgaa aaaggaagag tatgagtatt caacatttcc gtgtcgccct tattcccttt    4320
tttgcggcat tttgccttcc tgttttttgct cacccagaaa cgctggtgaa agtaaaagat    4380
gctgaagatc agttgggtgc acgagtgggt tacatcgaac tggatctcaa cagcggtaag    4440
atccttgaga gttttcgccc cgaagaacgt tttccaatga tgagcacttt taaagttctg    4500
ctatgtggcg cggtattatc ccgtattgac gccgggcaag agcaactcgg tcgccgcata    4560
cactattctc agaatgactt ggttgagtac tcaccagtca cagaaaagca tcttacggat    4620
ggcatgacag taagagaatt atgcagtgct gccataacca tgagtgataa cactgcggcc    4680
aacttacttc tgacaacgat cggaggaccg aaggagctaa ccgcttttt gcacaacatg    4740
ggggatcatg taactcgcct tgatcgttgg gaaccggagc tgaatgaagc cataccaaac    4800
gacgagcgtg acaccacgat gcctgtagca atggcaacaa cgttgcgcaa actattaact    4860
ggcgaactac ttactctagc ttcccggcaa caattaatag actggatgga ggcggataaa    4920
gttgcaggac cacttctgcg ctcggccctt ccggctggct ggtttattgc tgataaatct    4980
ggagccggtg agcgtgggtc tcgcggtatc attgcagcac tggggccaga tggtaagccc    5040
tcccgtatcg tagttatcta cacgacgggg agtcaggcaa ctatggatga acgaaataga    5100
cagatcgctg agataggtgc ctcactgatt aagcattggt aactgtcaga ccaagtttac    5160
tcatatatac tttagattga ttttaaaactt catttttaat ttaaaaggat ctaggtgaag    5220
atccttttttg ataatctcat gaccaaaatc ccttaacgtg agttttcgtt ccactgagcg    5280
tcagaccccg tagaaaagat caaaggatct tcttgagatc cttttttttct gcgcgtaatc    5340
tgctgcttgc aaacaaaaaa accaccgcta ccagcggtgg tttgtttgcc ggatcaagag    5400
ctaccaactc tttttccgaa ggtaactggc ttcagcagag cgcagatacc aaatactgtt    5460
cttctagtgt agccgtagtt aggccaccac ttcaagaact ctgtagcacc gcctacatac    5520
ctcgctctgc taatcctgtt accagtggct gctgccagtg gcgataagtc gtgtcttacc    5580
gggttggact caagacgata gttaccggat aaggcgcagc ggtcgggctg aacgggggt     5640
tcgtgcacac agcccagctt ggagcgaacg acctacaccg aactgagata cctacagcgt    5700
gagctatgag aaagcgccac gcttcccgaa gggagaaagg cggacaggta tccggtaagc    5760
ggcagggtcg aacaggaga gcgcacgagg gagcttccag ggggaaacgc ctggtatctt     5820
tatagtcctg tcgggtttcg ccacctctga cttgagcgtc gatttttgtg atgctcgtca    5880
gggggcggag gcctatggaa aaacgccagc aacgcggcct ttttacggtt cctggccttt    5940
tgctggcctt ttgctcacat gttctttcct gcgttatccc ctgattctgt ggataaccgt    6000
attaccgcct ttgagtgagc tgataccgct cgccgcagcc gaacgaccga gcgcagcgag    6060
tcagtgagcg aggaagcgga agagcgccca atacgcaaac cgcctctccc gcgcgttgg    6120
ccgattcatt aatgcagctg gcacgacagg tttcccgact ggaaagcggg cagtgagcgc    6180
aacgcaatta atgtgagtta gctcactcat taggcacccc aggctttaca ctttatgctt    6240
ccggctcgta tgttgtgtgg aattgtgagc ggataacaat ttcacacagg aaacagctat    6300
gaccatgagg cgcgcc                                                   6317
```

```
SEQ ID NO: 389         moltype = DNA  length = 6638
FEATURE                Location/Qualifiers
misc_feature           1..6638
                       note = Description of Artificial Sequence: Synthetic
                       polynucleotide
source                 1..6638
                       mol_type = other DNA
                       organism = synthetic construct
SEQUENCE: 389
gattcgacat tgattattga ctagttatta atagtaatca attacggggt cattagttca   60
tagcccatat atggagttcc gcgttacata acttacggta aatggcccgc ctggctgacc  120
gcccaacgac ccccgcccat tgacgtcaat aatgacgtat gttcccatag taacgccaat  180
agggactttc cattgacgtc aatgggtgga gtatttacgg taaactgccc acttggcagt  240
acatcaagtg tatcatatgc caagtacgcc ccctattgac gtcaatgacg gtaaatggcc  300
cgcctggcat tatgcccagt acatgacctt atgggacttt cctacttggc agtacatcta  360
cgtattagtc atcgctatta ccatggtcga ggtgagcccc acgttctgct tcactctccc  420
catctcccccc ccctcccccac ccccaatttt gtatttattt atttttttaat tattttgtgc  480
agcgatgggg gcggggggg gggggggcg cgcgccrggs ggggsgggs gggggrggg  540
gsgggggggg gsgaggcgga gaggtgcggg ggcagccaat cagagcggcg cgctccgaaa  600
gtttcctttt atggcgaggc ggcggcggcg cggccctat aaaaagcgaa gcgcgcggcg  660
ggcgggagtc gctgcgcgct gccttcgccc cgtgccccgc tccgccgccg cctcgcgccg  720
cccgcccgg ctctgactga ccgcgttact cccacaggtg agcgggcggg acggcccttc  780
tcctccgggc tgtaattagc gcttggttta atgacggctt gtttcttttc tgtgctgcg  840
tgaaagcctt gaggggctcc gggagggccc tttgtgcggg gggagcggct cgggggtgc  900
gtgcgtgtgt gtgtgcgtgg ggagcgccgc gtgcggctcc gcgctgcccg gcggctgtga  960
gcgctgcggg cgcggcgcgg ggctttgtgc gctccgcagt gtgcgcgagg ggagccggc 1020
cggggcggt gccccgcggt gcggggggg ctgcgagggg aacaaaggct gcgtgcgggg 1080
tgtgtgcgtg gggggggtgag caggggtgt gggcgcgtcg gtcgggctgc aaccccccct 1140
gcacccccct ccccgagttg ctgagcacgg cccgacttcg ggtgcgggc tccgtacggg 1200
gcgtggcgcg gggctcgccg tgccgggcgg ggggtggccg caggtgggg tgccgggcgg 1260
ggcgggggccg cctcgggccg gggagggctc ggggagggg cgcggcggcc ccggagcgc 1320
cggcggctgt cgaggcgcgg cgagccgcag ccattgcctt ttatggtaat cgtgcgagag 1380
ggcgcaggga cttcctttgt cccaaatctg tgcggagccg aaatctggga ggcgccgccg 1440
cacccctct agcgggcgcg gggcgaagcg gtgcggcgcc ggcaggaagg aaatgggcgg 1500
ggagggcctt cgtgcgtcgc cgcgccgccg tccccttctc cctctccagc ctcggggctg 1560
tccgcggggg gacggctgcc ttcggggggg acggggcagg gcggggttcg gcttctggcg 1620
tgtgaccggc ggctctagag cctctgctaa ccatgttcat gccttcttct ttttcctaca 1680
gatccttaat taataatacg actcactata ggggtcgac ccgccaccat gccccaagaag 1740
aaacggaaag tgatgagccc ctttatcgcc ccggacgtgc ccgagcacct cctgacact 1800
gtgcgcgtct ttctgtacgc ccgtcagagt aaaggacggt cagatggatc tgacgtgtcc 1860
accgaagcac agctcgctgc cggacgggcc cttgttgcct caagaaacgc acaagggga 1920
gctagatgga tggtggcggg cgaattcgtg gatgtgggca gatcaggggtg ggaccccgaat 1980
gtgacacgcg ccgacttcga aagaatgatg ggcgaggtgc gcgccggtga gggagacgta 2040
gtggtggtta atgaactgag tcgccttacg aggaagggcg cccacgacgc tctggagatc 2100
gataacgaac tcaaaaaaca cggtgtgcgg ttcatgagcg tgctgaaacc attcctggat 2160
accagcaccc caatcggtgt cgcgatcttt gccctgattg ccgcgctcgc taaacaggat 2220
tcagaccttaa aagctgagcg gctgaaggg gctaaagatg agatcgctgc cttgggggt 2280
gtgcacagct catctgcgcc attcggcatg agggcggtca gaaagaaagt ggataacctg 2340
gtcatatctg ttctggagcc tgatgaggac aacccgacc acgttgagct tgtggaacgg 2400
atggctaaga tgtctttcga aggcgtcagc gataacgcaa ttgccacaac atttgagaag 2460
gagaaaatcc cctctccggg gatgctgag agacgagcca cggagaagag gcttgcttct 2520
attaaggcac ggaggctcaa tggcgccgaa aagccgatca tgtggcgggc gcagacagtt 2580
agatggattc ttaaccatcc cgcgattggt ggattcgcat tcgagcgggt gaaacacgga 2640
aagcccaca tcaacgtgat acgaagagat cccggcggca aaccccttac ccctcacact 2700
ggtatcctgt ctggatccaa gtggttgaa ctccaggaga agagaagcgg gaaaaatctc 2760
tccgaccgca aaccaggtgc cgaagtgaa cctacgctgc tttccgggtg gagatttctg 2820
ggatgtcgga tatgcggtgg gtcaatgggc cagtcccaag ggggccgtaa gaggaatggg 2880
gacttggctg agggcaatta catgtgtgca aacccaaagg ggcacggcgg tctgagcgtc 2940
aagaggtctg agcttgatga attcgtggca tcaaaagtct gggcaggtt gcgcacggct 3000
gacatggagg atgaacatga ccaagcatgg attgcagctg cagctgaacg gtttgctttg 3060
cagcacgacc tggcggggt agctgacgag cgacgggag aacaagctca cctgataac 3120
gttcggagat caataaaaga tctccaggcg gataggaagg caggtctcta cgtgggacgc 3180
gaagaactgg agacctggcg cagtaccgtc ctgcaatata agctacgga ggctgagtgt 3240
actactaggt tggctgagct ggatgaaaaa atgaatggat ccaccgggt gccttcagaa 3300
tggttagcg gcgaggaccc aaccgcgaa ggaggcatat gggcgagctg ggatgtctat 3360
gagcgccggg agtttctcag cttttttttg gactccgtaa tggttgacag gggcagacat 3420
cctgaaacca gaaatatat accattgaaa gacgggtga ccttaaagtg ggcggagctg 3480
ttaaggaag agatgaagc aagcgaggc acagaacggg agctggcagc tctttaggtc 3540
agagctcgct gatcagcctc gactgtgcct tctagttgcc agccatcgt tgtttgcccc 3600
tcccccgtgc cttccttgac cctggaaggt gccactccca ctgtccttc ctaataaaat 3660
gaggaaattg catcgcattg tctgagtagg tgtcattcta ttctgggggg tgggtggg 3720
caggacagca aggggagga ttgggaagac aatagcaggc atgctgggga tgcggtggc 3780
tctatgcttt ctgagccgga aagaaccagc tggggctcag gatccactag ttctagcctc 3840
gaggctagag cggccgccac tggccgtcgt tttacaacgt cgtgactggg aaaaccctgg 3900
cgttacccaa cttaatcgcc ttgcagcaca tccccccttc gccagctggc gtaatagcga 3960
agaggcccgc accgatcgcc cttcccaaca gttgcgcagc ctgaatggcg aatgggacgc 4020
gccctgtagc ggcgcattaa gcgcggcggg tgtggtggtt acgcgcagcg tgaccgctac 4080
acttgccagc gccctagcgc ccgctccttt cgctttcttc ccttccttc tcgccacgtt 4140
```

```
cgccggcttt cccgtcaag ctctaaatcg ggggctccct ttaggggttcc gatttagtgc    4200
tttacggcac ctcgacccca aaaaacttga ttagggtgat ggttcacgta gtgggccatc    4260
gccctgatag acggttttc gcccttgac gttggagtcc acgttcttta atagtggact     4320
cttgttccaa actggaacaa cactcaaccc tatctcggtc tattctttg atttataagg     4380
gattttgccg atttcggcct attggttaaa aaatgagctg atttaacaaa aatttaacgc    4440
gaattttaac aaaatattaa cgcttacrmk tymsrtkssm cwttymggsg aaatgtgcgc    4500
ggaacccta tttgtttatt tttctaaata cattcaaata tgtatccgct catgagacaa    4560
taaccctgat aaatgcttca ataatattga aaaggaaga gtatgagtat tcaacatttc     4620
cgtgtcgccc ttattccctt ttttgcggca ttttgccttc ctgttttgc tcacccagaa     4680
acgctggtga aagtaaaaga tgctgaagat cagttgggtg cacgagtggg ttacatcgaa    4740
ctggatctca acagcggtaa gatcctgag agttttcgcc ccgaagaacg ttttccaatg    4800
atgagcactt ttaaagttct gctatgtggc gcggtattat cccgtattga cgccgggcaa    4860
gagcaactcg gtcgccgcat acactattct cagaatgact tggttgagta ctcaccagtc    4920
acagaaaagc atcttacgga tggcatgaca gtaagagaat tatgcagtgc tgccataacc    4980
atgagtgata acactgcggc caacttactt ctgacaacaa tcggaggacc gaaggagcta    5040
accgcttttt tgcacaacat gggggatcat gtaactcgcc ttgatcgttg ggaaccggag    5100
ctgaatgaag ccataccaaa cgacgagcgt gacaccacga tgcctgtagc aatggcaaca    5160
acgttgcgca aactattaac tggcgaacta cttactctag cttcccggca acaattaata    5220
gactggatgg aggcggataa agttgcagga ccacttctgc gctcggccct tccggctggc    5280
tggtttattg ctgataaatc tggagccggt gagcgtgggt ctcgcggtat cattgcagca    5340
ctggggccag atggtaagcc ctcccgtatc gtagttatct acacgacggg gagtcaggca    5400
actatggatg aacgaaatag acagatcgct gagataggtg cctcactgat taagcattgg    5460
taactgtcag accaagttta ctcatatata ctttagattg atttaaaact tcatttttaa    5520
tttaaaagga tctaggtgaa gatcctttt gataatctca tgaccaaaat cccttaacgt    5580
gagttttcgt tccactgagc gtcagacccc gtagaaaaga tcaaaggatc ttcttgagat    5640
ccttttttc tgcgcgtaat ctgctgcttg caaacaaaaa aaccaccgct accagcggtg    5700
gtttgtttgc cggatcaaga gctaccaact ctttttccga aggtaactgg cttcagcaga    5760
gcgcagatac caaatactgt tcttctagtg tagccgtagt taggccacca cttcaagaac    5820
tctgtagcac cgcctacata cctcgctctg ctaatcctgt taccagtggc tgctgccagt    5880
ggcgataagt cgtgtcttac cgggttggac tcaagacgat agttaccgga taaggcgcag    5940
cggtcgggct gaacggggg ttcgtgcaca cagcccagct tggagcgaac gacctacacc    6000
gaactgagat acctacagcg tgagctatga gaaagcgcca cgcttcccga agggagaaag    6060
gcggacaggt atccggtaag cggcagggtc ggaacaggag agcgcacgag ggagcttcca    6120
gggggaaacg cctggtatct ttatagtcct gtcgggtttc gccacctctg acttgagcgt    6180
cgattttttgt gatgctcgtc agggggggcgg agcctatgga aaaacgccag caacgcggcc    6240
tttttacggt tcctggcctt ttgctggcct tttgctcaca tgttctttcc tgcgttatcc    6300
cctgattctg tggataaccg tattaccgcc tttgagtgag ctgataccgc tcgccgcagc    6360
cgaacgaccg agcgcagcga gtcagtgagc gaggaagcgg aagagcgccc aatacgcaaa    6420
ccgcctctcc ccgcgcgttg gccgattcat taatgcagct ggcacgacag gtttcccgac    6480
tggaaagcgg gcagtgagcg caacgcaatt aatgtgagtt agctcactca ttaggcaccc    6540
caggctttac actttatgct tccggctcgt atgttgtgtg gaattgtgag cggataacaa    6600
tttcacacag gaaacagcta tgaccatgag gcgcgccg                            6638

SEQ ID NO: 390          moltype = DNA   length = 9530
FEATURE                 Location/Qualifiers
misc_feature            1..9530
                        note = Description of Artificial Sequence: Synthetic
                        polynucleotide
source                  1..9530
                        mol_type = other DNA
                        organism = synthetic construct
SEQUENCE: 390
taatcagcat catgatgtgg taccacatca tgatgctgat tataagaatg cggccgccac      60
actctagtgg atctcgagtt aataattcag aagaactcgt caagaaggcg atagaaggcg     120
atgcgctgcg aatcgggagc ggcgataccg taaagcggta ggaagcggtc agcccattcg     180
ccgccaagct cttcagcaat atcacgggta gccaacgcta tgtcctgata gcggtccgcc     240
acacccagcc ggccacagtc gatgaatcca gaaaagcggc catttccac catgatattc      300
ggcaagcagg catcgccatg ggtcacgacg agatcctcgc cgtcgggcat gctcgccttg     360
agcctggcga acagttcggc tggcgcgagc ccctgatgct cttcgtccag atcatcctga     420
tcgacaagac cggcttccat ccgagtacgt gtctgcgtca tgcgatgttt cgcttggtgg     480
tcgaatgggc aggtagccgg atcaagcgta tgcagccgcc gcattgcatc agccatgatg     540
gatactttct cggcaggagc aaggtgtaga tgacatggag atcctgcccc ggcacttcgc     600
ccaatagcag ccagtccctt cccgcttcag tgacaacgtc gagcacagct gcgcaaggaa     660
cgcccgtcgt ggccagccac gatagccgcg ctgcctcgtc ttgcagttca ttcagggcac     720
cggacaggtc ggtcttgaca aaaagaaccg ggcgcccctg cgctgacagc cggaacacgg     780
cggcatcaga gcagccgatt gtctgttgtg cccagtcata gccgaatagc ctctccaccc     840
aagcggccgg agaacctgcg tgcaatccat cttgttcaat catgcgaaac gatcctcatc     900
ctgtctcttg atcagagctt gatccctgc gccatcagat ccttggcggc gagaaagcca     960
tccagtttac tttgcagggc ttcccaacct taccagaggg cgccccagct ggcaattccg    1020
gttcgcttgc tgtccataaa accgcccagt ctagctatcg ccatgtaagc ccactgcaag    1080
ctacctgctt tctctttgcg cttgcgtttt cccttgtcca gatagcccag tagctgacat    1140
tcatccgggg tcagcaccgt ttctgcggac tggctttcta cgtgctcgag gggggccaaa    1200
cggtctccag cttggctgtt ttggcggatg agaagaagatt tcagcctga tacagattaa    1260
atcagaacgc agaagcggtc tgataaaaca gaatttgcct ggcggcagta gcgcggtggt    1320
cccacctgac cccatgccga actcagaagt gaaacgccgt agcgccgatg gtagtgtggt    1380
gtctccccat gcgagagtag ggaactgcca ggcatcaaat aaaacgaaag gctcagtcga    1440
aagactgggc ctttcgtttt atctgttgtt tgtcggtgaa cgctctcctg agtaggacaa    1500
atccgccggg agcggatttg aacgttgcga agcaacggcc cggagggtgg cggcaggac    1560
gcccgccata aactgccagg catcaaatta agcagaaggc catcctgacg gatggccttt    1620
```

```
ttgcgtttct acaaactctt ttgtttattt ttctaaatac attcaaatat gtatccgctc   1680
atgaccaaaa tcccttaacg tgagttttcg ttccactgag cgtcagaccc cgtagaaaag   1740
atcaaaggat cttcttgaga tccttttttt ctgcgcgtaa tctgctgctt gcaaacaaaa   1800
aaaccaccgc taccagcggt ggtttgtttg ccggatcaag agctaccaac tcttttccg    1860
aaggtaactg gcttcagcag agcgcagata ccaaatactg tccttctagt gtagccgtag   1920
ttaggccacc acttcaagaa ctctgtagca ccgcctacat acctcgctct gctaatcctg   1980
ttaccagtgg ctgctgccag tggcgataag tcgtgtctta ccgggttgga ctcaagacga   2040
tagttaccgg ataaggcgca gcggtcgggc tgaacggggg gttcgtgcac acagcccagc   2100
ttggagcgaa cgacctacac cgaactgaga tacctacagc gtgagctatg agaaagcgcc   2160
acgcttcccg aagggagaaa ggcggacagg tatccggtaa gcggcagggt cggaacagga   2220
gagcgcacga gggagcttcc aggggaaac gcctggtatc tttatagtcc tgtcgggttt    2280
cgccacctct gacttgagcg tcgattttg tgatgctcgt caggggggcg agcctatgg     2340
aaaaacgcca gcaacgcggc cttttacgg ttcctggcct tttgctggcc ttttgctcac    2400
atgttctttc ctgcgttatc ccctgattct gtggataacc gtattaccgc ctttgagtga   2460
gctgataccg ctcgccgcag ccgaacgacc gagcgcagcg agtcagtgag cgaggaagcg   2520
gaagagcgcc tgatgcggta ttttctcctt acgcatctgt gcggtatttc acaccgcata   2580
tggtgcactc tcagtacaat ctgctctgat gccgcatagt taagccagta tacactccgc   2640
tatcgctacg tgactgggtc atggctgcgc cccgacaccc gccaacaccc gctgacgcgc   2700
cctgacgggc ttgtctgctc ccggcatccg cttacagaca agctgtgacc gtctccggga   2760
gctgcatgtg tcagaggttt tcaccgtcat caccgaaacg cgcgaggcag cagatcaatt   2820
cgcgcgcgaa ggcgaagcgg catgcataat gtgcctgtca aatggacgaa gcagggattc   2880
tgcaaaccct atgctactcc gtcaagccgt caattgtctg attcgttacc aattatgaca   2940
acttgacggc tacatcattc actttttctt cacaaccggc acggaactcg ctcgggctgc   3000
ccccggtgca ttttttaaat acccgcgaga aatagagttg atcgtcaaaa ccaacattgc   3060
gaccgacggt ggcgatagc atccgggtgg tgctcaaaag cagcttcgcc tggctgatac    3120
gttggtcctc gcgccagctt aagacgctaa tccctaactg ctggcggaaa agatgtgaca   3180
gacgcgacgg cgacaagcaa acatgctgtg cgacgctggc gatacattac cctgttatcc   3240
ctagatgaca ttaccctgtt atcccagatg acattaccct gttatccctta gatgacatta   3300
ccctgttatc cctagatgac atttaccctg ttatccctag atgacattac cctgttatcc   3360
cagatgacat taccctgtta tccctagata cattaccccc ttatcccaga tgacatacc    3420
tgttatccct agatgacatt accctgttat cccagatgac attaccctgt tatccctaga   3480
tacattaccc tgttatccca gatgacatac cctgttatcc ctagatgaca ttaccctgtt   3540
atcccagatg acattaccct gttatcccta gatacattac cctgttatcc cagatgacat   3600
accctgttat ccctagatga cattaccctg ttatcccaga tgacattacc ctgttatccc   3660
tagatacatt accctgttat cccagatgac atacccgtt atccctagat gacattaccc    3720
tgttatccca gatgacatta ccctgttatc cctagataca ttaccctgtt atcccagatg   3780
acataccctt ttatccctag atgacattac cctgttatcc cagatgacat accctgttata 3840
tccctagata cattaccctg ttatcccaga tgacatacc tgttatccct agatgacatt   3900
accctgttat cccagataaa ctcaatgatg atgatgatga tggtcgagac tcagcggccg   3960
cggtgccagg gcgtgccctt gggctcccg ggcgcgacta taagctgcga gcaacttcac    4020
ttgggtatgc cggcggtagc gctgagggcc tatttcccat gattccttca tatttgcata   4080
tacgataca ggctgttaga gagataattg gaattaattt gactgtaaac acaaagatat    4140
tagtacaaaa tacgtgacgt agaaagtaat aatttcttgg gtagtttgca gttttaaaat   4200
tatgttttaa aatggactat catatgctta ccgtaacttg aaagtatttc gatttcttgg   4260
ctttatatat cttgtggaaa ggacgaaaca ccgggtcttc gagaagacct gttttagagc   4320
tagaaatcgt ggttcgcacc gactcggtgc cacagcaagt taaataagg ctagtccgtt    4380
atcaacttga aaaagtggca ccgagtcggt gcttttttga attcgctagc taggtcttga   4440
aaggagtggg aattggctcc ggtgccgtc agtgggcaga gcgcacatcg cccacagtcc    4500
ccgagaagtt ggggggaggg gtcggcaatt gatccggtgc ctagagaagg tggcgcgggg   4560
taaactggga aagtgatgtc gtgtactggc tccgcctttt cccgagggt ggggggagaac    4620
cgtatataag tgcagtagtc gccgtgaacg ttctttttcg caacgggttt ggcgccaaaa   4680
cacaggaccg gttctagagc gctgccacca tggacaagaa gtacagcatc ggcctgaca    4740
tcggcaccaa ctctgtgggc tgggccgtga tcaccgacga gtacaaggtg cccagcaaga   4800
aattcaaggt gctgggcaac accgaccggc acagcatcaa gaagaacctg atcggagccc   4860
tgctgttcga cagcggcgaa acagccgagg ccaccccggc gaagaaccc gccagaagaa    4920
gatacaccag acggaagaac cggatctgct atctgcaaga gatcttcagc aacgagatgg   4980
ccaaggtgga cgacagcttc ttccacagac tggaagagtc cttcctggtg aagaggata    5040
agaagcacga gcggcacccc atcttcggca acatcgtgga cgaggtggcc taccacgaga   5100
agtacccac catctaccac ctgagaaaga aactggtgga cagcaccgac aaggccgacc    5160
tgcggctgat ctatctggcc ctggcccaca tgatcaagtt ccggggccac ttcctgatcg   5220
agggcgacct gaaccccgac aacagcgacg tggacaagct gttcatccag ctggtgcaga   5280
cctacaacca gctgttcgag gaaaacccca tcaacgccag cggcgtggac gccaaggcca   5340
tcctgtctgc cagactgagc aagagcagac ggctggaaaa tctgatcgcc cagctgcccg   5400
gcgagaagaa gaatggcctg ttcggaaacc tgattgccct tgaccccca                5460
acttcaagag caacttcgac ctggccgagg atgccaaact gcagctgagc aaggacacct   5520
acgacgacga cctggacaac ctgctggccc agatcggcga ccagtacgcc gacctgtttc   5580
tggccgccaa gaacctgtcc gacgccatcc tgctgagcga catcctgaga gtgaacaccg   5640
agatcaccaa ggcccccctg agcgcctcta tgatcaagag atacgacgag caccaccagg   5700
acctgaccct gctgaaagct ctcgtgcggc agcagctgcc tgagaagtac aaagagattt   5760
tcttcgacca gagcaagaac ggctacgccg ctacattga cggcggagcc agccaggaag   5820
agttctacaa gttcatcaag cccatcctgg aaaagatgga cggcaccgag gaactgctcg   5880
tgaagctgaa cagagaggac ctgctgcgga agcagcggac cttcgacaac ggcagcatcc   5940
cccaccagat ccacctggga gagctgcacg ccattctgcg gcgccaggaa gatttttacc   6000
cattcctgaa ggacaaccgg gaaaagatcg agaagatcct gacctttcgc atccctact    6060
acgtgggccc tctggccagg ggaaacagca gattcgcctg gatgaccaga aagagcgagg   6120
aaaccatcac ccctggaac ttcgaggaag tggtggacaa gggcgcttcc gcccagagct    6180
tcatcgagcg gatgaccaac ttcgataaga acctgcccaa cgagaaggtg ctgcccaagc   6240
acagcctgct gtacgagtac ttcaccgtgt ataacgagct gaccaaagtg aaatacgtga   6300
ccgagggaat gagaaagccc gccttcctga gcggcgagca gaaaaaggcc atcgtggacc   6360
```

```
tgctgttcaa gaccaaccgg aaagtgaccg tgaagcagct gaaagaggac tacttcaaga   6420
aaatcgagtg cttcgactcc gtggaaatct ccggcgtgga agatcggttc aacgcctccc   6480
tgggcacata ccacgatctg ctgaaaatta tcaaggacaa ggacttcctg gacaatgagg   6540
aaaacgagga cattctggaa gatatcgtgc tgacctgac actgtttgag gacagagaga    6600
tgatcgagga acggctgaaa acctatgccc acctgttcga cgacaaagtg atgaagcagc   6660
tgaagcggcg gagatacacc ggctgggca ggctgagccg gaagctgatc aacggcatcc    6720
gggacaagca gtccggcaag acaatcctgg atttcctgaa gtccgacggc ttcgccaaca   6780
gaaacttcat gcagctgatc cacgacgaca gcctgacctt taaagaggac atccagaaag   6840
cccaggtgtc cggccagggc gatagcctgc acgagcacat tgccaatctg gccggcagcc   6900
cgccattaa gaagggcatc ctgcagacag tgaaggtggt ggacgagctc gtgaaagtga    6960
tgggccggca caagcccgag aacatcgtga tcgaaatggc cagagagaac cagaccaccc   7020
agaagggaca gaagaacagc cgcgagagaa tgaagcggat cgaagagggc atcaaagagc   7080
tgggcagcca gatcctgaaa gaacaccccg tggaaaacac ccagctgcag aacgagaagc   7140
tgtacctgta ctacctgcag aatgggcggg atatgtacgt ggaccaggaa ctggacatca   7200
accggctgtc cgactacgat gtggaccata tcgtgcctca gagcttctct aaggacgact   7260
ccatcgacaa caaggtgctg accagaagcg acaagaaccg gggcaagagc gacaacgtgc   7320
cctccgaaga ggtcgtgaag aagatgaaga actactggcg gcagctgctg aacgccaagc   7380
tgattaccca gagaaagttc gacaatctga ccaaggccga ggaggcggc ctgagcgaac    7440
tggataaggc cggcttcatc aagagacagc tggtggaaac ccggcagatc acaaagcacg   7500
tggcacagat cctggactcc cggatgaaca ctaagtacga cgagaatgac aagctgatcc   7560
gggaagtgaa agtgatcacc ctgaagtcca gctggtgtc cgatttccgg aaggatttcc    7620
agttttacaa agtgcgggag atcaacaact accaccagc ccagaacgcc tacctgaacg     7680
ccgtcgtggg aaccgccctg atcaaaaagt accctaagct ggaaagcgag ttcgtgtacg   7740
gcgactacaa ggtgtacgac gtgcggaaga tgatcgccaa gagcgagcag gaaatcggca   7800
aggctaccgc caagtacttc ttctacagca acatcatgaa cttttttcaag accgagatta   7860
ccctggccca cggcgagatc cggaagcggc ctctgatcga gacaaacggc gaaaccggag   7920
agatcgtgtg ggataagggc cgggattttg ccaccgtgcg gaaagtgctg agcatgcccc   7980
aagtgaatat cgtgaaaaag accgaggtgc agacaggcgg cttcagcaaa gagtctatcc   8040
tgcccaagag aacagcgat aagctgatcg ccagaaagaa ggactgggac cctaagaagt    8100
acggcggctt cgacagcccc accgtggcct attctgtgct ggtggtggcc aaagtggaaa   8160
agggcaagtc caagaaactg aagagtgtga aagagctgct ggggatcacc atcatggaaa   8220
gaagcagctt cgaagaagat cccatcgact ttctggaagc caagggctac aaagaagtga   8280
aaaaggacct gatcatcaag ctgcctaagt actcctgtt cgagctggaa aacggccgga    8340
agagaatgct ggcctctgcc ggcgaactgc agaaggaaa cgaactggcc ctgcccctcca   8400
aatatgtgaa cttcctgtac ctggccagcc actatgagaa gctgaagggc tcccccgagg   8460
ataatgagca gaaacagctg tttgtggaac agcacaagca ctaccggac gagatcatcg     8520
agcagatcag cgagttctcc aagagagtga tcctggccga cgctaatctg gacaaagtgc   8580
tgtccgccta caacaagcac cgggataagc ccatcagaga gcaggccgag aatatcatcc   8640
acctgttac cctgaccaat ctgggagccc tgccgcctt caagtacttt gacaccacca    8700
tcgaccggaa gaggtacacc agcaccaaaa ggtgctgaa cgccaccctg atccaccaga   8760
gcatcaccgg cctgtacgag acacggatcg acctgtctca gctgggaggc gacaagcgac   8820
ctgccgccac aaagaaggct ggacaggcta agaagaagaa agattacaaa gacgatgacg   8880
ataagtaact agagctcgct gatcagcctc gactgtgcct tctagttgcc agccatctgt   8940
tgtttgcccc tcccccgtgc cttccttgac cctggaaggt gccactccca ctgtcctttc   9000
ctaataaaat gaggaaattg catcgcattg tctgagtagg tgtcattcta ttctgggggg   9060
tggggtgggg caggacagca aggggagga ttgggaagag aatagcaggc atgctgggga    9120
ctgaggcgga aagaaccagc tgtggaatgt gtgtcagtta gggtgtggaa agtccccagg   9180
ctccccagca ggcagaagta tgcaaagcat gcatctcaat tagtcagcaa ccaggtgtgg   9240
aaagtcccca ggctcccag caggcagaag tatgcaaagc atgcatctca attagtcagc    9300
aaccatagtc ccgcccctaa ctccgcccat cccgcccta ctccgccca gttccgccca    9360
ttctccgccc catggctgac taatttttt tatttatgca gaggccgagg ccgcctcggc    9420
ctctgagcta ttccagaagt agtgaggagg cttttttgga ggcctaggct tttgcaaaaa   9480
gcttgggccc gccccaactg gggtaacctt tgagttctct cagttggggg              9530

SEQ ID NO: 391        moltype = DNA   length = 5722
FEATURE               Location/Qualifiers
misc_feature          1..5722
                      note = Description of Artificial Sequence: Synthetic
                      polynucleotide
source                1..5722
                      mol_type = other DNA
                      organism = synthetic construct
SEQUENCE: 391
tgatcccctg cgccatcaga tccttggcgg cgagaaagcc atccagttta ctttgcaggg     60
cttcccaacc ttaccagagg gcgccccagc tggcaattcc ggttcgcttg ctgtccataa    120
aaccgcccag tctagctatc gccatgtaag cccactgcaa gctacctgct ttctctttgc    180
gcttgcgttt tcccttgtcc agatagccca gtagctgaca ttcatccggg gtcagcaccg    240
tttctgcgga ctggctttct acgtgctcga gggggccaa acggtctcca gcttggctgt     300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca atccgccgg gagcggattt     600
gaacgttgcg aagcaacggc ccggagggtg cgggcaggca gccgcccgca t aaactgcgcag     660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc cgtagaaaa gatcaaagga tcttcttgag     840
atccttttt tctgcgcgta atctgctgct tgcaaacaaa aaaaccaccg ctaccagcgg     900
tggtttgttt gccggatcaa gagctaccaa ctctttttc cgaaggtaact ggcttcagca    960
```

```
gagcgcagat accaaatact gtccttctag tgtagccgta gttaggccac cacttcaaga  1020
actctgtagc accgcctaca tacctcgctc tgctaatcct gttaccagtg gctgctgcca  1080
gtggcgataa gtcgtgtctt accgggttgg actcaagacg atagttaccg gataaggcgc  1140
agcggtcggc ctgaacgggg ggttcgtgca cacagcccag cttggagcga acgacctaca  1200
ccgaactgag atacctacag cgtgaactat gagaaagcgc cacgcttccc gaagggagaa  1260
aggcggacag gtatccggta agcggcaggg tcggaacagg agagcgcacg agggagcttc  1320
caggggaaa cgcctggtat ctttatagtc ctgtcgggtt tcgccacctc tgacttgagc  1380
gtcgattttt gtgatgctcg tcagggggc ggagcctatg gaaaaacgcc agcaacgcgg  1440
ccttttacg gttcctggcc ttttgctggc cttttgctca catgttcttt cctgcgttat  1500
cccctgattc tgtggataac cgtattaccg cctttgagtg agctgatacc gctcgccgca  1560
gccgaacgac cgagcgcagc gagtcagtga gcgaggaagc ggaagagcgc ctgatgcggt  1620
attttctcct tacgcatctg tgcggtattt cacaccgcat atggtgcact ctcagtacaa  1680
tctgctctga tgccgcatag ttaagccagt atacactccg ctatcgctac gtgactgggt  1740
catggctgcg ccccgacacc cgccaacacc cgctgacgcg ccctgacggg cttgtctgct  1800
cccggcatcc gcttacagac aagctgtgac cgtctccggg agctgcatgt gtcagaggtt  1860
ttcaccgtca tcaccgaaac gcgcgaggca gcagatcaat tcgcgcgcga aggcgaagcg  1920
gcatgcataa tgtgcctgtc aaatggacga agcagggatt ctgcaaaccc tatgctactc  1980
cgtcaagccg tcaattgtct gattcgttac caattatgac aacttgacgg ctacatcatt  2040
cactttttct tcacaaccgg cacgaactc gctcggctg ccccggtgc atttttttaaa  2100
tacccgcgag aaatagagtt gatcgtcaaa accaacattg cgaccgacgg tggcgatagg  2160
catccggtg gtgctcaaaa gcagcttcgc ctggctgata cgttggtcct cgcgccagct  2220
taagacgcta atccctaact gctggcggaa aagatgtgac agacgcgacg gcgacaagca  2280
aacatgctgt gcgacgctgg cgatacatta ccctgttatc cctagatgac attaccctgt  2340
tatcccagat gacattaccc tgttatccct agatgacatt accctgttat ccctagatga  2400
catttaccct gttatcccta gatgacatta ccctgttatc ccagatgaca ttaccctgtt  2460
atccctagat acattaccct gttatcccag atgacatacc tgttatccta gatgacat  2520
taccctgtta tcccagatga cattaccctg ttatccctag atacattacc ctgttatccc  2580
agatgacata ccctgttatc cctagatgac attaccctgt tatcccagat gacattaccc  2640
tgttatccct agatacatta ccctgttatc ccagatgaca ccctgttata tccctagtg  2700
acattaccct gttatcccag atgacattac cctgttatcc ctagatacat taccctgtta  2760
tcccagatga catccctgt tatccctaga tgacattacc ctgttatccc agatgacatt  2820
accctgttat ccctagatac attaccctgt tatcccagat gacatacct gttatccta  2880
gatgacatta ccctgttatc ccagatgaca ttaccctgtt atccctagat acattaccct  2940
gttatcccag atgacatacc ctgttatccc tagatgacat taccctgtta tcccagataa  3000
actcaatgat gatgatgatg atggtcgaga ctcagcggcc gcggtgccag ggcgtgccct  3060
tgggctcccc gggcgcggtc ctttgggcgc taactgcgtg cgcgctggga attggcgcta  3120
attgcgcgtg cgcgctggga ctcaaggcgc taactgcgcg tgcgttctgg ggcccggggt  3180
gccgcggcct gggctgggc gaaggcgggc tcggccggaa ggggtggggt cgccgcggct  3240
cccggggcct tgcgcgcact tcctgcccga gccgctgccc gccgcgaggg tgtggccgctg  3300
cgtgcgcgcg cgccgacccg gcgctgtttg aaccgggcgg aggcggggct ggcgcccggt  3360
tgggaggggg ttggggcctg gcttcctgcc gcgcgccgcg gggacgcctc cgaccagtgt  3420
ttgccttttta tggtaataac gcggccggcc cggcttcctt tgtccccaat ctgggcgcgc  3480
gccggcgccc cctggcggcc taaggactcg gcgcgccgga agtggccagg gcgggggcga  3540
cctcggctca cagcgcgccc ggctattctc gcagctcgcc accatgcccg ccatgaagat  3600
cgagtgccgc atcaccggca ccctgaacgg cgtggagttc gagctggtgg gcggcggaga  3660
gggcacccc gagcagggcc gcatgaccaa caagatgaag agcaccaaag cgccctgac  3720
cttcagcccc tacctgctga gccacgtgat gggctacggc ttctaccact tcggccacta  3780
ccccagcggc tacgagaacc ccttcctgca cgccatcaac aacggcgct acaccaacac  3840
ccgcatcgag aagtacgagg acggcggcgt gctgcacgtg agcttcagct accgctacga  3900
ggccggccgc gtgatcggcg acttcaaggt ggtgggcacc ggcttccccg aggacagcgt  3960
gatcttcacc gacaagatca tccgcagcaa cgccaccgtg gagcacctgc accccatggg  4020
cgataacgtg ctggtgggca gttcgcccg caccttcagc ctgcgcgacg gcggctacta  4080
cagcttcgtg gtggacagcc acatgcactt caagagcgcc atccacccca gcatcctgca  4140
gaacgggggc cccatgttcg ccttccgccg cgtggaggag ctgcacagca acaccgagct  4200
gggcatcgtg gagtaccagc acgccttcaa gacccccatc gccttcgccg gatctcgagc  4260
tcgaaccatg gatgatgata tcgccgcgct cgtcgtcgac aacggctccg gcatgtgcaa  4320
ggccggcttc gcgggcgacg atgccccccg ggccgtcttc ccctccatcg tgggcgccc  4380
caggcaccag gtaggggagc tggctgggtg gggcagcccc gggagcgggc gggaggcaag  4440
ggcgctttct ctgcacagga gcctcccggt ttccggggtg gggctgcgc ccgtgctcag  4500
ggcttcttgt cctttccttc ccagggcgtg atggtcagaa tgggtcagaa ggattcctat  4560
gtgggcgacg aggccagag caagagaggc atcctcaccc tgaagtaccc catcgagcac  4620
ggcatcgtca ccaactggga cgacatgag aaaatctggc accacacctt ctacaatgag  4680
ctgcgtgtgt ctcccgagga gcaccccgtg ctgctgaccg aggccccct gaaccccaag  4740
gccaaccgga gaagatgac tcagccccaa ctggggtaac ctttgagttc tctcagttgg  4800
gggtaatcag catcatgatg tggtaccaca tcatgatgct gattataaga atgcggccgc  4860
cacactctag tggatctcga gttaataatt cagaagaact cgtcaagaag gcgatagaag  4920
gcgatgcgct gcgaatcggg agcggcgata ccgtaaagca cgaggaagcg gtcagcccat  4980
tcgccgccaa gctcttcagc aatatcacgg gtagccaacg ctatgtcctg atagcggtca  5040
gccacaccca gccggccaca gtcgatgaat ccagaaaagc ggccattttc caccatgata  5100
ttcggcaagc aggcatcgcc atgggtcacg acgagatcct cgccgtcggg catgctcgcc  5160
ttgagcctgg cgaacagttc ggctggcgcg agccctgat gctcttcgtc cagatcatcc  5220
tgatcgacaa gaccggcttc catccgagta cgtgctcgct cgatgcgatg tttcgcttgg  5280
tggtcgaatg ggcaggtagc cggatcaagc gtatgcagcc gccgcattgc atcagccatg  5340
atggatactt tctcggcagg agcaaggtgt agatgacatg gagcctcgcc ccggcactt  5400
cgcccaatag cagccagtcc cttcccgctt cagtgacaac gtcgagcaca gctgcgcaag  5460
gaacgcccgt cgtggccagc cacgatagcc gcgctgcctc gtcttgcagt tcattcaggg  5520
caccggacag gtcggtcttg acaaaaagaa ccgggcgccc ctgcgctgac agccggaaca  5580
cggcggcatc agagcagccg attgtctgtt gtgcccagtc atagccgaat agcctctcca  5640
cccaagcggc cggagaacct gcgtgcaatc catcttgttc aatcatgcga aacgatcctc  5700
```
atcctgtctc ttgatcagag ct 5722

| SEQ ID NO: 392 | moltype = DNA length = 15424 |
| --- | --- |
| FEATURE | Location/Qualifiers |
| misc_feature | 1..15424 |
| | note = Description of Artificial Sequence: Synthetic polynucleotide |
| source | 1..15424 |
| | mol_type = other DNA |
| | organism = synthetic construct |

SEQUENCE: 392

```
tcgacggtat cgataagctt gatatcgaat tcctgcagcc cgggggatcc actagttcta   60
gagcggccgc caccgcggtg gagctccagc ttttgttccc tttagtgagg gttaatttcg  120
agcttggcgt aatcatggtc atagctgttt cctgtgtgaa attgttatcc gctcacaatt  180
ccacacaaca tacgagccgg aagcataaag tgtaaagcct ggggtgccta atgagtgagc  240
taactcacat taattgcgtt gcgctcactg cccgctttcc agtcgggaaa cctgtcgtgc  300
cagctgcatt aatgaatcgg ccaacgcgcg ggagaggcg gtttgcgtat gggcgctct  360
tccgcttcct cgctcactga ctcgctgcgc tcggtcgttc ggctgcggcg agcggtatca  420
gctcactcaa aggcggtaat acggttatcc acagaatcag gggataacgc aggaaagaac  480
atgtgagcaa aaggccagca aaaggccagg aaccgtaaaa aggccgcgtt gctggcgttt  540
ttccataggc tccgcccccc tgacgagcat cacaaaaatc gacgctcaag tcagaggtgg  600
cgaaacccga caggactata aagataccag gcgtttcccc ctggaagctc cctcgtgcgc  660
tctcctgttc cgaccctgcc gcttaccgga tacctgtccg cctttctccc ttcgggaagc  720
gtggcgcttt ctcatagctc acgctgtagg tatctcagtt cggtgtaggt cgttcgctcc  780
aagctgggct gtgtgcacga accccccgtt cagcccgacc gctgcgcctt atccggtaac  840
tatcgtcttg agtccaaccc ggtaagacac gacttatcgc cactggcagc agccactggt  900
aacaggatta gcagagcgag gtatgtaggc ggtgctacag agttcttgaa gtggtggcct  960
aactacggct acactagaag gacagtattt ggtatctgcg ctctgctgaa gccagttacc 1020
ttcggaaaaa gagttggtag ctcttgatcc ggcaaacaaa ccaccgctgg tagcggtggt 1080
ttttttgttt gcaagcagca gattacgcgc agaaaaaaag gatctcaaga agatcctttg 1140
atcttttcta cggggtctga cgctcagtgg aacgaaaact cacgttaagg gattttggtc 1200
atgagattat caaaaaggat cttcacctag atccttttaa attaaaaatg aagttttaaa 1260
tcaatctaaa gtatatatga gtaaacttgg tctgacagtt accaatgctt aatcagtgag 1320
gcacctatct cagcgatctg tctatttcgt tcatccatag ttgcctgact ccccgtcgtg 1380
tagataacta cgatacggga gggcttacca tctggcccca gtgctgcaat gataccgcga 1440
gacccacgct caccggctcc agatttatca gcaataaacc agccagccgg aagggccgag 1500
cgcagaagtg gtcctgcaac tttatccgcc tccatccagt ctattaattg ttgccgggaa 1560
gctagagtaa gtagttcgcc agttaatagt ttgcgcaacg ttgttgccat tgctacaggc 1620
atcgtggtgt cacgctcgtc gtttggtatg gcttcattca gctccggttc ccaacgatca 1680
aggcgagtta catgatcccc catgttgtgc aaaaaagcgg ttagctcctt cggtcctccg 1740
atcgttgtca gaagtaagtt ggccgcagtg ttatcactca tggttatggc agcactgcat 1800
aattctctta ctgtcatgcc atccgtaaga tgcttttctg tgactggtga gtactcaacc 1860
aagtcattct gagaatagtg tatgcggcga ccgagttgct cttgcccggc gtcaatacgg 1920
gataataccg cgccacatag cagaacttta aaagtgctca tcattggaaa acgttcttcg 1980
gggcgaaaac tctcaaggat cttaccgctg ttgagatcca gttcgatgta acccactcgt 2040
gcacccaact gatcttcagc atcttttact ttcaccagcg tttctgggtg agcaaaaaca 2100
ggaaggcaaa atgccgcaaa aaagggaata agggcgacac ggaaatgttg aatactcata 2160
ctcttccttt ttcaatatta ttgaagcatt tatcagggtt attgtctcat gagcggatac 2220
atatttgaat gtatttagaa aaataaacaa ataggggttc cgcgcacatt tccccgaaaa 2280
gtgccacctg acgtctaaga aaccattatt atcatgacat taacctataa aaataggcgt 2340
atcacgaggc cctttcgtct tcaagaattc tcatgtttga cagcttatca tcgataagct 2400
ttaatgcggt agtttatcac agttaaattg ctaacgcagt caggcaccgt gtatgaaatc 2460
taacaatgcg ctcatcgtca tcctcggcac cgtcaccctg gatgctgtag gcataggctt 2520
ggttatgccg gtactgccgg cctcttgcg gatatcgtc cattccgaca gcatcgccag 2580
tcactgagtc gtgctgctag cgctatatgc gttgatgcaa tttctatgcg cacccgttct 2640
cggagcactg tccgaccgct ttggccgccg cccagtcctg ctcgcttcgc tacttggagc 2700
cactatcgac tacgcgatca tggcgaccac accgtcctg tggatccggc gcacaccaaa 2760
aacgtcactt tgccacatc cgtcgcttac atgtgttccg ccacacttgc aacatcacac 2820
ttccgccaca ctactacgtc acccgccccg ttcccacgcc ccgcgccacg tcacaaactc 2880
caccccctca ttatcatatt ggcttcaatc caaatataat catcaataat ataccttatt 2940
ttggattgaa gccaatatga taatgagggg gtgagtttg tgacgtggcg cggggcgtgg 3000
gaacggggcg ggtgacgtag gttttagggc ggagtaactt gtatgtgttg ggaattgtag 3060
ttttcttaaa atgggaagtt acgtaacgtg gaaaacgga agtgacgatt tgaggaagtt 3120
gtgggttttt tggctttcgt ttctgggcgt aggttcgtc gcggttttct gggtgttttt 3180
tgtggactttt aaccgttacg tcatttttta gtcctatata tactcgctct gcacttggcc 3240
cttttttaca ctgtgactga ttgagctggt gccgtgtcga gtggtgtttt tttaataggt 3300
tttctttttt actggtaagg ctgactgtta ggctgccgct gtgaagcgct gtatgttgtt 3360
ctggagcggg agggtgctat tttgcctagg caggagggtt tcaggtgtt ttatgtgttt 3420
ttctctccta ttaattttgt tataccttcct atggggggtg tcacgttgtc tctacgccgg 3480
cgggtatgta ttccccgggg ctatttcggt cgcttttag cactgaccga tgaatcaacc 3540
tgatgtgttt accgagtctt acattatgac tccggacatg accgaggagc tgtcggtggt 3600
gcttttaat cacggtgacc agttttttta cggtcacgcc ggcatggccg tagtccgtct 3660
tatgcttata agggttgttt ttcctgttgt aagacaggct tctaatgttt aaatgttttt 3720
ttgttatttt attttgtt tatgcagaaa cccgcagaca tgtttgagag aaaaatggtg 3780
tcttttttctg tggtggttcc ggagcttacc tgcctttatc tgcatgagca tgactacgat 3840
gtgctttctt ttttgcgcga ggctttgcct gattttttga gcagcacctt gcattttata 3900
tcgccgccca tgcaacaaag cttacatcgg ggctacgctg gttagcatag ctccgagtat 3960
gcgtgtcata atcagtgtgg gttcttttgt caaggttcct ggcggggaag tggccgcgct 4020
ggtccgtgca gacctgcacg attatgttca gctggccctg cgaagggacc tacgggatcg 4080
```

```
cggtattttt gttaatgttc cgcttttgaa tcttatacag gtctgtgagg aacctgaatt   4140
tttgcaatca tgattcgctg cttgaggctg aaggtggagg gcgctctgga gcagattttt   4200
acaatggccg gacttaatat tcgggatttg cttagagata tattgagaag gtggcgagat   4260
gagaattatt tgggcatggt tgaaggtgct ggaatgttta tagaggagat tcaccctgaa   4320
gggtttagcc tttacgtcca cttggacgtg agggccgttt gccttttgga agccattgtg   4380
caacatctta caaatgccat tatctgttct ttggctgtag agtttgacca cgccaccgga   4440
ggggagcgcg ttcacttaat agatcttcat ttttgaggttt tggataatct tttggaataa   4500
aaaaaaaaac atggttcttc cagctcttcc cgctcctccc gtgtgtgact cgcagaacga   4560
atgtgtaggt tggctgggtg tggcttattc tgcggtggtg gatgttatca gggcagcggc   4620
gcatgaagga gtttacatag aacccgaagc caggggggcgc ctggatgctt tgagagagtg   4680
gatatactac aactactaca cagagcgatc taagcggcga gaccggagac gcagatctgt   4740
ttgtcacgcc cgcacctggt tttgcttcag gaaatatgac tacgtccggc gttccatttg   4800
gcatgacact acgaccaaca cgatctcggt tgtctcggcg cactccgtac agtagggatc   4860
gtctacctcc ttttgagaca gaaacccgcg ctaccatact ggaggatcat ccgctgctgc   4920
ccgaatgtaa cactttgaca atgcacaacg tgagttacgt gcgaggtctt ccctgcagtg   4980
tgggatttac gctgattcag gaatggggttg ttccctggga tatggttcta acgcgggagg   5040
agcttgtaat cctgaggaag tgtatgcacg tgtgcctgtg ttgtgccaac attgatatca   5100
tgacgagcat gatgatccat ggttacgagt cctgggctct ccactgtcat tgttccagtc   5160
ccggttccct gcagtgtata gccggcgggc aggttttggc cagctggttt aggatggtgg   5220
tggatggcgc catgtttaat cagaggtttta tatggtaccg ggaggtggtg aattacaaca   5280
tgccaaaaga ggtaatgttt atgtccagcg tgtttatgag gggtcgccac ttaatctacc   5340
tgcgcttgtg gtatgatggc cacgtgggtt ctgtgtccc ccatgagc tttggataca   5400
gcgccttgca ctgtgggatt ttgaacaata ttgtggtgct gtgctgcagt tactgtgctg   5460
atttaagtga gatcagggtg cgctgctgtg cccggaggac aaggcgcctt atgctgcggg   5520
cggtgcgaat catcgctgag gagaccactg ccatgttgta ttcctgcagg acggagcggc   5580
ggcggcagca gtttattcgc gcgctgctgc agcaccaccg ccctatcctg atgcacgatt   5640
atgactctac ccccatgtag gcgtggactt ctccttcgcc gcccgttaag caaccgcaag   5700
ttggacagca gcctgtggct cagcagctgg acagcgacat gaacttaagt gagctgcccg   5760
gggagtttat taatatcact gatgagcgtt tggctcgaca ggaaaccgtg tggaatataa   5820
cacctaagaa tatgtctgtt acccatgata tgatgctttt taaggccagc cggggagaaa   5880
ggactgtgta ctctgtgtgt tgggaggag gtggcaggtt gaatactagg gttctgtgag   5940
tttgattaag gtacggtgat ctgtataagc tatgtggtgg tggggctata ctactgaatg   6000
aaaaatgact tgaaattttc tgcaattgaa aaataaacac gttgaaacat aacacaaacg   6060
attctttatt cttgggcaat gtatgaaaaa gtgtaagagg atgtggcaaa tatttcatta   6120
atgtagttgt ggccagacca gtcccatgaa aatgacatag agtatgcact tggagttgtg   6180
tctcctgttt cctgtgtacc gtttagtgta atggtagtg ttacaggttt agttttgtct   6240
ccgtttaagt aaacttgact gacaatgtta cttttggcag ttttaccgtg agattttgga   6300
taagctgata ggttaggcat aaatccaaca gcgtttgtat aggctgtgcc ttcagtaaga   6360
tctccatttc taaagttcca atattctggg tccaggaagg aatttgtttag tagcactcca   6420
ttttcgtcaa atcttataat aagatgagca ctttgaactg ttccagatat tggagccaaa   6480
ctgccttttaa cagccaaaac tgaaactgta gcaagtattt gactgccaca ttttgttaag   6540
accaaagtga gtttagcatc tttctctgca tttagtctac agttaggaga tggagctggt   6600
gtggtccaca aagttagctt atcattattt ttgtttccta ctgtaatggc acctgctgctg   6660
tcaaaactaa ggccagttcc tagtttagga accatagcct tgtttgaatc aaattctagg   6720
ccatggccaa ttttttgttt gagggggattt gtgtttggtg cattaggtga accaaattca   6780
agcccatctc ctgcattaat ggctatggct gtagcgtcaa acatcaaccc cttggcagtg   6840
cttaggttaa cctcaagctt tttggaattg tttgaagctg taaacaagta aaggcctttg   6900
ttgtagttaa tatccaagtt gtgggctgag tttataaaaa gagggccctg tcctagtctt   6960
agattatgtt ggttttgagc atcaaacgga taactaacat caagtataag gcgtctgttt   7020
tgagaatcaa tccttagtcc tcctgctaca ttaagttgca tattgccttg tgaatcaaaa   7080
cccaaggctc cagtaacttt agtttgcaag gaagtattat taatagtcac acctggacca   7140
gttgctacgg tcaaagtgtt taggtcgtct gttacatgca aaggagcccc gtactttagt   7200
cctagttttc cattttgtgt ataaatgggc tctttcaagt caatgcccaa gctaccagtg   7260
gcagtagtta gagggggtga ggcagtgata gtaagggtac tgctatcggt ggtggtgagg   7320
gggcctgatg tttgcagggc tagctttcct tctgacactg tgagggggtcc ttgggtggca   7380
atgctaagtt tggagtcgtg cacggttagc gggggcctgtg attgcatgat gagtgtgttg   7440
cccgcgacca ttagaggtgc ggcggcagcc acagttaggg cttctgaggt aactgtgagg   7500
ggtgcagata tttccaggtt tatgtttgac ttggtttttt tgagaggtgg gctcacagtg   7560
gttacatttt gggaggtaag gttgccggcc tcgtccagag agaggccgtt gcccatttg   7620
agcgcaagca tgccattgga ggtaactaga ggttcggata ggcgcaaaga gagtaccca   7680
gggggactct cttgaaaccc attggggat acaaagggag gagtaagaaa aggcacagtt   7740
ggaggaccgg tttccgtgtc atatggatac acggggttga aggtatcttc agacggtctt   7800
gcgcgcttca tctgcaacaa catgaagata gtgggtgcgg atggacagga acaggaggaa   7860
actgacattc catttagatt gtggagaaag tttgcagcca ggaggaagct gcaataccag   7920
agctgggagg agggcaagga ggtgctgctg aataaactgg acagaaattt gctaactgat   7980
tttaagtaag tgatgcttta ttatttttt ttattagtta aagggaataa gatcccggg   8040
tactctagtt aattaactag aggatcttga tgtaatccaa ggttaggaca gttgcaaatc   8100
acagtgagaa cacagggtcc cctgtcccgc tcaactagca gggggcgctg ggtaaactcc   8160
cgaatcaggc tacgggcaag ctctccctgg gcggtaagcc ggaggccgtg gccgggggcc   8220
tcgatatgat cctcgggcaa ttcaaagtag caaaactcac cggagtcgcg ggcaaagcac   8280
ttgtggcggc gacagtggac caggtgtttc aggcgcagtt gctctgcctc tccacttaac   8340
attcagtcgt agccgtccgc cgagtccttt accgcgtcaa agttaggaat aaattgatcc   8400
ggatagtggc cgggaggtcc cgagaagggg ttaaagtaga ccgatggcac aaactcctca   8460
ataaattgca gagttccaat gcctccagag caggcaggg aggacgaggt ctgcagagtt   8520
aggattgcct gacgagcgt gaatgaagga cggccggcgc cgccgatctg aaatgtcccg   8580
tccgacgga accaagcga ggagctcacc gactcgtcgt tgagctgaat acctcgccct   8640
ctgattgtca ggtgagttat accctgcccg ggcgaccgca ccctgtgacg aaagccgccc   8700
gcaagctgcg cccctgagtt agtcatctga acttcggcct gggcgtctct gggaagtacc   8760
acagtggtgg gagcgggact ttcctggtac accagggcag cgggccaact acgggggatta   8820
```

```
aggttattac gaggtgtggt ggtaatagcc gcctgttcca agagaattcg gtttcggtgg   8880
gcgcggattc cgttgacccg ggatatcatg tggggtcccg cgctcatgta gtttattcgg   8940
gttgagtagt cttgggcagc tccagccgca agtcccattt gtggctggta actccacatg   9000
tagggcgtgg gaatttcctt gctcataatg gcgctgacga caggtgctgg cgccgggtgt   9060
ggccgctgga gatgacgtag ttttcgcgct taaatttgag aaagggcgcg aaactagtcc   9120
ttaagagtca gcgcgcagta tttactgaag agagcctccg cgtcttccag cgtgcgccga   9180
agctgatctt cgcttttgtg atacaggcag ctgcgggtga gggatcgcag agacctgttt   9240
tttattttca gctcttgttc ttggcccctg ctctgttgaa atatagcata cagagtggga   9300
aaaatcctgt ttctaagctc gcgggtcgat acgggttcgt tgggcgccag acgcagcgct   9360
cctcctcctg ctgctgccgc cgctgtggat ttcttgggct ttgtcagagt cttgctatcc   9420
ggtcgccttt gcttctgtgt ggccgctgct gttgctgccg ctgccgctgc cgccggtgca   9480
gtatgggctg tagagatgac ggtagtaatg caggatgtta cggggggaagg ccacgccgtg   9540
atggtagaga agaaagcggc gggcgaagga gatgttgccc ccacagtctt gcaagcaagc   9600
aactatggcg ttcttgtgcc cgcgccatga gcggtagcct tggcgctgtt gttgctcttg   9660
ggctaacggc ggcggctgct tggacttacc ggccctggtt ccagtggtgt cccatctacg   9720
gttgggtcgg cgaacgggca gtgccggcgg cgcctgagga gcggaggttg tagccatgct   9780
ggaaccggtt gccgatttct ggggcgccgg cgaggggaat gcgaccgagg gtgacggtgt   9840
ttcgtctgac acctcttcga cctcggaagc ttcctcgtct aggctctccc agtcttccat   9900
catgtcctcc tcctcctcgt ccaaaacctc ctctgcctga ctgtcccagt attcctcctc   9960
gtccgtgggt ggcggcggca gctgcagctt ctttttgggt gccatcctgg gaagcaaggg  10020
cccgcggctg ctgctgatag ggctgcgcg gcgggggggat tgggttgagc tcctcgccgg  10080
actggggtc caagtaaacc ccccgtccct ttcgtagcag aaactcttgg cgggctttgt  10140
tgatggcttg caattggcca agaatgtggc cctgggtaat gacgcaggcg gtaagctccg  10200
catttggcgg gcgggattgg tcttcgtaga acctaatctc gtgggcgtgg tagtcctcag  10260
gtacaaattt gcgaaggtaa gccgacgtcc acagccccgg agtgagtttc aaccccggag  10320
ccgcgganctt ttcgtcaggc gagggaccct gcagctcaaa ggtaccgata atttgactt  10380
cgttaagcag ctgcgaattg caaaccaggg agcggtgcgg ggtgcatagg ttgcagcgac  10440
agtgacactc cagtagaccg tcaccgctca cgtcttccat tatgtcagag tggtaggcaa  10500
ggtagttggc tagctgcaga aggtagcagt ggccccaaag cggcggaggg cattcgcggt  10560
acttaatggg cacaaagtcg ctaggaagtg cacagcaggt ggcgggcaa attcctgagc  10620
gctctaggat aaagttccta aagttctgca acatgctttg actggtgaag tctggcagac  10680
cctgttgcag ggttttaagc aggcgttcgg ggaaaatgat gtccgccagg tgcgcggcca  10740
cggagcgctc gttgaaggcc gtccataggt ccttcaagtt ttgctttagc agtttctgca  10800
gctccttgag gttgcactcc tccaagcact gctgccaaac gcccatggcc gtctgccagg  10860
tgtagcatag aaataagtaa acgcagtcgc ggacgtagtc gcggcgcgcc tcgcccttga  10920
gcgtggaatg aagcacgttt tgcccaaggc ggttttcgtg caaaattcca aggtaggaga  10980
ccaggttgca gagctccacg ttggagatct tgcaggcctg gcgtacgtag ccctgtcgaa  11040
aggtgtagtg caatgttttcc tctagcttgc gctgcatctc cgggtcagca aagaaccgct  11100
gcatgcactc aagctccacg gtaacgagca ctgcggccat cattagtttg cgtcgctcct  11160
ccaagtcggc aggctcgcgc gtttgaagcc agccgcgctag ctgctcgtcg ccaactgcgg  11220
gtaggccctc ctctgtttgt tcttgcaaat ttgcatccct ctccaggggc tgcgcacggc  11280
gcacgatcag ctcactcatg actgtgctca tgaccttggg gggtaggtta agtgccgggt  11340
aggcaaagtg ggtgacctcg atgctgcgtt ttagtacggc ggtgcgcgcg ttgtcaccct  11400
cgagttccac caacactcca gagtgacttt cattttcgct gttttcctgt tgcagagcgt  11460
ttgccgcgcg cttctcgtcg cgtccaagac cctcaaagat ttttggcact tcgttgagcg  11520
aggcgatatc aggtatgaca gcgccctgcc gcaaggccag ctgcttgtcc gctcggctgc  11580
ggttggcacg gcaggatagg ggtatcttgc agttttggaa aaagatgtga taggtggcaa  11640
gcacctctgg cacggcaaat acggggtaga agttgaggcg cggggttgggc tcgcatgtgc  11700
cgttttcttg gcgtttgggg ggtacgcgcg gtgagaatag gtggcgttcg taggcaaggc  11760
tgacatccgc tatggcgagg ggcacatcgc tgcgctcttg caacgcgtcg cagataatgg  11820
cgcactggcg ctgcagatgc ttcaacagca cgtcgtctcc cacatctagg tagtcgccat  11880
gcctttcgtc ccccgcccg acttgttcct cgtttgcctc tgcgttgtcc tggtcttgct  11940
ttttatcctc tgttggtact gagcggtcct cgtcgtcttc gcttacaaaa cctgggtcct  12000
gctcgataat cacttcctcc tcctcaagcg ggggtgcctc gacggggaag gtggtaggcg  12060
cgttggcggc atcggtggag gcggtggtgg cgaactcaga ggggggcggt aggctgtcct  12120
tcttctcgac tgactccatg atcttttct gcctatagga gaaggaaatg gccagtcggg  12180
aagaggagca gcgcgaaacc accccccgagc gcggacgcgg tgcggcgcga cgtccccaa  12240
ccatggagga cgtgtcgtcc ccgtcccgt cgccgccgcc tccccgggcg cccccaaaaa  12300
agcggatgag gcgcgcgtatc gagtccgagg acgaggaaga ctcatcacaa gacgcgctgg  12360
tgccgcgcac acccagcccg cggccatcga cctcgccggc ggatttggcc attgcgccca  12420
agaagaaaaa gaagcgccct tctcccaagc ccgagcgccc gccatcacca gaggtaatcg  12480
tggacagcga ggaagaaaga gaagatgtgg cgctacaaat ggtgggttc agcaacccac  12540
cggtgctaat caagcatggc aaaggaggta agcgcacagt gcggcggctg aatgaagacg  12600
acccagtggc gcgtggttatg cggacgcaag aggaagagac agagcccagc gaagcggaaa  12660
gtgaaattac ggtgatgaac ccgctgagtg tgccgatcgt gtctgcgtgg gagaagggca  12720
tggaggctgc gcgcgcgctg atggacaagt accacgtgga taacgatcta aaggcgaact  12780
tcaaactact gcctgaccaa gtggaagctc tggcggccgt atgcaagacc tggctgaacg  12840
aggagcaccg cgggttgcag ctgaccttca ccagcaacaa gacctttgtg acgatgatgg  12900
ggcgattcct gcaggcgtac ctgcagtcgt ttgcagaggt gacctacaag catcacgagc  12960
ccacgggctg cgcgttgtgg ctgcaccgct gcgctgagat cgaaggcgag cttaagtgtc  13020
tacacggaag cattatgata aataaggagc acgtgattga aatggatgtg acgagcgaaa  13080
acgggcagcg cgcgctgaag gagcagtcta gcaaggccaa gatcgtgaag aaccggtggg  13140
gccgaaatgt ggtgcagatc tccaacaccg acgcaaggtg ctgcgtgcac gacgcggcct  13200
gtccggccaa tcagttttcc gccaagtctt gggcaatgtt ctttctgaag gcgcaaagg  13260
ctcaggtggc ttttaagcag atcaaggctt ttatgcagge gctgtatcct aacgcccaga  13320
ccgggcacgg tcacctttttg atgccactac ggtgcgagtg caactcaaag cctgggcacg  13380
cgcccttttt gggaaggcag ctaccaaagt tgactccgtt cgccctgagc aacgcggagg  13440
acctggacgg ggatcgatc tccgacaaga gcgtgctggg cagcgtgcac cacccggcgc  13500
tgatagtgtt ccagtgctgc aaccctgtgt atcgcaactc gcgcgcgcag ggcggaggcc  13560
```

```
ccaactgcga cttcaagata tcggcgcccg acctgctaaa cgcgttggtg atggtgcgca   13620
gcctgtggag tgaaaacttc accgagctgc cgcggatggt tgtgcctgag tttaagtgga   13680
gcactaaaca ccagtatcgc aacgtgtccc tgccagtggc gcatagcgat gcgcggcaga   13740
accccttga tttttaaacg gcgcagacgg caagggtggg ggtaaataat cacccgagag    13800
tgtacaaata aaagcatttg cctttattga aagtgtctct agtacattat ttttacatgt   13860
ttttcaagtg acaaaaagaa gtggcgctcc taatctgcgc actgtggctg cggaagtagg   13920
gcgagtggcg ctccaggaag ctgtagagct gttcctggtt gcgacgcagg gtgggctgta   13980
cctggggact gttgagcatg gagttgggta ccccggtaat aaggttcatg gtggggttgt   14040
gatccatggg agtttgggc cagttggcaa aggcgtggag aaacatgcag cagaatagtc     14100
cacaggcggc cgagttgggc ccctgtacgc tttgggtgga cttttccagc gttatacagg   14160
ggtcgggga agaagcaatg gcgctacggc gcaggagtga ctcgtactca aactggtaaa    14220
cctgcttgag tcgctggtca gaaaagccaa agggctcaaa gaggtagcat gttttttgagt  14280
gcgggttcca ggcaaaggcc atccagtgta cgccccagt ctcggtccga gactcgaacc     14340
gggggtcccg cgactcaacc cttggaaaat aaccctccg ctacagggag cgagccactt     14400
aatgctttcg ctttccagcc taaccgctta cgctgcgcgc ggccagtggc caaaaaagct   14460
agcgcagcag ccgccgcgcc tggaaggaag ccaaaaggag cactccccg ttgtctgacg     14520
tcgcacacct gggttcgaca cgcgggcggt aaccgcatgg atcacggcgg acggccggat   14580
acggggctcg aaccccggtc gtccgccatg ataccctteg gaatttatcc accagaccac   14640
ggaagagtgc ccgcttacag gctctccttt tgcacggtag agcgtcaacg attgcgcgcg   14700
cctgaccggc cagagcgtcc cgaccatgga gcacttttg ccgctgcgca acatctggaa     14760
ccgcgtccgc gactttccgc gcgcctccac caccgccgcc ggcatcacct ggatgtccag   14820
gtacatctac ggatatcatc gccttatgtt ggaagatctc gaaacccgga cccggccac    14880
cctacgctgg cccctctacc gccagccgcc gccgcacttt ttggtgggat accagtacct   14940
ggtgcggact tgcaacgact acgtatttga ctcgagggct tactcgcgtc tcaggtacac   15000
cgagctctcg cagccgggtc accagaccgt taactggtcc gttatggcca actgcactta   15060
caccatcaac acgggcgcat accaccgctt tgtggacatg gatgacttcc agtctacccct  15120
cacgcaggtg cagcaggcca tattagccga gcgcgttgtc gccgacctag ccctgcttca   15180
gccgatgagg ggcttcgggg tcacacgcat gggaggaaga gggcgccacc tacggccaaa   15240
ctccgccgcc gccgcagcga tagatgcaag agatgcagga caagaggaag gagaagaaga   15300
agtgccggta gaaaggctca tgcaagacta ctacaaagac ctgcgccgat gtcaaaacga   15360
agcctggggc atggccgacc gcctgcgcat tcagcaggcc ggacccaagg acatggtgct   15420
tctg                                                                15424
SEQ ID NO: 393          moltype = DNA  length = 3849
FEATURE                 Location/Qualifiers
misc_feature            1..3849
                        note = Description of Artificial Sequence: Synthetic
                        polynucleotide
source                  1..3849
                        mol_type = other DNA
                        organism = synthetic construct
SEQUENCE: 393
cggcgtcaat acgggataat accgcgccac atagcagaac tttaaaagtg ctcatcattg   60
gaaaacgttc ttcggggcga aaactctcaa ggatcttacc gctgttgaga tccagttcga   120
tgtaacccac tcgtgcaccc aactgatctt cagcatcttt tactttcacc agcgtttctg   180
ggtgagcaaa acaggaagg caaatgccga caaaaaggg aataagggcg acacggaaat      240
gttgaatact catactcttc ctttttcaat attattgaa catttatcag ggttattgtc     300
tcatgagcgg atacatattt gaatgtattt agaaaaataa acaaataggg gttccgcgca   360
catttccccg aaaagtgcca cctaaattgt aagcgttaat attttgttaa aattcgcgtt   420
aaatttttgt taaatcagct cattttttaa ccaataggcc gaaatcggca aaatcccttta  480
taaatcaaaa gaatagaccg agatagggtt gagtgttgtt ccagtttgga acaagagtcc   540
actattaaag aacgtggact ccaacgtcaa agggcgaaaa accgtctatc agggcgatgg   600
cccactacgt gaaccatcac cctaatcaag tttttgggg tcgaggtgcc gtaaagcact     660
aaatcggaac cctaagggga gccccgatt tagagcttga cggggaaagc cggcgaacgt     720
ggcgagaaag gaagggaaga aagcgaaagg gcgggcgct agggccgctgg caagtgtagc   780
ggtcacgctg cgcgtaacca ccacaccgc cgcgcttaat gcgccgctac agggcgcgtc    840
ccattcgcca tcaggctgc gcaactgttg ggaagggcga tcgtgcggg cctcttcgct      900
attacgccag ctgcgcgctc gctcgctcac tgaggccgcc cggcaaagc ccgggcgtcg     960
ggcgaccttt ggtcgcccgg cctcagtgag cgagcgagcg cgcagagagg gagtggccaa   1020
ctccatcact agggggttcct tgtagttaat gattaaccg ccatgctact tatctacgta   1080
gccatgctct aggaagagta ccattgacgt caataatgac gtatgttccc atagtaacgc   1140
caataggac tttccattga cgtcaatggg tggagtattt acgtaaaact gcccacttgg    1200
cagtacatca agtgtatcag tggtttgtct ggtcaaccac cgcggtctca gtggtgtacg   1260
gtacaaaccc agctaccggt cgccaccatg cccgccatga gctgcgtcac ccgcatccgt   1320
ggcaccctga acggcgtgga gttcgagctg gtgggcggcg agagggcac ccccgagcag    1380
ggccgcatga ccaacaagat gaagagcacc aaaggcgccc tgacccttcag ccctacctg   1440
ctgagccacg tgatgggcta cggcttctac cacttcggca cctaccccag cggctacgag   1500
aacccctcc tgcacgccat caacaacggc ggctacacaa cacccgcat cgagaagtac     1560
gaggacggcg gcgtgctgca cgtgagcttc agctaccgct acgaggccgg ccgcgtgatc   1620
ggcgacttca aggtggtggg caccggcttc cccgaggaca gcgtgatctt caccgacaag   1680
atcatccgca gcaacgccac cgtggagcac ctgcaccca tgggcgataa cgtgctggtg   1740
ggcagcttcg cccgcacctt cagcctgcgc gacggcggct actacagctt cgtggtggac   1800
agccacatgc acttcaagag cgccatccac cccagcatcc tgcagaacgg gggccccatg   1860
ttcgccttcc gccgcgtgga ggagctgcac agcaacaccg agctgggcat cgtggagtac   1920
cagcacgcct tcaagacccc catcgccttc gccagatctc gagctcgatg agtttggaca   1980
aaccacaact agaatgcagt gaaaaaaatg ctttatttgt gaaatttgtg atgctattgc   2040
tttatttgtg gcccgggat cttcctagag catggctacg tagataagta gcatggcggg   2100
ttaatcatta actacaagga accctagtg atggagttgg ccactccctc tctgcgcgct   2160
cgctcgctca ctgaggccgg gcgaccaaag gtcgcccgac gcccgggctt tgcccgggcg   2220
```

```
gcctcagtga gcgagcgagc gcgcagctgc attaatgaat cggccaacgc gcggggagag  2280
gcggtttgcg tattgggcgc tcttccgctt cctcgctcac tgactcgctg cgctcggtcg  2340
ttcggctgcg gcgagcggta tcagctcact caaaggcggt aatacggtta tccacagaat  2400
caggggataa cgcaggaaag aacatgtgag caaaaggcca gcaaaaggcc aggaaccgta  2460
aaaaggccgc gttgctggcg ttttccata  ggctccgccc ccctgacgag catcacaaaa  2520
atcgacgctc aagtcagagg tggcgaaacc cgacaggact ataaagatac caggcgtttc  2580
cccctggaag ctccctcgtg cgctctcctg ttccgaccct gccgcttacc ggatacctgt  2640
ccgcctttct cccttcggga agcgtggcgc tttctcatag ctcacgctgt aggtatctca  2700
gttcggtgta ggtcgttcgc tccaagctgg gctgtgtgca cgaaccccc  gttcagcccg  2760
accgctgcgc cttatccggt aactatcgtc ttgagtccaa cccggtaaga cacgacttat  2820
cgccactggc agcagccact ggtaacagga ttagcagagc gaggtatgta ggcggtgcta  2880
cagagttctt gaagtggtgg cctaactacg gctacactag aagaacagta tttggtatct  2940
gcgctctgct gaagccagtt accttcggaa aaagagttgg tagctcttga tccggcaaac  3000
aaaccaccgc tggtagcggt ggttttttt  tttgcaagca gcagattacg cgcagaaaaa  3060
aaggatctca agaagatcct ttgatctttt ctacggggtc tgacgctcag tggaacgaaa  3120
actcacgtta agggattttg gtcatgagat tatcaaaaag gatcttcacc tagatccttt  3180
taaattaaaa atgaagtttt aaatcaatct aaagtatata tgagtaaact tggtctgaca  3240
gttaccaatg cttaatcagt gaggcaccta tctcagcgat ctgtctattt cgttcatcca  3300
tagttgcctg actccccgtc gtgtagataa ctacgatacg ggagggctta ccatctggcc  3360
ccagtgctgc aatgataccg cgagacccac gctcaccggc tccagattta tcagcaataa  3420
accagccagc cggaagggcc gagcgcagaa gtggtcctgc aactttatcc gcctccatcc  3480
agtctattaa ttgttgccgg gaagctagag taagtagttc gccagttaat agtttgcgca  3540
acgttgttgc cattgctaca ggcatcgtgg tgtcacgctc gtcgtttggt atggcttcat  3600
tcagctccgg ttcccaacga tcaaggcgag ttacatgatc cccatgttg  tgcaaaaaag  3660
cggttagctc cttcggtcct ccgatcgttg tcagaagtaa gttggccgca gtgttatcac  3720
tcatggttat ggcagcactg cataattctc ttactgtcat gccatccgta agatgctttt  3780
ctgtgactgg tgagtactca accaagtcat tctgagaata gtgtatgcgg cgaccgagtt  3840
gctcttgcc                                                         3849
```

SEQ ID NO: 394      moltype = DNA  length = 7336
FEATURE             Location/Qualifiers
misc_feature        1..7336
                    note = Description of Artificial Sequence: Synthetic
                    polynucleotide
source              1..7336
                    mol_type = other DNA
                    organism = synthetic construct
SEQUENCE: 394

```
atgccggggt tttacgagat tgtgattaag gtccccagcg accttgacga gcatctgccc   60
ggcatttctg acagctttgt gaactgggtg gccgagaagg aatgggagtt gccgccagat  120
tctgacatgg atctgaatct gattgagcag gcaccctga  ccgtggccga gaagctgcag  180
cgcgacttc  tgacgaatg  gcgccgtgtg agtaaggccc cggaggctct tttctttgtg  240
caatttgaga agggagagag ctacttccac atgcacgtgc tcgtggaaac caccggggtg  300
aaatccatgg ttttgggacg tttcctgagt cagattcgcg aaaaactgat tcagagaatt  360
taccgcggga tcgagccgac tttgccaaac tggttcgcgg tcacaaagac cagaaatggc  420
gccgaggcg  ggaacaaggt ggtggatgag tgctacatcc ccaattactt gctccccaaa  480
acccagcctg agctccagtg ggcgtggact aaatatgaac agtatttaag cgcctgtttg  540
aatctcacgg agcgtaaacg gttggtggcg cagcatctga cgcacgtgtc gcagacgcag  600
gagcagaaca aagagaatca gaatcccaat tctgatgcgc cggtgatcag atcaaaaact  660
tcagccaggt acatggagct ggtcgggtgg ctcgtggaca aggggattac ctcggagaag  720
cagtggatcc aggaggacca ggcctcatac atctccttca tgcggcctc  caactcgcgg  780
tcccaaatca aggctgcctt ggacaatgcg ggaaagatta tgagcctgac taaaaccgcc  840
cccgactacc tggtgggcca gcagcccgtg gaggacattt ccagcaatcg gatttataaa  900
attttggaac taaacgggta cgatcccaa  tatgcggctt ccgtctttct gggatgggc   960
acgaaaaagt tcggcaagag gaacaccatc tggctgtttg ggcctgcaac taccggaaag 1020
accaacatcg cggaggccat agcccacact gtgcccttct acgggtgcgt aaactgacc  1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agacttttc  cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac tcagacgcg  1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
caacctctct gagggcattc gcgagtggtg ggcgctgaaa cctggagccc gaagcccaa  1980
agccaaccag caaaagcagg acgacggccg gggtctggtg cttcctggct acaagtacct 2040
cggacccttc aacggactcg acaaggggga gcccgtcaac gcggcggacg cagcggccct 2100
cgagcacgac aaggtctacg accagcagct caaggcggga gacaatccgt acctgcggta 2160
taaccacgcc gacgccgagt tccaggagcg tctgcaagaa gatacgtctt ttgggggcaa 2220
cctcgggcga gcagtcttcc aggccaagaa gcgggttctc gaacctctcg gtctggttga 2280
ggaaggcgct aagacggctc ctggaaagaa gagaccggta gagccatcac cccagcgttc 2340
tccagactcc tctacgggca tcggcaagaa aggccaacag cccgccagaa aaagactcaa 2400
ttttggtcag actggcgact cagagtcagt tccagaccct caacctctcg gagaacctcc 2460
```

```
agcagcgccc tctggtgtgg gacctaatac aatggctgca ggcggtgggc caccaatggc  2520
agacaataac gaaggcgccg acggagtggg tagttcctcg ggaaattggc attgcgattc  2580
cacatggctg ggcgacagag tcatcaccac cagcacccga acctgggccc tgcccaccta  2640
caacaaccac ctctacaagc aaatctccaa cgggacatcg gaggagcca ccaacgacaa  2700
cacctacttc ggctacagca cccccctggg gtattttgac tttaacagat tccactgcca  2760
cttttcacca cgtgactggc agcgactcat caacaacaac tggggattcc ggcccaagag  2820
actcagcttc aagctcttca acatccaggt caaggaggtc acgcagaatg aaggcaccaa  2880
gaccatcgcc aataacctca ccagcaccat ccaggtgttt acggactcgg agtaccagct  2940
gccgtacgtt ctcggctctg cccaccaggg ctgcctgcct ccgttcccgg cggacgtgtt  3000
catgattccc cagtacggct acctaacact caacaacggt agtcaggccg tgggacgctc  3060
ctccttctac tgcctggaat actttccttc gcagatgctg agaaccggca acaacttcca  3120
gtttacttac accttcgagg acgtgccttt ccacagcagc tacgcccaca gccagagctt  3180
ggaccggctg atgaatcctc tgattgacca gtacctgtac tacttgtctc ggactcaaac  3240
aacaggaggc acggcaaata cgcagactct gggcttcagc caaggtgggc ctaatacaat  3300
ggccaatcag gcaaagaact ggctgccagg accctgttac cgccaacaac gcgtctcaac  3360
gacaaccggg caaaacaaca atagcaactt tgcctggact gctgggacca aataccatct  3420
gaatggaaga aattcattgg ctaatcctgg catcgctatg caacacaca aagacgacga  3480
ggagcgtttt tttcccagta acgggatcct gattttttgc aaacaaaatg ctgccagaga  3540
caatgcggat tacagcgatg tcatgctcac cagcgaggaa gaaatcaaaa ccactaaccc  3600
tgtggctaca gaggaatacg gtatcgtggc agataacttg cagcagcaaa cacggctcc  3660
tcaaattgga actgtcaaca gccagggggc cttacccggt atggtctggc agaacccgga  3720
cgtgtacctg cagggtccca tctgggccaa gattcctcac acggacggca acttccacca  3780
gtctccgctg atgggcggct ttggcctgaa acatcctccg cctcagatcc tgatcaagaa  3840
cacgcctgta cctgcggatc ctccgaccac cttcaaccag tcaaagctga actctttcat  3900
cacgcaatac agcaccggac aggtcagcgt ggaaattgaa tgggagctgc agaaggaaaa  3960
cagcaagcgc tggaacccg agatccagta cacctccaac tactacaaat ctacaagtgt  4020
ggactttgct gttaatacag aaggcgtgta ctctgaaccc cgccccattg gcacccgtta  4080
cctcacccgt aatctgtaat tgcctgttaa tcaataaacc ggttgattcg tttcagttga  4140
actttggtct ctgcgaaggg cgaattcgtt taaacctgca ggactagagg tcctgtatta  4200
gaggtcacgt gagtgttttg cgacattttg cgacaccatg tggtcacgct gggtatttaa  4260
gcccgagtga gcacgcaggg tctccatttt gaagcgggag gtttgaacgc gcagccgcca  4320
agccgaattc tgcagatatc catcacactg gcggccgctc gactagagcg gccgccaccg  4380
cggtggagct ccagcttttg ttccctttag tgagggttaa ttgcgcgctt ggcgtaatca  4440
tggtcatagc tgtttcctgt gtgaaattgt tatccgctca caattccaca acatacga  4500
gccgaagca taaagtgtaa agcctggggt gcctaatgag tgagctaact cacattaatt  4560
gcgttgcgct cactgcccgc tttccagtcg ggaaacctgt cgtgccagct gcattaatga  4620
atcggccaac gcgcggggag aggcggtttg cgtattgggc gctcttccgc ttcctcgctc  4680
actgactcgc tgcgctcggt cgttcggctg cggcgagcgg tatcagctca ctcaaaggcg  4740
gtaatacggt tatccacaga atcagggat aacgcaggaa agaacatgtg agcaaaaggc  4800
cagcaaaagg ccaggaaccg taaaaaggcc gcgttgctgg cgtttttcca taggctccgc  4860
cccccctgacg agcatcacaa aaatcgacgc tcaagtcaga ggtggcgaaa cccgacagga  4920
ctataaagat accaggcgtt tccccctgga agctccctcg tgcgctctcc tgttccgacc  4980
ctgccgctta ccggatacct gtccgccttt ctcccttcgg gaagcgtggc gctttctcat  5040
agctcacgct gtaggtatct cagttcggtg taggtcgttc gctccaagct gggctgtgtg  5100
cacgaacccc ccgttcagcc cgaccgctgc gccttatccg gtaactatcg tcttgagtcc  5160
aacccggtaa gacacgactt atcgccactg gcagcagcca ctggtaacag gattagcaga  5220
gcgaggtatg taggcggtgc tacagagttc ttgaagtggt ggcctaacta cggctacact  5280
agaagaacag tatttggtat ctgcgctctg ctgaagccag ttaccttcgg aaaaagagtt  5340
ggtagctctt gatccggcaa acaaaccacc gctggtagcg gtggtttttt tgtttgcaag  5400
cagcagatta cgcgcagaaa aaaaggatct caagaagatc ctttgatctt ttctacgggg  5460
tctgacgctc agtggaacga aaactcacgt taagggattt tggtcatgag attatcaaaa  5520
aggatcttca cctagatcct ttaaattaa aaatgaagtt ttaaatcaat ctaaagtata  5580
tatgagtaaa cttggtctga cagttaccaa tgcttaatca gtgaggcacc tatctcagcg  5640
atctgtctat ttcgttcatc catagttgcc tgactcccg tcgtgtagat aactacgata  5700
cgggagggct taccatctgg ccccagtgct gcaatgatac cgcgagaccc acgctcaccg  5760
gctccagatt tatcagcaat aaaccagcca gccggaaggg ccgagcgcag aagtggtcct  5820
gcaactttat ccgcctccat ccagtctatt aattgttgcc gggaagctag agtaagtagt  5880
tcgccagtta atagtttgcg caacgttgtt gccattgcta caggcatcgt ggtgtcacgc  5940
tcgtcgtttg gtatggcttc attcagctcc ggttcccaac gatcaaggcg agttacatga  6000
tcccccatgt tgtgcaaaaa agcggttagc tccttcggtc ctccgatcgt tgtcagaagt  6060
aagttggccg cagtgttatc actcatggtt atggcagcac tgcataattc tcttactgtc  6120
atgccatccg taagatgctt ttctgtgact ggtgagtact caaccaagtc attctgagaa  6180
tagtgtatgc ggcgaccgag ttgctcttgc ccggcgtcaa tacgggataa taccgcgcca  6240
catgcagaa ctttaaaagt gctcatcatt ggaaaacgtt cttcggggcg aaaactctca  6300
aggatcttac cgctgttgag atccagttcg atgtaaccca ctcgtgcacc caactgatct  6360
tcagcatctt ttactttcac cagcgtttct gggtgagcaa aaacaggaag gcaaaatgcc  6420
gcaaaaaagg gaataagggc gacacggaaa tgttgaatac tcatactctt ccttttcaa  6480
tattattgaa gcatttatca gggttattgt ctcatgagcg gatacatatt tgaatgtatt  6540
tagaaaaata aacaatagg ggttccgcgc acatttcccc gaaaagtgcc acctaaattg  6600
taagcgttaa tattttgtta aaattcgcgt taaattttg ttaaatcagc tcatttttta  6660
accaataggc cgaaatcggc aaaatccctt ataaatcaaa agaatagacc gagatagggt  6720
tgagtgttgt tccagtttgg aacaagagtc cactattaaa gaacgtggac tccaacgtca  6780
aagggcgaaa aaccgtctat cagggcgatg gcccactacg tgaaccatca ccctaatcaa  6840
gttttttggg gtcgaggtgc cgtaaagcac taaatcctaaaggg agccccccgat  6900
ttagagcttg acggggaaag ccggcgaacg tggcgagaaa ggaagggaag aaagcgaaag  6960
gagcgggcgc tagggcgctg gcaagtgtag cggtcacgct gcgcgtaacc accacaccgg  7020
ccgcgcttaa tgcgccgcta cagggcgcgt cccattcgcc attcaggctg cgcaactgtt  7080
gggaagggcg atcggtgcgg gcctcttcgc tattacgcca gctggcgaaa gggggatgtg  7140
ctgcaaggcg attaagttgg gtaacgccag gttttccca gtcacgacgt tgtaaaacga  7200
```

```
cggccagtga gcgcgcgtaa tacgactcac tatagggcga attgggtacc gggcccccc   7260
tcgatcgagg tcgacggtat cgggggagct cgcagggtct ccatttttgaa gcgggaggtt  7320
tgaacgcgca gccgcc                                                   7336

SEQ ID NO: 395          moltype = DNA  length = 969
FEATURE                 Location/Qualifiers
misc_feature            1..969
                        note = Description of Artificial Sequence: Synthetic
                         polynucleotide
source                  1..969
                        mol_type = other DNA
                        organism = synthetic construct
SEQUENCE: 395
ccccaactgg ggtaaccttt gggctccccg ggcgcgacta taagctgcga gcaacttcac   60
ttgggtatgc cggcggtagc gcttaccgtt cgtataatgt atgctatacg aagttatccg  120
aagccgctag cggtggtttg tctggtcaac caccgcggtc tcagtggtgt acggtacaaa  180
cccagctacc ggtcgccacc atgcccgcca tgaagatcga gtgccgcatc accggcaccg  240
tgaacggcgt ggagttcgag ctggtgggcg gcggagaggg caccccgag cagggccgca   300
tgaccaacaa gatgaagagc accaaaggcc cctgacctt cagcccctac ctgctgagcc   360
acgtgatggg ctacggcttc taccacttcg gcacctaccc cagccggcta c gagaacccct 420
tcctgcacgc catcaacaac ggcggctaca ccaacacccg catcgagaag tacgaggacg  480
gcggcgtgct gcacgtgagc ttcagctacc gctacgaggc cggccgcgtg atcggcgact  540
tcaaggtggt gggcaccggc ttccccgagg acagcgtgat cttcaccgac aagatcatcc  600
gcagcaacgc caccgtggag cacctgcacc ccatgggcga taacgtgctg gtgggcagct  660
tcgcccgcac cttcagcctg cgcgacgcg gctactacag cttcgtggtg acagccaca   720
tgcacttcaa gagcgccatc caccccagca tcctgcagca gggggcccc atgttcgcat  780
tccgccgcgt ggaggagctg cacagcaaca ccgagctggg catcgtggag taccagcacg  840
ccttcaagac ccccatcgcc ttcgccagat ctcgagctcg atgagtttgg acaaaccaca  900
actagaatgc agtgaaaaaa atgctttatt tgtgaaattt gtgatgctat tgctttatt   960
gtgggcccg                                                          969

SEQ ID NO: 396          moltype = DNA  length = 4769
FEATURE                 Location/Qualifiers
misc_feature            1..4769
                        note = Description of Artificial Sequence: Synthetic
                         polynucleotide
source                  1..4769
                        mol_type = other DNA
                        organism = synthetic construct
SEQUENCE: 396
tgatcccctg cgccatcaga tccttggcgg cgagaaagcc atccagttta ctttgcaggg   60
cttcccaacc ttaccagagg gcgccccagc tggcaattcc ggttcgcttg ctgtccataa  120
aaccgccag tctagctatc gccatgtaag cccactgcaa gctacctgct ttctctttgc   180
gcttgcgttt tcccttgtcc agatagccca gtagctgaca ttcatccggg gtcagcaccg  240
tttctgcgga ctggctttct acgtgctcga gggggccaa acggtctcca gcttggctgt  300
tttggcggat gagagaagat tttcagcctg atacagatta aatcagaacg cagaagcggt  360
ctgataaaac agaatttgcc tggcgcagt agcgcggtg tcccacctga ccccatgccg  420
aactcagaag tgaaacgccg tagcgccgat ggtagtgtgg ggtctcccca tgcgagagta  480
gggaactgcc aggcatcaaa taaaacgaaa ggctcagtcg aaagactggg cctttcgttt  540
tatctgttgt ttgtcggtga acgctctcct gagtaggaca aatccgccgg gagcggattt  600
gaacgttgcg aagcaacggc ccggagggtg gcgggcaagca cgcccgccat aaactgccag  660
gcatcaaatt aagcagaagg ccatcctgac ggatggcctt tttgcgtttc tacaaactct  720
tttgtttatt tttctaaata cattcaaata tgtatccgct catgaccaaa atcccttaac  780
gtgagttttc gttccactga gcgtcagacc ccgtagaaaa gatcaaagga tcttcttgag  840
atccttttt tctgcgcgta atctgctgct tgcaaacaaa aaaaccaccg ctaccagcga  900
tggtttgttt gccggatcaa gagctaccaa ctctttttcc gaaggtaact ggcttcagca  960
gagcgcagat accaaatact gtccttctag tgtagccgta gttaggccac cacttcaaga 1020
actctgtagc accgcctaca tacctcgctc tgctaatcct gttaccagtg gctgctgcca 1080
gtggcgataa gtcgtgtctt accgggttgg actcaagacg atagttaccg gataaggcgc 1140
agcggtcggg ctgaacgggg ggttcgtgca cacagcccag cttggagcga acgacctaca 1200
ccgaactgag atacctacag cgtgagctat gagaaagcgc cacgcttccc gaagggagaa 1260
aggcggacag gtatccggta agcggcaggg tcggaacagg agagcgcacg agggagcttc 1320
cagggggaaa cgcctggtat ctttatagtc ctgtcgggtt tcgccacctc tgacttgagc 1380
gtcgattttt gtgatgctcg tcagggggc ggagcctatg gaaaaacgcc agcaacgcgg 1440
cctttttacg gttcctggcc ttttgctggc cttttgctca catgttcttt cctgcgttat 1500
cccctgattc tgtggataac cgtattaccg cctttgagtg agctgatacc gctcgccgca 1560
gccgaacgac cgagcgcagc gagtcagtga gcgaggaagc ggaagagcgc ctgatgcggt 1620
attttctcct tacgcatctg tgcggtattt cacaccgcat atggtgcact ctcagtacaa 1680
tctgctctga tgccgcatag ttaagccagt atacactccg ctatcgctac gtgactggtt 1740
catggctgcg ccccgacacc cgccaacacc cgctgacgcg ccctgacggg cttgtctgct 1800
cccggcatcc gcttacagac aagctgtgac cgtctccggg agctgcatgt gtcagaggtt 1860
ttcaccgtca tcaccgaaac gcgcgaggca gcagatcaat tcgcgcgcga aggcgaagcg 1920
gcatgcataa tgtgcctgtc aaatggacga agcagggatt ctgcaaaccc tatgctactc 1980
cgtcaagcgt caattgtct gattcgttac caattatgac aacttgacgg ctacatcatt 2040
cacttttttct tcacaaccgg cacgaactc gctcggctg ccccggtgc attttttaaa 2100
tacccgcgag aaatagagtt gatcgtcaaa accaacattg cgaccgacgg tggcgatagg 2160
catccgggt gtgctcaaaa gcagcttcgc ctggctgata cgttggtcct cgcgccagct 2220
taagacgcta atccctaact gctggcgaaa agatgtgac agacgcgacg gcgacaagca 2280
aacatgctgt gcgacgctgg cgatacatta ccctgttatc cctagatgac attaccctgt 2340
```

```
tatcccagat gacattaccc tgttatccct agatgacatt accctgttat ccctagatga  2400
catttaccct gttatcccta gatgacatta ccctgttatc ccagatgaca ttaccctgtt  2460
atccctagat acattaccct gttatcccag atgacatacc ctgttatccc tagatgacat  2520
taccctgtta tcccagatga cattaccctg ttatccctag atacattacc ctgttatccc  2580
agatgacata ccctgttatc cctagatgac attaccctgt tatcccagat gacattaccc  2640
tgttatccct agatacatta ccctgttatc ccagatgaca taccctgtta tccctagatg  2700
acattaccct gttatcccag atgacattac cctgttatcc ctagatacat taccctgtta  2760
tcccagatga catacccctgt tatccctaga tgacattacc ctgttatccc agatgacatt  2820
accctgttat ccctagatac attaccctgt tatcccagat gacataccct gttatcccta  2880
gatgacatta ccctgttatc ccagatgaca ttaccctgtt atccctagat acattaccct  2940
gttatcccag atgacatacc ctgttatccc tagatgacat accctgtta tcccagataa  3000
actcaatgat gatgatgatg atggtcgaga ctcagcggcc gcggtgccag ggcgtgccct  3060
tgggctcccc gggcgcgatg cccgccatga agatcgagtg ccgcatcacc ggcaccctga  3120
acggcgtgga gttcgagctg gtgggcggcg agagggcca ccccgagcag ggccgcatga  3180
ccaacaagat gaagagcacc aaaggcgccc tgaccttcag cccctacctg ctgagccacg  3240
tgatgggcta cggcttctac cacttcggca cctaccccag cggctacgag aacccctcc  3300
tgcacgccat caacaacggc ggctacacca caccccgcat cgagaagtac gaggacggcg  3360
gcgtgctgca cgtgagcttc agctaccgct acgaggccgc ggcgacttca  3420
aggtggtggg caccggcttc cccgaggaca cgtgatctt caccgacaag atcatccgca  3480
gcaacgccac cgtggagcac ctgcacccca tgggcgataa cgtgctggtg ggcagcttcg  3540
cccgcacctt cagcctgcgc gacggcggct actacagctt cgtggtggac agccacatgc  3600
acttcaagag cgccatccac cccagcatcc tgcagaacgg gggcccatg ttcgcctcc  3660
gccgcgtgga ggagctgcac agcaacaccg agctgggcat cgtggagtac cagcacgcct  3720
tcaagacccc catcgccttc gccagatctc gagctcgagg tggtttgtct ggtcaaccac  3780
cgcggtctca gtggtgtacg gtacaaaccc accccaactg gggtaacctt tgagttctct  3840
cagttggggg taatcagcat catgatgtgg taccacatca tgatgctgat tataagaatg  3900
cggccgccac actctagtgg atctcgagtt aataattcag aagaactcgt caagaaggcg  3960
atagaaggcg atgcgctgcg aatcgggagc ggcgataccg taaagcacga ggaagcggtc  4020
agcccattcg ccgccaagct cttcagcaat atcacgggta gccaacgcta tgtcctgata  4080
gcggtccgcc acacccagcc ggccacagtc gatgaatcca gaaaagcggc catttccac  4140
catgatattc ggcaagcagg catcgccatg ggtcacgacg agatcctcgc cgtcgggcat  4200
gctcgccttg agcctggcga acagttcggc tggcgcgagc ccctgatgct cttcgtccag  4260
atcatcctga tcgacaagac cggcttccat ccgagtacgt gctcgctcga tgcgatgttt  4320
cgcttggtgg tcgaatgggc aggtagccgg atcaagcgta tgcagccgcc gcattgcatc  4380
agccatgatg gatactttct cggcaggagc aaggtgtaga tgacatggag atcctgcccc  4440
ggcacttcgc ccaatagcag ccagtccctt cccgcttcag tgacaacgtc gagcacagct  4500
gcgcaaggaa cgcccgtcgt ggccagccac gatagccgcg ctgcctcgtc ttgcagttca  4560
ttcagggcac cggacaggtc ggtcttgaca aaaagaaccg ggcgcccctg cgctgacagc  4620
cggaacacgg cggcatcaga gcagccgatt gtctgttgtg cccagtcata gccgaatagc  4680
ctctccaccc aagcggccgg agaacctgcg tgcaatccat cttgttcaat catgcgaaac  4740
gatcctcatc ctgtctcttg atcagagct                                    4769

SEQ ID NO: 397          moltype = DNA  length = 797
FEATURE                 Location/Qualifiers
misc_feature            1..797
                        note = Description of Artificial Sequence: Synthetic
                         polynucleotide
source                  1..797
                        mol_type = other DNA
                        organism = synthetic construct
SEQUENCE: 397
ccccaactgg ggtaaccttt gggctccccg ggcgcgatgg tgagcaaggg cgaggaggat   60
aacatggcca tcatcaagga gttcatgcgc ttcaaggtgc acatggaggg ctccgtgaac  120
ggccacgagt tcgagatcga gggcgagggc gaggccgcc cctacgaggg cacccagacc  180
gccaagctga aggtgaccaa gggtggcccc ctgcccttcg cctgggacat cctgtcccct  240
cagttcatgt acggctccaa ggcctacgtg aagcaccccg ccgacatccc cgactacttg  300
aagctgtcct tccccgaggg cttcaagtgg gagcgcgtga tgaacttcga ggacggcggc  360
gtggtgaccg tgacccagga ctcctccctg caggacggcg agttcatcta caaggtgaag  420
ctgcgcggca ccaacttccc ctccgacggc cccgtaatgc agaagaagac catgggctgg  480
gaggcctcct ccgagcggat gtaccccgag gacggcgcg tgaagggcga gatcaagcag  540
aggctgaagc tgaaggacgg cggccactac gacgctgagg tcaagaccac ctacaaggcc  600
aagaagcccg tgcagctgcc cggcgcctac aacgtcaaca tcaagttgga catcacctcc  660
cacaacgagg actacaccat cgtggaacag tacgaacgcg ccgagggccg ccactccacc  720
ggcggcatgg acgagctgta caagggtggt tgtctggtc aaccaccgcg agctcagtgg  780
tgtacggtac aaaccca                                                 797

SEQ ID NO: 398          moltype = DNA  length = 815
FEATURE                 Location/Qualifiers
misc_feature            1..815
                        note = Description of Artificial Sequence: Synthetic
                         polynucleotide
source                  1..815
                        mol_type = other DNA
                        organism = synthetic construct
SEQUENCE: 398
ccccaactgg ggtaaccttt gggctccccg ggcgcggccg ccaccatggt gtccaagggt   60
gaggaacttt ttaccggagt ggtgccgata ctggtagagc tggatggcga cgtaaacggg  120
cacaagttca gtgtacgggg agagggcgag ggcgacgcta cgaatgggaa attgactttg  180
aaatttattt gcaccacggg caaattgccg gtcccgtggc caactttggt tacgaccttg  240
```

```
acctatggcg ttcagtgttt ctcacggtac ccagaccaca tgaaacagca tgactttttt    300
aagtcagcga tgccggaggg atatgtgcaa gaacggacta tctcatttaa agatgatggc    360
acatataaga caagagcgga agtcaaattc gaaggggaca ccctcgtcaa tcgaatagaa    420
ctcaaggaa tagacttcaa agaagatggt aatatactgg ggcacaaact cgaatacaat    480
ttcaacagtc ataacgtcta catcactgcc gacaaacaaa aaaatgggat caaagcgaac    540
ttcaaaatcc gacataatgt cgaggatggg agcgtccaac tggcagacca ttaccagcaa    600
aatactccaa taggtgatgg tccagtgctt ttgccagata tcattatct tagctatcag    660
agcaagttga gtaaggatcc gaatgaaaag cgagatcaca tggtcttgct ggagtttgtt    720
acggcggctg gtatcacact tggtatggat gaattgtaca agggtggttt gtctggtcaa    780
ccaccgcgga ctcagtggtg tacggtacaa accca                               815

SEQ ID NO: 399           moltype = DNA  length = 1660
FEATURE                  Location/Qualifiers
misc_feature             1..1660
                         note = Description of Artificial Sequence: Synthetic
                         polynucleotide
source                   1..1660
                         mol_type = other DNA
                         organism = synthetic construct
SEQUENCE: 399
ccccaactgg ggtaacccttt gggctccccg ggcgcggcca ccatgaaatg ggttactttc     60
atatctctgt tgttttttgtt ttcctctagt tccagggcca tgccgtcttc tgtctcgtgg    120
ggcatcctcc tgctggcagg cctgtgctgc ctggtccctg tctccctggc tgaggatccc    180
cagggagatg ctgccagaa gacagataca tccaccatg atcaggatca cccaaccttc    240
aacaagatca cccccaacct ggctgagttc gccttcagcc tataccgcca gctggcacac    300
cagtccaaca gcaccaatat cttcttctcc ccagtgctacc agc ctttgcaatg    360
ctctccctgg ggaccaaggc tgacactcac gatgaaatcc tggagggcct gaatttcaac    420
ctcacggaga ttccggaggc tcagatccat gaaggcttcc aggaactcct ccgtaccctc    480
aaccagccag acagccagct ccagctgacc accggcaatg gcctgttcct cagcgagggc    540
ctgaagctag tggataagtt tttgaaggat gttaaaaagt tgtaccactc agaagccttc    600
actgtcaact tcggggacac cgaagagcc aagaaacaga tcaacgatta cgtggagaag    660
ggtactcaag ggaaaattgt ggatttggtc aaggagcttg acagagacac agttttttgct    720
ctggtgaatt acatcttctt taaaggcaaa tgggagagac cctttgaagt caaggacacc    780
gaggaagaga acttccacgt ggaccaggtg accaccgtga aggtgcctat gatgaagcgt    840
ttaggcatgt ttaacatcca gcactgtaag aagctgtcca gctgggtgct gctgatgaaa    900
tacctgggca tgccaccgc catcttcttc ctgcctgatg aggggaaact acagcacctg    960
gaaaatgaac tcacccacga tatcatcacc aagttcctgg aaaatgaaga cagaaggtct   1020
gccagcttac atttacccaa actgtccatt actggaacct atgatctgaa gagcgtcctg   1080
ggtcaactgg gcatcactaa ggtcttcagc aatggggctg aacctctccgg ggtcacagag   1140
gaggcacccc tgaagctctc caaggccgtg cataagctg tgctgaccat cgacgagaaa   1200
gggactgaag ctgctgggc catgtttta gaggccatac ccatgtctat ccccccgag     1260
gtcaagttca acaaaccctt tgtcttctta atgattgaac aaaataccaa gtctcccctc   1320
ttcatgggaa aagtggtgaa tcccacccaa aaataagaat tctaactaga gctcgctgat   1380
cagcctcgac tgtgccttct agttgccagc catctgttgt ttgcccctcc ccgtgcctt   1440
ccttgaccct ggaaggtgcc actcccactg tcctttccta ataaaatgag gaaattgcat   1500
cgcattgtct gagtaggtgt cattctattc tgggggtgg ggtggggcag gacagcaagg   1560
gggaggattg ggaagagaat agcaggcatg ctggggagcg agctcgaggt ggtttgtctg   1620
gtcaaccacc gcggtctcag tggtgtacgg tacaaaccca                         1660

SEQ ID NO: 400           moltype = DNA  length = 4906
FEATURE                  Location/Qualifiers
misc_feature             1..4906
                         note = Description of Artificial Sequence: Synthetic
                         polynucleotide
source                   1..4906
                         mol_type = other DNA
                         organism = synthetic construct
SEQUENCE: 400
ccccaactgg ggtaacccttt gggctccccg ggcgcggcca ccatgaaatg ggttactttc     60
atatctctgt tgttttttgtt ttcctctagt tccagggcca tgacgaggat tttgacagct    120
ttcaaagtgg tgaggacact gaagactggt tttggcttta ccaatgtgac tgcacaccaa    180
aaatggaaat tttcaagacc tggcatcagg ctcctttctg tcaaggcaca gacagcacac    240
attgtcctg aagatggaac taagatgaaa ggttactcct ttggccatcc atcctctgtt    300
gctggtgaag tggtttttaa tactggcctg ggaggtgacc cagaagctat tactgaccc    360
gcctacaaag gacagattct cacaatggcc aaccctatta ttgggaatgg tggagctcct    420
gatactactg ctctgatga actgggactt agcaaatatt ggagtctaa tggaatcaag    480
gtttcaggtt tgctggtgct ggattatagt aaagactaca accactggct ggctaccaag    540
agtttagggc aatggctaca ggaagaaaag gttcctgcaa tttatggagt ggacacaaga    600
atgctgacta aaataattcg ggataaggt accatgctga gaagattga atttgaaggt    660
cagcctgtgg attttgtgga tccaaataaa cagaatttga ttgctgaggt ttcaaccaag    720
gatgtcaaag tgtacggcaa aggaaacccc acaaagtgg tagctgtaga ctgtgggatt    780
aaaaacaatg taatccgcct gctagtaaag cgaggagctg aagtgcactt agttccctgg    840
aaccatgatt tcaccaagat ggagtatgat gggatttga tcgcgggagg accggggaac    900
ccagctcttg cagaaccact aattcagaat gtcagaaaga ttttggagag tgatcgcaa    960
gagccattgt ttggaatcag tacaggaaac ttaataacag gattggctgc tggtgccaaa   1020
acctacaaga tgtccatggc caacagaggg cagaatcagc tgttttttgaa tatcacaaac   1080
aaacaggctt tcattactgc tcagaatcat ggctatgcct ggacaacac cctcctgct    1140
ggctggaaac cacttttttgt gaatgtcaac gatcaaacaa atgaggggat tatgcatgag   1200
agcaaacccc tcttcgctgt gcagttccac ccagaggtca ccccgggggcc aatagacact   1260
```

```
gagtacctgt ttgattcctt tttctcactg ataaagaaag gaaaagctac caccattaca  1320
tcagtcttac cgaagccagc actagttgca tctcgggttg aggtttccaa agtccttatt  1380
ctaggatcag gaggtctgtc cattggtcag gctggagaat ttgattactc aggatctcaa  1440
gctgtaaaag ccatgaagga agaaaatgtc aaaactgttc tgatgaaccc aaacattgca  1500
tcagtccaga ccaatgaggt gggcttaaag caagcggata ctgtctactt tcttcccatc  1560
acccctcagt ttgtcacaga ggtcatcaag gcagaacagc cagatgggtt aattctgggc  1620
atgggtggcc agacagctct gaactgtgga gtggaactat tcaagagagg tgtgctcaag  1680
gaatatggtg tgaaagtcct gggaacttca gttgagtcca ttatggctac ggaagacagg  1740
cagctgtttt cagataaact aaatgagatc aatgaaaaga ttgctccaag ttttgcagtg  1800
gaatcgattg aggatgcact gaaggcagca gacaccattg gctacccagt gatgatccgt  1860
tccgcctatg cactgggtgg gttaggctca ggcatctgtc ccaacagaga gactttgatg  1920
gacctcagca caaaggcctt tgctatgacc aaccaaattc tggtggagaa gtcagtgaca  1980
ggttggaaag aaatagaata tgaagtggtt cgagatgctg atgcaaattg tgtcactgtc  2040
tgtaacatgg aaaatgttga tgccatgggt gttcacacag gtgactcagt tgttgtggct  2100
cctgcccaga cactctccaa tgccgagttt cagatgttga gacgtacttc aatcaatgat  2160
gttcgccact tgggcattgt gggtgaatgc aacattcagt ttgcccttca tcctacctca  2220
atggaatact gcatcattga agtgaatgcc agactgtccc gaagctctgc tctggcctca  2280
aaagccactg gctacccatt ggcattcatt gctgcaaaga ttgccctagg aatcccactt  2340
ccagaaatta agaacgtcgt atccgggaag acatcagcct gttttgaacc tagcctggat  2400
tacatggtca ccaagattcc ccgctgggat cttgaccgtt tcatggaac atctagccga  2460
attggtagct ctatgaaaag tgtaggagag gtcatggcta ttggtcgtac ctttgaggag  2520
agtttccaga aagctttacg gatgtgccac ccatctactag aaggtttcac tccccgtctc  2580
ccaatgaaca aagaatggcc atctaattta gatcttagaa aagagttgtc tgaaccaagc  2640
agcacgcgta tctatgccat tgccaaggcc attgatgaca acatgtccct tgatgagatt  2700
gagaagctca catacattga caagtggttt ttgtataaga tgcgtgatat tttaaacatg  2760
gaaaagcac tgaaaggcct caacagtgag tccatgacag aagaaaccct gaaaagggca  2820
aaggagattg ggttctcaga taagcagatt tcaaaatgcc ttgggctcac tgaggcccag  2880
acaagggagc tgaggttaaa gaaaaacatc caccccttggg ttaaacagat tgatacactg  2940
gctgcagaat acccatcagt aacaaactat ctctatgtta cctacaatgg tcaggagcat  3000
gatgtcaatt ttgatgacca tggaatgatg gtgctaggtc gtgtccata tcacattggc  3060
agcagtgtgg aatttgattg gtgtgctgtc tctagtatcc gcacactgcg tcaacttggc  3120
aagaagacgg tggtggtgaa ttgcaatcct gagactgtga gcacagactt tgatgagtgt  3180
gacaaactgt actttgaaga gttgtccttg gagagaatcc tagacatcta ccatcaggag  3240
gcatgtggtg gctgcatcat atcagttgga ggccagattc caaacaacct ggcagttcct  3300
ctatacaaga atggtgtcaa gatcatgggc acaagccccc tgcagatcga cagggctgag  3360
gatcgctcca tcttctcagc tgtcttggat gagctgaagg tggctcaggc accttggaaa  3420
gctgttaata ctttgaatga agcactgaaa tttgcaaagt ctgtggacta cccctgcttg  3480
ttgaggcctt ccctatgtttt gagtgggtct gctatgaatg tggtattctc tgaggatgag  3540
atgaaaaaat tcctagaaga ggcgactaga gtttctcagg agcacccagt ggtgctgaca  3600
aaatttgttg aaggggcccg agaagtagaa atggacgctg ttggcaaaga tggaagggtt  3660
atctctcatg ccatctctga acatgttgaa gatgcaggtg tccactcggg agatgccact  3720
ctgatgctgc ccacacaaac catcagccaa ggggccattg aaaaggtgaa ggatgctacc  3780
cggaagattg caaaggcttt tgccatctct ggtccattca acgtccaatt tcttgtcaaa  3840
ggaaatgatg tcttggtgat tgagtgtaac ttgagagctt ctcgatcctt ccccttgtt  3900
tccaagactc ttggggttga cttcattgat gtggccacca aggtgatgat tggagagaat  3960
gttgatgaga acatcttcc aacattggac catcccataa ttcctgctga ctatgttgca  4020
attaaggctc ccatgtttc ctggccccgg ttgagggat ctgaccccat tctgagatgt  4080
gagatggctt ccactggaga ggtggcttgc tttggtgaag gtattcatac agccttccta  4140
aaggcaatgc tttccacagg atttaagata ccccagaaag gcatcctgat aggcatccag  4200
caatcattcc ggccaagatt ccttggtgtg gctgaacaat tacacaatga aggttttcaag  4260
ctgtttgcca cggaagccac atcagactgg ctcaacgcca acaatgtccc tgccacccca  4320
gtggcatggc cgtctcaaga aggacagaat cccagcctct cttccatcag aaaattgatt  4380
agagatggca gcattgacct agtgattaac cttcccaaca acaactaa atttgtccat  4440
gataattatg tgattcggag gacagctgtt gatagtggaa tccctctcct cactaatttt  4500
caggtgacca aacttttgc tgaagctgtg cagaaatctc gcaaggtgga ctccaagagt  4560
cttttccact acaggcagta cagtgctgga aaagcagcat aggaattcta actagagctc  4620
gctgatcagc ctcgactgtg ccttctagtt gccagccatc tgttgtttgc ccctcccccg  4680
tgccttcctt gaccctggaa ggtgccactc ccactgtcct ttcctaataa aatgaggaaa  4740
ttgcatcgca ttgtctgagt aggtgtcatt ctattctggg gggtggggtg gggcaggaca  4800
gcaagggggag ggattgggaa gagaatagca ggcatgctgg ggagcgagct cgaggtggtt  4860
tgtctggtca accaccgcgg tctcagtggt gtacggtaca aaccca         4906

SEQ ID NO: 401          moltype = DNA   length = 4882
FEATURE                 Location/Qualifiers
misc_feature            1..4882
                        note = Description of Artificial Sequence: Synthetic
                        polynucleotide
source                  1..4882
                        mol_type = other DNA
                        organism = synthetic construct
SEQUENCE: 401
ccccaactgg ggtaaccttt gggctccccg ggcgcgacta taagctgcga gcaacttcac   60
ttgggtatgc cggcggtagc gcttaccgtt cgtataatgt atgctatacg aagttatccg  120
aagccgctag cggtggtttg tctggtcaac caccgcggtc tcagtggtgt acggtacaaa  180
cccacccgag agaccatgca gaggtcgcct ctggaaaagg ccagcgttgt ctccaaactt  240
ttctttagct ggactagacc catccttcgt aaaggataca gacagcgcct ggaattgtca  300
gacatatacc aaatcccttc tgttgattct gctgacaatc tatctgaaaa attggaaaga  360
gaatgggata gagagctggc ttcaaagaaa aatcctaaac tcattaatgc ccttcggcga  420
tgttttttct ggagatttat gttctatgga atctttttat atttagggga agtcaccaaa  480
```

```
gcagtacagc ctctcttact gggaagaatc atagcttcct atgacccgga taacaaggag    540
gaacgctcta tcgcgattta tctaggcata ggcttatgcc ttctctttat tgtgaggaca    600
ctgctcctac acccagccat ttttggcctt catcacattg gaatgcagat gagaatagct    660
atgtttagtt tgatttataa gaagacttta aagctgtcaa gccgtgttct agataaaata    720
agtattggac aacttgttag tctcctttcc aacaacctga acaaatttga tgaaggactt    780
gcattggcac atttcgtgtg gatcgctcct ttgcaagtgg cactcctcat ggggctaatc    840
tgggagttgt tacaggcgtc tgccttctgt ggacttggtt tcctgatagt ccttgccctt    900
tttcaggctg ggctagggag aatgatgatg aagtacagag atcagagagc tgggaagatc    960
agtgaaagac ttgtgattac ctcagaaatg attgaaaata tccaatctgt taaggcatac   1020
tgctgggaag aagcaatgga aaaaatgatt gaaaacttaa gacaaacaga actgaaactg   1080
actcggaagg cagccatgt  gagatacttc aatagctcag ccttcttctt ctcagggttc   1140
tttgtggtgt ttttatctgt gcttcccta  gcactaatca aaggaatcat cctccggaaa   1200
atattcacca ccatctcatt ctgcattgtt ctgcgcatgg cggtcactcg gcaatttccc   1260
tgggctgtac aaacatggta tgactctctt ggagcaataa acaaaataca gagtttctta   1320
caaaagcaag aatataagac attggaatat aacttaacga ctacagaagt agtgatggag   1380
aatgtaacag ccttctggga ggagggattt ggggaattat ttgagaaagc aaaacaaaac   1440
aataacaata gaaaaacttc taatggtgat gacagcctct tcttcagtaa tttctcactt   1500
cttggtactc ctgtcctgaa agatattaat ttcaagatag aaagaggaca gttgttggcg   1560
gttgctggat ccactggagc aggcaagact tcacttctaa tggtgattat gggagaactg   1620
gagccttcag agggtaaaat taagcacagt ggaagaattt cattctgttc tcagttttcc   1680
tggattatgc ctggcaccat taagaaaaat atcatctttg gtgtttccta tgatgaatat   1740
agatacagaa gcgtcatcaa agcatgccaa ctagaagagg acatctccaa gtttgcagag   1800
aaagacaata tagttcttgg agaaggtgga atcacactgt gtggaggtca acgagcaaga   1860
atttctttag caagagcagt atacaaagat gctgatttgt atttattaga ctctcctttt   1920
ggatacctag acgtattgac tgagaaggag atcttcgagt cctgcgtttg caagcttatg   1980
gccaataaga caagaatcct ggttacaagt aagtgaagaa acctgaagaa ggccgataag   2040
attctgatcc tgcacgaggg atcttcatac ttctacggca ctttcagcga gcttcagaac   2100
ttgcaacctg atttctctag caagcttatg ggctgcgact cctttgatca gttctctgcc   2160
gagcgtcgca actccattct gaccgaaaca ctgcataggt ttttccctcga gggcgacgca   2220
ccagtgtctt ggactgagac taagaagcag agcttcagac aaaccggcga attcggtgga   2280
aagagaaaga acagtatcct gaaccccatt aattcaattc ggaagttcag tatcgttcag   2340
aaaacgcctc ttcagatgaa cgggattgag gaagactcag acgaaccgct gaaaggcga    2400
ctctcattgg ttcctgacag tgaacaaggg gaagctattc tcccccggat ttcagtaatt   2460
tccacaggtc cgactctgca agcccggaga agacaatccg tgttgaatct tatgacccat   2520
tccgtgaatc aggggcaaaa tatccataga aagactactg cctctacgag gaaggtatcc   2580
cttgcacccc aagccaatct gacggagctc gacatctact ctcgccgcct gtcccaggag   2640
acaggactgg agattagcga ggagatcaat gaagaggatc tgaaagaatg tttcttcgac   2700
gacatggaat ccatccctgc cgtcacgacg tggaatacct atttgcgtta catcacggta   2760
cataaaagtc tgatattcgt cctgatctgg tgtcttgtga tcttcctcgc tgaagtcgca   2820
gccagcctgg tcgttctttg gctgctcggg aataccccct tgcaggataa gggaaactcc   2880
acccactctc ggaacaatag ttacgccgtc atcattactt ccacttcctc atactacgta   2940
ttctatatat atgtcgggt  cgctgataca ctgctggcca tgggcttctt tcgcggcctg   3000
ccgctcgtcc acacgctgat aactgtctcc aagatctgc  atcataagat gctgcactca   3060
gtgctgcagg ctccaatgag tacactgaat actcttaagg ctgcggcat  cctgaaccgc   3120
tttagtaagg acatcgccat acttgacgat ctcttgcccc tgacaatctt cgatttta    3180
caactccttt tgatcgttat cggggcgatc gctgtggttg ctgtgttcg  gccatatata   3240
ttcgtagcta ctgttcccgt catcgtcgcg ttcatcatgc tccgtgccta ctttctgcag   3300
acgtcccaac agctgaagca gctcgagagc gagggacggt cccccatatt tacgcacttg   3360
gtaactagtc tgaaggggct gtggactctg agagcatttg gtcgacaacc atatttcgag   3420
acctctcttc ataaggccct caacctgcac accgcgaatt ggtttctgta tttgagtacg   3480
ttgcggtggt ttcagatgcg catcgagatg atattcgtga tattctttat cgcagtcaga   3540
tttatcagca tcctgactac gggcgaggga gaggtcgcg  tgggcatcat actcacgctc   3600
gctatgaaca ttatgagcac cctgcaatgg gccgtgaata gctctatcga cgttgacagt   3660
cttatgcgat ctgtgagccg agtctttaag ttcattgaca tgccaacaga aggtaaacct   3720
accaagtcaa ccaaaccata caagaatggc caactctcga aagttatgat tattgagaat   3780
tcacacgtga agaaagatga catctggccc tcaggggggcc aaatgactgt caaagatctc   3840
acagcaaaat acacagaagg tggaaatgcc atattagaga cattccctt  ctcaataagt   3900
cctggccaga gggtggggcct cttgggaaga actggatcag ggaagagtac tttgttatca   3960
gcttttttga gactactgaa cactgaagga gaaatccaga tcgatggtgt gtcttgggat   4020
tcaataactt tgcaacagtg gaggaaagcc tttggagtga taccacagaa agtatttatt   4080
ttttctggaa catttagaaa aaacttggat ccctatgaac agtggagtga tcaagaaata   4140
tggaaagttg cagatgaggt tgggctcaga tctgtgatag aacagtttcc tgggaagctt   4200
gactttgtcc ttgtggatgg gggctgtgtc ctaagccatg ccacaagca gttgatgtgc   4260
ttggctagat ctgttctcag taaggcgaag atcttgctga ttgataacc cagtgctcat   4320
ttggatccag taacatacca aataattaga agaactctaa aacaagcatt tgctgattgc   4380
acagtaattc tctgtgaaca caggataaa  gcaatgctgg aatgccaaca atttttggtc   4440
atagaagaga acaaagtgcg gcagtacgat tccatccaga aactgctgaa cgagaggagc   4500
ctcttccggc aagccatcag ccctccgac  agggtgaagc tctttcccca ccggaactca   4560
agcaagtgca agtctaagcc ccagattgct gctctgaaag aggagacaga agaagaggtg   4620
caagatacaa ggcttagac  ccgctgatca gcctcgactg tgccttctag ttgccagcca   4680
tctgttgttt gcccctcccc cgtgccttcc ttgaccctgg aaggtgccac tcccactgtc   4740
cttcctaat  aaaatgagaa aattgcatcg cattgtctga gtaggtgtca ttctattctg   4800
gggggtgggg tggggcagga cagcaagggg gaggattggg aagacaatag caggcatgct   4860
ggggatgcgg tgggctctat gg                                            4882

SEQ ID NO: 402        moltype = DNA   length = 1594
FEATURE               Location/Qualifiers
misc_feature          1..1594
                      note = Description of Artificial Sequence: Synthetic
```

|   |   |   |
|---|---|---|
| | polynucleotide | |
| source | 1..1594 | |
| | mol_type = other DNA | |
| | organism = synthetic construct | |

SEQUENCE: 402

```
cccccaactgg ggtaaccttt gggctccccg ggcgcggttc cggatccgga gagggcaggg   60
gatctctcct tacttgtggc gacgtggagg agaaccccgg ccccatgagc atcggcctcc  120
tgtgctgtgc agccttgtct ctcctgtggg caggtccagt gaatgctggt gtcactcaga  180
ccccaaaatt ccaggtcctg aagacaggac agagcatgac actgcagtgt gcccaggata  240
tgaaccatga atacatgtcc tggtatcgac aagaccccag catgggcctg aggctgattc  300
attactcagt tggtgctggt atcactgacc aaggagaagt ccccaatggc tacaatgtct  360
ccagatcaac cacagaggat ttcccgctca ggctgctgtc ggctgctccc tcccagacat  420
ctgtgtactt ctgtgccagc agttacgtcg ggaacaccgg ggagctgttt tttggagaag  480
gctctaggct gaccgtactg gaggacctga aaaacgtgct cccacccgag gtcgctgtgt  540
ttgagccatc agaagcagag atctcccaca cccaaaaggc cacactggta tgcctggcca  600
caggcttcta ccccgaccac gtggagctga gctggtgggt gaatgggaag gaggtgcaca  660
gtggggtcag cacagacccg cagccsctca aggagcagcc cgcccctcaat gactccagat  720
actgcctgag cagccgcctg agggtctcgg ccaccttctg gcagaacccc cgcaaccact  780
tccgctgtca agtccagttc tacgggtctc tggagaatga cgagtggacc caggataggg  840
ccaaacccgt cacccagatc gtcagcgccg aggcctgggg tagagcagac tgtggcttca  900
cctccgagtc ttaccagcaa ggggtcctgt ctgccaccat cctctatgag atcttgctag  960
ggaaggccac cttgtatgcc gtgctggtca gtgccctcgt gctgatggct atggtcaaga 1020
gaaaggattc cagaggccgg gccaagcggt ccggatccgg agccaccaac ttcagcctgc 1080
tgaagcaggc cggcgacgtg gaggagaacc ccggccccat ggagccctc ttgggcctgc 1140
ttatcctttg gctgcagctg caatgggtga gcagcaaaca ggaggtgacg cagattcctg 1200
cagctctgag tgtcccagaa ggagaaaact tggttctcaa ctgcagtttc actgatagcg 1260
ctatttacaa cctccagtgg tttaggcagg accctgggaa aggtctcaca tctctgttgt 1320
ttattcagtc aagtcagaga gagcaaacaa gtggaagact taatgcctcg ctggataaat 1380
catcaggacg tagtacttta tacattgcag cttctcagcc tggtgactca gccacctacc 1440
tctgtgctgt gagagccctg tacggaggaa gctacatacc tacatttgga agaggaacca 1500
gccttattgt tcatccgtat atccagaacc ctgaccctgc gggtggtttg tctggtcaac 1560
caccgcggtc tcagtggtgt acggtacaaa ccca                              1594
```

| | | |
|---|---|---|
| SEQ ID NO: 403 | moltype = DNA length = 19 | |
| FEATURE | Location/Qualifiers | |
| misc_feature | 1..19 | |
| | note = Description of Artificial Sequence: Synthetic oligonucleotide | |
| source | 1..19 | |
| | mol_type = other DNA | |
| | organism = synthetic construct | |

SEQUENCE: 403

```
ttgagcgggc ccccaccgt                                                  19
```

| | | |
|---|---|---|
| SEQ ID NO: 404 | moltype = DNA length = 393 | |
| FEATURE | Location/Qualifiers | |
| misc_feature | 1..393 | |
| | note = Description of Artificial Sequence: Synthetic polynucleotide | |
| source | 1..393 | |
| | mol_type = other DNA | |
| | organism = synthetic construct | |

SEQUENCE: 404

```
atgactcact atcaggcctt gcttttggac acgaccgggt ccagttcgg accggtggta    60
gccctgaacc cggctacgct gctcccactg cctgaggaag ggctgcaaca caactgcctt  120
gatgggacag gtggcggtgg tgtcaccgtc aagtttcaagt acaagggtga ggaacttgaa  180
gttgatatta gcaaaatcaa gaaggtttgg cgcgttggta aaatgatatc ttttacttat  240
gacgacaacg gcaagacagg tagaggggca gtgtctgaga agacgcccc caaggagctg  300
ttgcaaatgt tggaaaagtc tgggaaaaag tctggcggct caaaaagaac cgccgacggc  360
agcgaattcg agcccaagaa gaagaggaaa gtc                                393
```

| | | |
|---|---|---|
| SEQ ID NO: 405 | moltype = DNA length = 11 | |
| FEATURE | Location/Qualifiers | |
| misc_feature | 1..11 | |
| | note = Description of Artificial Sequence: Synthetic probe | |
| source | 1..11 | |
| | mol_type = other DNA | |
| | organism = synthetic construct | |

SEQUENCE: 405

```
cgacgacggc g                                                          11
```

| | | |
|---|---|---|
| SEQ ID NO: 406 | moltype = DNA length = 16 | |
| FEATURE | Location/Qualifiers | |
| misc_feature | 1..16 | |
| | note = Description of Artificial Sequence: Synthetic probe | |
| source | 1..16 | |
| | mol_type = other DNA | |
| | organism = synthetic construct | |

SEQUENCE: 406

```
tttatttgtg ggcccg                                                         16

SEQ ID NO: 407          moltype = DNA   length = 15
FEATURE                 Location/Qualifiers
misc_feature            1..15
                        note = Description of Artificial Sequence: Synthetic probe
source                  1..15
                        mol_type = other DNA
                        organism = synthetic construct
SEQUENCE: 407
tcgagtgccg catca                                                          15

SEQ ID NO: 408          moltype = DNA   length = 17
FEATURE                 Location/Qualifiers
misc_feature            1..17
                        note = Description of Artificial Sequence: Synthetic probe
source                  1..17
                        mol_type = other DNA
                        organism = synthetic construct
SEQUENCE: 408
aaagtggtga ggacact                                                        17

SEQ ID NO: 409          moltype = DNA   length = 15
FEATURE                 Location/Qualifiers
misc_feature            1..15
                        note = Description of Artificial Sequence: Synthetic probe
source                  1..15
                        mol_type = other DNA
                        organism = synthetic construct
SEQUENCE: 409
aacccacccg agaga                                                          15

SEQ ID NO: 410          moltype = DNA   length = 66
FEATURE                 Location/Qualifiers
misc_feature            1..66
                        note = Description of Artificial Sequence: Synthetic
                         oligonucleotide
source                  1..66
                        mol_type = other DNA
                        organism = synthetic construct
SEQUENCE: 410
ggaagcggag ctactaactt cagcctgctg aagcaggctg gcgacgtgga ggagaaccct         60
ggacct                                                                    66

SEQ ID NO: 411          moltype = DNA   length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 411
gggggaggag gttctggagg cggaggctcc ggaggcggag ggtca                         45

SEQ ID NO: 412          moltype = DNA   length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 412
ggaggtggcg ggagc                                                          15

SEQ ID NO: 413          moltype = DNA   length = 15
FEATURE                 Location/Qualifiers
misc_feature            1..15
                        note = Description of Artificial Sequence: Synthetic
                         oligonucleotide
source                  1..15
                        mol_type = other DNA
                        organism = synthetic construct
SEQUENCE: 413
cccgcaccag cgcct                                                          15

SEQ ID NO: 414          moltype = DNA   length = 45
FEATURE                 Location/Qualifiers
```

```
misc_feature              1..45
                          note = Description of Artificial Sequence: Synthetic
                            oligonucleotide
source                    1..45
                          mol_type = other DNA
                          organism = synthetic construct
SEQUENCE: 414
gaggcagctg ccaaggaagc cgctgccaag gaggcggccg caaag                           45

SEQ ID NO: 415            moltype = DNA  length = 48
FEATURE                   Location/Qualifiers
misc_feature              1..48
                          note = Description of Artificial Sequence: Synthetic
                            oligonucleotide
source                    1..48
                          mol_type = other DNA
                          organism = synthetic construct
SEQUENCE: 415
agtgggagcg agacccctgg gactagcgag tcagctacac ccgaaagc                        48

SEQ ID NO: 416            moltype = DNA  length = 54
FEATURE                   Location/Qualifiers
misc_feature              1..54
                          note = Description of Artificial Sequence: Synthetic
                            oligonucleotide
source                    1..54
                          mol_type = other DNA
                          organism = synthetic construct
SEQUENCE: 416
gggggtcag gtggatccgg cggaagtggc ggatccggtg gatctggcgg cagt                  54

SEQ ID NO: 417            moltype = DNA  length = 15
FEATURE                   Location/Qualifiers
misc_feature              1..15
                          note = Description of Artificial Sequence: Synthetic
                            oligonucleotide
source                    1..15
                          mol_type = other DNA
                          organism = synthetic construct
SEQUENCE: 417
gaagctgctg ctaag                                                            15

SEQ ID NO: 418            moltype = AA  length = 22
FEATURE                   Location/Qualifiers
REGION                    1..22
                          note = Description of Artificial Sequence: Synthetic peptide
source                    1..22
                          mol_type = protein
                          organism = synthetic construct
SEQUENCE: 418
GSGATNFSLL KQAGDVEENP GP                                                    22

SEQ ID NO: 419            moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 419
GGGGSGGGGS GGGGS                                                            15

SEQ ID NO: 420            moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 420
GGGGS                                                                        5

SEQ ID NO: 421            moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
```

```
SEQUENCE: 421
PAPAP                                                                           5

SEQ ID NO: 422          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 422
EAAAKEAAAK EAAAK                                                                15

SEQ ID NO: 423          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 423
SGSETPGTSE SATPES                                                               16

SEQ ID NO: 424          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 424
GGSGGSGGSG GSGGSGGS                                                             18

SEQ ID NO: 425          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 425
EAAAK                                                                           5

SEQ ID NO: 426          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 426
GLSGQPPRSP SSGSSG                                                               16

SEQ ID NO: 427          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 427
GGLSGQPPRS PSSGSSG                                                              17

SEQ ID NO: 428          moltype = RNA  length = 88
FEATURE                 Location/Qualifiers
misc_feature            1..88
                        note = Description of Artificial Sequence: Synthetic
                         oligonucleotide
source                  1..88
                        mol_type = other RNA
                        organism = synthetic construct
SEQUENCE: 428
gacgagcgcg gcgatatcat catccatggc cggatgatcc tgacgacgga gaccgccgtc              60
gtcgacaagc cggcctgagc tgcgagaa                                                 88

SEQ ID NO: 429          moltype = RNA  length = 20
FEATURE                 Location/Qualifiers
misc_feature            1..20
                        note = Description of Artificial Sequence: Synthetic
```

```
                    oligonucleotide
source              1..20
                    mol_type = other RNA
                    organism = synthetic construct
SEQUENCE: 429
gaagccggcc ttgcacatgc                                              20

SEQ ID NO: 430      moltype = DNA  length = 95
FEATURE             Location/Qualifiers
source              1..95
                    mol_type = unassigned DNA
                    organism = Homo sapiens
SEQUENCE: 430
gcgcgcccgg ctattctcgc agctcaccat ggatgatgat atcgccgcgc tcgtcgtcga  60
caacggctcc ggcatgtgca aggccggctt cgcgg                             95

SEQ ID NO: 431      moltype = RNA  length = 20
FEATURE             Location/Qualifiers
misc_feature        1..20
                    note = Description of Artificial Sequence: Synthetic
                     oligonucleotide
source              1..20
                    mol_type = other RNA
                    organism = synthetic construct
SEQUENCE: 431
accactcgac gctcttatcg                                              20
```